US011434282B2

(12) United States Patent
Croote et al.

(10) Patent No.: US 11,434,282 B2
(45) Date of Patent: *Sep. 6, 2022

(54) ALLERGEN-SPECIFIC ANTIBODIES

(71) Applicants: Chan Zuckerberg Biohub, Inc., San Francisco, CA (US); The Board of Trustees of the Leland Stanford Junior University, Stanford, CA (US)

(72) Inventors: Derek Croote, Stanford, CA (US); Stephen R. Quake, San Francisco, CA (US); Kari Nadeau, Stanford, CA (US); Spyros Darmanis, San Francisco, CA (US); David N. Cornfield, Stanford, CA (US)

(73) Assignees: Chan Zuckerberg Biohub, Inc., San Francisco, CA (US); The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/351,058

(22) Filed: Jun. 17, 2021

(65) Prior Publication Data

US 2021/0317199 A1 Oct. 14, 2021

Related U.S. Application Data

(63) Continuation of application No. 17/056,384, filed as application No. PCT/US2019/032951 on May 17, 2019.

(60) Provisional application No. 62/673,713, filed on May 18, 2018.

(51) Int. Cl.
| | |
|---|---|
| *C07K 16/18* | (2006.01) |
| *C07K 16/14* | (2006.01) |
| *C07K 16/16* | (2006.01) |
| *A61K 39/395* | (2006.01) |
| *A61K 49/00* | (2006.01) |
| *C12N 5/0781* | (2010.01) |
| *G01N 33/50* | (2006.01) |
| *G01N 33/569* | (2006.01) |

(52) U.S. Cl.
CPC ........ *C07K 16/18* (2013.01); *A61K 39/39575* (2013.01); *A61K 49/0004* (2013.01); *C07K 16/14* (2013.01); *C07K 16/16* (2013.01); *C12N 5/0635* (2013.01); *G01N 33/5052* (2013.01); *G01N 33/56961* (2013.01); *C07K 2317/21* (2013.01); *C07K 2317/33* (2013.01); *C07K 2317/34* (2013.01); *C07K 2317/52* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 6,180,370 | B1 * | 1/2001 | Queen | A61P 31/12 435/69.6 |
| 6,849,259 | B2 * | 2/2005 | Haurum | C07K 16/18 424/133.1 |
| 8,604,174 | B2 | 12/2013 | Babcook et al. | |
| 2013/0295097 | A1 | 11/2013 | Orengo et al. | |
| 2016/0058377 | A1 | 3/2016 | Butte et al. | |

FOREIGN PATENT DOCUMENTS

| | | |
|---|---|---|
| WO | 2016209773 A1 | 12/2016 |
| WO | 2018/118713 A1 | 6/2018 |
| WO | 2018150029 A1 | 8/2018 |

OTHER PUBLICATIONS

Janeway, Charles A. "Immunobiology: The Immune System in Health and Disease." 2005 (Year: 2005).*
Sela-Culang et al. Frontiers in immunology 4 (2013): 302 (Year: 2013).*
Stryer, Biochemistry 4th, WH Freeman, New York. 1995 (Year: 1995).*
Colman, Peter M. Research in Immunology 145.1 (1994): 33-36 (Year: 1994).*
Janeway, Charles A. "Immunobiology: The Immune System in Health and Disease." 2001 (Year: 2001).*
Kipriyanov, Sergey M., and Fabrice Le Gall. "Generation and production of engineered antibodies." Molecular biotechnology 26.1 (2004): 39-60. (Year: 2004).*
Peng, Juan, et al. "Development of a monoclonal antibody-based sandwich ELISA for peanut allergen Ara h 1 in food." International Journal of Environmental Research and Public Health 10.7 (2013): 2897-2905. (Year: 2013).*
Abcam, "Human Ig Isotyping Antibody Array (8 Targets)—Quantitative (ab197452)", Available Online At: (URL: https://www.google.com/search? q=antibody+isotyping+kit+human+including+IgD&sxsrf=ACYBGNQjMWILMPnAh51 UHpkUBLfmglf95g%3A1571169654664&source=lnt&tbs=cdr%3A1%2Ccd_min%3A%2Ccd_max%3A5%2F 17%2F2018&tbm, 2019, 2 pages.
Hoh et al., "Single B Cell Deconvolution of Peanut-Specific Antibody Responses in Allergic Patients", J Allergy Clin Immunol, vol. 137, No. 1, Jan. 2016, pp. 157-167.
Kurup et al., "Fungal Allergens And Peptide Epitopes", Peptides, vol. 21, No. 4, 2000, pp. 589-599.

(Continued)

*Primary Examiner* — Michael Szperka
*Assistant Examiner* — Lia E Taylor
(74) *Attorney, Agent, or Firm* — Kilpatrick Townsend & Stockton LLP

(57) ABSTRACT

In one aspect, methods of generating human monoclonal antibodies that specifically binds to an allergen are provided. In some embodiments, the monoclonal antibodies are generated from sequences identified from isolated single B cells from a human subject who is allergic to the allergen.

7 Claims, 33 Drawing Sheets

Specification includes a Sequence Listing.

(56) References Cited

OTHER PUBLICATIONS

Mattoo et al., "De Novo Oligoclonal Expansions of Circulating Plasmablasts in Active and Relapsing Igg4-Related Disease", J Allergy Clin Immunol, vol. 134, No. 3, Sep. 2014, pp. 679-687.
PCT/US2019/032951, "International Search Report and Written Opinion" by ISA/US, dated Nov. 12, 2019, 21 pages.
Zhang et al., "Blocking Allergic Reaction through Targeting Surface-Bound IgE with Low-Affinity Anti-IgE Antibodies", J Immunol, vol. 198, No. 10, May 15, 2007, pp. 3823-3834.
Bublin et al., "IgE cross-reactivity between the major peanut allergen Ara h 2 and the 750 nonhomologous allergens Ara h 1 and Ara h 3", J Allergy Clin Immunol, Jul. 2013, pp. 118-124, vol. 132, Issue 1.
Dekosky et al., In-Depth Determination and Analysis of the Human Paired Heavy- and Light-Chain Antibody Repertoire, Nature Medicine, vol. 21, No. 1, Jan. 2015, pp. 86-93.
Steinitz, Human Monoclonal Antibodies Methods and Protocols, XP055260491, Jan. 1, 2014.
EP Patent Application 19804534.6, Supplemental Partial European Search Report, dated Feb. 17, 2022, 24 pages.
EP Patent Application 19804534.6, Supplemental European Search Report, dated May 20, 2022, 24 pages.

\* cited by examiner

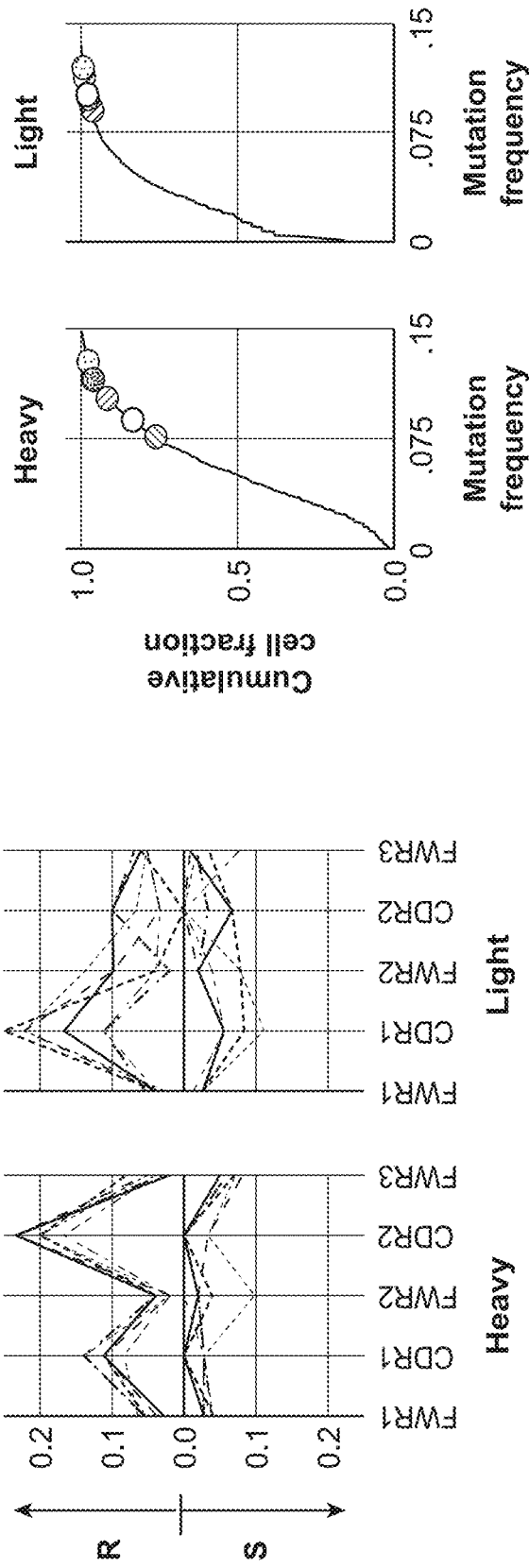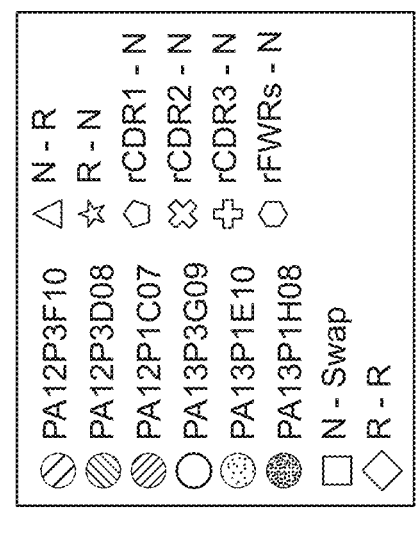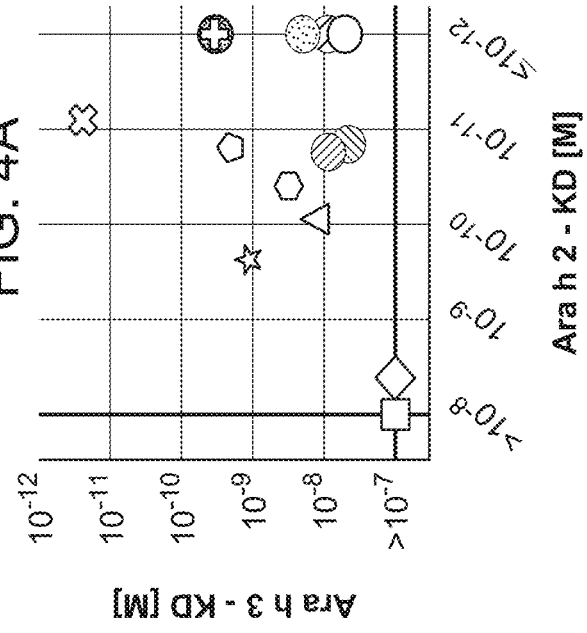
FIG. 4A
FIG. 4B
FIG. 4C

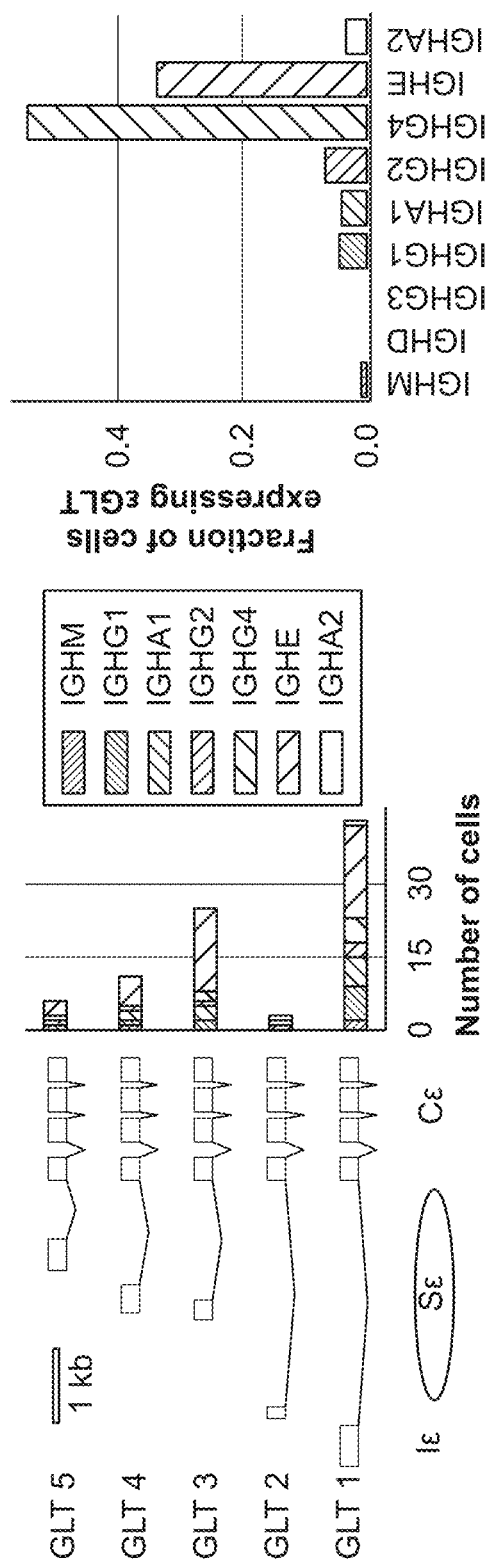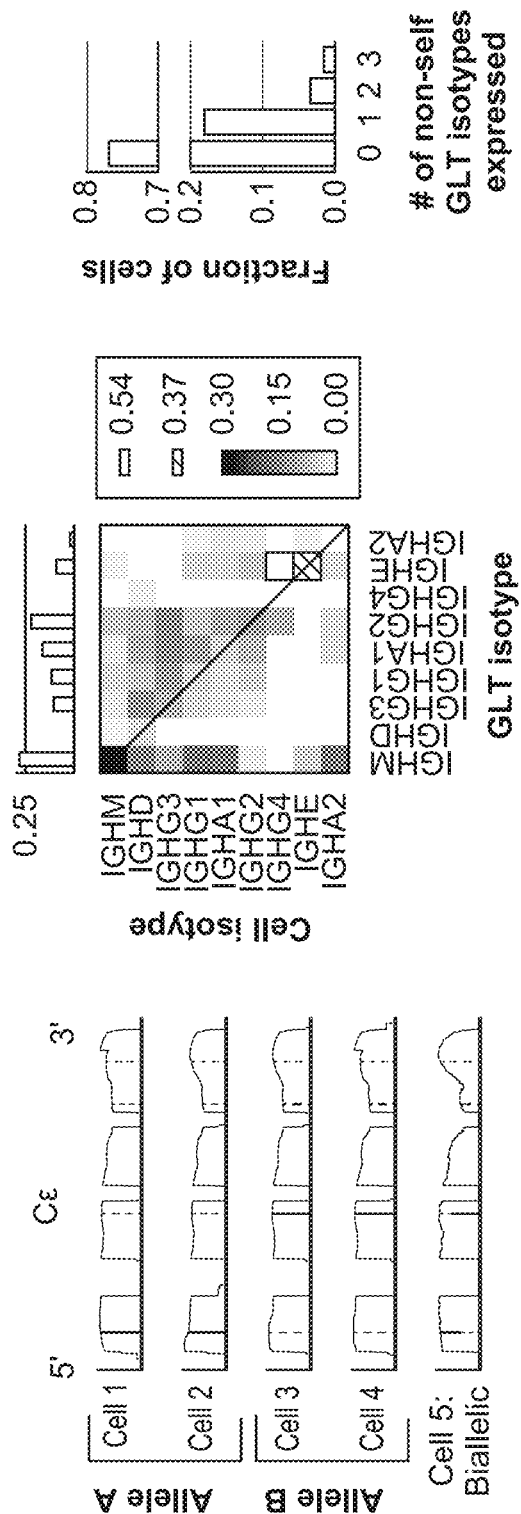
FIG. 5A
FIG. 5B
FIG. 5C
FIG. 5D
FIG. 5E

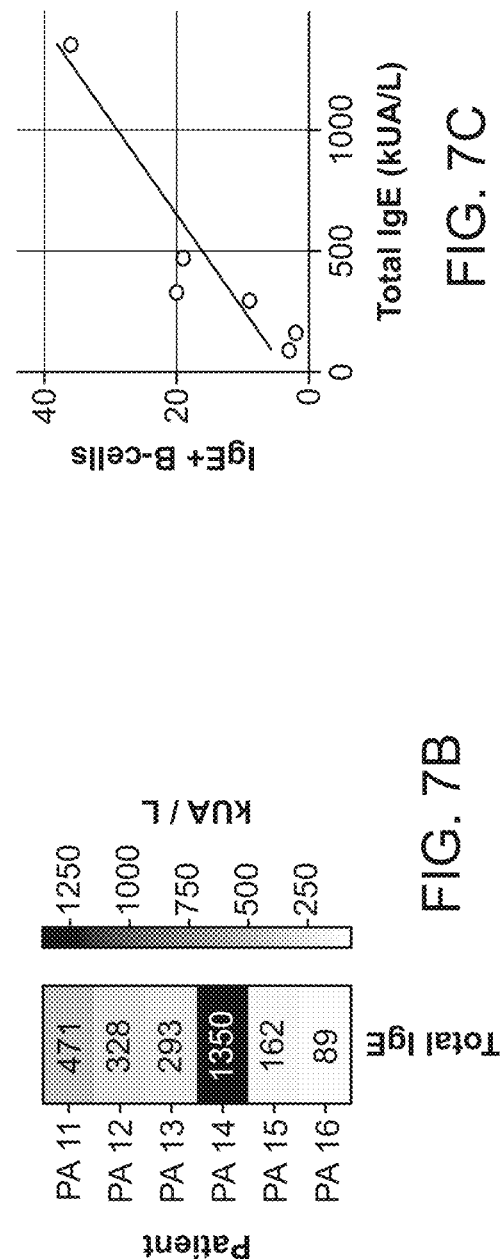
FIG. 7A
FIG. 7B
FIG. 7C

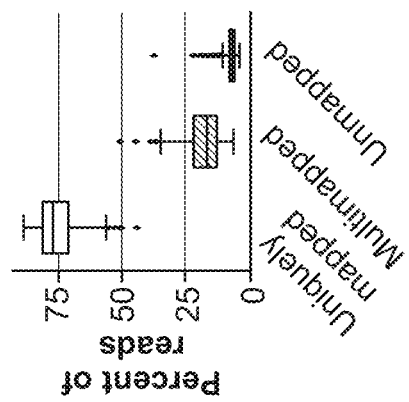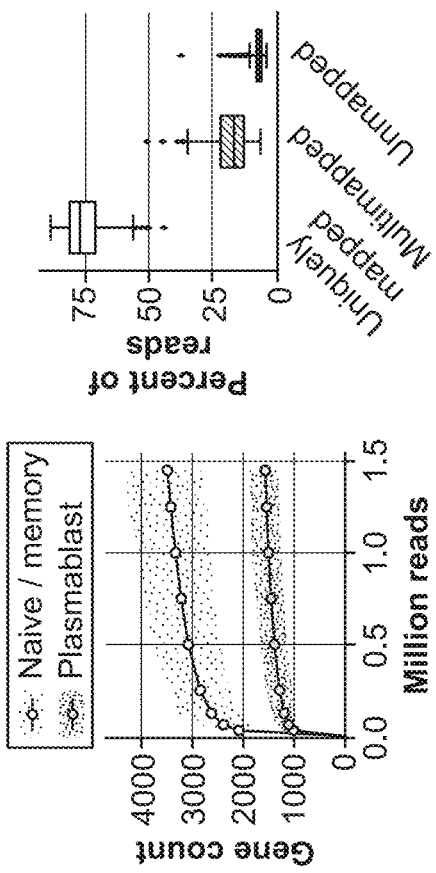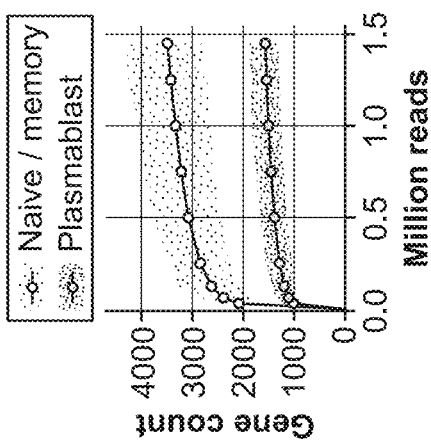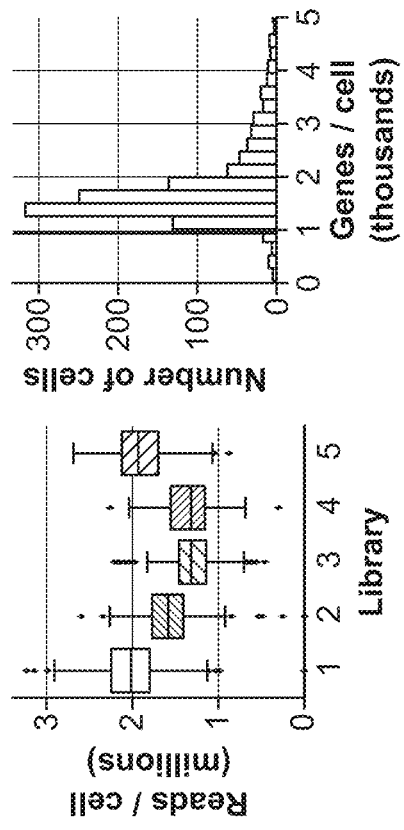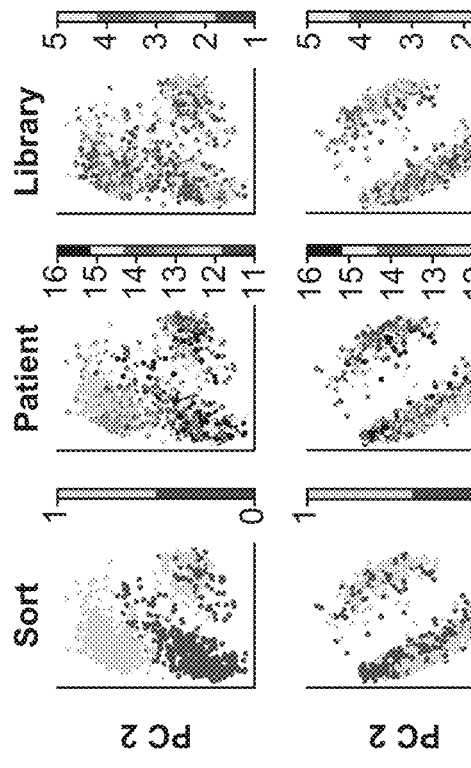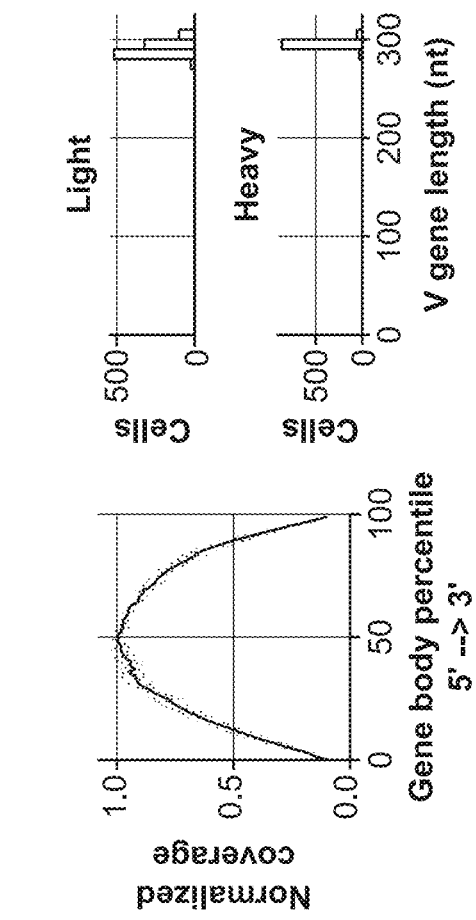
FIG. 9A  FIG. 9B  FIG. 9C  FIG. 9D  FIG. 9E  FIG. 9F  FIG. 9G

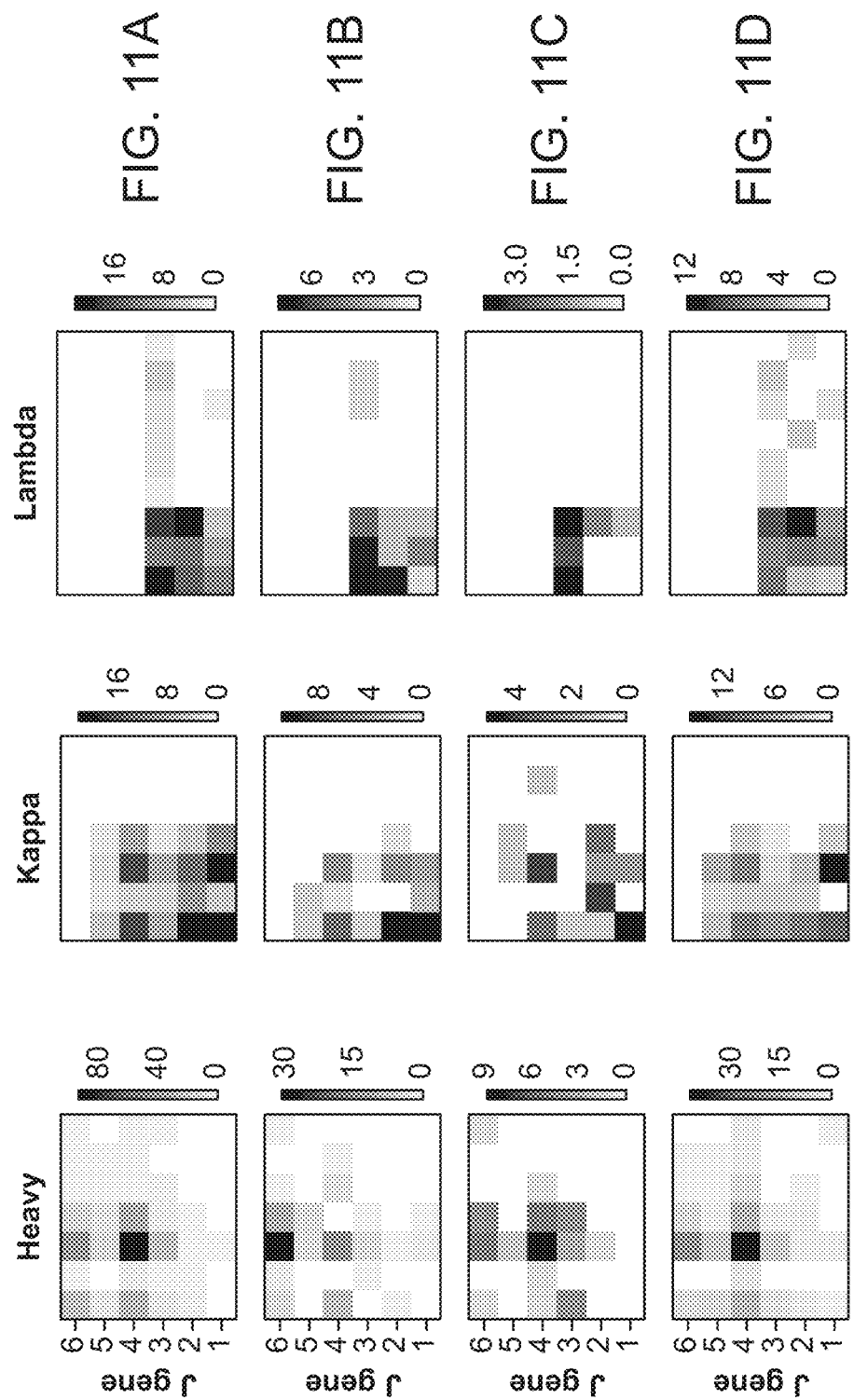

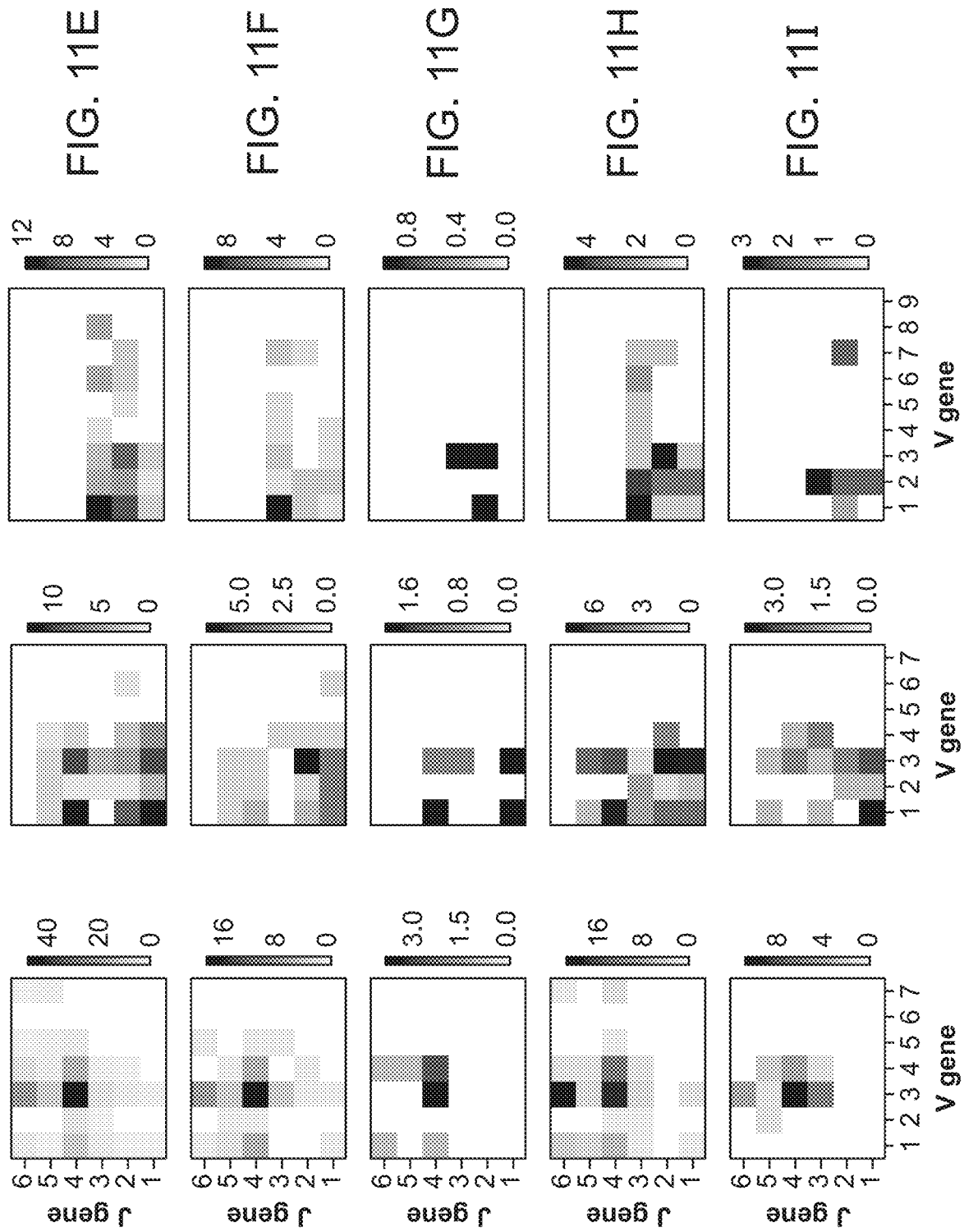

```
TACTGTGCGAAAGTTCTTGACTACACAGTGAATTTCATTACTATTACGGTTTGAGCGTCTGGGGCCAAGGGACCACGCGGTCCCCGTCTCCTCAG    PA12P3F10(SEQ ID NO:933)
TACTGTGCGAAAGTTCTTGACTACACAATGAGTACTACTCTCTACTTCGGTATGACGTGAAGACGACCACGGTCACCGTCTCCTCAG            PA12P3D08(SEQ ID NO:934)
TACTGTGCGAAGGTCCTTGACTACACAGTACTCCTATTATTACGGTATGACGTCTGGGGCCAAGGGACCACGGTCACCGTCTCCTCAG           PA12P1C07(SEQ ID NO:935)
TACTGTGCGAAGGTCCTTGACTACACAGTACTCCTATTATTACGGTATGACGTCTGGGGCCAAGGGACCACGGTCACCGTCTCTCCTCAG         PA13P1H06(SEQ ID NO:936)
TACTGTGCTAAGGTCCTTGACTACACAGTGCATTCTCCTATTATTAGGGATGACGTCTGGGGCCAAGGGACCACGGTCATCGTCTCCTCAG        PA13P1E10(SEQ ID NO:937)
TATTGTGCGAAAGTCCTTGACTACACAGTATTTCTATTACTATTCCGGCCTGGACGTCTGGGGCCAAGGGACCACGGTCACCGTCTCCTCAG       PA13P3G09(SEQ ID NO:938)

TACTGTGCGAAAGA                                                                                       IGHV30-30*18(SEQ ID NO:939)
              TYCT                                                                                   Nontemplated (inferred)(SEQ ID NO:940)
                  TGACTACAGTAACTAC                                                                   IGHD4-11*01(SEQ ID NO:941)
                                  ATTACTACTACTACGGTATGGACGTCTGGGGCCAAGGGACCACGGTCACCGTCTCCTCAG       IGHJ6*02(SEQ ID NO:942)
 Y  C  A  K                                                                                          Translated: V (SEQ ID NO:943)
             V  L  D  Y  S  N  Y                                                                     Translated: Nontemplated + D (SEQ ID NO:944)
                                 N  Y  Y  Y  Y  Y  G  M  D  V  W  G  Q  G  T  T  V  T  V  S  S      Translated: J (SEQ ID NO:945)

Y  C  A  K  V  L  D  Y  S  N  Y  N  Y  Y  Y  Y  Y  G  M  D  V  W  G  Q  G  T  T  V  T  V  S  S     Inferred naive rearrangement (SEQ ID NO:946)

Y  C  A  K  V  L  D  Y  S  E  F  H  Y  Y  Y  Y  Y  G  L  D  V  W  G  Q  G  T  T  V  T  V  S  S     Translated: PA12P3F10(SEQ ID NO:947)
 Y  C  A  K  V  L  D  Y  N  E  Y  S  L  Y  Y  Y  Y  Y  G  M  D  V  W  G  Q  G  T  A  V  T  V  S  S  Translated: PA12P3D08(SEQ ID NO:948)
 Y  C  A  K  V  L  D  Y  S  E  Y  S  R  Y  Y  Y  Y  Y  G  F  G  M  D  V  W  G  Q  G  T  T  V  L  V  S  S  Translated: PA12P1C07(SEQ ID NO:949)
 Y  C  A  K  V  L  D  Y  S  R  Y  S  A  F  S  Y  Y  Y  Y  G  M  D  V  W  G  Q  G  T  T  V  T  V  S  S  Translated: PA13P1H08(SEQ ID NO:950)
 Y  C  A  K  V  L  D  Y  S  I  F  Y  Y  Y  Y  F  G  L  D  V  W  G  Q  G  T  T  V  T  V  S  S     Translated: PA13P1E10(SEQ ID NO:951)
 Y  C  A  K  V  L  D  Y  S  I  F  Y  Y  Y  Y  F  G  L  D  V  W  G  Q  G  T  T  V  T  V  S  S     Translated: PA13P3G09(SEQ ID NO:952)
```

Reverted: EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPPYTFGQGTKLEIK (SEQ ID NO:61)

Native: EIVLTQSPGTLSLSPGGRGTLSCRHSQTINNAHLAWYQHKPGQAPRLLIYGSSERATGVPDRFSGSGSGSDFTLTISSLEAEDFAVYYCQHYGRSPPYTFGPGTKLDIK (SEQ ID NO:5)

FIG. 13D

Swap: EIVLTQSPATLSLSPGERATLSCRASQSVSSYLAWYQQKPGQAPRLLIYDASNRATGIPARFSGSGSGTDFTLTISSLEPEDFAVYYCQQRSNWPPGFTFGPGTKVDIK (SEQ ID NO:970)

FIG. 13E

Goat anti-human IgG (H+L) DyLight680 (1:5000),
mouse monoclonal anti-HA (12CA5) DyLight800 (1:2000)

Human IgG1 antibody, 1 µg/ml

ALLERGEN-SPECIFIC ANTIBODIES

CROSS REFERENCE TO RELATED APPLICATIONS

This application is a continuation of application Ser. No. 17/056,384 filed Nov. 17, 2020 (pending), which is the § 371 U.S. National Stage of PCT Application No. PCT/US2019/032951, filed May 17, 2019, which published under serial no. WO 2019/222679 on Nov. 21, 2019. The PCT application claims the priority benefit of U.S. Provisional Patent Application No. 62/673,713, filed May 18, 2018. The aforesaid priority applications are hereby incorporated herein by reference in their entirety for all purposes.

REFERENCE TO A SEQUENCE LISTING

The Sequence Listing written in file 103182-1134892-000710WO_SL.txt created on Nov. 15, 2019, 480 KB, machine format IBM-PC, MS-Windows operating system, is hereby incorporated by reference in its entirety for all purposes.

BACKGROUND OF THE INVENTION

Allergies are a growing health concern worldwide and are characterized by a misdirected adaptive immune response towards otherwise harmless proteins. For food allergies in particular, individuals must be diligent in avoiding allergen exposure or otherwise risk potentially fatal allergic reactions. No cure for allergies exist, and although desensitization regimens such as immunotherapy have shown some clinical benefit, there is a need for a fast, effective intervention that can improve the quality of life for allergic individuals.

BRIEF SUMMARY OF THE INVENTION

In one aspect, the present disclosure provides methods of generating a human monoclonal antibody that specifically binds to an allergen. In some embodiments, the method comprises:
  (a) isolating single B cells from a sample from a human subject, wherein the subject is allergic to the allergen;
  (b) generating cDNAs from the single B cells of step (a), wherein the cDNA sequences comprise a first sequence that encodes all or part of an immunoglobulin heavy chain and a second sequence that encodes all or part of an immunoglobulin light chain;
  (c) determining the sequences of the cDNAs from step (b);
  (d) analyzing the sequences determined in step (c) to identify single B cells comprising a first sequence that comprises an IgE constant region or an IgG4 constant region;
  (e) identifying, from the single B cells of step (d), (i) a heavy chain variable region sequence in the immunoglobulin heavy chain that comprises an IgE constant region or an IgG4 constant region, and (ii) a light chain variable region sequence in an immunoglobulin light chain that is co-expressed with the immunoglobulin heavy chain in the same single B cell;
  (f) expressing antibodies comprising the heavy chain variable region sequence and the light chain variable region sequence from step (e); and
  (g) identifying one or more antibodies from step (f) that specifically bind to the allergen.

In some embodiments, step (a) comprises sorting cells in the sample by fluorescent activated cell sorting (FACS). In some embodiments, step (a) comprises selecting single B cells for expression of cell surface IgE and/or cell surface IgG4. In some embodiments, step (a) comprises isolating antibody-secreting B cells and/or memory B cells.

In some embodiments, the method comprises isolating single B cells that are selected for expression of cell surface IgE and identifying a sequence encoding an immunoglobulin heavy chain that comprises an IgE constant region. In some embodiments, step (a) comprises contacting cells from the sample with an anti-human CD19 antibody and an anti-human IgE antibody and selecting for CD19$^+$ IgE-expressing B cells. In some embodiments, the method comprises isolating single B cells that express a B cell marker and that are negative for non-IgE isotypes. In some embodiments, step (a) comprises contacting cells from the sample with an anti-human CD19 antibody, an anti-human IgM antibody, an anti-human IgG antibody, an anti-human IgA antibody, and an anti-human IgD antibody and selecting for CD19$^+$IgM$^-$IgG$^-$IgA$^-$IgD$^-$ B cells.

In some embodiments, the method comprises isolating single B cells that are selected for expression of cell surface IgG4 and identifying a sequence encoding an immunoglobulin heavy chain that comprises an IgG4 constant region. In some embodiments, step (a) comprises contacting cells from the sample with an anti-human CD19 antibody and an anti-human IgG4 antibody and selecting for CD19$^+$IgG4-expressing B cells. In some embodiments, the method comprises isolating single B cells that express a B cell marker and that are negative for non-IgG4 isotypes. In some embodiments, step (a) comprises contacting cells from the sample with an anti-human CD19 antibody, an anti-human IgM antibody, an anti-human IgE antibody, an anti-human IgA antibody, an anti-human IgD antibody, an anti-human IgG1 antibody, an anti-human IgG2 antibody, and an anti-human IgG3 antibody and selecting for CD19$^+$IgM$^-$IgE$^-$IgA$^-$IgD$^-$IgG1$^-$IgG2$^-$IgG3$^-$ B cells.

In some embodiments, step (b) comprises reverse transcribing cDNAs from RNA from the single B cells and amplifying the cDNAs. In some embodiments, the RNA is mRNA. In some embodiments, the method comprises amplifying immunoglobulin heavy chain and light chain sequences from the single B cells. In some embodiments, the method comprises amplifying the transcriptomes of the single B cells.

In some embodiments, step (f) comprises expressing the heavy chain variable region sequence and the light chain variable region sequence from step (e) in a host cell and purifying the antibodies. In some embodiments, step (f) comprises expressing antibodies comprising the heavy chain variable region sequence and the light chain variable region sequence from step (e) and an IgG4 constant region or an IgG1 constant region.

In some embodiments, the method further comprises substituting the constant region of an antibody identified in step (g) with a wild-type IgG4 constant region or a modified IgG4 constant region.

In some embodiments, the sample comprises peripheral blood. In some embodiments, the sample comprises tissue (e.g., tonsil tissue).

In some embodiments, the allergen is a food allergen, a plant allergen, a fungal allergen, an animal allergen, a drug allergen, a cosmetic allergen, or a latex allergen. In some embodiments, the allergen is a food allergen selected from the group consisting of a milk allergen, an egg allergen, a nut allergen, a fish allergen, a shellfish allergen, a soy allergen, a legume allergen, a seed allergen, and a wheat allergen. In some embodiments, the food allergen is a peanut allergen. In some embodiments, the food allergen is a tree nut allergen. In some embodiments, the food allergen is a milk allergen. In some embodiments, the allergen is a fungal allergen. In some embodiments, the fungal allergen is an *Aspergillus* allergen.

In another aspect, monoclonal antibodies produced according to a method disclosed herein are provided.

In yet another aspect, pharmaceutical compositions comprising a monoclonal antibody produced according to a method disclosed herein are provided. In some embodiments, the pharmaceutical composition comprises a plurality of monoclonal antibodies, wherein each monoclonal antibody is produced according to a method disclosed herein and wherein the monoclonal antibodies recognize different epitopes or specifically bind to different antigens (e.g., different allergens within the same type or class of allergen or in different types or classes of allergens).

In still another aspect, monoclonal antibodies, or antigen-binding portions thereof, that specifically bind to an allergen are provided. In some embodiments, the antibody comprises:
  (a) a heavy chain variable region sequence that is derived from an immunoglobulin heavy chain from an IgE- or IgG4-producing single B cell from a human subject who is allergic to the allergen;
  (b) a heavy chain IgG constant region sequence;
  (c) a light chain variable region sequence that is derived from an immunoglobulin light chain from the IgE-producing or IgG4-producing single B cell from a human subject; and
  (d) a light chain constant region sequence that is of the same class as the immunoglobulin light chain of (c).

In some embodiments, the antibody or the antigen-binding portion thereof specifically binds to an allergen with a binding affinity ($K_D$) of less than 1 nM. In some embodiments the antibody or the antigen-binding portion thereof specifically binds to an allergen with a binding affinity (KD) of less than 250 nM, less than 100 nM, less than 50 nM, less than 10 nM, or less than 5 nM. In some embodiments, the antibody binds to the allergen with a binding affinity (KD) from 1 nM to 250 nM. In some embodiments, the allergen is a food allergen, a plant allergen, a fungal allergen, an animal allergen, a dust mite allergen, a drug allergen, a cosmetic allergen, or a latex allergen. In some embodiments, the allergen is a food allergen selected from the group consisting of a milk allergen, an egg allergen, a nut allergen, a fish allergen, a shellfish allergen, a soy allergen, a legume allergen, a seed allergen, and a wheat allergen. In some embodiments, the food allergen is a peanut allergen or a tree nut allergen. In some embodiments, the food allergen is a milk allergen. In some embodiments, the allergen is a fungal allergen. In some embodiments, the fungal allergen is an *Aspergillus* antigen. In some embodiments, the antibody is cross-reactive with two different antigens. In some embodiments, the antibody is cross-reactive with a first antigen of a first allergen type and a second antigen of a second allergen type that is different from the first allergen type. In some embodiments, the antibody is cross-reactive with a peanut allergen and a tree nut allergen. In some embodiments, the antibody is cross-reactive with two or more tree nut antigens.

In some embodiments, the antibody comprises a heavy chain variable region sequence and a light chain variable region sequence that are derived from an IgE-producing human B cell or from an IgG4-producing human B cell.

In yet another aspect, monoclonal antibodies, or antigen-binding portions thereof, that specifically binds to a peanut allergen are provided. In some embodiments, the antibody binds to the peanut allergen with a binding affinity ($K_D$) of less than 1 nM. In some embodiments the antibody or the antigen-binding portion thereof specifically binds to an peanut allergen with a binding affinity (KD) of less than 250 nM, less than 100 nM, less than 50 nM, less than 10 nM, or less than 5 nM. In some embodiments, the antibody binds to the peanut allergen with a binding affinity (KD) from 1 nM to 250 nM.

In some embodiments, the antibody or the antigen-binding portion thereof specifically binds to the peanut allergen Ara h 2, Ara h 3, or Ara h 1. In some embodiments, the antibody or the antigen-binding portion thereof specifically binds to Ara h 2 with a $K_D$ of less than 100 pM. In some embodiments, the antibody or the antigen-binding portion thereof is cross-reactive with at least two peanut allergens. In some embodiments, the antibody or the antigen-binding portion thereof is cross-reactive with Ara h 2 and Ara h 3. In some embodiments, the antibody or the antigen-binding portion thereof specifically binds to Ara h 2 with a $K_D$ of less than 1 nM and specifically binds to Ara h 3 with a $K_D$ of less than 1 µM. In some embodiments, the antibody or the antigen-binding portion thereof binds to an epitope that comprises the amino acid motif DPYSPS (SEQ ID NO:704). Furthermore, additional peanut-specific antibodies were discovered during these experiments. Antibodies PA12P3E09 and PA12P3E11 bound peanut extract with little to no binding to natural peanut allergen Ara h 2, while antibodies PA12P1D02, PA12P1G11, PA13P1H03, PA12P3C01, and PA12P3E04 bound strongly to both peanut extract and natural peanut allergen Ara h 2. In some embodiments the peanut specific antibody binds to peanut extract, but does not bind natural peanut allergen Ara h 2.

In some embodiments, the antibody comprises:
  a heavy chain CDR1 comprising the amino acid sequence of any one of SEQ ID NOs:2, 10, 17, 25, 33, 41, 47, 58, 113, 129, 199, 341, 348, 409, 459, or 593;
  a heavy chain CDR2 comprising the amino acid sequence of any one of SEQ ID NOs:3, 11, 18, 26, 34, 48, 59, 130, 200, 342, 349, 410, 460, 539, or 594;
  a heavy chain CDR3 comprising the amino acid sequence of any one of SEQ ID NOs:4, 12, 19, 27, 35, 42, 49, 55, 60, 131, 201, 350, 411, 461, 540, or 595;
  a light chain CDR1 comprising the amino acid sequence of any one of SEQ ID NOs:6, 14, 21, 29, 37, 44, 51, 62, 133, 203, 343, 352, 413, 463, 542, or 597;
  a light chain CDR2 comprising the amino acid sequence of any one of SEQ ID NOs:7, 15, 22, 30, 38, 52, 78, 86, 126, 149, 196, 345, 353, or 598; and
  a light chain CDR3 comprising the amino acid sequence of any one of SEQ ID NOs:8, 23, 31, 39, 45, 53, 63, 134, 204, 346, 354, 414, 464, 543, or 599.

In some embodiments, the antibody comprises heavy chain and light chain CDR sequences contained within the heavy chain variable region and light chain variable region sequence pairs selected from the group consisting of SEQ ID NOs: 1 and 5; 9 and 13; 16 and 20; 24 and 28; 32 and 36; 40 and 43; 46 and 50; 54 and 56; 57 and 61; 57 and 5; 1 and 61; 64 and 5; 65 and 5; 66 and 5; 67 and 5; 128 and 132; 340 and 344; 347 and 351; 406 and 407; 408 and 412; 458 and 462; 538 and 541; and 592 and 596. In some embodiments, the antibody comprises a heavy chain CDR1-3 and a light chain CDR1-3 comprising the amino acid sequences of:
(a) SEQ ID NOs: 2, 3, 4, 6, 7, and 8, respectively; or
(b) SEQ ID NOs: 10, 11, 12, 14, 15, and 8, respectively; or
(c) SEQ ID NOs: 17, 18, 19, 21, 22, and 23, respectively; or
(d) SEQ ID NOs: 25, 26, 27, 29, 30, and 31, respectively; or
(e) SEQ ID NOs: 33, 34, 35, 37, 38, and 39, respectively; or
(f) SEQ ID NOs: 41, 34, 35, 37, 38, and 39, respectively; or
(g) SEQ ID NOs: 47, 48, 49, 51, 52, and 53, respectively; or
(h) SEQ ID NOs: 47, 48, 55, 51, 52, and 53, respectively; or
(i) SEQ ID NOs: 58, 59, 60, 62, 30, and 63, respectively; or
(j) SEQ ID NOs: 58, 59, 60, 6, 7, and 8, respectively; or
(k) SEQ ID NOs: 2, 3, 4, 62, 30, and 63, respectively; or
(l) SEQ ID NOs: 58, 3, 4, 6, 7, and 8, respectively; or
(m) SEQ ID NOs: 2, 59, 4, 6, 7, and 8, respectively; or
(n) SEQ ID NOs: 2, 3, 60, 6, 7, and 8, respectively; or
(o) SEQ ID NOs:129, 130, 131, 133, 126, and 134, respectively; or
(p) SEQ ID NOs:341, 342, 343, 345, 78, and 346, respectively; or
(q) SEQ ID NOs:348, 349, 350, 352, 353, and 354, respectively; or
(r) SEQ ID NOs:199, 200, 201, 203, 149, and 204, respectively; or
(s) SEQ ID NOs:409, 410, 411, 413, 86, and 414, respectively; or
(t) SEQ ID NOs:459, 460, 461, 463, 196, and 464, respectively; or
(u) SEQ ID NOs:113, 539, 540, 542, 196, and 543, respectively; or
(v) SEQ ID NOs:593, 594, 595, 597, 598, and 599, respectively.

In some embodiments, the antibody comprises a heavy chain variable region comprising an amino acid sequence that has at least 90% sequence identity to any one of SEQ ID NOs:1, 9, 16, 24, 32, 40, 46, 54, 57, 64, 65, 66, 67, 128, 340, 347, 406, 408, 458, 538, or 592. In some embodiments, the antibody comprises a light chain variable region comprising an amino acid sequence that has at least 90% sequence identity to any one of SEQ ID NOs:5, 13, 20, 28, 36, 43, 50, 56, 61, 132, 344, 351, 407, 412, 462, 541, or 596.

In some embodiments, the antibody comprises:
(a) a heavy chain variable region comprising an amino acid sequence that has at least 90% sequence identity to SEQ ID NO:1 and a light chain variable region comprising an amino acid sequence that has at least 90% sequence identity to SEQ ID NO:5; or
(b) a heavy chain variable region comprising an amino acid sequence that has at least 90% sequence identity to SEQ ID NO:9 and a light chain variable region comprising an amino acid sequence that has at least 90% sequence identity to SEQ ID NO:13; or
(c) a heavy chain variable region comprising an amino acid sequence that has at least 90% sequence identity to SEQ ID NO:16 and a light chain variable region comprising an amino acid sequence that has at least 90% sequence identity to SEQ ID NO:20; or
(d) a heavy chain variable region comprising an amino acid sequence that has at least 90% sequence identity to SEQ ID NO:24 and a light chain variable region comprising an amino acid sequence that has at least 90% sequence identity to SEQ ID NO:28; or
(e) a heavy chain variable region comprising an amino acid sequence that has at least 90% sequence identity to SEQ ID NO:32 and a light chain variable region comprising an amino acid sequence that has at least 90% sequence identity to SEQ ID NO:36; or
(f) a heavy chain variable region comprising an amino acid sequence that has at least 90% sequence identity to SEQ ID NO:40 and a light chain variable region comprising an amino acid sequence that has at least 90% sequence identity to SEQ ID NO:43; or
(g) a heavy chain variable region comprising an amino acid sequence that has at least 90% sequence identity to SEQ ID NO:46 and a light chain variable region comprising an amino acid sequence that has at least 90% sequence identity to SEQ ID NO:50; or
(h) a heavy chain variable region comprising an amino acid sequence that has at least 90% sequence identity to SEQ ID NO:54 and a light chain variable region comprising an amino acid sequence that has at least 90% sequence identity to SEQ ID NO:56; or
(i) a heavy chain variable region comprising an amino acid sequence that has at least 90% sequence identity to SEQ ID NO:57 and a light chain variable region comprising an amino acid sequence that has at least 90% sequence identity to SEQ ID NO:61; or
(j) a heavy chain variable region comprising an amino acid sequence that has at least 90% sequence identity to SEQ ID NO:57 and a light chain variable region comprising an amino acid sequence that has at least 90% sequence identity to SEQ ID NO:5; or
(k) a heavy chain variable region comprising an amino acid sequence that has at least 90% sequence identity to SEQ ID NO:1 and a light chain variable region comprising an amino acid sequence that has at least 90% sequence identity to SEQ ID NO:61; or
(l) a heavy chain variable region comprising an amino acid sequence that has at least 90% sequence identity to SEQ ID NO:64 and a light chain variable region comprising an amino acid sequence that has at least 90% sequence identity to SEQ ID NO:5; or
(m) a heavy chain variable region comprising an amino acid sequence that has at least 90% sequence identity to SEQ ID NO:65 and a light chain variable region comprising an amino acid sequence that has at least 90% sequence identity to SEQ ID NO:5; or
(n) a heavy chain variable region comprising an amino acid sequence that has at least 90% sequence identity to SEQ ID NO:66 and a light chain variable region comprising an amino acid sequence that has at least 90% sequence identity to SEQ ID NO:5; or
(o) a heavy chain variable region comprising an amino acid sequence that has at least 90% sequence identity to SEQ ID NO:67 and a light chain variable region comprising an amino acid sequence that has at least 90% sequence identity to SEQ ID NO:5; or
(p) a heavy chain variable region comprising an amino acid sequence that has at least 90% sequence identity to SEQ ID NO:128 and a light chain variable region comprising an amino acid sequence that has at least 90% sequence identity to SEQ ID NO:132; or
(q) a heavy chain variable region comprising an amino acid sequence that has at least 90% sequence identity to SEQ ID NO:340 and a light chain variable region comprising an amino acid sequence that has at least 90% sequence identity to SEQ ID NO:344; or
(r) a heavy chain variable region comprising an amino acid sequence that has at least 90% sequence identity to SEQ ID NO:347 and a light chain variable region comprising an amino acid sequence that has at least 90% sequence identity to SEQ ID NO:351; or
(s) a heavy chain variable region comprising an amino acid sequence that has at least 90% sequence identity to SEQ ID NO:406 and a light chain variable region comprising an amino acid sequence that has at least 90% sequence identity to SEQ ID NO:407; or
(t) a heavy chain variable region comprising an amino acid sequence that has at least 90% sequence identity to SEQ ID NO:408 and a light chain variable region comprising an amino acid sequence that has at least 90% sequence identity to SEQ ID NO:412; or
(u) a heavy chain variable region comprising an amino acid sequence that has at least 90% sequence identity to SEQ ID NO:458 and a light chain variable region comprising an amino acid sequence that has at least 90% sequence identity to SEQ ID NO:462; or
(v) a heavy chain variable region comprising an amino acid sequence that has at least 90% sequence identity to SEQ ID NO:538 and a light chain variable region comprising an amino acid sequence that has at least 90% sequence identity to SEQ ID NO:541; or
(w) a heavy chain variable region comprising an amino acid sequence that has at least 90% sequence identity to SEQ ID NO:592 and a light chain variable region comprising an amino acid sequence that has at least 90% sequence identity to SEQ ID NO:596.

In still another aspect, monoclonal antibodies, or antigen-binding portions thereof, that specifically binds to a tree nut allergen are provided. In some embodiments, the antibody binds to the tree nut allergen with a binding affinity ($K_D$) of less than 250 nM, less than 100 nM, less than 50 nM, less than 10 nM, or less than 5 nM. In some embodiments, the antibody binds to the tree nut allergen with a binding affinity ($K_D$) of less than 1 nM. In some embodiments, the antibody binds to the tree nut allergen with a binding affinity ($K_D$) from 1 nM to 250 nM. In some embodiments, the tree nut allergen is cashew, pistachio, pecan, walnut, hazelnut, and/or macadamia nut.

In some embodiments, the antibody comprises:
a heavy chain CDR1 comprising the amino acid sequence of any one of SEQ ID NOs:113, 167, 175, 227, 311, 318, 438, 466, 621, 665, or 692;
a heavy chain CDR2 comprising the amino acid sequence of any one of SEQ ID NOs: 168, 176, 200, 312, 319, 439, 539, 666, or 693;
a heavy chain CDR3 comprising the amino acid sequence of any one of SEQ ID NOs: 169, 177, 228, 313, 320, 440, 467, 540, 667, or 694;
a light chain CDR1 comprising the amino acid sequence of any one of SEQ ID NOs: 171, 179, 230, 315, 322, 442, 469, 542, 623, 669, or 696;
a light chain CDR2 comprising the amino acid sequence of any one of SEQ ID NOs: 30, 94, 149, 172, 180, 196, 323, or 670; and
a light chain CDR3 comprising the amino acid sequence of any one of SEQ ID NOs: 173, 181, 231, 316, 324, 443, 470, 543, 624, 671, or 697.

In some embodiments, the antibody comprises a heavy chain CDR1-3 and a light chain CDR1-3 comprising the amino acid sequences of:

(a) SEQ ID NOs: 692, 693, 694, 696, 94, and 697, respectively; or
(b) SEQ ID NOs:318, 319, 320, 322, 323, and 324, respectively; or
(c) SEQ ID NOs:227, 200, 228, 230, 149, and 231, respectively; or
(d) SEQ ID NOs:113, 539, 540, 542, 196, and 543, respectively; or
(e) SEQ ID NOs:311, 312, 313, 315, 94, and 316, respectively; or
(f) SEQ ID NOs:665, 666, 667, 669, 670, and 671, respectively; or
(g) SEQ ID NOs:466, 200, 467, 469, 149, and 470, respectively; or
(h) SEQ ID NOs:167, 168, 169, 171, 172, and 173, respectively; or
(i) SEQ ID NOs:621, 176, 177, 623, 180, and 624, respectively; or
(j) SEQ ID NOs:175, 176, 177, 179, 180, and 181, respectively; or
(k) SEQ ID NOs:438, 439, 440, 442, 30, and 443, respectively.

In some embodiments, the antibody comprises a heavy chain variable region comprising an amino acid sequence that has at least 90% sequence identity to any one of SEQ ID NOs:166, 174, 226, 310, 317, 437, 465, 538, 620, 664, or 691. In some embodiments, the antibody comprises a light chain variable region comprising an amino acid sequence that has at least 90% sequence identity to any one of SEQ ID NOs:170, 178, 229, 314, 321, 441, 468, 541, 622, 668, or 695.

In some embodiments, the antibody comprises:
(a) a heavy chain variable region comprising an amino acid sequence that has at least 90% sequence identity to SEQ ID NO:691 and a light chain variable region comprising an amino acid sequence that has at least 90% sequence identity to SEQ ID NO:695; or
(b) a heavy chain variable region comprising an amino acid sequence that has at least 90% sequence identity to SEQ ID NO:317 and a light chain variable region comprising an amino acid sequence that has at least 90% sequence identity to SEQ ID NO:321; or
(c) a heavy chain variable region comprising an amino acid sequence that has at least 90% sequence identity to SEQ ID NO:226 and a light chain variable region comprising an amino acid sequence that has at least 90% sequence identity to SEQ ID NO:229; or
(d) a heavy chain variable region comprising an amino acid sequence that has at least 90% sequence identity to SEQ ID NO:538 and a light chain variable region comprising an amino acid sequence that has at least 90% sequence identity to SEQ ID NO:541; or
(e) a heavy chain variable region comprising an amino acid sequence that has at least 90% sequence identity to SEQ ID NO:310 and a light chain variable region comprising an amino acid sequence that has at least 90% sequence identity to SEQ ID NO:314; or
(f) a heavy chain variable region comprising an amino acid sequence that has at least 90% sequence identity to SEQ ID NO:664 and a light chain variable region comprising an amino acid sequence that has at least 90% sequence identity to SEQ ID NO:668; or
(g) a heavy chain variable region comprising an amino acid sequence that has at least 90% sequence identity to SEQ ID NO:465 and a light chain variable region comprising an amino acid sequence that has at least 90% sequence identity to SEQ ID NO:468; or (h) a heavy chain variable region comprising an amino acid sequence that has at least 90% sequence identity to SEQ ID NO:166 and a light chain variable region comprising an amino acid sequence that has at least 90% sequence identity to SEQ ID NO:170; or (i) a heavy chain variable region comprising an amino acid sequence that has at least 90% sequence identity to SEQ ID NO:620 and a light chain variable region comprising an amino acid sequence that has at least 90% sequence identity to SEQ ID NO:622; or (j) a heavy chain variable region comprising an amino acid sequence that has at least 90% sequence identity to SEQ ID NO:174 and a light chain variable region comprising an amino acid sequence that has at least 90% sequence identity to SEQ ID NO:178; or (k) a heavy chain variable region comprising an amino acid sequence that has at least 90% sequence identity to SEQ ID NO:437 and a light chain variable region comprising an amino acid sequence that has at least 90% sequence identity to SEQ ID NO:441.

In yet another aspect, monoclonal antibodies, or antigen-binding portions thereof, that specifically binds to a milk allergen are provided. In some embodiments, the antibody binds to the milk allergen with a binding affinity (KD) of less than 250 nM, less than 100 nM, less than 50 nM, less than 10 nM, or less than 5 nM. In some embodiments, the antibody binds to the milk allergen with a binding affinity ($K_D$) of less than 1 nM. In some embodiments, the antibody binds to the milk allergen with a binding affinity (KD) from 1 nM to 250 nM.

In some embodiments, the antibody comprises:
a heavy chain CDR1 comprising the amino acid sequence of any one of SEQ ID NOs: 121, 750, 757, 765, 772, 779, 785, 793, 800, 807, 814, 821, 833, 838, 846, 853, 860, 868, 874, 881, 889, 895, 903, 911, 918, or 926;
a heavy chain CDR2 comprising the amino acid sequence of any one of SEQ ID NOs: 378, 532, 751, 758, 766, 773, 786, 794, 801, 808, 815, 822, 826, 839, 847, 854, 861, 875, 882, 890, 896, 904, 912, 919, or 927;
a heavy chain CDR3 comprising the amino acid sequence of any one of SEQ ID NOs: 752, 759, 767, 774, 780, 787, 795, 802, 809, 816, 827, 840, 848, 855, 862, 869, 876, 883, 891, 897, 905, 913, 920, or 928;
a light chain CDR1 comprising the amino acid sequence of any one of SEQ ID NOs: 523, 754, 761, 769, 776, 782, 789, 797, 804, 811, 818, 829, 835, 842, 850, 857, 864, 871, 878, 885, 899, 907, 915, 922, or 930;
a light chain CDR2 comprising the amino acid sequence of any one of SEQ ID NOs: 22, 30, 94, 110, 149, 186, 196, 389, 404, 509, 662, 682, 762, 790, 830, 843, 865, 886, 900, 908, 923, or 931; and
a light chain CDR3 comprising the amino acid sequence of any one of SEQ ID NOs: 755, 763, 770, 777, 783, 791, 798, 805, 812, 819, 824, 831, 836, 844, 851, 858, 866, 872, 879, 887, 893, 901, 909, 916, 924, or 932.

In some embodiments, the antibody comprises a heavy chain CDR1-3 and a light chain CDR1-3 comprising the amino acid sequences of:
(a) SEQ ID NOs: 800, 801, 802, 804, 110, and 805, respectively; or
(b) SEQ ID NOs:121, 826, 827, 829, 830, and 831, respectively; or
(c) SEQ ID NOs:833, 826, 827, 835, 149, and 836, respectively; or
(d) SEQ ID NOs:853, 854, 855, 857, 662, and 858, respectively; or
(e) SEQ ID NOs:860, 861, 862, 864, 865, and 866, respectively; or
(f) SEQ ID NOs:868, 378, 869, 871, 682, and 782, respectively.

In some embodiments, the antibody comprises a heavy chain variable region comprising an amino acid sequence that has at least 90% sequence identity to any one of SEQ ID NOs:749, 756, 764, 771, 778, 784, 792, 799, 806, 813, 820, 825, 832, 837, 845, 852, 859, 867, 873, 880, 888, 894, 902, 910, 917, or 925. In some embodiments, the antibody comprises a light chain variable region comprising an amino acid sequence that has at least 90% sequence identity to any one of SEQ ID NOs:753, 760, 768, 775, 781, 788, 796, 803, 810, 817, 823, 828, 834, 841, 849, 856, 863, 870, 877, 884, 892, 898, 906, 914, 921, or 929.

In some embodiments, the antibody comprises:
(a) a heavy chain variable region comprising an amino acid sequence that has at least 90% sequence identity to SEQ ID NO:799 and a light chain variable region comprising an amino acid sequence that has at least 90% sequence identity to SEQ ID NO:803; or
(b) a heavy chain variable region comprising an amino acid sequence that has at least 90% sequence identity to SEQ ID NO:825 and a light chain variable region comprising an amino acid sequence that has at least 90% sequence identity to SEQ ID NO:828; or
(c) a heavy chain variable region comprising an amino acid sequence that has at least 90% sequence identity to SEQ ID NO:832 and a light chain variable region comprising an amino acid sequence that has at least 90% sequence identity to SEQ ID NO:834; or
(d) a heavy chain variable region comprising an amino acid sequence that has at least 90% sequence identity to SEQ ID NO:852 and a light chain variable region comprising an amino acid sequence that has at least 90% sequence identity to SEQ ID NO:856; or
(e) a heavy chain variable region comprising an amino acid sequence that has at least 90% sequence identity to SEQ ID NO:859 and a light chain variable region comprising an amino acid sequence that has at least 90% sequence identity to SEQ ID NO:863; or
(f) a heavy chain variable region comprising an amino acid sequence that has at least 90% sequence identity to SEQ ID NO:867 and a light chain variable region comprising an amino acid sequence that has at least 90% sequence identity to SEQ ID NO:870.

In some embodiments, the antibody is an antibody that competes with a monoclonal antibody as disclosed herein for binding to an allergen (e.g., for binding to a food allergen such as a peanut allergen, a tree nut allergen, or a milk allergen).

In yet another aspect, monoclonal antibodies, or antigen-binding portions thereof, that specifically binds to a fungal allergen are provided. In some embodiments, the fungal allergen is an *Aspergillus* allergen. In some embodiments, the antibody binds to the fungal allergen (e.g., *Aspergillus* allergen) with a binding affinity (KD) of less than 250 nM, less than 100 nM, less than 50 nM, less than 10 nM, or less than 5 nM. In some embodiments, the antibody binds to the fungal allergen (e.g., *Aspergillus* allergen) with a binding affinity ($K_D$) of less than 1 nM. In some embodiments, the antibody binds to the fungal allergen with a binding affinity (KD) from 1 nM to 250 nM.

In some embodiments, the antibody or the antigen-binding portion thereof specifically binds to the allergen *Aspergillus fumigatus, Aspergillus niger*, and/or *Aspergillus nidu-*

*lans.* In some embodiments, the antibody specifically binds to the allergen *Aspergillus fumigatus* 1 (Asp f 1).

In some embodiments, the antibody comprises:
a heavy chain CDR1 comprising the amino acid sequence of any one of SEQ ID NOs:710, 718, 726, 734, or 742;
a heavy chain CDR2 comprising the amino acid sequence of any one of SEQ ID NOs:711, 719, 727, 735, or 743;
a heavy chain CDR3 comprising the amino acid sequence of any one of SEQ ID NOs:712, 720, 728, 736, or 744;
a light chain CDR1 comprising the amino acid sequence of any one of SEQ ID NOs:714, 722, 730, 738, or 746;
a light chain CDR2 comprising the amino acid sequence of any one of SEQ ID NOs:715, 723, 731, 739, or 747; and
a light chain CDR3 comprising the amino acid sequence of any one of SEQ ID NOs:716, 724, 732, 740, or 748.

In some embodiments, the antibody comprises heavy chain and light chain CDR sequences contained within the heavy chain variable region and light chain variable region sequence pairs selected from the group consisting of SEQ ID NOs:709 and 713; 717 and 721; 725 and 729; 733 and 737; and 741 and 745. In some embodiments, the antibody comprises a heavy chain CDR1-3 and a light chain CDR1-3 comprising the amino acid sequences of:
(a) SEQ ID NOs: 710, 711, 712, 714, 715, and 716, respectively; or
(b) SEQ ID NOs:718, 719, 720, 722, 723, and 724, respectively; or
(c) SEQ ID NOs:726, 7272, 728, 730, 731, and 732, respectively; or
(d) SEQ ID NOs:734, 735, 736, 738, 739, and 740, respectively; or
(e) SEQ ID NOs:742, 743, 744, 746, 747, and 748, respectively.

In some embodiments, the antibody comprises a heavy chain variable region comprising an amino acid sequence that has at least 90% sequence identity to any one of SEQ ID NOs:709, 717, 725, 733, or 741. In some embodiments, the antibody comprises a light chain variable region comprising an amino acid sequence that has at least 90% sequence identity to any one of SEQ ID NOs:713, 721, 729, 737, or 745.

In some embodiments, the antibody comprises:
(a) a heavy chain variable region comprising an amino acid sequence that has at least 90% sequence identity to SEQ ID NO:709 and a light chain variable region comprising an amino acid sequence that has at least 90% sequence identity to SEQ ID NO:713; or
(b) a heavy chain variable region comprising an amino acid sequence that has at least 90% sequence identity to SEQ ID NO:717 and a light chain variable region comprising an amino acid sequence that has at least 90% sequence identity to SEQ ID NO:721; or
(c) a heavy chain variable region comprising an amino acid sequence that has at least 90% sequence identity to SEQ ID NO:725 and a light chain variable region comprising an amino acid sequence that has at least 90% sequence identity to SEQ ID NO:729; or
(d) a heavy chain variable region comprising an amino acid sequence that has at least 90% sequence identity to SEQ ID NO:733 and a light chain variable region comprising an amino acid sequence that has at least 90% sequence identity to SEQ ID NO:737; or
(e) a heavy chain variable region comprising an amino acid sequence that has at least 90% sequence identity to SEQ ID NO:741 and a light chain variable region comprising an amino acid sequence that has at least 90% sequence identity to SEQ ID NO:745.

In some embodiments, the antibody is an antibody that competes with a monoclonal antibody as disclosed herein for binding to a fungal allergen (e.g., for binding to an *Aspergillus* allergen).

In another aspect, pharmaceutical compositions comprising a monoclonal antibody or antigen-binding portion as disclosed herein are provided. In some embodiments, the pharmaceutical composition comprises a plurality of monoclonal antibodies as disclosed herein, wherein the monoclonal antibodies recognize different epitopes or specifically bind to different antigens (e.g., different allergens within the same type or class of allergen or in different types or classes of allergens).

In another aspect, antibody-drug conjugates comprising a monoclonal antibody or antigen-binding portion thereof as disclosed herein are provided. In some embodiments, the antibody-drug conjugate comprises a monoclonal antibody or antigen-binding portion thereof that specifically binds to a fungal allergen as disclosed herein and further comprises an anti-fungal agent. In some embodiments, the anti-fungal agent is Amphotericin B.

In still another aspect, isolated polynucleotides comprising a nucleotide sequence encoding a monoclonal antibody as disclosed herein. Also provided herein are vectors and host cells comprising a polynucleotide as disclosed herein.

In another aspect, therapeutic methods are provided. In some embodiments, the therapeutic method is a method of reducing one or more allergy symptoms in a subject. In some embodiments, the therapeutic method is a method of reducing one or more allergy symptoms in a subject having a peanut allergy. In some embodiments, the therapeutic method is a method of reducing one or more allergy symptoms in a subject having a tree nut allergy. In some embodiments, the therapeutic method is a method of reducing one or more allergy symptoms in a subject having a fungal allergy. In some embodiments, the therapeutic method is a method of reducing one or more allergy symptoms in a subject having a milk allergy. In some embodiments, the method comprises administering to the subject a therapeutically effective amount of a monoclonal antibody or pharmaceutical composition as disclosed herein.

In another aspect, kits are provided. In some embodiments, the kit comprises a monoclonal antibody or pharmaceutical composition as disclosed herein. In some embodiments, the kit is for use in practicing a therapeutic method as disclosed herein.

BRIEF DESCRIPTION OF THE DRAWINGS

FIGS. 4A-4C. High affinity, cross-reactive IgE antibody convergence in two unrelated individuals (PA12 & PA13). Antibody patterns are conserved among panels. (A) Frequency of silent (S) and replacement (R) mutations by region. (B) Mutation frequency percentiles compared to all class-switched antibodies. (C) Dissociation constants (KDs) for major allergenic peanut proteins Ara h 2 and Ara h 3 for six convergent antibodies as well as eight variants of PA13P1H08. Shortened antibody variant names are designated as "heavy-light," using the following abbreviations: N=native, R=reverted, FWRs=framework regions. An "r" prefix indicates only that region has been reverted.

FIGS. 5A-5E. Germline transcription reveals class switch priming in single B cells. (A) Identity of CE germline transcript splice donors along with the number of cells, by isotype, expressing each. (B) Fraction of cells expressing εGLTs by isotype. (C) Example from individual PA11 where identification of phased variants within IgE constant region exons enables subsequent verification of biallelic GLT expression in other B cells from the same patient. (D) Global germline transcription state heatmap indicating the fraction of cells of a given isotype expressing a given GLT. Above: GLT isotype expression frequency relative to all GLT isotypes; excludes self-isotype GLT expression. (E) Histogram of the number of non-self GLT isotypes expressed in each cell.

FIGS. 7A-7C. Plasma IgE levels. (A) Allergen-specific and allergen component (hazelnut, peanut) concentrations. (B) Total IgE concentration. (C) Positive correlation between total plasma IgE level and the number confirmed IgE+ B cells. Each point is an individual.

FIGS. 9A-9G. Single cell RNA-seq data overview and quality control. (A) Cells were sequenced in 5 libraries to a depth of ~1-2 million reads/cell. (B) Genes per cell histogram. Cells expressing fewer than 950 genes were discarded. (C) Rarefaction curve depicting the number of genes detected as a function of sequencing depth for eight randomly selected cells in each B cell subtype. Solid lines and shaded area represent mean and 95% confidence interval for the gene count, respectively. (D) Read mapping distribution for retained cells. Most reads mapped uniquely (Ensembl reference annotation) and multimapped reads largely belonged to RNA18S5 repeats on chr21 and unplaced scaffolds. (E) Read mapping across gene bodies showed minimal 3' or 5' bias. (F) V gene assembly length histogram by chain. (G) PCA on the top 500 most variable genes before (top) and after (bottom) batch correction.

FIGS. 11A-11K. B cell comparisons across isotypes. (A-I) Number of cells with a given V and J gene by isotype and chain. (A) IGHM. (B) IGHD. (C) IGHG3. (D) IGHG1. (E) IGHA1. (F) IGHG2. (G) IGHG4. (H) IGHE. (I) IGHA2. (J) Heavy chain mutation frequency by isotype. (K) Relative utilization of the lambda and kappa light chain by isotype.

FIGS. 13A-13E. Sequences of heavy and light chains used in constructing PA13P1H08 antibody variants. (A) Derivation of the inferred naïve heavy chain CDR3 and surrounding amino acids. (B) Native and reverted heavy chain sequences, in addition to sequences where region(s) of the heavy chain have been reverted to the inferred naïve rearrangement. Labels with an "r" prefix indicate only that region has been reverted. FWRs=frameworks. (C) Derivation of the inferred naïve light chain CDR3 and surrounding amino acids. (D) Native and reverted light chain sequences. (E) Sequence of a light chain taken from another antibody, PA12P4H03, which we confirmed did not to bind any peanut allergens by ELISA.

TABLE 1

Figure 1:
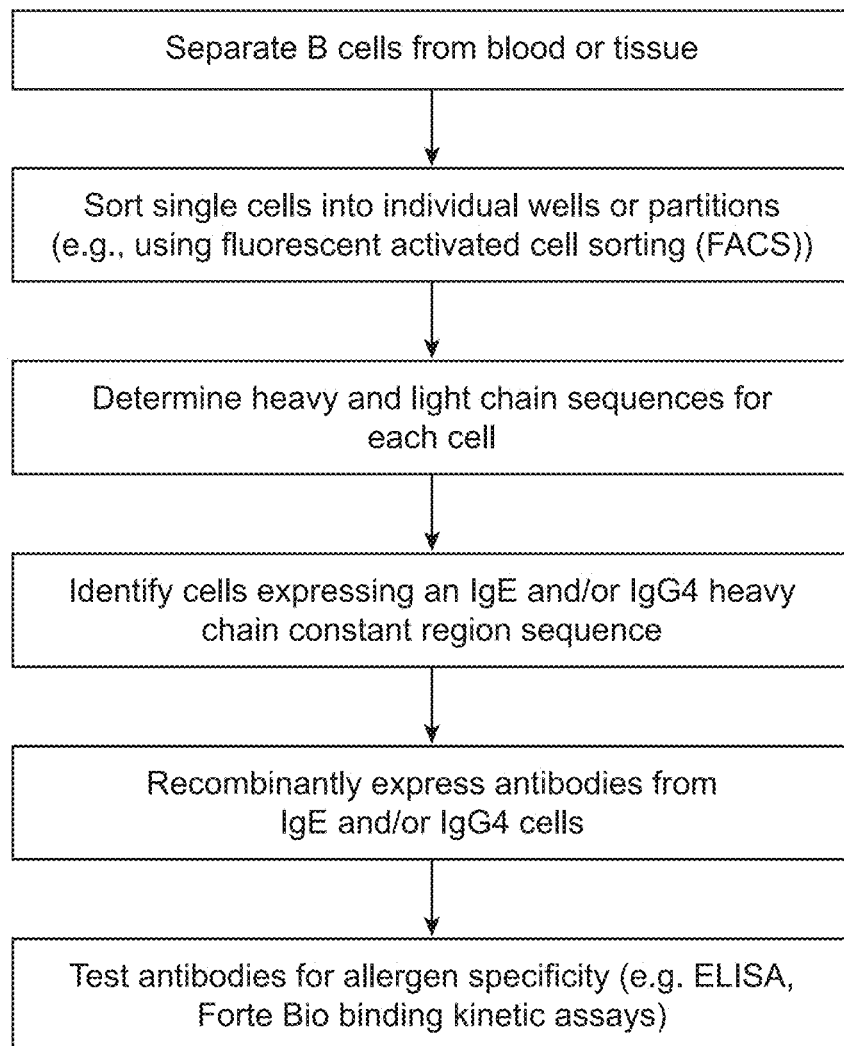
FIG. 1. Flowchart of exemplary workflow for method of generating allergen-specific monoclonal antibodies.

Table 1 includes protein and nucleic acid sequences discussed herein. Polypeptide sequences are provided using the standard one-letter code. One of ordinary skill in the art provided with an amino acid sequence will understand that the amino acid sequence may be encoded by a defined set of nucleotide sequences such that the reader and inventors have posession of the nucleotide sequences encoding each amino acid sequence. A nucleic acid sequence encoding a polynucleotide may be a naturally occurring human sequence. In some embodiments a nucleic acid sequence encoding a polynucleotide is not a naturally occurring human sequence. A nucleic acid sequence encoding a polynucleotide may be a sequence that is codon optimized for expression in human cells or specific cell types, eukaryotic cells, bacteria cells, or otherwise. Codon optimization, which replaces one codon by another codon encoding the same amino acid and having a higher frequency of occurrence in the particular host cell, can be performed to improve the ability of the host to produce the polypeptide encoded by the nucleic acid (see, e.g., Mauro, *BioDrugs* 32(1):69-81, 2018 and Kato, *Int J Mol Sci.* 20(4), 2019).

In certain embodiments it is contemplated that variant sequences may be used in methods and compositions disclosed herein. For example, in one aspect, an antibody with a heavy chain variable region comprising an amino acid sequence that has at least 90% sequence identity to SEQ ID NO:1 and a light chain variable region comprising an amino acid sequence that has at least 90% sequence identity to SEQ ID NO:5 is described. A degree of sequence identity or similarity can be determined using art-known methods. In one approach, the identity of two nucleotide or polypeptide sequences or subsequences is calculated as the percentage of positions that are identical or equivalent after the sequences have been aligned, introducing gaps, if necessary, to achive maximum percent sequence identity. Methods of sequence alignment are art-known methods, and include, but are not limited to the Needleman-Wunsch global alignment algorithm (Needleman and Wunsch (1970) J. Mol. Biol. 48(3): 443-453 (30)), the Smith and Waterman local homology search algorithm (Smith, Temple F. & Waterman, Michael S. (1981) J. Mol. Biol. 147 (1): 195-197.), manual alignment and inspection, or computerized implementations of these algorithms, such as the "needle" program, distributed as part of the EMBOSS software package (Rice, P. et al., Trends in Genetics 16(6): 276-277 (31), versions 6.3.1 available from EMBnet at various sources).

It is contemplated that, in certain embodiments, a method or composition described herein will differ from a polypeptide sequence provided herein (e.g., in Table 1) by one or more amino acid substitutions. In some embodiments a sequence will have at least 90% sequence identity (or other degree of sequence identity disclosed hereinbelow) to a sequence or combination of sequences described herein. In one embodiment the polypeptide sequence differs from a reference sequence (e.g., in Table 1) by one amino acid substitution. In one embodiment the polypeptide sequence differs from a reference sequence (e.g., in Table 1) by two amino acid substitutions. In one embodiment the polypeptide sequence differs from a reference sequence by two amino acid substitutions. In one embodiment the polypeptide sequence differs from a reference sequence by three amino acid substitutions. In one embodiment the polypeptide sequence differs from a reference sequence by four amino acid substitutions. In one embodiment the polypeptide sequence differs from a reference sequence by five amino acid substitutions. In one embodiment the polypeptide sequence differs from a reference sequence by six amino acid substitutions. In one embodiment the polypeptide sequence differs from a reference sequence by seven amino acid substitutions. In one embodiment the polypeptide sequence differs from a reference sequence by eight amino acid substitutions. In one embodiment the polypeptide sequence differs from a reference sequence by nine amino acid substitutions. In one embodiment the polypeptide sequence differs from a reference sequence by ten amino acid substitutions. In certain embodiments the polypeptide sequence differs from a reference sequence by 1-10 amino acid substitutions, sometimes 1-5 amino acid substitutions. In some cases, amino acid substitutions are selected that do not change a basic property (e.g., binding specificity) relative to the reference sequence. In some cases, amino acid substitutions are selected that change binding affinity but not binding specificity. In some cases substitutions are selected to change a property (e.g., substitutions that affect effector function or half-life) as known in the art or described herein below. In some embodiments the amino acid substitutions are conservative substitutions. A conservative amino add substitution is recognized in the art as a substitution of one amino add for another amino add that has similar properties, such as polarity, charge, hydrophobicity, and aromaticity. A conservative amino add substitution can also be made based on the side chain characteristics of the amino add, such as containing sulfur, hydroxyl, or amide. Non-limiting examples of conservative amino add substitutions are set out below.

| Amino acid property | Amino acid |
| --- | --- |
| Polar-uncharged | Cys, Ser, Thr, Met, Asn, Gln |
| Polar-charged | Asp, Glu, Lys, Arg |
| Non-polar | Gly, Ala, Pro, Ile, Leu, Val |
| Aromatic | His, Phe, Trp, Tyr |
| Aliphatic | Ala, Leu, Ile, Val, Pro |
| Positively charged | Lys, Arg, His |
| Negatively charged | Asp, Glu |
| Sulfur-containing | Met |
| Hydroxyl-containing | Ser, Thr, Tyr |
| Amide-containing | Asn, Gln |
| Sulfhydryl containing | Cys |

DETAILED DESCRIPTION OF THE INVENTION

I. Introduction

In one aspect, the present disclosure provides human allergen-specific monoclonal antibodies and methods for generating human allergen-specific monoclonal antibodies from single IgE- or IgG4-expressing human B cells. IgE antibodies, the least abundant class of antibodies in humans, are known to cause the symptoms of allergic reactions. For example, food allergy symptoms ranging from urticaria to potentially fatal anaphylaxis result from the degranulation of mast cells and basophils induced by the recognition of allergic food proteins by surface-bound IgE antibodies. Despite this central role in immunity and allergic disease, human IgE antibodies remain poorly characterized due to their scarcity. Fitzsimmons et al., *Front Immunol.*, 2014, 5:61. Similarly, there is a lack of knowledge, but growing interest, surrounding the IgG4 isotype due to its potential role in mediating the reduced clinical allergen reactivity that accompanies immunotherapy and early allergen exposure through antigen blocking. Tordesillas et al., *Immunity*, 2017, 47:32-50.

The present disclosure provides therapeutic methods for treating a human subject having an allergy or reducing one or more allergy symptoms in a human subject with one or more of the allergen-specific monoclonal antibodies or antigen-binding portions thereof as disclosed herein. In some embodiments and without intending to be boud by a particular mechanism, the allergen-specific monoclonal antibodies disclosed herein are used therapeutically as blocking antibodies, which is often referred to as passive immunotherapy.

As described herein, the methods of the disclosure can be used to generate, from a sample from a human subject having an allergy to an antigen of interest, a pool of genotype-confirmed IgE or IgG4 single B cells that are candidates for producing antibodies having high affinity for an allergen of interest. As described in the Examples section below, it has been found that analyzing the cDNA sequences of immunoglobulin heavy chain constant regions to identify the isotype of single B cells avoids the problem of isotype mischaracterization that is known to occur when B cell isotype is determined based on sorting cells by cell surface markers (e.g., as is typically done in FACS cell surface staining). This problem of isotype mischaracterization is known to be especially pervasive for IgE B cells because the marker CD23 is a "low-affinity" IgE receptor that captures IgE on the surface of non-IgE B cells. See, Berkowska et al., *J Allergy Clin Immunol*, 2014, 134:688-697. Thus, the methods of the present disclosure generate a pool of single B cells that are much more likely to produce antibodies having high affinity for the allergen. Furthermore, it has been found that antibodies generated according to the methods disclosed herein are among the highest affinity native human antibodies discovered to date and exhibit cross-reactivity to different antigens.

II. Definitions

The terminology used herein is for the purpose of describing particular embodiments only, and is not intended to be limiting, because the scope of the present invention will be limited only by the appended claims. Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings unless a contrary intention is apparent. In some cases, terms with commonly understood meanings are defined herein for clarity and/or for ready reference, and the inclusion of such definitions herein should not be construed as representing a substantial difference over the definition of the term as generally understood in the art.

All numerical designations, e.g., pH, temperature, time, concentration, and molecular weight, including ranges, are approximations which are varied (+) or (−) by increments of 0.1 or 1.0, as appropriate. It is to be understood, although not always explicitly stated that all numerical designations are preceded by the term "about."

The singular forms "a," "an," and "the" include plural referents unless the context clearly dictates otherwise. Thus, for example, reference to "a compound" includes a plurality of compounds.

The term "comprising" is intended to mean that the compounds, compositions and methods include the recited elements, but not excluding others. "Consisting essentially of" when used to define compounds, compositions and methods, shall mean excluding other elements that would materially affect the basic and novel characteristics of the claimed invention. "Consisting of" shall mean excluding any element, step, or ingredient not specified in the claim. Embodiments defined by each of these transition terms are within the scope of this invention.

The term "allergen" refers to a substance that induces an immune response in a subject that results in an allergic reaction by the subject.

As used herein, the term "antibody" refers to a polypeptide encoded by an immunoglobulin gene or functional fragments thereof that specifically binds and recognizes an antigen. The term "antibody," as used herein, also includes antibody fragments that retain binding specificity, including but not limited to Fab, F(ab')$_2$, Fv, and scFv. The recognized immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises two identical pairs of polypeptide chains, each pair having one "light" chain (about 25 kDa) and one "heavy" chain (about 50-70 kDa). The N-terminus of each chain defines a variable region of about 100 to 110 or more amino acids primarily responsible for antigen recognition. Thus, the terms "variable heavy chain" or "VH" refer to the variable region of an immunoglobulin heavy chain, including an Fv, scFv, dsFv or Fab; while the terms "variable light chain" or "VL" refer to the variable region of an immunoglobulin light chain, including an Fv, scFv, dsFv or Fab.

The term "variable region" refers to a domain in an antibody heavy chain or light chain that gives an antibody its specificity for binding to an antigen. Typically, an antibody variable region comprises four conserved "framework" regions interspersed with three hypervariable "complementarity determining regions."

The term "complementarity determining region" or "CDR" refers to the three hypervariable regions in each chain that interrupt the four framework regions established by the light and heavy chain variable regions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found.

As noted, the part of a variable region not contained in the CDRs is called the framework. The "framework regions" of different light or heavy chains are relatively conserved within a species. The framework region of an antibody, that is the combined framework regions of the constituent light and heavy chains, serves to position and align the CDRs in three-dimensional space. Framework sequences can be obtained from public DNA databases or published references that include germline antibody gene sequences. For example, germline DNA sequences for human heavy and light chain variable region genes can be found in the "VBASE2" germline variable gene sequence database for human and mouse sequences.

The amino acid sequences of the CDRs and framework regions can be determined using various well known definitions in the art. The position and length of the CDRs have been precisely defined by Kabat et al., Sequences of Proteins of Immunological Interest, U.S. Department of Health and Human Services, 1983, 1987, and others. See, e.g., Johnson and Wu, *Nucleic Acids Res.* 2000 Jan. 1; 28(1): 214-218; Johnson et al., Nucleic Acids Res., 29:205-206 (2001); Chothia & Lesk, (1987) *J. Mol. Biol.* 196, 901-917; Chothia et al. (1989) Nature 342, 877-883; Chothia et al. (1992) J. Mol. Biol. 227, 799-817; Al-Lazikani et al., *J. Mol. Biol* 1997, 273(4)); and MacCallum et al., *J. Mol. Biol.,* 262: 732-745 (1996). Also see international ImMunoGeneTics database (IMGT), AbM, and observed antigen contacts.

The terms "antigen-binding portion" and "antigen-binding fragment" are used interchangeably herein and refer to one or more fragments of an antibody that retains the ability to specifically bind to an antigen (e.g., an allergen, e.g., Ara h 2 or Ara h 3). Examples of antibody-binding fragments include, but are not limited to, a Fab fragment (a monovalent fragment consisting of the VL, VH, CL, and CH1 domains), F(ab')$_2$ fragment (a bivalent fragment comprising two Fab fragments linked by a disulfide bridge at the hinge region), a single chain Fv (scFv), a disulfide-linked Fv (dsFv), complementarity determining regions (CDRs), VL (light chain variable region), VH (heavy chain variable region), nanobodies, and any combination of those or any other functional portion of an immunoglobulin peptide capable of binding to target antigen. Antibodies and antigen-binding portions thereof include domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains. Exemplary configurations of variable and constant domains that may be found within an antigen-binding fragment of an antibody of the present invention include: (a) VH-CHI; (b) VH-CH2; (c) VH-CH3; (d) VH-CH1-CH2; (e) VH-Ch1-Ch2-Ch3; (f) VH-Ch2-Ch3; (g) VH-CL; (h) VL-CH1; (i) VL-Ch2; (X) VL-Ch3; (j) VL-CH1-CH2; (k) VL-CH1-CH2-CH3; (I) VL-CH2-CH3; and (m) VL-CL (see, e.g., FUNDAMENTAL IMMUNOLOGY (Paul ed., 4th ed. 2001), Gruber et al. (1994) *J Immunol.* 152:5368-5374; McCartney, et al., 1995 *Protein Eng.* 8:301-314; Shukra et al., 2014, "Production of recombinant antibodies using bacteriophages" *Eur J Microbiol Immunol* (Bp). 4(2): 91-98; Todorovska, 2001, "Design and application of diabodies, triabodies and tetrabodies for cancer targeting" *J Immunol Methods;* 248(1-2): 47-66; Salvador et al., 2019, "Nanobody: outstanding features for diagnostic and therapeutic applications" *Anal Bioanal Chem.* 411(9):1703-1713; Gill et al., 2006, "Biopharmaceutical drug discovery using novel protein scaffolds." *Curr Opin Biotechnol.,* (6):653-8; and Ubah et al., 2016, "Phage Display Derived IgNAR V Region Binding Domains for Therapeutic Development" *Curr Pharm Des.* 22(43):6519-6526, each of which is incorporated by reference herein.

The term "epitope" refers to the area or region of an antigen to which an antibody specifically binds, i.e., an area or region in physical contact with the antibody, and can include a few amino acids or portions of a few amino acids, e.g., 5 or 6, or more, e.g., 20 or more amino acids, or portions of those amino acids. In some cases, the epitope includes non-protein components, e.g., from a carbohydrate, nucleic acid, or lipid. In some cases, the epitope is a three-dimensional moiety. Thus, for example, where the target is a protein, the epitope can be comprised of consecutive amino acids, or amino acids from different parts of the protein that are brought into proximity by protein folding (e.g., a discontinuous epitope).

A "monoclonal antibody" refers to antibodies produced by a single clone of cells or a single cell line and consisting of or consisting essentially of antibody molecules that are identical in their primary amino acid sequence. In some embodiments, a monoclonal antibody preparation comprises a population of antibodies that are identical and bind to the same epitope of an antigen, except for mutations that arise during monoclonal antibody production. Unless otherwise specified or clear from context, the term 'monoclonal antibody' includes synthetic antibodies and antigen binding fragments thereof.

A "human antibody" refers to an antibody having variable and constant regions derived from human germline immunoglobulin sequences. A human antibody of the present disclosure may include amino acid residues not encoded by human germline immunoglobulin sequences (e.g., mutations introduced by random or site-directed mutagenesis in vitro or by somatic mutations in vivo). The term "human antibody" is not intended to include chimeric or humanized antibodies in which CDR sequences derived from the germline or immune cells of a non-human species (e.g., mouse) have been grafted onto human framework sequences.

The term "specifically binds" refers to a molecule (e.g., an antibody or antibody fragment) that binds to a target with greater affinity, avidity, more readily, and/or with greater duration to that target in a sample than it binds to a non-target compound. In some embodiments, an antibody or antigen-binding portion thereof that specifically binds a target (e.g., an allergen, e.g., Ara h 2 or Ara h 3) is an antibody or antigen-binding portion that binds to the target with at least 2-fold greater affinity than non-target compounds, e.g., at least 3-fold, 4-fold, 5-fold, 6-fold, 7-fold, 8-fold, 9-fold, 10-fold, 20-fold, 25-fold, 50-fold or greater affinity. For example, in some embodiments, an antibody that specifically binds to an allergen target, such as Ara h 2 or Ara h 3, will typically bind to the allergen target with at least a 2-fold greater affinity than to a non-allergen target. It will be understood by a person of ordinary skill in the art that an antibody that specifically or preferentially binds to a first target may or may not specifically or preferentially bind to a second target.

The term "binding affinity," as used herein, refers to the strength of a non-covalent interaction between two molecules, e.g., an antibody (or an antigen-binding fragment thereof) and an antigen. Thus, for example, the term may refer to 1:1 interactions between an antibody (or an antigen-binding fragment thereof) and an antigen, unless otherwise indicated or clear from context. Binding affinity may be quantified by measuring an equilibrium dissociation constant ($K_D$), which refers to the dissociation rate constant ($k_d$, time$^{-1}$) divided by the association rate constant ($k_a$, time$^{-1}$ M$^{-1}$). $K_D$ can be determined by measurement of the kinetics of complex formation and dissociation, e.g., using Surface Plasmon Resonance (SPR) methods, e.g., a Biacore™ system; kinetic exclusion assays such as KinExA®; and Bio-Layer interferometry (e.g., using the ForteBio® Octet platform). As used herein, "binding affinity" includes not only formal binding affinities, such as those reflecting 1:1 interactions between an antibody (or an antigen-binding fragment thereof) and an antigen, but also apparent affinities for which Kos are calculated that may reflect avid binding.

The term "cross-reacts," as used herein, refers to the ability of an antibody to bind to two or more antigens. As a non-limiting example, in some embodiments, an antibody that specifically binds to a first allergen target (e.g., a first peanut allergen, such as Ara h 2) can exhibit cross-reactivity with a second allergen target (e.g., a second peanut allergen, such as Ara h 3).

The term "isolated," as used with reference to a nucleic acid or protein (e.g., antibody), denotes that the nucleic acid or protein is essentially free of other cellular components with which it is associated in the natural state. It is preferably in a homogeneous state. Purity and homogeneity are typically determined using analytical chemistry techniques such as electrophoresis (e.g., polyacrylamide gel electrophoresis) or chromatography (e.g., high performance liquid chromatography). In some embodiments, an isolated nucleic acid or protein (e.g., antibody) is at least 85% pure, at least 90% pure, at least 95% pure, or at least 99% pure.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins, wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the terms "nucleic acid" and "polynucleotide" are used interchangeably. Use of the term "polynucleotide" includes oligonucleotides (i.e., short polynucleotides). This term also refers to deoxyribonucleotides, ribonucleotides, and naturally occurring variants, and can also refer to synthetic and/or non-naturally occurring nucleic acids (i.e., comprising nucleic acid analogues or modified backbone residues or linkages), such as, for example and without limitation, phosphorothioates, phosphoramidates, methyl phosphonates, chiral-methyl phosphonates, 2-O-methyl ribonucleotides, peptide-nucleic acids (PNAs), and the like. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (see, e.g., Batzer et al., *Nucleic Acid Res.* 19:5081 (1991); Ohtsuka et al, *J. Biol. Chem.* 260:2605-2608 (1985); Rossolini et al, *Mol. Cell. Probes* 8:91-98 (1994)).

The term "sample," as used herein, refers to a biological sample obtained from a human or non-human mammalian subject. In some embodiments, a sample comprises blood, blood fractions or blood products (e.g., serum, plasma, platelets, red blood cells, peripheral blood mononuclear cells and the like); sputum or saliva; stool, urine, other biological fluids (e.g., lymph, saliva, prostatic fluid, gastric fluid, intestinal fluid, renal fluid, lung fluid, cerebrospinal fluid, and the like), tissue (e.g., kidney, lung, liver, heart, brain, nervous tissue, thyroid, eye, skeletal muscle, cartilage, or bone tissue), cultured cells (e.g., primary cultures, explants, transformed cells, or stem cells), or a biopsy sample.

The terms "subject" and "patient," as used interchangeably herein, refer to a mammal, including but not limited to humans, non-human primates, rodents (e.g., rats, mice, and guinea pigs), rabbits, cows, pigs, horses, and other mammalian species. In one embodiment, the subject or patient is a human.

The terms "treat," "treating," and "treatment" refer to any indicia of success in the treatment or amelioration of an injury, disease, or condition, including any objective or subjective parameter such as abatement; remission; diminishing of symptoms or making the injury, disease, or condition more tolerable to the subject; slowing in the rate of degeneration or decline; making the final point of degeneration less debilitating; and/or improving a subject's physical or mental well-being. The treatment or amelioration of symptoms can be based on objective or subjective parameters. The effect of treatment can be compared to an individual or pool of individuals not receiving the treatment, or to the same patient prior to treatment or at a different time during treatment.

The term "pharmaceutical composition" refers to a composition suitable for administration to a subject. In general, a pharmaceutical composition is sterile, and preferably free of contaminants that are capable of eliciting an undesirable response with the subject. Pharmaceutical compositions can be designed for administration to subjects in need thereof via a number of different routes of administration, including oral, intravenous, buccal, rectal, parenteral, intraperitoneal, intradermal, intratracheal, intramuscular, subcutaneous, inhalational, and the like.

The term "pharmaceutically acceptable excipient" refers to a non-active pharmaceutical ingredient that is biologically or pharmacologically compatible for use in humans or animals, such as, but not limited to a buffer, carrier, or preservative.

As used herein, a "therapeutic amount" or "therapeutically effective amount" of an agent (e.g., a monoclonal antibody as disclosed herein) is an amount of the agent that treats, ameliorates, abates, remits, improves patient survival, increases survival time or rate, diminishes symptoms, makes an injury, disease, or condition (e.g., an allergy) more tolerable, slows the rate of degeneration or decline, or improves a patient's physical or mental well-being. For example, for the given parameter, a therapeutically effective amount will show an increase or decrease of therapeutic effect at least 5%, 10%, 15%, 20%, 25%, 40%, 50%, 60%, 75%, 80%, 90%, or 100%. Therapeutic efficacy can also be expressed as "-fold" increase or decrease. For example, a therapeutically effective amount can have at least a 1.2-fold, 1.5-fold, 2-fold, 5-fold, or more effect over a control.

The terms "administer," "administered," or "administering" refer to methods of delivering agents, compounds, or compositions to the desired site of biological action. These methods include, but are not limited to, topical delivery, parenteral delivery, intravenous delivery, intradermal delivery, intramuscular delivery, rectal delivery, or intraperitoneal delivery. Administration techniques that are optionally employed with the agents and methods described herein, include e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

III. Methods of Generating Allergen-Specific Antibodies

In one aspect, methods of generating allergen-specific monoclonal antibodies from a human sample are provided. In some embodiments, the method comprises:
  (a) isolating single B cells from a sample from a human subject, wherein the subject is allergic to the allergen;
  (b) generating cDNAs from the single B cells of step (a), wherein the cDNA sequences comprise a first sequence that encodes all or part of an immunoglobulin heavy chain and a second sequence that encodes all or part of an immunoglobulin light chain;
  (c) determining the sequences of the cDNAs from step (b);
  (d) analyzing the sequences determined in step (c) to identify single B cells comprising a first sequence that comprises an IgE constant region or an IgG4 constant region;
  (e) identifying, from the single B cells of step (d), (i) a heavy chain variable region sequence in the immunoglobulin heavy chain that comprises an IgE constant region or an IgG4 constant region, and (ii) a light chain variable region sequence in an immunoglobulin light chain that is co-expressed with the immunoglobulin heavy chain in the same single B cell;
  (f) expressing antibodies comprising the heavy chain variable region sequence and the light chain variable region sequence from step (e); and
  (g) identifying one or more antibodies from step (f) that specifically bind to the allergen.

Subject Populations and Samples

In some embodiments, the method of generating allergen-specific monoclonal antibodies comprises isolating B cells from a biological sample from a human subject. In some embodiments, the sample comprises whole blood, peripheral blood, or a leukapheresis product. In some embodiments, the sample comprises peripheral blood mononuclear cells (PBMCs). In some embodiments, the sample comprises a tissue from the human subject, e.g., tonsil tissue, spleen, or bone marrow. Methods of isolating B cells from blood and tissue samples are described in the art. See, e.g., Heine et al., *Curr Protoc. Immunol.*, 2011, 94:7.5.1-7.5.14; and Zuccolo et al., *BMC Immunol*, 2009, 10:30, doi:10.1186/1471-2172-10-30.

In some embodiments, the allergen-specific antibodies are generated from a human subject having an allergy to the allergen. In some embodiments, the human subject having an allergy is an adult. In some embodiments, the human subject having an allergy is a juvenile. In some embodiments, the human subject has an allergy to a food allergen, a plant allergen, a fungal allergen, an animal allergen, a dust mite allergen, a drug allergen, a cosmetic allergen, or a latex allergen. In some embodiments, the human subject has allergies to two or more allergens, e.g., to two or more of a food allergen, a plant allergen, a fungal allergen, an animal allergen, a dust mite allergen, a drug allergen, a cosmetic allergen, or a latex allergen. In some embodiments, the human subject has allergies to 2, 3, 4, 5, 6, 7, 8, 9, 10 or more allergens. In some embodiments, the human subject has allergies to two or more different types of antigens (allergens) in a class of allergen, e.g., allergies to two or more different food allergens (e.g., allergies to two or more different peanut antigens, or allergies to a peanut allergen and a non-peanut allergen such as a tree nut, egg, or milk allergen), or allergies to two more different fungal allergens (e.g., allergies to two or more different species of *Aspergillus*). In some embodiments, the human subject has allergies to two more different classes of allergens (e.g., allergies to one or more food allergens and to one or more plant allergens). In some embodiments, the human subject has allergies to only one class of allergens (e.g., the subject has allergies to one or more food allergens but not to non-food allergens, or the subject has allergies to one or more fungal allergens but not to non-fungal allergens).

In some embodiments, the human subject has an allergy to a food allergen. In some embodiments, the food allergen is a milk allergen, an egg allergen, a nut allergen, a tree nut allergen, a fish allergen, a shellfish allergen, a soy allergen, a legume allergen, a seed allergen, or a wheat allergen. In some embodiments, the food allergen is a peanut allergen.

In some embodiments, the human subject has an allergy to a plant allergen or a fungal allergen. In some embodiments, the allergen is a fungal allergen (e.g., *Aspergillus*, e.g., *Asp. fumigatus, Asp. niger*, or *Asp. nidulans*). In some embodiments, the allergen is a pollen allergen (e.g., tree pollen, grass pollen, or weed pollen) or a mold allergen. In some embodiments, the human subject has an allergy to an animal allergen. In some embodiments, the allergen is a dander allergen or an insect sting.

In some embodiments, the method of generating allergen-specific monoclonal antibodies does not comprise immunizing the human subject with the allergen or exposing the human subject to the allergen prior to obtaining the sample from the subject.

B Cell Isolation and Screening

In some embodiments, single B cells are isolated from the sample from the subject having an allergy to the allergen. In some embodiments, the single B cells are separated into separate partitions, e.g., separate wells of a multi-well plate, encapsulated into droplets, or dispersed into microwells. In some embodiments, at least 10, 50, 100, 500, 1,000, 5,000, or 10,000 B cells or more are isolated from a sample and are separated into separate partitions.

In some embodiments, the isolating step comprises sorting cells in the sample by fluorescent activated cell sorting (FACS). FACS sorting can be used to sort cells based on cell surface marker expression, cell size, and/or granularity and deliver cells individually to a well, e.g., a 96-well or 384-well tissue culture or PCR plate. Methods of isolating and purifying cell populations by FACS are described in the art. See, e.g., Basu et al., *J Vis Exp*, 2010, 41:1546, doi: 10.3791/1546.

In some embodiments, a droplet microfluidic platform can be used to dispense single B cells into separate droplets. In some embodiments, the nucleic acids (e.g., mRNA) of a single cell in a droplet is labeled with a nucleotide sequence that is unique to the droplet, e.g., a Unique Molecular Identifier barcode nucleotide sequence, thereby enabling downstream processing steps for the sequences from multiple B cells to be performed in a single reaction container. Methods of encapsulating single cells in droplets are described in the art. See, e.g., Macosko et al., *Cell*, 2015, 161: 1202-1214; Zhang et al., *Scientific Reports*, 2017, 7:41192, doi:10.1038/srep41192.

In some embodiments, cells are dispersed into microwells designed to trap a single cell. Methods of single cell microwell trapping are described in the art. See, e.g. Han et al., Cell, 2018, 172:5, doi:10.1016/j.cell.2018.02.001.

In some embodiments, cells from the sample are screened for the presence, absence, or level of expression of one or more markers and single B cells are isolated based on the presence or level of expression of the one or more B cell markers (e.g., one, two, three, four, five, six, seven, eight, or more markers). In some embodiments, cells are screened for the presence, absence, or level of expression of one or more cell surface B cell markers, such as but not limited to CD19, CD20, CD21, CD22, CD23, CD24, CD40, CD72, or CD79. In some embodiments, a cell is determined to be a B cell if the cell is positive for one or more of the B cell markers, e.g., is positive for one or more of CD19, CD20, CD21, CD22, CD23, CD24, CD40, CD72, or CD79. In some embodiments, single CD19$^+$ B cells are isolated.

In some embodiments, cells from the sample are screened for the presence, absence, or level of expression of one or more immunoglobulin isotypes, such as but not limited to IgE, IgG, IgM, IgA, or IgD or a subclass thereof. In some embodiments, the single B cells that are isolated are selected for expression of cell surface IgE and/or for expression of cell surface IgG4. In some embodiments, single B cells are isolated without selecting for expression of one or more immunoglobulin isotypes (e.g., without selecting for expression of cell surface IgE and/or for expression of cell surface IgG4).

IgE Selection

In some embodiments, the method comprises isolating single B cells that are selected for expression of cell surface IgE. In some embodiments, the isolating step comprises contacting cells of the sample with an anti-human IgE antibody and selecting for cells that express IgE on the cell surface. In some embodiments, the isolating step comprises contacting cells of the sample with antibody against a B cell marker (e.g., an antibody against CD19, CD20, CD21, CD22, CD23, CD24, CD40, CD72, or CD79) and an anti-human IgE antibody and selecting for cells that express the B cell marker and that express IgE on the cell surface. In some embodiments, the isolating step comprises contacting cells of the sample with an anti-human CD19 antibody and an anti-human IgE antibody and selecting for CD19$^+$IgE-expressing B cells.

In some embodiments, the isolating step comprises contacting cells of the sample with antibody against a B cell marker (e.g., an antibody against CD19, CD20, CD21, CD22, CD23, CD24, CD40, CD72, or CD79), an anti-human IgE antibody, and an antibody against one or more immunoglobulin isotypes (e.g., an anti-human IgG antibody, an anti-human IgM antibody, an anti-human IgA antibody, and/or an anti-human IgD antibody) or subclass thereof and selecting for cells that express the B cell marker, that express IgE on the cell surface, and that do not express detectable levels of the one or more other immunoglobulin isotypes being screened for. In some embodiments, the isolating step comprises contacting cells of the sample with an anti-human CD19 antibody, an anti-human IgE antibody, and one or more of an anti-human IgG antibody, an anti-human IgM antibody, an anti-human IgA antibody, or an anti-human IgD antibody, and selecting for CD19$^+$IgE-expressing B cells that are negative for IgG, IgM, IgA, or IgD cell surface expression.

In some embodiments, the isolating step comprises contacting cells from the sample with an anti-human CD19 antibody, an anti-human IgE antibody, an anti-human IgM antibody, and an anti-human IgG antibody and selecting for CD19$^+$IgM$^-$IgG$^-$ IgE-expressing B cells. In some embodiments, the isolating step comprises contacting cells from the sample with an anti-human CD19 antibody, an anti-human IgE antibody, an anti-human IgM antibody, an anti-human IgG antibody, an anti-human IgA antibody, and an anti-human IgD antibody and selecting for CD19$^+$IgM$^-$IgG$^-$IgA$^-$IgD$^-$ IgE-expressing B cells.

In some embodiments, the isolating step comprises contacting cells of the sample with antibody against a B cell marker (e.g., an antibody against CD19, CD20, CD21, CD22, CD23, CD24, CD40, CD72, or CD79) and antibodies against non-IgE isotypes (e.g., an anti-human IgG antibody, an anti-human IgM antibody, an anti-human IgA antibody, and an anti-human IgD antibody) or subclass thereof, and selecting for cells that express the B cell marker and that do not express detectable levels of the non-IgE isotypes. In some embodiments, the isolating step comprises contacting cells from the sample with an anti-human CD19 antibody, an anti-human IgM antibody, an anti-human IgG antibody, an anti-human IgA antibody, and an anti-human IgD antibody and selecting for CD19$^+$IgM$^-$IgG$^-$IgA$^-$IgD$^-$ B cells.

In some embodiments, the method comprises isolating IgE-expressing B cells that are antibody-secreting B cells (e.g., plasmablasts or plasma cells). In some embodiments, the method comprises isolating IgE-expressing B cells that are memory B cells. In some embodiments, the method comprises isolating IgE-expressing antibody-secreting B cells and IgE-expressing memory B cells.

IgG4 Selection

In some embodiments, the method comprises isolating single B cells that are selected for expression of cell surface IgG4. In some embodiments, the isolating step comprises contacting cells of the sample with an anti-human IgG4 antibody and selecting for cells that express IgG4 on the cell surface. In some embodiments, the isolating step comprises contacting cells of the sample with an antibody against a B cell marker (e.g., an antibody against CD19, CD20, CD21, CD22, CD23, CD24, CD40, CD72, or CD79) and an anti-human IgG4 antibody and selecting for cells that express the B cell marker and that express IgG4 on the cell surface. In some embodiments, the isolating step comprises contacting cells of the sample with an anti-human CD19 antibody and an anti-human IgG4 antibody and selecting for CD19$^+$IgG4-expressing B cells.

In some embodiments, the isolating step comprises contacting cells of the sample with an antibody against a B cell marker (e.g., an antibody against CD19, CD20, CD21, CD22, CD23, CD24, CD40, CD72, or CD79), an anti-human IgG4 antibody, and an antibody against one or more IgG subclasses (e.g., an anti-human IgG1 antibody, an anti-human IgG2 antibody, an anti-human IgG3 antibody) and selecting for cells that express the B cell marker, that express IgG4 on the cell surface, and that do not express detectable levels of the one or more other IgG subclasses being screened for. In some embodiments, the isolating step comprises contacting cells from the sample with an anti-human CD19 antibody, an anti-human IgG1 antibody, an anti-human IgG2 antibody, an anti-human IgG3 antibody, and an anti-human IgG4 antibody and selecting for CD19$^+$IgG1$^-$IgG2$^-$IgG3$^-$IgG4-expressing B cells.

In some embodiments, the isolating step comprises contacting cells of the sample with an antibody against a B cell marker (e.g., an antibody against CD19, CD20, CD21, CD22, CD23, CD24, CD40, CD72, or CD79), an anti-human IgG4 antibody, and an antibody against one or more immunoglobulin isotypes (e.g., an anti-human IgE antibody, an anti-human IgM antibody, an anti-human IgA antibody, and/or an anti-human IgD antibody) or subclass thereof and selecting for cells that express the B cell marker, that express IgG4 on the cell surface, and that do not express detectable levels of the one or more other immunoglobulin isotypes being screened for. In some embodiments, the isolating step comprises contacting cells of the sample with an anti-human CD19 antibody, an anti-human IgG4 antibody, and one or more of an anti-human IgE antibody, an anti-human IgM antibody, an anti-human IgA antibody, or an anti-human IgD antibody, and selecting for CD19$^+$IgG4-expressing B cells that are negative for IgE, IgM, IgA, or IgD cell surface expression.

In some embodiments, the isolating step comprises contacting cells from the sample with an anti-human CD19 antibody, an anti-human IgG4 antibody, an anti-human IgM antibody, and an anti-human IgG antibody and selecting for CD19$^+$IgM$^-$IgE$^-$ IgG4-expressing B cells. In some embodiments, the isolating step comprises contacting cells from the sample with an anti-human CD19 antibody, an anti-human IgG4 antibody, an anti-human IgM antibody, an anti-human IgE antibody, an anti-human IgA antibody, and an anti-human IgD antibody and selecting for CD19$^+$IgM$^-$IgE$^-$IgA$^-$IgD$^-$ IgG4-expressing B cells.

In some embodiments, the isolating step comprises contacting cells of the sample with an antibody against a B cell marker (e.g., an antibody against CD19, CD20, CD21, CD22, CD23, CD24, CD40, CD72, or CD79) and antibodies against non-IgG isotypes (e.g., an anti-human IgE antibody, an anti-human IgM antibody, an anti-human IgA antibody, and an anti-human IgD antibody) or non-IgG4 isotypes thereof, and selecting for cells that express the B cell marker and that do not express detectable levels of the non-IgG or non-IgG4 isotypes. In some embodiments, the isolating step comprises contacting cells from the sample with an anti-human CD19 antibody, an anti-human IgM antibody, an anti-human IgE antibody, an anti-human IgA antibody, and an anti-human IgD antibody and selecting for CD19$^+$IgM$^-$IgE$^-$IgA$^-$IgD$^-$ B cells. In some embodiments, the isolating step comprises contacting cells from the sample with an anti-human CD19 antibody, an anti-human IgM antibody, an anti-human IgE antibody, an anti-human IgA antibody, an anti-human IgD antibody, an anti-human IgG1 antibody, an anti-human IgG2 antibody, and an anti-human IgG3 antibody and selecting for CD19$^+$IgM$^-$IgE$^-$IgA$^-$IgD$^-$ IgG1$^-$IgG2$^-$IgG3$^-$ B cells.

In some embodiments, the method comprises isolating IgG4-expressing B cells that are antibody-secreting B cells. In some embodiments, the method comprises isolating IgG4-expressing B cells that are memory B cells. In some embodiments, the method comprises isolating IgG4-expressing antibody-secreting B cells and IgG4-expressing memory B cells.

Generating and Sequencing cDNAs

In some embodiments, cDNAs are generated from the isolated single B cells from the sample (e.g., from single B cells that have been screened for expression of an immunoglobulin isotype such as IgE or IgG4, or from single B cells that have not been screened for expression of an immunoglobulin isotype). In some embodiments, cDNA libraries are prepared from the single B cells. In some embodiments, for the cDNAs that are generated for each single B cell, the cDNA sequences comprise a sequence that encodes an immunoglobulin heavy chain and a sequence that encodes an immunoglobulin light chain.

In some embodiments, cDNAs are generated by reverse transcribing cDNA sequences from RNA (e.g., total RNA or mRNA) from the single B cell and amplifying the cDNA sequences. For generating cDNAs, in some embodiments, the single B cells are lysed and cDNA sequences are reverse transcribed from mRNA present in the cell lysate. In some embodiments, RNA is isolated from the single B cell and cDNAs are reverse transcribed from the isolated RNA.

In some embodiments, the method comprises amplifying the transcriptome of the single B cell. For example, in some embodiments, the method comprises reverse transcribing RNA (e.g., polyadenylated mRNA) to synthesize cDNAs, then amplifying the cDNA, e.g., by PCR. Exemplary methods for reverse transcribing polyadenylated mRNA and amplifying the transcriptome of a single cell are described in Darmanis et al., *Cell Reports,* 2017, 21:1399-1410, and in Picelli et al., *Nature Protocols,* 9, 2014, 171-181.

In some embodiments, the method comprises amplifying immunoglobulin heavy chain and light chain sequences from the single B cells. For example, in some embodiments, the method comprises reverse transcribing RNA (e.g., total RNA) to synthesize cDNAs, then amplifying the cDNAs, e.g., by PCR, using primers for immunoglobulin heavy chain variable regions and constant regions. In some embodiments, the method comprises reverse transcribing RNA using immunoglobulin-specific primers (e.g., constant region-specific primers) to synthesize cDNAs comprising immunoglobulin sequences, then amplifying the cDNAs using primers for immunoglobulin heavy chain variable regions and constant regions. An exemplary method for amplifying immunoglobulin heavy chain and light chain sequences from a single cell is described in Tiller et al., *J. Immunol. Methods,* 2008, 329:112-124.

After the cDNAs are generated, in some embodiments, the method comprises determining the sequences of the cDNAs. In some embodiments, the cDNAs are subjected to sequencing. In some embodiments, the method comprises sequencing the transcriptomes of the single B cells. In some embodiments, the method comprises sequencing target genes (e.g., immunoglobulin genes, e.g., immunoglobulin heavy chain variable regions and constant regions and immunoglobulin light chain variable regions and constant regions).

Sequencing methods, including methods for high-throughput sequencing, are known in the art. For example, such sequencing technologies include, but are not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics,* 92: 255 (2008), herein incorporated by reference in its entirety.

In some embodiments, sequencing comprises high-throughput sequencing. In high-throughput sequencing, parallel sequencing reactions using multiple templates and multiple primers allows rapid sequencing of genomes or large portions of genomes. High throughput sequencing methods include methods that typically use template amplification and those that do not. Sequencing methods that utilize amplification include pyrosequencing commercialized by Roche as the 454 technology platforms (e.g., GS 20 and GS FLX), clonal array formation and sequencing by synthesis (SBS) chemistry commercialized by Illumina with systems such as the NextSeq, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and platforms commercialized by VisiGen, Oxford Nanopore Technologies Ltd., Life Technologies/Ion Torrent, and Pacific Biosciences, respectively.

In some embodiments, an Illumina sequencing platform, such as NextSeq, is used. This sequencing technology utilizes clonal array formation and sequencing by synthesis to produce sequences on a large scale. In this method, sequencing templates are immobilized on a flow cell surface, then solid-phase amplification creates copies of each template molecule (up to 1,000 identical copies) in close proximity, forming dense "clusters" of polynucleotide sequences. For sequencing the clusters, fluorescently-labeled nucleotides are used to sequences the clusters on the flow cell surface in parallel. For each sequencing cycle, a single labeled reversible terminator-bound dNTP is added to the nucleic acid chain. The sequence of incorporated nucleotides is determined by detection of post-incorporation fluorescence, then the fluorescent dye is removed prior to the next cycle of dNTP addition, resulting in base-by-base sequencing. Typically sequence read length ranges from about 30 nucleotides to over 150 nucleotides. For a target cDNA of interest having a longer length, the sequence can be bioinformatically reassembled based on overlaps between the short sequencing reads to determine the sequence of the full-length target cDNA.

Identifying B Cells Having an IgE or IgG4 Isotype

In some embodiments, after the sequences of cDNAs have been determined for the single B cells, the method comprises analyzing the sequences of the cDNAs to identify single B cells that express an immunoglobulin heavy chain having a constant region that is of the IgE isotype and/or of the IgG4 isotype. As described herein, it has been found that determining the isotype of the B cell based on the sequence of the heavy chain transcript, rather than FACS immunoglobulin surface staining, substantially reduces the number of false positive IgE cells in the B cell population, and thus results in a population of B cells that is much more likely to yield antibodies that specifically bind to the allergen to which the human subject who is the source of the B cells is allergic.

In some embodiments, the method comprises identifying a sequence encoding an immunoglobulin heavy chain that comprises an IgE constant region. In some embodiments, the method comprises identifying a sequence encoding an immunoglobulin heavy chain that comprises an IgG4 constant region. In some embodiments, the cDNA sequence is analyzed by comparing the sequence to a known IgE constant region sequence or to a known IgG4 constant region sequence. For example, a comparison of a cDNA sequence of interest (e.g., a "test" sequence from a B cell) can be compared to a known IgE or IgG4 constant region sequence (e.g., a "reference" sequence) by aligning the sequences. Methods of alignment of sequences for comparison are known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site.

For comparing a test sequence to an IgE or IgG4 constant region reference sequence, in some embodiments, the reference sequence is published sequence such as an IgE or IgG4 constant region sequence that is publicly available in the ImMunoGeneTics (IMGT) database. See, e.g., Camacho et al., *BMC Bioinformatics*, 2009, 10:421; Lefranc et al., *Nucleic Acids Res*, 2009, 37:D1006-1012. Methods of analyzing test sequences to identify sequences comprising an immunoglobulin heavy chain constant region that is of the IgE isotype and/or of the IgG4 isotype are also described in Table 1 below.

In some embodiments, in addition to analyzing sequences to identify and select single B cells comprising an immunoglobulin heavy chain sequence that comprises an IgE constant region or an IgG4 constant region, the method further comprises determining the sequences and/or levels of expression of one or more other genes in the single B cell. For example, in some embodiments, the method comprises determining the sequences and/or levels of expression of a set of genes that are a "signature" for a particular type of B cell.

In some embodiments, for a B cell that is identified as having an immunoglobulin heavy chain that comprises an IgE constant region or an IgG4 constant region, the method further comprises identifying, from the same B cell, the heavy chain variable region sequence that is expressed by the cell and the light chain variable region sequence that is expressed by the cell.

Antibody Expression

Typically, for a single B cell that is identified as having a cDNA that comprises an IgE or IgG4 constant region sequence, the heavy chain variable region and light chain variable region sequences from the single B cell are candidate antibody sequences for having specificity to the allergen of interest. Thus, in some embodiments, the method comprises expressing antibodies comprising the heavy chain variable region and light chain variable region sequences from the single B cell and identifying whether the expressed antibody specifically binds to the allergen of interest. Methods for the expression and purification of recombinant antibodies are described in the art. See, e.g., Frenzel et al., *Front Immunol.*, 2013, 4:217, doi:10.3389/fimmu.2013.00217; Siegemund et al., *Methods Mol Biol.*, 2014, 1131:273-295.

In some embodiments, the heavy chain variable region and light chain variable region sequences from the single B cell are amplified from the single B cell and cloned into an expression vector. In some embodiments, the heavy chain variable region and light chain variable region sequences from the single B cell are synthesized. In some embodiments, the heavy chain variable region sequence and/or light chain variable region sequence is codon-optimized, e.g., to increase antibody expression by the expression system. See, e.g., Ayyar et al., *Methods*, 2017, 116:51-62.

The heavy chain variable region and light chain variable region sequences from the single B cell can be expressed using any number of expression systems, including prokaryotic and eukaryotic expression systems. In some embodiments, the expression system is a mammalian cell expression, such as a hybridoma, or a CHO or HEK293 cell expression system. Many such systems are widely available from commercial suppliers. Cell expression systems are also described in the art. See, e.g., Kunert and Reinhart, 2016, "Advances in recombinant antibody manufacturing" *Appl Microbiol Biotechnol.* 100:3451-61; Jager et al., *BMC Proc.*, 2015, 9:P40, doi:10.1186/1753-6561-9-59-P40; and references cited therein. In some embodiments, the heavy chain and light chain are expressed using a single vector, e.g., in a di-cistronic expression unit, or under the control of different promoters. In other embodiments, the heavy chain and light chain are be expressed using separate vectors. In some embodiments, an expression vector for expressing heavy chain variable region sequence and/or light chain variable region sequence as disclosed herein is a vector that comprises a constant region of a desired heavy chain isotype or light chain subclass. For example, a heavy chain variable region sequence as disclosed herein can be cloned into a vector that comprises a human IgG (e.g., IgG1, IgG2, IgG3, or IgG4) heavy chain constant region, and a light chain variable region sequence as disclosed herein can be cloned into a vector that comprises a human lambda or kappa light chain constant region.

After an antibody comprising a heavy chain variable region sequence and a light chain variable region sequence from the single B cell as disclosed herein is expressed and purified, in some embodiments, the method comprises determining whether the antibody specifically binds to the allergen. Methods for analyzing binding affinity and binding kinetics are known in the art. See, e.g., Ernst et al., Determination of Equilibrium Dissociation Constants, *Therapeutic Monoclonal Antibodies* (Wiley & Sons ed. 2009). These methods include, but are not limited to, solid-phase binding assays (e.g., ELISA assay), immunoprecipitation, surface plasmon resonance (SPR, e.g., Biacore™ (GE Healthcare, Piscataway, N.J.)), kinetic exclusion assays (e.g. KinExA®), flow cytometry, fluorescence-activated cell sorting (FACS), BioLayer interferometry (e.g., Octet™ (FortéBio, Inc., Menlo Park, Calif.)), and Western blot analysis. SPR techniques are reviewed, e.g., in Hahnfeld et al. Determination of Kinetic Data Using SPR Biosensors, *Molecular Diagnosis of Infectious Diseases* (2004). In a typical SPR experiment, one interactant (target or targeting agent) is immobilized on an SPR-active, gold-coated glass slide in a flow cell, and a sample containing the other interactant is introduced to flow across the surface. When light of a given wavelength is shined on the surface, the changes to the optical reflectivity of the gold indicate binding, and the kinetics of binding. In some embodiments, kinetic exclusion assays are used to determine affinity. This technique is described, e.g., in Darling et al., *Assay and Drug Development Technologies* Vol. 2, number 6 647-657 (2004). In some embodiments, BioLayer interferometry assays are used to determine affinity. This technique is described, e.g., in Wilson et al., *Biochemistry and Molecular Biology Education*, 38:400-407 (2010); Dysinger et al., *J. Immunol. Methods*, 379:30-41 (2012).

In some embodiments, the expressed antibody specifically binds to the allergen with high affinity. In some embodiments, the antibody has a binding affinity ($K_D$) for the allergen that is less than 250 nM, less than 100 nM, less than 50 nM, less than 10 nM, less than 5 nM, less than 1 nM, less than 500 pM, less than 250 pM, less than 150 pM, less than 100 pM, less than 50 pM, less than 40 pM, less than 30 pM, less than 20 pM, less than about 10 pM, or less than 1 pM. In some embodiments, the antibody binds to the allergen with a binding affinity (KD) from 1 nM to 250 nM.

Nucleic Acids, Vectors, and Host Cells

In some embodiments, the allergen-specific monoclonal antibodies as described herein are prepared using recombinant methods. Accordingly, in some aspects, the invention provides isolated nucleic acids comprising a nucleic acid sequence encoding any of the allergen-specific monoclonal antibodies as described herein (e.g., any one or more of the CDRs described herein); vectors comprising such nucleic acids; and host cells into which the nucleic acids are introduced that are used to replicate the antibody-encoding nucleic acids and/or to express the antibodies. In some embodiments, the host cell is eukaryotic, e.g., a human cell such as HEK-293.

In some embodiments, a polynucleotide (e.g., an isolated polynucleotide) comprises a nucleotide sequence encoding an antibody or antigen-binding portion thereof as described herein (e.g., as described in Section IV below). In some embodiments, the polynucleotide comprises a nucleotide sequence encoding one or more amino acid sequences (e.g., CDR, heavy chain variable region, or light chain variable region) disclosed in Table 1 below.

In a further aspect, methods of making an allergen-specific monoclonal antibody as described herein are provided. In some embodiments, the method includes culturing a host cell as described herein (e.g., a host cell expressing a polynucleotide or vector as described herein) under conditions suitable for expression of the antibody. In some embodiments, the antibody is subsequently recovered from the host cell (or host cell culture medium).

Suitable vectors containing polynucleotides encoding antibodies of the present disclosure, or fragments thereof, include cloning vectors and expression vectors. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Examples include plasmids and bacterial viruses, e.g., pUC18, pUC19, Bluescript (e.g., pBS SK+) and its derivatives, mpl8, mpl9, pBR322, pMB9, ColE1, pCR1, RP4, phage DNAs, and shuttle vectors such as pSA3 and pAT28. Cloning vectors are available from commercial vendors such as BioRad, Stratagene, and Invitrogen.

Expression vectors generally are replicable polynucleotide constructs that contain a nucleic acid of the present disclosure. The expression vector may replicate in the host cells either as episomes or as an integral part of the chromosomal DNA. Suitable expression vectors include but are not limited to plasmids, viral vectors, including adenoviruses, adeno-associated viruses, retroviruses, and any other vector.

IV. Monoclonal Antibodies that Specifically Bind to Allergens

In another aspect, allergen-specific monoclonal antibodies, and antigen-binding portions thereof, that are generated from a human sample according to a method disclosed herein are provided. In some embodiments, the monoclonal antibody is an antibody that is generated according to the methods disclosed in Section III above. In some embodiments, the monoclonal antibody is an antibody that is generated from a sample from a human subject having an allergy to a food allergen, a plant allergen, a fungal allergen, an animal allergen, a dust mite allergen, a drug allergen, a cosmetic allergen, or a latex allergen, and the monoclonal antibody specifically binds to the food allergen, plant allergen, fungal allergen, animal allergen, dust mite allergen, drug allergen, cosmetic allergen, or latex allergen.

In some embodiments, an antibody described herein is a full-length antibody, a Fab, a Fab', a F(ab')2, a Fab'-SH, an Fv, a single-chain antibody, or a single chain Fv (scFv) antibody. In some embodiments, an antibody described herein comprises an IgG4 constant region. In some embodiments, an antibody described herein is a monospecific antibody. In some embodiments, an antibody described herein is a multispecific antibody. In particular, an antibody described herein can be a bispecific antibody that binds to two different allergens. For example, in some embodiments, an antibody described herein can bind to a peanut allergen and a tree nut allergen. In some embodiments, an antibody described herein can bind to a peanut allergen and a milk allergen. In some embodiments, an antibody described herein can bind to a peanut allergen and a fungal allergen. In some embodiments, an antibody described herein can bind to a tree nut allergen and a milk allergen. In some embodiments, an antibody described herein can bind to a tree nut allergen and a fungal allergen. In some embodiments, an antibody described herein can bind to a milk allergen and a fungal allergen.

In some embodiments, the monoclonal antibody or antigen-binding portion thereof is an allergen-specific antibody that comprises a heavy chain variable region sequence and a light chain variable region sequence that are identified according to a process comprising:
(a) isolating single B cells from a sample from a human subject, wherein the subject is allergic to the allergen;
(b) generating cDNAs from the single B cells of step (a), wherein the cDNA sequences comprise a first sequence that encodes all or part of an immunoglobulin heavy chain and a second sequence that encodes all or part of an immunoglobulin light chain;
(c) determining the sequences of the cDNAs from step (b);
(d) analyzing the sequences determined in step (c) to identify single B cells comprising a first sequence that comprises an IgE constant region or an IgG4 constant region;
(e) identifying, from the single B cells of step (d), (i) a heavy chain variable region sequence in the immunoglobulin heavy chain that comprises an IgE constant region or an IgG4 constant region, and (ii) a light chain variable region sequence in an immunoglobulin light chain that is co-expressed with the immunoglobulin heavy chain in the same single B cell.

In some embodiments, the heavy chain variable region and the light chain variable region are from a B cell comprising an immunoglobulin that comprises an IgE constant region. In some embodiments, the heavy chain variable region and the light chain variable region are from a B cell comprising an immunoglobulin that comprises an IgG4 constant region.

In some embodiments, the monoclonal antibody or antigen-binding portion thereof is an allergen-specific antibody that comprises:
(a) a heavy chain variable region sequence that is derived from an immunoglobulin heavy chain from an IgE- or IgG4-producing single B cell from a human subject who is allergic to the allergen;
(b) a heavy chain IgG constant region sequence;
(c) a light chain variable region sequence that is derived from an immunoglobulin light chain from the IgE- or IgG4-producing single B cell from a human subject;
(d) a light chain constant region sequence that is of the same class as the immunoglobulin light chain of (c).

In some embodiments, the monoclonal antibody comprises a heavy chain variable region sequence and a light chain variable region sequence that are derived from an IgE-producing human B cell. In some embodiments, the monoclonal antibody comprises a heavy chain variable region sequence and a light chain variable region sequence that are derived from an IgG4-producing human B cell.

Characteristics of Allergen-Specific Monoclonal Antibodies

In some embodiments, the monoclonal antibody is an antibody that specifically binds to a food allergen, a plant allergen, a fungal allergen, an animal allergen, a dust mite allergen, a drug allergen, a cosmetic allergen, or a latex allergen. In some embodiments, the monoclonal antibody is an antibody that specifically binds to a food allergen, such as a milk allergen, an egg allergen, a nut allergen, a fish allergen, a shellfish allergen, a soy allergen, a legume allergen, a seed allergen, or a wheat allergen. In some embodiments, the monoclonal antibody specifically binds to a peanut allergen. In some embodiments, the monoclonal antibody specifically binds to a milk allergen. In some embodiments, the monoclonal antibody specifically binds to an egg allergen.

In some embodiments, the monoclonal antibody specifically binds to the allergen (e.g., a food allergen, a plant allergen, a fungal allergen, an animal allergen, a dust mite allergen, a drug allergen, a cosmetic allergen, or a latex allergen) with a binding affinity ($K_D$) of less than 100 nM, less than 50 nM, less than 10 nM, less than 5 nM, less than 1 nM, less than 500 pM, less than 250 pM, less than 150 pM, less than 100 pM, less than 50 pM, less than 40 pM, less than 30 pM, less than 20 pM, less than about 10 pM, or less than 1 pM. In some embodiments, the antibody binds to the allergen with a binding affinity (KD) from 1 nM to 250 nM.

In some embodiments, the monoclonal antibody exhibits cross-reactivity with at least two different antigens (e.g., allergens), e.g., at least two food allergens, at least two plant allergens, at least two fungal allergens, at least two animal allergens, at least two dust mite allergens, at least two drug allergens, at least two cosmetic allergens, or at least two latex allergens. In some embodiments, the monoclonal antibody exhibits cross-reactivity with at least two milk allergens, at least two egg allergens, at least two nut allergens, at least two fish allergens, at least two shellfish allergens, at least two soy allergens, at least two legume allergens, at least two seed allergens, or at least two wheat allergens. It will be appreciated by a person of ordinary skill in the art that many different allergens, such as many plant food allergens, can be grouped within a small number of protein families. For example, more than half of all plant food allergens can be categorized into one of the following four structural protein families: the prolamin superfamily, the cupin superfamily, profilins, and Bet v-1-related proteins. It will also be appreciated by a person of ordinary skill in the art that for a particular type of allergen (e.g., a "peanut" allergen), there can be more than one peptide or protein that is an allergen. As a non-limiting example, there are 12 known peanut allergens. See, Mueller et al., *Curr Allergy Asthma Rep,* 2014, 14:429. In some embodiments, the monoclonal antibody exhibits cross-reactivity with two or more different antigens that are different types or classes of antigens. As a non-limiting example, in some embodiments, a monoclonal antibody exhibits cross-reactivity with an antigen that is a peanut allergen and an antigen that is a nut (e.g., tree nut) allergen.

In embodiments in which the monoclonal antibody exhibits cross-reactivity with at least two different antigens (e.g., allergens), in some embodiments the monoclonal antibody specifically binds to at least one of the allergens with a $K_D$ of less than 100 nM, less than 50 nM, less than 10 nM, less than 5 nM, less than 1 nM, less than 500 pM, less than 250 pM, less than 150 pM, less than 100 pM, less than 50 pM, less than 40 pM, less than 30 pM, less than 20 pM, less than about 10 pM, or less than 1 pM. In some embodiments, the monoclonal antibody specifically binds to the first antigen (e.g., first allergen) with a $K_D$ of less than 100 nM, less than 50 nM, less than 10 nM, less than 5 nM, less than 1 nM, less than 500 pM, less than 250 pM, less than 150 pM, less than 100 pM, less than 50 pM, less than 40 pM, less than 30 pM, less than 20 pM, less than about 10 pM, or less than 1 pM. In some embodiments, the monoclonal antibody specifically binds to the second antigen (e.g., second allergen) with a $K_D$ of less than 1 µM, less than 500 nM, less than 100 nM, less than 10 nM, or less than 1 nM.

Engineered Variations in Variable Regions

In some embodiments, the heavy chain variable region and/or the light chain variable region of the monoclonal antibody has an identical sequence to the heavy chain variable region and/or the light chain variable region encoded by the IgE-producing or IgG4-producing single B cell from the human subject having an allergy to the allergen. In some embodiments, the heavy chain variable region and/or the light chain variable region of the monoclonal antibody comprises one or more modifications, e.g., amino acid substitutions, deletions, or insertions.

As described in the Examples section below, the heavy chain variable region sequence and/or light chain variable region sequence of an antibody described herein (e.g., a peanut allergen-specific monoclonal antibody such as Clone PA13P1H08, Clone PA13P1E10, Clone PA12P3F10, Clone PA13P3G09, Clone PA12P3D08, Clone PA12P1C07, Clone PA15P1D12, Clone PA15P1D05, or a Clone PA13P1H08 variant) can be engineered to comprise one or more variations in the heavy chain variable region sequence and/or light chain variable region sequence. In some embodiments, the engineered variation(s) improves the binding affinity of the antibody for the allergen. In some embodiments, the engineered variation(s) improves the cross-reactivity of the antibody for a second allergen.

In some embodiments, the engineered variation is a variation in one or more CDRs, e.g., an amino acid substitution in a heavy chain CDR and/or a light chain CDR as described herein. In some embodiments, the engineered variation is a variation in one or more framework regions, e.g., an amino acid substitution in a heavy chain framework region and/or a light chain framework region. In some embodiments, the engineered variation is a reversion of a region of the heavy chain and/or light chain sequence to the inferred naïve sequence. Methods for determining an inferred naïve immunoglobulin sequence are described in the art. See, e.g., Magnani et al., *PLoS Negl Trop Dis,* 2017, 11:e0005655, doi:10.1371/journal.pntd.0005655.

In some embodiments, affinity maturation is used to engineer further mutations that enhance the binding affinity of the antibody for the allergen or enhance the cross-reactivity of the antibody for a second allergen. Methods for performing affinity maturation are known in the art. See, e.g., Renaut et al., *Methods Mol Biol,* 2012, 907:451-461.

Constant Regions and Isotype Switching

In some embodiments, the monoclonal antibody comprises a heavy chain variable region sequence and a light chain variable region sequence that are derived from an IgE-producing human B cell or from an IgG4-producing human B cell, and further comprises a kappa or lambda light chain constant region. In some embodiments, the light chain constant region (kappa or lambda) is from the same type of light chain (i.e., kappa or lambda) as the light chain variable region that was derived from the IgE-producing human B cell or from an IgG4-producing human B cell; as a non-limiting example, if an IgE-producing human B cell comprises a kappa light chain, then the monoclonal antibody that is produced comprises the light chain variable region from the IgE-producing B cell and further comprises a kappa light chain constant region.

In some embodiments, the monoclonal antibody comprises a heavy chain variable region sequence and a light chain variable region sequence that are derived from an IgE-producing human B cell or from an IgG4-producing human B cell, and further comprises a heavy chain constant region having an IgG isotype (e.g., IgG4), an IgA isotype (e.g., IgA1), an IgM isotype, an IgD isotype, or that is derived from an IgG, IgA, IgM, or IgD isotype (e.g., is a modified IgG4 constant region). It will be appreciated by a person of ordinary skill in the art that the different heavy chain isotypes (IgA, IgD, IgE, IgG, and IgM) have different effector functions that are mediated by the heavy chain constant region, and that for certain uses it may be desirable to have an antibody that has the effector function of a particular isotype (e.g., IgG).

In some embodiments, the monoclonal antibody comprises a native (i.e., wild-type) human IgG, IgA, IgM, or IgD constant region. In some embodiments, the monoclonal antibody comprises a native human IgG1 constant region, a native human IgG2 constant region, a native human IgG3 constant region, a native human IgG4 constant region, a native human IgA1 constant region, a native human IgA2 constant region, a native human IgM constant region, or a native human IgD constant region. In some embodiments, the monoclonal antibody comprises a heavy chain constant region that comprises one or more modifications. It will be appreciated by a person of ordinary skill in the art that modifications such as amino acid substitutions can be made at one or more residues within the heavy chain constant region that modulate effector function. In some embodiments, the modification reduces effector function, e.g., results in a reduced ability to induce certain biological functions upon binding to an Fc receptor expressed on an effector cell that mediates the effector function. In some embodiments, the modification (e.g., amino acid substitution) prevents in vivo Fab arm exchange, which can introduce undesirable effects and reduce the therapeutic efficacy of the antibody. See, e.g., Silva et al., *J Biol Chem*, 2015, 280:5462-5469.

In some embodiments, the monoclonal antibody comprises a native (i.e., wild-type) human IgM constant region, human IgD constant region, human IgG constant region that is derived from IgG1, IgG2, IgG3, or IgG4, or human IgA constant region that is derived from IgA1 or IgA2 and comprises one or more modifications that modulate effector function. In some embodiments the monoclonal antibody comprises a human IgM constant region, human IgD constant region, human IgG constant region that is derived from IgG1, IgG2, IgG3, or IgG4, or human IgA constant region that is derived from IgA1 or IgA2. In some embodiments, the monoclonal antibody comprises a native (i.e., wild-type) human IgM constant region, human IgD constant region, human IgG constant region that is derived from IgG1, IgG2, IgG3, or IgG4, or human IgA constant region that is derived from IgA1 or IgA2 and comprises one, two, three, four, five, six, seven, eight, nine, ten or more modifications (e.g., amino acid substitutions). In some embodiments the constant regions includes variations (e.g., one, two, three, four, five, six, seven, eight, nine, ten or more amino acid substitutions) that reduce effector function.

In some embodiments, a monoclonal antibody comprises CDR sequences, a heavy chain variable region, and/or a light chain variable region from an antibody from an IgE or IgG4 B cell as described herein (e.g., as disclosed in Table 1 below) and further comprises a heavy chain constant region and/or a light chain constant region that is heterologous to the antibody from the IgE or IgG4 B cell from which the CDR sequences and/or variable region sequences are derived. For example, in some embodiments, the monoclonal antibody comprises the CDR sequences and/or variable region sequences of an antibody from an IgE B cell, and further comprises a heavy chain constant region and a light chain constant region that is heterologous to the antibody from the IgE B cell (e.g., the heavy chain constant region and/or light chain constant region is a wild-type or modified IgG1, IgG2, IgG3, or IgG4 constant region, or the heavy chain constant region and/or light chain constant region comprises one or more modifications (e.g., amino acid substitutions) relative to the native constant region of the antibody from the IgE B cell).

Antibodies that Specifically Bind to Peanut and/or Tree Nut Allergens

In some embodiments, a monoclonal antibody or antigen-binding portion thereof as disclosed herein specifically binds to a peanut allergen and/or a tree nut allergen. In some embodiments, the monoclonal antibody specifically binds to a peanut allergen. In some embodiments, the monoclonal antibody specifically binds to a peanut allergen that is Ara h 1, Ara h 2, Ara h 3, or Ara h 6.

In some embodiments, the monoclonal antibody exhibits cross-reactivity with at least two peanut allergens. In some embodiments, the monoclonal antibody exhibits cross-reactivity with two or more of the peanut allergens Ara h 1, Ara h 2, Ara h 3, and Ara h 6. In some embodiments, the monoclonal antibody specifically binds to at least one of the peanut allergens with a $K_D$ of less than 100 nM, less than 50 nM, less than 10 nM, less than 5 nM, less than 1 nM, less than 500 pM, less than 250 pM, less than 150 pM, less than 100 pM, less than 50 pM, less than 40 pM, less than 30 pM, less than 20 pM, less than about 10 pM, or less than 1 pM. In some embodiments, the monoclonal antibody specifically binds to a first peanut allergen with a $K_D$ of less than 100 nM (e.g., less than 50 nM, less than 10 nM, less than 5 nM, or less than 1 nM) and specifically binds to a second peanut allergen with a $K_D$ of less than 1 μM (e.g., less than 500 nM, less than 100 nM, less than 10 nM, or less than 1 nM). In some embodiments, the monoclonal antibody specifically binds to Ara h 2 with a $K_D$ of less than 100 nM (e.g., less than 50 nM, less than 10 nM, less than 5 nM, or less than 1 nM) and specifically binds to Ara h 1, Ara h 3, or Ara h 6 with a $K_D$ of less than 1 μM (e.g., less than 500 nM, less than 100 nM, less than 10 nM, or less than 1 nM).

In some embodiments, the monoclonal antibody recognizes an epitope that comprises or consists of the amino acid motif DPYSPS (SEQ ID NO:704). In some embodiments, the monoclonal antibody recognizes an epitope that comprises or consists of the amino acid sequence DSYGRDPYSPS (SEQ ID NO:705), YSPSQDPYSPS (SEQ ID NO:706), or PDRRDPYSPS (SEQ ID NO:707).

In some embodiments, the monoclonal antibody or antigen-binding portion thereof specifically binds to a tree nut allergen. In some embodiments, the tree nut allergen is a cashew, pistachio, almond, pine nut, pecan, walnut, hazelnut, or macadamia nut allergen. In some embodiments, the monoclonal antibody exhibits cross-reactivity with at least two tree nut allergens. In some embodiments, the monoclonal antibody exhibits cross-reactivity with both cashew and pistachio allergens. In some embodiments, the monoclonal antibody exhibits cross-reactivity with both pecan and walnut allergens. In some embodiments, the monoclonal antibody exhibits cross-reactivity with two or more of pecan, walnut, hazelnut, and macadamia nut allergens. In some embodiments, the monoclonal antibody specifically binds to at least one of the tree nut allergens with a $K_D$ of less than 100 nM, less than 50 nM, less than 10 nM, less than 5 nM, less than 1 nM, less than 500 pM, less than 250 pM, less than 150 pM, less than 100 pM, less than 50 pM, less than 40 pM, less than 30 pM, less than 20 pM, less than about 10 pM, or less than 1 pM.

In some embodiments, the monoclonal antibody or antigen-binding portion thereof specifically binds to a peanut allergen and to a tree nut allergen. In some embodiments, the monoclonal antibody specifically binds to a peanut allergen and to one or more (e.g., 1, 2, 3, 4, or more) of a cashew, pistachio, almond, pine nut, pecan, walnut, hazelnut, or macadamia nut allergen.

Peanut-Specific Antibody Sequences

In some embodiments, a monoclonal antibody that specifically binds to a peanut allergen (e.g., that specifically binds to Ara h 1, Ara h 2, Ara h 3, or Ara h 6) comprises heavy chain CDRs and/or light chain CDRs that are disclosed in Table 1 below. In some embodiments, a monoclonal antibody that specifically binds to a peanut allergen comprises a light chain variable region sequence and/or a heavy chain variable region sequence that is disclosed in Table 1 below. In some embodiments, a monoclonal antibody that specifically binds to a peanut allergen comprises: a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity to a heavy chain variable region sequence disclosed in Table 1 and comprises a CDR1, a CDR2, and a CDR3 that is identical to the CDRs of that heavy chain variable region sequence, and a light chain variable region comprising an amino acid sequence that has at least 70% sequence identity (e.g., at least 75%, 80%, 85%, 90%, 91%, 92%, 93%, 94%, 95%, 96%, 97%, 98%, or 99% sequence identity to a light chain variable region sequence disclosed in Table 1 and comprises a CDR1, a CDR2, and a CDR3 that is identical to the CDRs of that light chain variable region sequence.

In some embodiments, a monoclonal antibody that specifically binds to a peanut allergen (e.g., that specifically binds to Ara h 1, Ara h 2, Ara h 3, or Ara h 6) comprises a light chain sequence, or a portion thereof, and/or a heavy chain sequence, or a portion thereof, derived from any of the following antibodies described herein: Clone PA13P1H08, Clone PA13P1E10, Clone PA12P3F10, Clone PA13P3G09, Clone PA12P3D08, Clone PA12P1C07, Clone PA15P1D12, Clone PA15P1D05, a variant of Clone PA13P1H08 (e.g., an R-R variant, an R-N variant, an N-R variant, an rCDR1-N variant, an rCDR2-N variant, an rCDR3-N variant, or an rFWRs-N variant of Clone PA13P1H08), Clone PA12P4D02, Clone PA12P3E09, Clone PA12P3E11, Clone PA12P1D02, Clone PA12P1G11, Clone PA13P1H03, Clone PA12P3C01, or Clone PA12P3E04. The amino acid sequences of the CDR, light chain variable domain (VL), and heavy chain variable domain (VH) of Clone PA13P1H08, Clone PA13P1E10, Clone PA12P3F10, Clone PA13P3G09, Clone PA12P3D08, Clone PA12P1C07, Clone PA15P1D12, Clone PA15P1D05, Clone PA13P1H08 variants, Clone PA12P4D02, Clone PA12P3E09, Clone PA12P3E11, Clone PA12P1D02, Clone PA12P1G11, Clone PA13P1H03, Clone PA12P3C01, and Clone PA12P3E04 are set forth in Table 1 below.

In some embodiments, a monoclonal antibody that specifically binds to a peanut allergen comprises one or more (e.g., one, two, three, four, five, or all six) of:
(a) a heavy chain CDR1 comprising the amino acid sequence of any one of SEQ ID NOs:2, 10, 17, 25, 33, 41, 47, 58, 113, 129, 199, 341, 348, 409, 459, or 593;
(b) a heavy chain CDR2 comprising the amino acid sequence of any one of SEQ ID NOs:3, 11, 18, 26, 34, 48, 59, 130, 200, 342, 349, 410, 460, 539, or 594;
(c) a heavy chain CDR3 comprising the amino acid sequence of any one of SEQ ID NOs:4, 12, 19, 27, 35, 42, 49, 55, 60, 131, 201, 350, 411, 461, 540, or 595;
(d) a light chain CDR1 comprising the amino acid sequence of any one of SEQ ID NOs:6, 14, 21, 29, 37, 44, 51, 62, 133, 203, 343, 352, 413, 463, 542, or 597;
(e) a light chain CDR2 comprising the amino acid sequence of any one of SEQ ID NOs:7, 15, 22, 30, 38, 52, 78, 86, 126, 149, 196, 345, 353, or 598; and
(f) a light chain CDR3 comprising the amino acid sequence of any one of SEQ ID NOs:8, 23, 31, 39, 45, 53, 63, 134, 204, 346, 354, 414, 464, 543, or 599.

In some embodiments, a monoclonal antibody that specifically binds to a peanut allergen comprises a heavy chain CDR1-3 and a light chain CDR1-3 comprising the amino acid sequences of:
(a) SEQ ID NOs: 2, 3, 4, 6, 7, and 8, respectively; or
(b) SEQ ID NOs: 10, 11, 12, 14, 15, and 8, respectively; or
(c) SEQ ID NOs: 17, 18, 19, 21, 22, and 23, respectively; or
(d) SEQ ID NOs: 25, 26, 27, 29, 30, and 31, respectively; or
(e) SEQ ID NOs: 33, 34, 35, 37, 38, and 39, respectively; or
(f) SEQ ID NOs: 41, 34, 35, 37, 38, and 39, respectively; or
(g) SEQ ID NOs: 47, 48, 49, 51, 52, and 53, respectively; or
(h) SEQ ID NOs: 47, 48, 55, 51, 52, and 53, respectively; or
(i) SEQ ID NOs: 58, 59, 60, 62, 30, and 63, respectively; or
(j) SEQ ID NOs: 58, 59, 60, 6, 7, and 8, respectively; or
(k) SEQ ID NOs: 2, 3, 4, 62, 30, and 63, respectively; or
(l) SEQ ID NOs: 58, 3, 4, 6, 7, and 8, respectively; or
(m) SEQ ID NOs: 2, 59, 4, 6, 7, and 8, respectively; or
(n) SEQ ID NOs: 2, 3, 60, 6, 7, and 8, respectively; or
(o) SEQ ID NOs:129, 130, 131, 133, 126, and 134, respectively; or
(p) SEQ ID NOs:341, 342, 343, 345, 78, and 346, respectively; or
(q) SEQ ID NOs:348, 349, 350, 352, 353, and 354, respectively; or
(r) SEQ ID NOs:199, 200, 201, 203, 149, and 204, respectively; or
(s) SEQ ID NOs:409, 410, 411, 413, 86, and 414, respectively; or
(t) SEQ ID NOs:459, 460, 461, 463, 196, and 464, respectively; or
(u) SEQ ID NOs:113, 539, 540, 542, 196, and 543, respectively; or
(v) SEQ ID NOs:593, 594, 595, 597, 598, and 599, respectively.

In some embodiments, a monoclonal antibody that specifically binds to a peanut allergen comprises a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity) to any one of SEQ ID NOs:1, 9, 16, 24, 32, 40, 46, 54, 57, 64, 65, 66, 67, 128, 340, 347, 406, 408, 458, 538, or 592. In some embodiments, a monoclonal antibody that specifically binds to a peanut allergen comprises a light chain variable region comprising an amino acid sequence that has at least 75% sequence identity (e.g., at least 75%, 80%, 85%, 90%, 91%, 92%, 93%, 94%, 95%, 96%, 97%, 98%, or 99% sequence identity) to any one of SEQ ID NOs:5, 13, 20, 28, 36, 43, 50, 56, 61, 132, 344, 351, 407, 412, 462, 541, or 596. In some embodiments, a monoclonal antibody that specifically binds to a peanut allergen comprises a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity) to any one of SEQ ID NOs:1, 9, 16, 24, 32, 40, 46, 54, 57, 64, 65, 66, 67, 128, 340, 347, 406, 408, 458, 538, or 592, and comprises a light chain variable region comprising an amino acid sequence that has at least 75% sequence identity (e.g., at least 80%, 85%, 90%, 91%, 92%, 93%, 94%, 95%, 96%, 97%, 98%, or 99% sequence identity) to any one of SEQ ID NOs: 5, 13, 20, 28, 36, 43, 50, 56, 61, 132, 344, 351, 407, 412, 462, 541, or 596.

In some embodiments, a monoclonal antibody that specifically binds to a peanut allergen comprises a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity) to any one of SEQ ID NOs: 1, 9, 16, 24, 32, 40, 46, 54, 57, 64, 65, 66, 67, 128, 340, 347, 406, 408, 458, 538, or 592 and comprises a CDR1, a CDR2, and a CDR3 that is identical to the CDRs of that SEQ ID NO. In some embodiments, a monoclonal antibody that specifically binds to a peanut allergen comprises a light chain variable region comprising an amino acid sequence that has at least 70% sequence identity (e.g., at least 75%, 80%, 85%, 90%, 91%, 92%, 93%, 94%, 95%, 96%, 97%, 98%, or 99% sequence identity) to any one of SEQ ID NOs: 5, 13, 20, 28, 36, 43, 50, 56, 61, 132, 344, 351, 407, 412, 462, 541, or 596 and comprises a CDR1, a CDR2, and a CDR3 that is identical to the CDRs of that SEQ ID NO. In some embodiments, a monoclonal antibody that specifically binds to a peanut allergen comprises:

(a) a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity) to any one of SEQ ID NOs: 1, 9, 16, 24, 32, 40, 46, 54, 57, 64, 65, 66, 67, 128, 340, 347, 406, 408, 458, 538, or 592 and that comprises a CDR1, a CDR2, and a CDR3 that is identical to the CDRs of that SEQ ID NO; and (b) a light chain variable region comprising an amino acid sequence that has at least 75% sequence identity (e.g., at least 80%, 85%, 90%, 91%, 92%, 93%, 94%, 95%, 96%, 97%, 98%, or 99% sequence identity) to any one of SEQ ID NOs: 5, 13, 20, 28, 36, 43, 50, 56, 61, 132, 344, 351, 407, 412, 462, 541, or 596 and that comprises a CDR1, a CDR2, and a CDR3 that is identical to the CDRs of that SEQ ID NO.

Clone PA13P1H08

In some embodiments, a monoclonal antibody that specifically binds to a peanut allergen comprises a heavy chain CDR1 comprising the amino acid sequence of SEQ ID NO:2, a heavy chain CDR2 comprising the amino acid sequence of SEQ ID NO:3, a heavy chain CDR3 comprising the amino acid sequence of SEQ ID NO:4, a light chain CDR1 comprising the amino acid sequence of SEQ ID NO:6, a light chain CDR2 comprising the amino acid sequence of SEQ ID NO:7, and a light chain CDR3 comprising the amino acid sequence of SEQ ID NO:8.

In some embodiments, the antibody comprises:

(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:1, and that comprises a heavy chain CDR1, CDR2, and CDR3 comprising the amino acid sequences of SEQ ID NOs:2, 3, and 4, respectively; and (b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:5, and that comprises the light chain CDR1, CDR2, and CDR3 comprising the amino acid sequences of SEQ ID NOs:6, 7, and 8, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:1, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:5. In some embodiments, the antibody comprises a heavy chain variable region comprising the amino acid sequence of SEQ ID NO:1 and comprises a light chain variable region comprising the amino acid sequence of SEQ ID NO:5.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:2, 3, 4, 6, 7, and 8, respectively, or an antibody comprising a heavy chain variable region comprising the amino acid sequence of SEQ ID NO:1 and further comprising a light chain variable region comprising the amino acid sequence of SEQ ID NO:5).

Clone PA13P1E10

In some embodiments, a monoclonal antibody that specifically binds to a peanut allergen comprises a heavy chain CDR1 comprising the amino acid sequence of SEQ ID NO:10, a heavy chain CDR2 comprising the amino acid sequence of SEQ ID NO:11, a heavy chain CDR3 comprising the amino acid sequence of SEQ ID NO:12, a light chain CDR1 comprising the amino acid sequence of SEQ ID NO:14, a light chain CDR2 comprising the amino acid sequence of SEQ ID NO:15, and a light chain CDR3 comprising the amino acid sequence of SEQ ID NO:8.

In some embodiments, the antibody comprises:

(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:9, and that comprises a heavy chain CDR1, CDR2, and CDR3 comprising the amino acid sequences of SEQ ID NOs:10, 11, and 12, respectively; and (b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:13, and that comprises the light chain CDR1, CDR2, and CDR3 comprising the amino acid sequences of SEQ ID NOs:14, 15, and 8, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:9, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:13. In some embodiments, the antibody comprises a heavy chain variable region comprising the amino acid sequence of SEQ ID NO:9 and comprises a light chain variable region comprising the amino acid sequence of SEQ ID NO:13.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:10, 11, 12, 14, 15, and 8 respectively, or an antibody comprising a heavy chain variable region comprising the amino acid sequence of SEQ ID NO:9 and further comprising a light chain variable region comprising the amino acid sequence of SEQ ID NO:13).

Clone PA12P3F10

In some embodiments, a monoclonal antibody that specifically binds to a peanut allergen comprises a heavy chain CDR1 comprising the amino acid sequence of SEQ ID NO:17, a heavy chain CDR2 comprising the amino acid sequence of SEQ ID NO:18, a heavy chain CDR3 comprising the amino acid sequence of SEQ ID NO:19, a light chain CDR1 comprising the amino acid sequence of SEQ ID NO:21, a light chain CDR2 comprising the amino acid sequence of SEQ ID NO:22, and a light chain CDR3 comprising the amino acid sequence of SEQ ID NO:23.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:16, and that comprises a heavy chain CDR1, CDR2, and CDR3 comprising the amino acid sequences of SEQ ID NOs:17, 18, and 19, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:20, and that comprises the light chain CDR1, CDR2, and CDR3 comprising the amino acid sequences of SEQ ID NOs:21, 22, and 23, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:16, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:20. In some embodiments, the antibody comprises a heavy chain variable region comprising the amino acid sequence of SEQ ID NO:16 and comprises a light chain variable region comprising the amino acid sequence of SEQ ID NO:20.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:17, 18, 19, 21, 22, and 23, respectively, or an antibody comprising a heavy chain variable region comprising the amino acid sequence of SEQ ID NO:16 and further comprising a light chain variable region comprising the amino acid sequence of SEQ ID NO:20).

Clone PA13P3G09

In some embodiments, a monoclonal antibody that specifically binds to a peanut allergen comprises a heavy chain CDR1 comprising the amino acid sequence of SEQ ID NO:25, a heavy chain CDR2 comprising the amino acid sequence of SEQ ID NO:26, a heavy chain CDR3 comprising the amino acid sequence of SEQ ID NO:27, a light chain CDR1 comprising the amino acid sequence of SEQ ID NO:29, a light chain CDR2 comprising the amino acid sequence of SEQ ID NO:30, and a light chain CDR3 comprising the amino acid sequence of SEQ ID NO:31.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:24, and that comprises a heavy chain CDR1, CDR2, and CDR3 comprising the amino acid sequences of SEQ ID NOs:25, 26, and 27, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:28, and that comprises the light chain CDR1, CDR2, and CDR3 comprising the amino acid sequences of SEQ ID NOs:29, 30, and 31, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:24, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:28. In some embodiments, the antibody comprises a heavy chain variable region comprising the amino acid sequence of SEQ ID NO:24 and comprises a light chain variable region comprising the amino acid sequence of SEQ ID NO:28.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:25, 26, 27, 29, 30, and 31, respectively, or an antibody comprising a heavy chain variable region comprising the amino acid sequence of SEQ ID NO:24 and further comprising a light chain variable region comprising the amino acid sequence of SEQ ID NO:28).

Clone PA12P3D08

In some embodiments, a monoclonal antibody that specifically binds to a peanut allergen comprises a heavy chain CDR1 comprising the amino acid sequence of SEQ ID NO:33, a heavy chain CDR2 comprising the amino acid sequence of SEQ ID NO:34, a heavy chain CDR3 comprising the amino acid sequence of SEQ ID NO:35, a light chain CDR1 comprising the amino acid sequence of SEQ ID NO:37, a light chain CDR2 comprising the amino acid sequence of SEQ ID NO:38, and a light chain CDR3 comprising the amino acid sequence of SEQ ID NO:39.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:32, and that comprises a heavy chain CDR1, CDR2, and CDR3 comprising the amino acid sequences of SEQ ID NOs:33, 34, and 35, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:36, and that comprises the light chain CDR1, CDR2, and CDR3 comprising the amino acid sequences of SEQ ID NOs:37, 38, and 39, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:32, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:36. In some embodiments, the antibody comprises a heavy chain variable region comprising the amino acid sequence of SEQ ID NO:32 and comprises a light chain variable region comprising the amino acid sequence of SEQ ID NO:36.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:33, 34, 35, 37, 38, and 39, respectively, or an antibody comprising a heavy chain variable region comprising the amino acid sequence of SEQ ID NO:32 and further comprising a light chain variable region comprising the amino acid sequence of SEQ ID NO:36).

Clone PA12P1C07

In some embodiments, a monoclonal antibody that specifically binds to a peanut allergen comprises a heavy chain CDR1 comprising the amino acid sequence of SEQ ID NO:41, a heavy chain CDR2 comprising the amino acid sequence of SEQ ID NO:34, a heavy chain CDR3 comprising the amino acid sequence of SEQ ID NO:42, a light chain CDR1 comprising the amino acid sequence of SEQ ID NO:44, a light chain CDR2 comprising the amino acid sequence of SEQ ID NO:30, and a light chain CDR3 comprising the amino acid sequence of SEQ ID NO:45.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:40, and that comprises a heavy chain CDR1, CDR2, and CDR3 comprising the amino acid sequences of SEQ ID NOs:41, 34, and 42, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:43, and that comprises the light chain CDR1, CDR2, and CDR3 comprising the amino acid sequences of SEQ ID NOs:44, 30, and 45, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:40, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:43. In some embodiments, the antibody comprises a heavy chain variable region comprising the amino acid sequence of SEQ ID NO:40 and comprises a light chain variable region comprising the amino acid sequence of SEQ ID NO:43.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:41, 34, 42, 44, 30, and 45, respectively, or an antibody comprising a heavy chain variable region comprising the amino acid sequence of SEQ ID NO:40 and further comprising a light chain variable region comprising the amino acid sequence of SEQ ID NO:43).

Clone PA15P1D12

In some embodiments, a monoclonal antibody that specifically binds to a peanut allergen comprises a heavy chain CDR1 comprising the amino acid sequence of SEQ ID NO:47, a heavy chain CDR2 comprising the amino acid sequence of SEQ ID NO:48, a heavy chain CDR3 comprising the amino acid sequence of SEQ ID NO:49, a light chain CDR1 comprising the amino acid sequence of SEQ ID NO:51, a light chain CDR2 comprising the amino acid sequence of SEQ ID NO:52, and a light chain CDR3 comprising the amino acid sequence of SEQ ID NO:53.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:46, and that comprises a heavy chain CDR1, CDR2, and CDR3 comprising the amino acid sequences of SEQ ID NOs:47, 48, and 49, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:50, and that comprises the light chain CDR1, CDR2, and CDR3 comprising the amino acid sequences of SEQ ID NOs:51, 52, and 53, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:46, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:50. In some embodiments, the antibody comprises a heavy chain variable region comprising the amino acid sequence of SEQ ID NO:46 and comprises a light chain variable region comprising the amino acid sequence of SEQ ID NO:50.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:41, 34, 42, 44, 30, and 45, respectively, or an antibody comprising a heavy chain variable region comprising the amino acid sequence of SEQ ID NO:46 and further comprising a light chain variable region comprising the amino acid sequence of SEQ ID NO:50).

Clone PA15P1D05

In some embodiments, a monoclonal antibody that specifically binds to a peanut allergen comprises a heavy chain CDR1 comprising the amino acid sequence of SEQ ID NO:47, a heavy chain CDR2 comprising the amino acid sequence of SEQ ID NO:48, a heavy chain CDR3 comprising the amino acid sequence of SEQ ID NO:55, a light chain CDR1 comprising the amino acid sequence of SEQ ID NO:51, a light chain CDR2 comprising the amino acid sequence of SEQ ID NO:52, and a light chain CDR3 comprising the amino acid sequence of SEQ ID NO:53.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:54, and that comprises a heavy chain CDR1, CDR2, and CDR3 comprising the amino acid sequences of SEQ ID NOs:47, 48, and 55, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:56, and that comprises the light chain CDR1, CDR2, and CDR3 comprising the amino acid sequences of SEQ ID NOs:51, 52, and 53, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:54, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:56. In some embodiments, the antibody comprises a heavy chain variable region comprising the amino acid sequence of SEQ ID NO:54 and comprises a light chain variable region comprising the amino acid sequence of SEQ ID NO:56.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:47, 48, 55, 51, 52, and 53, respectively, or an antibody comprising a heavy chain variable region comprising the amino acid sequence of SEQ ID NO:54 and further comprising a light chain variable region comprising the amino acid sequence of SEQ ID NO:56).

Variant Sequences

In some embodiments, the allergen-specific monoclonal antibody comprises one or more variations (e.g., amino acid substitutions) in one or more CDR, heavy chain, and/or light chain sequences as disclosed herein (e.g., one or more mutations in one or more CDR, heavy chain, and/or light chain sequences of Clone PA13P1H08, Clone PA13P1E10, Clone PA12P3F10, Clone PA13P3G09, Clone PA12P3D08, Clone PA12P1C07, Clone PA15P1D12, Clone PA15P1D05). In some embodiments, one or more substitutions are made in a CDR, heavy chain, or light chain sequence of Clone PA13P1H08. As described in the Examples section below, variants were made of Clone PA13P1H08, in which one or more regions in the heavy chain and/or light chain were reverted to the inferred naïve rearrangement. It was found that antibody sequences comprising a naïve light chain or heavy chain sequence were capable of binding to the peanut allergen Ara h 2. It was also surprisingly found that a variant of Clone PA13P1H08 comprising a reverted CDR-H2 sequence exhibited significantly improved cross-reactivity to a second peanut allergen (Ara h 3) in addition to having sub-nanomolar affinity for the Ara h 2 peanut allergen. Thus, in some embodiments, the mutation is an amino acid substitution that reverts at least a portion of the sequence of the clone from its "native" form (i.e., the CDR, heavy chain variable region, or light chain variable region sequence of the clone as disclosed in Table 1) to the inferred naïve immunoglobulin sequence.

In some embodiments, an allergen-specific monoclonal antibody comprises one or more variant sequences of a Clone PA13P1H08 variant as disclosed herein. In some embodiments, the antibody comprises one of the sequences of Clone PA13P1H08 variant "R-R," in which both the heavy chain variable region and the light chain variable region of Clone PA13P1H08 are reverted back to the inferred naïve rearrangement. In some embodiments, the antibody comprises a reverted heavy chain variable region sequence comprising SEQ ID NO:57. In some embodiments, the antibody comprises a reverted light chain variable region sequence comprising SEQ ID NO:61.

In some embodiments, the antibody comprises one of the sequences of Clone PA13P1H08 variant "R-N," in which the heavy chain variable region of Clone PA13P1H08 is reverted back to the inferred naïve rearrangement and the light chain variable region retains the native sequence of Clone PA13P1H08 (i.e., SEQ ID NO:5). In some embodiments, the antibody comprises one of the sequences of Clone PA13P1H08 variant "N-R," in which the heavy chain variable region retains the native sequence of Clone PA13P1H08 (i.e., SEQ ID NO:1), and the light chain variable region is reverted back to the inferred naïve rearrangement of Clone PA13P1H08.

In some embodiments, the antibody comprises one or more reverted CDR sequences, e.g., one or more reverted heavy chain CDR sequences, and/or one or more reverted light chain CDR sequences. In some embodiments, the antibody comprises one or more of a reverted CDR-H1 comprising SEQ ID NO:58, a reverted CDR-H2 comprising SEQ ID NO:59, or a reverted CDR-H3 comprising SEQ ID NO:60. In some embodiments, the antibody comprises one or more of a reverted CDR-L1 comprising SEQ ID NO:62, a reverted CDR-L2 comprising SEQ ID NO:30, or a reverted CDR-L3 comprising SEQ ID NO:63. In some embodiments, the antibody comprises one or more reverted framework regions, e.g., the heavy chain variable region comprising reverted framework regions of SEQ ID NO:67.

In some embodiments, a monoclonal antibody that specifically binds to a peanut allergen comprises a heavy chain CDR1 comprising the amino acid sequence of SEQ ID NO:2 or SEQ ID NO:58, a heavy chain CDR2 comprising the amino acid sequence of SEQ ID NO:3 or SEQ ID NO:59, a heavy chain CDR3 comprising the amino acid sequence of SEQ ID NO:4 or SEQ ID NO:60, a light chain CDR1 comprising the amino acid sequence of SEQ ID NO:6 or SEQ ID NO:62, a light chain CDR2 comprising the amino acid sequence of SEQ ID NO:7 or SEQ ID NO:30, and a light chain CDR3 comprising the amino acid sequence of SEQ ID NO:8 or SEQ ID NO:63.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:1, SEQ ID NO:57, SEQ ID NO:64, SEQ ID NO:65, SEQ ID NO:66, or SEQ ID NO:67, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:5 or SEQ ID NO:61. In some embodiments, the antibody comprises a heavy chain variable region comprising the amino acid sequence of SEQ ID NO:57 and comprises a light chain variable region comprising the amino acid sequence of SEQ ID NO:61. In some embodiments, the antibody comprises a heavy chain variable region comprising the amino acid sequence of SEQ ID NO:57 and comprises a light chain variable region comprising the amino acid sequence of SEQ ID NO:5. In some embodiments, the antibody comprises a heavy chain variable region comprising the amino acid sequence of SEQ ID NO:1 and comprises a light chain variable region comprising the amino acid sequence of SEQ ID NO:61. In some embodiments, the antibody comprises a heavy chain variable region comprising the amino acid sequence of SEQ ID NO:64 and comprises a light chain variable region comprising the amino acid sequence of SEQ ID NO:5. In some embodiments, the antibody comprises a heavy chain variable region comprising the amino acid sequence of SEQ ID NO:65 and comprises a light chain variable region comprising the amino acid sequence of SEQ ID NO:5. In some embodiments, the antibody comprises a heavy chain variable region comprising the amino acid sequence of SEQ ID NO:66 and comprises a light chain variable region comprising the amino acid sequence of SEQ ID NO:5. In some embodiments, the antibody comprises a heavy chain variable region comprising the amino acid sequence of SEQ ID NO:67 and comprises a light chain variable region comprising the amino acid sequence of SEQ ID NO:5.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:65, and that comprises a heavy chain CDR1, CDR2, and CDR3 comprising the amino acid sequences of SEQ ID NOs:2, 59, and 4, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:5, and that comprises the light chain CDR1, CDR2, and CDR3 comprising the amino acid sequences of SEQ ID NOs:6, 7, and 8, respectively.

Tree Nut-Specific Antibody Sequences

In some embodiments, a monoclonal antibody that specifically binds to a tree nut allergen (e.g., that specifically binds to a cashew, pistachio, almond, pine nut, pecan, walnut, hazelnut, or macadamia nut allergen) comprises heavy chain CDRs and/or light chain CDRs that are disclosed in Table 1 below. In some embodiments, a monoclonal antibody that specifically binds to a tree nut allergen comprises a light chain variable region sequence and/or a heavy chain variable region sequence that is disclosed in Table 1 below. In some embodiments, a monoclonal antibody that specifically binds to a tree nut allergen comprises: a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity to a heavy chain variable region sequence disclosed in Table 1 and comprises a CDR1, a CDR2, and a CDR3 that is identical to the CDRs of that heavy chain variable region sequence, and a light chain variable region comprising an amino acid sequence that has at least 70% sequence identity (e.g., at least 75%, 80%, 85%, 90%, 91%, 92%, 93%, 94%, 95%, 96%, 97%, 98%, or 99% sequence identity to a light chain variable region sequence disclosed in Table 1 and comprises a CDR1, a CDR2, and a CDR3 that is identical to the CDRs of that light chain variable region sequence.

In some embodiments, a monoclonal antibody that specifically binds to a tree nut allergen comprises a light chain sequence, or a portion thereof, and/or a heavy chain sequence, or a portion thereof, derived from any of the following antibodies described herein: Clone PA14P3H08, Clone PA11P1D11, Clone PA11P1G10, Clone PA12P4D02, Clone PA11P1D12, Clone PA11P1F03, Clone PA11P1C04, Clone PA11P1G04, Clone PA11P1E01, Clone PA11P1C11, or Clone PA11P1CO3. The amino acid sequences of the CDR, light chain variable domain (VL), and heavy chain variable domain (VH) of Clone PA14P3H08, Clone PA11P1D11, Clone PA11P1G10, Clone PA12P4D02, Clone PA11P1D12, Clone PA11P1F03, Clone PA11P1C04, Clone PA11P1G04, Clone PA11P1E01, Clone PA11P1C11, and Clone PA11P1CO3 are set forth in Table 1 below.

In some embodiments, a monoclonal antibody that specifically binds to a tree nut allergen comprises one or more (e.g., one, two, three, four, five, or all six) of:
(a) a heavy chain CDR1 comprising the amino acid sequence of any one of SEQ ID NOs: 113, 167, 175, 227, 311, 318, 438, 466, 621, 665, or 692;
(b) a heavy chain CDR2 comprising the amino acid sequence of any one of SEQ ID NOs: 168, 176, 200, 312, 319, 439, 539, 666, or 693;
(c) a heavy chain CDR3 comprising the amino acid sequence of any one of SEQ ID NOs: 169, 177, 228, 313, 320, 440, 467, 540, 667, or 694;
(d) a light chain CDR1 comprising the amino acid sequence of any one of SEQ ID NOs: 171, 179, 230, 315, 322, 442, 469, 542, 623, 669, or 696;
(e) a light chain CDR2 comprising the amino acid sequence of any one of SEQ ID NOs: 30, 94, 149, 172, 180, 196, 323, or 670; and
(f) a light chain CDR3 comprising the amino acid sequence of any one of SEQ ID NOs: 173, 181, 231, 316, 324, 443, 470, 543, 624, 671, or 697.

In some embodiments, a monoclonal antibody that specifically binds to a tree nut allergen comprises a heavy chain variable region comprising an amino acid sequence that comprises the sequence of, or has at least 75% sequence identity (e.g., at least 80%, 85%, 90%, 91%, 92%, 93%, 94%, 95%, 96%, 97%, 98%, or 99% sequence identity) to, any one of SEQ ID NOs:166, 174, 226, 310, 317, 437, 465, 538, 620, 664, or 691. In some embodiments, a monoclonal antibody that specifically binds to a peanut allergen comprises a light chain variable region comprising an amino acid sequence that comprises the sequence of, or has at least 75% sequence identity (e.g., at least 75%, 80%, 85%, 90%, 91%, 92%, 93%, 94%, 95%, 96%, 97%, 98%, or 99% sequence identity) to, any one of SEQ ID NOs:170, 178, 229, 314, 321, 441, 468, 541, 622, 668, or 695. In some embodiments, a monoclonal antibody that specifically binds to a peanut allergen comprises a heavy chain variable region comprising an amino acid sequence that comprises the sequence of, or has at least 75% sequence identity (e.g., at least 80%, 85%, 90%, 91%, 92%, 93%, 94%, 95%, 96%, 97%, 98%, or 99% sequence identity to, any one of SEQ ID NOs:166, 174, 226, 310, 317, 437, 465, 538, 620, 664, or 691, and comprises a light chain variable region comprising an amino acid sequence that comprises the sequence of, or has at least 75% sequence identity (e.g., at least 80%, 85%, 90%, 91%, 92%, 93%, 94%, 95%, 96%, 97%, 98%, or 99% sequence identity) to, any one of SEQ ID NOs:170, 178, 229, 314, 321, 441, 468, 541, 622, 668, or 695.

In some embodiments, a monoclonal antibody that specifically binds to a tree nut allergen comprises:
(a) a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity) to any one of SEQ ID NOs:166, 174, 226, 310, 317, 437, 465, 538, 620, 664, or 691 and that comprises a CDR1, a CDR2, and a CDR3 that is identical to the CDRs of that SEQ ID NO; and
(b) a light chain variable region comprising an amino acid sequence that has at least 75% sequence identity (e.g., at least 80%, 85%, 90%, 91%, 92%, 93%, 94%, 95%, 96%, 97%, 98%, or 99% sequence identity) to any one of SEQ ID NOs:170, 178, 229, 314, 321, 441, 468, 541, 622, 668, or 695 and that comprises a CDR1, a CDR2, and a CDR3 that is identical to the CDRs of that SEQ ID NO.

In some embodiments, the monoclonal antibody specifically binds to a pecan, walnut, hazelnut, and/or macadamia nut allergen and comprises one or more (e.g., one, two, three, four, five, or all six) of:
(a) a heavy chain CDR1 comprising the amino acid sequence of any one of SEQ ID NOs: 113, 227, 311, 318, 665, or 692;
(b) a heavy chain CDR2 comprising the amino acid sequence of any one of SEQ ID NOs: 200, 312, 319, 539, 666, or 693;
(c) a heavy chain CDR3 comprising the amino acid sequence of any one of SEQ ID NOs: 228, 313, 320, 540, 667, or 694;
(d) a light chain CDR1 comprising the amino acid sequence of any one of SEQ ID NOs: 230, 315, 322, 542, 669, or 696;
(e) a light chain CDR2 comprising the amino acid sequence of any one of SEQ ID NOs: 94, 149, 196, 323, or 670; and
(f) a light chain CDR3 comprising the amino acid sequence of any one of SEQ ID NOs: 231, 316, 324, 543, 671, or 697.

In some embodiments, a monoclonal antibody that specifically binds to a pecan, walnut, hazelnut, and/or macadamia nut allergen comprises a heavy chain variable region comprising an amino acid sequence that comprises the sequence of, or has at least 75% sequence identity (e.g., at least 80%, 85%, 90%, 91%, 92%, 93%, 94%, 95%, 96%, 97%, 98%, or 99% sequence identity) to any one of SEQ ID NOs: 226, 310, 317, 538, 664, or 691. In some embodiments, a monoclonal antibody that specifically binds to a pecan, walnut, hazelnut, and/or macadamia nut allergen comprises a light chain variable region comprising an amino acid sequence that comprises the sequence of, or has at least 75% sequence identity (e.g., at least 75%, 80%, 85%, 90%, 91%, 92%, 93%, 94%, 95%, 96%, 97%, 98%, or 99% sequence identity) to, any one of SEQ ID NOs: 229, 314, 321, 541, 668, or 695. In some embodiments, a monoclonal antibody that specifically binds to a pecan, walnut, hazelnut, and/or macadamia nut allergen comprises a heavy chain variable region comprising an amino acid sequence that comprises the sequence of, or has at least 75% sequence identity (e.g., at least 80%, 85%, 90%, 91%, 92%, 93%, 94%, 95%, 96%, 97%, 98%, or 99% sequence identity to, any one of SEQ ID NOs: 226, 310, 317, 437, 538, 664, or 691, and comprises a light chain variable region comprising an amino acid sequence that comprises the sequence of, or has at least 75% sequence identity (e.g., at least 80%, 85%, 90%, 91%, 92%, 93%, 94%, 95%, 96%, 97%, 98%, or 99% sequence identity) to, any one of SEQ ID NOs: 229, 314, 321, 541, 668, or 695.

In some embodiments, the monoclonal antibody specifically binds to a cashew and/or pistachio allergen and comprises one or more (e.g., one, two, three, four, five, or all six) of:
(a) a heavy chain CDR1 comprising the amino acid sequence of any one of SEQ ID NOs: 167, 175, 227, 438, 466, or 621;
(b) a heavy chain CDR2 comprising the amino acid sequence of any one of SEQ ID NOs: 168, 176, 200, or 439;
(c) a heavy chain CDR3 comprising the amino acid sequence of any one of SEQ ID NOs: 169, 177, 440, or 467;
(d) a light chain CDR1 comprising the amino acid sequence of any one of SEQ ID NOs: 171, 179, 442, 469, or 623;
(e) a light chain CDR2 comprising the amino acid sequence of any one of SEQ ID NOs: 30, 149, 172, or 180; and
(f) a light chain CDR3 comprising the amino acid sequence of any one of SEQ ID NOs: 173, 181, 443, 470, or 624.

In some embodiments, a monoclonal antibody that specifically binds to a cashew and/or pistachio allergen comprises a heavy chain variable region comprising an amino acid sequence that comprises the sequence of, or has at least 75% sequence identity (e.g., at least 80%, 85%, 90%, 91%, 92%, 93%, 94%, 95%, 96%, 97%, 98%, or 99% sequence identity) to, any one of SEQ ID NOs:166, 174, 437, 465, or 620. In some embodiments, a monoclonal antibody that specifically binds to a cashew and/or pistachio allergen comprises a light chain variable region comprising an amino acid sequence that comprises the sequence of, or has at least 75% sequence identity (e.g., at least 75%, 80%, 85%, 90%, 91%, 92%, 93%, 94%, 95%, 96%, 97%, 98%, or 99% sequence identity) to, any one of SEQ ID NOs:170, 178, 441, 468, or 622. In some embodiments, a monoclonal antibody that specifically binds to a cashew and/or pistachio allergen comprises a heavy chain variable region comprising an amino acid sequence that comprises the sequence of, or has at least 75% sequence identity (e.g., at least 80%, 85%, 90%, 91%, 92%, 93%, 94%, 95%, 96%, 97%, 98%, or 99% sequence identity to, any one of SEQ ID NOs:166, 174, 437, 465, or 620, and comprises a light chain variable region comprising an amino acid sequence that comprises the sequence of, or has at least 75% sequence identity (e.g., at least 80%, 85%, 90%, 91%, 92%, 93%, 94%, 95%, 96%, 97%, 98%, or 99% sequence identity) to, any one of SEQ ID NOs:170, 178, 441, 468, or 622.

In some embodiments, a monoclonal antibody that specifically binds to a tree nut allergen comprises a heavy chain CDR1-3 and a light chain CDR1-3 comprising the amino acid sequences of:
(a) SEQ ID NOs:692, 693, 694, 696, 94, and 697, respectively; or
(b) SEQ ID NOs:318, 319, 320, 322, 323, and 324, respectively; or
(c) SEQ ID NOs:227, 200, 228, 230, 149, and 231, respectively; or
(d) SEQ ID NOs:113, 539, 540, 542, 196, and 543, respectively; or
(e) SEQ ID NOs:311, 312, 313, 315, 94, and 316, respectively; or
(f) SEQ ID NOs:665, 666, 667, 669, 670, and 671, respectively; or
(g) SEQ ID NOs:466, 200, 467, 469, 149, and 470, respectively; or
(h) SEQ ID NOs:167, 168, 169, 171, 172, and 173, respectively; or
(i) SEQ ID NOs:621, 176, 177, 623, 180, and 624, respectively; or
(j) SEQ ID NOs:175, 176, 177, 179, 180, and 181, respectively; or
(k) SEQ ID NOs:438, 439, 440, 442, 30, and 443, respectively.

Clone PA14P3H08

In some embodiments, a monoclonal antibody that specifically binds to a tree nut allergen comprises a heavy chain CDR1 comprising the amino acid sequence of SEQ ID NO:692, a heavy chain CDR2 comprising the amino acid sequence of SEQ ID NO:693, a heavy chain CDR3 comprising the amino acid sequence of SEQ ID NO:694, a light chain CDR1 comprising the amino acid sequence of SEQ ID NO:696, a light chain CDR2 comprising the amino acid sequence of SEQ ID NO:94, and a light chain CDR3 comprising the amino acid sequence of SEQ ID NO:697. In some embodiments, the monoclonal antibody binds to two or more tree nut allergens. In some embodiments, the monoclonal antibody binds to a pecan, walnut, hazelnut, and/or macadamia nut allergen.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:691, and that comprises a heavy chain CDR1, CDR2, and CDR3 comprising the amino acid sequences of SEQ ID NOs:692, 693, and 694, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:695, and that comprises the light chain CDR1, CDR2, and CDR3 comprising the amino acid sequences of SEQ ID NOs:696, 94, and 697, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:691, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:695. In some embodiments, the antibody comprises a heavy chain variable region comprising the amino acid sequence of SEQ ID NO:691 and comprises a light chain variable region comprising the amino acid sequence of SEQ ID NO:695.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:692, 693, 694, 696, 95, and 697, respectively, or an antibody comprising a heavy chain variable region comprising the amino acid sequence of SEQ ID NO:691 and further comprising a light chain variable region comprising the amino acid sequence of SEQ ID NO:695).

Clone PA11P1D11

In some embodiments, a monoclonal antibody that specifically binds to a tree nut allergen comprises a heavy chain CDR1 comprising the amino acid sequence of SEQ ID NO:318, a heavy chain CDR2 comprising the amino acid sequence of SEQ ID NO:319, a heavy chain CDR3 comprising the amino acid sequence of SEQ ID NO:320, a light chain CDR1 comprising the amino acid sequence of SEQ ID NO:322, a light chain CDR2 comprising the amino acid sequence of SEQ ID NO:323, and a light chain CDR3 comprising the amino acid sequence of SEQ ID NO:324. In some embodiments, the monoclonal antibody binds to two or more tree nut allergens. In some embodiments, the monoclonal antibody binds to a pecan, walnut, hazelnut, and/or macadamia nut allergen.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:317, and that comprises a heavy chain CDR1, CDR2, and CDR3 comprising the amino acid sequences of SEQ ID NOs:318, 319, and 320, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:321, and that comprises the light chain CDR1, CDR2, and CDR3 comprising the amino acid sequences of SEQ ID NOs:322, 323, and 324, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:317, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:321. In some embodiments, the antibody comprises a heavy chain variable region comprising the amino acid sequence of SEQ ID NO:317 and comprises a light chain variable region comprising the amino acid sequence of SEQ ID NO:321.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:318, 319, 320, 322, 323, and 324, respectively, or an antibody comprising a heavy chain variable region comprising the amino acid sequence of SEQ ID NO:317 and further comprising a light chain variable region comprising the amino acid sequence of SEQ ID NO:321).

Clone PA11P1G10

In some embodiments, a monoclonal antibody that specifically binds to a tree nut allergen comprises a heavy chain CDR1 comprising the amino acid sequence of SEQ ID NO:227, a heavy chain CDR2 comprising the amino acid sequence of SEQ ID NO:200, a heavy chain CDR3 comprising the amino acid sequence of SEQ ID NO:228, a light chain CDR1 comprising the amino acid sequence of SEQ ID NO:230, a light chain CDR2 comprising the amino acid sequence of SEQ ID NO:149, and a light chain CDR3 comprising the amino acid sequence of SEQ ID NO:231. In some embodiments, the monoclonal antibody binds to two or more tree nut allergens. In some embodiments, the monoclonal antibody binds to a pecan, walnut, hazelnut, and/or macadamia nut allergen.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:226, and that comprises a heavy chain CDR1, CDR2, and CDR3 comprising the amino acid sequences of SEQ ID NOs:227, 200, and 228, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:229, and that comprises the light chain CDR1, CDR2, and CDR3 comprising the amino acid sequences of SEQ ID NOs:230, 149, and 231, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:226, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:229. In some embodiments, the antibody comprises a heavy chain variable region comprising the amino acid sequence of SEQ ID NO:226 and comprises a light chain variable region comprising the amino acid sequence of SEQ ID NO:229.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:227, 200, 228, 230, 149, and 231, respectively, or an antibody comprising a heavy chain variable region comprising the amino acid sequence of SEQ ID NO:226 and further comprising a light chain variable region comprising the amino acid sequence of SEQ ID NO:229).

Clone PA12P4D02

In some embodiments, a monoclonal antibody that specifically binds to a tree nut allergen comprises a heavy chain CDR1 comprising the amino acid sequence of SEQ ID NO:113, a heavy chain CDR2 comprising the amino acid sequence of SEQ ID NO:539, a heavy chain CDR3 comprising the amino acid sequence of SEQ ID NO:540, a light chain CDR1 comprising the amino acid sequence of SEQ ID NO:542, a light chain CDR2 comprising the amino acid sequence of SEQ ID NO:196, and a light chain CDR3 comprising the amino acid sequence of SEQ ID NO:543. In some embodiments, the monoclonal antibody binds to two or more tree nut allergens. In some embodiments, the monoclonal antibody binds to a pecan, walnut, hazelnut, and/or macadamia nut allergen.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:538, and that comprises a heavy chain CDR1, CDR2, and CDR3 comprising the amino acid sequences of SEQ ID NOs:113, 539, and 540, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:541, and that comprises the light chain CDR1, CDR2, and CDR3 comprising the amino acid sequences of SEQ ID NOs:542, 196, and 543, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:538, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:541. In some embodiments, the antibody comprises a heavy chain variable region comprising the amino acid sequence of SEQ ID NO:538 and comprises a light chain variable region comprising the amino acid sequence of SEQ ID NO:541.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:113, 539, 540, 542, 196, and 543, respectively, or an antibody comprising a heavy chain variable region comprising the amino acid sequence of SEQ ID NO:538 and further comprising a light chain variable region comprising the amino acid sequence of SEQ ID NO:541).

Clone PA11P1D12

In some embodiments, a monoclonal antibody that specifically binds to a tree nut allergen comprises a heavy chain CDR1 comprising the amino acid sequence of SEQ ID NO:692, a heavy chain CDR2 comprising the amino acid sequence of SEQ ID NO:693, a heavy chain CDR3 comprising the amino acid sequence of SEQ ID NO:694, a light chain CDR1 comprising the amino acid sequence of SEQ ID NO:696, a light chain CDR2 comprising the amino acid sequence of SEQ ID NO:94, and a light chain CDR3 comprising the amino acid sequence of SEQ ID NO:697. In some embodiments, the monoclonal antibody binds to two or more tree nut allergens. In some embodiments, the monoclonal antibody binds to a pecan, walnut, hazelnut, and/or macadamia nut allergen.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:310, and that comprises a heavy chain CDR1, CDR2, and CDR3 comprising the amino acid sequences of SEQ ID NOs:311, 312, and 313, respectively; and (b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:314, and that comprises the light chain CDR1, CDR2, and CDR3 comprising the amino acid sequences of SEQ ID NOs:315, 94, and 316, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:310, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:314. In some embodiments, the antibody comprises a heavy chain variable region comprising the amino acid sequence of SEQ ID NO:310 and comprises a light chain variable region comprising the amino acid sequence of SEQ ID NO:314.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:311, 312, 313, 315, 94, and 316, respectively, or an antibody comprising a heavy chain variable region comprising the amino acid sequence of SEQ ID NO:310 and further comprising a light chain variable region comprising the amino acid sequence of SEQ ID NO:314).

Clone PA11P1F03

In some embodiments, a monoclonal antibody that specifically binds to a tree nut allergen comprises a heavy chain CDR1 comprising the amino acid sequence of SEQ ID NO:665, a heavy chain CDR2 comprising the amino acid sequence of SEQ ID NO:666, a heavy chain CDR3 comprising the amino acid sequence of SEQ ID NO:667, a light chain CDR1 comprising the amino acid sequence of SEQ ID NO:669, a light chain CDR2 comprising the amino acid sequence of SEQ ID NO:670, and a light chain CDR3 comprising the amino acid sequence of SEQ ID NO:671. In some embodiments, the monoclonal antibody binds to two or more tree nut allergens. In some embodiments, the monoclonal antibody binds to a pecan, walnut, hazelnut, and/or macadamia nut allergen.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:664, and that comprises a heavy chain CDR1, CDR2, and CDR3 comprising the amino acid sequences of SEQ ID NOs:665, 666, and 667, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:668, and that comprises the light chain CDR1, CDR2, and CDR3 comprising the amino acid sequences of SEQ ID NOs:669, 670, and 671, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:664, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:668. In some embodiments, the antibody comprises a heavy chain variable region comprising the amino acid sequence of SEQ ID NO:664 and comprises a light chain variable region comprising the amino acid sequence of SEQ ID NO:668.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:665, 666, 667, 669, 670, and 671, respectively, or an antibody comprising a heavy chain variable region comprising the amino acid sequence of SEQ ID NO:664 and further comprising a light chain variable region comprising the amino acid sequence of SEQ ID NO:668).

Clone PA11P1C04

In some embodiments, a monoclonal antibody that specifically binds to a tree nut allergen comprises a heavy chain CDR1 comprising the amino acid sequence of SEQ ID NO:466, a heavy chain CDR2 comprising the amino acid sequence of SEQ ID NO:200, a heavy chain CDR3 comprising the amino acid sequence of SEQ ID NO:467, a light chain CDR1 comprising the amino acid sequence of SEQ ID NO:469, a light chain CDR2 comprising the amino acid sequence of SEQ ID NO:149, and a light chain CDR3 comprising the amino acid sequence of SEQ ID NO:470. In some embodiments, the monoclonal antibody binds to two or more tree nut allergens. In some embodiments, the monoclonal antibody binds to a cashew and/or a pistachio allergen.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:465, and that comprises a heavy chain CDR1, CDR2, and CDR3 comprising the amino acid sequences of SEQ ID NOs:466, 200, and 467, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:468, and that comprises the light chain CDR1, CDR2, and CDR3 comprising the amino acid sequences of SEQ ID NOs:469, 149, and 470, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:465, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:468. In some embodiments, the antibody comprises a heavy chain variable region comprising the amino acid sequence of SEQ ID NO:465 and comprises a light chain variable region comprising the amino acid sequence of SEQ ID NO:468.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:466, 200, 467, 469, 149, and 470, respectively, or an antibody comprising a heavy chain variable region comprising the amino acid sequence of SEQ ID NO:465 and further comprising a light chain variable region comprising the amino acid sequence of SEQ ID NO:468).

Clone PA11P1G04

In some embodiments, a monoclonal antibody that specifically binds to a tree nut allergen comprises a heavy chain CDR1 comprising the amino acid sequence of SEQ ID NO:167, a heavy chain CDR2 comprising the amino acid sequence of SEQ ID NO:168, a heavy chain CDR3 comprising the amino acid sequence of SEQ ID NO:169, a light chain CDR1 comprising the amino acid sequence of SEQ ID NO:171, a light chain CDR2 comprising the amino acid sequence of SEQ ID NO:172, and a light chain CDR3 comprising the amino acid sequence of SEQ ID NO:173. In some embodiments, the monoclonal antibody binds to two or more tree nut allergens. In some embodiments, the monoclonal antibody binds to a cashew and/or a pistachio allergen.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:166, and that comprises a heavy chain CDR1, CDR2, and CDR3 comprising the amino acid sequences of SEQ ID NOs:167, 168, and 169, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:170, and that comprises the light chain CDR1, CDR2, and CDR3 comprising the amino acid sequences of SEQ ID NOs:171, 172, and 173, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:166, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:170. In some embodiments, the antibody comprises a heavy chain variable region comprising the amino acid sequence of SEQ ID NO:166 and comprises a light chain variable region comprising the amino acid sequence of SEQ ID NO:170.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:167, 168, 169, 171, 172, and 173, respectively, or an antibody comprising a heavy chain variable region comprising the amino acid sequence of SEQ ID NO:166 and further comprising a light chain variable region comprising the amino acid sequence of SEQ ID NO:170).

Clone PA11P1E01

In some embodiments, a monoclonal antibody that specifically binds to a tree nut allergen comprises a heavy chain CDR1 comprising the amino acid sequence of SEQ ID NO:621, a heavy chain CDR2 comprising the amino acid sequence of SEQ ID NO:176, a heavy chain CDR3 comprising the amino acid sequence of SEQ ID NO:177, a light chain CDR1 comprising the amino acid sequence of SEQ ID NO:623, a light chain CDR2 comprising the amino acid sequence of SEQ ID NO:180, and a light chain CDR3 comprising the amino acid sequence of SEQ ID NO:624. In some embodiments, the monoclonal antibody binds to two or more tree nut allergens. In some embodiments, the monoclonal antibody binds to a cashew and/or a pistachio allergen.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:620, and that comprises a heavy chain CDR1, CDR2, and CDR3 comprising the amino acid sequences of SEQ ID NOs:621, 176, and 177, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:622, and that comprises the light chain CDR1, CDR2, and CDR3 comprising the amino acid sequences of SEQ ID NOs:623, 180, and 624, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:620, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:622. In some embodiments, the antibody comprises a heavy chain variable region comprising the amino acid sequence of SEQ ID NO:620 and comprises a light chain variable region comprising the amino acid sequence of SEQ ID NO:622.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:621, 176, 177, 623, 180, and 624, respectively, or an antibody comprising a heavy chain variable region comprising the amino acid sequence of SEQ ID NO:620 and further comprising a light chain variable region comprising the amino acid sequence of SEQ ID NO:622).

Clone PA11P1C11

In some embodiments, a monoclonal antibody that specifically binds to a tree nut allergen comprises a heavy chain CDR1 comprising the amino acid sequence of SEQ ID NO:175, a heavy chain CDR2 comprising the amino acid sequence of SEQ ID NO:176, a heavy chain CDR3 comprising the amino acid sequence of SEQ ID NO:177, a light chain CDR1 comprising the amino acid sequence of SEQ ID NO:179, a light chain CDR2 comprising the amino acid sequence of SEQ ID NO:180, and a light chain CDR3 comprising the amino acid sequence of SEQ ID NO:181. In some embodiments, the monoclonal antibody binds to two or more tree nut allergens. In some embodiments, the monoclonal antibody binds to a cashew and/or a pistachio allergen.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:174, and that comprises a heavy chain CDR1, CDR2, and CDR3 comprising the amino acid sequences of SEQ ID NOs:175, 176, and 177, respectively; and (b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:178, and that comprises the light chain CDR1, CDR2, and CDR3 comprising the amino acid sequences of SEQ ID NOs:179, 180, and 181, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:174, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:178. In some embodiments, the antibody comprises a heavy chain variable region comprising the amino acid sequence of SEQ ID NO:174 and comprises a light chain variable region comprising the amino acid sequence of SEQ ID NO:178.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:175, 176, 177, 179, 180, and 181, respectively, or an antibody comprising a heavy chain variable region comprising the amino acid sequence of SEQ ID NO:174 and further comprising a light chain variable region comprising the amino acid sequence of SEQ ID NO:178).

Clone PA11P1CO3

In some embodiments, a monoclonal antibody that specifically binds to a tree nut allergen comprises a heavy chain CDR1 comprising the amino acid sequence of SEQ ID NO:438, a heavy chain CDR2 comprising the amino acid sequence of SEQ ID NO:439, a heavy chain CDR3 comprising the amino acid sequence of SEQ ID NO:440, a light chain CDR1 comprising the amino acid sequence of SEQ ID NO:442, a light chain CDR2 comprising the amino acid sequence of SEQ ID NO:30, and a light chain CDR3 comprising the amino acid sequence of SEQ ID NO:443. In some embodiments, the monoclonal antibody binds to two or more tree nut allergens. In some embodiments, the monoclonal antibody binds to a cashew and/or a pistachio allergen.

In some embodiments, the antibody comprises:

(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:437, and that comprises a heavy chain CDR1, CDR2, and CDR3 comprising the amino acid sequences of SEQ ID NOs:438, 439, and 440, respectively; and (b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:441, and that comprises the light chain CDR1, CDR2, and CDR3 comprising the amino acid sequences of SEQ ID NOs:442, 30, and 443, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:437, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:441. In some embodiments, the antibody comprises a heavy chain variable region comprising the amino acid sequence of SEQ ID NO:437 and comprises a light chain variable region comprising the amino acid sequence of SEQ ID NO:441.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:438, 439, 440, 442, 30, and 443, respectively, or an antibody comprising a heavy chain variable region comprising the amino acid sequence of SEQ ID NO:437 and further comprising a light chain variable region comprising the amino acid sequence of SEQ ID NO:441).

Antibodies that Specifically Bind to Milk Allergens

In some embodiments, the monoclonal antibody or antigen-binding portion thereof specifically binds to a milk allergen (e.g., cow's milk allergen). In some embodiments, a monoclonal antibody that specifically binds to a milk allergen comprises heavy chain CDRs and/or light chain CDRs that are disclosed in Table 1 below. In some embodiments, a monoclonal antibody that specifically binds to a milk allergen comprises a light chain variable region sequence and/or a heavy chain variable region sequence that is disclosed in Table 1 below. In some embodiments, a monoclonal antibody that specifically binds to a milk allergen comprises: a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity to a heavy chain variable region sequence disclosed in Table 1 and comprises a CDR1, a CDR2, and a CDR3 that is identical to the CDRs of that heavy chain variable region sequence, and a light chain variable region comprising an amino acid sequence that has at least 70% sequence identity (e.g., at least 75%, 80%, 85%, 90%, 91%, 92%, 93%, 94%, 95%, 96%, 97%, 98%, or 99% sequence identity to a light chain variable region sequence disclosed in Table 1 and comprises a CDR1, a CDR2, and a CDR3 that is identical to the CDRs of that light chain variable region sequence.

In some embodiments, a monoclonal antibody that specifically binds to a milk allergen comprises a light chain sequence, or a portion thereof, and/or a heavy chain sequence, or a portion thereof, derived from any of the following antibodies described herein: Clone PA01P2C05, Clone PA01P2B03, Clone PA01P2A12, Clone PA01P2C12, Clone PA01P2E10, Clone PA01P2C09, Clone PA01P2D06, Clone PA01P2E08, Clone PA01P2A05, Clone PA01P2B04, Clone PA01P2E05, Clone PA01P2D04, Clone PA01P2B12, Clone PA01P2D11, Clone PA01P2B10, Clone PA01P2D10, Clone PA01P2D09, Clone PA01P2B05, Clone PA01P4C11, Clone PA01P3E08, Clone PA01P2E06, Clone PA01P2E07, Clone PA01P2G07, Clone PA01P2B09, Clone PA01P2C04, or Clone PA01P2H08. The amino acid sequences of the CDR, light chain variable domain (VL), and heavy chain variable domain (VH) of Clone PA01P2C05, Clone PA01P2B03, Clone PA01P2A12, Clone PA01P2C12, Clone PA01P2E10, Clone PA01P2C09, Clone PA01P2D06, Clone PA01P2E08, Clone PA01P2A05, Clone PA01P2B04, Clone PA01P2E05, Clone PA01P2D04, Clone PA01P2B12, Clone PA01P2D11, Clone PA01P2B10, Clone PA01P2D10, Clone PA01P2D09, Clone PA01P2B05, Clone PA01P4C11, Clone PA01P3E08, Clone PA01P2E06, Clone PA01P2E07, Clone PA01P2G07, Clone PA01P2B09, Clone PA01P2C04, and Clone PA01P2H08 are set forth in Table 1 below.

In some embodiments, a monoclonal antibody that specifically binds to a peanut allergen comprises one or more (e.g., one, two, three, four, five, or all six) of:
- (a) a heavy chain CDR1 comprising the amino acid sequence of any one of SEQ ID NOs: 121, 750, 757, 765, 772, 779, 785, 793, 800, 807, 814, 821, 833, 838, 846, 853, 860, 868, 874, 881, 889, 895, 903, 911, 918, or 926;
- (b) a heavy chain CDR2 comprising the amino acid sequence of any one of SEQ ID NOs: 378, 532, 751, 758, 766, 773, 786, 794, 801, 808, 815, 822, 826, 839, 847, 854, 861, 875, 882, 890, 896, 904, 912, 919, or 927;
- (c) a heavy chain CDR3 comprising the amino acid sequence of any one of SEQ ID NOs: 752, 759, 767, 774, 780, 787, 795, 802, 809, 816, 827, 840, 848, 855, 862, 869, 876, 883, 891, 897, 905, 913, 920, or 928;
- (d) a light chain CDR1 comprising the amino acid sequence of any one of SEQ ID NOs: 523, 754, 761, 769, 776, 782, 789, 797, 804, 811, 818, 829, 835, 842, 850, 857, 864, 871, 878, 885, 899, 907, 915, 922, or 930;
- (e) a light chain CDR2 comprising the amino acid sequence of any one of SEQ ID NOs: 22, 30, 94, 110, 149, 186, 196, 389, 404, 509, 662, 682, 762, 790, 830, 843, 865, 886, 900, 908, 923, or 931; and
- (f) a light chain CDR3 comprising the amino acid sequence of any one of SEQ ID NOs: 755, 763, 770, 777, 783, 791, 798, 805, 812, 819, 824, 831, 836, 844, 851, 858, 866, 872, 879, 887, 893, 901, 909, 916, 924, or 932.

In some embodiments, a monoclonal antibody that specifically binds to a milk allergen comprises a heavy chain CDR1-3 and a light chain CDR1-3 comprising the amino acid sequences of:
- (a) SEQ ID NOs:750, 751, 752, 754, 196, and 755, respectively; or
- (b) SEQ ID NOs:757, 758, 759, 761, 762, and 763, respectively; or
- (c) SEQ ID NOs:765, 766, 767, 769, 30, and 770, respectively; or
- (d) SEQ ID NOs:772, 773, 774, 776, 389, and 777, respectively; or
- (e) SEQ ID NOs:779, 532, 780, 782, 404, and 783, respectively; or
- (f) SEQ ID NOs:785, 786, 787, 789, 790, and 791, respectively; or
- (g) SEQ ID NOs:793, 794, 795, 797, 30, and 798, respectively; or
- (h) SEQ ID NOs:800, 801, 802, 804, 110, and 805, respectively; or
- (i) SEQ ID NOs:807, 808, 809, 811, 509, and 812, respectively; or
- (j) SEQ ID NOs:814, 815, 816, 818, 94, and 819, respectively; or
- (k) SEQ ID NOs:821, 822, 787, 776, 790, and 824, respectively; or
- (l) SEQ ID NOs:121, 826, 827, 829, 830, and 831, respectively; or
- (m) SEQ ID NOs:833, 826, 827, 835, 149, and 836, respectively; or
- (n) SEQ ID NOs:838, 839, 840, 842, 843, and 844, respectively; or
- (o) SEQ ID NOs:846, 847, 848, 850, 196, and 851, respectively; or
- (p) SEQ ID NOs:853, 854, 855, 857, 662, and 858, respectively; or
- (q) SEQ ID NOs:860, 861, 862, 864, 865, and 866, respectively; or
- (r) SEQ ID NOs:868, 378, 869, 871, 682, and 872, respectively; or
- (s) SEQ ID NOs:874, 875, 876, 878, 22, and 879, respectively; or
- (t) SEQ ID NOs:881, 882, 883, 885, 886, and 887, respectively; or
- (u) SEQ ID NOs:889, 890, 891, 523, 762, and 893, respectively; or
- (v) SEQ ID NOs:895, 896, 897, 899, 900, and 901, respectively; or
- (w) SEQ ID NOs:903, 904, 905, 907, 908, and 909, respectively; or
- (x) SEQ ID NOs:911, 912, 913, 915, 149, and 916, respectively; or
- (y) SEQ ID NOs:918, 919, 920, 922, 923, and 924, respectively; or
- (z) SEQ ID NOs:926, 927, 928, 930, 931, and 932, respectively.

In some embodiments, a monoclonal antibody that specifically binds to a milk allergen comprises a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity) to any one of SEQ ID NOs:749, 756, 764, 771, 778, 784, 792, 799, 806, 813, 820, 825, 832, 837, 845, 852, 859, 867, 873, 880, 888, 894, 902, 910, 917, or 925. In some embodiments, a monoclonal antibody that specifically binds to a milk allergen comprises a light chain variable region comprising an amino acid sequence that has at least 75% sequence identity (e.g., at least 75%, 80%, 85%, 90%, 91%, 92%, 93%, 94%, 95%, 96%, 97%, 98%, or 99% sequence identity) to any one of SEQ ID NOs:753, 760, 768, 775, 781, 788, 796, 803, 810, 817, 823, 828, 834, 841, 849, 856, 863, 870, 877, 884, 892, 898, 906, 914, 921, or 929. In some embodiments, a monoclonal antibody that specifically binds to a milk allergen comprises a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity) to any one of SEQ ID NOs:749, 756, 764, 771, 778, 784, 792, 799, 806, 813, 820, 825, 832, 837, 845, 852, 859, 867, 873, 880, 888, 894, 902, 910, 917, or 925, and comprises a light chain variable region comprising an amino acid sequence that has at least 75% sequence identity (e.g., at least 80%, 85%, 90%, 91%, 92%, 93%, 94%, 95%, 96%, 97%, 98%, or 99% sequence identity) to any one of SEQ ID NOs:753, 760, 768, 775, 781, 788, 796, 803, 810, 817, 823, 828, 834, 841, 849, 856, 863, 870, 877, 884, 892, 898, 906, 914, 921, or 929.

In some embodiments, a monoclonal antibody that specifically binds to a milk allergen comprises a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity) to any one of SEQ ID NOs:749, 756, 764, 771, 778, 784, 792, 799, 806, 813, 820, 825, 832, 837, 845, 852, 859, 867, 873, 880, 888, 894, 902, 910, 917, or 925 and comprises a CDR1, a CDR2, and a CDR3 that is identical to the CDRs of that SEQ ID NO. In some embodiments, a monoclonal antibody that specifically binds to a milk allergen comprises a light chain variable region comprising an amino acid sequence that has at least 70% sequence identity (e.g., at least 75%, 80%, 85%, 90%, 91%, 92%, 93%, 94%, 95%, 96%, 97%, 98%, or 99% sequence identity) to any one of SEQ ID NOs:753, 760, 768, 775, 781, 788, 796, 803, 810, 817, 823, 828, 834, 841, 849, 856, 863, 870, 877, 884, 892, 898, 906, 914, 921, or 929 and comprises a CDR1, a CDR2, and a CDR3 that is identical to the CDRs of that SEQ ID NO.

In some embodiments, a monoclonal antibody that specifically binds to a milk allergen comprises:

(a) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:749 or that has the sequence of SEQ ID NO:749, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:753 or that has the sequence of SEQ ID NO:753; or (b) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:756 or that has the sequence of SEQ ID NO:756, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:760 or that has the sequence of SEQ ID NO:760; or (c) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:764 or that has the sequence of SEQ ID NO:764, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:768 or that has the sequence of SEQ ID NO:768; or (d) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:771 or that has the sequence of SEQ ID NO:771, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:775 or that has the sequence of SEQ ID NO:775; or (e) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:778 or that has the sequence of SEQ ID NO:778, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:781 or that has the sequence of SEQ ID NO:781; or (f) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:784 or that has the sequence of SEQ ID NO:784, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:788 or that has the sequence of SEQ ID NO:788; or (g) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:792 or that has the sequence of SEQ ID NO:792, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:796 or that has the sequence of SEQ ID NO:796; or (h) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:799 or that has the sequence of SEQ ID NO:799, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:803 or that has the sequence of SEQ ID NO:803; or (i) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:806 or that has the sequence of SEQ ID NO:806, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:810 or that has the sequence of SEQ ID NO:810; or (j) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:813 or that has the sequence of SEQ ID NO:813, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:817 or that has the sequence of SEQ ID NO:817; or (k) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:820 or that has the sequence of SEQ ID NO:820, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:823 or that has the sequence of SEQ ID NO:823; or (l) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:825 or that has the sequence of SEQ ID NO:825, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:828 or that has the sequence of SEQ ID NO:828; or (m) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:832 or that has the sequence of SEQ ID NO:832, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:834 or that has the sequence of SEQ ID NO:834; or (n) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:837 or that has the sequence of SEQ ID NO:837, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:841 or that has the sequence of SEQ ID NO:841; or (o) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:845 or that has the sequence of SEQ ID NO:845, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:849 or that has the sequence of SEQ ID NO:849; or (p) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:852, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:856 or that has the sequence of SEQ ID NO:856; or (q) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:859 or that has the sequence of SEQ ID NO:859, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:863 or that has the sequence of SEQ ID NO:863; or (r) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:867 or that has the sequence of SEQ ID NO:867, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:870 or that has the sequence of SEQ ID NO:870; or (s) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:873 or that has the sequence of SEQ ID NO:873, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:877 or that has the sequence of SEQ ID NO:877; or (t) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:880 or that has the sequence of SEQ ID NO:880, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:884 or that has the sequence of SEQ ID NO:884; or (u) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:888 or that has the sequence of SEQ ID NO:888, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:892 or that has the sequence of SEQ ID NO:892; or (v) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:894 or that has the sequence of SEQ ID NO:894, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:898 or that has the sequence of SEQ ID NO:898; or (w) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:902 or that has the sequence of SEQ ID NO:902, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:906 or that has the sequence of SEQ ID NO:906; or (x) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:910 or that has the sequence of SEQ ID NO:910, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:914 or that has the sequence of SEQ ID NO:914; or (y) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:917 or that has the sequence of SEQ ID NO:917, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:921 or that has the sequence of SEQ ID NO:921; or (z) a heavy chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:925 or that has the sequence of SEQ ID NO:925, and a light chain variable region comprising an amino acid sequence that has at least 90% (e.g., at least 75%, 80%, 85%, 90%, 91%, 92%, 93%, 94%, 95%, 96%, 97%, 98%, or 99%) sequence identity to SEQ ID NO:929 or that has the sequence of SEQ ID NO:929.

Clone PA01P2D09

In some embodiments, a monoclonal antibody that specifically binds to a milk allergen comprises a heavy chain CDR1 comprising the amino acid sequence of SEQ ID NO:860, a heavy chain CDR2 comprising the amino acid sequence of SEQ ID NO:861, a heavy chain CDR3 comprising the amino acid sequence of SEQ ID NO:862, a light chain CDR1 comprising the amino acid sequence of SEQ ID NO:864, a light chain CDR2 comprising the amino acid sequence of SEQ ID NO:865, and a light chain CDR3 comprising the amino acid sequence of SEQ ID NO:866.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:859, and that comprises a heavy chain CDR1, CDR2, and CDR3 comprising the amino acid sequences of SEQ ID NOs:860, 861, and 862, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:863, and that comprises the light chain CDR1, CDR2, and CDR3 comprising the amino acid sequences of SEQ ID NOs:864, 865, and 866, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:859, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:863. In some embodiments, the antibody comprises a heavy chain variable region comprising the amino acid sequence of SEQ ID NO:859 and comprises a light chain variable region comprising the amino acid sequence of SEQ ID NO:863.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:860, 861, 862, 864, 865, and 866, respectively, or an antibody comprising a heavy chain variable region comprising the amino acid sequence of SEQ ID NO:859 and further comprising a light chain variable region comprising the amino acid sequence of SEQ ID NO:863).

Clone PA01P2D04

In some embodiments, a monoclonal antibody that specifically binds to a milk allergen comprises a heavy chain CDR1 comprising the amino acid sequence of SEQ ID NO:121, a heavy chain CDR2 comprising the amino acid sequence of SEQ ID NO:826, a heavy chain CDR3 comprising the amino acid sequence of SEQ ID NO:827, a light chain CDR1 comprising the amino acid sequence of SEQ ID NO:829, a light chain CDR2 comprising the amino acid sequence of SEQ ID NO:830, and a light chain CDR3 comprising the amino acid sequence of SEQ ID NO:831.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:825, and that comprises a heavy chain CDR1, CDR2, and CDR3 comprising the amino acid sequences of SEQ ID NOs:121, 826, and 827, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:828, and that comprises the light chain CDR1, CDR2, and CDR3 comprising the amino acid sequences of SEQ ID NOs:829, 830, and 831, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:825, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:828. In some embodiments, the antibody comprises a heavy chain variable region comprising the amino acid sequence of SEQ ID NO:825 and comprises a light chain variable region comprising the amino acid sequence of SEQ ID NO:828.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:121, 826, 827, 829, 830, and 831, respectively, or an antibody comprising a heavy chain variable region comprising the amino acid sequence of SEQ ID NO:825 and further comprising a light chain variable region comprising the amino acid sequence of SEQ ID NO:828).

Clone PA01P2B12

In some embodiments, a monoclonal antibody that specifically binds to a milk allergen comprises a heavy chain CDR1 comprising the amino acid sequence of SEQ ID NO:833, a heavy chain CDR2 comprising the amino acid sequence of SEQ ID NO:826, a heavy chain CDR3 comprising the amino acid sequence of SEQ ID NO:827, a light chain CDR1 comprising the amino acid sequence of SEQ ID NO:835, a light chain CDR2 comprising the amino acid sequence of SEQ ID NO:149, and a light chain CDR3 comprising the amino acid sequence of SEQ ID NO:836.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:832, and that comprises a heavy chain CDR1, CDR2, and CDR3 comprising the amino acid sequences of SEQ ID NOs:833, 826, and 827, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:834, and that comprises the light chain CDR1, CDR2, and CDR3 comprising the amino acid sequences of SEQ ID NOs:835, 149, and 836, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:832, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:834. In some embodiments, the antibody comprises a heavy chain variable region comprising the amino acid sequence of SEQ ID NO:832 and comprises a light chain variable region comprising the amino acid sequence of SEQ ID NO:834.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:833, 826, 827, 835, 149, and 836, respectively, or an antibody comprising a heavy chain variable region comprising the amino acid sequence of SEQ ID NO:832 and further comprising a light chain variable region comprising the amino acid sequence of SEQ ID NO:834).

Clone PA01P2B05

In some embodiments, a monoclonal antibody that specifically binds to a milk allergen comprises a heavy chain CDR1 comprising the amino acid sequence of SEQ ID NO:868, a heavy chain CDR2 comprising the amino acid sequence of SEQ ID NO:378, a heavy chain CDR3 comprising the amino acid sequence of SEQ ID NO:869, a light chain CDR1 comprising the amino acid sequence of SEQ ID NO:871, a light chain CDR2 comprising the amino acid sequence of SEQ ID NO:682, and a light chain CDR3 comprising the amino acid sequence of SEQ ID NO:872.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:867, and that comprises a heavy chain CDR1, CDR2, and CDR3 comprising the amino acid sequences of SEQ ID NOs:868, 378, and 869, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:870, and that comprises the light chain CDR1, CDR2, and CDR3 comprising the amino acid sequences of SEQ ID NOs:871, 682, and 872, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:867, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:870. In some embodiments, the antibody comprises a heavy chain variable region comprising the amino acid sequence of SEQ ID NO:867 and comprises a light chain variable region comprising the amino acid sequence of SEQ ID NO:870.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:868, 378, 869, 871, 682, and 872, respectively, or an antibody comprising a heavy chain variable region comprising the amino acid sequence of SEQ ID NO:867 and further comprising a light chain variable region comprising the amino acid sequence of SEQ ID NO:870).

Clone PA01P2D10

In some embodiments, a monoclonal antibody that specifically binds to a milk allergen comprises a heavy chain CDR1 comprising the amino acid sequence of SEQ ID NO:853, a heavy chain CDR2 comprising the amino acid sequence of SEQ ID NO:854, a heavy chain CDR3 comprising the amino acid sequence of SEQ ID NO:855, a light chain CDR1 comprising the amino acid sequence of SEQ ID NO:857, a light chain CDR2 comprising the amino acid sequence of SEQ ID NO:662, and a light chain CDR3 comprising the amino acid sequence of SEQ ID NO:858.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:852, and that comprises a heavy chain CDR1, CDR2, and CDR3 comprising the amino acid sequences of SEQ ID NOs:853, 854, and 855, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:856, and that comprises the light chain CDR1, CDR2, and CDR3 comprising the amino acid sequences of SEQ ID NOs:857, 662, and 858, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:852, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:856. In some embodiments, the antibody comprises a heavy chain variable region comprising the amino acid sequence of SEQ ID NO:852 and comprises a light chain variable region comprising the amino acid sequence of SEQ ID NO:856.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:853, 854, 855, 857, 662, and 858, respectively, or an antibody comprising a heavy chain variable region comprising the amino acid sequence of SEQ ID NO:852 and further comprising a light chain variable region comprising the amino acid sequence of SEQ ID NO:856).

Clone PA01P2E08

In some embodiments, a monoclonal antibody that specifically binds to a milk allergen comprises a heavy chain CDR1 comprising the amino acid sequence of SEQ ID NO:800, a heavy chain CDR2 comprising the amino acid sequence of SEQ ID NO:801, a heavy chain CDR3 comprising the amino acid sequence of SEQ ID NO:802, a light chain CDR1 comprising the amino acid sequence of SEQ ID NO:804, a light chain CDR2 comprising the amino acid sequence of SEQ ID NO:110, and a light chain CDR3 comprising the amino acid sequence of SEQ ID NO:805.

In some embodiments, the antibody comprises:
  (a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:799, and that comprises a heavy chain CDR1, CDR2, and CDR3 comprising the amino acid sequences of SEQ ID NOs:800, 801, and 802, respectively; and
  (b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:803, and that comprises the light chain CDR1, CDR2, and CDR3 comprising the amino acid sequences of SEQ ID NOs:804, 110, and 805, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:799, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:803. In some embodiments, the antibody comprises a heavy chain variable region comprising the amino acid sequence of SEQ ID NO:799 and comprises a light chain variable region comprising the amino acid sequence of SEQ ID NO:803

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:800, 801, 802, 804, 110, and 805, respectively, or an antibody comprising a heavy chain variable region comprising the amino acid sequence of SEQ ID NO:799 and further comprising a light chain variable region comprising the amino acid sequence of SEQ ID NO:803).

Antibodies that Specifically Bind to Fungal Allergens

In some embodiments, the monoclonal antibody or antigen-binding portion thereof specifically binds to a fungal allergen. In some embodiments, the monoclonal antibody specifically binds to a fungal allergen that is an *Aspergillus fumigatus, Aspergillus niger*, or *Aspergillus nidulans* allergen (e.g., an extract of *Aspergillus fumigatus, Aspergillus niger*, or *Aspergillus nidulans*). In some embodiments, the fungal allergen is *Aspergillus fumigatus* 1 (Asp f 1), e.g., a purified recombinant allergen *Aspergillus fumigatus* 1 (rAsp f 1).

In some embodiments, the monoclonal antibody exhibits cross-reactivity with at least two fungal allergens. In some embodiments, the monoclonal antibody exhibits cross-reactivity with two or more *Aspergillus* allergens (e.g., two or more species of *Aspergillus*). In some embodiments, the monoclonal antibody exhibits cross-reactivity with two or more of the fungal allergens *Aspergillus fumigatus, Aspergillus niger*, and *Aspergillus nidulans*. In some embodiments, the monoclonal antibody specifically binds to at least one of the fungal allergens with a $K_D$ of less than 100 nM, less than 50 nM, less than 10 nM, less than 5 nM, less than 1 nM, less than 500 pM, less than 250 pM, less than 150 pM, less than 100 pM, less than 50 pM, less than 40 pM, less than 30 pM, less than 20 pM, less than about 10 pM, or less than 1 pM.

Antibody Sequences

In some embodiments, a monoclonal antibody that specifically binds to a fungal allergen (e.g., that specifically binds to an *Aspergillus* allergen) comprises heavy chain CDRs and/or light chain CDRs that are disclosed in Table 1 below. In some embodiments, a monoclonal antibody that specifically binds to a fungal allerge (e.g., an *Aspergillus* allergen) comprises a light chain variable region sequence and/or a heavy chain variable region sequence that is disclosed in Table 1 below. In some embodiments, a monoclonal antibody that specifically binds to a fungal allergen (e.g., an *Aspergillus* allergen) comprises: a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity to a heavy chain variable region sequence disclosed in Table 1 and comprises a CDR1, a CDR2, and a CDR3 that is identical to the CDRs of that heavy chain variable region sequence, and a light chain variable region comprising an amino acid sequence that has at least 70% sequence identity (e.g., at least 75%, 80%, 85%, 90%, 91%, 92%, 93%, 94%, 95%, 96%, 97%, 98%, or 99% sequence identity to a light chain variable region sequence disclosed in Table 1 and comprises a CDR1, a CDR2, and a CDR3 that is identical to the CDRs of that light chain variable region sequence.

In some embodiments, a monoclonal antibody that specifically binds to a fungal allergen (e.g., that specifically binds to an *Aspergillus* allergen) comprises a light chain sequence, or a portion thereof, and/or a heavy chain sequence, or a portion thereof, derived from any of the following antibodies described herein: Clone 1003320101_D6, Clone 1003320105_D6, Clone 1003320107_C5, Clone 1003320107_F3, or Clone 1003320107_F8. The amino acid sequences of the CDR, light chain variable domain (VL), and heavy chain variable domain (VH) of Clone 1003320101_D6, Clone 1003320105_D6, Clone 1003320107_C5, Clone 1003320107_F3, and Clone 1003320107_F8 are set forth in Table 1 below.

In some embodiments, a monoclonal antibody that specifically binds to a fungal allergen comprises one or more (e.g., one, two, three, four, five, or all six) of:
  (a) a heavy chain CDR1 comprising the amino acid sequence of any one of SEQ ID NOs:710, 718, 726, 734, or 742;

a heavy chain CDR2 comprising the amino acid sequence of any one of SEQ ID NOs:711, 719, 727, 735, or 743;
a heavy chain CDR3 comprising the amino acid sequence of any one of SEQ ID NOs:712, 720, 728, 736, or 744;
a light chain CDR1 comprising the amino acid sequence of any one of SEQ ID NOs:714, 722, 730, 738, or 746;
a light chain CDR2 comprising the amino acid sequence of any one of SEQ ID NOs:715, 723, 731, 739, or 747; and
a light chain CDR3 comprising the amino acid sequence of any one of SEQ ID NOs:716, 724, 732, 740, or 748.

In some embodiments, a monoclonal antibody that specifically binds to a fungal allergen comprises a heavy chain CDR1-3 and a light chain CDR1-3 comprising the amino acid sequences of:
(a) SEQ ID NOs: 710, 711, 712, 714, 715, and 716, respectively; or
(b) SEQ ID NOs:718, 719, 720, 722, 723, and 724, respectively; or
(c) SEQ ID NOs:726, 7272, 728, 730, 731, and 732, respectively; or
(d) SEQ ID NOs:734, 735, 736, 738, 739, and 740, respectively; or
(e) SEQ ID NOs:742, 743, 744, 746, 747, and 748, respectively.

In some embodiments, a monoclonal antibody that specifically binds to a fungal allergen comprises a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity to any one of SEQ ID NOs:709, 717, 725, 733, or 741. In some embodiments, a monoclonal antibody that specifically binds to a fungal allergen comprises a light chain variable region comprising an amino acid sequence that has at least 75% sequence identity (e.g., at least 75%, 80%, 85%, 90%, 91%, 92%, 93%, 94%, 95%, 96%, 97%, 98%, or 99% sequence identity to any one of SEQ ID NOs:713, 721, 729, 737, or 745. In some embodiments, a monoclonal antibody that specifically binds to a fungal allergen comprises a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity to any one of SEQ ID NOs:709, 717, 725, 733, or 741 and comprises a light chain variable region comprising an amino acid sequence that has at least 75% sequence identity (e.g., at least 80%, 85%, 90%, 91%, 92%, 93%, 94%, 95%, 96%, 97%, 98%, or 99% sequence identity to any one of SEQ ID NOs:713, 721, 729, 737, or 745.

In some embodiments, a monoclonal antibody that specifically binds to a fungal allergen comprises a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity to any one of SEQ ID NOs:709, 717, 725, 733, or 741 and comprises a CDR1, a CDR2, and a CDR3 that is identical to the CDRs of that SEQ ID NO. In some embodiments, a monoclonal antibody that specifically binds to a fungal allergen comprises a light chain variable region comprising an amino acid sequence that has at least 70% sequence identity (e.g., at least 75%, 80%, 85%, 90%, 91%, 92%, 93%, 94%, 95%, 96%, 97%, 98%, or 99% sequence identity to any one of SEQ ID NOs:713, 721, 729, 737, or 745 and comprises a CDR1, a CDR2, and a CDR3 that is identical to the CDRs of that SEQ ID NO. In some embodiments, a monoclonal antibody that specifically binds to a fungal allergen comprises:

(a) a heavy chain variable region comprising an amino acid sequence that has at least 75% sequence identity (e.g., at least 80%, 85%, 90%, 91%, 92%, 93%, 94%, 95%, 96%, 97%, 98%, or 99% sequence identity to any one of SEQ ID NOs:709, 717, 725, 733, or 741 and that comprises a CDR1, a CDR2, and a CDR3 that is identical to the CDRs of that SEQ ID NO; and (b) a light chain variable region comprising an amino acid sequence that has at least 75% sequence identity (e.g., at least 80%, 85%, 90%, 91%, 92%, 93%, 94%, 95%, 96%, 97%, 98%, or 99% sequence identity to any one of SEQ ID NOs:713, 721, 729, 737, or 745 and that comprises a CDR1, a CDR2, and a CDR3 that is identical to the CDRs of that SEQ ID NO.

Clone 1003320101 D6

In some embodiments, a monoclonal antibody that specifically binds to a fungal allergen (e.g., *Aspergillus* allergen) comprises a heavy chain CDR1 comprising the amino acid sequence of SEQ ID NO:710, a heavy chain CDR2 comprising the amino acid sequence of SEQ ID NO:711, a heavy chain CDR3 comprising the amino acid sequence of SEQ ID NO:712, a light chain CDR1 comprising the amino acid sequence of SEQ ID NO:714, a light chain CDR2 comprising the amino acid sequence of SEQ ID NO:715, and a light chain CDR3 comprising the amino acid sequence of SEQ ID NO:716. In some embodiments, the antibody specifically binds to the fungal allergen *Aspergillus fumigatus*.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:709, and that comprises a heavy chain CDR1, CDR2, and CDR3 comprising the amino acid sequences of SEQ ID NOs:710, 711, and 712, respectively; and
(b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:713, and that comprises the light chain CDR1, CDR2, and CDR3 comprising the amino acid sequences of SEQ ID NOs:714, 715, and 716, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:709, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:713. In some embodiments, the antibody comprises a heavy chain variable region comprising the amino acid sequence of SEQ ID NO:709 and comprises a light chain variable region comprising the amino acid sequence of SEQ ID NO:713.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:710, 711, 712, 714, 715, and 716, respectively, or an antibody comprising a heavy chain variable region comprising the amino acid sequence of SEQ ID NO:709 and further comprising a light chain variable region comprising the amino acid sequence of SEQ ID NO:713).

Clone 1003320105 D6

In some embodiments, a monoclonal antibody that specifically binds to a fungal allergen (e.g., *Aspergillus* allergen) comprises a heavy chain CDR1 comprising the amino acid sequence of SEQ ID NO:718, a heavy chain CDR2 comprising the amino acid sequence of SEQ ID NO:719, a heavy chain CDR3 comprising the amino acid sequence of SEQ ID NO:720, a light chain CDR1 comprising the amino acid sequence of SEQ ID NO:722, a light chain CDR2 comprising the amino acid sequence of SEQ ID NO:723, and a light chain CDR3 comprising the amino acid sequence of SEQ ID NO:724. In some embodiments, the antibody specifically binds to the fungal allergen *Aspergillus fumigatus*.

In some embodiments, the antibody comprises:
  (a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:717, and that comprises a heavy chain CDR1, CDR2, and CDR3 comprising the amino acid sequences of SEQ ID NOs:718, 719, and 720, respectively; and
  (b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:721, and that comprises the light chain CDR1, CDR2, and CDR3 comprising the amino acid sequences of SEQ ID NOs:722, 723, and 724, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:717, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:721. In some embodiments, the antibody comprises a heavy chain variable region comprising the amino acid sequence of SEQ ID NO:717 and comprises a light chain variable region comprising the amino acid sequence of SEQ ID NO:721.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:718, 719, 720, 722, 723, and 724, respectively, or an antibody comprising a heavy chain variable region comprising the amino acid sequence of SEQ ID NO:717 and further comprising a light chain variable region comprising the amino acid sequence of SEQ ID NO:721).

Clone 1003320107 C5

In some embodiments, a monoclonal antibody that specifically binds to a fungal allergen (e.g., *Aspergillus* allergen) comprises a heavy chain CDR1 comprising the amino acid sequence of SEQ ID NO:726, a heavy chain CDR2 comprising the amino acid sequence of SEQ ID NO:727, a heavy chain CDR3 comprising the amino acid sequence of SEQ ID NO:728, a light chain CDR1 comprising the amino acid sequence of SEQ ID NO:730, a light chain CDR2 comprising the amino acid sequence of SEQ ID NO:731, and a light chain CDR3 comprising the amino acid sequence of SEQ ID NO:732. In some embodiments, the antibody specifically binds to the fungal allergen *Aspergillus fumigatus*. In some embodiments, the antibody specifically binds to the fungal allergen *Aspergillus niger*. In some embodiments, the antibody specifically binds to the fungal allergen *Aspergillus nidulans*. In some embodiments, the antibody specifically binds to a recombinant *Aspergillus* antigen (e.g., rAsp f 1). In some embodiments, the antibody specifically binds cross-reactively to more than one of *Aspergillus fumigatus, Aspergillus niger, Aspergillus nidulans*, or a recombinant *Aspergillus* antigen (e.g., rAsp f 1).

In some embodiments, the antibody comprises:
  (a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:725, and that comprises a heavy chain CDR1, CDR2, and CDR3 comprising the amino acid sequences of SEQ ID NOs:726, 727, and 728, respectively; and
  (b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:729, and that comprises the light chain CDR1, CDR2, and CDR3 comprising the amino acid sequences of SEQ ID NOs:730, 731, and 732, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:725, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:729. In some embodiments, the antibody comprises a heavy chain variable region comprising the amino acid sequence of SEQ ID NO:725 and comprises a light chain variable region comprising the amino acid sequence of SEQ ID NO:729.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:726, 727, 728, 730, 731, and 732, respectively, or an antibody comprising a heavy chain variable region comprising the amino acid sequence of SEQ ID NO:725 and further comprising a light chain variable region comprising the amino acid sequence of SEQ ID NO:729).

Clone 1003320107 F3

In some embodiments, a monoclonal antibody that specifically binds to a fungal allergen (e.g., *Aspergillus* allergen) comprises a heavy chain CDR1 comprising the amino acid sequence of SEQ ID NO:734, a heavy chain CDR2 comprising the amino acid sequence of SEQ ID NO:735, a heavy chain CDR3 comprising the amino acid sequence of SEQ ID NO:736, a light chain CDR1 comprising the amino acid sequence of SEQ ID NO:738, a light chain CDR2 comprising the amino acid sequence of SEQ ID NO:739, and a light chain CDR3 comprising the amino acid sequence of SEQ ID NO:740. In some embodiments, the antibody specifically binds to a recombinant *Aspergillus* antigen (e.g., rAsp f 1).

In some embodiments, the antibody comprises:
  (a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:733, and that comprises a heavy chain CDR1, CDR2, and CDR3 comprising the amino acid sequences of SEQ ID NOs:734, 735, and 736, respectively; and (b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:737, and that comprises the light chain CDR1, CDR2, and CDR3 comprising the amino acid sequences of SEQ ID NOs:738, 739, and 740, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:733, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:737. In some embodiments, the antibody comprises a heavy chain variable region comprising the amino acid sequence of SEQ ID NO:733 and comprises a light chain variable region comprising the amino acid sequence of SEQ ID NO:737.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:734, 735, 736, 738, 739, and 740, respectively, or an antibody comprising a heavy chain variable region comprising the amino acid sequence of SEQ ID NO:733 and further comprising a light chain variable region comprising the amino acid sequence of SEQ ID NO:737).

Clone 1003320107 F8

In some embodiments, a monoclonal antibody that specifically binds to a fungal allergen (e.g., *Aspergillus* allergen) comprises a heavy chain CDR1 comprising the amino acid sequence of SEQ ID NO:742, a heavy chain CDR2 comprising the amino acid sequence of SEQ ID NO:743, a heavy chain CDR3 comprising the amino acid sequence of SEQ ID NO:744, a light chain CDR1 comprising the amino acid sequence of SEQ ID NO:746, a light chain CDR2 comprising the amino acid sequence of SEQ ID NO:747, and a light chain CDR3 comprising the amino acid sequence of SEQ ID NO:748. In some embodiments, the antibody specifically binds to the fungal allergen *Aspergillus fumigatus*.

In some embodiments, the antibody comprises:
(a) a heavy chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:741, and that comprises a heavy chain CDR1, CDR2, and CDR3 comprising the amino acid sequences of SEQ ID NOs:74222, 743, and 744, respectively; and (b) a light chain variable region that comprises an amino acid sequence that has at least 70% sequence identity (e.g., at least 70%, 75%, 80%, 85%, 90%, 91%, 92%, 93%, 94%, 95%, 96%, 97%, 98%, or 99% sequence identity) to SEQ ID NO:745, and that comprises the light chain CDR1, CDR2, and CDR3 comprising the amino acid sequences of SEQ ID NOs:746, 747, and 748, respectively.

In some embodiments, the antibody comprises a heavy chain variable region comprising an amino acid sequence that has at least 90% sequence identity (e.g., at least 91%, 92%, 93%, 94%, 95%, 96%, 97%, 98%, or 99% sequence identity) to SEQ ID NO:741, and comprises a light chain variable region comprising an amino acid sequence that has at least 90% sequence identity (e.g., at least 91%, 92%, 93%, 94%, 95%, 96%, 97%, 98%, or 99% sequence identity) to SEQ ID NO:745. In some embodiments, the antibody comprises a heavy chain variable region comprising the amino acid sequence of SEQ ID NO:741 and comprises a light chain variable region comprising the amino acid sequence of SEQ ID NO:745.

In some embodiments, the antibody is an antibody that competes for binding with an antibody as described herein (e.g., an antibody comprising a heavy chain CDR1-3 and a light chain CDR1-3 comprising the amino acid sequences of SEQ ID NOs:742, 743, 744, 746, 747, and 748, respectively, or an antibody comprising a heavy chain variable region comprising the amino acid sequence of SEQ ID NO:741 and further comprising a light chain variable region comprising the amino acid sequence of SEQ ID NO:745).

Antigen-Binding Fragments

In some embodiments, an antibody as disclosed herein (e.g., an antibody as disclosed in Section IV that binds to a food allergen, plant allergen, fungal allergen, animal allergen, dust mite allergen, drug allergen, cosmetic allergen, or latex allergen) is an antigen-binding portion (also referred to herein as an antigen-binding fragment). Examples of antigen-binding fragments include, but are not limited to, a Fab, a F(ab')$_2$, a Fv, a scFv, a bivalent scFv, a single domain antibody, or a diabody. Various techniques have been developed for the production of antigen-binding fragments. Traditionally, these fragments were derived via proteolytic digestion of intact antibodies (see, e.g., Morimoto et al., *J. Biochem. Biophys. Meth.*, 24:107-117 (1992); and Brennan et al., Science, 229:81 (1985)). However, these fragments can now be produced directly using recombinant host cells. For example, antigen-binding fragments can be isolated from antibody phage libraries. Alternatively, Fab'-SH fragments can be directly recovered from *E. coli* cells and chemically coupled to form F(ab')2 fragments (see, e.g., Carter et al., *BioTechnology*, 10:163-167 (1992)). According to another approach, F(ab')$_2$ fragments can be isolated directly from recombinant host cell culture. Other techniques for the production of antigen-binding fragments are known in the art.

Antibody Conjugates

In some embodiments, the antibody or antigen-binding fragment can be conjugated to another molecule, e.g., polyethylene glycol (PEGylation) or serum albumin, to provide an extended half-life in vivo. Examples of PEGylation of antigen-binding fragments are provided in Knight et al. Platelets 15:409, 2004 (for abciximab); Pedley et al., *Br. J. Cancer* 70:1126, 1994 (for an anti-CEA antibody); Chapman et al., *Nature Biotech.* 17:780, 1999; and Humphreys, et al., *Protein Eng. Des.* 20: 227, 2007).

In some embodiments, antibody-drug conjugates comprising a monoclonal antibody or antigen-binding fragment as described herein are provided. In some embodiments, a monoclonal antibody or antigen-binding fragment (e.g., an antibody or antigen-binding fragment that specifically binds to a food allergen or a fungal allergen) is covalently linked to a cytotoxic drug. In some embodiments, the antibody or antigen-binding fragment is an antibody that specifically binds to a fungal allergen and the drug is an anti-fungal drug. Suitable anti-fungal drugs include, but are not limited to, Amphotericin B, azole anti-fungals (e.g., ketoconazole, fluconazole, isavuconazole, itraconazole, posaconazole, or voriconazole), echinocandins (e.g., anidulafungin, caspofungin, or micafungin), and flucytosine. Methods for making antibody-drug conjugates are described, e.g., in Chudasama et al., *Nature Chemistry*, 2016, 8:114-119; WO 2013/068874; and U.S. Pat. No. 8,535,678.

Synthetic Antibodies, Antibody Compositions, and Antibody-Producing Cells

Certain antibodies described herein are derived from B cells isolated from human subjects who have been exposed to allergen(s). In certain embodiments, antibodies, antibody compositions, and cells of the invention are distinguishable from naturally occurring antibodies, compositions and cells in one or more respects. The distinguishable antibodies, compositions, and cells may be referred to as "synthetic," or may be identified by the proviso that the antibody or composition "is not naturally occurring" or affirmatively as "non-naturally occurring." As used herein the terms "corresponding antibody," and "corresponding to" describes the relationship between (1) an antibody characterized by six specific CDR sequences and produced by immune cells of a study subject described in the Examples below and (2) a synthetic antibody comprising the same six CDR sequences.

Synthetic Antibodies

Synthetic antibodies of the invention may differ in structure from naturally occurring antibodies with the same CDRs. That is, synthetic antibodies identified by specified CDRs may be structurally different from antibodies comprising the specified CDRs that are produced by cells of the study subject described in the Examples below. Possible differences include:

Variable Region Sequences that Differ Corresponding Naturally Occurring Antibodies In one approach, an antibody heavy chain comprises the CDRs of a clone described herein (e.g., PA13P1E10) with the proviso that the antibody heavy chain does not comprise the heavy chain variable region sequence associated with the clone described herein. For illustration, in one embodiment an antibody that comprises the CDRs of Clone PA13P1E10 does not have a heavy chain variable region that comprises SEQ ID NO:9. In another approach, an antibody light chain comprises the CDRs of a clone described herein (e.g., PA13P1E10) with the proviso that the antibody light chain does not comprise the light chain variable region sequence associated with the clone described herein. For illustration, in one embodiment an antibody that comprises the CDRs of Clone PA13P1E10 does not have a light chain variable region that comprises SEQ ID NO:13). In one approach both the heavy chain and the light chain variable region of an antibody of the invention have an amino acid sequence other than the sequence disclosed herein.

Lambda and Kappa Light Chains

In some embodiments the synthetic antibody comprises lambda type light chains. In some embodiments the synthetic antibody comprises kappa type light chains.

Isotypes

In some embodiments the synthetic antibody with specified CDRs is an isotype other the isotype(s) found associated with the study subject from which B cells with the specified CDRs was derived. In some embodiments the antibody disclosed herein is an isotype other than IgG1. In some embodiments the antibody disclosed herein is an isotype other than IgG2. In some embodiments the antibody disclosed herein is an isotype other than IgG3. In some embodiments the antibody disclosed herein is an isotype other than IgG4. In some embodiments the antibody disclosed herein is an isotype other than IgM. In some embodiments the antibody disclosed herein is an isotype other than IgA.

Allotypes

In some embodiments the synthetic antibody with specified CDRs is an allotype other the allotype(s) found associated with the study subject from which B cells with the specified CDRs was derived. In some embodiments, the synthetic antibody of the invention comprises an allotype selected from those listed in Table 2, below, which is different from an allotype of antibodies from the corresponding study subject. In some embodiments the synthetic antibody of the invention comprises any individual allotype selected from those listed in Table 2, with the proviso that the allotype differs from the corresponding allotype of antibodies from a study subject.

TABLE 2

Human immunoglobulin allotypes

| Isotype/type Allotypes | Heavy chains | | | IgA A2m | Light chains Km |
|---|---|---|---|---|---|
| | IgG1 G1m | IgG2 G2m | IgG3 G3m | | |
| | 1(a) | 23(n) | 21(g1) | 1 | 1 |
| | 2(x) | | 28(g5) | 2 | 2 |
| | 3(f) | | 11(b0) | | 3 |
| | 17(z) | | 5(b1) | | |
| | | | 13 (b3) | | |
| | | | 14 (b4) | | |
| | | | 10 (b5) | | |
| | | | 15(s) | | |
| | | | 16(t) | | |
| | | | 6(c3) | | |
| | | | 24(c5) | | |
| | | | 26(u) | | |
| | | | 27 (v) | | |

NB: Alphabetical notation given within brackets. From: Jefferis and Marie-Paule Lefranc, 2009, "Human immunoglobulin allotypes: Possible implications for immunogenicity" mAbs 1(4): 332-338, incorporated herein by reference.

Constant Domain Variants

Synthetic antibodies of the invention may comprise variations in heavy chain constant regions to change the properties of the synthetic antibody relative to the corresponding naturally occurring antibody. Exemplary changes include mutations to modulate antibody effector function (e.g., complement-based effector function or FcγR-based effector function), alter half-like, modulate coengagement of antigen and FcγRs, introduce or remove glycosylation motifs (glycoengineering). See Fonseca et al., 2018, "Boosting half-life and effector functions of therapeutic antibodies by Fc-engineering: An interaction-function review" *Intl Biol Macromol.* 19:306-311; Wang et al., 2018, "IgG Fc engineering to modulate antibody effector functions" *Protein Cell* 2018, 9(1):63-73; Schlothauer, 2016, "Novel human IgG1 and IgG4 Fc-engineered antibodies with completely abolished immune effector functions," *Protein Engineering, Design and Selection* 29(10):457-466; Tam et al., 2017, "Functional, Biophysical, and Structural Characterization of Human IgG1 and IgG4 Fc Variants with Ablated Immune Functionality" *Antibodies* 6, 12, each incorporated herein by reference for all purposes.

Synthetic Antibody Compositions

Synthetic antibody compositions of the invention may differ from naturally occurring compositions in at least one or more of the following respects: (i) composition comprises antibodies that are purified, i.e., separated from tissue or cellular material with which they are associated in the human body, and optionally in an manufactured excipient or medium; and/or (ii) antibody compositions of the invention contain a single species of antibody (are monoclonal) such that all antibodies in the composition have the same structure and specificity;

Synthetic Antibody-Producing Cells

Antibodies described herein may be produced by recombinant expression in a human or non-human cell. Synthetic antibody-producing cells include non-human cells expressing heavy chains, light chains, or both heavy and light chains; human cells that are not immune cells heavy chains, light chains, or both heavy and light chains; and human B cells that produce heavy chains or light chains, but not both heavy and light chains. Synthetic antibodies of the invention may be are heterologously expressed, in vitro or in vivo, in cells other than human B cells, such as non-human cells and human cells other than B cells, optionally other than immune cells, and optionally in cells other than cells in a B cell lineage.

V. Methods of Use

In another aspect, the present disclosure provides therapeutic methods for treating a human subject with one or more of the allergen-specific monoclonal antibodies or antigen-binding portions thereof as disclosed herein. In some embodiments, methods of treating an allergy are provided. In some embodiments, methods of reducing one or more allergy symptoms in a subject are provided. In some embodiments, the allergen-specific monoclonal antibodies disclosed herein are used therapeutically as blocking antibodies, which is often referred to as passive immunotherapy. Without being bound to a particular theory, it is hypothesized that the allergen-specific monoclonal antibodies disclosed herein block allergen binding to IgE or outcompete endogenous IgE for allergen binding, which in turns prevents or reduces initiation of the allergic cascade. Without intending to be bound by a particular mechanism in some embodiments antibodies of the invention provide therapeutic benefit by binding inhibitory receptors on mast cells and/or basophils.

In some embodiments, the method comprises administering to the subject a therapeutically effective amount of one or more allergen-specific monoclonal antibodies as disclosed herein (e.g., one or more allergen-specific monoclonal antibodies as disclosed in Section IV above). In some embodiments, the method comprises administering to the subject a therapeutically effective amount of a pharmaceutical composition comprising one or more allergen-specific monoclonal antibodies as disclosed herein (e.g., a pharmaceutical composition as disclosed in Section VI below).

In some embodiments, the method comprises administering to the subject a therapeutically effective amount of an allergen-specific monoclonal antibody that is a human IgG isotype, such as a human IgG4 isotype, or antigen-binding portion thereof comprising at least a portion of a human IgG or IgG4 isotype constant region sequence.

In some embodiments, the method comprises administering to the subject a therapeutically effective amount of an allergen-specific monoclonal antibody or antigen-binding portion thereof. In some embodiments, the method comprises administering to the subject two or more allergen-specific monoclonal antibodies (e.g., in a pharmaceutical composition comprising the two or more allergen-specific monoclonal antibodies). In some embodiments, the method comprises administering two or more antibodies that specifically bind to the same allergen. In some embodiments, the method comprises administering two or more antibodies that specifically bind to different epitopes of the same allergen. In some embodiments, the method comprises administering two or more antibodies that specifically bind to two or more different allergens.

In some embodiments, the therapeutic antibody is an antibody that comprises CDR sequences, a heavy chain variable region, and/or a light chain variable region as described herein (e.g., as disclosed in Table 1 below) and further comprises a native or modified IgM, IgD, IgG3, IgG1, IgA1, IgG2, IgG4, or IgA2 heavy chain constant region.

In some embodiments, the therapeutic antibody is conjugated to a drug, e.g., as described in Section IV above.

In some embodiments, the human subject to be treated is an adult. In some embodiments, the human subject is a juvenile.

In some embodiments, a human subject to be treated has an allergy to a food allergen, a plant allergen, a fungal allergen, an animal allergen, a dust mite allergen, a drug allergen, a cosmetic allergen, or a latex allergen. In some embodiments, the human subject has an allergy to a food allergen. In some embodiments, the food allergen is a milk allergen, an egg allergen, a nut allergen, a fish allergen, a shellfish allergen, a soy allergen, a legume allergen, a seed allergen, or a wheat allergen. In some embodiments, the food allergen is a peanut allergen. In some embodiments, the food allergen is a milk allergen. In some embodiments, the food allergen is an egg allergen. In some embodiments, the human subject has an allergy to a plant allergen or a fungal allergen (e.g., an *Aspergillus* allergen). In some embodiments, the allergen is a pollen allergen (e.g., tree pollen, grass pollen, or weed pollen) or a mold allergen. In some embodiments, the human subject has an allergy to an animal allergen. In some embodiments, the allergen is a dander allergen or an insect sting.

In some embodiments, the human subject to be treated has allergies to two or more allergens, e.g., to two or more of a food allergen, a plant allergen, a fungal allergen, an animal allergen, a dust mite allergen, a drug allergen, a cosmetic allergen, or a latex allergen. In some embodiments, the human subject has allergies to 2, 3, 4, 5, 6, 7, 8, 9, 10 or more allergens. In some embodiments, the human subject has allergies to two or more different types of antigens (allergens) in a class of allergen, e.g., allergies to two or more different food allergens (e.g., allergies to two or more different peanut antigens, or allergies to a peanut allergen and a non-peanut allergen such as an egg or milk allergen). In some embodiments, the human subject has allergies to two more different classes of allergens (e.g., allergies to one or more food allergens and to one or more plant allergens). In some embodiments, a human subject has an allergy to 1, 2, 3, 4, 5, 6, 7, 8, 9, 10 or more allergens in the same class of allergen but does not have any known allergies to allergens in other classes of allergens. For example, in some embodiments, a human subject has an allergy to 1, 2, 3, 4, 5, 6, 7, 8, 9, 10 or more food allergens but does not have any known allergies to non-food allergens. In some embodiments, a human subject has an allergy to 1, 2, 3, 4, 5, 6, 7, 8, 9, 10 or more fungal allergens but does not have any known allergies to non-fungal allergens.

In some embodiments, the therapeutic methods disclosed herein reduce one or more symptoms of the allergy in the subject. It will be appreciated by a person of ordinary skill in the art that the symptom(s) associated with an allergic reaction can vary depending upon the type of allergen that induces the allergic reaction. Examples of allergic reaction symptoms include, but are not limited to, hives, rashes, eczema flare, redness of skin, itchy mouth, itchy eyes, nausea, vomiting, diarrhea, stomach pain, nasal congestion, runny nose, stuffy nose, sneezing, cough, fatigue, sore throat, swelling of the lips, tongue, or throat, headaches, trouble swallowing, shortness of breath, wheezing, drop in blood pressure, or weak pulse. In some embodiments, the therapeutic methods disclosed herein reduce the severity of one or more symptoms of the allergy. In some embodiments of the therapeutic methods described herein, the allergy symptoms in the subject comprise one or more of runny nose, skin hives, skin redness, skin swelling, itching or tingling in or around the mouth and/or throat, difficulty swallowing, watery eyes, diarrhea, stomach cramps, nausea, vomiting, tightening of the throat, shortness of breath or wheezing, shortness of breath, and anaphylaxis. In some embodiments, the therapeutic methods disclosed herein reduce the length of duration of one or more symptoms of the allergy.

In some embodiments, the therapeutic methods disclosed herein reduce one or more symptoms of allergic reaction to an allergen such as a food allergen (e.g., a peanut allergen), such as but not limited to hives, rashes, eczema flare, redness of skin, itchy mouth, nausea, vomiting, diarrhea, stomach pain, nasal congestion, runny nose, sneezing, dry cough, swelling of the lips, tongue, or throat, trouble swallowing, shortness of breath, wheezing, drop in blood pressure, or weak pulse. In some embodiments, administration of one or more allergen-specific monoclonal antibodies as disclosed herein reduces the severity of one or more of the symptoms and/or reduces the length of duration of one or more of the symptoms.

In some embodiments, an allergen-specific monoclonal antibody as disclosed herein is administered to a human subject at a therapeutically effective amount or dose. In some embodiments, a daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. Determination of an effective amount is well within the capability of those skilled in the art.

The route of administration of an antibody or composition comprising an antibody as described herein can be dermal or transdermal, inhalational, intestinal, intravenous, intramuscular, intraperitoneal, intrathecal, intralesional, intrabronchial, nasal, ocular or otic delivery, oral, rectal, subcutaneous, topical, transmucosal, or any other methods known in the art. In some embodiments, the antibody or composition is administered by infusion (e.g., intravenously) or by injection (e.g., subcutaneously). In some embodiments, the route of administration of an antibody or composition comprising an antibody in any of the methods described herein is subcutaneous, intravenous, or intranasal.

In some embodiments, administration of a single dose of an antibody or composition comprising an antibody as described herein is effective to treat the allergy or reduce one or more symptoms of the allergy. In some embodiments, multiple doses of the antibody or composition are administered. In some embodiments, a second dose is administered at least 1 day, 2 days, 3 days, 4 days, 5 days, 6 days, 7 days or longer, e.g., at least 1 week, 2 weeks, 3 weeks, 4 weeks, 5 weeks, 6 weeks, 7 weeks, 8 weeks, or longer, after administration of the first dose. In some embodiments, an antibody or composition comprising an antibody as described herein is administered to a subject about every 1, 2, 3, 4, 5, 6, 7, 8, 9, or 10 week(s). In some embodiments, an antibody or composition comprising an antibody as described herein is administered to a subject over an extended period of time, e.g., for at least 30, 40, 50, 60, 70, 80, 90, 100, 150, 200, 250, 300, 350 days or longer.

In some embodiments, in any of the methods described herein, the subject is further administered an additional agent, e.g., an antihistamine, an epinephrine, a decongestant, a bronchial dilator, or a corticosteroid. In some embodiments, the monoclonal antibody and the additional agent are administered substantially simultaneously, i.e., in the same pharmaceutical composition or in separation pharmaceutical compositions that are administered at substantially the same time (e.g., administered within seconds of each other). In some embodiments, the monoclonal antibody and the additional agent are administered separately. In some embodiments, the monoclonal antibody is administered first, followed by administering of the additional agent. In some embodiments, the additional agent is administered first, followed by administering of the monoclonal antibody.

In some embodiments, in any of the methods described herein, the methods can further comprise a step of assessing the reduction of the allergy symptoms (e.g., allergy symptoms related to a peanut allergy, a tree nut allergy, a milk allergy, or a fungal allergy) in the subject. In some embodiments, the reduction of the allergy symptoms can be measured by a Total Nasal Symptom Score (TNSS), which is made from patient assessment of four symptoms graded on a 0 (none) to 3 (severe) scale for congestion, itching, and rhinorrhea, and 0 (none) to 3 (5 or more sneezes) for sneezing. Each of the four symptoms is evaluated using the following scale of 0=None, 1=Mild, 2=Moderate, or 3=Severe. The TNSS has a possible score of 0-12. In other embodiments, the reduction of the allergy symptoms can be measured by a Visual Analog Scale (VAS) nasal symptoms score, which is often used to classify allergy burden into mild, moderate, and severe. A VAS nasal symptoms score ranging from 0 (no nasal symptoms) to 100 (maximal nasal symptoms) can be used to assess the severity of combined nasal symptoms. In other embodiments, the reduction of the allergy symptoms can be measured by peak nasal inspiratory flow (PNIF), which uses a nasal spirometer to measure the nasal airflow (measured as 1/min) in a patient. In yet other embodiments, the reduction of the allergy symptoms can be measured by an allergen skin test, such as a skin prick test (SPT), which uses the presence and degree of cutaneous reactivity as a marker for sensitization within target organs, such as eyes, nose, lung, gut and skin. When relevant allergens (e.g., a peanut allergen, a tree nut allergen, a milk allergen, or a fungal allergen) are introduced into the skin, allergic reactions on the skin produce a wheal and flare response that can be quantitated, for example, using the diameter of the wheal. In yet other embodiments, the reduction of the allergy symptoms can be measured by basophil activation test, which utilizes flow cytometry to quantify the expression of markers of activation on the surface of basophils following allergen stimulation. In yet other embodiments, the reduction of the allergy symptoms can be measured by oral food challenge, which involves administering escalating doses of an allergen to an allergic individual under the supervision of a trained allergist or immunologist. An oral food challenge may be conducted according to an open, single-blind, or double-blind format, with the gold-standard being both double-blind and placebo-controlled.

In yet another aspect, the present disclosure provides diagnostic and detection methods using one or more of the allergen-specific monoclonal antibodies or antigen-binding portions thereof as disclosed herein. In some embodiments, an allergen-specific monoclonal antibody or antigen-binding portion thereof is used to detect whether a sample from a subject has allergic reactivity to an allergen (e.g., a food allergen such as a peanut allergen, tree nut allergen, or milk allergen), a plant allergen, a fungal allergen, an animal allergen, a dust mite allergen, a drug allergen, a cosmetic allergen, or a latex allergen. In some embodiments, the allergen-specific monoclonal antibody or antigen-binding portion thereof is used to detect whether a sample from a subject has allergic reactivity to a specific epitope of the allergen (e.g., using an antibody that is known to bind to a specific epitope of the allergen). In some embodiments, the method comprises contacting a sample from the subject (e.g., a blood or plasma sample) with an allergen-specific monoclonal antibody or antigen-binding portion as disclosed herein.

VI. Compositions and Kits

In another aspect, compositions and kits comprising one or more allergen-specific monoclonal antibodies or antigen-binding portions thereof that are generated from human B cells are provided.

Pharmaceutical Compositions

In some embodiments, pharmaceutical compositions comprising one or more allergen-specific monoclonal antibodies or antigen-binding portions thereof are provided. In some embodiments, the pharmaceutical composition comprises a monoclonal antibody as described herein, e.g., as disclosed in Section IV above. In some embodiments, the pharmaceutical composition is for use in a method of reducing one or more allergy symptoms in a subject (e.g., allergy symptoms due to an allergy to a food allergen, a plant allergen, a fungal allergen, an animal allergen, a dust mite allergen, a drug allergen, a cosmetic allergen, or a latex allergen). In some embodiments, the pharmaceutical composition is for use in a method of reducing one or more allergy symptoms in a subject having a food allergy, e.g., a peanut allergy. In some embodiments, the pharmaceutical composition is for use in a method of reducing one or more allergy symptoms in a subject having an allergy to two more allergens (e.g., two or more food allergens, e.g., peanut allergy and tree nut allergy). In some embodiments, the pharmaceutical composition is for use in a method of reducing one or more allergy symptoms in a subject having a fungal allergy.

In some embodiments, the pharmaceutical composition comprises two or more monoclonal antibodies or antigen-binding portions thereof as described herein (e.g., 2, 3, 4, 5, 6, 7, 8, 9, 10 or more antibodies or antigen-binding portions thereof). In some embodiments, the composition comprises two or more monoclonal antibodies that specifically bind to the same allergen. In some embodiments, the composition comprises two or more monoclonal antibodies that specifically bind to different epitopes of the same allergen. In some embodiments, the composition comprises two or more monoclonal antibodies that specifically bind to two or more different allergens. It will also be appreciated by a person of ordinary skill in the art that for a particular type or class of allergen, e.g., a type of food allergen such as a peanut allergen, there can be more than one substance (e.g., peptide or protein) within that type or class of allergen that induces an allergic response. In some embodiments, a composition comprises two or more monoclonal antibodies that specifically bind to different allergens within a particular type or class of allergen, e.g., two or more different peptides or proteins that are allergens of the same type or class (e.g., two or more different proteins that are peanut allergens). In some embodiments, the composition comprises two or more monoclonal antibodies that specifically bind to the same first allergen and further comprises one or more monoclonal antibodies that specifically bind to a second allergen.

Guidance for preparing formulations can be found in any number of handbooks for pharmaceutical preparation and formulation that are known to those of skill in the art. See, e.g., *Remington: The Science and Practice of Pharmacy*, 21st Edition, Philadelphia, Pa. Lippincott Williams & Wilkins, 2005.

In some embodiments, the pharmaceutical composition further comprises one or more pharmaceutically acceptable carriers, adjuvants, and/or vehicles appropriate for the particular route of administration for which the composition is to be employed. In some embodiments, the carrier, adjuvant, and/or vehicle is suitable for intravenous, intramuscular, oral, intraperitoneal, transdermal, topical, or subcutaneous administration. In some embodiments, the pharmaceutical composition is formulated for intravenous or subcutaneous administration. Methods of formulating antibodies for injection or infusion (e.g., subcutaneous or intramuscular injection or by intravenous infusion) are also described in the art. See, e.g., US 2013/0209465, Pharmaceutically acceptable carriers are well-known in the art. See, e.g., *Handbook of Pharmaceutical Excipients* ($5^{th}$ ed., Ed. Rowe et al., Pharmaceutical Press, Washington, D.C.). Examples of pharmaceutically acceptable carriers include, but are not limited to, aqueous solutions, e.g., water or physiologically compatible buffers such as Hanks's solution, Ringer's solution, or physiological saline buffer.

Typically, a pharmaceutical composition for use in in vivo administration is sterile. Sterilization can be accomplished according to methods known in the art, e.g., heat sterilization, steam sterilization, sterile filtration, or irradiation.

Dosages and desired drug concentration of pharmaceutical compositions of the disclosure may vary depending on the particular use envisioned. The determination of the appropriate dosage or route of administration is well within the skill of one in the art. Suitable dosages are also described in Section V above.

In some embodiments, an antibody formulation comprising one or more allergen-specific monoclonal antibodies or antigen-binding portions thereof as disclosed herein are provided. In some embodiments, the antibody formulation comprises an antibody or antigen-binding portion thereof; and a buffer.

In some embodiments, the buffer is an acetate, citrate, histidine, succinate, phosphate, or hydroxymethylaminomethane buffer. In some embodiments, the antibody formulation further comprises one or more additional excipients such as a salt, a surfactant, polyol/disaccharide/polysaccharides, amino acids, and/or an antioxidant. In some embodiments, the antibody formulation comprises a surfactant such as polysorbate 80 (Tween 80), polysorbate 20 (Tween 20), or poloxamer 188. In some embodiments, the antibody formulation comprises a polyol/disaccharide/polysaccharide such as mannitol, sorbitol, sucrose, trehalose, or dextran 40. In some embodiments, the antibody formulation comprises a salt such as sodium chloride. In some embodiments, the antibody formulation comprises an amino acid such as glycine or arginine. In some embodiments, the antibody formulation comprises an antioxidant such as ascorbic acid, methionine, or ethylenediaminetetraacetic acid (EDTA). In some embodiments, the antibody formulation is a lyophilized formulation. In some embodiments, the antibody formulation is a liquid formulation.

Kits

In some embodiments, kits comprising one or more allergen-specific monoclonal antibodies or antigen-binding portions thereof as disclosed herein, or a pharmaceutical composition comprising one or more allergen-specific monoclonal antibodies or antigen-binding portions thereof as disclosed herein, are provided. In some embodiments, the kit comprises a monoclonal antibody as described herein, e.g., as disclosed in Section IV above. In some embodiments, the kit comprises two or more monoclonal antibodies or antigen-binding portions thereof (e.g., 2, 3, 4, 5, 6, 7, 8, 9, 10 or more antibodies or antigen-binding portions thereof) as described herein. In some embodiments, the kit is for use in a method of reducing one or more allergy symptoms in a subject (e.g., allergy symptoms due to an allergy to a food allergen, a plant allergen, a fungal allergen, an animal allergen, a dust mite allergen, a drug allergen, a cosmetic allergen, or a latex allergen). In some embodiments, the kit is for use in a method of reducing one or more allergy symptoms in a subject having a food allergy, e.g., a peanut allergy. In some embodiments, the kit is for use in a method of reducing one or more allergy symptoms in a subject having a fungal allergy. In some embodiments, the kit is for use in a method of reducing one or more allergy symptoms in a subject having an allergy to two or more allergens (e.g., two or more food allergens, e.g., a peanut allergen and a tree nut allergen).

In some embodiments, the kits can further comprise instructional materials containing directions (i.e., protocols) for the practice of the methods of this invention (e.g., instructions for using the kit for treating an allergy). While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

VII. Examples

The following examples are offered to illustrate, but not to limit, the claimed invention.

Example 1—Single Cell Transcriptomic Analysis of Human IgE Producing Cells and Their Antibodies from Allergic Individuals Abstract IgE antibodies provide immunity from helminth infections, but also can cause life-threatening allergic reactions. Despite their importance to human health, these antibodies and the cells that produce them remain enigmatic due to their scarcity in humans; much of our knowledge of their properties is derived from model organisms. Herein the isolation of IgE producing B cells from the blood of individuals with food allergies is described, followed by a detailed study of their properties by single cell RNA sequencing (scRNAseq). It has been discovered that IgE B cells are deficient in membrane immunoglobulin expression and that the IgE plasmablast state is more immature than that of other antibody producing cells. Through recombinant expression of monoclonal antibodies derived from single cells, cross-reactive IgE antibodies specific for both major peanut allergens Ara h 2 and Ara h 3 were discovered and characterized; these are among the highest affinity native human antibodies discovered to date. Surprisingly, an example of convergent evolution in unrelated individuals who independently evolved nearly identical antibodies to peanut allergens was found. Finally, it was discovered that splicing within B cells of all isotypes reveals polarized germline transcription of the IgE, but not IgG4, isotype as well as several examples of biallelic expression of germline transcripts. These results offer insights into IgE B cell transcriptomics, clonality and regulation, provide a striking example of adaptive immune convergence, and offer an approach for accelerating mechanistic disease understanding by characterizing a rare B cell population underlying IgE-mediated disease at single cell resolution.

Introduction

The IgE antibody class is the least abundant of all isotypes in humans and plays an important role in host defense against parasitic worm infections (1), but it can also become misdirected towards otherwise harmless antigens. Food allergies are one example of this misdirection, where symptoms ranging from urticaria to potentially fatal anaphylaxis result from the degranulation of mast cells and basophils induced by the recognition of allergic food proteins by surface-bound IgE antibodies. Despite this central role in immunity and allergic disease, human IgE antibodies remain poorly characterized due to their scarcity (2). Bulk epitope mapping experiments have revealed that IgE antibodies are polyclonal and epitopes are heterogeneous (3); however, individuals with the same allergy tend to recognize a core set of one or a few allergenic proteins (4). Recent studies applying bulk fluorescence activated cell sorting (FACS) immunophenotyping (5,6) and immune repertoire deep sequencing (7) have inferred IgE B cell origins, while studies performing peanut allergen specific single cell sorting (8,9) have described clonal families to which IgE antibodies belong. However, none have successfully isolated single IgE producing cells or the paired heavy and light chain sequences that comprise individual IgE antibodies, leaving unanswered questions as to the functional properties of such antibodies, transcriptional programs of these cells, and the degree to which any of these features are shared across individuals. Similarly, there is a lack of knowledge, but growing interest, surrounding the IgG4 isotype due to its potential role in mediating the reduced clinical allergen reactivity that accompanies immunotherapy and early allergen exposure through antigen blocking (10). Here we report the first successful isolation and transcriptomic characterization of single IgE and IgG4 producing B cells from humans. We combined single cell RNA sequencing (scRNA-seq) with functional antibody assays to elucidate mechanisms underlying the regulation of IgE and to discover high affinity, cross-reactive peanut specific antibodies in unrelated individuals.

Characterization of Single B Cells from Peripheral Blood

Figure 6:
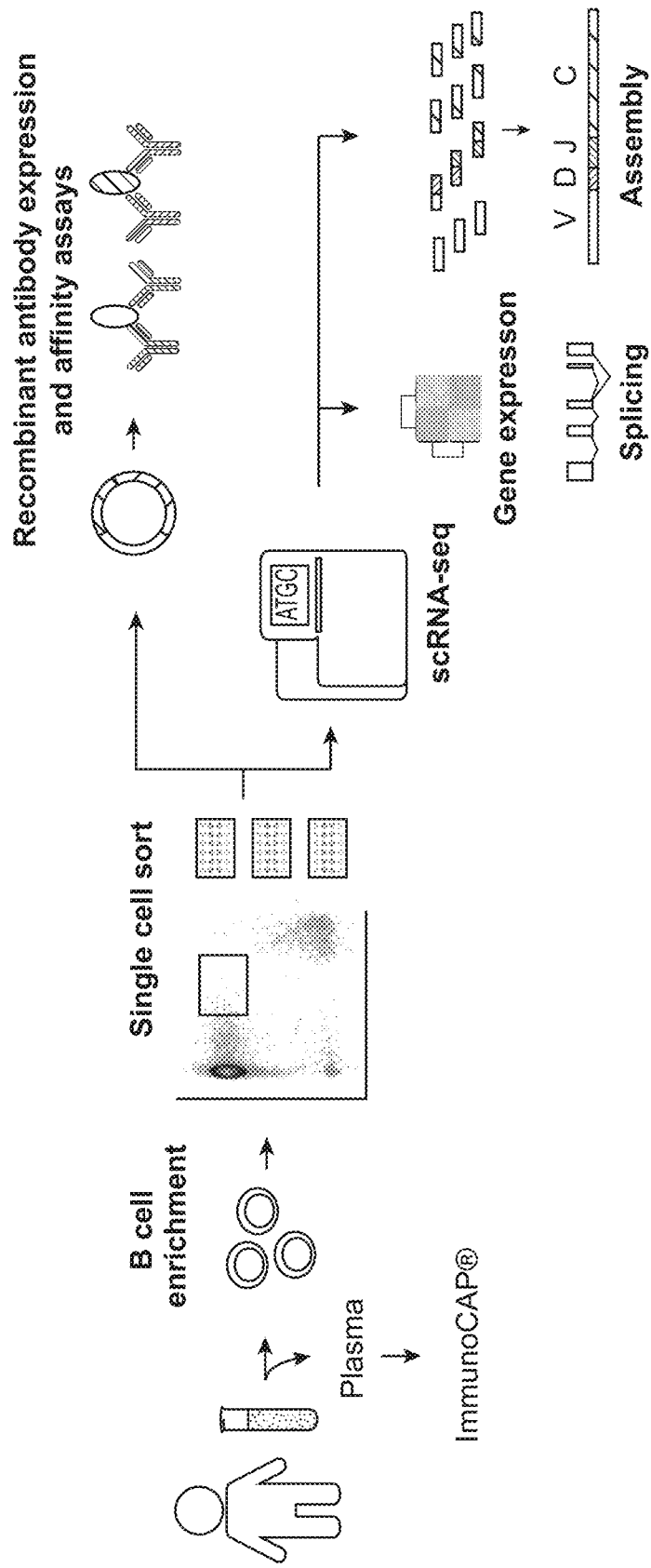
FIG. 6. Study overview. Plasma was extracted from fresh blood to measure circulating IgE levels, while the cellular fraction was enriched for B cells prior to FACS. Single cells were sorted into individual wells of a 96 well plate and processed with scRNA-seq, generating sequencing reads that were aligned to the genome to calculate gene expression and assess splicing as well as assembled in order to reconstruct heavy and light chain sequences. Specificity and affinity data were generated for recombinantly expressed antibodies.
Figure 8A:
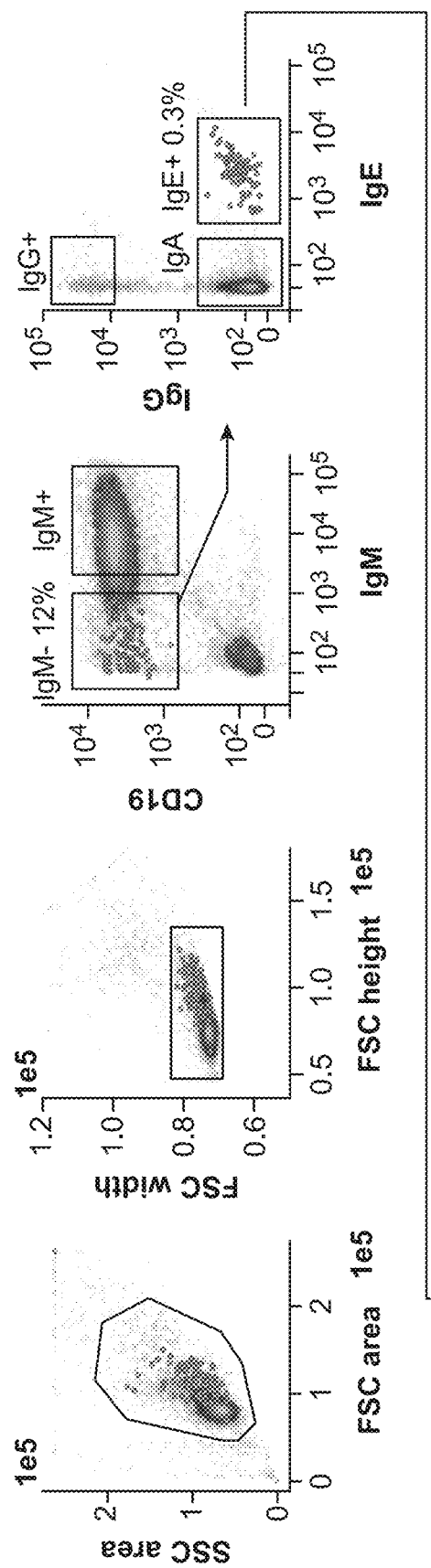
FIGS. 8A-8C. FACS gating and analysis. (A) Gating strategy for sorting single B cells. IgE+ B cells have been overlaid as dark gray dots. (B) Isotype identity within the final IgE gate as determined by heavy chain transcript assembly. ND=not determined. (C) For reference, putative basophils (CD19−IgE+) display higher IgE surface expression than IgE+ B cells.
Figure 8C:
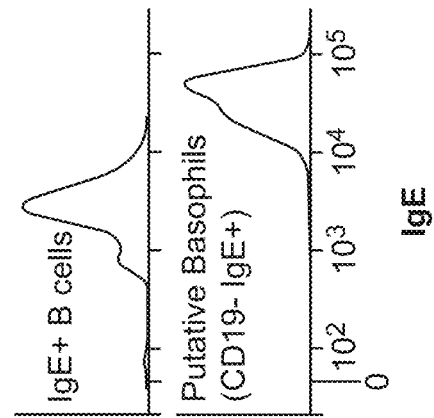
Figure 8B:
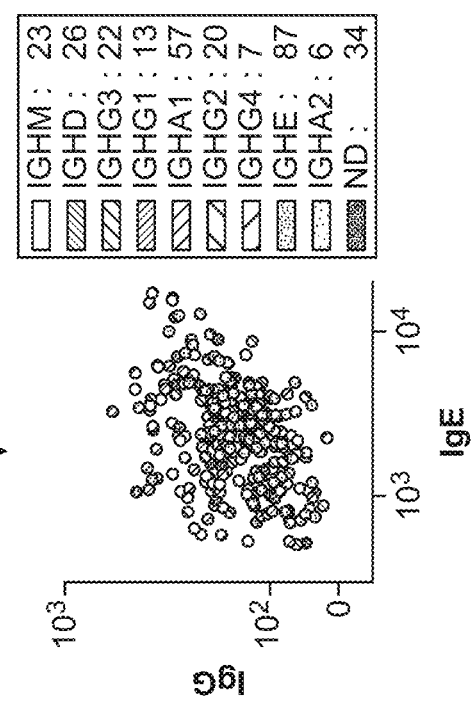
Figure 10A:
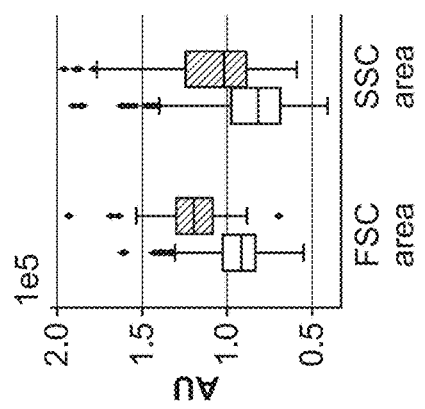
FIGS. 10A-10D. Auxiliary data supporting B cell subtype classification. PBs (striped) have greater FACS forward and side scatter (A), more cDNA after SmartSeq2 preamplification (B), and have greater gene expression of antibody light and heavy chains (C) as compared to the naive/memory B cell subset (non-striped). (D) Top differentially expressed genes for each subset.
Figure 10B:
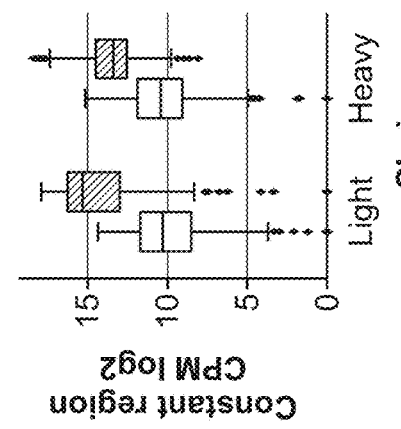
Figure 10C:
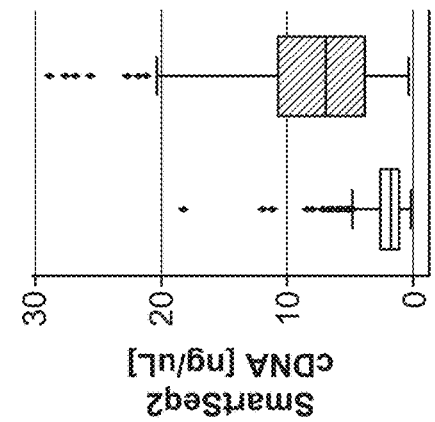
Figure 10D:
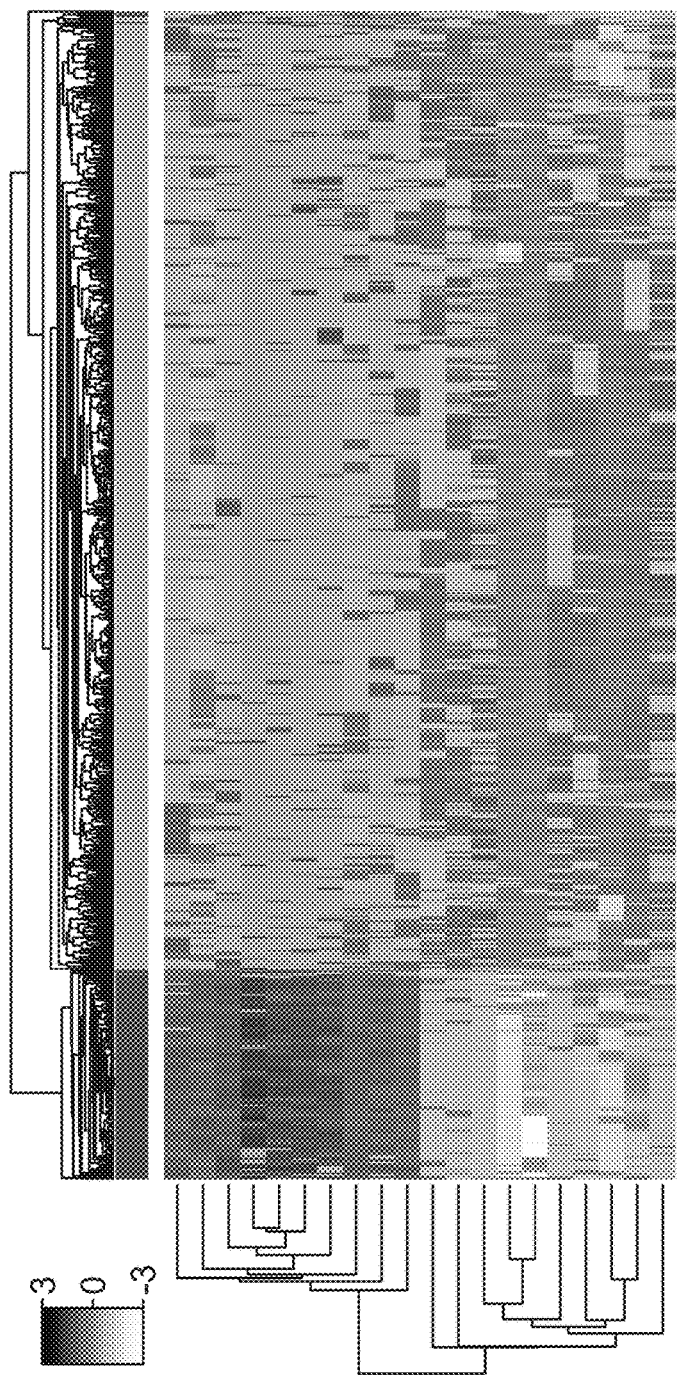
Figure 11J:
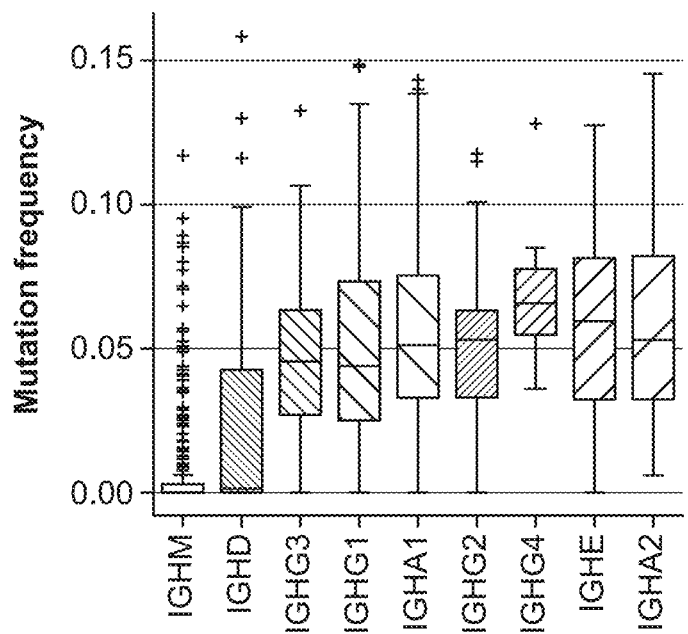
Figure 11K:
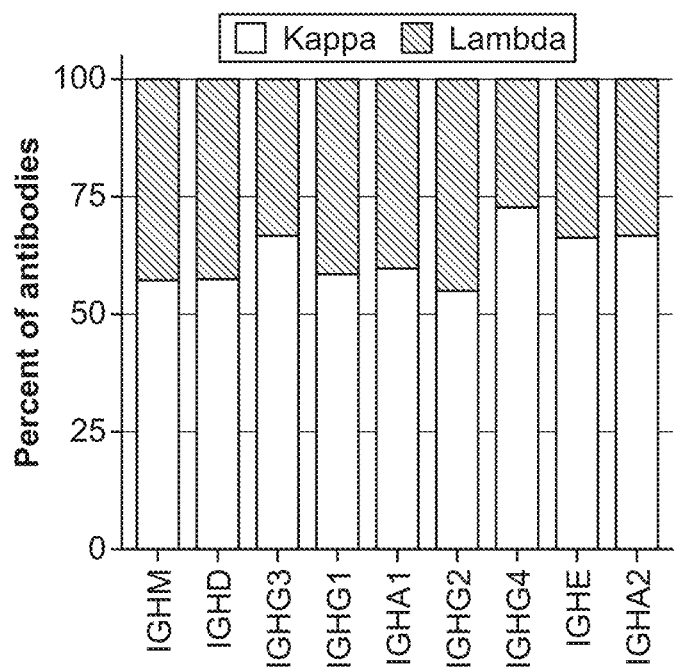

We performed scRNA-seq on B cells isolated from the peripheral blood of food allergic individuals, which enabled us to characterize each cell's gene expression, splice variants, and heavy and light chain antibody sequences (FIG. 6). Fresh peripheral blood from six peanut allergic individuals was first separated into plasma and cellular fractions; plasma was stored and later used for allergen-specific IgE concentration measurements (FIGS. 7A-7C), while the cellular fraction was enriched for B cells prior to FACS (see Materials and Methods). CD19+ B cells of all isotypes were sorted exclusively based on immunoglobulin surface expression, but with an emphasis on maximizing IgE B cell capture (FIGS. 8A-8C). Because cellular identity was determined from scRNA-seq rather than a complex, many-color gating scheme, we were able to sort and capture cells with high sensitivity. This approach makes the prospect of IgE B cell capture accessible for many laboratories without stringent requirements on FACS gate purity.

Single cells were sorted into 96 well plates, processed using a modified version of the SmartSeq2 protocol (11) and sequenced on an Illumina NextSeq with 2×150 bp reads to an average depth of 1-2 million reads per cell (FIGS. 9A-9G). Sequencing reads were independently aligned and assembled to produce a gene expression count table and reconstruct antibody heavy and light chains, respectively (FIG. 6, Materials and Methods). Using STAR (12) for alignment also facilitated the assessment of splicing within single cells. Cells were stringently filtered to remove those of low quality, putative basophils, and those lacking a single productive heavy and light chain, yielding a total of 973 cells for further analysis (Materials and Methods). The isotype identity of each cell was determined by its productive heavy chain assembly, which avoids misclassification of isotype based on FACS immunoglobulin surface staining (FIG. 8B), a problem which is especially pervasive for IgE B cells due to CD23, the "low-affinity" IgE receptor that captures IgE on the surface of non-IgE B cells (6).

Figure 2A:
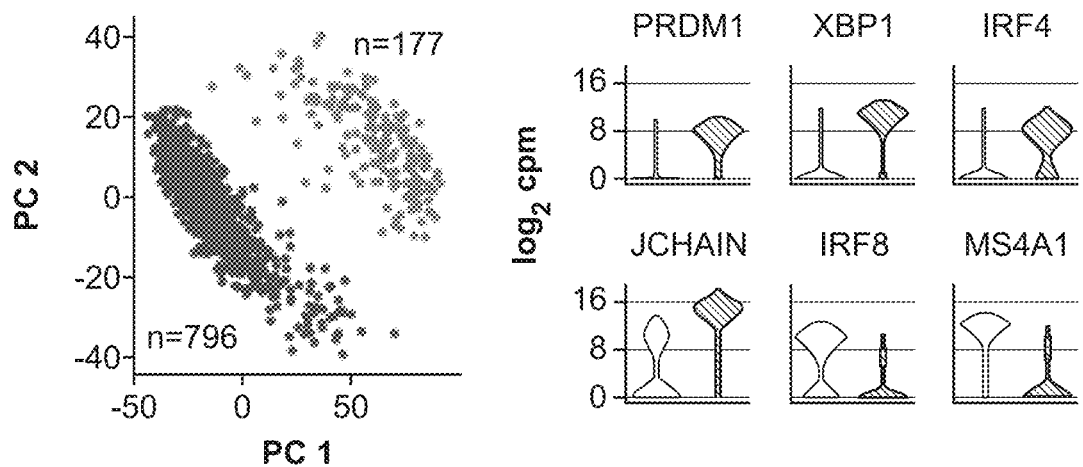
FIGS. 2A-2G. Characterization of single B cells isolated from fresh human peripheral blood. (A) Principal component analysis (left) separates naive/memory (black dots) and plasmablast (PB, gray dots) B cell subsets identified by expression of established transcription factors and marker genes (right; non-striped for naive/memory B cells and striped for plasmablast (PB) B cells). (B) Isotype of B cells, black dots for IGHE and gray dots for other isotypes. (C) Number of cells belonging to each subtype in (A) by isotype (non-striped for naive/memory B cells and striped for plasmablast (PB) B cells). (D-G) Analysis of clonal families (CFs). (D) Distribution of the number of cells per CF. (E) Fraction of cells of each isotype that belong to a multi-member CF. (F) Isotype, B cell subtype, mutational frequency, and patient of origin of each cell within multi-member CFs. CFs referred to in the text are labeled. (G) Heavy (right) and light (left) chain CDR3 sequences and similarity heatmap for CFs in (F).

Principal component analysis of normalized gene expression following batch effect correction (FIGS. 9A-9G and Materials and Methods) separated cells into two distinct clusters (FIG. 2A) identifiable as plasmablasts (PBs) and naive/memory B cells. PBs expressed the triad of transcription factors BLIMP1 (PRDM1), XBP1, and IRF4 that drive plasma cell differentiation (13), as well as genes associated with antibody secretion, such as the J chain, while naive and memory cells expressed the canonical mature B cell surface marker CD20 (MS4A1), as well as transcription factor IRF8, which antagonizes the PB fate and instead promotes a germinal center response (14). Additional data corroborated this cell subtype assignment; PBs had greater FACS forward and side scatter in agreement with their larger size and increased granularity, PB cDNA concentrations were higher following preamplification, and PBs expressed more antibody heavy and light chain transcripts (FIGS. 10A-10D).

Figures 2B, 2C:
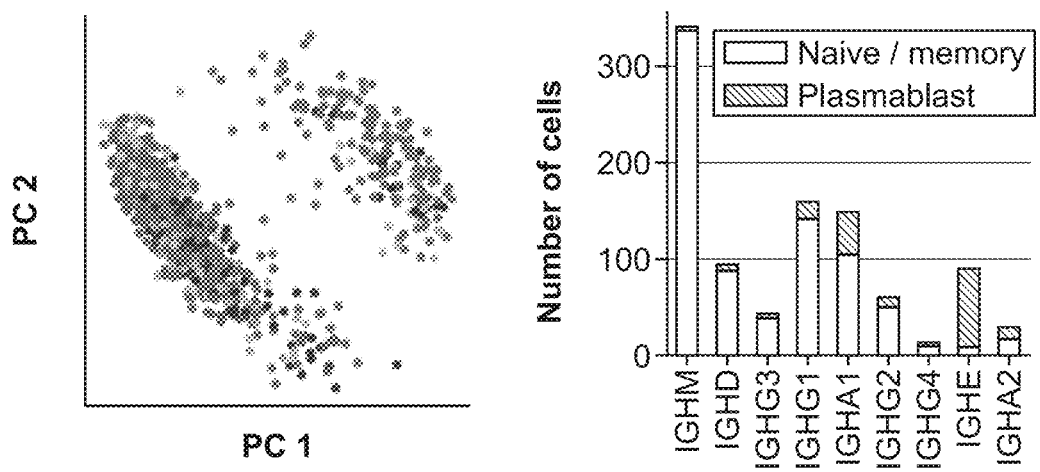

We assessed isotype distribution within each B cell subtype and found that, in stark contrast to other isotypes, IgE B cells overwhelmingly belonged to the PB subtype (FIG. 2B-2C). This discovery is consistent with observations of preferential differentiation of IgE B cells into PBs in mice (15). Subtype proportions for other isotypes followed expectations: IgM B cells, which are primarily naive, had the lowest PB percentages, while IgA B cells had the highest in accordance with their secretory role in maintaining mucosal homeostasis. Interestingly, we found that the number of circulating IgE B cells for each individual correlated with total plasma IgE levels (FIG. 7C); a similar phenomenon has been noted in cases of hyper-IgE syndrome (16).

Figure 2D:
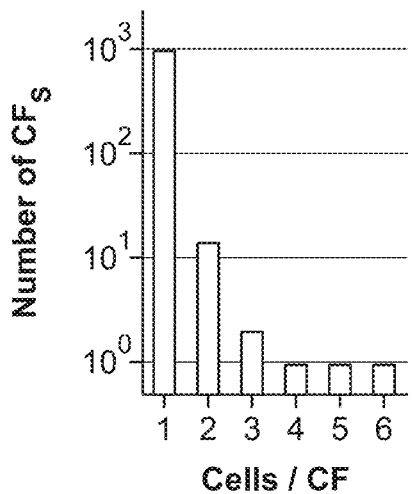
Figure 2E:
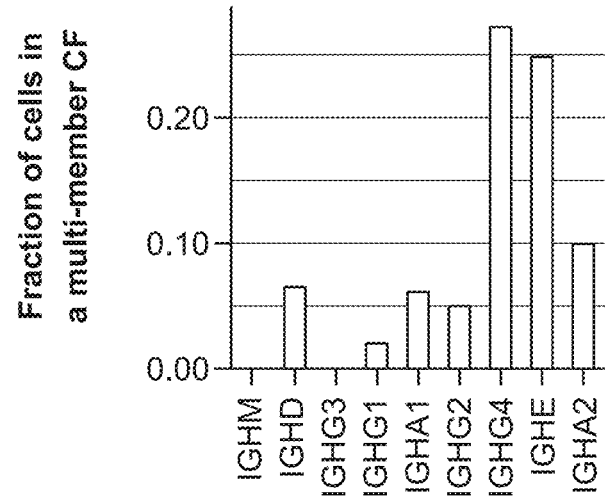
Figure 2F:
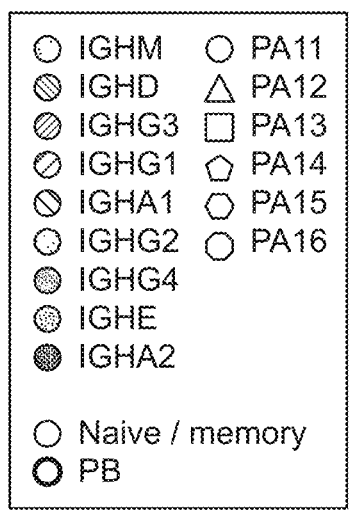
Figure 2F:
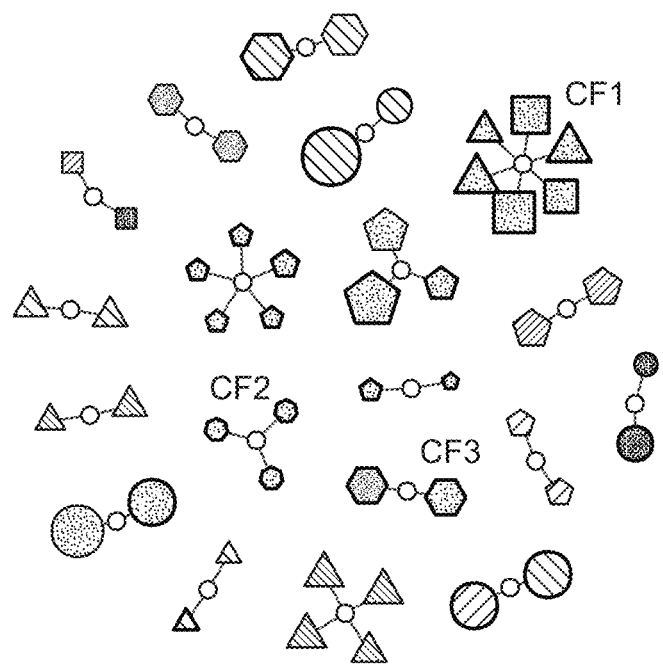
Figure 2G:
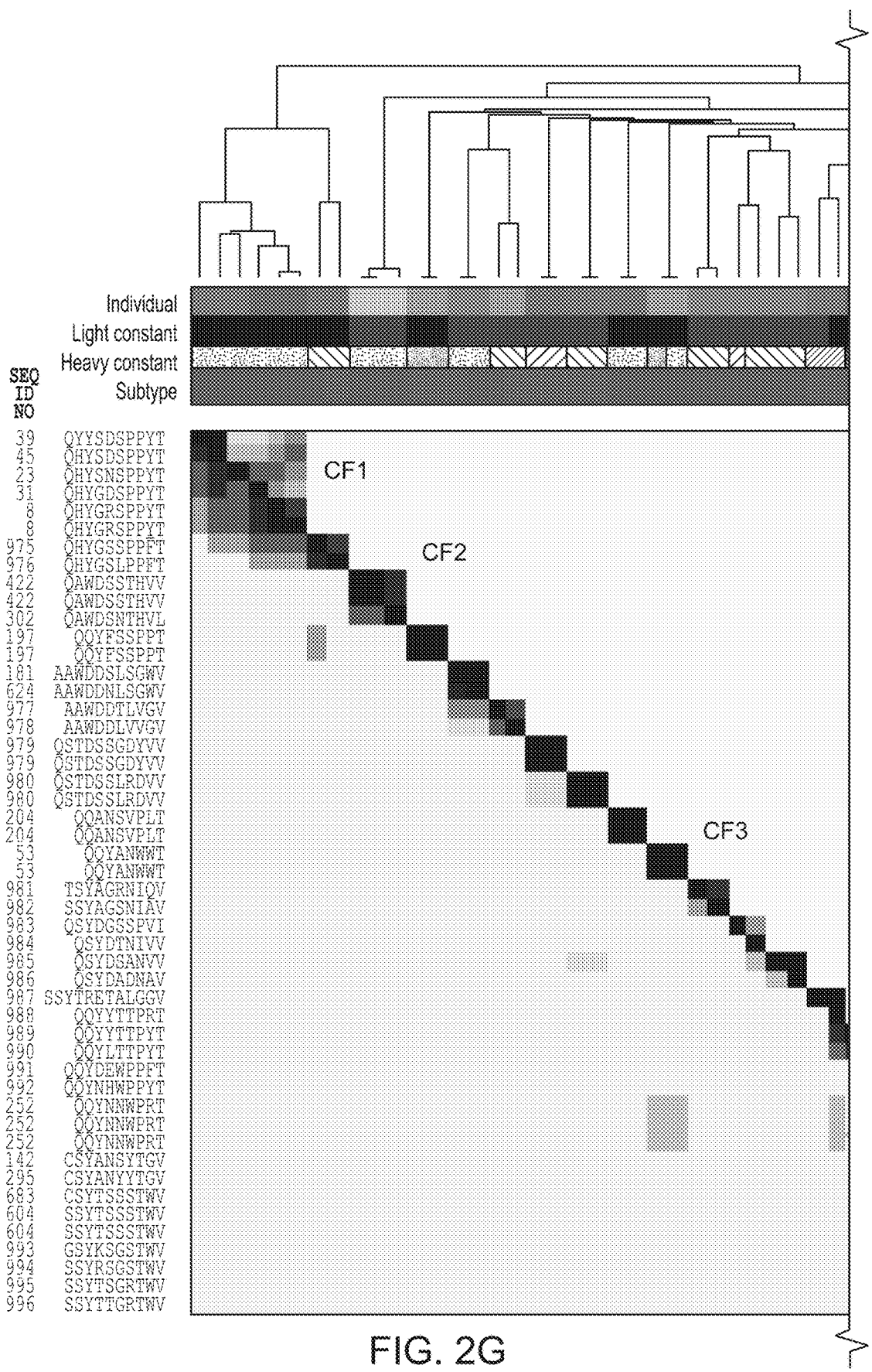
Figure 2G:
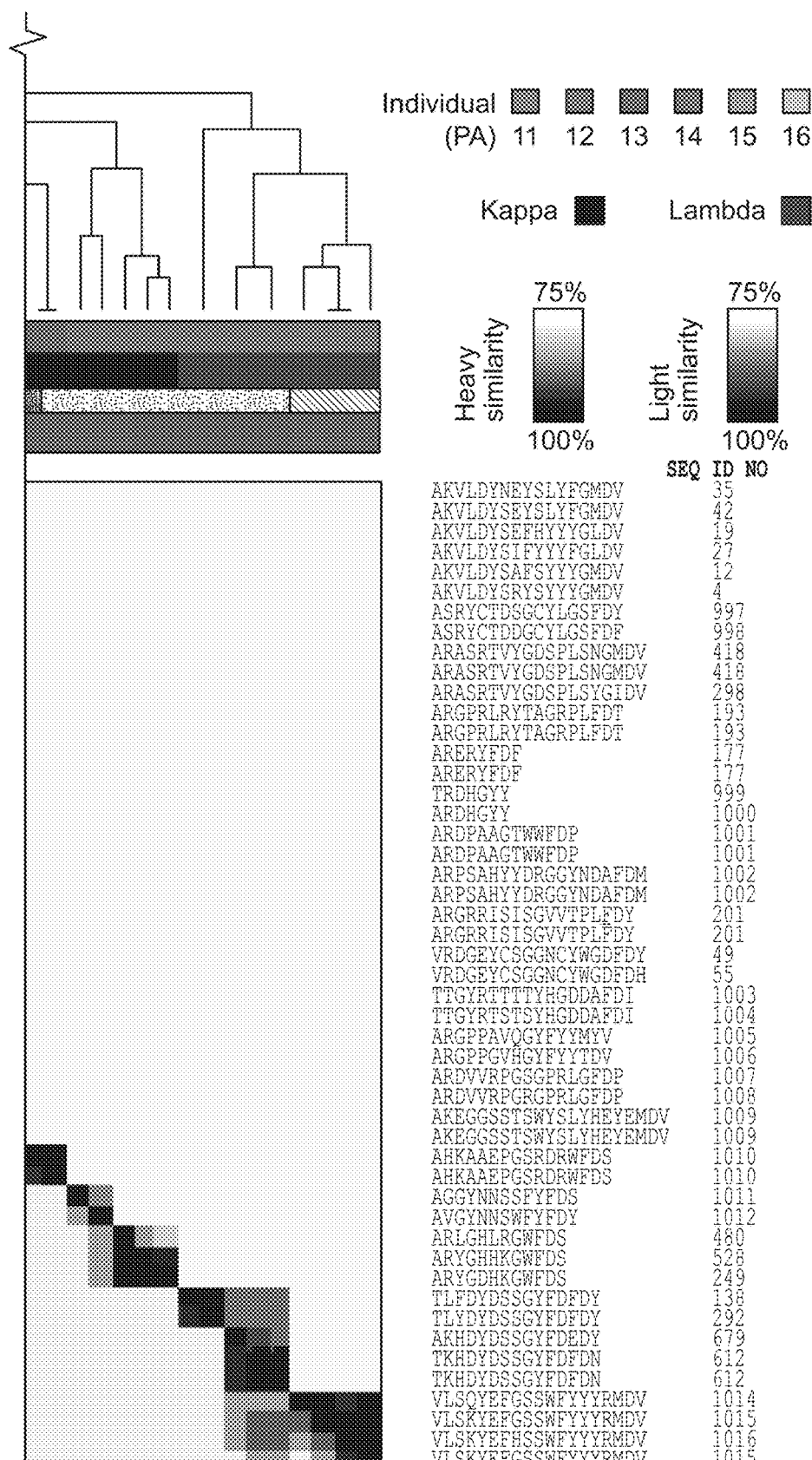

By clustering antibodies into clonal families (CFs) we were able to observe elements of classical germinal center phenomenon such as somatic hypermutation, class switching, and fate determination in our data. Antibody heavy chain sequences were first divided by V and J genes and were clustered if their amino acid CDR3 sequences shared at least 75% similarity. Only 49 heavy chains formed CFs with multiple members, although this was not surprising given the vast diversity of potential immunoglobulin gene rearrangements (FIG. 2D). We found that in contrast to other isotypes, IgE and IgG4 were surprisingly clonal as over 20% of IgE and IgG4 antibodies belonged to such multi-member CFs (FIG. 2E). Multi-member CFs were diverse; they contained between two and six sequences, had variable isotype membership (node pattern), and had a comprehensive distribution of mutational frequency (node size). CFs were specific to an individual (node shape), with the exception of one CF (CF1) that contained six heavily mutated IgE PB sequences: three each from individuals PA12 and PA13, as discussed in depth later. Four CFs illustrated the two possible terminal differentiation pathways of germinal centers in that they contained both PBs and memory B cells. Other CFs contained cells belonging to multiple isotypes, with one of particular interest (CF3), discussed later, that contained an IgE PB and an IgG4 PB. Validating the premise of CFs as a collection of cells with similar origin, we found light chain CDR3 sequences were often comparable within families (FIG. 2G).

Figure 3A:
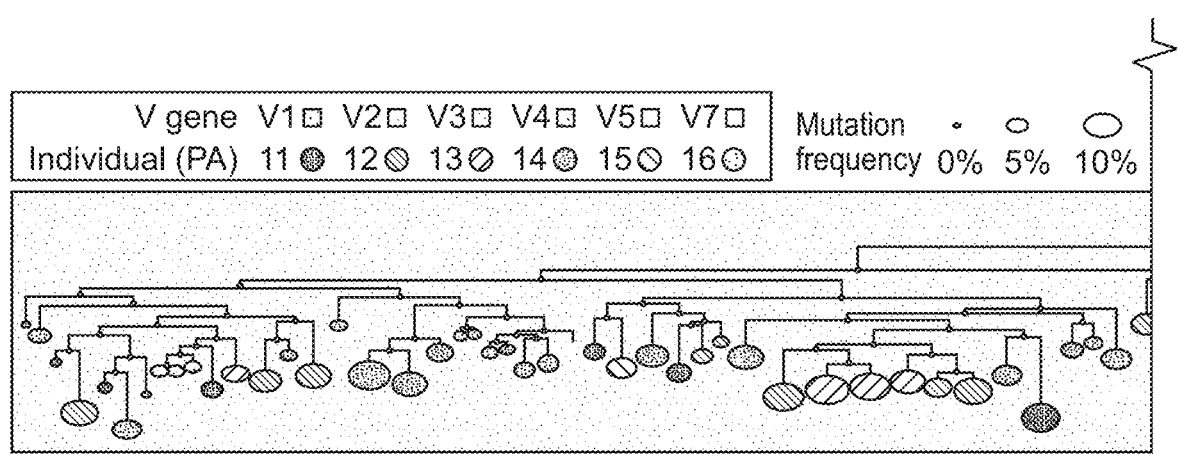
FIGS. 3A-3G. Characterization of 89 IgE antibodies from single B cells. (A) Phylogenetic depiction of antibody heavy chains arranged by IGHV gene (background pattern), patient of origin (node pattern), and mutation frequency (node size). (B) Heatmap indicating number of cells with a given heavy and light chain CDR3 length. (C) Heavy and light chain mutation frequency of each cell. (D) Silent (S) and replacement (R) mutations by region within heavy and light chains. (E) Differential gene expression between IgE PBs and PBs of other isotypes. Positive log fold change indicates genes enriched in IgE PBs. (F) Heavy chain constant region coverage histograms for naïve/memory B cells (top) and PBs (bottom) by isotype, with loci oriented in the 5' to 3' direction. Mean normalized read depth and 95% confidence interval are indicated by solid lines and shaded area, respectively, for the number of cells (n) inscribed. Membrane exons are the two most 3' exons of each isotype. (G) Summary of (F), but depicting the fraction of cells of each isotype with any membrane exon coverage.
Figure 3B:
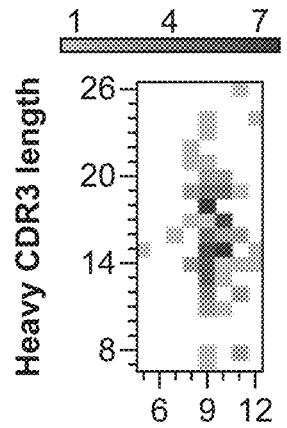
Figure 3C:
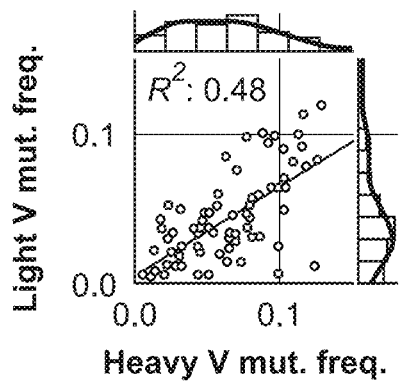
Figure 3D:
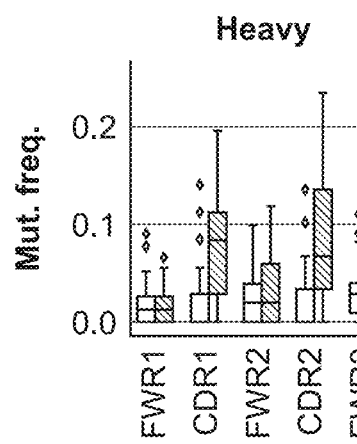

IgE antibodies varied widely in gene usage, CDR3 lengths, and mutation frequency (FIGS. 3A-3C). There was moderate correlation between the mutation frequency of heavy and light chains within single cells (FIG. 3C), with evidence of selection via an enrichment of replacement mutations relative to silent mutations in the heavy chain CDR1 and CDR2 that was absent in framework (FWR) regions. Light chains were similarly enriched for replacement mutations in the CDR1 and, to a lesser degree, FWR1 (FIG. 3D). Compared to other isotypes, IgE B cells had a similar distribution of heavy chain mutation frequency, relative utilization of the lambda versus kappa light chains, and heavy chain V and J gene usage (FIGS. 11A-11K).

B Cell Intrinsic Factors Define IgE Cell State

Figure 3F:
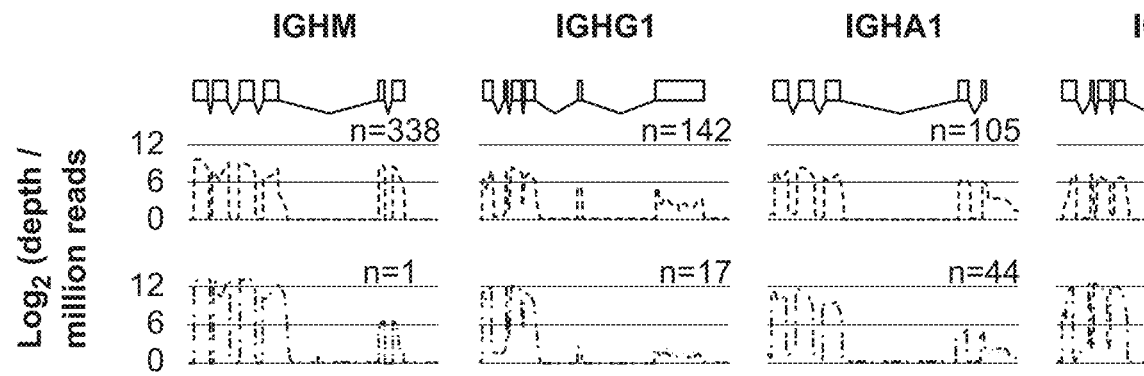
Figure 3A:
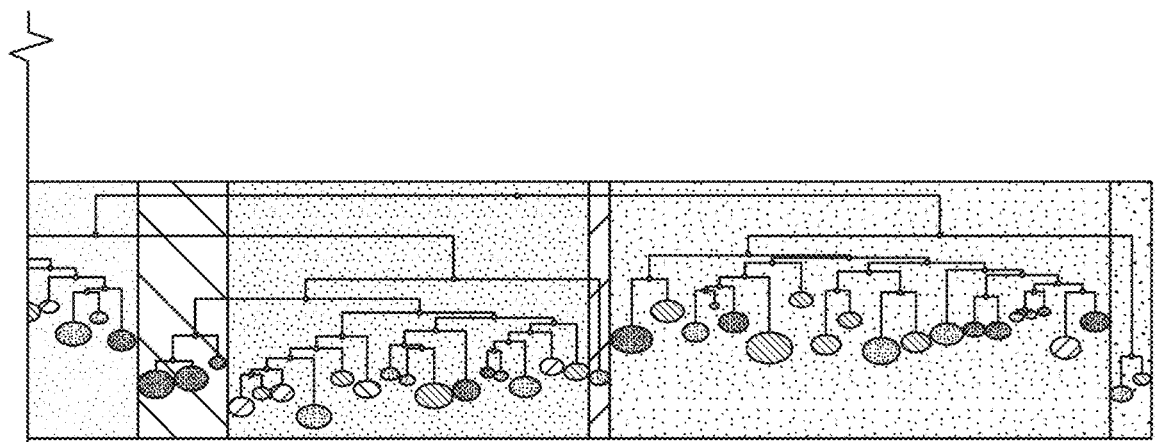
Figure 3D:
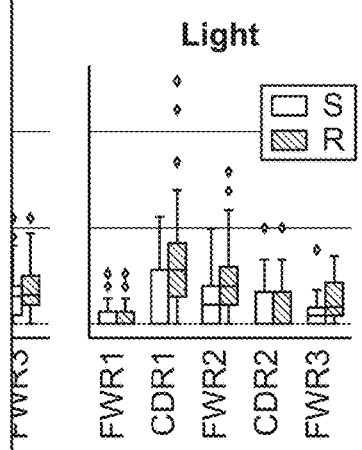
Figure 3E:
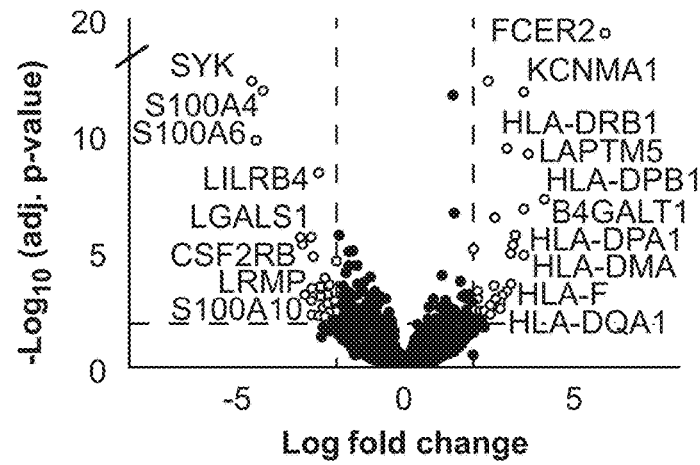
Figure 3F:
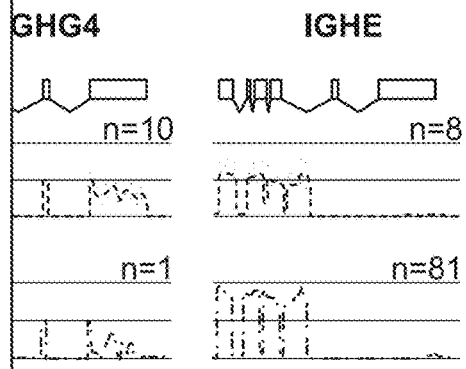

To elucidate B cell intrinsic factors affecting PB activation, survival, and differentiation, we assessed genes differentially expressed between IgE PBs and PBs of other isotypes (FIG. 3E). A host of MHC genes were robustly upregulated in IgE PBs, suggesting a more immature transcriptional program given the established loss of MHC-II during the maturation of PBs to plasma cells (17) (18) (19). FCER2 (CD23), the "low-affinity" IgE receptor was also highly upregulated, although its precise role within IgE PBs is unclear; autoinhibition of IgE production could result from membrane CD23-mediated co-ligation of membrane IgE (mIgE) and CD21 (20). IgE production could also be upregulated through antagonistic effects of soluble CD23 (21), which is produced following cleavage by ADAM10 (22), a disintegrin and metalloproteinase domain-containing protein that we find is co-expressed in a subset of IgE PBs. LAPTM5, a negative regulator of B cell activation, BCR expression, and antibody production (23), was upregulated, which suggests compromised activation and proliferation capacity of IgE PBs. Downregulated genes included LILRB4 (24), galectin 1 (LGALS1), which supports plasma cell survival (25), and the S100 proteins S100A4, S100A6, and S100A10, which may indicate reduced proliferative and survival signaling (26,27). One of the most significantly downregulated genes in IgE PBs was spleen associated tyrosine kinase (SYK), which plays an essential role in BCR signal transduction (28) and is necessary for naïve differentiation into plasma cells and for memory B cell survival (29). Taken together, this gene expression program shows that the IgE PB cell state is immature relative to other PBs with weakened activation, proliferation, and survival capacity. It also provides a potential transcriptomic mechanism for the hypothesized short-lived IgE PB phenotype described in mouse models of allergy (15).

B cell intrinsic factors also regulate IgE production in murine models via impaired memory formation (30,31).

Figure 3G:
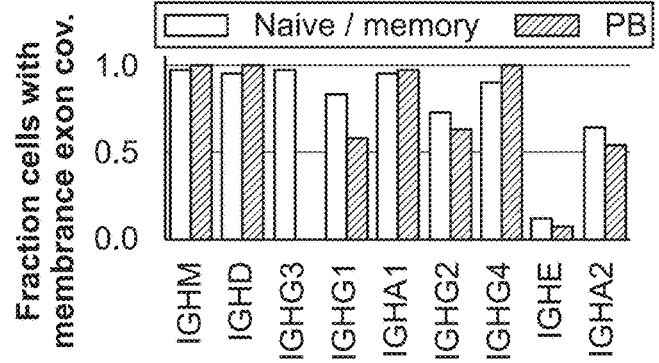

Indeed, we found human IgE B cells belonging to the naïve/memory subset were deficient in heavy chain membrane immunoglobulin exon splicing compared to other common isotypes. Furthermore, membrane exon splicing was detected at low levels in non-IgE PBs, but not in IgE PBs (FIGS. 3F and 3G). In fact, the absence of mIgE splicing rendered us unable to assess the relative utilization of the two splice variants of mIgE known to have distinct signaling characteristics (32,33). The lack of mature mIgE transcripts could be explained by poor processing of pre-mRNA (34) and is consistent with low IgE surface protein we measured by FACS; indeed, mIgE surface protein levels on true IgE B cells did not exceed those of some non-IgE B cells presumably displaying surface IgE as a result of CD23-mediated capture (FIG. 8B). Together, these results suggest that the scarcity of circulating memory IgE B cells in vivo could result from impaired membrane IgE expression that compromises IgE B cell entry into the memory compartment and/or memory B cell survival. Murine studies support such a hypothesis, having shown IgE responses are reduced by removal or modification of mIgE domains, but augmented by the exchange of these domains for those of IgG1 (35).

Characterization of Peanut-Specific IgE and IgG4 Antibodies

Surprisingly, our clonal analysis produced one CF of cells belonging to multiple individuals (CF1, FIGS. 2F and 2G), which contained three IgE PBs from individual PA12 and three IgE PBs from individual PA13. The antibodies produced by these six cells were highly similar as all utilized the IGHV3-30*18 and IGHJ6*02 heavy chain genes as well as the IGKV3-20*01 and IGKJ2*01 light chain genes, with pairwise CDR3 amino acid sequence identity ranging from 65% to 94% for the heavy chain and 70% to 100% for the light chain. These antibodies were also highly mutated and enriched in replacement mutations within the complementarity determining regions of both chains (FIG. 4A). In fact, compared to all other class switched antibodies, these were amongst the most mutated: the heavy chains were in the 76th percentile or above for mutation frequency, while all of the light chains were in the 96th percentile or above (FIG. 4B).

We recombinantly expressed the six IgE antibodies belonging to this convergent clonal family in order to assess whether they bind the natural forms of the major allergenic peanut (*Arachis hypogaea*) proteins Ara h 1, Ara h 2, or Ara h 3. Of all characterized peanut allergens, Ara h 2 is the most commonly recognized by allergic individuals and is the most clinically relevant both in terms of immunological response (36) and discriminating allergic status (37,38). Using an indirect ELISA as a semi-quantitative screen for binding, we found these six antibodies bound strongly to Ara h 2, moderately to Ara h 3, and very weakly to Ara h 1 (FIGS. 12A-12H). We then used biolayer interferometry to determine dissociation constants of each antibody for Ara h 2 and Ara h 3, with resulting affinities of 17 picomolar (pM) to sub-pM for Ara h 2 and micromolar to sub-nanomolar for Ara h 3 (FIG. 4C and FIGS. 12A-12G). These affinities are comparable to some of the highest affinity native human antibodies discovered for pathogens such as HIV, influenza, and malaria (39-43). Additionally, high affinity to multiple peanut allergens should be advantageous if such antibodies or variants thereof were to be used therapeutically as blocking antibodies intended to outcompete endogenous IgE for allergenic protein, an approach recently shown to be efficacious for treatment of cat allergy (44).

To investigate the degree to which each chain and the mutations therein affect the binding properties, we recombinantly expressed eight variants of antibody PA13P1H08, each with one or more regions in the heavy and/or light chain reverted to the inferred naïve rearrangement. Reversion of the heavy chain CDR3 was performed based on the aforementioned heavy chain V and J gene segments as well as the IGHD4-11*01 D gene and inferred nontemplated nucleotides TYCT between the V and D genes. Reversion of the light chain CDR3 was performed based on the aforementioned light chain V and J genes. Retaining the native heavy chain while swapping the light chain with another kappa light chain abrogated binding to both allergenic proteins, while reverting both chains eliminated Ara h 3 specificity and dramatically reduced Ara h 2 affinity (FIG. 4C). Reverting only the heavy or light chain reduced the affinity to Ara h 2 and Ara h 3, but disproportionately; light chain mutations contributed more to Ara h 3 affinity than did heavy chain mutations. We also found a synergistic contribution of heavy chain mutations to affinity as independent reversion of the CDR1, CDR2, CDR3 or framework region(s) each caused minor decreases in affinity. Interestingly, reversion of the heavy chain CDR2 increased Ara h 3 affinity, while only marginally decreasing Ara h 2 affinity. These results indicate that the naively recombined antibody sequence is capable of binding the most clinically relevant peanut allergen Ara h 2, but mutations, especially in the light chain, are necessary for generating high affinity antibodies which are cross-reactive towards Ara h 3. More broadly, this shows that two unrelated individuals produced an identically rearranged naive B cell that bound Ara h 2 and underwent class switching, affinity maturation, differentiation, and clonal expansion, eventually resulting in the presence of multiple circulating IgE PBs secreting high affinity antibodies with cross-reactivity towards Ara h 3.

We also expressed antibodies from two other CFs. CF2 contained three IgE PBs from individual PA16 (two of which were identical), but their recombinantly expressed antibodies did not bind Ara h 1, 2, or 3, which was unsurprising given this individual had low plasma peanut-specific IgE levels as well as IgE specific to other allergens (FIGS. 7A-7C). On the other hand, CF3 contained an IgE PB (PA15P1D05) and IgG4 PB (PA15P1D12), the recombinantly expressed antibodies from which did not bind Ara h 1, but bound Ara h 3 with nanomolar affinity and Ara h 2 with sub-nanomolar affinity (FIGS. 12A-12H). Interestingly, these two antibodies utilize the same light chain V gene and a highly similar heavy chain V gene (IGHV3-30-3*01) as the six convergent antibodies of CF1, which provides additional support for the importance of these V genes in Ara h 2 binding. Moreover, the presence of peanut-specific IgE and IgG4 in the same CF within an allergic individual provides a unique example of antagonist cell fate given the roles of IgE and IgG4 in allergic reactivity and potentially decreased sensitization, respectively.

Polarized Germline Transcription and Class Switch Priming

Figure 14:
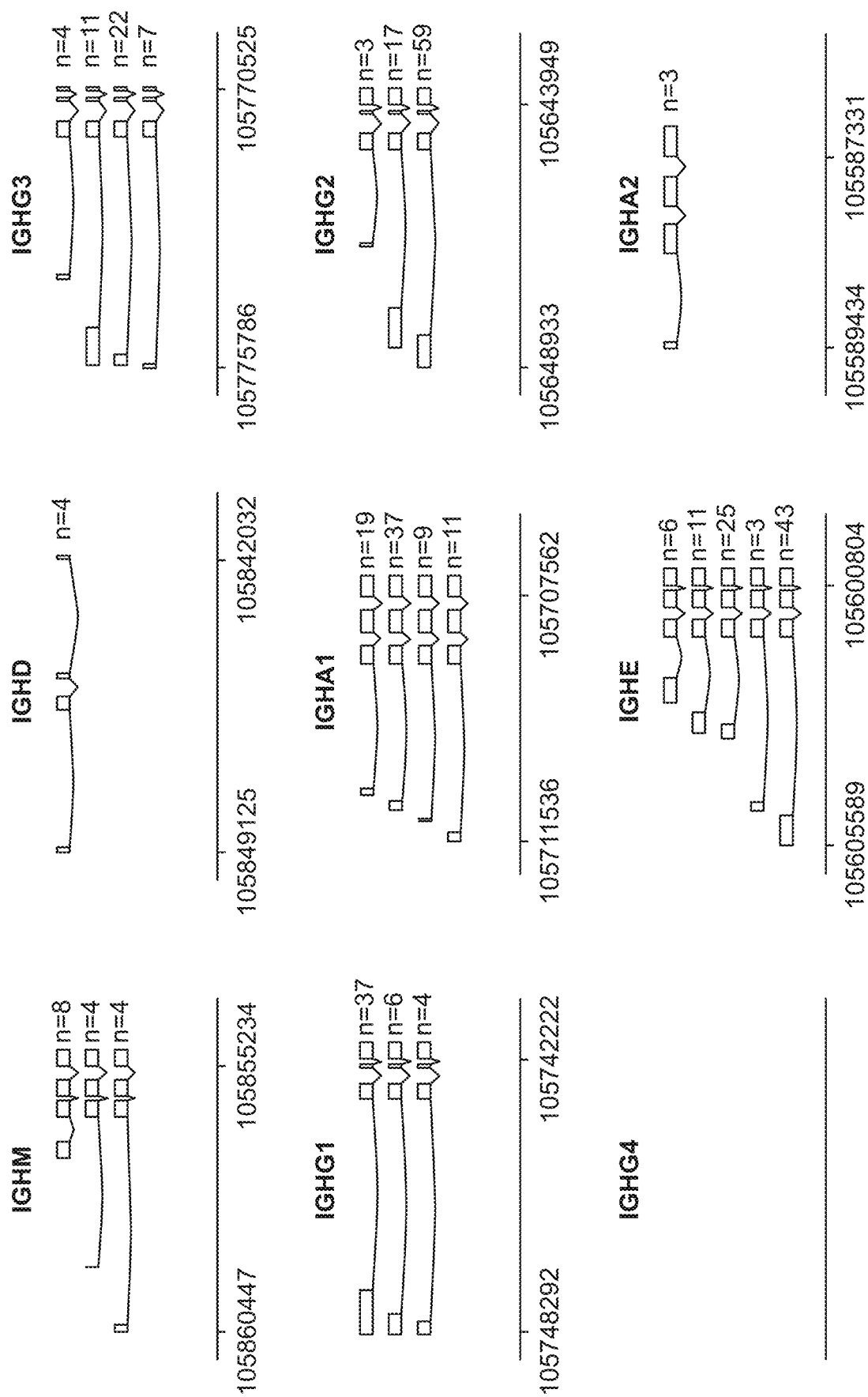
FIG. 14. GLT splicing for all isotypes. Note that only the first three constant region exons are shown for each isotype for clarity.

Tailored responses of the adaptive immune system are possible in part due to the ability of activation-induced cytidine deaminase (AID) to initiate class switch recombination (CSR) in B cells, leading to the production of antibodies with specific effector functions. CSR is preceded by cytokine-induced germline transcription, where nonproductive germline transcripts (GLTs) that contain an I-exon, switch (S) region, and heavy chain constant region exons guide AID to the S region (45). Importantly, GLT processing is necessary for CSR (46,47) and canonically results in two species: an intronic S region lariat and a mature polyadenylated transcript consisting of the I exon spliced to the constant region exons (48). In our scRNA-seq data, we observe multiple splice isoforms of the latter, where the proximal constant region exon serves as the exclusive splice acceptor for multiple splice donors. IgE had the largest number of distinct GLTs at five (FIG. 5A and FIG. 14), which we confirmed through Sanger sequencing; these were expressed in numerous cells of varying isotypes and across all individuals, but at nonuniform frequencies (FIG. 5A). The 1-exon was the most common splice donor site (FIG. 5A, GLT #1) and it is known that 1-exons can provide multiple splice donors (49-51), but εGLT splice donors within the switch region were also observed.

Figure 15:
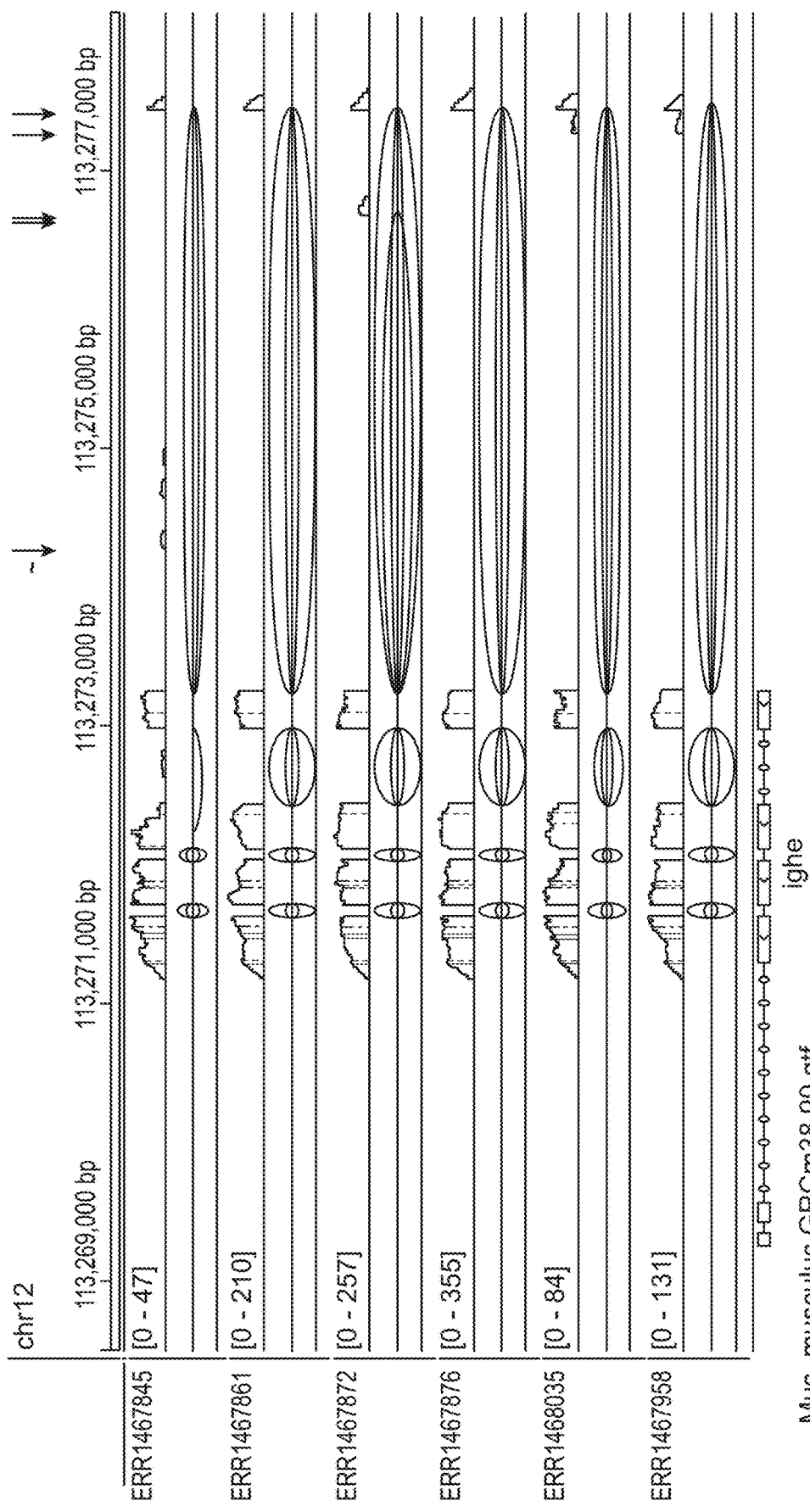
FIG. 15. IGV coverage histograms and splice junctions for the ighe constant region locus showing εGLTs in single murine B cells stimulated with IL-4, LPS, and BAFF (Wu et al. 2017). Arrows indicate ighe GLT splice donors.

We found independent evidence for multiple IgE GLT splice donors in a previously published scRNA-seq dataset from murine B cells harvested 24 h after simulation to class switch (52) (FIG. 15). We also assessed variation in the isotypes expressing εGLTs. The IgG4 isotype had the highest proportion of cells expressing an εGLT (FIG. 5B), while IgE B cells themselves also commonly expressed εGLTs. The remainder of isotypes had fairly low expression of εGLTs.

GLT production is not limited to the IgE locus; we extended our analysis to all isotypes, enabling the construction of a global class switch priming state diagram (FIG. 5D) that illustrates the fraction of cells of each isotype that produce a GLT of their own (self) or another isotype. We observe that, in contrast to IgE, we find almost no IgG4 GLT expression in these allergic individuals. We also observe elevated IgG2 GLT production, which can be explained by splicing of the CH1 IgG2 exon to an upstream lincRNA. Interestingly, we observe that GLT expression arising from the alternate allele is common, as evidenced by common expression of IgM GLTs as well as GLTs of other isotypes upstream of a class switched isotype (signal below the diagonal in FIG. 5D). Mirroring the landscape of human class switching (53), we observe the trend for GLT production to be higher for proximal downstream isotypes rather than distant downstream isotypes. Unlike previous reports (54), we found that cells with GLT expression tend to be polarized towards the expression of a single GLT isotype, although we did not detect any non-self GLT production in most cells (FIG. 5E).

The study of B lymphocyte transcriptomes at single cell resolution offers other advantages; for example, we discovered multiple instances of biallelic GLT expression though heavy chain constant region haplotype phasing in single B cells from in individuals who had heterozygous single nucleotide variants within these loci. An example of this process that demonstrates biallelic εGLT expression is shown in FIG. 5C.

Characterization of Tree Nut-Specific IgE and IgG4 Antibodies

Given that some subjects had plasma IgE against other allergens in addition to peanut (FIG. 7A), we assessed whether recombinant monoclonal antibodies from subjects PA11, PA12, PA13, PA14, PA15, and PA16 bound to allergen extracts derived not only from peanut, but other allergents as well, including cashew, pistachio, latex, BSA, soy, sesame, milk, egg, almond, pine nuts, pecan, walnut, hazelnut, and macadamia. The results of an indirect ELISA are shown in FIG. 12H. A total of 89 antibodies were tested, although only those with any OD value above 0.25 are shown in FIG. 12H. Antibodies not depicted include: PA12P1D04, PA12P1G02, PA16P1B09, PA16P1E11, PA16P1E12, PA11P1C01, PA11P1C12, PA11P1C06, PA11P1C08, PA11P1D07, PA11P1E08, PA11P1F10, PA11P1F02, PA11P1G06, PA11P1G07, PA13P2H10, PA15P1C03, PA15P1E01, PA15P1E02, PA13P1C01, PA13P1C09, PA13P1D02, PA13P1E06, PA14P1C10, PA14P1C12, PA14P1C02, PA14P1C04, PA14P1C06, PA14P1C07, PA14P1C08, PA14P1D10, PA14P1D02, PA14P1D07, PA14P1D09, PA14P1E10, PA14P1E11, PA14P1E12, PA14P1E04, PA14P1E06, PA14P1E08, PA14P1E09, PA14P1F10, PA14P1F11, PA14P1F05, PA14P1F07, PA14P1G01, PA14P1G11, PA14P1G12, PA14P1G03, PA14P1H01, PA14P1H11, PA14P1H12, PA14P1H02, PA14P1H05, PA14P1H09, PA12P3C05, PA12P3C09, PA12P3D11, PA12P3D09, PA12P3E06, PA12P3E07, PA12P3F02, PA12P3F07, PA13P3G04, PA14P3F10, PA14P3F02, PA14P3H10, PA14P3H12, PA12P4G03, and PA12P4G06.

As shown in FIG. 12H, several antibodies exhibited specificity for multiple tree nut allergens. The antibody PA14P3H08 bound strongly to pecan, walnut, hazelnut, and macadamia allergens; the antibody PA11P1D11 bound to pecan, walnut, and macadamia allergens; the antibodies PA11P1E01, PA11P1C11, and PA11P1C03 each strongly bound to cashew and pistachio allergens; and the antibody PA11P1C04 more weakly bound to cashew and pistachio allergens. Some antibodies exhibited specificity for both peanut and tree nut allergens. For example, the antibody PA11P1G10 strongly bound to both pecan and walnut allergens and also bound (albeit more weakly) to peanut allergen, while the antibody PA12P4D02 strongly bound to peanut allergen and more weakly bound to walnut allergen while not binding natural peanut allergen Ara h 2. Other antibodies exhibited specificity for a single tree nut allergen. For example, antibody PA11P1G04 bound to pistachio allergen, PA11P1F03 bound to pecan allergen, and PA11P1D12 bound to macadamia allergen. Furthermore, additional peanut-specific antibodies were discovered during these experiments. Antibodies PA12P3E09 and PA12P3E11 bound peanut extract with little to no binding to natural peanut allergen Ara h 2, while antibodies PA12P1D02, PA12P1G11, PA13P1H03, PA12P3C01, and PA12P3E04 bound strongly to both peanut extract and natural peanut allergen Ara h 2.

Conclusion

Using scRNA-seq, we provide the first transcriptomic characterization of circulating human IgE B cells and the antibodies they produce. Our data suggests two mechanisms underlying IgE regulation in humans: membrane immunoglobulin expression deficiency and an IgE PB gene expression program suggestive of weakened activation, proliferation, and survival capacity. These results are largely consistent with extensive studies of mIgE signaling and IgE memory in murine models of allergy, and provide evidence supporting the use of animal models for this disease. (55-59). Furthermore, the ability to capture GLT splice variant, polarization, and biallelic expression information within single B cells presents an exciting application of scRNA-seq for future mechanistic studies of GLT and CSR.

Insight into convergent evolution of high affinity antibodies in unrelated individuals can guide vaccine design and lead to strategies for population-level passive immunity; it is also a process that has been argued to occur in response to a number of pathogens such as influenza (60), HIV (43), and *Streptococcus pneumoniae* (61). Here we found a striking case of convergence where two unrelated individuals produced high affinity, cross-reactive, peanut-specific antibodies comprised of identical gene rearrangements within respective heavy and light chains. A third individual has Ara h 2-specific antibodies that utilize a similar heavy V gene and the same light chain V gene. Although this is a small sample size, there is evidence supporting the importance of these genes within the peanut-allergic population more broadly: one independent dataset of IgE heavy chain sequences from peanut allergic individuals (62) contains IgE heavy chains that utilize identical V and J genes and share at least 70% CDR3 identity with one or more of the six convergent antibodies in our dataset (FIG. 16); another dataset (9) contains Ara h 2 specific antibodies belonging to IgG and IgM B cells that utilize similar IGHV3-30 genes.

Cross-inhibition experiments with purified allergens and plasma IgE have shown that cross-reactivity of IgE antibodies may also be common within peanut allergic individuals (63) and the antibodies we have isolated here offer a clear example of these findings. Furthermore, the fact that these high affinity antibodies were being produced by secretory IgE PBs found in circulation contributes to an understanding of how minute amounts of allergen are capable of eliciting severe allergic reactions. We also expect that either these antibodies themselves or engineered variants of them may find application as therapeutics; recent clinical results have shown that engineered allergen-specific IgG antibodies can be administered to humans and provide effective treatment for cat-whisker allergies, perhaps by outcompeting the native IgE for antigen (44).

Methods

Study Subjects

All study subjects were consented and screened through the Stanford IRB approved-protocol. Participants were eligible if they had a peanut allergy confirmed by an oral food challenge and board certified allergist. Peanut allergic individuals with reported reactivity to peanut ranged in age from 8 to 17, and in some cases exhibited sensitivities to other food allergens (FIGS. 7A-7C).

Plasma IgE Measurement and B Cell Isolation

Both plasma and cellular fractions were extracted from up to 45 mL of fresh peripheral blood collected in K2 EDTA tubes. For plasma extraction, blood was transferred to 15 mL falcon tubes and spun at 1600 g for 10 min. The upper plasma layer was extracted, transferred to 2 mL Eppendorf protein LoBind tubes and spun again at 16000 g to further purify the plasma fraction. The resulting supernatant was moved to fresh tubes before being put on dry ice and later transferred to −80° C. Allergen-specific plasma IgE measurements were performed by CLIA-licensed Johns Hopkins University Dermatology, Allergy, and Clinical Immunology (DACI) Reference Laboratory using the ImmunoCAP system. To purify B cells remaining after plasma extraction, RosetteSep human B cell enrichment cocktail (Stemcell Technologies), a negative selection antibody cocktail, was added after the plasma fraction was replaced with PBS+2% fetal bovine serum (FBS). After a 20 min incubation, the blood was then diluted two-fold with PBS+2% FBS before being transferred to Sepmate 50 mL tubes (Stemcell Technologies) containing 15 mL Ficoll-Plaque PLUS (GE Healthcare Life Sciences). An enriched B cell population was achieved after a 10 min, 1200 g spin with the brake on and transferred a fresh tube. Residual red blood cells were then removed using ACK lysis buffer (ThermoFisher) and cells were washed with stain buffer (BD Biosciences). Cells were stained on ice with the following BioLegend antibodies according to the manufacturer's instructions: PE anti-human IgE clone MHE-18, Brilliant Violent 421 anti-human CD19 clone HIB19, APC anti-human IgM clone MHM-88, and Alexa Fluor 488 anti-human IgG clone M1310G05. Cells were washed twice more prior to sorting.

Flow Cytometry and Single Cell Sorting

Single cell sorts were performed on a FACSAria II Special Order Research Product (BD Biosciences) with a 5 laser configuration (355, 405, 488, 561, and 640 nm excitation). Fluorophore compensation was performed prior to each sort using OneComp eBeads (ThermoFisher), although minimal compensation was required due to the fluorophore panel and laser configuration. Equivalent laser power settings were used for each sort. Cells were sorted using "single cell" purity mode into chilled 96 well plates (Biorad HSP9641) containing lysis buffer (11) and ERCC synthetic RNA spike-in mix (ThermoFisher). Plates were spun and put on dry ice immediately before storage at −80° C.

cDNA Generation, Library Preparation, and Sequencing

A modified version of the SmartSeq2 protocol (64) was used as previously described (11). In total, 1165 cells were sequenced across 5 runs using 2×150 bp Illumina High Output kits on an Illumina NextSeq.

Sequencing Read Alignment, Gene Expression, and Splicing

Sequencing reads were aligned to the genome in order to determine gene expression, identify splice variants, and assess read coverage. To produce the gene expression counts table, reads were first aligned to the GRCh38 human genome using STAR v2.5.3a (12) run in 2-pass mode. Gene counts were then determined using htseq-count (65) run in intersection-nonempty mode. The GTF annotation file supplied to both STAR and htseq-count was the Ensembl 90 release manually cleaned of erroneous Ig transcripts e.g. those annotated as either a V gene or constant region but containing both V gene and constant region exons. During STAR genome generation an additional splice junction file was provided that included splicing between all combinations of heavy chain CH1 exons and IGHJ genes to improve read mapping across these junctions. Gene expression was normalized using log 2 counts per million after removing counts belonging to ERCCs. Cells with fewer than 950 expressed genes were excluded prior to analysis, as were putative basophils, identified by high FACS IgE, absent or poor quality antibody assemblies, and expression of histidine decarboxylase (HDC) and Charcot-Leyden crystal protein/Galectin-10 (CLC). Batch effects mostly affecting the naive/memory B cell subset were noted between sorts by clustering using PCA on the 500 most variable genes; this gene set was enriched in genes known to be affected by sample processing such as FOS, FOSB, JUN, JUNB, JUND, HSPA8 (66). PCA following the exclusion of genes differentially expressed between sort batches (Mann-Whitney test, p-value<0.01 after Bonferroni correction) yielded well-mixed populations within both the naive/memory and PB cell clusters not biased by sort batch, individual, or sequencing library (FIG. 9G). For differential expression analysis between IgE and non-IgE PBs, genes expressed in at least 10 PBs were analyzed by voom-limma (67) with sort batch and sequencing library were supplied as technical covariates. Constant region genes, such as IGHE and IGHA1, were excluded given these are differentially expressed by design of the comparison being made.

Analysis of splicing, including GLT expression, relied upon splice junctions called by STAR. Junctions were discarded if they contained fewer than three unique reads and GLT splice donors were only considered if observed in at least three cells. Biallelic expression of GLTs was determined based on heterozygous expression of variants discovered within heavy chain constant regions using bcftools (68).

Antibody Heavy and Light Chain Assembly

In addition to alignment, sequencing reads were also independently assembled in order to reconstruct full length heavy and light chain transcripts. BASIC (69) was used as the primary assembler given its intended use for antibody reconstruction, while Bridger (70), a whole transcriptome assembler, was used as an alternative when BASIC did not assemble a functional heavy and/or light chain. The heavy chain isotype or light chain type (lambda or kappa) was determined using a BLAST (71) database of heavy and light chain constant regions constructed from IMGT sequences (72). Here it is important to note the necessity of isotype determination using heavy chain transcript presence rather than FACS immunoglobulin surface staining: only 30% of B cells in the IgE B cell sort gate were in fact producing IgE transcripts (FIG. 8B). This likely results from the presence of surface-bound IgE captured by CD23 on non-IgE B cells, and while acid-washing can remove IgE bound by CD23 (73), we avoided this harsh treatment in order minimize transcriptomic perturbations to the cells. Immunoglobulin variable domain gene segment assignment was performed using IgBLAST (74) v1.8.0 using a database of human germline gene segments from IMGT. IgBLAST output was parsed with Change-0 and mutation frequency was called with SHazaM (75). Cells without a single productive heavy and single productive light chain, which were all members of the naive/memory cell cluster, were excluded, leaving a final total of 973 cells. The workflow engine Snakemake (76) was used to execute these analysis pipelines.

Recombinant Antibody Expression

Select antibodies were expressed recombinantly for specificity and affinity assays. All heavy chains were expressed as human IgG1, while light chains were expressed as either lambda or kappa as appropriate. Heavy and light chain sequences were synthesized by Genscript after codon optimization and were transiently transfected in HEK293-6E cells. Antibodies were purified with RoboColumn Eshmuno® A columns (EMD Millipore) and were confirmed under reducing and non-reducing conditions by SDS-PAGE and by western blots with goat anti-human IgG-HRP and goat anti-human kappa-HRP or goat anti-human lambda-HRP as appropriate.

Functional Antibody Characterization

ELISAs were performed one of two ways. For antibodies derived from CF1, CF2, or CF3, purified peanut allergens were used to semi-quantitatively assess peanut allergen binding. Purified natural Ara h 1 (NA-AH1-1), Ara h 2 (NA-AH2-1) and Ara h 3 (NA-AH3-1), purchased from Indoor Biotechnologies, were immobilized overnight at 4° C. using 50 μL at a concentration of 2 ng/μL. Following 3 washes, wells were blocked with 100 μL of PBST (ThermoFisher)+2% BSA for 2 hours. After two washes, 100 μL of primary antibodies were incubated for 2 hours at a concentration of 2 ng/μL in blocking buffer. Following 4 washes, 100 μL of rabbit anti-human HRP (abcam #ab6759) or rabbit anti-mouse HRP (abcam #ab6728) secondary antibodies were incubated for 2 hours at a dilution of 1/1000 in blocking buffer. After 5 washes, 150 μL of 1-Step ABTS Substrate Solution (ThermoFisher) was added to the wells. Color development was measured at 405 nm on a plate reader after 8-20 min and reported OD values are after subtraction of signal from no-antibody wells. Negative controls included immobilized BSA as an antigen, as well as a human isotype control primary antibody (abcam #ab206195). One random IgM/IgK antibody we recombinantly expressed (PA12P4H3) also did not exhibit any binding. Positive controls consisted of monoclonal mouse antibodies 2C12, 1C4, and 1E8 (Indoor Biotechnologies) specific for Ara h 1, Ara h 2, and Ara h 3, respectively.

For ELISAs testing recombinant antibodies against a broad panel of allergen extracts, the following was performed. First, the allergens were obtained. Raw nut allergens, sesame seeds, peanuts, non-fat dry milk, and soy flour were purchased at a local grocery market, while spray-dried whole egg was purchased from the National Institute of Standards and Technology (RM 8445), and liquid latex containing natural rubber centrifuged latex and water was obtained from Amazon. If necessary, a mortar and pestle was used to grind solid allergens, following which 100 mg was added to a 2 mL Eppendorf Protein LoBind tube along with a 5 mm stainless steel bead and 1.7 mL PBS. A TissueLyser system (Qiagen) was used to homogenize the sample at 30 Hz for 10 min. Subsequently, the samples were spun for 20 min at 20000 g and 4° C. The aqueous layer was then transferred to a fresh tube. The protein concentrations of these allergen extracts were then determined using the Pierce 660 nm protein assay kit (ThermoFisher) in microplate format according to the manufacturer's instructions. ELISAs were performed in 384 well format according to the following steps. First, 20 μL of 15 allergens and BSA were incubated overnight at at 4° C. at a concentration of 2 ng/μL each. The plate was then washed 3 times with 62.5 μL of 1×PBST per well per wash using an Integra VIAFLO. Wells were then blocked for 2 hrs using 50 μL of a blocking buffer consisting of 1×PBST and 2% BSA. Next, 20 μL of recombinant antibodies were incubated at a concentration of 2 ng/μL in blocking buffer. Following 4 washes, 20 μL of rabbit anti-human HRP (abcam #ab6759) diluted 1/1000 in blocking buffer was incubated for 2 hours. Following 5 washes, 40 μL of ABTS was added and 405 nm plate absorbance was measured using the BioTek Neo2.

Kinetic characterization of antibody interactions with natural purified allergenic peanut proteins was achieved using biolayer interferometry on a ForteBio Octet 96 using anti-human IgG Fc capture (AHC) biosensors with 1×PBST as the assay buffer. The assay was run with the following protocol: up to 600s baseline, 120-150s antibody load, 120-300s baseline, associations of up to 300s, and variable length dissociations that lasted up to 30 min for high affinity antibody-antigen interactions. Biosensors were regenerated by cycling between buffer and pH 1.5 glycine following each experiment. Antibodies were loaded at a concentration of 10-25 nM, while optimal peanut protein concentrations were determined experimentally (FIGS. 12A-12H). Data were processed using ForteBio software using a 1:1 binding model and global fit after reference sensor (ligand, but no analyte) subtraction.

Example 2—Consensus Ara h 2 Binding Motif for Monoclonal Antibody PA13P1H08

Methods

Linear epitope mapping of the recombinant IgG1 PA13P1H08 antibody was performed against Ara h 2 and Ara h 3 sequences linked and elongated with neutral GSGSGSG linkers at the N- and C-termini to avoid truncated peptides. The linked antigen sequences were translated into linear 15 amino acid peptides with a peptide-peptide overlap of 14 amino acids. The resulting Ara h 2 and Ara h 3 peptide microarray contained 668 different peptides printed in duplicate (1,336 peptide spots) as well as 90 spots of influenza virus hemagglutinin (HA) peptide YPYDVPDYAG framing the microarray as internal quality controls.

The microarray was first subjected to 15 min pre-swelling in washing buffer (PBS, pH 7.4 with 0.05% Tween 20), followed by 30 min in blocking buffer (Rockland blocking buffer MB-070). The microarray was incubated with the PA13P1H08 IgG1 antibody at a concentration of 1 μg/ml in incubation buffer (washing buffer with 10% blocking buffer)

for 16 h at 4° C. with shaking at 140 rpm. The microarray was then stained with secondary goat anti-human IgG (H+L) DyLight680 antibody (1:5000) and control mouse monoclonal anti-HA (12CA5) DyLight800 antibody (1:2000) for 45 min in incubation buffer at room temperature. Read-out was performed with the LI-COR Odyssey Imaging System with the following parameters: scanning offset 0.65 mm, resolution 21 µm, scanning intensities of 7/7 (red=700 nm/green=800 nm). Quantification of spot intensities and peptide annotation were done with PepSlide® Analyzer.

An identical copy of the peptide microarray was subjected to the above procedure without incubation of the PA13P1H08 antibody. This served as a control to analyze background interactions of the secondary and control antibodies with the 668 different peptides of both antigens.

Results

Figure 17A:
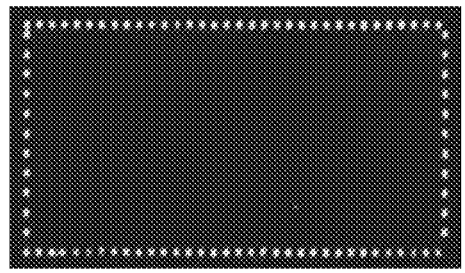
FIG. 17A. Microarray scan confirming the absence of background interactions of the secondary goat anti-human IgG and the control mouse monoclonal anti-HA antibody with antigen-derived peptides. The control antibody gave rise to the expected HA control spot pattern framing the peptide microarray (white dots).
Figure 17B:
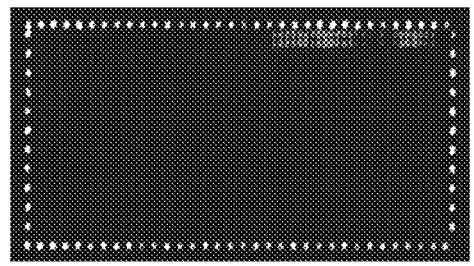
FIGS. 17B and 17C. Microarray epitope mapping of PA13P1H08 to Ara h 2 ("Ah2") and Ara h 3 ("Ah3") peptides. (B) Microarray scan illustrating antibody binding to antigen peptides (light gray) as well as the expected HA control spot pattern (white dots). (C) Microarray fluorescence intensity by antigen peptide. Ara h 2 motifs with high intensity are annotated.
Figure 17C:
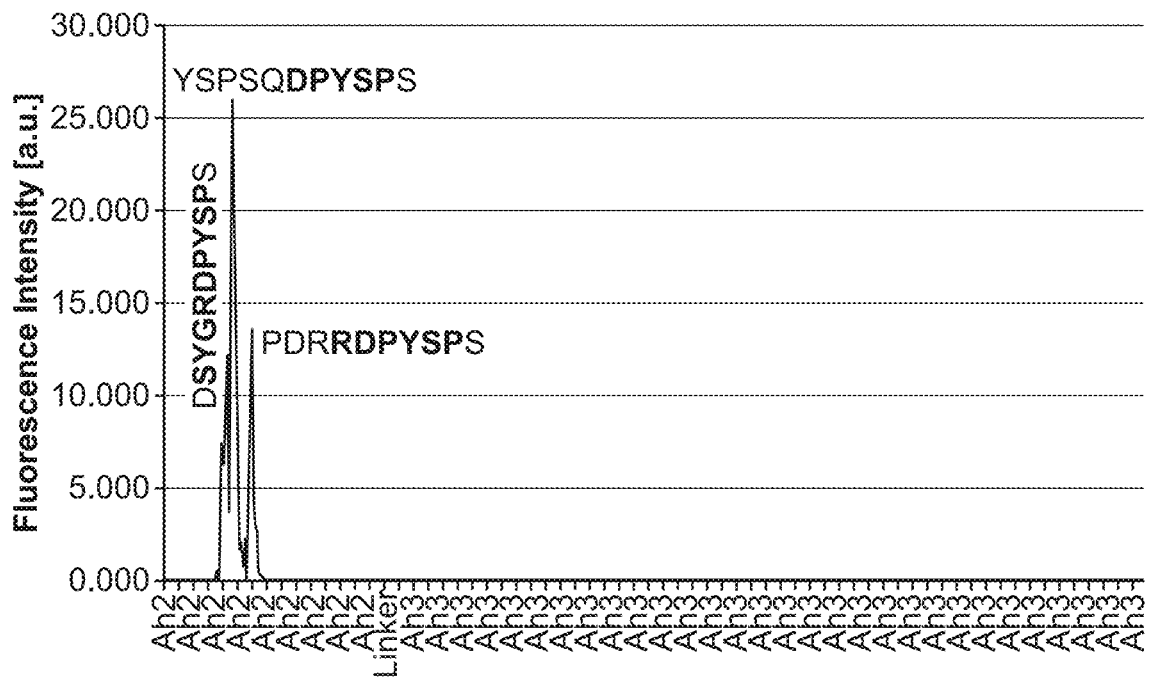

To assess whether the PA13P1H08 antibody, and by extension antibodies similar to PA13P1H08, could be binding linear peanut allergen epitope(s), we synthesized a microarray containing 15 amino acid peptides from peanut allergens Ara h 2 and Ara h 3. We found secondary and control antibody staining of the Ara h 2 and Ara h 3 peptide microarray did not highlight any background interactions that could interfere with the main assay (FIG. 17A). In contrast, we observed a strong PA13P1H08 antibody response with high signal-to-noise ratios to the very similar consensus motifs DSYGRDPYSPS, YSPSQDPYSPS, and PDRRDPYSPS of Ara h 2. The similar responses were found in a region with multiple repeat units with the common DPYSPS motif (FIGS. 17B and 17C). This motif occurs three times in the Ara h 2 isoform Ara h 2.0201 (SEQ ID NO:708; WHO/IUIS allergen nomenclature; Uniprot ID: Q6PSU2-1).

Example 3—*Aspergillus*-Specific Antibodies Derived from Human IgE B Cells

Figure 18:
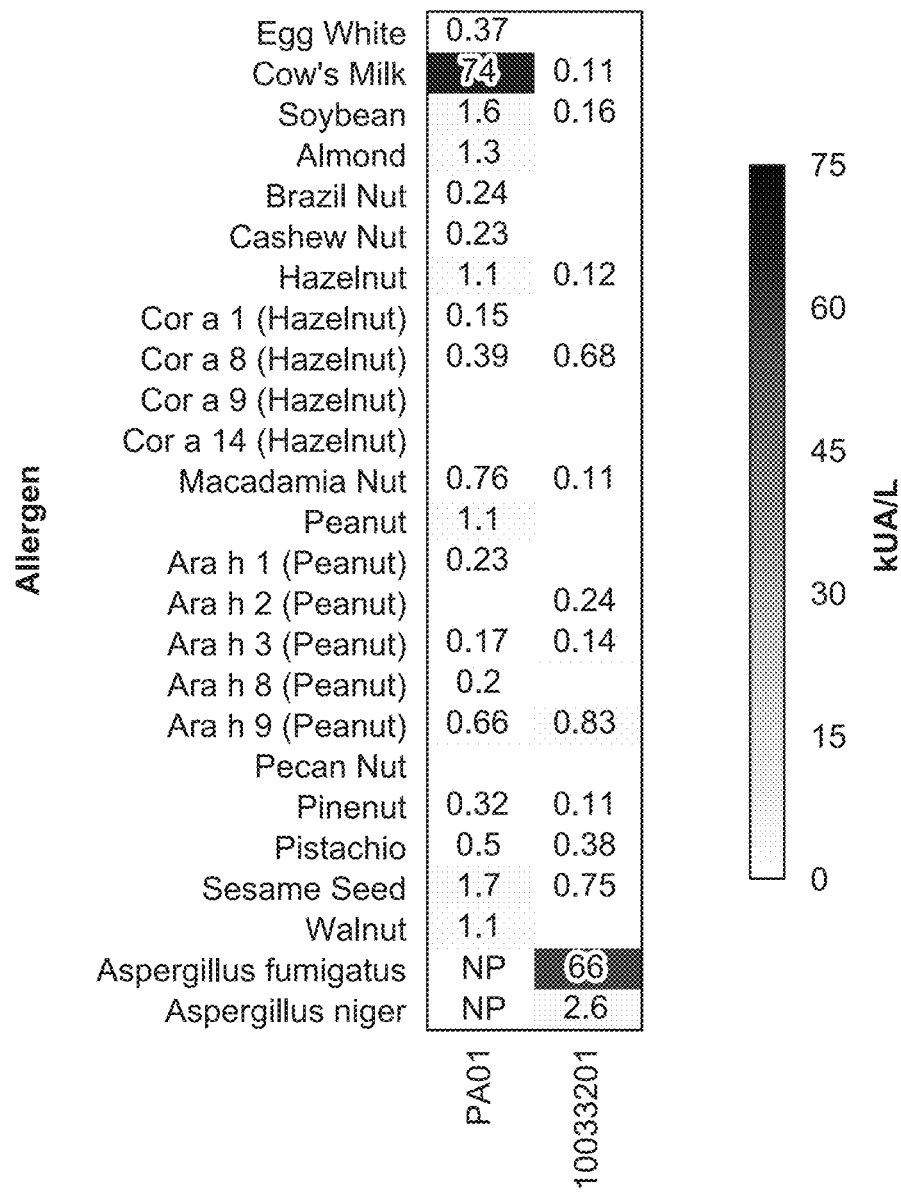
FIG. 18. Plasma IgE levels for milk allergic subject PA01 and *Aspergillus* study subject 10033201 against common food allergens as well as *Aspergillus fumigatus* and *Aspergillus niger*. NP=not performed. Total IgE was 353 kU/L and 3528 kU/L for PA01 and 10033201, respectively. The assay was performed by CLIA-licensed Johns Hopkins University Dermatology, Allergy, and Clinical Immunology Reference Laboratory using the ImmunoCAP system.

This example describes the generation and characterization of *Aspergillus*-specific antibodies derived from human IgE B cells. The methods of Example 1 were used to obtain *Aspergillus*-specific antibodies, with the following differences: the blood from which B cells were isolated originated from a subject (subject number 10033201) with allergic reactivity to *Aspergillus*, rather than a food allergy. Accordingly, the subject's plasma was tested for *Aspergillus*-specific IgE as well as for common food allergens and as shown in FIG. 18, plasma IgE levels indicate *Aspergillus* sensitization but no confounding food sensitizations.

Figure 19:
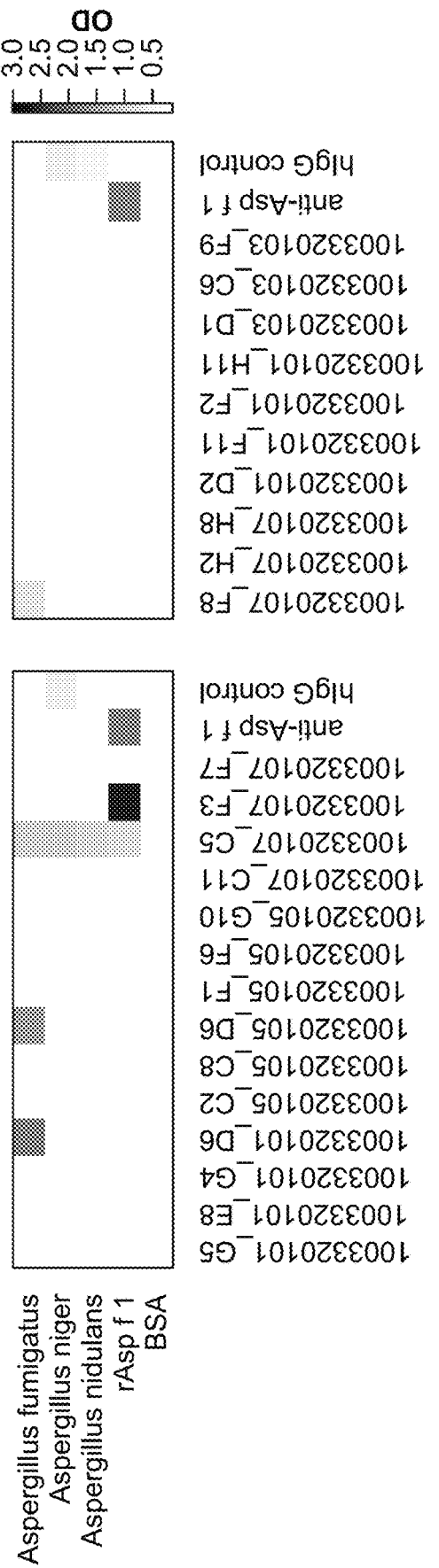
FIG. 19. Indirect ELISA showing binding of recombinant monoclonal antibodies (columns) to antigens (rows). Antigens include extracts of *Aspergillus fumigatus, Aspergillus niger*, and *Aspergillus nidulans*, as well as a purified recombinant allergen *Aspergillus fumigatus* 1 (rAsp f 1). Bovine serum albumin (BSA) serves as a negative antigen control. A monoclonal antibody against Asp f 1 ("anti-Asp f 1") serves as a positive control against this allergen. Higher values indicate stronger binding. OD=optical density. hIgG=human IgG isotype control.

Functional assays (ELISAs) were performed as described in Example 1 to semi-quantitatively assess the obtained antibodies' specificity for statically grown, defatted, powdered, and dried *Aspergillus* species purchased from Stallergenes Greer as well as recombinant *Aspergillus fumigatus* antigen Asp f 1 purchased from Indoor Biotechnologies. As shown in FIG. 19, the monoclonal antibody clones 1003320101_D6, 1003320105_D6, and 1003320107_F8 each exhibited specific binding to *Aspergillus fumigatus*. Clone 1003320107_F3 exhibited specific binding to purified recombinant allergen *Aspergillus fumigatus* 1 (rAsp f 1). Furthermore, clone 1003320107_C5 specifically bound to each of the allergens *Aspergillus fumigatus*, *Aspergillus niger*, and *Aspergillus nidulans* and to rAsp F 1. These results demonstrate that the method disclosed herein for generating antibodies from single IgE- or IgG4-expressing human B cells is able to robustly isolate allergen-specific antibodies independent of the type of allergic disease.

Example 4—Milk Allergen-Specific Antibodies Derived from Human IgE B Cells

This example describes the generation and characterization of milk-specific antibodies derived from human IgE B cells. The methods of Example 1 were used to obtain milk-specific antibodies, with the following differences: the blood from which B cells were isolated originated from a subject (PA01) with allergic reactivity to cow's milk but not to other food allergens. The subject's plasma was tested for common food allergens, including milk. As shown in FIG. 18, plasma IgE levels from the subject indicate milk sensitization but no other confounding food sensitizations.

Figure 20:
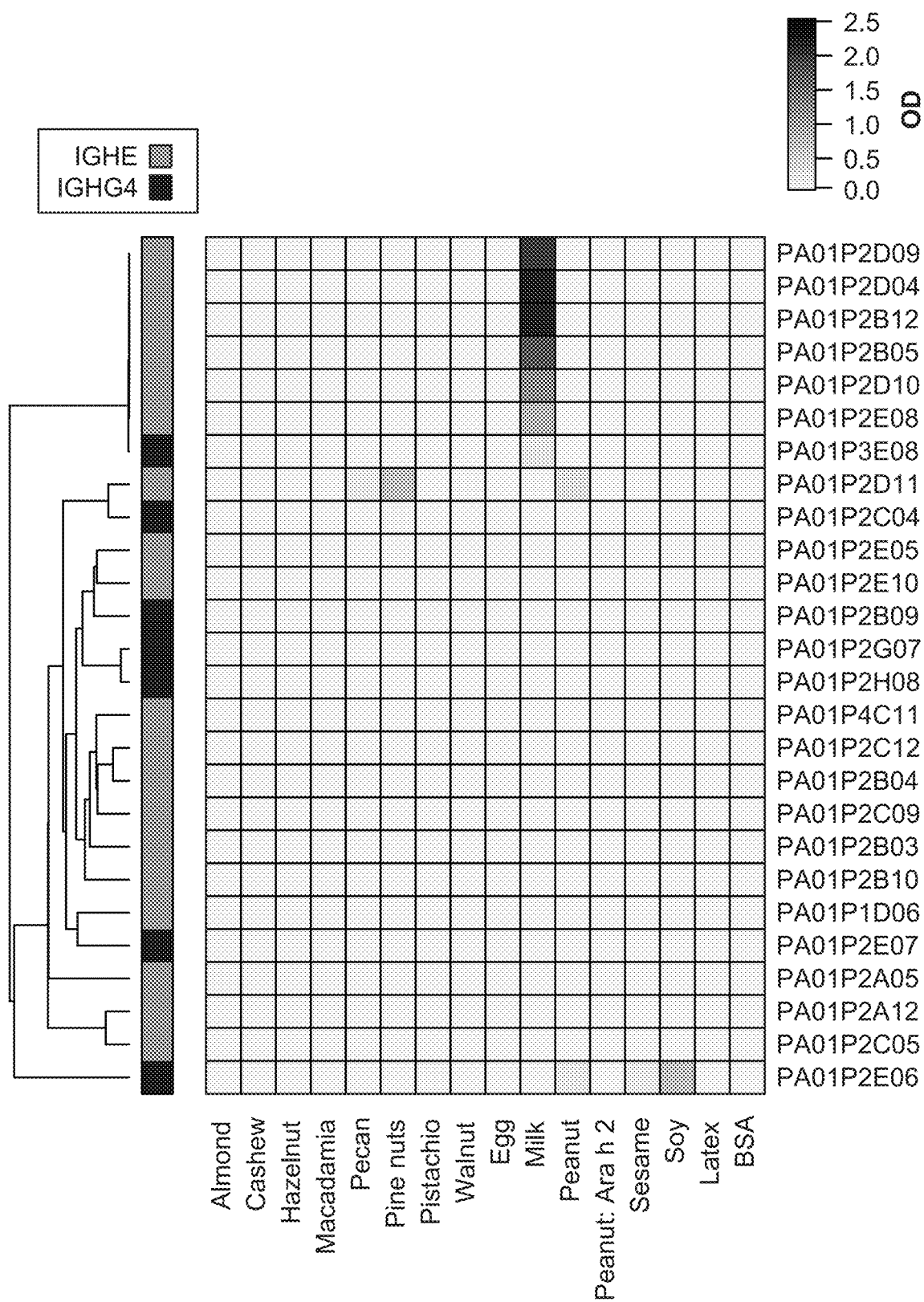
FIG. 20. Indirect ELISA showing binding of recombinant monoclonal antibodies from subject PA01 (rows) to allergen extracts, natural peanut allergen Ara h 2, and BSA (columns). The isotype of each antibody is shown to the left. Higher values indicate stronger binding. OD=optical density. Depicted values represent those after subtraction of human IgG isotype control.

Functional assays (ELISAs) were performed as described in Example 1 to semi-quantitatively assess the specificity of the obtained IgE and IgG4 antibodies. As shown in FIG. 20, the monoclonal antibod clones PA01P2D09, PA01P2D04, PA01P2B12, PA01P2B05, and PA01P2D10 each strongly bound to milk extract, while the antibody PA01P2E08 bound moderately. These results demonstrate that the method disclosed herein for generating antibodies from single IgE- or IgG4-expressing human B cells is able to robustly isolate allergen-specific antibodies independent of the type of allergic disease.

REFERENCES

1. Fitzsimmons C M, Falcone F H, Dunne D W. Helminth Allergens, Parasite-Specific IgE, and Its Protective Role in Human Immunity. Front Immunol. 2014 Feb. 14; 5:61.
2. Eckl-Dorna J, Niederberger V. What is the source of serum allergen-specific IgE? Curr Allergy Asthma Rep. 2013 June; 13(3):281-287.
3. Shreffler W G, Beyer K, Chu T-H T, Burks A W, Sampson H A. Microarray immunoassay: association of clinical history, in vitro IgE function, and heterogeneity of allergenic peanut epitopes. J Allergy Clin Immunol. 2004 April; 113(4):776-782.
4. Croote D, Quake S R. Food allergen detection by mass spectrometry: the role of systems biology. npj Syst Biol Appl. 2016 Sep. 29; 2:16022.
5. Heeringa J J, Rijvers L, Arends N J, Driessen G J, Pasmans S G, van Dongen J J M, et al. IgE-expressing memory B cells and plasmablasts are increased in blood of children with asthma, food allergy, and atopic dermatitis. Allergy. 2018 Jan. 30;
6. Berkowska M A, Heeringa J J, Hajdarbegovic E, van der Burg M, Thio H B, van Hagen P M, et al. Human IgE(+) B cells are derived from T cell-dependent and T cell-independent pathways. J Allergy Clin Immunol. 2014 September; 134(3):688-697.e6.
7. Looney T J, Lee J-Y, Roskin K M, Hoh R A, King J, Glanville J, et al. Human B-cell isotype switching origins of IgE. J Allergy Clin Immunol. 2016 February; 137(2): 579-586.e7.
8. Patil S U, Ogunniyi A O, Calatroni A, Tadigotla V R, Ruiter B, Ma A, et al. Peanut oral immunotherapy transiently expands circulating Ara h 2-specific B cells with a homologous repertoire in unrelated subjects. J Allergy Clin Immunol. 2015 July; 136(1):125-134.e12.
9. Hoh R A, Joshi S A, Liu Y, Wang C, Roskin K M, Lee J-Y, et al. Single B-cell deconvolution of peanut-specific antibody responses in allergic patients. J Allergy Clin Immunol. 2016 January; 137(1):157-167.

10. Tordesillas L, Berin M C, Sampson H A. Immunology of food allergy. Immunity. 2017 Jul. 18; 47(1):32-50.
11. Darmanis S, Sloan S A, Croote D, Mignardi M, Chernikova S, Samghababi P, et al. Single-Cell RNA-Seq Analysis of Infiltrating Neoplastic Cells at the Migrating Front of Human Glioblastoma. Cell Rep. 2017 Oct. 31; 21(5):1399-1410.
12. Dobin A, Davis C A, Schlesinger F, Drenkow J, Zaleski C, Jha S, et al. STAR: ultrafast universal RNA-seq aligner. Bioinformatics. 2013 Jan. 1; 29(1):15-21.
13. Nutt S L, Hodgkin P D, Tarlinton D M, Corcoran L M. The generation of antibody-secreting plasma cells. Nat Rev Immunol. 2015 March; 15(3):160-171.
14. Xu H, Chaudhri V K, Wu Z, Biliouris K, Dienger-Stambaugh K, Rochman Y, et al. Regulation of bifurcating B cell trajectories by mutual antagonism between transcription factors IRF4 and IRF8. Nat Immunol. 2015 December; 16(12):1274-1281.
15. Erazo A, Kutchukhidze N, Leung M, Christ A P G, Urban J F, Curotto de Lafaille M A, et al. Unique maturation program of the IgE response in vivo. Immunity. 2007 Feb. 8; 26(2):191-203.
16. Horst A, Hunzelmann N, Arce S, Herber M, Manz R A, Radbruch A, et al. Detection and characterization of plasma cells in peripheral blood: correlation of IgE+ plasma cell frequency with IgE serum titre. Clin Exp Immunol. 2002 December; 130(3):370-378.
17. Manz R, Löhning M, Cassese G, Thiel A, Radbruch A. Survival of long-lived plasma cells is independent of antigen. Int Immunol. 1998 Nov. 1; 10(11):1703-1711.
18. Medina F, Segundo C, Campos-Caro A, González-García I, Brieva J A. The heterogeneity shown by human plasma cells from tonsil, blood, and bone marrow reveals graded stages of increasing maturity, but local profiles of adhesion molecule expression. Blood. 2002 Mar. 15; 99(6):2154-2161.
19. Calame K L, Lin K-I, Tunyaplin C. Regulatory mechanisms that determine the development and function of plasma cells. Annu Rev Immunol. 2003; 21:205-230.
20. Gould H J, Sutton B J. IgE in allergy and asthma today. Nat Rev Immunol. 2008 March; 8(3):205-217.
21. Cooper A M, Hobson P S, Dutton M R, Kao M W, Drung B, Schmidt B, et al. Soluble CD23 controls IgE synthesis and homeostasis in human B cells. J Immunol. 2012 Apr. 1; 188(7):3199-3207.
22. Weskamp G, Ford J W, Sturgill J, Martin S, Docherty A J P, Swendeman S, et al. ADAM10 is a principal "sheddase" of the low-affinity immunoglobulin E receptor CD23. Nat Immunol. 2006 December; 7(12):1293-1298.
23. Ouchida R, Kurosaki T, Wang J-Y. A role for lysosomal-associated protein transmembrane 5 in the negative regulation of surface B cell receptor levels and B cell activation. J Immunol. 2010 Jul. 1; 185(1):294-301.
24. Cella M, Döhring C, Samaridis J, Dessing M, Brockhaus M, Lanzavecchia A, et al. A novel inhibitory receptor (ILT3) expressed on monocytes, macrophages, and dendritic cells involved in antigen processing. J Exp Med. 1997 May 19; 185(10):1743-1751.
25. Anginot A, Espeli M, Chasson L, Mancini S J C, Schiff C. Galectin 1 modulates plasma cell homeostasis and regulates the humoral immune response. J Immunol. 2013 Jun. 1; 190(11):5526-5533.
26. Leśniak W, Słomnicki Ł P, Filipek A. S100A6—new facts and features. Biochem Biophys Res Commun. 2009 Dec. 25; 390(4):1087-1092.
27. Boye K, Maelandsmo G M. S100A4 and metastasis: a small actor playing many roles. Am J Pathol. 2010 February; 176(2):528-535.
28. Geahlen R L. Syk and pTyr'd: Signaling through the B cell antigen receptor. Biochim Biophys Acta. 2009 July; 1793(7):1115-1127.
29. Ackermann J A, Nys J, Schweighoffer E, McCleary S, Smithers N, Tybulewicz V U. Syk tyrosine kinase is critical for B cell antibody responses and memory B cell survival. J Immunol. 2015 May 15; 194(10):4650-4656.
30. Yang Z, Sullivan B M, Allen C D C. Fluorescent in vivo detection reveals that IgE(+) B cells are restrained by an intrinsic cell fate predisposition. Immunity. 2012 May 25; 36(5):857-872.
31. He J-S, Subramaniam S, Narang V, Srinivasan K, Saunders S P, Carbajo D, et al. IgG1 memory B cells keep the memory of IgE responses. Nat Commun. 2017 Sep. 21; 8(1):641.
32. Poggianella M, Bestagno M, Burrone O R. The extracellular membrane-proximal domain of human membrane IgE controls apoptotic signaling of the B cell receptor in the mature B cell line A20. J Immunol. 2006 Sep. 15; 177(6):3597-3605.
33. Batista F D, Anand S, Presani G, Efremov D G, Burrone O R. The two membrane isoforms of human IgE assemble into functionally distinct B cell antigen receptors. J Exp Med. 1996 Dec. 1; 184(6):2197-2205.
34. Karnowski A, Achatz-Straussberger G, Klockenbusch C, Achatz G, Lamers M C. Inefficient processing of mRNA for the membrane form of IgE is a genetic mechanism to limit recruitment of IgE-secreting cells. Eur J Immunol. 2006 July; 36(7):1917-1925.
35. Wu L C, Zarrin A A. The production and regulation of IgE by the immune system. Nat Rev Immunol. 2014 April; 14(4):247-259.
36. Koppelman S J, Wensing M, Ertmann M, Knulst A C, Knol E F. Relevance of Ara h1, Ara h2 and Ara h3 in peanut-allergic patients, as determined by immunoglobulin E Western blotting, basophil-histamine release and intracutaneous testing: Ara h2 is the most important peanut allergen. Clin Exp Allergy. 2004 April; 34(4):583-590.
37. Nicolaou N, Murray C, Belgrave D, Poorafshar M, Simpson A, Custovic A. Quantification of specific IgE to whole peanut extract and peanut components in prediction of peanut allergy. Journal of Allergy and Clinical Immunology. 2011 March; 127(3):684-685.
38. Dang T D, Tang M, Choo S, Licciardi P V, Koplin J J, Martin P E, et al. Increasing the accuracy of peanut allergy diagnosis by using Ara h 2. J Allergy Clin Immunol. 2012 April; 129(4):1056-1063.
39. Wrammert J, Smith K, Miller J, Langley W A, Kokko K, Larsen C, et al. Rapid cloning of high-affinity human monoclonal antibodies against influenza virus. Nature. 2008 May 29; 453(7195):667-671.
40. Murugan R, Buchauer L, Triller G, Kreschel C, Costa G, Pidelaserra Martí G, et al. Clonal selection drives protective memory B cell responses in controlled human malaria infection. Sci Immunol. 2018 Feb. 16; 3(20).
41. Kaur K, Zheng N-Y, Smith K, Huang M, Li L, Pauli N T, et al. High Affinity Antibodies against Influenza Characterize the Plasmablast Response in SLE Patients After Vaccination. PLoS ONE. 2015 May 7; 10(5):e0125618.
42. Mouquet H, Klein F, Scheid J F, Warncke M, Pietzsch J, Oliveira T Y K, et al. Memory B cell antibodies to HIV-1 gp140 cloned from individuals infected with clade A and B viruses. PLoS ONE. 2011 Sep. 8; 6(9):e24078.

43. Scheid J F, Mouquet H, Ueberheide B, Diskin R, Klein F, Oliveira T Y K, et al. Sequence and structural convergence of broad and potent HIV antibodies that mimic CD4 binding. Science. 2011 Sep. 16; 333(6049):1633-1637.
44. Orengo J M, Radin A R, Kamat V, Badithe A, Ben L H, Bennett B L, et al. Treating cat allergy with monoclonal IgG antibodies that bind allergen and prevent IgE engagement. Nat Commun. 2018 Apr. 12; 9(1):1421.
45. Yewdell W T, Chaudhuri J. A transcriptional serenAID: the role of noncoding RNAs in class switch recombination. Int Immunol. 2017 Apr. 1; 29(4):183-196.
46. Hein K, Lorenz M G, Siebenkotten G, Petry K, Christine R, Radbruch A. Processing of switch transcripts is required for targeting of antibody class switch recombination. J Exp Med. 1998 Dec. 21; 188(12):2369-2374.
47. Lorenz M, Jung S, Radbruch A. Switch transcripts in immunoglobulin class switching. Science. 1995 Mar. 24; 267(5205):1825-1828.
48. Zheng S, Vuong B Q, Vaidyanathan B, Lin J-Y, Huang F-T, Chaudhuri J. Non-coding RNA Generated following Lariat Debranching Mediates Targeting of AID to DNA. Cell. 2015 May 7; 161(4):762-773.
49. Collins J T, Dunnick W A. Germline transcripts of the murine immunoglobulinγ 2a gene: structure and induction by IFN-γ. Int Immunol. 1993; 5(8):885-891.
50. Gaff C, Gerondakis S. RNA splicing generates alternate forms of germline immunoglobulin alpha heavy chain transcripts. Int Immunol. 1990; 2(12):1143-1148.
51. Gauchat J F, Lebman D A, Coffman R L, Gascan H, de Vries J E. Structure and expression of germline epsilon transcripts in human B cells induced by interleukin 4 to switch to IgE production. J Exp Med. 1990 Aug. 1; 172(2):463-473.
52. Wu Y L, Stubbington M J T, Daly M, Teichmann S A, Rada C. Intrinsic transcriptional heterogeneity in B cells controls early class switching to IgE. J Exp Med. 2017 January; 214(1):183-196.
53. Horns F, Vollmers C, Croote D, Mackey S F, Swan G E, Dekker C L, et al. Lineage tracing of human B cells reveals the in vivo landscape of human antibody class switching. elife. 2016 Aug. 2; 5.
54. Fear D J, McCloskey N, O'Connor B, Felsenfeld G, Gould H J. Transcription of Ig germline genes in single human B cells and the role of cytokines in isotype determination. J Immunol. 2004 Oct. 1; 173(7):4529-4538.
55. Laffleur B, Duchez S, Tarte K, Denis-Lagache N, Péron S, Carrion C, et al. Self-Restrained B Cells Arise following Membrane IgE Expression. Cell Rep. 2015 Feb. 12;
56. Haniuda K, Fukao S, Kodama T, Hasegawa H, Kitamura D. Autonomous membrane IgE signaling prevents IgE-memory formation. Nat Immunol. 2016 Jul. 18; 17(9):1109-1117.
57. Tong P, Granato A, Zuo T, Chaudhary N, Zuiani A, Han S S, et al. IgH isotype-specific B cell receptor expression influences B cell fate. Proc Natl Acad Sci USA. 2017 Oct. 3; 114(40):E8411-E8420.
58. Yang Z, Robinson M J, Chen X, Smith G A, Taunton J, Liu W, et al. Regulation of B cell fate by chronic activity of the IgE B cell receptor. elife. 2016 Dec. 9; 5.
59. Laffleur B, Debeaupuis O, Dalloul Z, Cogné M. B cell intrinsic mechanisms constraining ige memory. Front Immunol. 2017 Nov. 13; 8:1277.
60. Jackson K J L, Liu Y, Roskin K M, Glanville J, Hoh R A, Seo K, et al. Human responses to influenza vaccination show seroconversion signatures and convergent antibody rearrangements. Cell Host Microbe. 2014 Jul. 9; 16(1):105-114.
61. Zhou J, Lottenbach K R, Barenkamp S J, Lucas A H, Reason D C. Recurrent variable region gene usage and somatic mutation in the human antibody response to the capsular polysaccharide of *Streptococcus pneumoniae* type 23F. Infect Immun. 2002 August; 70(8):4083-4091.
62. Kiyotani K, Mai T H, Yamaguchi R, Yew P Y, Kulis M, Orgel K, et al. Characterization of the B-cell receptor repertoires in peanut allergic subjects undergoing oral immunotherapy. J Hum Genet. 2018 February; 63(2):239-248.
63. Bublin M, Kostadinova M, Radauer C, Hafner C, Szépfalusi Z, Varga E-M, et al. IgE cross-reactivity between the major peanut allergen Ara h 2 and the nonhomologous allergens Ara h 1 and Ara h 3. J Allergy Clin Immunol. 2013 July; 132(1):118-124.
64. Picelli S, Faridani O R, Björklund A K, Winberg G, Sagasser S, Sandberg R. Full-length RNA-seq from single cells using Smart-seq2. Nat Protoc. 2014 Jan. 2; 9(1):171-181.
65. Anders S, Pyl P T, Huber W. HTSeq—a Python framework to work with high-throughput sequencing data. Bioinformatics. 2015 Jan. 15; 31(2):166-169.
66. Van den Brink S C, Sage F, Vértesy Á, Spanjaard B, Peterson-Maduro J, Baron C S, et al. Single-cell sequencing reveals dissociation-induced gene expression in tissue subpopulations. Nat Methods. 2017 Sep. 29; 14(10):935-936.
67. Ritchie M E, Phipson B, Wu D, Hu Y, Law C W, Shi W, et al. limma powers differential expression analyses for RNA-sequencing and microarray studies. Nucleic Acids Res. 2015 Apr. 20; 43(7):e47.
68. Li H. A statistical framework for SNP calling, mutation discovery, association mapping and population genetical parameter estimation from sequencing data. Bioinformatics. 2011 Nov. 1; 27(21):2987-2993.
69. Canzar S, Neu K E, Tang Q, Wilson P C, Khan A A. BASIC: BCR assembly from single cells. Bioinformatics. 2017 Feb. 1; 33(3):425-427.
70. Chang Z, Li G, Liu J, Zhang Y, Ashby C, Liu D, et al. Bridger: a new framework for de novo transcriptome assembly using RNA-seq data. Genome Biol. 2015 Feb. 11; 16:30.
71. Camacho C, Coulouris G, Avagyan V, Ma N, Papadopoulos J, Bealer K, et al. BLAST+: architecture and applications. BMC Bioinformatics. 2009 Dec. 15; 10:421.
72. Lefranc M-P, Giudicelli V, Ginestoux C, Jabado-Michaloud J, Folch G, Bellahcene F, et al. IMGT, the international ImMunoGeneTics information system. Nucleic Acids Res. 2009 January; 37(Database issue):D1006-12.
73. Katona I M, Urban J F, Scher I, Kanellopoulos-Langevin C, Finkelman F D. Induction of an IgE response in mice by *Nippostrongylus brasiliensis*: characterization of lymphoid cells with intracytoplasmic or surface IgE. J Immunol. 1983 January; 130(1):350-356.

74. Ye J, Ma N, Madden T L, Ostell J M. IgBLAST: an immunoglobulin variable domain sequence analysis tool. Nucleic Acids Res. 2013 July; 41(Web Server issue): W34-40.
75. Gupta N T, Vander Heiden J A, Uduman M, Gadala-Maria D, Yaari G, Kleinstein S H. Change-O: a toolkit for analyzing large-scale B cell immunoglobulin repertoire sequencing data. Bioinformatics. 2015 Oct. 15; 31(20): 3356-3358.
76. Köster J, Rahmann S. Snakemake—a scalable bioinformatics workflow engine. Bioinformatics. 2012 Oct. 1; 28(19):2520-2522.

TABLE 1

Sequence Listing

| SEQ ID NO | Sequence | Description |
|---|---|---|
| 1 | QVQLVNSGGGVVQPGRSLRLSCVASGFTFSTFGIHWVRQAPGKGLEWVAVH ISNDGEKSESADSVKGRFTPSRDNSKNTVYLQMNNLRVEDTAVYYCAKVL DYSRYSYYYGMDVWGQGTTVIVSS | Heavy chain variable region for clone PA13P1H08 and N-R variant of PA13P1H08 |
| 2 | GFTFSTFG | CDR-H1 for clone PA13P1H08 and PA13P1H08 variants N-R, rCDR2-N, rCDR3-N, rFWRs-N |
| 3 | ISNDGEKS | CDR-H2 for clone PA13P1H08 and PA13P1H08 variants N-R, rCDR1-N, rCDR3-N |
| 4 | AKVLDYSRYSYYYGMDV | CDR-H3 for clone PA13P1H08 and PA13P1H08 variants N-R, rCDR1-N, rCDR2-N |
| 5 | EIVLTQSPGTLSLSPGGRGTLSCRTSQTINNAHLAWYQHKPGQAPRLLIY GSSERATGVPDRFSGSGSGSDFTLTISSLEAEDFAVYYCQHYGRSPPYTF GPGTKLDIK | Light chain variable region for clone PA13P1H08 and PA13P1H08 variants R-N, rCDR1-N, rCDR2-N, rCDR3-N, rFWRs-N |
| 6 | QTINNAH | CDR-L1 for clone PA13P1H08 and PA13P1H08 variants R-N, rCDR1-N, rCDR2-N, rCDR3-N, rFWRs-N |
| 7 | GSS | CDR-L2 for clone PA13P1H08 and PA13P1H08 variants R-N, rCDR1-N, rCDR2-N, rCDR3-N, rFWRs-N |
| 8 | QHYGRSPPYT | CDR3-L3 for clone PA13P1H08 and PA13P1H08 variants R-N, rCDR1-N, rCDR2-N, rCDR3-N, rFWRs-N |
| 9 | QVQLVDSGGGVVQPGKSLRLSCVGSGFTFRTFGIHWVRQAPGKGLEWVAV ISNDGGNSASADSVKGRFTTSRDNSKNTVYLQINSLRPEDTAIYYCAKVL DYSAFSYYYGMDVWGQGTTVIVSS | Clone PA13P1E10 - Heavy chain variable region |
| 10 | GFTFRTFG | Clone PA13P1E10 -CDR-H1 |
| 11 | ISNDGGNS | Clone PA13P1E10 -CDR-H2 |
| 12 | AKVLDYSAFSYYYGMDV | Clone PA13P1E10 -CDR-H3 |
| 13 | EIVLTQSPGTLSLSPGERGTLSCRTSQPISRAHLAWYQHKAGQAPRLLIY GSTERAAGIPERFSGGGSGSDFTLTISSLEAEDFAVYYCQHYGRSPPYTF GQGTKVEIK | Clone PA13P1E10 - light chain variable region |
| 14 | QPISRAH | Clone PA13P1E10 -CDR-L1 |
| 15 | GST | Clone PA13P1E10 -CDR-L2 |
| 8 | QHYGRSPPYT | Clone PA13P1E10 -CDR-L3 |
| 16 | QVQLVESGGGVVQPGGSLTLSCVGSGFTFSHYAIHWVRQAPGKGLEWVAV ISNVGTTRDYADSLKGRLTISRENSQSTVFLQMNSLRADDTAIYYCAKVL DYSEFHYYYGLDVWGQGTAVAVSS | Clone PA12P3F10 - Heavy chain variable region |
| 17 | GFTFSHYA | Clone PA12P3F10 - CDR-H1 |
| 18 | ISNVGTTR | Clone PA12P3F10 - CDR-H2 |
| 19 | AKVLDYSEFHYYYGLDV | Clone PA12P3F10 - CDR-H3 |
| 20 | EIVLTQSPGTLSLSPGQRVTLSCRVSQAIPTMYVAWYQQRPGQAPRLLIY GTSSRATGIPDRFSGGGSGTDFTLTINRLEPEDIAVYYCQHYSNSPPYTF GPGTKLEIK | Clone PA12P3F10 - light chain variable region |

TABLE 1-continued

Sequence Listing

| SEQ ID NO | Sequence | Description |
|---|---|---|
| 21 | QAIPTMY | Clone PA12P3F10 - CDR-L1 |
| 22 | GTS | Clone PA12P3F10 - CDR-L2 |
| 23 | QHYSNSPPYT | Clone PA12P3F10 - CDR-L3 |
| 24 | QEQLVESGGGVVHPGGSLRLSCVASAFTFNRFGMHWVRQAPGKGLEWVAVISNDGRSQDYADSVKGRFIISRDNSKNTLYLQLNSLRFEDTAVYYCAKVLDYSIFYYYFGLDVWGQGTTVTVSS | Clone PA13P3G09 - Heavy chain variable region |
| 25 | AFTFNRFG | Clone PA13P3G09 - CDR-H1 |
| 26 | ISNDGRSQ | Clone PA13P3G09 - CDR-H2 |
| 27 | AKVLDYSIFYYYFGLDV | Clone PA13P3G09 - CDR-H3 |
| 28 | EVVLTQSPGSLSLSPGERATLSCRAGQSLSSKFLAWYQHKPGQAPRLLIYGASTRATGVPDRFSGSGSGTDFSLIISRVEPEDFAVYYCQHYGDSPPYTFGQGTKVEMK | Clone PA13P3G09 - light chain variable region |
| 29 | QSLSSKF | Clone PA13P3G09 - CDR-L1 |
| 30 | GAS | CDR-L2 for clone PA13P3G09 and PA13P1H08 variants R-R, N-R |
| 31 | QHYGDSPPYT | Clone PA13P3G09 - CDR-L3 |
| 32 | QVQLVESGGGVVQPGKSLRLSCAASAFTFRRFAMHWVRQAPGKGLEWVAVISDNGLREDYEDSVKGRFTISRDNSQNTLYLQMNGLRAEDTAVYYCAKVLDYNEYSLYFGMDVWGQGTTVTVSS | Clone PA12P3D08 - Heavy chain variable region |
| 33 | AFTFRRFA | Clone PA12P3D08 - CDR-H1 |
| 34 | ISDNGLRE | Clone PA12P3D08 - CDR-H2 |
| 35 | AKVLDYNEYSLYFGMDV | Clone PA12P3D08 - CDR-H3 |
| 36 | EVVLTQSPATLSLSPGERATLSCRTSQAISNNFLAWYQQRPGQPPRLLIYASSRRATDTPDRFTGSGSGTDFTLTITRLEPEDFAVYFCQYYSDSPPYTFGPGTKLEIK | Clone PA12P3D08 - light chain variable region |
| 37 | QAISNNF | Clone PA12P3D08 - CDR-L1 |
| 38 | ASS | Clone PA12P3D08 - CDR-L2 |
| 39 | QYYSDSPPYT | Clone PA12P3D08 - CDR-L3 |
| 40 | QVQLEESGGGVVQPGKSLRLSCVASAFTFKRFAMHWVRQAPGKGLEWVAVISDNGLREDYEDSVKGRFTISRDNSKDTLYLQMNSLRPEDTAIYYCAKVLDYSEYSLYFGMDVWGQGTTVLVSS | Clone PA12P1C07 - Heavy chain variable region |
| 41 | AFTFKRFA | Clone PA12P1C07 - CDR-H1 |
| 34 | ISDNGLRE | Clone PA12P1C07 - CDR-H2 |
| 42 | AKVLDYSEYSLYFGMDV | Clone PA12P1C07 - CDR-H3 |
| 43 | EIVLTQSPAILSLSPGDRATLSCRTSQTVNSNFLAWYQQKPGQAPRLLIYGASRRAIDIPDRFTGSGSGTEFTLTIARLEPEDFAVYSCQHYSDSPPYTFGQGTKLEIK | Clone PA12P1C07 - light chain variable region |
| 44 | QTVNSNF | Clone PA12P1C07 - CDR-L1 |
| 30 | GAS | Clone PA12P1C07 - CDR-L2 |
| 45 | QHYSDSPPYT | Clone PA12P1C07 - CDR-L3 |
| 46 | QVHLVESGGGVVQPGRSLGLSCAASGFTFNYYAIHWVRQAPGKGLEWVAVVSFDGNIIYYADSVKGRFNISRDNSKNTVNLQMNSLRADDTAVYYCVRDGEYCSGGNCYWGDFDYWGQGTLVTVSP | Clone PA15P1D12 - Heavy chain variable region |
| 47 | GFTFNYYA | Clone PA15P1D12 - CDR-H1 |

TABLE 1-continued

Sequence Listing

| SEQ ID NO | Sequence | Description |
|---|---|---|
| 48 | VSFDGNII | Clone PA15P1D12 - CDR-H2 |
| 49 | VRDGEYCSGGNCYWGDFDY | Clone PA15P1D12 - CDR-H3 |
| 50 | EIVLTQSPGTLSLSPGERATLSCRASQSISSEYLTWFQQKPGQAPRLLIY GAFNRATGIPDRFSGSGSGTDFTLTISSLEPEDFAVYYCQQYANWWTFGQ GTKVEIK | Clone PA15P1D12 - light chain variable region |
| 51 | QSISSEY | Clone PA15P1D12 - CDR-L1 |
| 52 | GAF | Clone PA15P1D12 - CDR-L2 |
| 53 | QQYANWWT | Clone PA15P1D12 - CDR-L3 |
| 54 | QVHLVESGGGVVQPGRSLGLSCVASGFTFNYYAIHWVRQAPGKGLEWVAV VSFDGNIIYYADSVKGRFNISRDNSKNTVNLQMNSLRPDDTAVYYCVRDG EYCSGGNCYWGDFDHWGQGSLVTVSP | Clone PA15P1D05 - Heavy chain variable region |
| 47 | GFTFNYYA | Clone PA15P1D05 - CDR-H1 |
| 48 | VSFDGNII | Clone PA15P1D05 - CDR-H2 |
| 55 | VRDGEYCSGGNCYWGDFDH | Clone PA15P1D05 - CDR-H3 |
| 56 | EIVLTQSPATLSLSPGERATLSCRASQSISSEYLTWFQQKPGQAPRLLIY GAFNRATGIPDRFSGSGSGTDFTLTISSLEPEDFAVYYCQQYANWWTFGQ GTKVEIK | Clone PA15P1D05 - light chain variable region |
| 51 | QSISSEY | Clone PA15P1D05 - CDR-L1 |
| 52 | GAF | Clone PA15P1D05 - CDR-L2 |
| 53 | QQYANWWT | Clone PA15P1D05 - CDR-L3 |
| 57 | QVQLVESGGGVVQPGRSLRLSCAASGFTFSSYGMHWVRQAPGKGLEWVAV ISYDGSNKYYADSVKGRFTISRDNSKNTLYLQMNSLRAEDTAVYYCAKVL DYSNYYYYGMDVWGQGTTVTVSS | Heavy chain variable region for R-R and R-N variants of PA13P1H08 |
| 58 | GFTFSSYG | CDR-H1 for PA13P1H08 variants R-R, R-N, rCDR1-N |
| 59 | ISYDGSNK | CDR-H2 for PA13P1H08 variants R-R, R-N, rCDR2-N |
| 60 | AKVLDYSNYYYYGMDV | CDR-H3 for PA13P1H08 variants R-R, R-N, rCDR3-N |
| 61 | EIVLTQSPGTLSLSPGERATLSCRASQSVSSSYLAWYQQKPGQAPRLLIY GASSRATGIPDRFSGSGSGTDFTLTISRLEPEDFAVYYCQQYGSSPPYTF GQGTKLEIK | Light chain variable for region R-R and N-R variants of PA13P1H08 |
| 62 | QSVSSSY | CDR-L1 for PA13P1H08 variants R-R, N-R |
| 63 | QQYGSSPPYT | CDR-L3 for PA13P1H08 variants R-R, N-R |
| 64 | QVQLVNSGGGVVQPGRSLRLSCVASGFTFSSYGIHWVRQAPGKGLEWVAV ISNDGEKSESADSVKGRFTPSRDNSKNTVYLQMNNLRVEDTAVYYCAKVL DYSRYSYYYGMDVWGQGTTVIVSS | Heavy chain variable region for PA13P1H08 variant rCDR1-N |
| 65 | QVQLVNSGGGVVQPGRSLRLSCVASGFTFSTFGIHWVRQAPGKGLEWVAV ISYDGSNKESADSVKGRFTPSRDNSKNTVYLQMNNLRVEDTAVYYCAKVL DYSRYSYYYGMDVWGQGTTVIVSS | Heavy chain variable region for PA13P1H08 variant rCDR2-N |
| 66 | QVQLVNSGGGVVQPGRSLRLSCVASGFTFSTFGIHWVRQAPGKGLEWVAV ISNDGEKSESADSVKGRFTPSRDNSKNTVYLQMNNLRVEDTAVYYCAKVL DYSNYYYYGMDVWGQGTTVIVSS | Heavy chain variable region for PA13P1H08 variant rCDR3-N |
| 67 | QVQLVESGGGVVQPGRSLRLSCAASGFTFSTFGMHWVRQAPGKGLEWVAV ISNDGEKSYADSVKGRFTISRDNSKNTLYLQMNSLRAEDTAVYYCAKVL DYSRYSYYYGMDVWGQGTTVTVSS | Heavy chain variable region for PA13P1H08 variant rFWRs-N |

TABLE 1-continued

Sequence Listing

| SEQ ID NO | Sequence | Description |
|---|---|---|
| 68 | GCCTCCACACAGAGCCCATCCGTCTTCCCCTTGACCCGCTGCTGCAAAAA<br>CATTCCCTCCAATGCCACCTCCGTGACTCTGGGCTGCCTGGCCACGGGCT<br>ACTTCCCGGAGCCGGTGATGGTGACCTGGGACACAGGCTCCCTCAACGGG<br>ACAACTATGACCTTACCAGCCACCACCCTCACGCTCTCTGGTCACTATGC<br>CACCATCAGCTTGCTGACCGTCTCGGGTGCGTGGGCCAAGCAGATGTTCA<br>CCTGCCGTGTGGCACACACTCCATCGTCCACAGACTGGGTCGACAACAAA<br>ACCTTCAGCGTCTGCTCCAGGGACTTCACCCCGCCCACCGTGAAGATCTT<br>ACAGTCGTCCTGCGACGGCGGCGGGCACTTCCCCCCGACCATCCAGCTCC<br>TGTGCCTCGTCTCTGGGTACACCCCAGGGACTATCAACATCACCTGGCTG<br>GAGGACGGGCAGGTCATGGACGTGGACTTGTCCACCGCCTCTACCACGCA<br>GGAGGGTGAGCTGGCCTCCACACAAAGCGAGCTCACCCTCAGCCAGAAGC<br>ACTGGCTGTCAGACCGCACCTACACCTGCCAGGTCACCTATCAAGGTCAC<br>ACCTTTGAGGACAGCACCAAGAAGTGTGCAGATTCCAACCCGAGAGGGGT<br>GAGCGCCTACCTAAGCCGGCCCAGCCCGTTCGACCTGTTCATCCGCAAGT<br>CGCCCACGATCACCTGTCTGGTGGTGGACCTGGCACCCAGCAAGGGGACC<br>GTGAACCTGACCTGGTCCCGGGCCAGTGGGAAGCCTGTGAACCACTCCAC<br>CAGAAAGGAGGAGAAGCAGCGCAATGGCACGTTAACCGTCACGTCCACCC<br>TGCCGGTGGGCACCCGAGACTGGATCGAGGGGGAGACCTACCAGTGCAGG<br>GTGACCCACCCCCACCTGCCCAGGGCCCTCATGCGGTCCACGACCAAGAC<br>CAGCGGCCCGCGTGCTGCCCCGGAAGTCTATGCGTTTGCGACGCCGGAGT<br>GGCCGGGGAGCCGGGACAAGCGCACCCTCGCCTGCCTGATCCAGAACTTC<br>ATGCCTGAGGACATCTCGGTGCAGTGGCTGCACAACGAGGTGCAGCTCCC<br>GGACGCCCGGCACAGCACGACGCAGCCCCGCAAGACCAAGGGCTCCGGCT<br>TCTTCGTCTTCAGCCGCCTGGAGGTGACCAGGGCCGAATGGGAGCAGAAA<br>GATGAGTTCATCTGCCGTGCAGTCCATGAGGCAGCGAGCCCCTCACAGAC<br>CGTCCAGCGAGCGGTGTCTGTAAATCCCGGTAAA | Nucleotide sequence for IgE heavy chain constant region |
| 69 | ASTQSPSVFPLTRCCKNIPSNATSVTLGCLATGYFPEPVMVTWDTGSLNG<br>TTMTLPATTLTLSGHYATISLLTVSGAWAKQMFTCRVAHTPSSTDWVDNK<br>TFSVCSRDFTPPTVKILQSSCDGGGHFPPTIQLLCLVSGYTPGTINITWL<br>EDGQVMDVDLSTASTTQEGELASTQSELTLSQKHWLSDRTYTCQVTYQGH<br>TFEDSTKKCADSNPRGVSAYLSRPSPFDLFIRKSPTITCLVVDLAPSKGT<br>VNLTWSRASGKPVNHSTRKEEKQRNGTLTVTSTLPVGTRDWIEGETYQCR<br>VTHPHLPRALMRSTTKTSGPRAAPEVYAFATPEWPGSRDKRTLACLIQNF<br>MPEDISVQWLHNEVQLPDARHSTTQPRKTKGSGFFVFSRLEVTRAEWEQK<br>DEFICRAVHEAASPSQTVQRAVSVNPGK | Amino acid sequence for IgE heavy chain constant region |
| 70 | GCTTCCACCAAGGGCCCATCCGTCTTCCCCCTGGCGCCCTGCTCCAGGAG<br>CACCTCCGAGAGCACAGCCGCCCTGGGCTGCCTGGTCAAGGACTACTTCC<br>CCGAACCGGTGACGGTGTCGTGGAACTCAGGCGCCCTGACCAGCGGCGTG<br>CACACCTTCCCGGCTGTCCTACAGTCCTCAGGACTCTACTCCCTCAGCAG<br>CGTGGTGACCGTGCCCTCCAGCAGCTTGGGCACGAAGACCTACACCTGCA<br>ACGTAGATCACAAGCCCAGCAACACCAAGGTGGACAAGAGAGTTGAGTCC<br>AAATATGGTCCCCCATGCCCATCATGCCCAGCACCTGAGTTCCTGGGGGG<br>ACCATCAGTCTTCCTGTTCCCCCCAAAACCCAAGGACACTCTCATGATCT<br>CCCGGACCCCTGAGGTCACGTGCGTGGTGGTGGACGTGAGCCAGGAAGAC<br>CCCGAGGTCCAGTTCAACTGGTACGTGGATGGCGTGGAGGTGCATAATGC<br>CAAGACAAAGCCGCGGGAGGAGCAGTTCAACAGCACGTACCGTGTGGTCA<br>GCGTCCTCACCGTCCTGCACCAGGACTGGCTGAACGGCAAGGAGTACAAG<br>TGCAAGGTCTCCAACAAAGGCCTCCCGTCCTCCATCGAGAAAACCATCTC<br>CAAAGCCAAAGGGCAGCCCCGAGAGCCACAGGTGTACACCCTGCCCCCAT<br>CCCAGGAGGAGATGACCAAGAACCAGGTCAGCCTGACCTGCCTGGTCAAA<br>GGCTTCTACCCCAGCGACATCGCCGTGGAGTGGGAGAGCAATGGGCAGCC<br>GGAGAACAACTACAAGACCACGCCTCCCGTGCTGGACTCCGACGGCTCCT<br>TCTTCCTCTACAGCAGGCTAACCGTGGACAAGAGCAGGTGGCAGGAGGGG<br>AATGTCTTCTCATGCTCCGTGATGCATGAGGCTCTGCACAACCACTACAC<br>ACAGAAGAGCCTCTCCCTGTCTCTGGGTAAA | Nucleotide sequence for IgG4 heavy chain constant region |
| 71 | ASTKGPSVFPLAPCSRSTSESTAALGCLVKDYFPEPVTVSWNSGALTSGV<br>HTFPAVLQSSGLYSLSSVVTVPSSSLGTKTYTCNVDHKPSNTKVDKRVES<br>KYGPPCPSCPAPEFLGGPSVFLFPPKPKDTLMISRTPEVTCVVVDVSQED<br>PEVQFNWYVDGVEVHNAKTKPREEQFNSTYRVVSVLTVLHQDWLNGKEYK<br>CKVSNKGLPSSIEKTISKAKGQPREPQVYTLPPSQEEMTKNQVSLTCLVK<br>GFYPSDIAVEWESNGQPENNYKTTPPVLDSDGSFFLYSRLTVDKSRWQEG<br>NVFSCSVMHEALHNHYTQKSLSLSLGK | Amino acid sequence for IgG4 heavy chain constant region |
| 72 | QVQLVESGGGVVQPGRSLRLSCAASGFTFDTYGMHWVRQAPGKGPEWVAV<br>IWYDGTREDYADSVKGRFTVSRDNSKSTLFLQMNSLRADDTAVYYCAKEH<br>NTYFSDHIGRVGGMDVWGQGTTVIVSS | Clone PA14P1E12 - Heavy chain variable region |
| 73 | GFTFDTYG | Clone PA14P1E12 - CDR-H1 |
| 74 | IWYDGTRE | Clone PA14P1E12 - CDR-H2 |

TABLE 1-continued

Sequence Listing

| SEQ ID NO | Sequence | Description |
|---|---|---|
| 75 | AKEHNTYFSDHIGRVGGMDV | Clone PA14P1E12 - CDR-H3 |
| 76 | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQVLQTPPWTFGQGTQVEIK | Clone PA14P1E12 - light chain variable region |
| 77 | QSLLHSNGYNY | Clone PA14P1E12 - CDR-L1 |
| 78 | LGS | Clone PA14P1E12 - CDR-L2 |
| 79 | MQVLQTPPWT | Clone PA14P1E12 - CDR-L3 |
| 80 | QVQLVESGGGVVQPGRSLRLSCAGSGFTFNAYGLHWVRQAPGKGLEWVAGIYYDGSNKYYADSVKGRFAISRDNSQNTLYLEMNSLRVEDTAVYYCAKAGPIASIGTRHTFDHWGQGTLVTVSS | Clone PA14P1E10 - Heavy chain variable region |
| 81 | GFTFNAYG | Clone PA14P1E10 - CDR-H1 |
| 82 | IYYDGSNK | Clone PA14P1E10 - CDR-H2 |
| 83 | AKAGPIASIGTRHTFDH | Clone PA14P1E10 - CDR-H3 |
| 84 | DIVMTQSPDSLAVSLGERATINCKSSQSLLLNSNNKNYLAWYQQKPGQPPKLLIYWASTRESGVPDRFSGNGSVTDFTLTISGLQAEDVAVYYCHQYYTTSYTFGQGTKLEIK | Clone PA14P1E10 - light chain variable region |
| 85 | QSLLLNSNNKNY | Clone PA14P1E10 - CDR-L1 |
| 86 | WAS | Clone PA14P1E10 - CDR-L2 |
| 87 | HQYYTTSYT | Clone PA14P1E10 - CDR-L3 |
| 88 | QVQLVQSGAEVKKPGASVKISCKAVGYTFTSYYLHWVRQAPGQGLEWVGIIDPSRGHRNYAQGFQGRVTMTSDTSTSTVYMDLGSLRSEDTAVYYCARAPARDHFDNWGQGTPVTVSP | Clone PA14P1E11 - Heavy chain variable region |
| 89 | GYTFTSYY | Clone PA14P1E11 - CDR-H1 |
| 90 | IDPSRGHR | Clone PA14P1E11 - CDR-H2 |
| 91 | ARAPARDHFDN | Clone PA14P1E11 - CDR-H3 |
| 92 | DIQMTQSPSSLAASVGDRVTINCQASQDIRNCLNWYQQQPGKAPKLLIYDASILETGVPSRFSGSGSGTDFTFSISSLQPEDIATYYCQQCEDLPLTFGPGSKVDIK | Clone PA14P1E11 - light chain variable region |
| 93 | QDIRNC | Clone PA14P1E11 - CDR-L1 |
| 94 | DAS | Clone PA14P1E11 - CDR-L2 |
| 95 | QQCEDLPLT | Clone PA14P1E11 - CDR-L3 |
| 96 | QVQLVQSGAEVKQPGSSVKVSCKASGGTFRNSALSWVRQAPGQGLEWMGGIIPIFDTTNYAQEFQGRVTITADKSTTTAYMELSSLKSEDTAVYYCARGEGLPWLTYHYYGMDVWGQGTTVTVSS | Clone PA13P1C01 - Heavy chain variable region |
| 97 | GGTFRNSA | Clone PA13P1C01 - CDR-H1 |
| 98 | IIPIFDTT | Clone PA13P1C01 - CDR-H2 |
| 99 | ARGEGLPWLTYHYYGMDV | Clone PA13P1C01 - CDR-H3 |
| 100 | QAVLTQPSSLSASPGASASLTCTLRSGINIGTDRIYWFQQKPGSPPQYLLTYKSDSDEQRGSGVPSRFSGSKDVSANAGILLISGLQSEDEADYYCMIWHSSAWVFGGGTKLTVL | Clone PA13P1C01 - light chain variable region |
| 101 | SGINIGTDR | Clone PA13P1C01 - CDR-L1 |
| 102 | YKSDSDE | Clone PA13P1C01 - CDR-L2 |
| 103 | MIWHSSAWV | Clone PA13P1C01 - CDR-L3 |

TABLE 1-continued

Sequence Listing

| SEQ ID NO | Sequence | Description |
|---|---|---|
| 104 | QVQLQQWGAGLLKPSETLSLICAVYGGSLSGYHWSWIRQPPGKGLQWIGE ISHSGNAKYNPSLKSRVSISVHMSKNEFYLNLTSVTAADTAVYYCARGYC SGGSCYYKFWGQGTLVTVSS | Clone PA14P1F11 - Heavy chain variable region |
| 105 | GGSLSGYH | Clone PA14P1F11 - CDR-H1 |
| 106 | ISHSGNA | Clone PA14P1F11 - CDR-H2 |
| 107 | ARGYCSGGSCYYKF | Clone PA14P1F11 - CDR-H3 |
| 108 | QSVLTQPPSVSAAPGQKVTISCSGNSSNIGNNYVSWFQQLPGTAPKLLIY DNNKRPSGIPDRFSGSKSGTSATLGITGLQTGDEADYFCGTWDSSLRTGV FGGGTKLTVL | Clone PA14P1F11 - light chain variable region |
| 109 | SSNIGNNY | Clone PA14P1F11 - CDR-L1 |
| 110 | DNN | Clone PA14P1F11 - CDR-L2 |
| 111 | GTWDSSLRTGV | Clone PA14P1F11 - CDR-L3 |
| 112 | EVQLLESGGGLVQPGGSLRLSCAASGFTFSSYAMSWVRQAPGKGLEWVSL IYSGGSRTSYPDSVKGRFTISRDNSNTLFLQMNSLRVEDTAVYYCAKGG SSWLKMDYWGQGTLVIVSS | Clone PA14P1F10 - Heavy chain variable region |
| 113 | GFTFSSYA | Clone PA14P1F10 - CDR-H1 |
| 114 | IYSGGSRT | Clone PA14P1F10 - CDR-H2 |
| 115 | AKGGSSWLKMDY | Clone PA14P1F10 - CDR-H3 |
| 116 | QSVLTQPPSVSGAPGQRVTISCTGSSSNIGAGYDVQWYQHLPGTAPKLLIC FANTNRPSGVPDRFSGSKSGTSASLAITGLQAEDEADYYCQSYDSSLSGS VFGGGTKLTVL | Clone PA14P1F10 - light chain variable region |
| 117 | SSNIGAGYD | Clone PA14P1F10 - CDR-L1 |
| 118 | ANT | Clone PA14P1F10 - CDR-L2 |
| 119 | QSYDSSLSGSV | Clone PA14P1F10 - CDR-L3 |
| 120 | QVQLVQSGAEVKKPGASVRVSCSSSGYTFTGYYIHWVRQAPGQGLEYMGR INPHSGGTNYAQKFQGRVTMTRDTSTSTVYMELSSLRSDDTAVYYCAKEG TTAHIFNWFDPWGQGTLVTVSS | Clone PA13P1C09 - Heavy chain variable region |
| 121 | GYTFTGYY | Clone PA13P1C09 - CDR-H1 |
| 122 | INPHSGGT | Clone PA13P1C09 - CDR-H2 |
| 123 | AKEGTTAHIFNWFDP | Clone PA13P1C09 - CDR-H3 |
| 124 | DIQMTQSPSSLSASVGDRVTITCRASQSINSYLNWYQQKPGKAPNLLIYT ASSLQSGVPSRFSGSGSGTDFTLTISSLQPEDFATYYCQQSYTSLFTFGQ GTKLEIK | Clone PA13P1C09 - light chain variable region |
| 125 | QSINSY | Clone PA13P1C09 - CDR-L1 |
| 126 | TAS | Clone PA13P1C09 - CDR-L2 |
| 127 | QQSYTSLFT | Clone PA13P1C09 - CDR-L3 |
| 128 | QLQLQESGPGLVKPSETLSLTCTVSGVSINSTSYYWGWMRQPPGKGLEWI GNIYYTGTTYYNPSLNRRVSISGDTSKNQFSLSLTSVTAADTAVYYCAGP RRVTVFGILLMESFDVWSQGTMVTVSS | Clone PA13P1D02 - Heavy chain variable region |
| 129 | GVSINSTSYY | Clone PA13P1D02 - CDR-H1 |
| 130 | IYYTGTT | Clone PA13P1D02 - CDR-H2 |
| 131 | AGPRRVTVFGILLMESFDV | Clone PA13P1D02 - CDR-H3 |
| 132 | AIQMTQSPSSLSASVGDRVTITCRASQAIRDDLGWFQQKPGKAPKLLIYT ASTLQSGVPSRFSGGGSGTEFLTISSLQPEDIGTYYCLQDYGYPWTFGQ GTKVEIK | Clone PA13P1D02 - light chain variable region |

TABLE 1-continued

Sequence Listing

| SEQ ID NO | Sequence | Description |
|---|---|---|
| 133 | QAIRDD | Clone PA13P1D02 - CDR-L1 |
| 126 | TAS | Clone PA13P1D02 - CDR-L2 |
| 134 | LQDYGYPWT | Clone PA13P1D02 - CDR-L3 |
| 135 | EVQLLESGGGLVQPGGSLRLSCAASGFTFSNYALSWVRQAPGKGLEWVSA ISGRDASTYYADSVKGRFTISRDNSKNTLYLQMNSLRAEDTAVYYCTLFD YDSSGYFDFDYWGQGTLVTVSS | Clone PA14P1E04 - Heavy chain variable region |
| 136 | GFTFSNYA | Clone PA14P1E04 - CDR-H1 |
| 137 | ISGRDAST | Clone PA14P1E04 - CDR-H2 |
| 138 | TLFDYDSSGYFDFDY | Clone PA14P1E04 - CDR-H3 |
| 139 | QSALTQPRSVSGSPGQSVTISCTGTGSDVGGYNYVSWYQHHPGKAPKLII FDVTKRPSGVPDRFSGSKSGYTASLTISGLQAEDEAVYYCCSYANSYTGV FGTGTKVTVL | Clone PA14P1E04 - light chain variable region |
| 140 | GSDVGGYNY | Clone PA14P1E04 - CDR-L1 |
| 141 | DVT | Clone PA14P1E04 - CDR-L2 |
| 142 | CSYANSYTGV | Clone PA14P1E04 - CDR-L3 |
| 143 | QVQLVESGGGVVQPGGSLRLSCAASGFTFSSHVMHWVRQAPGKGLEWVAL ISLDGDDKYYADSVNGRVAISRDNSKNTLYLQVNSLRSDDTCVYYCARGG RWDYALDVWGQGTTVTVSS | Clone PA14P1E06 - Heavy chain variable region |
| 144 | GFTFSSHV | Clone PA14P1E06 - CDR-H1 |
| 145 | ISLDGDDK | Clone PA14P1E06 - CDR-H2 |
| 146 | ARGGRWDYALDV | Clone PA14P1E06 - CDR-H3 |
| 147 | EIVMTQSPATLSVSPGERATLSCRVSQSISNSLAWYQQKPGQVPRLLIYA ASTRATGIPARFSGSGSGTEFTLTISSLQSEDFAVYYCQQYNNWPRALTF GGGTKVEIK | Clone PA14P1E06 - light chain variable region |
| 148 | QSISNS | Clone PA14P1E06 - CDR-L1 |
| 149 | AAS | Clone PA14P1E06 - CDR-L2 |
| 150 | QQYNNWPRALT | Clone PA14P1E06 - CDR-L3 |
| 151 | QVQLVESGGGVVQPGRSLRLSCAASGFTFNDYAMHWVRQAPGKGPEWVAV ISYDGTNEYYMGSVKGRFTISRDNSKNMVNLQMNSLRPEDTAVYYCARDL AAWSRELLVFDQWGQGTLVTVSS | Clone PA11P1G06 - Heavy chain variable region |
| 152 | GFTFNDYA | Clone PA11P1G06 - CDR-H1 |
| 153 | ISYDGTNE | Clone PA11P1G06 - CDR-H2 |
| 154 | ARDLAAWSRELLVFDQ | Clone PA11P1G06 - CDR-H3 |
| 155 | ENVLTQSPGTLSLSPGEATLSCRASQSVPNTYLAWYQQKPGQAPRLLIY GASSRAAGIPDRFSGSGSGTDFTLTISRLEPEDFAVYYCQQYGRSPGTFG QGTKVEIK | Clone PA11P1G06 - light chain variable region |
| 156 | QSVPNTY | Clone PA11P1G06 - CDR-L1 |
| 30 | GAS | Clone PA11P1G06 - CDR-L2 |
| 157 | QQYGRSPGT | Clone PA11P1G06 - CDR-L3 |
| 158 | QAQVVESGGGVVQPGTSLRLSCEPSGFTLSDYGIHWVRQPPGKGLEWVAC IWHDGDRINYADSVKGRFTISRDESDKKVHLQMESLRTEDTAVYYCARGT LPRNCRGMRCYGEFDHYYYLDVWGTGTTVTVSS | Clone PA11P1G07 - Heavy chain variable region |
| 159 | GFTLSDYG | Clone PA11P1G07 - CDR-H1 |
| 160 | IWHDGDRI | Clone PA11P1G07 - CDR-H2 |

TABLE 1-continued

Sequence Listing

| SEQ ID NO | Sequence | Description |
|---|---|---|
| 161 | ARGTLPRNCRGMRCYGEFDHYYYLDV | Clone PA11P1G07 - CDR-H3 |
| 162 | QSVLTQPPSVSGAPGQRVTISCTGHSSNIGANSDVHWYQQLPLRAPKLLIC FGTINRASGVPDRFSGSRSGTSASLVISGLQPDDEADYYCQSYDRGLSAY VFGSGTRVDVL | Clone PA11P1G07 - light chain variable region |
| 163 | SSNIGANSD | Clone PA11P1G07 - CDR-L1 |
| 164 | GTI | Clone PA11P1G07 - CDR-L2 |
| 165 | QSYDRGLSAYV | Clone PA11P1G07 - CDR-L3 |
| 166 | EVQLVESGGGLVQPGGSLRLSCAASGFTFSSYWMSWVRQAPGKGLEWVANC IKQDGSEKDYVDSVKGRFTISRDNAKNSLYLQLNSLRAEDTAVYYCARER STQSSSWYVSSYYSYYGMDVWGQGTTVTVSS | Clone PA11P1G04 - Heavy chain variable region |
| 167 | GFTFSSYW | Clone PA11P1G04 - CDR-H1 |
| 168 | IKQDGSEK | Clone PA11P1G04 - CDR-H2 |
| 169 | ARERSTQSSSWYVSSYYSYYGMDV | Clone PA11P1G04 - CDR-H3 |
| 170 | SSELTQDPAVSVALGQTVTITCQGDSLRSFYASWYQQKPGQAPVFVIYGKC YNRPSGIPDRFSGSSSGNTASLTITGAQAEDEADYYCNSRDSSDNHLGVF GGGTKLTVL | Clone PA11P1G04 - light chain variable region |
| 171 | SLRSFY | Clone PA11P1G04 - CDR-L1 |
| 172 | GKY | Clone PA11P1G04 - CDR-L2 |
| 173 | NSRDSSDNHLGV | Clone PA11P1G04 - CDR-L3 |
| 174 | QVQLVQSGSELRKPGASVKLSCRTSGYTFIHFAMNWLRQAPGQGLEWLGWC INTHSGNPTYAQGFTGRFVFSLDVSAGTAYLEISGLKAEDTAVYYCARER YFDFWGQGALVAVSS | Clone PA11P1C11 - Heavy chain variable region |
| 175 | GYTFIHFA | Clone PA11P1C11 - CDR-H1 |
| 176 | INTHSGNP | Clone PA11P1C11 - CDR-H2 |
| 177 | ARERYFDF | Clone PA11P1C11 - CDR-H3 |
| 178 | QSVLTQPPSASGTPGQRVTISCSGTSSNIGKNFLYWYQQVPGTAPKLLIYC SSNQRPSGVPDRFSGSKSGTSASLAISGLRSEDEADYYCAAWDDSLSGWV FGGGTKVTVL | Clone PA11P1C11 - light chain variable region |
| 179 | SSNIGKNF | Clone PA11P1C11 - CDR-L1 |
| 180 | SSN | Clone PA11P1C11 - CDR-L2 |
| 181 | AAWDDSLSGWV | Clone PA11P1C11 - CDR-L3 |
| 182 | EVQLVESGGDLVQPGGSLRLSCAASGFTFSNYWMNWVRQPPGKGLVWVSRC ISGDGTGTSYADSVRGRFTISRDNAKSTLYLQVNSLSAEDTAVYYCTRDG GRDHPTPDAFDIWGQGTMVTVSS | Clone PA11P1C12 - Heavy chain variable region |
| 183 | GFTFSNYW | Clone PA11P1C12 - CDR-H1 |
| 184 | ISGDGTGT | Clone PA11P1C12 - CDR-H2 |
| 185 | TRDGGRDHPTPDAFDI | Clone PA11P1C12 - CDR-H3 |
| 186 | DVVMAQSPLSLPVTLGQPASISCRSSQSLVHSDGNTYLNWFQQRPGQSPRC RLIYKISNRDSGVPDRFSGSGSGTDFTLKISRVEAEDVGVYYCMQGTHWP RTFGQGTKLEIK | Clone PA11P1C12 - light chain variable region |
| 187 | QSLVHSDGNTY | Clone PA11P1C12 - CDR-L1 |
| 188 | KIS | Clone PA11P1C12 - CDR-L2 |
| 189 | MQGTHWPRT | Clone PA11P1C12 - CDR-L3 |

TABLE 1-continued

Sequence Listing

| SEQ ID NO | Sequence | Description |
|---|---|---|
| 190 | QVQLQQWGAGLLKPSETLSLTCVVSGGSFSTHYWNWIRQSPGKGLEWIGE INHSGNTNYNPSLTGRATISVATSKTQFSLRLNSVTAADTAVYFCARGPR LRYTAGRPLFDTWGQGTLVTVSS | Clone PA15P1G05 - Heavy chain variable region |
| 191 | GGSFSTHY | Clone PA15P1G05 - CDR-H1 |
| 192 | INHSGNT | Clone PA15P1G05 - CDR-H2 |
| 193 | ARGPRLRYTAGRPLFDT | Clone PA15P1G05 - CDR-H3 |
| 194 | DIQMTQSPSTLSASVGDRVTITCRASQSISAFLAWYQQKPGKAPNLVIYK ASSLDSGVPSTFSGSGSGTEYTLTISSLQPDDFATYYCQQYFSSPPTFGQ GTKVEMK | Clone PA15P1G05 - light chain variable region |
| 195 | QSISAF | Clone PA15P1G05 - CDR-L1 |
| 196 | KAS | Clone PA15P1G05 - CDR-L2 |
| 197 | QQYFSSPPT | Clone PA15P1G05 - CDR-L3 |
| 198 | QVQLQESGPGLVKPSQTLSLTCAVSGGSISSGGYYWSWIRQLPGKGLEWI GYIYYSGSTSYNPSLKSRVTISVDTSKNQLSLNLSSVTAADTAVYNCARG RRISISGVVTPLFDYWGQGTLVTVSS | Clone PA14P1F05 - Heavy chain variable region |
| 199 | GGSISSGGYY | Clone PA14P1F05 - CDR-H1 |
| 200 | IYYSGST | Clone PA14P1F05 - CDR-H2 |
| 201 | ARGRRISISGVVTPLFDY | Clone PA14P1F05 - CDR-H3 |
| 202 | DIQMTQSPSSVSASVGDRVTITCRASQGISSWLAWYQLKPGKAPKLLIYA ASSLQSGVPSRFSGSGSGTDFTLTISSLQPEDFATYYCQQANSVPLTFGG GTKVEIK | Clone PA14P1F05 - light chain variable region |
| 203 | QGISSW | Clone PA14P1F05 - CDR-L1 |
| 149 | AAS | Clone PA14P1F05 - CDR-L2 |
| 204 | QQANSVPLT | Clone PA14P1F05 - CDR-L3 |
| 205 | EVQLVESGGGLVKPGGSLRLSCAASGFTFSHYYLNWVRQAPGKGLEWVAC ISDRSENVYYADSVKGRFTISRDNAKNSLFLQMNNLRAEDTAIYYCARDM RELRPSADYWGQGTLVTVSS | Clone PA14P1F07 - Heavy chain variable region |
| 206 | GFTFSHYY | Clone PA14P1F07 - CDR-H1 |
| 207 | ISDRSENV | Clone PA14P1F07 - CDR-H2 |
| 208 | ARDMRELRPSADY | Clone PA14P1F07 - CDR-H3 |
| 209 | EIVLTQSPGTLSLSPGDRATLSCRASQSVDGNSLAWYQQKPGQAPRLLIS GASTRATGIPDRFSGSGSGTDFTLTISRLEPEDFVLYHCQLYTVSPRYTF GQGTKLEIK | Clone PA14P1F07 - light chain variable region |
| 210 | QSVDGNS | Clone PA14P1F07 - CDR-L1 |
| 30 | GAS | Clone PA14P1F07 - CDR-L2 |
| 211 | QLYTVSPRYT | Clone PA14P1F07 - CDR-L3 |
| 212 | QLQLQESGPGLVKPSETLSLTCTVSGGSISSDNYYWGWIRQPPGKGPLWI GTIFYNGDTYYNPSLKSQLNISVDPSKNQFSLKLTSVTAADTAIYYCTRH DSYSRGWYVTHWGQGTLVTVSS | Clone PA14P3H12 - Heavy chain variable region |
| 213 | GGSISSDNYY | Clone PA14P3H12 - CDR-H1 |
| 214 | IFYNGDT | Clone PA14P3H12 - CDR-H2 |
| 215 | TRHDSYSRGWYVTH | Clone PA14P3H12 - CDR-H3 |
| 216 | EIVLTQSPATLSLFPGERATLSCRASQSVTSYLAWYQQKPGQAPRLLIYD ASKRATGIPARFSGSGSGTDFTLTISSLEPEDFATYYCQQRSARQLFGGG TKVEIK | Clone PA14P3H12 - light chain variable region |

TABLE 1-continued

Sequence Listing

| SEQ ID NO | Sequence | Description |
|---|---|---|
| 217 | QSVTSY | Clone PA14P3H12 - CDR-L1 |
| 94 | DAS | Clone PA14P3H12 - CDR-L2 |
| 218 | QQRSARQL | Clone PA14P3H12 - CDR-L3 |
| 219 | EVQLVESGGGLVKPGGSLRLSCVASGLTFRNAWMTWVRQAPGKGLEWVGR IKSNVNGGTTDYAAPVRGRFTISRDDSRDTLYLQMNSLETEDTAMYYCTK DPPYTGGGYCQHWGLGTLVTVSS | Clone PA14P3H10 - Heavy chain variable region |
| 220 | GLTFRNAW | Clone PA14P3H10 - CDR-H1 |
| 221 | IKSNVNGGTT | Clone PA14P3H10 - CDR-H2 |
| 222 | TKDPPYTGGGYCQH | Clone PA14P3H10 - CDR-H3 |
| 223 | EIVLTQSPATLSLSPGESATLSCRASQSVSSCLAWYQQKPGQAPRLLIYD ASTRAPGIPGRFSGSGSGTDFTLAISSLEPEDFAVYYCQQCSNWPLTFGR GTRLEIK | Clone PA14P3H10 - light chain variable region |
| 224 | QSVSSC | Clone PA14P3H10 - CDR-L1 |
| 94 | DAS | Clone PA14P3H10 - CDR-L2 |
| 225 | QQCSNWPLT | Clone PA14P3H10 - CDR-L3 |
| 226 | QVQLQESGPGLVKPSQTLSLTCTVSGGSINTGAYYWSWIRQHPGKGLEWI GYIYYSGSTYYNPSLKSRVTISKDTSKNQFSLRLTSVTAADTAVYYCVRE KLTGAPDNWGQGTLVAVSS | Clone PA11P1G10 - Heavy chain variable region |
| 227 | GGSINTGAYY | Clone PA11P1G10 - CDR-H1 |
| 200 | IYYSGST | Clone PA11P1G10 - CDR-H2 |
| 228 | VREKLTGAPDN | Clone PA11P1G10 - CDR-H3 |
| 229 | DIQMTQSPSSLSASVGDRVTITCRASQGVSNYLAWFHQKPGKAPKSLIYA ASTLHDGVPSSFSGSGSGTEFTLTISDLQPEHFGTYYCEQYNSYPFTFGP GTTVDFK | Clone PA11P1G10 - light chain variable region |
| 230 | QGVSNY | Clone PA11P1G10 - CDR-L1 |
| 149 | AAS | Clone PA11P1G10 - CDR-L2 |
| 231 | EQYNSYPFT | Clone PA11P1G10 - CDR-L3 |
| 232 | QVQLVQSGAEVKKPGSSVKVSCKASGGPLSSYNFIWVRQAPGQGLEWMGG ILPVFDTTNYAQKFQGRVTITADKATSTSYMELSSLTSEDTAVYYCARAV GGTHYYYYGLDVWGQGTTVAVSS | Clone PA13P2H10 - Heavy chain variable region |
| 233 | GGPLSSYN | Clone PA13P2H10 - CDR-H1 |
| 234 | ILPVFDTT | Clone PA13P2H10 - CDR-H2 |
| 235 | ARAVGGTHYYYYGLDV | Clone PA13P2H10 - CDR-H3 |
| 236 | EIVMTQSPLSLPVTPGEPASISCRSSQSLLHGNGYNYVDWYLQRPGQPPQC LLIYLGSRRASGVPDRFSGSGSGTDFTLKISRVEADDLGVYYCMQALQTR VTFGPGTKVDIK | Clone PA13P2H10 - light chain variable region |
| 237 | QSLLHGNGYNY | Clone PA13P2H10 - CDR-L1 |
| 78 | LGS | Clone PA13P2H10 - CDR-L2 |
| 238 | MQALQTRVT | Clone PA13P2H10 - CDR-L3 |
| 239 | EVQLVQSGAEVKKPGESLKISCKGSGYSFMSYWIGWVRQKPGKGLEWMGI IFPGDSDTRYSPSFQGHVTISADKSITTAYLQWNSLEASDTAIYYCATLD GDYWGRGTLVTVSS | Clone PA14P1H02 - Heavy chain variable region |
| 240 | GYSFMSYW | Clone PA14P1H02 - CDR-H1 |
| 241 | IFPGDSDT | Clone PA14P1H02 - CDR-H2 |

TABLE 1-continued

Sequence Listing

| SEQ ID NO | Sequence | Description |
|---|---|---|
| 242 | ATLDGDY | Clone PA14P1H02 - CDR-H3 |
| 243 | DIVMTQSPDSLAVSLGERATINCRSSQSVLSSSSNKNYLGWYQQKPGQPPKLLIHWASTRAAGVPDRFSGSGTGTDFTLNISSLQAEDVAVYYCQQYHTTLPTFGQGTKLEIK | Clone PA14P1H02 - light chain variable region |
| 244 | QSVLSSSSNKNY | Clone PA14P1H02 - CDR-L1 |
| 86 | WAS | Clone PA14P1H02 - CDR-L2 |
| 245 | QQYHTTLPT | Clone PA14P1H02 - CDR-L3 |
| 246 | EVQLLESGGGLVQPGGSLRLSCAASGFTFRDSAMTWVRQAPGKGLEWVSTISGNGDTTYYADSVKGRFSIFRDNSRNTLYVQMNSLRAEDTAVYYCARYGDHKGWFDSWGQGTLVTVSS | Clone PA14P1H01 - Heavy chain variable region |
| 247 | GFTFRDSA | Clone PA14P1H01 - CDR-H1 |
| 248 | ISGNGDTT | Clone PA14P1H01 - CDR-H2 |
| 249 | ARYGDHKGWFDS | Clone PA14P1H01 - CDR-H3 |
| 250 | ELVMTQSPASLSVSPGEGATVSCRASQSVGSNLAWYQQKPGQGPRLLIYGASTRATGVPARFSGSGSGTEFTLTISSLQSEDFAVYYCQQYNNWPRTFGQGTKVEIK | Clone PA14P1H01 - light chain variable region |
| 251 | QSVGSN | Clone PA14P1H01 - CDR-L1 |
| 30 | GAS | Clone PA14P1H01 - CDR-L2 |
| 252 | QQYNNWPRT | Clone PA14P1H01 - CDR-L3 |
| 253 | QVQLVQSGAEVKKPGASVKVSCKASGYTFTSYYMHWVRQAPGQGLEWMGIINPSDGSKTYAQKFQGRVILTRDTSTSTVYMELSSLRSEDTAVYYCARGNGYSSSWYVNDYWGQGTLVTVSS | Clone PA14P1H09 - Heavy chain variable region |
| 89 | GYTFTSYY | Clone PA14P1H09 - CDR-H1 |
| 254 | INPSDGSK | Clone PA14P1H09 - CDR-H2 |
| 255 | ARGNGYSSSWYVNDY | Clone PA14P1H09 - CDR-H3 |
| 256 | DIVLTQSPGTLSLSPGERATLSCRASQSLTNSNFAWYQQIPGQAPRLLIYGASSRATGIPDRFSGSGSGTDFTLTISRLEPEDFVVYYCQQYGRSPITFGQGTRLEIK | Clone PA14P1H09 - light chain variable region |
| 257 | QSLTNSN | Clone PA14P1H09 - CDR-L1 |
| 30 | GAS | Clone PA14P1H09 - CDR-L2 |
| 258 | QQYGRSPIT | Clone PA14P1H09 - CDR-L3 |
| 259 | QVQLVESGGGVVQPGRSLRLSCAASGFTFTKYGMHWVRQAPGKGLEWVALISYDGNNKYYADSVRGRVTISRDNSKNTLYLQMDSLRAEDTAVYYCARGQDYPFWSGSTFEYWGQGTLVTVSS | Clone PA12P3D11 - Heavy chain variable region |
| 260 | GFTFTKYG | Clone PA12P3D11 - CDR-H1 |
| 261 | ISYDGNNK | Clone PA12P3D11 - CDR-H2 |
| 262 | ARGQDYPFWSGSTFEY | Clone PA12P3D11 - CDR-H3 |
| 263 | QAVVTQEPSLTVSPGGTVTLTCGSTTGAVTGGHFPYWIQQKPGQAPRTLICYDATNRHSWTPARFSGSLLGGKAALTLSGAQPEDEADYYCLLSYSSATFLIFGGGTKLTVL | Clone PA12P3D11 - light chain variable region |
| 264 | TGAVTGGHF | Clone PA12P3D11 - CDR-L1 |
| 265 | DAT | Clone PA12P3D11 - CDR-L2 |
| 266 | LLSYSSATFLI | Clone PA12P3D11 - CDR-L3 |

TABLE 1-continued

Sequence Listing

| SEQ ID NO | Sequence | Description |
|---|---|---|
| 267 | QVQLQESGPGLVKPSETLSLTCTVSGDSLSSGSYFWSWIRQPPGKGLEWIGYISFRGDTNYNPSLKSRVIISLDKSKNQFSLRLSSMTPADTAVYYCARSPWIQSWSYYFDYWGQGTLVTVSS | Clone PA12P3F02 - Heavy chain variable region |
| 268 | GDSLSSGSYF | Clone PA12P3F02 - CDR-H1 |
| 269 | ISFRGDT | Clone PA12P3F02 - CDR-H2 |
| 270 | ARSPWIQSWSYYFDY | Clone PA12P3F02 - CDR-H3 |
| 271 | DIQMTQSPSTVSASVGDRVTITCRASQRISSWLAWYQQKPGKAPKLLIYKASSLEGGVPSRFSGSGSGTEFTLTISSLQPDDFAIYYCQQYNGYPWTFGQGTKVEIK | Clone PA12P3F02 - light chain variable region |
| 272 | QRISSW | Clone PA12P3F02 - CDR-L1 |
| 196 | KAS | Clone PA12P3F02 - CDR-L2 |
| 273 | QQYNGYPWT | Clone PA12P3F02 - CDR-L3 |
| 274 | QVQLQESGPGLVKPSGTLSLTCAVSGGSISTDNWWSWVRQPPNKGLEWIGAIFQSGSTIYNPSLMSRVTISLDRSNNRFSLQLISVTAADTALYYCARSFHYGSGNYFEYLGQGTLVTVSS | Clone PA12P3F07 - Heavy chain variable region |
| 275 | GGSISTDNW | Clone PA12P3F07 - CDR-H1 |
| 276 | IFQSGST | Clone PA12P3F07 - CDR-H2 |
| 277 | ARASFHYGSGNYFEY | Clone PA12P3F07 - CDR-H3 |
| 278 | QSVLTQPPSVSAAPGQKVTISCSGSSSNVGTHHVSWYQQLPGTAPKLLIYENDKRPSGIPNRFSGSKSGTSATLAIIGLQTGDEADYYCGSWDSSLSAFWVFGGGTKLTVL | Clone PA12P3F07 - light chain variable region |
| 279 | SSNVGTHH | Clone PA12P3F07 - CDR-L1 |
| 280 | END | Clone PA12P3F07 - CDR-L2 |
| 281 | GSWDSSLSAFWV | Clone PA12P3F07 - CDR-L3 |
| 282 | QVQLVQSGAEVKKPGASVKVACKASGYTFTRYAMHWVRQAPGQRLEWMGWINAGNGNTKDSQKFQGRVTITRDTSASTVYMELSSLRSEDTAVYYCARGVPWGLGSYNFDYWGQGTLVSISS | Clone PA14P1G03 - Heavy chain variable region |
| 283 | GYTFTRYA | Clone PA14P1G03 - CDR-H1 |
| 284 | INAGNGNT | Clone PA14P1G03 - CDR-H2 |
| 285 | ARGVPWGLGSYNFDY | Clone PA14P1G03 - CDR-H3 |
| 286 | QTVVTQEPSLTVSPGGTVTLSCASNTGAVTSGYYPYWFQQKPGQAPRTLICYETSNKHPWTPARFSGSLLGGKAALTLSGVQPEDEAEYCCLLYYGGTWVFGGGTKLTVL | Clone PA14P1G03 - light chain variable region |
| 287 | TGAVTSGYY | Clone PA14P1G03 - CDR-L1 |
| 288 | ETS | Clone PA14P1G03 - CDR-L2 |
| 289 | LLYYGGTWV | Clone PA14P1G03 - CDR-L3 |
| 290 | EVQLLESGGGLVQPGGSLRLSCAASGFTFSSYALSWVRQAPGKGLEWVSACISGRDGNTYYADSVKGRFTISRDNSKNTLYLQMNSLRAEDTAVYYCTLYDYDSSGYFDFDYWGQGTLVTVSS | Clone PA14P1G01 - Heavy chain variable region |
| 113 | GFTFSSYA | Clone PA14P1G01 - CDR-H1 |
| 291 | ISGRDGNT | Clone PA14P1G01 - CDR-H2 |
| 292 | TLYDYDSSGYFDFDY | Clone PA14P1G01 - CDR-H3 |
| 293 | QSALTQPRSVSGSPGQSVTISCTGTSSDVGGFNYVSWYQQHPGKAPKLMIFDVTQRPSGVPDRFSGSKSGNTASLTISGLQAEDEADYHCCSYANYYTGVFGTGTRVTVL | Clone PA14P1G01 - light chain variable region |

TABLE 1-continued

Sequence Listing

| SEQ ID NO | Sequence | Description |
|---|---|---|
| 294 | SSDVGGFNY | Clone PA14P1G01 - CDR-L1 |
| 141 | DVT | Clone PA14P1G01 - CDR-L2 |
| 295 | CSYANYYTGV | Clone PA14P1G01 - CDR-L3 |
| 296 | EVQLVESGGGLVQPGGSLRLSCAASGFTFSNYWMHWVRQAPGKGLVWVSRINSDGSNIRFADSVKGRFTFSRDNANNTLYLQMNSLRAEDTAVYYCARASRTVYGDSPLSYGIDVWGQGTTVTVSS | Clone PA16P1F09 - Heavy chain variable region |
| 183 | GFTFSNYW | Clone PA16P1F09 - CDR-H1 |
| 297 | INSDGSNI | Clone PA16P1F09 - CDR-H2 |
| 298 | ARASRTVYGDSPLSYGIDV | Clone PA16P1F09 - CDR-H3 |
| 299 | SYALTQPPSVSVSPGQTASITCSGDKLGNKFACWYQQKPGRSPVLVIYQDSQRPTGIPERFSGSNSGNTATLTISGTQAMDEADYYCQAWDSNTHVLFGGGTKLTVL | Clone PA16P1F09 - light chain variable region |
| 300 | KLGNKF | Clone PA16P1F09 - CDR-L1 |
| 301 | QDS | Clone PA16P1F09 - CDR-L2 |
| 302 | QAWDSNTHVL | Clone PA16P1F09 - CDR-L3 |
| 303 | QVQLVESGGGVVQPGGSLRLSCAASGFTFSGYGMHWVRQAPGKGLEWVAFFSFDGSNTDYVDSVKGRFTISGDNSKNTLYLQMNSLRAEDTAVYYCVRDILVLPAAVSVFSGYYYGMDVWGQGTTVTVSS | Clone PA14P1G12 - Heavy chain variable region |
| 304 | GFTFSGYG | Clone PA14P1G12 - CDR-H1 |
| 305 | FSFDGSNT | Clone PA14P1G12 - CDR-H2 |
| 306 | VRDILVLPAAVSVFSGYYYGMDV | Clone PA14P1G12 - CDR-H3 |
| 307 | EIVLTQSPATLSLSPGERATLSCRASQSVRSYLAWYQQKPGQAPRLLIYDASNRATGIPARFSGSGSGTDFTLTISSLEPEDFAVYYCQHRSNWPITFGQGTRLEIK | Clone PA14P1G12 - light chain variable region |
| 308 | QSVRSY | Clone PA14P1G12 - CDR-L1 |
| 94 | DAS | Clone PA14P1G12 - CDR-L2 |
| 309 | QHRSNWPIT | Clone PA14P1G12 - CDR-L3 |
| 310 | QVQLRVSGPGLVNPSETLSLTCIVSGDSLRDYYWSWIRQSPGKGLEWIGYVTESGGAHYNPSLESRVTISVDASKTQFSLNLKSVTAADTAVYYCARDAYSSTWYTVGWFDPWGPGSLVTVSS | Clone PA11P1D12 - Heavy chain variable region |
| 311 | GDSLRDYY | Clone PA11P1D12 - CDR-H1 |
| 312 | VTESGGA | Clone PA11P1D12 - CDR-H2 |
| 313 | ARDAYSSTWYTVGWFDP | Clone PA11P1D12 - CDR-H3 |
| 314 | EIVLTQSPATLSLSPGERATLSCRASQDVGVYLAWYQQKPGQAPRLIIYDASDRVSGVPARFTGSGSGTDFTLTITSLEPEDFAVYFCQQRTSGLTFGGGTTLEIK | Clone PA11P1D12 - light chain variable region |
| 315 | QDVGVY | Clone PA11P1D12 - CDR-L1 |
| 94 | DAS | Clone PA11P1D12 - CDR-L2 |
| 316 | QQRTSGLT | Clone PA11P1D12 - CDR-L3 |
| 317 | QVELVESGGGVVQPGRSLRLSCVASGFTFSDYGMHWVRQAPGKGLEWVACIWFDGSSKYYADSVKGRFTISRDDSKNTVFMQMNNVRVEDTAVYYCAREWLGTEYFQNWGQGTLVTVSS | Clone PA11P1D11 - Heavy chain variable region |
| 318 | GFTFSDYG | Clone PA11P1D11 - CDR-H1 |
| 319 | IWFDGSSK | Clone PA11P1D11 - CDR-H2 |

TABLE 1-continued

Sequence Listing

| SEQ ID NO | Sequence | Description |
|---|---|---|
| 320 | AREQWLGTEYFQN | Clone PA11P1D11 - CDR-H3 |
| 321 | EIVMTQSPATLSLFPGERATLSCRASQSVAGNLAWYQQKPGQAPRLLIYEASTRATDIPARFSGSGSETEFTLTISSLQSEDFAVYYCQQYKKWLITFGQGTRLEIK | Clone PA11P1D11 - light chain variable region |
| 322 | QSVAGN | Clone PA11P1D11 - CDR-L1 |
| 323 | EAS | Clone PA11P1D11 - CDR-L2 |
| 324 | QQYKKWLIT | Clone PA11P1D11 - CDR-L3 |
| 325 | QLQLQQWGAGLVKPSETLSLTCTVSGGSLSGHFWSWIRQSPEKGLEWIGEINHSGRKNYNPSLMIRVDISIDTSKNQFSMRMTSLTAADSAVYYCARVGRNIVDTDDAFDVWGRGTLVTVSS | Clone PA12P1D02 - Heavy chain variable region |
| 326 | GGSLSGHF | Clone PA12P1D02 - CDR-H1 |
| 327 | INHSGRK | Clone PA12P1D02 - CDR-H2 |
| 328 | ARVGRNIVDTDDAFDV | Clone PA12P1D02 - CDR-H3 |
| 329 | EIVLTQSPGTLSLSPGDTVTLSCRASQTIDSIYLAWYQQRPGQAPRLLIYGASTRATGTPDRFSGGGSGTDFTLTITRLEPEDFAVYFCQQYGTSPPITFGRGTRLEIK | Clone PA12P1D02 - light chain variable region |
| 330 | QTIDSIY | Clone PA12P1D02 - CDR-L1 |
| 30 | GAS | Clone PA12P1D02 - CDR-L2 |
| 331 | QQYGTSPPIT | Clone PA12P1D02 - CDR-L3 |
| 332 | QVQLLQSGAEVKKPGASVKVSCKASGYTFTSYNIHWVRQAPGQSFEWMGWIHVGNGETKYSQNFQDRVAITRDTSANTVYMELSPLRSEDTALYYCVRDHVTAIVVGLFDPWGQGTLVTVSS | Clone PA12P1D04 - Heavy chain variable region |
| 333 | GYTFTSYN | Clone PA12P1D04 - CDR-H1 |
| 334 | IHVGNGET | Clone PA12P1D04 - CDR-H2 |
| 335 | VRDHVTAIVVGLFDP | Clone PA12P1D04 - CDR-H3 |
| 336 | QSALTQPASVSGSPGQSITISCSGTSTDVGAYKYVSWYQHHPGRSPKVILCYEVDNRPSGVSIRFSGSKSGNTASLTISGLRAEDEADYYCSSFTSSSTWVFGGGTKVTVL | Clone PA12P1D04 - light chain variable region |
| 337 | STDVGAYKY | Clone PA12P1D04 - CDR-L1 |
| 338 | EVD | Clone PA12P1D04 - CDR-L2 |
| 339 | SSFTSSSTWV | Clone PA12P1D04 - CDR-L3 |
| 340 | QVQLVQSGAEVKKPGSSVKVSCKASGGTFSSYSISWVRQAPGQGLEWMGGIIPIFGSGSYAQKFQGVTITADKSTSTAYMELSSLSSDDTAVYYCARGESPSNFVYYGMDVWGQGTTVTVSS | Clone PA12P3E09 - Heavy chain variable region |
| 341 | GGTFSSYS | Clone PA12P3E09 - CDR-H1 |
| 342 | IIPIFGSG | Clone PA12P3E09 - CDR-H2 |
| 343 | ARGESPSNFVYYGMDV | Clone PA12P3E09 - CDR-H3 |
| 344 | DIVLTQSPLSLPVTPGEPASISCRSSHSLLHSNGYNHLDWYLQKPGQSPQCLLIYLGSNRASGVPDRFSGSGSGTDFTLKISRVEAEDVGVYYCMQALLVTFGPGTKVDIK | Clone PA12P3E09 - light chain variable region |
| 345 | HSLLHSNGYNH | Clone PA12P3E09 - CDR-L1 |
| 78 | LGS | Clone PA12P3E09 - CDR-L2 |
| 346 | MQALLVT | Clone PA12P3E09 - CDR-L3 |

TABLE 1-continued

Sequence Listing

| SEQ ID NO | Sequence | Description |
|---|---|---|
| 347 | EVKVVESGGGLVQPGGSLRLSCAASEFTFTYYWMSWIRQAPGKGLEWVAN VNGDATEKYYVDSVKGRFTISRDNPKKTVYLQMNSLRVEDTAVYYCARVG TTVVNDGFDLWGLGTMVTVSS | Clone PA12P3E04 - Heavy chain variable region |
| 348 | EFTFTYYW | Clone PA12P3E04 - CDR-H1 |
| 349 | VNGDATEK | Clone PA12P3E04 - CDR-H2 |
| 350 | ARVGTTVVNDGFDL | Clone PA12P3E04 - CDR-H3 |
| 351 | SYVLTQSHSVSVAPGQTARITCGGENIGGKGVHWYQQKPGQAPLLVVSSD TGRRSVTPDRFSGSNSGDTATLIISRVEAGDEADYYCQVWDPTSEYVFGS GTKVTVL | Clone PA12P3E04 - light chain variable region |
| 352 | NIGGKG | Clone PA12P3E04 - CDR-L1 |
| 353 | SDT | Clone PA12P3E04 - CDR-L2 |
| 354 | QVWDPTSEYV | Clone PA12P3E04 - CDR-L3 |
| 355 | QLQLQESGSGLVKPSQTLSLTCAVSGGSISSGDYSWSWIRQPPGKGLEWI GFRYYSGTTFYNPSLESRLTISIDRSTNQFSLQLTSVTAADTAVYFCASF RPLLRFLDPEGLFEYWGQGILVTVSS | Clone PA12P3E07 - Heavy chain variable region |
| 356 | GGSISSGDYS | Clone PA12P3E07 - CDR-H1 |
| 357 | RYYSGTT | Clone PA12P3E07 - CDR-H2 |
| 358 | ASFRPLLRFLDPEGLFEY | Clone PA12P3E07 - CDR-H3 |
| 359 | ELVMTQSPATLSVSPGARATLSCRASPGANSHLAWYQQKPGQAPRLLIYG ASTRATGIPARFSGSGSGTEFTLTISSLQSEDFAVYYCQQYNDWPYTFGQ GTKLEIK | Clone PA12P3E07 - light chain variable region |
| 360 | PGANSH | Clone PA12P3E07 - CDR-L1 |
| 30 | GAS | Clone PA12P3E07 - CDR-L2 |
| 361 | QQYNDWPYT | Clone PA12P3E07 - CDR-L3 |
| 362 | QVQLVQSGAAVKKPGASVRISCEASGYTFTGYNIHWVRQAPGQGLEWMGW VNPNNGGTKFAQKFEGWVTMTVATSINTVYMELTGLKSGDTAVYFCARDH GDSFDQWGQGTLVTVSS | Clone PA12P3E06 - Heavy chain variable region |
| 363 | GYTFTGYN | Clone PA12P3E06 - CDR-H1 |
| 364 | VNPNNGGT | Clone PA12P3E06 - CDR-H2 |
| 365 | ARDHGDSFDQ | Clone PA12P3E06 - CDR-H3 |
| 366 | EIVLTQSPDTLSLSPGDRATLSCRASHSLNNDYLAWYQHRPGQAPRLLIY GTSHGATGIPDRFSGSGSGTDFTLTISRLETEDFAVYYCHHYGKSLFPFP GTKVDIK | Clone PA12P3E06 - light chain variable region |
| 367 | HSLNNDY | Clone PA12P3E06 - CDR-L1 |
| 22 | GTS | Clone PA12P3E06 - CDR-L2 |
| 368 | HHYGKSLFP | Clone PA12P3E06 - CDR-L3 |
| 369 | EVQLVESGGGLVQPGGSLKLSCAASGFTFSGSAMHWVRQASGKGLEWVGR IRSKANTYATAYAASVKGRFTISRDDSKNTAYLQMNSLKTEDTAVYYCTR KHTSGWYDRGGDVWGQGTTVTVSS | Clone PA14P1E08 - Heavy chain variable region |
| 370 | GFTFSGSA | Clone PA14P1E08 - CDR-H1 |
| 371 | IRSKANTYAT | Clone PA14P1E08 - CDR-H2 |
| 372 | TRKHTSGWYDRGGDV | Clone PA14P1E08 - CDR-H3 |
| 373 | DIQMTQSPSSLSASVGDRVTITCQASQDISNYLNWYQQKPGKAPKLLIYD ASNLETGVPSRFSGSGSGTDFTFTISSLQPEDIATYYCQQYDNLPLTFGG GTKVEIK | Clone PA14P1E08 - light chain variable region |

TABLE 1-continued

Sequence Listing

| SEQ ID NO | Sequence | Description |
|---|---|---|
| 374 | QDISNY | Clone PA14P1E08 - CDR-L1 |
| 94 | DAS | Clone PA14P1E08 - CDR-L2 |
| 375 | QQYDNLPLT | Clone PA14P1E08 - CDR-L3 |
| 376 | EVQLLESGGGLVQPGGSLRLSCAASGFTVSNYAMSWVRQAPGKGLEWVSAISGSGGSTYYADSVKGRFTISRDTSKNTLYLQMNSLRAEDTAVYYCAIDCTVTDAPLSYWGQGTLVTVSS | Clone PA14P1E09 - Heavy chain variable region |
| 377 | GFTVSNYA | Clone PA14P1E09 - CDR-H1 |
| 378 | ISGSGGST | Clone PA14P1E09 - CDR-H2 |
| 379 | AIDCTVTDAPLSY | Clone PA14P1E09 - CDR-H3 |
| 380 | AIQMTQSPSSLSPSVGDRVTITCRASQGIRNDLGWYQQKPGKAPKLLIYAASSLQSGVPSRFSGGGSGTDFTLTISSLQPEDFATYYCLQDYNYPRTFGQGTKVEIK | Clone PA14P1E09 - light chain variable region |
| 381 | QGIRND | Clone PA14P1E09 - CDR-L1 |
| 149 | AAS | Clone PA14P1E09 - CDR-L2 |
| 382 | LQDYNYPRT | Clone PA14P1E09 - CDR-L3 |
| 383 | QVQLEQSGAEVRKPGSSVKVSCKASGTTFSNHAMSWVRQAPGQGLEWMGGIIPLVDKSMYALKFQGRVTITADESRNTVYMELSSLGSEDTAVYYCARSFADITTFGFVVNFHYYYTLDVWGQGTPVTVSS | Clone PA14P1H05 - Heavy chain variable region |
| 384 | GTTFSNHA | Clone PA14P1H05 - CDR-H1 |
| 385 | IIPLVDKS | Clone PA14P1H05 - CDR-H2 |
| 386 | ARSFADITTFGFVVNFHYYYTLDV | Clone PA14P1H05 - CDR-H3 |
| 387 | NFMLTQPHSVSESPGKTVTISCTRSSGSIADNYVQWFQQRPGSAPTTLIYEDNRRPSGVPDRFSGSVDSSSNSASLTISGLKPEDEADYYCQSYDTTQRVFGGGTKLTVL | Clone PA14P1H05 - light chain variable region |
| 388 | SGSIADNY | Clone PA14P1H05 - CDR-L1 |
| 389 | EDN | Clone PA14P1H05 - CDR-L2 |
| 390 | QSYDTTQRV | Clone PA14P1H05 - CDR-L3 |
| 391 | QLQLQESGSRLVKPSQTLSLTCAVSGGSINSGGYSWSWIRQPPGKGLEWIGNIYHGETTHYNPSLKSRVTISIDKSKNQFSLKLTSVTAADTAVYYCARAPLGNYYDTSGYLQPFDYWGPGALVTVSS | Clone PA12P3C09 - Heavy chain variable region |
| 392 | GGSINSGGYS | Clone PA12P3C09 - CDR-H1 |
| 393 | IYHGETT | Clone PA12P3C09 - CDR-H2 |
| 394 | ARAPLGNYYDTSGYLQPFDY | Clone PA12P3C09 - CDR-H3 |
| 395 | DIQMTQSPSSLSASVGDRVTITCRASQGIINDLGWYQQRPGRAPTRLIYAASSLQSGVPSRFSGSGSGTEFTLTINSLQPADFATYFCLQYNSYPPTFGQGTKVEIK | Clone PA12P3C09 - light chain variable region |
| 396 | QGIIND | Clone PA12P3C09 - CDR-L1 |
| 149 | AAS | Clone PA12P3C09 - CDR-L2 |
| 397 | LQYNSYPPT | Clone PA12P3C09 - CDR-L3 |
| 398 | EVQLVESGGGVVRPGGSLRLSCAASGFIFRDHGMSWVRQAPGKGLEWVSGINWNGANTGYADSVKGRSTISRDNAKNSLYLQMSSLRADDTALYHCVSHDYYYGLDVWGPGTTVIVSS | Clone PA12P3C05 - Heavy chain variable region |
| 399 | GFIFRDHG | Clone PA12P3C05 - CDR-H1 |
| 400 | INWNGANT | Clone PA12P3C05 - CDR-H2 |

TABLE 1-continued

Sequence Listing

| SEQ ID NO | Sequence | Description |
|---|---|---|
| 401 | VSHDYYYGLDV | Clone PA12P3C05 - CDR-H3 |
| 402 | QSALTQPRSVSGSPGQSVTISCTGTSSDVGGDNYVSWYQQHPGKVPKLIIHDVSERPSGVPDRFSGSKSANTASLTISGLQADDEADYYCCSYAGTYTFGGGTRLTVL | Clone PA12P3C05 - light chain variable region |
| 403 | SSDVGGDNY | Clone PA12P3C05 - CDR-L1 |
| 404 | DVS | Clone PA12P3C05 - CDR-L2 |
| 405 | CSYAGTYT | Clone PA12P3C05 - CDR-L3 |
| 406 | QVQLQESGPGLVKPSQTLSLTCTVSGGSISSGGYYWSWIRQLPGKGLEWIGYIYYSGSTSYNPSLKSRVTISVDTSKNQLSLNLSSVTAADTAVYYCARGRRISISGVVTPLFDYWGQGTLVTSS | Clone PA14P1G11 - Heavy chain variable region |
| 199 | GGSISSGGYY | Clone PA14P1G11 - CDR-H1 |
| 200 | IYYSGST | Clone PA14P1G11 - CDR-H2 |
| 201 | ARGRRISISGVVTPLFDY | Clone PA14P1G11 - CDR-H3 |
| 407 | DIQMTQSPSSVSASVGDRVTITCRASQGISSWLAWYQQKPGKAPKLLIYAASSLQSGVPSRFSGSGSGTDFTLTISSLQPEDFATYYCQQANSVPLTFGGGTKVEIK | Clone PA14P1G11 - light chain variable region |
| 203 | QGISSW | Clone PA14P1G11 - CDR-L1 |
| 149 | AAS | Clone PA14P1G11 - CDR-L2 |
| 204 | QQANSVPLT | Clone PA14P1G11 - CDR-L3 |
| 408 | QVQLVQSGAEVKKPGASVKVSCQASGYTFTRYDINWVRQATGQGLEWMGWLNPKSGDTGYAQKFQGRVTMTRDTSISTAYMELTSLTSDDTAVYYCARGVDANHWGQGSLVTVSS | Clone PA12P3C01 - Heavy chain variable region |
| 409 | GYTFTRYD | Clone PA12P3C01 - CDR-H1 |
| 410 | LNPKSGDT | Clone PA12P3C01 - CDR-H2 |
| 411 | ARGVDANH | Clone PA12P3C01 - CDR-H3 |
| 412 | DIVVTQSPDSLAVSLGERATINCKSSQSIFDTSSNKNYLAWFRQRPGQPPQLLIYWASTRESGVPDRFSGSGSGTDFTLTISSLQAEDVAVYYCHQYYSLPHAFGQGTKLEIK | Clone PA12P3C01 - light chain variable region |
| 413 | QSIFDTSSNKNY | Clone PA12P3C01 - CDR-L1 |
| 86 | WAS | Clone PA12P3C01 - CDR-L2 |
| 414 | HQYYSLPHA | Clone PA12P3C01 - CDR-L3 |
| 415 | EAQLVESGGGLVQPGGSLRLSCAASGFTFSSYYIHWVRQAPGKGLVWVSRINSDGSSTRYADSVKGRFTISRDNAKNTLYLQMNSLRAEDTAVYFCARASRTVYGDSPLSNGMDVWGQGTKVTVSS | Clone PA16P1H09 - Heavy chain variable region |
| 416 | GFTFSSYY | Clone PA16P1H09 - CDR-H1 |
| 417 | INSDGSST | Clone PA16P1H09 - CDR-H2 |
| 418 | ARASRTVYGDSPLSNGMDV | Clone PA16P1H09 - CDR-H3 |
| 419 | SYELTQPPSVSVSPGQTASITCSGDKLGDKFACWYQQKPGHSPVLVIYQDDKRPSGIPERFSGSNSGNTATLTISGTQAMDEADYYCQAWDSSTHVVFGGGTKLTVL | Clone PA16P1H09 - light chain variable region |
| 420 | KLGDKF | Clone PA16P1H09 - CDR-L1 |
| 421 | QDD | Clone PA16P1H09 - CDR-L2 |
| 422 | QAWDSSTHVV | Clone PA16P1H09 - CDR-L3 |

TABLE 1-continued

Sequence Listing

| SEQ ID NO | Sequence | Description |
|---|---|---|
| 423 | EVQLVESGGGLVQPGGSLRLSCAASGFSFNTYNMNWVRQAPGKGLEWISD ITSSGSMRSYADAVKGRFTISRDNAKNSLHLQMNSLRVEDTAVYYCTRGW HDDLWSGYSYGLDVWGQGTTVTSS | Clone PA12P3D09 - Heavy chain variable region |
| 424 | GFSFNTYN | Clone PA12P3D09 - CDR-H1 |
| 425 | ITSSGSMR | Clone PA12P3D09 - CDR-H2 |
| 426 | TRGWHDDLWSGYSYGLDV | Clone PA12P3D09 - CDR-H3 |
| 427 | DIQMTQSPSSLSASVGDRVTITCRASQGIRNDLGWYQQRPGKAPRCLIYG ASSLQSGVPSRFSGSGSGTEFTLTISNLQAEDFATYYCLQHKSYPLTFGP GTKVDIK | Clone PA12P3D09 - light chain variable region |
| 381 | QGIRND | Clone PA12P3D09 - CDR-L1 |
| 30 | GAS | Clone PA12P3D09 - CDR-L2 |
| 428 | LQHKSYPLT | Clone PA12P3D09 - CDR-L3 |
| 429 | QLLLLGPGPGVVRPSETLSLTCNVSGHSITDSPYYWGWIRQAPGKGLEWI GHFYYSDYTYYNPSLKSRVNVSVDTSKNHLFLALTSVTAADTAVYYCARG FGGYDSPIWAIWGQGTLVTVSS | Clone PA13P3G04 - Heavy chain variable region |
| 430 | GHSITDSPYY | Clone PA13P3G04 - CDR-H1 |
| 431 | FYYSDYT | Clone PA13P3G04 - CDR-H2 |
| 432 | ARGFGGYDSPIWAI | Clone PA13P3G04 - CDR-H3 |
| 433 | SHAVTQPPSVSVAPGQTASLTCAGDDIEENTVHWYQQKPGQAPVLVIYYT TDRPSAIPERFFGSKSGNTATLSIARVEAGDEADYYCQVSDRVFGGGTKL TVL | Clone PA13P3G04 - light chain variable region |
| 434 | DIEENT | Clone PA13P3G04 - CDR-L1 |
| 435 | YTT | Clone PA13P3G04 - CDR-L2 |
| 436 | QVSDRV | Clone PA13P3G04 - CDR-L3 |
| 437 | EVQLVQSGGGLVKPGGSLRLSCAASGSTLTNYNINWVRQAPGKGLQWVSS ISGTRDYTYYADSVVGRFTISRDNAKNSVYLQMNSLRAEDTAVYYCARG EVGGDYDSYDWGQGTLVTVSS | Clone PA11P1C03 - Heavy chain variable region |
| 438 | GSTLTNYN | Clone PA11P1C03 - CDR-H1 |
| 439 | ISGTRDYT | Clone PA11P1C03 - CDR-H2 |
| 440 | ARGREVGGDYDSYD | Clone PA11P1C03 - CDR-H3 |
| 441 | DIQMTQSPSSLSASVGDRVTITCQASQDISTFLHWYQQKPGKAPSVLIYG ASDLKTGVPSRFSGSGSGTHFTLTISSLQPEDIATYYCQQYDHLPLTFGG GTKVEIK | Clone PA11P1C03 - light chain variable region |
| 442 | QDISTF | Clone PA11P1C03 - CDR-L1 |
| 30 | GAS | Clone PA11P1C03 - CDR-L2 |
| 443 | QQYDHLPLT | Clone PA11P1C03 - CDR-L3 |
| 444 | EVQLVESGGGLIQPGGSLRLSCAASGFTVSSNYMSWVRQAPGKGLEWVSV IYSGGSTYYADSVKGRFTISRDNSKNTLYLQMNSLRAEDTAVYYCARDSR LGWAYDAFDIWGQGTMVTVSS | Clone PA11P1C01 - Heavy chain variable region |
| 445 | GFTVSSNY | Clone PA11P1C01 - CDR-H1 |
| 446 | IYSGGST | Clone PA11P1C01 - CDR-H2 |
| 447 | ARDSRLGWAYDAFDI | Clone PA11P1C01 - CDR-H3 |
| 448 | DIVMTQSPLSLPVTPGEPASISCRSSQSLLHSNGYNYLDWYLQKPGQSPQ LLIYLGSNRASGVPDRFSGSGSGTDFTLKISRVEAEDVGVYYCMQDGTF QGTKVEIK | Clone PA11P1C01 - light chain variable region |

TABLE 1-continued

Sequence Listing

| SEQ ID NO | Sequence | Description |
|---|---|---|
| 77 | QSLLHSNGYNY | Clone PA11P1C01 - CDR-L1 |
| 78 | LGS | Clone PA11P1C01 - CDR-L2 |
| 449 | MQDGT | Clone PA11P1C01 - CDR-L3 |
| 450 | QVQLVQSGSELKKPGASVKASCKASGYTFSNYAVNWVRQAPGQGLEWMGW INTKTGNPTYGQGFTGRFVFSLDTSVSTAYLQISSLKAEDTAVYYCARAA DYGEPYYYGMDVWGQGTTVTVSS | Clone PA11P1C06 - Heavy chain variable region |
| 451 | GYTFSNYA | Clone PA11P1C06 - CDR-H1 |
| 452 | INTKTGNP | Clone PA11P1C06 - CDR-H2 |
| 453 | ARAADYGEPYYYGMDV | Clone PA11P1C06 - CDR-H3 |
| 454 | QSALTQPASVSGSPGQSITISCTGINSDVGSYNLVSWYQQHPGKAPKFMI YEGTKRPSGVSNRFSGSKSGHTASLTISGLQAEDEADYYCCSYAGTSTLV FGGGTKLTVL | Clone PA11P1C06 - light chain variable region |
| 455 | NSDVGSYNL | Clone PA11P1C06 - CDR-L1 |
| 456 | EGT | Clone PA11P1C06 - CDR-L2 |
| 457 | CSYAGTSTLV | Clone PA11P1C06 - CDR-L3 |
| 458 | EVQLVESGGGLVQPGGSLRLSCAASGFTFRNYWMNWVRQAPGKGLVWVSR INSEGSSTSYADPVKGRFTISRDNAKDTLYLQMDSLRAEDSAVYYCARIF NGYIHVGRDYWGQGTRVTVSS | Clone PA13P1H03 - Heavy chain variable region |
| 459 | GFTFRNYW | Clone PA13P1H03 - CDR-H1 |
| 460 | INSEGSST | Clone PA13P1H03 - CDR-H2 |
| 461 | ARIFNGYIHVGRDY | Clone PA13P1H03 - CDR-H3 |
| 462 | DIQMTQSPSTLSASIGDRVTITCRASESISNWLAWFQQKPGKAPKLLIYK ASNLESGVPSRFSGSGSGTEFTLTISSLQPDDFATYYCQQYNSNSQTFGQ GTKLDLK | Clone PA13P1H03 - light chain variable region |
| 463 | ESISNW | Clone PA13P1H03 - CDR-L1 |
| 196 | KAS | Clone PA13P1H03 - CDR-L2 |
| 464 | QQYNSNSQT | Clone PA13P1H03 - CDR-L3 |
| 465 | QVQLQESGPGLVKPSETLSLTCTVSGGSISSYYWNWIRQPPGKGLEWIGY IYYSGSTNYNPSLKSRATISVDTSKNQFSLKLSSVTAADTAVYYCARANL FGVALRRVLGPFDYWGQGTLVTVSS | Clone PA11P1C04 - Heavy chain variable region |
| 466 | GGSISSYY | Clone PA11P1C04 - CDR-H1 |
| 200 | IYYSGST | Clone PA11P1C04 - CDR-H2 |
| 467 | ARANLFGVALRRVLGPFDY | Clone PA11P1C04 - CDR-H3 |
| 468 | DIQMTQSPSSLSASVGDRVTIACRASQSIANYLNWYQQKPGKAPKLLIYA ASNLQSGVPSRFSGSGSGTDFTLTISSLQPEDFATYYCQQSYSTPYTFGQ GTKLEIK | Clone PA11P1C04 - light chain variable region |
| 469 | QSIANY | Clone PA11P1C04 - CDR-L1 |
| 149 | AAS | Clone PA11P1C04 - CDR-L2 |
| 470 | QQSYSTPYT | Clone PA11P1C04 - CDR-L3 |
| 471 | QVQLVESGGGVVQPGRSLRLSCAASGFSFRSYGMHWVRQAPGKGLEWVAC ISYDGSNKYYVDSVKGRFTISRDNSKNTLYVQMNSLTDEDTAVYYCARD GVTTRQFSYYYYGMDVWGQGTTVTVSS | Clone PA14P1D10 - Heavy chain variable region |
| 472 | GFSFRSYG | Clone PA14P1D10 - CDR-H1 |
| 59 | ISYDGSNK | Clone PA14P1D10 - CDR-H2 |

TABLE 1-continued

Sequence Listing

| SEQ ID NO | Sequence | Description |
|---|---|---|
| 473 | ARDRGVTTRQFSYYYYGMDV | Clone PA14P1D10 - CDR-H3 |
| 474 | AIRMTQSPSSFSASTGDRVTITCRASQSITSYLAWYQQKPGKAPKLLIYAASTLQSGLPSRFSGSGSGTDFTLTISGLQSEDFATYYCQQYYNYPQTFGQGTRVEIK | Clone PA14P1D10 - light chain variable region |
| 475 | QSITSY | Clone PA14P1D10 - CDR-L1 |
| 149 | AAS | Clone PA14P1D10 - CDR-L2 |
| 476 | QQYYNYPQT | Clone PA14P1D10 - CDR-L3 |
| 477 | EVQLLESGGQLVQPGGSLRLSCGAFGFTFGDAAMTWVRQAPGKGLEWVSTISGRGDETFSADSVKGRFTISRDNFKNMLYVQMNSLRAEDTATYYCARLGHLRGWFDSWGQGTLVTVSS | Clone PA14P1C10 - Heavy chain variable region |
| 478 | GFTFGDAA | Clone PA14P1C10 - CDR-H1 |
| 479 | ISGRGDET | Clone PA14P1C10 - CDR-H2 |
| 480 | ARLGHLRGWFDS | Clone PA14P1C10 - CDR-H3 |
| 481 | EIVMTQSPATLSVSPGERVTLSCRASQSVSSNLAWYQQKPGQAPRLLIYGASTRATGIPAGFSGSGSGTEFTLTISSLQSEDFAVYYCQQYNNWPRTFGQGTKVEIK | Clone PA14P1C10 - light chain variable region |
| 482 | QSVSSN | Clone PA14P1C10 - CDR-L1 |
| 30 | GAS | Clone PA14P1C10 - CDR-L2 |
| 252 | QQYNNWPRT | Clone PA14P1C10 - CDR-L3 |
| 483 | EVQLVESGGGLVKPGGSLRLSCAASGFTFSDAWMTWVRQAPGKGLEWVGRIKSKTDGGTTDYGAPVKGRFSISRDDSKNTLYLHMNSLKTEDTAVYYCTTKSPNSNWFPFYYYYMDVWGKGTTVTVSS | Clone PA11P1C08 - Heavy chain variable region |
| 484 | GFTFSDAW | Clone PA11P1C08 - CDR-H1 |
| 485 | IKSKTDGGTT | Clone PA11P1C08 - CDR-H2 |
| 486 | TTKSPNSNWFPFYYYYMDV | Clone PA11P1C08 - CDR-H3 |
| 487 | QSALTQPRSVSGSPGQSVTISCTGTSSDVGGYNFVSWYQQHPGKAPQLMIYDVTKRPSGVPDRFSGSKSGNTASLTISGLQAEDEGDYYCSYAASSLYVFGTGTKVTVL | Clone PA11P1C08 - light chain variable region |
| 488 | SSDVGGYNF | Clone PA11P1C08 - CDR-L1 |
| 141 | DVT | Clone PA11P1C08 - CDR-L2 |
| 489 | YSYAASSLYV | Clone PA11P1C08 - CDR-L3 |
| 490 | QLQLQESGPGLVKPSETLSLICTVSGGAITSSTFYWAWIRQPPGRGLEWIGSMYYSGSTYYNLSLKSRVIISVNTSKNQFSLTLTSATATDMAVYYCVRHTLHDYGSGSFPDYSYGMDVWGQGTTVTVSS | Clone PA14P3F10 - Heavy chain variable region |
| 491 | GGAITSSTFY | Clone PA14P3F10 - CDR-H1 |
| 492 | MYYSGST | Clone PA14P3F10 - CDR-H2 |
| 493 | VRHTLHDYGSGSFPDYSYGMDV | Clone PA14P3F10 - CDR-H3 |
| 494 | EIVLTQSPATLSLFPGERGTLSCRASQSVSSHLIWYQQKPGQAPRVLIFDATNRATGIPARFSGSGSGTDFTLTISNLEPEDYGVYYCQQRSNWPLTFGGGTKVEIK | Clone PA14P3F10 - light chain variable region |
| 495 | QSVSSH | Clone PA14P3F10 - CDR-L1 |
| 265 | DAT | Clone PA14P3F10 - CDR-L2 |
| 496 | QQRSNWPLT | Clone PA14P3F10 - CDR-L3 |

TABLE 1-continued

Sequence Listing

| SEQ ID NO | Sequence | Description |
|---|---|---|
| 497 | EVQLLESGGGLVQPGGSLKLSCVASGFTFSSYAMMWVRQAPGKGLEWISS ISSSGGSTYYADSVKGRFTISRDNSKNTLYLQMNSLRVEDTAVYYCAKS CSTTSCPRAFYYYGMDVWGQGTTVTVSS | Clone PA14P1D11 - Heavy chain variable region |
| 113 | GFTFSSYA | Clone PA14P1D11 - CDR-H1 |
| 498 | ISSSGGST | Clone PA14P1D11 - CDR-H2 |
| 499 | AKSHCSTTSCPRAFYYYGMDV | Clone PA14P1D11 - CDR-H3 |
| 500 | DIQMTQSPSSLSASVGDRVTITCRASQTITTYLNWYQQKPGKAPKLLIYA ASSLQSGVPSRFSGSGSGTDFTLSLSSLQPEDSATYYCQQSYSTLGAFGG GTKVEIK | Clone PA14P1D11 - light chain variable region |
| 501 | QTITTY | Clone PA14P1D11 - CDR-L1 |
| 149 | AAS | Clone PA14P1D11 - CDR-L2 |
| 502 | QQSYSTLGA | Clone PA14P1D11 - CDR-L3 |
| 503 | QVHLQESGPGLVKPSGTLSLTCTVSGGSISTYYWSWIRQPPGKGLEWIGY IYYGGTTNYNPSLKSRVTISVDTSKNQFSLRLRSVTAADTAVYYCAREID SRMDRWGQGTLVTVSS | Clone PA14P3F02 - Heavy chain variable region |
| 504 | GGSISTYY | Clone PA14P3F02 - CDR-H1 |
| 505 | IYYGGTT | Clone PA14P3F02 - CDR-H2 |
| 506 | AREIDSRMDR | Clone PA14P3F02 - CDR-H3 |
| 507 | SYALTQPPSVSVAPGKTARITCGGDNIGSKTVHWYHQKPGQAPVLVIYYD SNRPSGISERFSGSNSGNTATLTISRVEAGDEADYYCQVWDSNSDHRIFG GGTKLTVL | Clone PA14P3F02 - light chain variable region |
| 508 | NIGSKT | Clone PA14P3F02 - CDR-L1 |
| 509 | YDS | Clone PA14P3F02 - CDR-L2 |
| 510 | QVWDSNSDHRI | Clone PA14P3F02 - CDR-L3 |
| 511 | QVQLVQSGAEVRKPGSSVKVSCKASGGTFSNNPITWVRQAPGQGLEWMGW IIPIFNTTNYAQKFQGRVTITADESTSTAYMELSSLKSEDTALFYCARDR AHAYCNNGVCYTTDAFDVWGQGTLVTVSS | Clone PA12P1G11 - Heavy chain variable region |
| 512 | GGTFSNNP | Clone PA12P1G11 - CDR-H1 |
| 513 | IIPIFNTT | Clone PA12P1G11 - CDR-H2 |
| 514 | ARDRAHAYCNNGVCYTTDAFDV | Clone PA12P1G11 - CDR-H3 |
| 515 | ETVLTQSPATLSLSPGERATLSCRASQSVGRYLAWYQHKPGQAPRLLIYD ASNRATGIPARFSGSGSGTDFTLTISSLEPEDSAVYYCQQGTDWLTFGGG TKVEIK | Clone PA12P1G11 - light chain variable region |
| 516 | QSVGRY | Clone PA12P1G11 - CDR-L1 |
| 94 | DAS | Clone PA12P1G11 - CDR-L2 |
| 517 | QQGTDWLT | Clone PA12P1G11 - CDR-L3 |
| 518 | QVQLVESGGGLVKPGGSLRLSCAASGITFSDNYMTWIRQAPGKGLEWVSY ISSSGTNIFYADSLKGRFTISRDNAKNSLYLQMNSLRAEDTAVYYCARTL MTGSSLYFDYWGQGTQVTVSS | Clone PA13P1E06 - Heavy chain variable region |
| 519 | GITFSDNY | Clone PA13P1E06 - CDR-H1 |
| 520 | ISSSGTNI | Clone PA13P1E06 - CDR-H2 |
| 521 | ARTLMTGSSLYFDY | Clone PA13P1E06 - CDR-H3 |
| 522 | SYELTQPPSVSVSPGQTARITCSGDALPKQYAYWYQQKPGQAPVLVIYKD SERPSGIPERFSGSSSGTTVTLAISGVQAEDEADYYCQSADIRVTESVLF GGGTKLTVL | Clone PA13P1E06 - light chain variable region |

TABLE 1-continued

Sequence Listing

| SEQ ID NO | Sequence | Description |
|---|---|---|
| 523 | ALPKQY | Clone PA13P1E06 - CDR-L1 |
| 524 | KDS | Clone PA13P1E06 - CDR-L2 |
| 525 | QSADIRVTESVL | Clone PA13P1E06 - CDR-L3 |
| 526 | EVHLLESGGHLVQPGGSLRLACAVSGFTFSDSAMTWVRQAPGKGLEWVSTISGRGDETFFADSVKGRFSIFRDNSNSVLYVQMNSLRAEDTATYYCARYGHHKGWFDSWGQGTLVTVSS | Clone PA14P1C12 - Heavy chain variable region |
| 527 | GFTFSDSA | Clone PA14P1C12 - CDR-H1 |
| 479 | ISGRGDET | Clone PA14P1C12 - CDR-H2 |
| 528 | ARYGHHKGWFDS | Clone PA14P1C12 - CDR-H3 |
| 529 | EIVMTQSPATLSVSPGERATLSCRASQSVSSNLAWYQQKPGQAPRLLIYGASTRAIGIPAGFSGSGSGTEFTLTISSLQSEDSAVYYCQQYNNWPRTFGQGTKVEIK | Clone PA14P1C12 - light chain variable region |
| 482 | QSVSSN | Clone PA14P1C12 - CDR-L1 |
| 30 | GAS | Clone PA14P1C12 - CDR-L2 |
| 252 | QQYNNWPRT | Clone PA14P1C12 - CDR-L3 |
| 530 | QVQLVQSGTEVKKPGASVKVSCKASGYTFSSFGITWVRQAPGQGLEWMGWISAYNGNTKYAQAVQGRVTLTTDTSTTTAYMELRSLRSNDTAVYFCAREGIEHLVVEGRGPGGDCWGQGTLVIVSS | Clone PA11P1D07 - Heavy chain variable region |
| 531 | GYTFSSFG | Clone PA11P1D07 - CDR-H1 |
| 532 | ISAYNGNT | Clone PA11P1D07 - CDR-H2 |
| 533 | AREGIEHLVVEGRGPGGDC | Clone PA11P1D07 - CDR-H3 |
| 534 | SYELTQPPSVSVSPGQTARITCSGDALPKEYTSWYQQKSGQAPVLVIYEDIKRPSGIPERFSGSSSGTMASLTISGAQVDDEADYYCYSTDTSGDHKVFGGGTKLTVL | Clone PA11P1D07 - light chain variable region |
| 535 | ALPKEY | Clone PA11P1D07 - CDR-L1 |
| 536 | EDI | Clone PA11P1D07 - CDR-L2 |
| 537 | YSTDTSGDHKV | Clone PA11P1D07 - CDR-L3 |
| 538 | QVQLVESGGGVVQPGRSLRLSCAASGFTFSSYAMHWVRQAPGKGREWVAALSYDGSSTYYADSVKGRLTISRDNSKNTLYLQMNSLRAEDTAVYFCTRVPYGEGRAANDYWGQGTLVTVSS | Clone PA12P4D02 - Heavy chain variable region |
| 113 | GFTFSSYA | Clone PA12P4D02 - CDR-H1 |
| 539 | LSYDGSST | Clone PA12P4D02 - CDR-H2 |
| 540 | TRVPYGEGRAANDY | Clone PA12P4D02 - CDR-H3 |
| 541 | DIQMTQSPSTLSASVGDRVTITCRASQSIGSWLAWYQQKPGKAPKLLIYKASNIESGVPSRFSGSGSGTEFTLTISSLQPDDFATYYCQHYNTYSRSFGGGTEVAIK | Clone PA12P4D02 - light chain variable region |
| 542 | QSIGSW | Clone PA12P4D02 - CDR-L1 |
| 196 | KAS | Clone PA12P4D02 - CDR-L2 |
| 543 | QHYNTYSRS | Clone PA12P4D02 - CDR-L3 |
| 544 | QVQLVQSGAEVKTPGSSVKVSCTASGDSFSRYAINWVRQAPGQGLEWVGKIVPVFGAASYAQKFQGRVTITADESTSTVYMELSSLRSEDTAVYYCARGVKLSTMPPVYWGQGTLVTVSS | Clone PA15P1C03 - heavy chain variable region |
| 545 | GDSFSRYA | Clone PA15P1C03 - CDR-H1 |
| 546 | IVPVFGAA | Clone PA15P1C03 - CDR-H2 |

TABLE 1-continued

Sequence Listing

| SEQ ID NO | Sequence | Description |
|---|---|---|
| 547 | ARGIVKLSTMPPVY | Clone PA15P1C03 - CDR-H3 |
| 548 | DIVMTQTPLSLSVTPGQPASISCKSSQSLLHSDGKTYLYWYLQKPGQSPQCLLISEVSSRFSGVPDRFSGSGSGTDFTLKISRVEAEDVGVYYCMQGIHHLTFGPGTKVDIK | Clone PA15P1C03 - light chain variable region |
| 549 | QSLLHSDGKTY | Clone PA15P1C03 - CDR-L1 |
| 550 | EVS | Clone PA15P1C03 - CDR-L2 |
| 551 | MQGIHHLT | Clone PA15P1C03 - CDR-L3 |
| 552 | QVQLQESGPGLVKPSETLSLTCSVSGGSVSDSAYYWSWIRQPPGGGLEFIGYVYNSGSTNYNPSLKSRVTISVDTSKNQFSLSLSSLTAADTAVYYCARYCSSTSCYVRSSDVNWFDPWGQGTLVIVSS | Clone PA12P4G06 - heavy chain variable region |
| 553 | GGSVSDSAYY | Clone PA12P4G06 - CDR-H1 |
| 554 | VYNSGST | Clone PA12P4G06 - CDR-H2 |
| 555 | ARYCSSTSCYVRSSDVNWFDP | Clone PA12P4G06 - CDR-H3 |
| 556 | EIVLTQSPGTLSSSPGESATLSCRASQSLGTYLAWYQQKPGQAPRLLIYDASKRATGIPARFSGSGSGTDFTLTISSLEPEDFAVYYCHQRSHWLTFGGGTKVEIK | Clone PA12P4G06 - light chain variable region |
| 557 | QSLGTY | Clone PA12P4G06 - CDR-L1 |
| 94 | DAS | Clone PA12P4G06 - CDR-L2 |
| 558 | HQRSHWLT | Clone PA12P4G06 - CDR-L3 |
| 559 | EAQLLESGGGLVQPGGSLRLSCAASGFNFSNYAMTWVRQAPGKGLEWVSACISSGGGTTYYADSVKGRFTISRDNSKNTVYLQMNSLKDADSALYYCAKPGRAVVVRLSYFDSWGQGTLVTVSS | Clone PA16P1B09 - heavy chain variable region |
| 560 | GFNFSNYA | Clone PA16P1B09 - CDR-H1 |
| 561 | ISSGGGTT | Clone PA16P1B09 - CDR-H2 |
| 562 | AKPGRAVVVRLSYFDS | Clone PA16P1B09 - CDR-H3 |
| 563 | QSVLTQPPSVSAAPGQKVSISCSGSGSNIANHYVSWYQHLPGTAPKLLIYDNNKRPSGIPDRFSGSKSGTSATLGITGLQTGDEADYYCGTWDSSLTVVVFGGGTKLTVL | Clone PA16P1B09 - light chain variable region |
| 564 | GSNIANHY | Clone PA16P1B09 - CDR-L1 |
| 110 | DNN | Clone PA16P1B09 - CDR-L2 |
| 565 | GTWDSSLTVVV | Clone PA16P1B09 - CDR-L3 |
| 566 | QITLKESGPTLVKPTETLTLTCTFSGFSLTTSGVAVGWVRQPPGKALEWLALIYWDDDERYTPSLKSRLTITKDTSKSQVVLTMTNMDPVDTATYFCVHCEGPDILLVPAAYFFDFWGQGTLVTVSS | Clone PA12P4G03 - heavy chain variable region |
| 567 | GFSLTTSGVA | Clone PA12P4G03 - CDR-H1 |
| 568 | IYWDDDE | Clone PA12P4G03 - CDR-H2 |
| 569 | VHCEGPDILLVPAAYFFDF | Clone PA12P4G03 - CDR-H3 |
| 570 | EIVLTQSPGTLSLSPGDRATLSCRASQSVSRRYLAWYQQSPGQAPRLLISGASSRATGIPDRFSGSGSGTDFTLTISRLEPEDFAMYYCQQYGSSTGTFGQGTKVEMK | Clone PA12P4G03 - light chain variable region |
| 571 | QSVSRRY | Clone PA12P4G03 - CDR-L1 |
| 30 | GAS | Clone PA12P4G03 - CDR-L2 |
| 572 | QQYGSSTGT | Clone PA12P4G03 - CDR-L3 |

TABLE 1-continued

Sequence Listing

| SEQ ID NO | Sequence | Description |
|---|---|---|
| 573 | QVQLQESGPGLVKPSQTLSLTCTVSGGSISSSGYYWSWIRQHPGKGLEWIGYINYIGGTYYNPSLRSRVTMSVDTSKNQFSLRLSSVSAADTAVYYCASTHSYGDYSRDYYYGVDVWGQGTTVTISS | Clone PA11P1F10 - heavy chain variable region |
| 574 | GGSISSSGYY | Clone PA11P1F10 - CDR-H1 |
| 575 | INYIGGT | Clone PA11P1F10 - CDR-H2 |
| 576 | ASTHSYGDYSRDYYYGVDV | Clone PA11P1F10 - CDR-H3 |
| 577 | EIVLTQSPATLSLSPGDRATLSCRTSQSVSSSYLAWYQQKPGQAPRLLIYAASSRATGIPDRFSGSGSGTDFTLTISRLEPEDFAVYYCQQCAGSPFTFGPGTKVDLK | Clone PA11P1F10 - light chain variable region |
| 62 | QSVSSSY | Clone PA11P1F10 - CDR-L1 |
| 149 | AAS | Clone PA11P1F10 - CDR-L2 |
| 578 | QQCAGSPFT | Clone PA11P1F10 - CDR-L3 |
| 579 | QVQLVESGGGVVQPGRSLRLSCAASGFTFSDYAMHWVRQAPGKGLEWVACISYDGNHRYYADSVKGRFTISRDNSKNTLYLQMNSLRAEDTAVYYCARHPGLSIAVAGPFDYWGQGTLVTVSS | Clone PA12P1G02 - heavy chain variable region |
| 580 | GFTFSDYA | Clone PA12P1G02 - CDR-H1 |
| 581 | ISYDGNHR | Clone PA12P1G02 - CDR-H2 |
| 582 | ARHPGLSIAVAGPFDY | Clone PA12P1G02 - CDR-H3 |
| 583 | EIVMTQSPATLSVSPGERATLSCGASQSVSSNLAWYQQKPGQAPRLLFYGASTRATGIPARFSGSGSGTEFTLTISSLQSEDFALYYCQQYNNWPWTFGQGTKVDIK | Clone PA12P1G02 - light chain variable region |
| 482 | QSVSSN | Clone PA12P1G02 - CDR-L1 |
| 30 | GAS | Clone PA12P1G02 - CDR-L2 |
| 584 | QQYNNWPWT | Clone PA12P1G02 - CDR-L3 |
| 585 | QVQLVQSGAEVKKPGASVKVSCKASGYTFNRDGITWVRQAPGQGLEWMGWISANNDFTDYAQKFQGRLTMTTDTSTNTAYMELRSLRSDDTAVYYCARQVITVLQYSYGMDVWGQGTTVTVSS | Clone PA16P1E12 - heavy chain variable region |
| 586 | GYTFNRDG | Clone PA16P1E12 - CDR-H1 |
| 587 | ISANNDFT | Clone PA16P1E12 - CDR-H2 |
| 588 | ARQVITVLQYSYGMDV | Clone PA16P1E12 - CDR-H3 |
| 589 | DIQMTQFPSSLSASVGDRVTITCRASQSISRYLNWYQQTPGKAPKLLIYGASSLQSGVPSRFSGSGSGTDFTLTISSLQPEDFATYYCQQSDTAPLTFGGGTRVEIK | Clone PA16P1E12 - light chain variable region |
| 590 | QSISRY | Clone PA16P1E12 - CDR-L1 |
| 30 | GAS | Clone PA16P1E12 - CDR-L2 |
| 591 | QQSDTAPLT | Clone PA16P1E12 - CDR-L3 |
| 415 | EAQLVESGGGLVQPGGSLRLSCAASGFTFSSYYIHWVRQAPGKGLVWVSRINSDGSSTRYADSVKGRFTISRDNAKNTLYLQMNSLRAEDTAVYFCARASRTVYGDSPLSNGMDVWGQGTKVTVSS | Clone PA16P1E11 - heavy chain variable region |
| 416 | GFTFSSYY | Clone PA16P1E11 - CDR-H1 |
| 417 | INSDGSST | Clone PA16P1E11 - CDR-H2 |
| 418 | ARASRTVYGDSPLSNGMDV | Clone PA16P1E11 - CDR-H3 |
| 419 | SYELTQPPSVSVSPGQTASITCSGDKLGDKFACWYQQKPGHSPVLVIYQDCDKRPSGIPERFSGSNSGNTATLTISGTQAMDEADYYCQAWDSSTHVVFGGGTKLTVL | Clone PA16P1E11 - light chain variable region |

TABLE 1-continued

Sequence Listing

| SEQ ID NO | Sequence | Description |
|---|---|---|
| 420 | KLGDKF | Clone PA16P1E11 - CDR-L1 |
| 421 | QDD | Clone PA16P1E11 - CDR-L2 |
| 422 | QAWDSSTHVV | Clone PA16P1E11 - CDR-L3 |
| 592 | QVQLVESGGGLVTPGGSLRLSCTVSGFTLSDYYMSWIRQAPGKGLDWLSYISGSGDNKNYADSVRGRFTISRDNSKNSLYLQMNSLRAEDTAVYYCAREFPSGGYSPGVVLWGQGTLVTVSS | Clone PA12P3E11 - heavy chain variable region |
| 593 | GFTLSDYY | Clone PA12P3E11 - CDR-H1 |
| 594 | ISGSGDNK | Clone PA12P3E11 - CDR-H2 |
| 595 | AREFPSGGYSPGVVL | Clone PA12P3E11 - CDR-H3 |
| 596 | NFVLTQPHSVSESPGKTVTISCARSSGSIAGSFVQWYQQRPGSSPTTVIYEDTRRPSGVPDRFSGSIDSSSNSASLTISGLKTEDEADYYCQSYDSTNPWVFGGGTKLTVL | Clone PA12P3E11 - light chain variable region |
| 597 | SGSIAGSF | Clone PA12P3E11 - CDR-L1 |
| 598 | EDT | Clone PA12P3E11 - CDR-L2 |
| 599 | QSYDSTNPWV | Clone PA12P3E11 - CDR-L3 |
| 600 | EVQLLESGGGLVQPGGSLRLSCAASGFTFSSYAMSWVRQAPGKGLEWVSVIYSGGSRTYYADSAKGRFTISRDNSKNMLYLQMNSLRAEDTAVYYCTKNDYDSSGYFDFDNWGQGTLVTVSS | Clone PA14P1C06 - heavy chain variable region |
| 113 | GFTFSSYA | Clone PA14P1C06 - CDR-H1 |
| 114 | IYSGGSRT | Clone PA14P1C06 - CDR-H2 |
| 601 | TKNDYDSSGYFDFDN | Clone PA14P1C06 - CDR-H3 |
| 602 | QSALTQPASVSGSPGQSITISCTGTSSDVGGYNYVSWYQQHPGKAPKLMIYDVSNRPSGVSNRFSGSKSGNTASLTISGLQAEDEADYHCSSYTSSSTWVFGGGTKLTVL | Clone PA14P1C06 - light chain variable region |
| 603 | SSDVGGYNY | Clone PA14P1C06 - CDR-L1 |
| 404 | DVS | Clone PA14P1C06 - CDR-L2 |
| 604 | SSYTSSSTWV | Clone PA14P1C06 - CDR-L3 |
| 605 | EVQLLESGGGLVQPGGSLRLSCAASGFTFSSYAMSWVRQAPGKGLEWVSVVYSGGSGTYYADSVKGRFTISRDDSTNTLYLQMNSLRAEDTAVYYCAKDRDSFGELDLDSWGQGTLVSVSS | Clone PA14P1C07 - heavy chain variable region |
| 113 | GFTFSSYA | Clone PA14P1C07 - CDR-H1 |
| 606 | VYSGGSGT | Clone PA14P1C07 - CDR-H2 |
| 607 | AKDRDSFGELDLDS | Clone PA14P1C07 - CDR-H3 |
| 608 | DIVMTQSPDSLAVSLGERATINCKSSQSVLYSSKNKNYLAWYQQRPGQPPKLLIYWASTRESGVPDRFSGSGSGTDFTLTISSLQAEDVAVYYCLQYYNIPRTFGQGTKLEIK | Clone PA14P1C07 - light chain variable region |
| 609 | QSVLYSSKNKNY | Clone PA14P1C07 - CDR-L1 |
| 86 | WAS | Clone PA14P1C07 - CDR-L2 |
| 610 | LQYYNIPRT | Clone PA14P1C07 - CDR-L3 |
| 611 | EVQLLESGGGLVQPGGSLRLSCAASGFTFSSYALSWVRQPPGKGLEWVSVIYSGGSRTYYADAAKGRFTISRDNSKNMLYLQMNSLRAEDTAVYYCTKHDYDSSGYFDFDNWGQGTLVTVSS | Clone PA14P1C04 - heavy chain variable region |
| 113 | GFTFSSYA | Clone PA14P1C04 - CDR-H1 |
| 114 | IYSGGSRT | Clone PA14P1C04 - CDR-H2 |

TABLE 1-continued

Sequence Listing

| SEQ ID NO | Sequence | Description |
|---|---|---|
| 612 | TKHDYDSSGYFDFDN | Clone PA14P1C04 - CDR-H3 |
| 602 | QSALTQPASVSGSPGQSITISCTGTSSDVGGYNYVSWYQQHPGKAPKLMIYDVSNRPSGVSNRFSGSKSGNTASLTISGLQAEDEADYHCSSYTSSSTWVFGGGTKLTVL | Clone PA14P1C04 - light chain variable region |
| 603 | SSDVGGYNY | Clone PA14P1C04 - CDR-L1 |
| 404 | DVS | Clone PA14P1C04 - CDR-L2 |
| 604 | SSYTSSSTWV | Clone PA14P1C04 - CDR-L3 |
| 613 | EVQLVESGGGVARPGGSLRLSCAASGFTFDDYGMSWVRQAPGKGLEWVSGINWNGGSTNYADSVKGRFIISRDNGKNSLYLQMNSLRAEDTAFYHCARRGNFYYYGMDVWGQGTTVTVSS | Clone PA14P1C02 - heavy chain variable region |
| 614 | GFTFDDYG | Clone PA14P1C02 - CDR-H1 |
| 615 | INWNGGST | Clone PA14P1C02 - CDR-H2 |
| 616 | ARRGNFYYYGMDV | Clone PA14P1C02 - CDR-H3 |
| 617 | DIQMTQSPSSVSASVGDRVTITCRASQGNSTWLAWYQQKPGKAPELLIFDASNLQSGVPSRFSGSGSGTDFTLTISSLQPEDFATYYCQQAQRFPLTFGGGTKVEIK | Clone PA14P1C02 - light chain variable region |
| 618 | QGNSTW | Clone PA14P1C02 - CDR-L1 |
| 94 | DAS | Clone PA14P1C02 - CDR-L2 |
| 619 | QQAQRFPLT | Clone PA14P1C02 - CDR-L3 |
| 620 | QVQLVQSGSELRRPGASVKVSCKTSGYAFTHFAMNWLRQAPGQGLEWLGWINTHSGNPTYAQGFTGRIVFSLDTSAGTAYLEISSLKAEDTAVYYCARERYFDFWGQGTLVAVSS | Clone PA11P1E01 - heavy chain variable region |
| 621 | GYAFTHFA | Clone PA11P1E01 - CDR-H1 |
| 176 | INTHSGNP | Clone PA11P1E01 - CDR-H2 |
| 177 | ARERYFDF | Clone PA11P1E01 - CDR-H3 |
| 622 | QSVLTQPPSASGTPGQRVTISCSGTNSNIGKNFLYWYQQLPGTAPKLLIFSSNQRPSGVPDRFSGSKSGTSASLAISGLRSEDEADYYCAAWDDNLSGWVFGGGTKVTVL | Clone PA11P1E01 - light chain variable region |
| 623 | NSNIGKNF | Clone PA11P1E01 - CDR-L1 |
| 180 | SSN | Clone PA11P1E01 - CDR-L2 |
| 624 | AAWDDNLSGWV | Clone PA11P1E01 - CDR-L3 |
| 625 | QVQLQESGPGLVKPSEALSLICSVSDGSVSSGSYYWTWIRQPPGKGLEWIGCIHYSGRTNYNPSLKSRVTISIDTSKNQFSLQLSSVTAVDTAVYYCARDRGEYDFWRVRYYGMDVWGQGTTVTVSS | Clone PA11P1E08 - heavy chain variable region |
| 626 | DGSVSSGSYY | Clone PA11P1E08 - CDR-H1 |
| 627 | IHYSGRT | Clone PA11P1E08 - CDR-H2 |
| 628 | ARDRGEYDFWRVRYYGMDV | Clone PA11P1E08 - CDR-H3 |
| 629 | QSALTQPASVSGSPGQSITISCTGTSSDVGDYNYVSWYQQHPGKAPKLLIYDFSNRPSGVSDRFSGSKSGNTASLTISGLRAEDESDYYCTSYTNTNTRLFGGGTKLTVL | Clone PA11P1E08 - light chain variable region |
| 630 | SSDVGDYNY | Clone PA11P1E08 - CDR-L1 |
| 631 | DFS | Clone PA11P1E08 - CDR-L2 |
| 632 | TSYTNTNTRL | Clone PA11P1E08 - CDR-L3 |

TABLE 1-continued

Sequence Listing

| SEQ ID NO | Sequence | Description |
|---|---|---|
| 633 | QVQLVQSGAEVKKPGASVKVSCKASGYTFISYGLHWVRQAPGQRPEWMGWINAGNGNRKYSERFQARVTFTRDTSATTAYMELSSLRSEDTAVYYCARDRLTAAAHFDYWGQGTQVTVSS | Clone PA14P1C08 - heavy chain variable region |
| 634 | GYTFISYG | Clone PA14P1C08 - CDR-H1 |
| 635 | INAGNGNR | Clone PA14P1C08 - CDR-H2 |
| 636 | ARDRLTAAAHFDY | Clone PA14P1C08 - CDR-H3 |
| 637 | EIVMTQSPATLSVSLGERATLSCRASQSVSSDLAWYQQKPGQAPRLLMYGASTRATGFPARFTGSGSGPEFTLTISSLQSEDFAVYYCQQYNNWPFTFGGGTKVEIK | Clone PA14P1C08 - light chain variable region |
| 638 | QSVSSD | Clone PA14P1C08 - CDR-L1 |
| 30 | GAS | Clone PA14P1C08 - CDR-L2 |
| 639 | QQYNNWPFT | Clone PA14P1C08 - CDR-L3 |
| 640 | QITLKESGPTLVKPTQTLTLTCTFSGFSLTSSAVGVGWIRQPPGKALEWLALIYGDDDKRYSPSLKRRLTITKDTSKNQVVLTMTDVDPVDTATYYCAHRRLTIPLLMVAADAFDIWGPGTMVIVSS | Clone PA14P1H12 - heavy chain variable region |
| 641 | GFSLTSSAVG | Clone PA14P1H12 - CDR-H1 |
| 642 | IYGDDDK | Clone PA14P1H12 - CDR-H2 |
| 643 | AHRRLTIPLLMVAADAFDI | Clone PA14P1H12 - CDR-H3 |
| 644 | DIQMTQSPSTLSASVGDRVTITCRASQSVSRWLAWYQQKPGKAPKLLIYRASSLQSGVPSRFSGSGSGTEFTLTISSLQPDDFATYYCQQYSSFHTFGQGTKLEIK | Clone PA14P1H12 - light chain variable region |
| 645 | QSVSRW | Clone PA14P1H12 - CDR-L1 |
| 646 | RAS | Clone PA14P1H12 - CDR-L2 |
| 647 | QQYSSFHT | Clone PA14P1H12 - CDR-L3 |
| 648 | EVQLVESGGGLVQPGGSLRLSCAASGFIFSTYSMNWVRQAPGKGLEWVSYISSSSNTIYYADSVKGRFTISRDNAKNSLYLQMNSLRDADTAVYYCARDGRSGYFDDYWGQGTLVTVSS | Clone PA14P1H11 - heavy chain variable region |
| 649 | GFIFSTYS | Clone PA14P1H11 - CDR-H1 |
| 650 | ISSSSNTI | Clone PA14P1H11 - CDR-H2 |
| 651 | ARDGGRSGYFDDY | Clone PA14P1H11 - CDR-H3 |
| 652 | QLVLTQSPSASASLGASVKLTCTLSNGHINYAIAWHQQQPDKGPRYLLNLKSDGSHSKGDGIPDRFSGSSSGAERYLTISGLQSEDEADYYCQTWGTGIQVFGGGTKLTVL | Clone PA14P1H11 - light chain variable region |
| 653 | NGHINYA | Clone PA14P1H11 - CDR-L1 |
| 654 | LKSDGSH | Clone PA14P1H11 - CDR-L2 |
| 655 | QTWGTGIQV | Clone PA14P1H11 - CDR-L3 |
| 656 | QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGRGVWFGELFPFDYWGQGTLGTVSS | Clone PA14P1D02 - heavy chain variable region |
| 657 | GGSFSGYY | Clone PA14P1D02 - CDR-H1 |
| 658 | INHSGST | Clone PA14P1D02 - CDR-H2 |
| 659 | ARGRGVWFGELFPFDY | Clone PA14P1D02 - CDR-H3 |
| 660 | QGGLTQPPSVSKGLRQTATLTCTGNSNNVGNQGAAWLQQHQGHPPKLLSYRNNNRPSGISERFSASRSGNTASLTITGLQPEDEADYYCSAWDSSLSAVVFGGGTKLTVL | Clone PA14P1D02 - light chain variable region |

TABLE 1-continued

Sequence Listing

| SEQ ID NO | Sequence | Description |
|---|---|---|
| 661 | SNNVGNQG | Clone PA14P1D02 - CDR-L1 |
| 662 | RNN | Clone PA14P1D02 - CDR-L2 |
| 663 | SAWDSSLSAVV | Clone PA14P1D02 - CDR-L3 |
| 664 | QVQLQQWGAGLLKPSETLSLNCTVYHGSLSTSYWSWIRQPPGRGLEWIGE INDSGATNYNPSLKSRVIISVDTSKDQFSLKLTSVTAADTAMYYCARAPL LWVGESFFYYFDSWGQGILVTVSS | Clone PA11P1F03 - heavy chain variable region |
| 665 | HGSLSTSY | Clone PA11P1F03 - CDR-H1 |
| 666 | INDSGAT | Clone PA11P1F03 - CDR-H2 |
| 667 | ARAPLLWVGESFFYYFDS | Clone PA11P1F03 - CDR-H3 |
| 668 | DIQMTQSPSSLSASVGDRVSITCRAGQSIDTYLNWYQHKPGKAPDLLIYT TSTLHSGVPSRFSGSGSGTDFTLTITSLQPEDFAIYYCQQSYKSPYTFGQ GTKVEIK | Clone PA11P1F03 - light chain variable region |
| 669 | QSIDTY | Clone PA11P1F03 - CDR-L1 |
| 670 | TTS | Clone PA11P1F03 - CDR-L2 |
| 671 | QQSYKSPYT | Clone PA11P1F03 - CDR-L3 |
| 672 | QVQLVQSGAEVKKPGASVKVSCKASGYTFTSYYMHWVRQAPGQGLEWMGI INPSGGTTSSAQKFQGRVTMTRDTSTSTVYMELSSLRSEDTALYYCARDR EQKVGGAPLHWGQGTLVTVSS | Clone PA11P1F02 - heavy chain variable region |
| 89 | GYTFTSYY | Clone PA11P1F02 - CDR-H1 |
| 673 | INPSGGTT | Clone PA11P1F02 - CDR-H2 |
| 674 | ARDREQKVGGAPLH | Clone PA11P1F02 - CDR-H3 |
| 675 | DIQMTQSPSSLSASVGDRVTITCQASQDISNYLNWYQQKPGKAPKLLIYD ASNLETGVPSRFSGSGSGTDFSFTISSLQPEDIATYYCQQYDNFALTFGG GTKVEIK | Clone PA11P1F02 - light chain variable region |
| 374 | QDISNY | Clone PA11P1F02 - CDR-L1 |
| 94 | DAS | Clone PA11P1F02 - CDR-L2 |
| 676 | QQYDNFALT | Clone PA11P1F02 - CDR-L3 |
| 677 | EVQLLESGGGLVQPGVSLRLSCAASGFTFSSYAMSWVRQAPGKGLEWVSV IYSGGNIIYYADSVKGRFTISRDNSKNTLYLQIDNLRAEDTALYYCAKHD YDSSGYFDFDYWGHGTLVTVSS | Clone PA14P1D07 - heavy chain variable region |
| 113 | GFTFSSYA | Clone PA14P1D07 - CDR-H1 |
| 678 | IYSGGNII | Clone PA14P1D07 - CDR-H2 |
| 679 | AKHDYDSSGYFDFDY | Clone PA14P1D07 - CDR-H3 |
| 680 | QSALTQPASVSGSPGQSITISCTGTSRDVGGYNYVSWYQQHPGKAPKLMI YDVNNRPSGVSNRFSGSKSGNTASLTISGLQAEDEADYFCCSYTSSSTWV FGGGTKLTVL | Clone PA14P1D07 - light chain variable region |
| 681 | SRDVGGYNY | Clone PA14P1D07 - CDR-L1 |
| 682 | DVN | Clone PA14P1D07 - CDR-L2 |
| 683 | CSYTSSSTWV | Clone PA14P1D07 - CDR-L3 |
| 684 | QVQLQESGPGLVKPSGTLSLTCAVSGASISNSAWWNWVRQPPRGGLEWVG EIYPSGSTNYTPSLKSRATILLDESRNEFSLKLNSVTAADTAVYYCARGR LEDCNGGVCYFFDNWGQGILVSVSS | Clone PA14P1D09 - heavy chain variable region |
| 685 | GASISNSAW | Clone PA14P1D09 - CDR-H1 |
| 686 | IYPSGST | Clone PA14P1D09 - CDR-H2 |

TABLE 1-continued

Sequence Listing

| SEQ ID NO | Sequence | Description |
|---|---|---|
| 687 | ARGRLEDCNGGVCYFFDN | Clone PA14P1D09 - CDR-H3 |
| 688 | DIEMTQSPSTLSASVGDRVTITCRANYGIGAWLAWYQQKPGKAPKLLIYKASTLESGVPLRFSGSGSGTEFTLSISGLQPDDFATYYCHQYSTYPITFGQGTRLEIK | Clone PA14P1D09 - light chain variable region |
| 689 | YGIGAW | Clone PA14P1D09 - CDR-L1 |
| 196 | KAS | Clone PA14P1D09 - CDR-L2 |
| 690 | HQYSTYPIT | Clone PA14P1D09 - CDR-L3 |
| 691 | QVQLVESGGGVVQPGRSLTLSCAASGFNFKTYGMHWVRQAPGKGLEWVAVIYHDGNDKFYADSVKGRFTISRDNSKNTLYVQMSSLRADDTAIYYCAKGIFSSGYHYGMDVWGQGTAVIVSS | Clone PA14P3H08 - heavy chain variable region |
| 692 | GFNFKTYG | Clone PA14P3H08 - CDR-H1 |
| 693 | IYHDGNDK | Clone PA14P3H08 - CDR-H2 |
| 694 | AKGIFSSGYHYGMDV | Clone PA14P3H08 - CDR-H3 |
| 695 | DIQMTQSPSSLSASLGDSVTITCLASQGIKEFLSWFQQKPGQAPKLLIYDASSSHSGVPSRFSGSGSATHFTLTISSLQPDDIATYYCQQYHQVPLTFGQGTRLEIK | Clone PA14P3H08 - light chain variable region |
| 696 | QGIKEF | Clone PA14P3H08 - CDR-L1 |
| 94 | DAS | Clone PA14P3H08 - CDR-L2 |
| 697 | QQYHQVPLT | Clone PA14P3H08 - CDR-L3 |
| 190 | QVQLQQWGAGLLKPSETLSLTCVVSGGSFSTHYWNWIRQSPGKGLEWIGEINHSGNTNYNPSLTGRATISVATSKTQFSLRLNSVTAADTAVYFCARGPRLRYTAGRPLFDTWGQGTLVTVSS | Clone PA15P1E01 - heavy chain variable region |
| 191 | GGSFSTHY | Clone PA15P1E01 - CDR-H1 |
| 192 | INHSGNT | Clone PA15P1E01 - CDR-H2 |
| 193 | ARGPRLRYTAGRPLFDT | Clone PA15P1E01 - CDR-H3 |
| 194 | DIQMTQSPSTLSASVGDRVTITCRASQSISAFLAWYQQKPGKAPNLVIYKASSLDSGVPSTFSGSGSGTEYTLTISSLQPDDFATYYCQQYFSSPPTFGQGTKVEMK | Clone PA15P1E01 - light chain variable region |
| 195 | QSISAF | Clone PA15P1E01 - CDR-L1 |
| 196 | KAS | Clone PA15P1E01 - CDR-L2 |
| 197 | QQYFSSPPT | Clone PA15P1E01 - CDR-L3 |
| 698 | EVRLVESGGGLIQPGGSLRLSCAASGFNVSSDYMNWVRQAPGKGLEWVSVLYSSGFTYYADSVRGRFTISRDNSKNTLYLQMNSLRAEDTAVYYCARVALFGEPLVDSWGQGTLVTVSS | Clone PA15P1E02 - heavy chain variable region |
| 699 | GFNVSSDY | Clone PA15P1E02 - CDR-H1 |
| 700 | LYSSGFT | Clone PA15P1E02 - CDR-H2 |
| 701 | ARVALFGEPLVDS | Clone PA15P1E02 - CDR-H3 |
| 702 | EIVMTQSPATLSVSPGERATLSCRASQSVSSNLAWYQQKPGQAPRLLIYGAISRATGIPARFSGSGSGTEFTLTISSLQSEDFAIYYCQQYNNWPWTFGQGTKVEIK | Clone PA15P1E02 - light chain variable region |
| 482 | QSVSSN | Clone PA15P1E02 - CDR-L1 |
| 703 | GAI | Clone PA15P1E02 - CDR-L2 |
| 584 | QQYNNWPWT | Clone PA15P1E02 - CDR-L3 |

TABLE 1-continued

Sequence Listing

| SEQ ID NO | Sequence | Description |
|---|---|---|
| 704 | DPYSPS | Binding motif sequence for PA13P1H08 |
| 705 | DSYGRDPYSPS | Binding motif sequence for PA13P1H08 |
| 706 | YSPSQDPYSPS | Binding motif sequence for PA13P1H08 |
| 707 | PDRRDPYSPS | Binding motif sequence for PA13P1H08 |
| 708 | RQQWELQGDRRCQSQLERANLRPCEQHLMQKIQRDEDSYGRDPYSPSQDPYSPSQDPDRRDPYSPSPYDRRGAGSSQHQERCCNELNEFENNQRCMCEALQQIMENQSDRLQGRQQEQQFKRELRNLPQQCGLRAPQRCDLEVESGGRDRY | Ara h 2 isoform Ara h 2.0201 (DPYSPS motif underlined) |
| 709 | EVQLVASGGGLIHPGGSLRLSCEASGFSFSRFWMYWVRQSPGEGLVWVARLSGDGTVTNYADSMEGRVTISRDNVKNTLFLEMNSLREGDTGIYYCARKDCPSLSCQLDYWGQGVQVTVSS | Clone 1003320101_D6 heavy chain variable region sequence |
| 710 | GFSFSRFW | Clone 1003320101_D6 CDR-H1 |
| 711 | LSGDGTVT | Clone 1003320101_D6 CDR-H2 |
| 712 | ARKDCPSLSCQLDY | Clone 1003320101_D6 CDR-H3 |
| 713 | QSVLTQPPSVSAAPGQKVTISCSGSTSNIGKNYVSWYQHFPGAAPKLLIFDNDKRPSGIPDRFSGSRSGTSATLDITGLQTGDEADYFCATWDSRLSADVFGSGTTVSVL | Clone 1003320101_D6 light chain variable region sequence |
| 714 | TSNIGKNY | Clone 1003320101_D6 CDR-L1 |
| 715 | DND | Clone 1003320101_D6 CDR-L2 |
| 716 | ATWDSRLSADV | Clone 1003320101_D6 CDR-L3 |
| 717 | EVQLLESGGGLVQPGGSLRLSCAASGFNFSNFAVSWVRQTPGKGLEWVSAILGSRSVTYYADSVKGRFTISRDKSKNALYLQMDSLRAEDTAIYYCAKLFFMPYSHDDSGDYWGQGTLVAVSS | Clone 1003320105_D6 heavy chain variable region sequence |
| 718 | GFNFSNFA | Clone 1003320105_D6 CDR-H1 |
| 719 | ILGSRSVT | Clone 1003320105_D6 CDR-H2 |
| 720 | AKLFFMPYSHDDSGDY | Clone 1003320105_D6 CDR-H3 |
| 721 | QLVLTQSPSASASLGASVKLTCTLSSDHRSYAIAWHQQQPGKGPRYLMKVNRDGSHIKGDGIPHRFSGSSSVTERYLIISSLQSEDEADYYCQSWDTGIQVFGGGTRLTVV | Clone 1003320105_D6 light chain variable region sequence |
| 722 | SDHRSYA | Clone 1003320105_D6 CDR-L1 |
| 723 | VNRDGSH | Clone 1003320105_D6 CDR-L2 |
| 724 | QSWDTGIQV | Clone 1003320105_D6 CDR-L3 |
| 725 | QVQLQESGLGLVKPSGTLSLTCAVSGGPMNSSYWWSWVRQSPGGGLEWIGQISHYTNTKYNPSFKNRVSISIDKSKNEFSLRLTYVTGADTGVYYCVGERDWKDPNWFDPWGQGRLVTVSS | Clone 1003320107_C5 heavy chain variable region sequence |
| 726 | GGPMNSSYW | Clone 1003320107_C5 CDR-H1 |
| 727 | ISHYTNT | Clone 1003320107_C5 CDR-H2 |
| 728 | VGERDWKDPNWFDP | Clone 1003320107_C5 CDR-H3 |
| 729 | QSVLTQPPSVSGAPGQRVTISCTGSNSNIGAGQDVHWYQHFPGTAPKLVIYGNSNRPSGVPDRFSGSKSGTSASLAISGLQADDEADYYCQSYDKSLSSSLFGGGTKLTVL | Clone 1003320107_C5 light chain variable region sequence |
| 730 | NSNIGAGQD | Clone 1003320107_C5 CDR-L1 |

TABLE 1-continued

Sequence Listing

| SEQ ID NO | Sequence | Description |
|---|---|---|
| 731 | GNS | Clone 1003320107_C5 CDR-L2 |
| 732 | QSYDKSLSSSL | Clone 1003320107_C5 CDR-L3 |
| 733 | QVQLQESGPGLVKPSETLSLSCNVSGGSIRGHYWSWIRQSPGKRLEWLGYIYQSGYTKYNPSLKSRVSISLDTSKNKFSLNLKSVTTADTAVYYCAGRVAERGGDQFDFWGQGTLVTVSS | Clone 1003320107_F3 heavy chain variable region sequence |
| 734 | GGSIRGHY | Clone 1003320107_F3 CDR-H1 |
| 735 | IYQSGYT | Clone 1003320107_F3 CDR-H2 |
| 736 | AGRVAERGGDQFDF | Clone 1003320107_F3 CDR-H3 |
| 737 | SYELTQSPSLSVSPGQTASITCSGENLGEKHASWYQQKSGQSPVLVIYQDTKRPAGIPERFSGSNSGSTATLTISGTQPMDEADYFCQAWDANTANVIFGGGTMLTVL | Clone 1003320107_F3 light chain variable region sequence |
| 738 | NLGEKH | Clone 1003320107_F3 CDR-L1 |
| 739 | QDT | Clone 1003320107_F3 CDR-L2 |
| 740 | QAWDANTANVI | Clone 1003320107_F3 CDR-L3 |
| 741 | EVQLVESGGGLVQPGGSLKLSCAASGFTFSGSTIHWVRQTSGKGLEWVGRCIGSKATSYATAYAASVKGRFTISRDDSKNTAYLQMNSLKTEDTAVYFCTRRYYDTTKSVLVVSDSWGQGTLVTVSS | Clone 1003320107_F8 heavy chain variable region sequence |
| 742 | GFTFSGST | Clone 1003320107_F8 CDR-H1 |
| 743 | IGSKATSYAT | Clone 1003320107_F8 CDR-H2 |
| 744 | TRRYYDTTKSVLVVSDS | Clone 1003320107_F8 CDR-H3 |
| 745 | SYELTQPPSMSVSPGQTARITCSGDVLAKQFAYWYQQKPGQAPVLVIYKDSERPSGIPERFSGSSSGTIITLTISGVQAEDEADYYCQSADSSGTSWVFGGGTKLTVL | Clone 1003320107_F8 light chain variable region sequence |
| 746 | VLAKQF | Clone 1003320107_F8 CDR-L1 |
| 747 | KDS | Clone 1003320107_F8 CDR-L2 |
| 748 | QSADSSGTSWV | Clone 1003320107_F8 CDR-L3 |
| 749 | QLLLQESGPGLVKPSETLSLSCTVSAGSITSINYSWGWIRQPPGKGLEWIASVYFSGSIYYNPSLKSRVAISVDTSKNTFSLNLTSVTAADTAVYYCARLRLDTGRDSSGLSYREHFDYWAQGTLVTVSS | Clone PA01P2C05 heavy chain variable region sequence |
| 750 | AGSITSINYS | Clone PA01P2C05 CDR-H1 |
| 751 | VYFSGSI | Clone PA01P2C05 CDR-H2 |
| 752 | ARLRLDTGRDSSGLSYREHFDY | Clone PA01P2C05 CDR-H3 |
| 753 | DIQMTQSPSTLSASVGDRVTITCRASQSIGMWLAWFQQKPGKAPKLLIYKASTLESGVPSRFSGSGSGTEFTLTINSLQPDDFATYYCQQYNSYLFTFGPGTKVDIK | Clone PA01P2C05 light chain variable region sequence |
| 754 | QSIGMW | Clone PA01P2C05 CDR-L1 |
| 196 | KAS | Clone PA01P2C05 CDR-L2 |
| 755 | QQYNSYLFT | Clone PA01P2C05 CDR-L3 |
| 756 | EVQLVQSGAEVKKPGESLKISCKGSGYNFTSSWIGWVRQMPGKGLEWMGIIHPGDSDTRYSPSFQGQVTISADKSLTTAFLQWSSLKTSDTAIYYCARHGSTMLWGDAFDIWGQGTMVTVSS | Clone PA01P2B03 heavy chain variable region sequence |
| 757 | GYNFTSSW | Clone PA01P2B03 CDR-H1 |
| 758 | IHPGDSDT | Clone PA01P2B03 CDR-H2 |
| 759 | ARHGSTMLWGDAFDI | Clone PA01P2B03 CDR-H3 |

TABLE 1-continued

Sequence Listing

| SEQ ID NO | Sequence | Description |
|---|---|---|
| 760 | SYELTQPPSVSLSPGQTARITCSGDALPKHYAYWYQQKPGQAPVLVIYKDCTERPSGIPERFSGSSSGTTVTLTISGVQAEDEADYYCQSSDSTGEVFGGGTKLTVL | Clone PA01P2B03 light chain variable region sequence |
| 761 | ALPKHY | Clone PA01P2B03 CDR-L1 |
| 762 | KDT | Clone PA01P2B03 CDR-L2 |
| 763 | QSSDSTGEV | Clone PA01P2B03 CDR-L3 |
| 764 | QVQLVQSGAEVKKPGASVMLSCKASGYIFTNSDINWVRQAPGQGPEWMGWMNPKSGNTGYEQKFQGRVTMTTNTSISTAYMELSRLRSEDTAVYYCARSTGAVAGNFDYWGQGTPVTVSS | Clone PA01P2A12 heavy chain variable region sequence |
| 765 | GYIFTNSD | Clone PA01P2A12 CDR-H1 |
| 766 | MNPKSGNT | Clone PA01P2A12 CDR-H2 |
| 767 | ARSTGAVAGNFDY | Clone PA01P2A12 CDR-H3 |
| 768 | EIVMTQSPATLSVSLGDRATLSCRASQSISRNLAWYQQKPGQAPRLLIYGCASIRITDIPARFSGSGSGTEFTLTISSLQSEDFAIYFCQQYNNWRTFGQGTRVELK | Clone PA01P2A12 light chain variable region sequence |
| 769 | QSISRN | Clone PA01P2A12 CDR-L1 |
| 30 | GAS | Clone PA01P2A12 CDR-L2 |
| 770 | QQYNNWRT | Clone PA01P2A12 CDR-L3 |
| 771 | HVQLQESGPGLVKSSETLSLTCNVSSDSFSDHYWSWVRQPAGKGLQWLGRCIYNTGTTTYNPSLNRRITMSVDTSKNQFSLRLTSVTAADTAVYYCAARHYHDKTIWGQGTLVTVSS | Clone PA01P2C12 heavy chain variable region sequence |
| 772 | SDSFSDHY | Clone PA01P2C12 CDR-H1 |
| 773 | IYNTGTT | Clone PA01P2C12 CDR-H2 |
| 774 | AARHYHDKTI | Clone PA01P2C12 CDR-H3 |
| 775 | NFMLTQPHSVSESPGKTVTISCTRSSGSIASNYVQWYQQRPGSPPTTVIYCEDNQRPSGVPDRFSGSIDSSSNSASLTISGLKPEDEADFYCQSYDSDDREVFGGGTRLTVL | Clone PA01P2C12 light chain variable region sequence |
| 776 | SGSIASNY | Clone PA01P2C12 CDR-L1 |
| 389 | EDN | Clone PA01P2C12 CDR-L2 |
| 777 | QSYDSDDREV | Clone PA01P2C12 CDR-L3 |
| 778 | QVQLVQSGAEVKKPGASVKVSCKASGYTFTTYGISWVRQAPGQGLEWMGWCISAYNGNTTYAQNFHARVTMTTDTSTSTAYMELRSLRSDDTAVYFCARTSARTITIFGVLIPAGLNLDYWGQGTLVTVSS | Clone PA01P2E10 heavy chain variable region sequence |
| 779 | GYTFTTYG | Clone PA01P2E10 CDR-H1 |
| 532 | ISAYNGNT | Clone PA01P2E10 CDR-H2 |
| 780 | ARTSARTITIFGVLIPAGLNLDY | Clone PA01P2E10 CDR-H3 |
| 781 | QSALTQPASVSGSPGQSITISCTGIGSDVGRYNYVSWYQQHPGKAPKFMICYDVSNRPSGVSNRFSASKSGNTASLTISGLQAEDEADYYCSSYTSTSTLVFGGGTKLTVL | Clone PA01P2E10 light chain variable region sequence |
| 782 | GSDVGRYNY | Clone PA01P2E10 CDR-L1 |
| 404 | DVS | Clone PA01P2E10 CDR-L2 |
| 783 | SSYTSTSTLV | Clone PA01P2E10 CDR-L3 |
| 784 | QVDLVESGGGYVKSGGSLRLSCAASGFRFSDYYMSWVRQAPGKGLEWLSHISSDSSDTNYADSVKGRFSISRDNAKNSVFLQMNTLRAEDTAVYYCARNALTNAYDMSGFRNWGQGILVTVSS | Clone PA01P2C09 heavy chain variable region sequence |

TABLE 1-continued

Sequence Listing

| SEQ ID NO | Sequence | Description |
|---|---|---|
| 785 | GFRFSDYY | Clone PA01P2C09 CDR-H1 |
| 786 | ISSDSSDT | Clone PA01P2C09 CDR-H2 |
| 787 | ARNALTNAYDMSGFRN | Clone PA01P2C09 CDR-H3 |
| 788 | NFMLTQPHSVSESPGKTVILSCTRSSGSIATNYVRWYQQRPGSAPTTVIYEDSRRPSSVPDRFSGSIDSSSNSASLTISGLRTEDEADYYCQSFDTSSRKVVVFGGGTKLTVL | Clone PA01P2C09 light chain variable region sequence |
| 789 | SGSIATNY | Clone PA01P2C09 CDR-L1 |
| 790 | EDS | Clone PA01P2C09 CDR-L2 |
| 791 | QSFDTSSRKVV | Clone PA01P2C09 CDR-L3 |
| 792 | QVTLRESGPALVEVTQTVTLTCNFSGFSLHTRGMYVNWIRQPPGKALEWLAVINWDDDKYYTPSLKNRLTISKDTSKNQVVLTMTNMDPVDTATYYCARTDYGGYGPEGFDYWGQGTLVTVSS | Clone PA01P1D06 heavy chain variable region sequence |
| 793 | GFSLHTRGMY | Clone PA01P1D06 CDR-H1 |
| 794 | INWDDDK | Clone PA01P1D06 CDR-H2 |
| 795 | ARTDYGGYGPEGFDY | Clone PA01P1D06 CDR-H3 |
| 796 | EIVMTQSPATLSVSPGESATLSCRASQSVRSNLAWYQQKPGQAPRLLIYGASTRAPGVPARFTGSESGREFTLTISSLQSEDFAVYYCQQYNNWPPYTFGQGTKLEIK | Clone PA01P1D06 light chain variable region sequence |
| 797 | QSVRSN | Clone PA01P1D06 CDR-L1 |
| 30 | GAS | Clone PA01P1D06 CDR-L2 |
| 798 | QQYNNWPPYT | Clone PA01P1D06 CDR-L3 |
| 799 | QVQLVESGGGVVQPGRSLRLSCVASGFDLNAYGMHWVRQAPGKGLDWVAACTSRGGTKKYYADSVKGRFTISRDVSKNTLYLQMGSLRTGDTAIYYCGVGMEDVFDIWGQGTMVTVSP | Clone PA01P2E08 heavy chain variable region sequence |
| 800 | GFDLNAYG | Clone PA01P2E08 CDR-H1 |
| 801 | TSRGGTKK | Clone PA01P2E08 CDR-H2 |
| 802 | GVGMEDVFDI | Clone PA01P2E08 CDR-H3 |
| 803 | QSVLTQPPSVSAAPGQKVTISCSENNSNIGNRNVSWYQQLPGKAPKLFIYDNNERPSGIPARFSGSKSGTSATLVITGLQTGDEADYYCGTWDRSLSVWVFGGGTKLTVL | Clone PA01P2E08 light chain variable region sequence |
| 804 | NSNIGNRN | Clone PA01P2E08 CDR-L1 |
| 110 | DNN | Clone PA01P2E08 CDR-L2 |
| 805 | GTWDRSLSVWV | Clone PA01P2E08 CDR-L3 |
| 806 | QVQLQESGPGLVKPSQTLSLTCTVSGGSMRSGDYYWSWIRQPPGKGLEWIGYIYFTGSSYYNPSLKSRATISVDTSKNQFSLKLNSVTAADTAVYFCARGVDVDLTFFDCWGHGTLVTVSS | Clone PA01P2A05 heavy chain variable region sequence |
| 807 | GGSMRSGDYY | Clone PA01P2A05 CDR-H1 |
| 808 | IYFTGSS | Clone PA01P2A05 CDR-H2 |
| 809 | ARGVDVDLTFFDC | Clone PA01P2A05 CDR-H3 |
| 810 | SYVLTQPPSVSLAPGKTARITCGGNNIGNKSVHWYQQKPGQAPVLVIYYDSDRPSGIPERFSGSNSGNTATLTINRVEAGDEADYHCQVWDSSTDHRVFGEGTKLTVL | Clone PA01P2A05 light chain variable region sequence |
| 811 | NIGNKS | Clone PA01P2A05 CDR-L1 |
| 509 | YDS | Clone PA01P2A05 CDR-L2 |

TABLE 1-continued

Sequence Listing

| SEQ ID NO | Sequence | Description |
|---|---|---|
| 812 | QVWDSSTDHRV | Clone PA01P2A05 CDR-L3 |
| 813 | QVQLQQWGAGLLKPSETLSLTCTVIGTSFSNYYWSWIRQPPGKGLQWIGEITHSDSANYNPSLKSRVIISIDSSKNQLSLNLSSVTAADTAVYYCARGSKDYYDRSTFSWFDPWGQGTLVTVSS | Clone PA01P2B04 heavy chain variable region sequence |
| 814 | GTSFSNYY | Clone PA01P2B04 CDR-H1 |
| 815 | ITHSDSA | Clone PA01P2B04 CDR-H2 |
| 816 | ARGSKDYYDRSTFSWFDP | Clone PA01P2B04 CDR-H3 |
| 817 | EIVMTQSPATLSVSPGERATLSCRASQNISNKLAWYQQKPGQAPRLLIYDASTRATGVPARFSCSVSGTAFTLTINRLQSEDFAVYYCQQYYYWPPPYTFGHGTKLEIK | Clone PA01P2B04 light chain variable region sequence |
| 818 | QNISNK | Clone PA01P2B04 CDR-L1 |
| 94 | DAS | Clone PA01P2B04 CDR-L2 |
| 819 | QQYYYWPPPYT | Clone PA01P2B04 CDR-L3 |
| 820 | QVQLVESGGGFVKPGGSLRLSCAVSGFTFSDYYMSWVRQAPGKGLEWLSHISSDGSDTNYADSVKGRFSISRDNAKNSVFLQMNTLRVEDTAVYYCARNALTNAYDMSGFRNWGQGTLVTVSS | Clone PA01P2E05 heavy chain variable region sequence |
| 821 | GFTFSDYY | Clone PA01P2E05 CDR-H1 |
| 822 | ISSDGSDT | Clone PA01P2E05 CDR-H2 |
| 787 | ARNALTNAYDMSGFRN | Clone PA01P2E05 CDR-H3 |
| 823 | NFMLTQPHSVSESPGKTVILSCTRSSGSIASNYVRWYQQRPGSAPTTVIYEDSRRPSSVPDRFSGSIDSSSNSASLTISGLKTEDEADYYCQSFDSSSRKVVFGGGTKLTVL | Clone PA01P2E05 light chain variable region sequence |
| 776 | SGSIASNY | Clone PA01P2E05 CDR-L1 |
| 790 | EDS | Clone PA01P2E05 CDR-L2 |
| 824 | QSFDSSSRKVV | Clone PA01P2E05 CDR-L3 |
| 825 | QVQLLQSGPEVKQPGASVQVSCQTSGYTFTGYYIHWVRQAPGQGLEWVGWINPNRGHTNYGPAFQGRLTLTADTSSSTAYLELTRLRSDDTAVYYCARDLTGGRDAFEIWGQGTMLIVSS | Clone PA01P2D04 heavy chain variable region sequence |
| 121 | GYTFTGYY | Clone PA01P2D04 CDR-H1 |
| 826 | INPNRGHT | Clone PA01P2D04 CDR-H2 |
| 827 | ARDRLTGGRDAFEI | Clone PA01P2D04 CDR-H3 |
| 828 | DIQLTQSPSSLSASVGDRVTITCRASQSISSYLNWYQQKPGKAPKLLISVASSLQDGVPPRFSGSRSGTEFTLTISSLQPEDFAIYYCQQSYSLSWTFGQGTKVEIK | Clone PA01P2D04 light chain variable region sequence |
| 829 | QSISSY | Clone PA01P2D04 CDR-L1 |
| 830 | VAS | Clone PA01P2D04 CDR-L2 |
| 831 | QQSYSLSWT | Clone PA01P2D04 CDR-L3 |
| 832 | QVQLVQSGAEVKQPGASVQVACQTSGYIFTAYYIHWLRQAPGQGLEWVGWINPNRGHTNYAPGFQGRLTLTADTSSSTAYLALTRLASDDTAVYYCARDLTGGRDAFEIWGQGTMLIVSS | Clone PA01P2B12 heavy chain variable region sequence |
| 833 | GYIFTAYY | Clone PA01P2B12 CDR-H1 |
| 826 | INPNRGHT | Clone PA01P2B12 CDR-H2 |
| 827 | ARDRLTGGRDAFEI | Clone PA01P2B12 CDR-H3 |

TABLE 1-continued

Sequence Listing

| SEQ ID NO | Sequence | Description |
|---|---|---|
| 834 | DIQLTQSPSSLSASVGDRVTITCRASQSVSSYLNWYQQKPGEAPKLLISA ASSLQDGVPPRFSGSRSGTEFTLTISSLQPEDFAIYYCQQSYSLWWTFGQ GTKVEIK | Clone PA01P2B12 light chain variable region sequence |
| 835 | QSVSSY | Clone PA01P2B12 CDR-L1 |
| 149 | AAS | Clone PA01P2B12 CDR-L2 |
| 836 | QQSYSLWWT | Clone PA01P2B12 CDR-L3 |
| 837 | QLQLQESGSGLVKPSQTLSLTCDVSGDSMNDDVYTWSWIRQPPGRGLEWI GYISHTGNTFYNSSLQSRVTMSVDTSKNQFSLKLSSVTIADTAVYYCARL TFLFSAPFSSFNWFDPWGQGILVTVSS | Clone PA01P2D11 heavy chain variable region sequence |
| 838 | GDSMNDDVYT | Clone PA01P2D11 CDR-H1 |
| 839 | ISHTGNT | Clone PA01P2D11 CDR-H2 |
| 840 | ARLTFLFSAPFSSFNWFDP | Clone PA01P2D11 CDR-H3 |
| 841 | QSVLTQPPSVSGAPGQTITISCTGTPSNFGADYDVHWYQQRPGTAPKLLI FADKHRPSGVPDRFSGSRSGTSASLAISGLQAEDEADYYCQSYDSGVVGL WVFGGGTKVTVL | Clone PA01P2D11 light chain variable region sequence |
| 842 | PSNFGADYD | Clone PA01P2D11 CDR-L1 |
| 843 | ADK | Clone PA01P2D11 CDR-L2 |
| 844 | QSYDSGVVGLWV | Clone PA01P2D11 CDR-L3 |
| 845 | QVQLQQWGAGLLKPSETLSLTCGVHGGSLNNYYWSWIRQPPGKGLEWIGE VYHSGSINYNPSLKSRVIMSVDTSKNQFSFNLSSVTAADTAVYYCARGAY DSRGFWILDAFNTWGQGTMVIVSS | Clone PA01P2B10 heavy chain variable region sequence |
| 846 | GGSLNNYY | Clone PA01P2B10 CDR-H1 |
| 847 | VYHSGSI | Clone PA01P2B10 CDR-H2 |
| 848 | ARGAYDSRGFWTLDAFNT | Clone PA01P2B10 CDR-H3 |
| 849 | DIQMTQSPSALSASLGDRVTITCRASESINSWLAWYQQKPGKAPKLLIYK ASTLESGVPSRFSGSGSGTEFTLTISSLQPDDFATYYCHQYNRYSYTFGQ GTKLDIK | Clone PA01P2B10 light chain variable region sequence |
| 850 | ESINSW | Clone PA01P2B10 CDR-L1 |
| 196 | KAS | Clone PA01P2B10 CDR-L2 |
| 851 | HQYNRYSYT | Clone PA01P2B10 CDR-L3 |
| 852 | EVLLLESGGGLVHPGGTLRLSCAASGFTFRNSAMTWVRQAPGKGLEWVSS IGGSGAKSYYADSVKGRFTISRDNSKNTLYLEMNTLRVDDTAIYYCAKDQ LNCYDLWSGDYCWFDTWGQGTLVTVSS | Clone PA01P2D10 heavy chain variable region sequence |
| 853 | GFTFRNSA | Clone PA01P2D10 CDR-H1 |
| 854 | IGGSGAKS | Clone PA01P2D10 CDR-H2 |
| 855 | AKDQLNCYDLWSGDYCWFDT | Clone PA01P2D10 CDR-H3 |
| 856 | QSVLIQPPSASGTPGQRVTISCSGSNSNIGSNYVCWYQHLPGGAPKLLIY RNNQRPSGVPDRFSGSKSGTSASLAISGLRSEDEADYYCAAWDDSLSGSW VFGGGTKLTVL | Clone PA01P2D10 light chain variable region sequence |
| 857 | NSNIGSNY | Clone PA01P2D10 CDR-L1 |
| 662 | RNN | Clone PA01P2D10 CDR-L2 |
| 858 | AAWDDSLSGSWV | Clone PA01P2D10 CDR-L3 |
| 859 | EVQLLESGGGLVQPGGSLRLSCAVSGLKFSSYAMSWVRQAPGKGLEWVSC VSGSSGSTFYAVSVEGRFSISRDNSNNMLYMDHSLRVEDTAKYYCAKV GWYYDRNGNRRPKGFRAFDVWGQGTMVIVSS | Clone PA01P2D09 heavy chain variable region sequence |

TABLE 1-continued

Sequence Listing

| SEQ ID NO | Sequence | Description |
|---|---|---|
| 860 | GLKFSSYA | Clone PA01P2D09 CDR-H1 |
| 861 | VSGSSGST | Clone PA01P2D09 CDR-H2 |
| 862 | AKVVGWYYDRNGNRRPKGFRAFDV | Clone PA01P2D09 CDR-H3 |
| 863 | QSVLTQPPSASGTPGQRITIACSGTTSNIGGNSVNWYQQFPGAAPRLLIF DYDQRPSGVPARFSGSSSGSSGYLAISGLQSEDEADYYCSSWDDNLNGWV FGGGTKLTVL | Clone PA01P2D09 light chain variable region sequence |
| 864 | TSNIGGNS | Clone PA01P2D09 CDR-L1 |
| 865 | DYD | Clone PA01P2D09 CDR-L2 |
| 866 | SSWDDNLNGWV | Clone PA01P2D09 CDR-L3 |
| 867 | EVQLLESGGGLVQPGGSLRLSCVASGFTFSGHAMSWVRQAPGKGLEWVSGC ISGSGGSTYYADSVKGRFTISRDNSKKTVDLQMNNLRAEDTAIYYCAKDL HFDTSGYYYSMIFDYWGQGTLVPVSS | Clone PA01P2B05 heavy chain variable region sequence |
| 868 | GFTFSGHA | Clone PA01P2B05 CDR-H1 |
| 378 | ISGSGGST | Clone PA01P2B05 CDR-H2 |
| 869 | AKDLHFDTSGYYYSMIFDY | Clone PA01P2B05 CDR-H3 |
| 870 | QSALAQPASVGSPGQSITISCTGTSSDISDYNYVSWYQQHPGKAPKLILC YDVNNRPSGVSSRFSGSKSGDTASLTISGLQPEDEADYYCSSYTSTKIFG GGTKVTVL | Clone PA01P2B05 light chain variable region sequence |
| 871 | SSDISDYNY | Clone PA01P2B05 CDR-L1 |
| 682 | DVN | Clone PA01P2B05 CDR-L2 |
| 872 | SSYTSTKI | Clone PA01P2B05 CDR-L3 |
| 873 | EVQLLESGGGLLQLGGSLRLSCAASGFTFSSYVMSWVRQAPGKGLEWVSL ITGSGGNTYYADSVKGRFTISRDNSKNTLFLQMNSLRVEDTAIYYCVKT FYDSSGYYFHDAFHIWGQGTMVTVSS | Clone PA01P4C11 heavy chain variable region sequence |
| 874 | GFTFSSYV | Clone PA01P4C11 CDR-H1 |
| 875 | ITGSGGNT | Clone PA01P4C11 CDR-H2 |
| 876 | VKTDFYDSSGYYFHDAFHI | Clone PA01P4C11 CDR-H3 |
| 877 | QTVVTQEPSLTVSPGGTVTLTCASSTGSVTSGYYPNWFQQKPGQAPRTLIC YGTSNKHSWTPARFSGSLLGGKAALTLSDVQPEDEAEYYCLLYYGGAYVF GTGTKVTVL | Clone PA01P4C11 light chain variable region sequence |
| 878 | TGSVTSGYY | Clone PA01P4C11 CDR-L1 |
| 22 | GTS | Clone PA01P4C11 CDR-L2 |
| 879 | LLYYGGAYV | Clone PA01P4C11 CDR-L3 |
| 880 | QVQLVQSGAEVKKPGASVKVSCKASGYTFIRYDIHWVRQATGQGLEWMGW MNPNNGKSGFAQKFEGRVTLTRNTSVTSTYMQLSSLGLEDTAVYYCVRAG YSYGWGFDYWGQGSLVTVSS | Clone PA01P3E08 heavy chain variable region sequence |
| 881 | GYTFIRYD | Clone PA01P3E08 CDR-H1 |
| 882 | MNPNNGKS | Clone PA01P3E08 CDR-H2 |
| 883 | VRAGYSYGWGFDY | Clone PA01P3E08 CDR-H3 |
| 884 | NFTLTQPHSVSGSPGKTVTISCTRSSGGIASSHVQWYQQRPASAPTTLIF EDDQRSSGVPDRFSGSIDTSSNSAYLTISGLEAEDEADYYCQSYDNSMWV FGGGSKVTVL | Clone PA01P3E08 light chain variable region sequence |
| 885 | SGGIASSH | Clone PA01P3E08 CDR-L1 |
| 886 | EDD | Clone PA01P3E08 CDR-L2 |

TABLE 1-continued

Sequence Listing

| SEQ ID NO | Sequence | Description |
|---|---|---|
| 887 | QSYDNSMWV | Clone PA01P3E08 CDR-L3 |
| 888 | HVQLVQSGADVKKPGSSVKVSCKFSGGTFNNDSINWVRQAPGQGLEWMGVIMPFFGATRFAPKFQGRVILTADKFTSTGYMELGSLKSDDTAVYYCARDKPPDDKWADYGMDVWGQGTTVTVSS | Clone PA01P2E06 heavy chain variable region sequence |
| 889 | GGTFNNDS | Clone PA01P2E06 CDR-H1 |
| 890 | IMPFFGAT | Clone PA01P2E06 CDR-H2 |
| 891 | ARDKPPDDKWADYGMDV | Clone PA01P2E06 CDR-H3 |
| 892 | SYELTQPPSVSVSPGQTARITCSGDALPKQYVYWYQQKTGQAPVLVIYKDTERPSGIPERFSGSTSGTTVTLTISGVQADDEADYFCQSADRNANYRVFGGGTKLTVL | Clone PA01P2E06 light chain variable region sequence |
| 523 | ALPKQY | Clone PA01P2E06 CDR-L1 |
| 762 | KDT | Clone PA01P2E06 CDR-L2 |
| 893 | QSADRNANYRV | Clone PA01P2E06 CDR-L3 |
| 894 | QLQLQESGSGLVKPSQTLSLTCAVSGGSITSGTYSWTWIRQSPEKGLEWIGYIYYTGSTYYNPSLGRRVTISGDTSNNEFSLNLKSVTAADTAVYYCARGIHRGGVLDFWGQGILVTVSS | Clone PA01P2E07 heavy chain variable region sequence |
| 895 | GGSITSGTYS | Clone PA01P2E07 CDR-H1 |
| 896 | IYYTGST | Clone PA01P2E07 CDR-H2 |
| 897 | ARGIHRGGVLDF | Clone PA01P2E07 CDR-H3 |
| 898 | EIVLTQSPATLPLSPGERATLSCRASQSLDKYLAWYQQKPGQAPRLLIYDTSKRATGIPARFSGSGSGTDFTLTISSLEPEDFAVYFCQQRNNWPPYTFGQGTKVEMK | Clone PA01P2E07 light chain variable region sequence |
| 899 | QSLDKY | Clone PA01P2E07 CDR-L1 |
| 900 | DTS | Clone PA01P2E07 CDR-L2 |
| 901 | QQRNNWPPYT | Clone PA01P2E07 CDR-L3 |
| 902 | QVLLVQSGSEVKNPGASIRVSCKTSGYMFTNNGIAWVREVPTQGLEWMGWISTYSGATHYAPNLHGRITMTADTSASTAYMELRSLQSGDTGVYYCARLWFGKLGLDFWGQGTQVTVSS | Clone PA01P2G07 heavy chain variable region sequence |
| 903 | GYMFTNNG | Clone PA01P2G07 CDR-H1 |
| 904 | ISTYSGAT | Clone PA01P2G07 CDR-H2 |
| 905 | ARLWFGKLGLDF | Clone PA01P2G07 CDR-H3 |
| 906 | QSVLTQPPSASGTPGQRVIISCSGSTSNIGTKTVNWYQHLPGTAPKLLIYNNNQRPSGVPDRFSGSKSGTSASLTISGLQSEDEADYYCAAWDDSLNGRGLFGPGTKVTVL | Clone PA01P2G07 light chain variable region sequence |
| 907 | TSNIGTKT | Clone PA01P2G07 CDR-L1 |
| 908 | NNN | Clone PA01P2G07 CDR-L2 |
| 909 | AAWDDSLNGRGL | Clone PA01P2G07 CDR-L3 |
| 910 | QVEVVESGGGVVQPGKSLRLSCAASGFKFNVYGIHWVRQAPGKGLEWVACVWYDGSNKYYADSVKGRFTISRDNSKNTTYLQMDSLRVDDTAVYYCARELQYSNYDYFYAMDVWGQGTTVTVSS | Clone PA01P2B09 heavy chain variable region sequence |
| 911 | GFKFNVYG | Clone PA01P2B09 CDR-H1 |
| 912 | VWYDGSNK | Clone PA01P2B09 CDR-H2 |
| 913 | ARELQYSNYDYFYAMDV | Clone PA01P2B09 CDR-H3 |

TABLE 1-continued

Sequence Listing

| SEQ ID NO | Sequence | Description |
|---|---|---|
| 914 | DIQMTQSPPSLSASVGDRVTITCRASQDIDNYLVWFQQKPGRAPKSLIYA ASSLQSGVPSKFSGSGSGTEFTLTISSLQPEDFATYYCQQYNSFPYTFGQ GTKLEIK | Clone PA01P2B09 light chain variable region sequence |
| 915 | QDIDNY | Clone PA01P2B09 CDR-L1 |
| 149 | AAS | Clone PA01P2B09 CDR-L2 |
| 916 | QQYNSFPYT | Clone PA01P2B09 CDR-L3 |
| 917 | QVQLQESGPGLVKPSETLSLTCSVSGGSISSHYWSWIRQPPGRGLEWIAY ISYSGRTKYNPSLKSRVTISEDTSKNQFSLKLSSVTPADTAVYYCARIYG DYGPFIDYWGQGTLVTVSS | Clone PA01P2C04 heavy chain variable region sequence |
| 918 | GGSISSHY | Clone PA01P2C04 CDR-H1 |
| 919 | ISYSGRT | Clone PA01P2C04 CDR-H2 |
| 920 | ARIYGDYGPFIDY | Clone PA01P2C04 CDR-H3 |
| 921 | DIQMTQSPSSLSASVGDRVTITCRASQTISTYLNWYQQKPGTAPMLLIYG AYSLHSGVPSRFSGSGSGTDFTLTISSLQPEDFATYYCQQSSSLPLTFGG GTKVEIK | Clone PA01P2C04 light chain variable region sequence |
| 922 | QTISTY | Clone PA01P2C04 CDR-L1 |
| 923 | GAY | Clone PA01P2C04 CDR-L2 |
| 924 | QQSSSLPLT | Clone PA01P2C04 CDR-L3 |
| 925 | QEQLQESGPGLVKPSQTLSLTCTVSGGSISSGDHYWSWLRQTPGKGLEWI GYIYYRGNTNYNPSLESRITMSVDTSKNQFSLKLSSVTAADTGVYYCARD RRLLFWFGQGPETFDIWGPGTMVTVSS | Clone PA01P2H08 heavy chain variable region sequence |
| 926 | GGSISSGDHY | Clone PA01P2H08 CDR-H1 |
| 927 | IYYRGNT | Clone PA01P2H08 CDR-H2 |
| 928 | ARDRRLLFWFGQGPETFDI | Clone PA01P2H08 CDR-H3 |
| 929 | DIQMTQSPSILSASVGDRVTITCRASQNINHWLAWYQQKPGKAPKLLIYM ASSLENGVPSRFSGSGSGTEFTLTISSLQPDDFATYYCQQYNSYSGTFGH GTKVDIK | Clone PA01P2H08 light chain variable region sequence |
| 930 | QNINHW | Clone PA01P2H08 CDR-L1 |
| 931 | MAS | Clone PA01P2H08 CDR-L2 |
| 932 | QQYNSYSGT | Clone PA01P2H08 CDR-L3 |
| 933 | TACTGTGCGAAAGTTCTTGACTACAGTGAATTTCATTACTATTACGGTTT GGACGTCTGGGGCCAAGGGACCGCGGTCGCCGTCTCCTCAG | FIG. 13A PA12P3F10 |
| 934 | TACTGTGCGAAAGTTCTTGACTACAATGAGTACTCTCTACTTCGGTAT GGACGTCTGGGGCCAAGGGACCACGGTCACCGTCTCCTCAG | FIG. 13A PA12P3D08 |
| 935 | TACTGTGCGAAAGTTCTTGACTACAGTGAATACTCTCTACTTCGGTAT GGACGTCTGGGGCCAAGGGACCACGGTCCTTGTCTCCTCAG | FIG. 13A PA12P1C07 |
| 936 | TACTGTGCGAAGGTCCTTGACTACAGTAGGTACTCCTATTATTACGGGAT GGACGTCTGGGGCCAGGGGACCACGGTCATCGTCTCCTCAG | FIG. 13A PA13P1H08 |
| 937 | TACTGTGCTAAGGTCCTTGACTACAGTGCATTCTCCTATTATTATGGGAT GGACGTCTGGGGCCAGGGGACCACGGTCATCGTCTCCTCAG | FIG. 13A PA13P1E10 |
| 938 | TATTGTGCGAAAGTCCTTGACTACAGTATTTTCTATTACTATTTCGGCCT GGACGTCTGGGGCCAAGGGACCACGGTCACCGTCTCCTCAG | FIG. 13A PA13P3G09 |
| 939 | TACTGTGCGAAAGA | FIG. 13A IGHV30-30*18 |
| 940 | TYCT | FIG. 13A Nontennplated (inferred) |

TABLE 1-continued

Sequence Listing

Figures 13B, 13C:
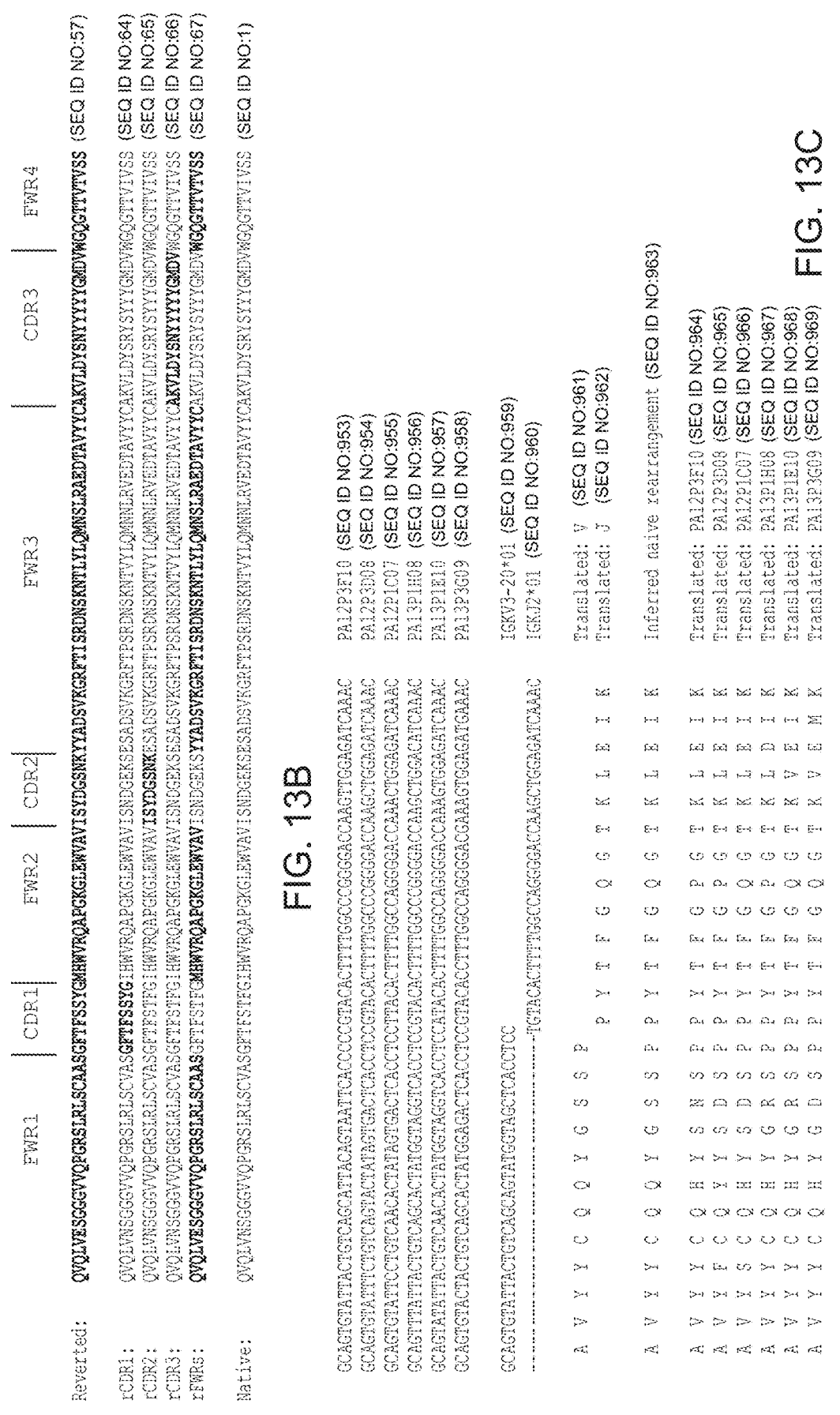

| SEQ ID NO | Sequence | Description |
|---|---|---|
| 941 | TGACTACAGTAACTAC | FIG. 13A IGHD4-11*01 |
| 942 | ATTACTACTACTACTACGGTATGGACGTCTGGGGCCAAGGGACCACGGTCACCGTCTCCTCAG | FIG. 13A IGHJ6*02 |
| 943 | YCAK | FIG. 13A Translated: V |
| 944 | VLDYSNY | FIG. 13A Translated: Nontemplated + D |
| 945 | NYYYYYGMDVWGQGTTVTVSS | FIG. 13A Translated: J |
| 946 | YCAKVLDYSNYYYYYGMDVWGQGTTVTVSS | FIG. 13A Inferred naive rearrangement |
| 947 | YCAKVLDYSEFHYYYGLDVWGQGTAVAVSS | FIG. 13A Translated: PA12P3F10 |
| 948 | YCAKVLDYNEYSLYFGMDVWGQGTTVTVSS | FIG. 13A Translated: PA12P3D08 |
| 949 | YCAKVLDYSEYSLYFGMDVWGQGTTVLVSS | FIG. 13A Translated: PA12P1C07 |
| 950 | YCAKVLDYSRYSYYYGMDVWGQGTTVIVSS | FIG. 13A Translated: PA13P1H08 |
| 951 | YCAKVLDYSAFSYYYGMDVWGQGTIVIVSS | FIG. 13A Translated: PA13P1E10 |
| 952 | YCAKVLDYSIFYYYFGLDVWGQGTTVTVSS | FIG. 13A Translated: PA13P3G09 |
| 953 | GCAGTGTATTACTGTCAGCATTACAGTAATTCACCCCCGTACACTTTTGGCCCGGGGACCAAGTTGGAGATCAAAC | FIG. 13C PA12P3F10 |
| 954 | GCAGTGTATTTCTGTCAGTACTATAGTGACTCACCTCCGTACACTTTTGGCCCGGGGACCAAGCTGGAGATCAAAC | FIG. 13C PA12P3D08 |
| 955 | GCAGTGTATTCCTGTCAACACTATAGTGACTCACCTCCTTACACTTTTGGCCAGGGGACCAAACTGGAGATCAAAC | FIG. 13C PA12P1C07 |
| 956 | GCAGTTTATTACTGTCAGCACTATGGTAGGTCACCTCCGTACACTTTTGGCCCGGGGACCAAGCTGGACATCAAAC | FIG. 13C PA13P1H08 |
| 957 | GCAGTATATTACTGTCAACACTATGGTAGGTCACCTCCATACACTTTTGGCCAGGGGACCAAAGTGGAGATCAAAC | FIG. 13C PA13P1E10 |
| 958 | GCAGTGTACTACTGTCAGCACTATGGAGACTCACCTCCGTACACCTTTTGGCCAGGGGACGAAAGTGGAGATGAAAC | FIG. 13C PA13P3G09 |
| 959 | GCAGTGTATTACTGTCAGCAGTATGGTAGCTCACCTCC | FIG. 13C IGKV3-20*01 |
| 960 | TGTACACTTTTGGCCAGGGGACCAAGCTGGAGATCAAAC | FIG. 13C IGKJ2*01 |
| 961 | AVYYCQQYGSSP | FIG. 13C Translated: V |
| 962 | PYTFGQGTKLEIK | FIG. 13C Translated: J |
| 963 | AVYYCQQYGSSPPYTFGQGTKLEIK | FIG. 13C Inferred naive rearrangement |
| 964 | AVYYCQHYSNSPPYTFGPGTKLEIK | FIG. 13C Translated: PA12P3F10 |
| 965 | AVYFCQYYSDSPPYTFGPGTKLEIK | FIG. 13C Translated: PA12P3D08 |
| 966 | AVYSCQHYSDSPPYTFGQGTKLEIK | FIG. 13C Translated: PA12P1C07 |
| 967 | AVYYCQHYGRSPPYTFGPGTKLDIK | FIG. 13C Translated: PA13P1H08 |
| 968 | AVYYCQHYGRSPPYTFGQGTKVEIK | FIG. 13C Translated: PA13P1E10 |
| 969 | AVYYCQHYGDSPPYTFGQGTKVEMK | FIG. 13C Translated: PA13P3G09 |
| 970 | EIVLTQSPATLSLSPGERATLSCRASQSVSSYLAWYQQKPGQAPRLLIYDFIASNRATGIPARFSGSGSGTDFTLTISSLEPEDFAVYYCQQRSNWPPGFTFGPGTKVDIK | FIG. 13E swap |
| 971 | AKVMDYDIFKNYFGLDV | FIG. 16 |

TABLE 1-continued

Sequence Listing

Figure 12A:
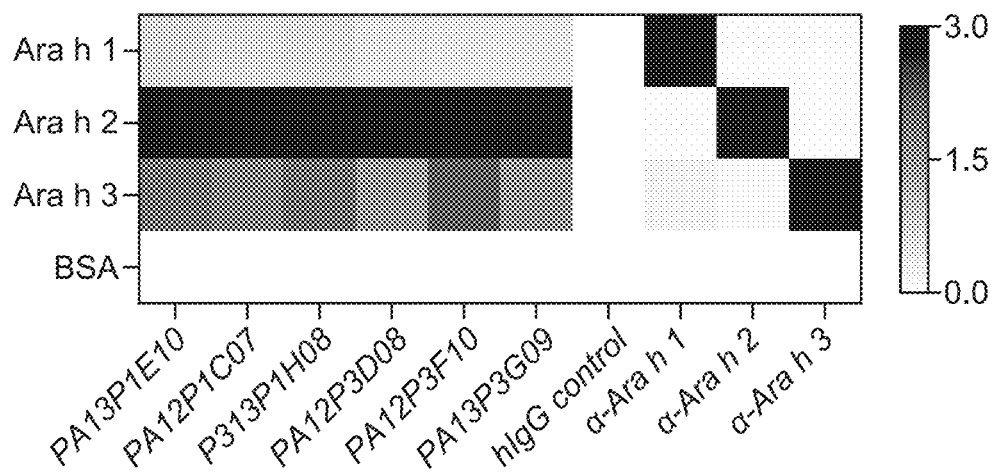
FIGS. 12A-12H. Antibody specificity and affinity characterizations. (A) Semi-quantitative indirect ELISAs of convergent antibodies, controls, PA13P1H08 variants, and antibodies from other clonal families. Human IgG isotype control (abcam #ab206195) served as a negative control, while positive controls included anti-Ara h mouse monoclonal antibodies purchased from Indoor Biotechnologies. (B-G) Kinetic characterization of antibody binding to Ara h 2 (B-D) and Ara h 3 (E-G) using biolayer interferometry. Antibodies are named and described herein. (H) Indirect ELISA showing binding of recombinant monoclonal antibodies from subjects PA11, PA12, PA13, PA14, PA15, and PA16 (rows) to allergen extracts, natural peanut allergen Ara h 2, and bovine serum albumin (BSA) (columns). The isotype of each antibody is shown to the left. Higher values indicate stronger binding. OD=optical density. Depicted values represent those after subtraction of human IgG isotype control. Only the tested antibodies with any OD value above 0.25 are shown.
Figure 12A:
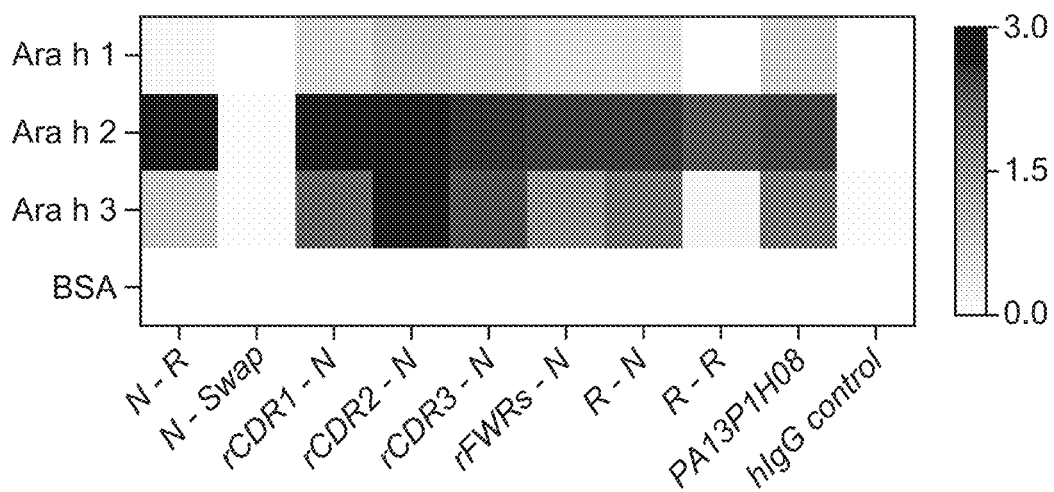
Figure 12B:
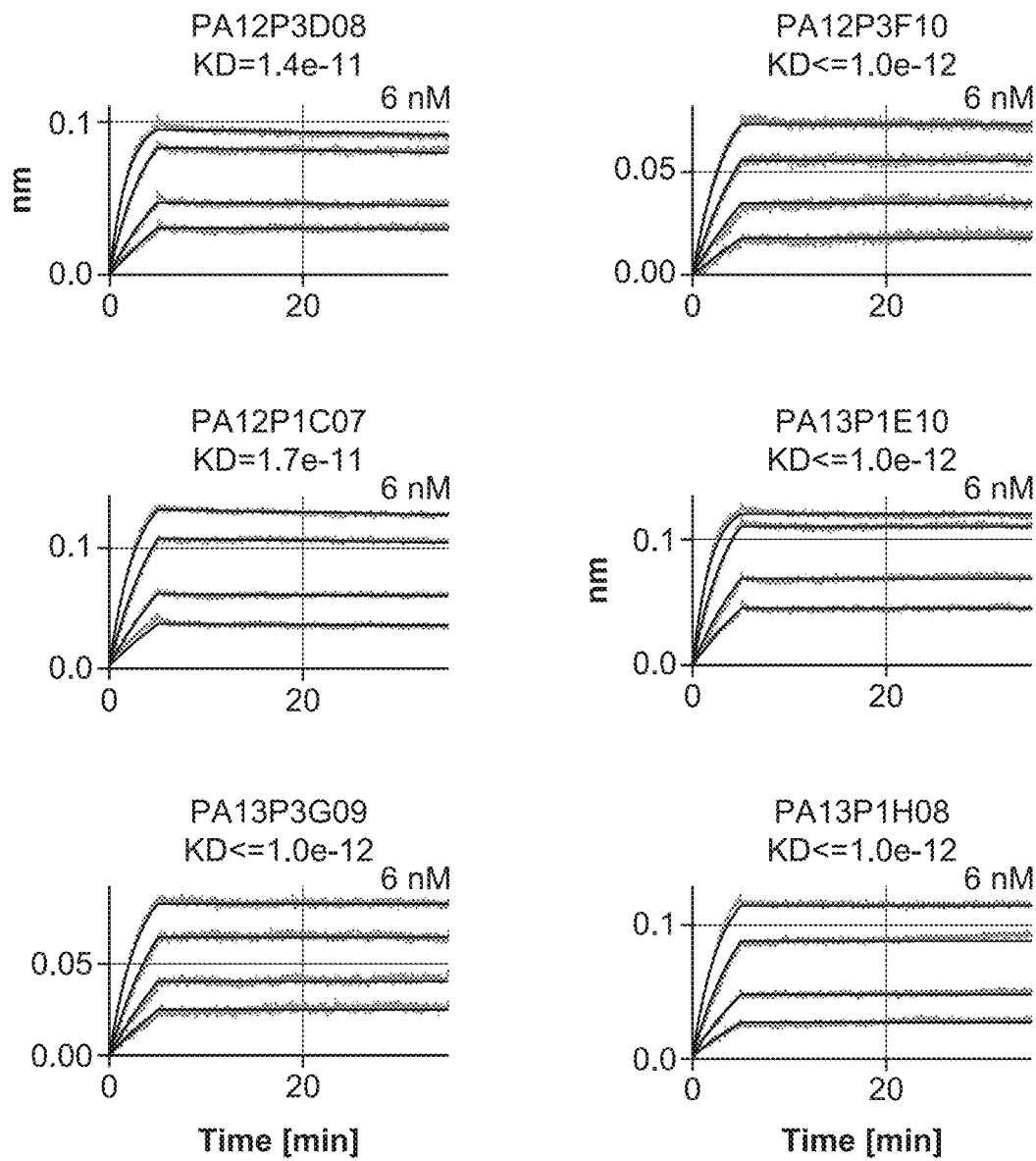
Figure 12C:
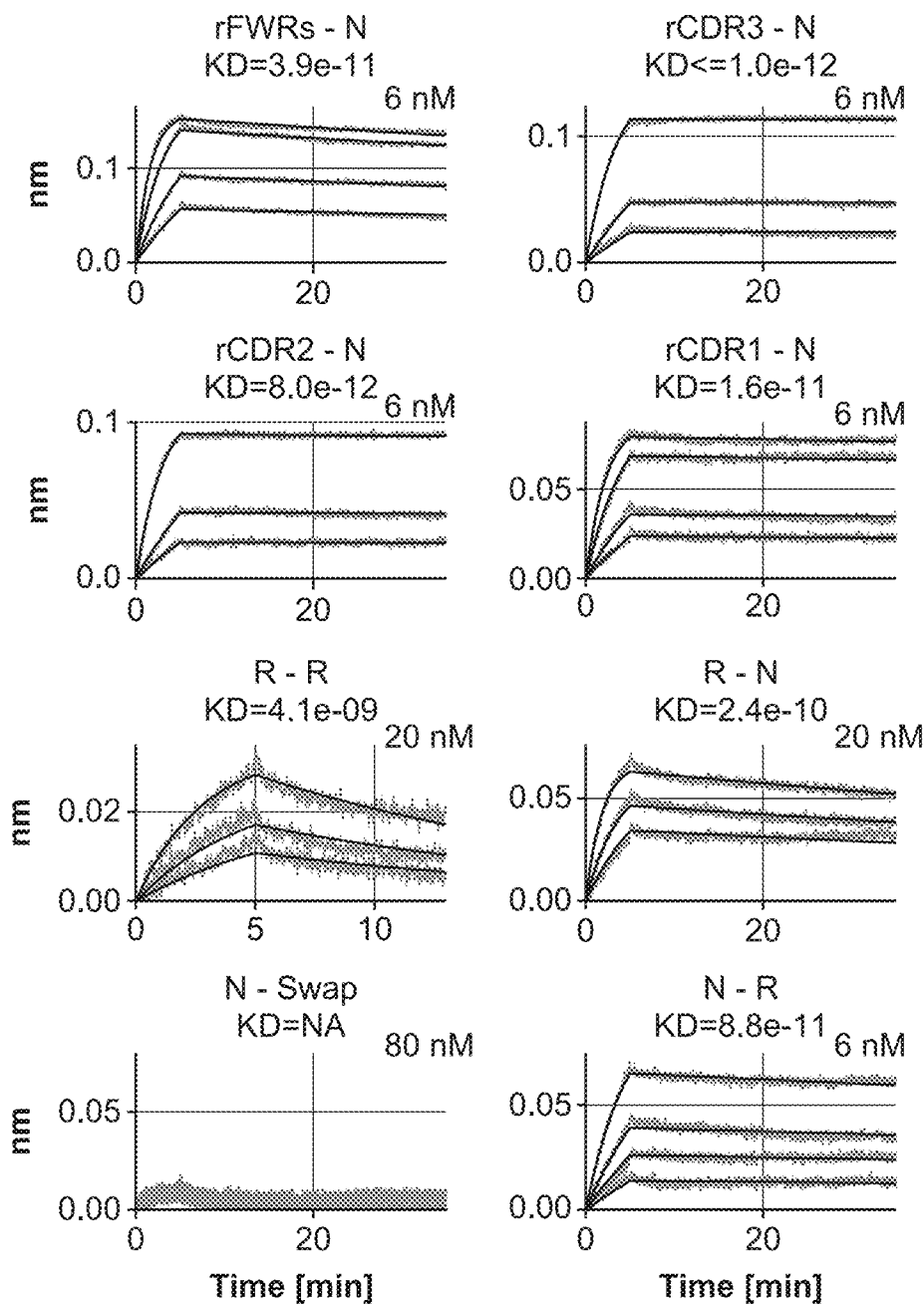
Figure 12D:
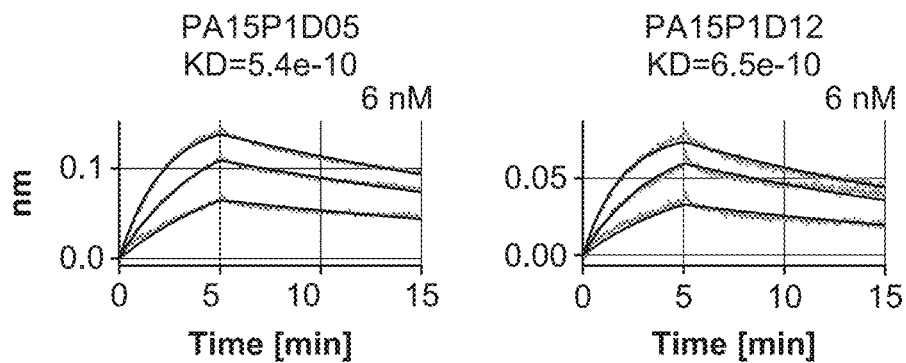
Figure 12E:
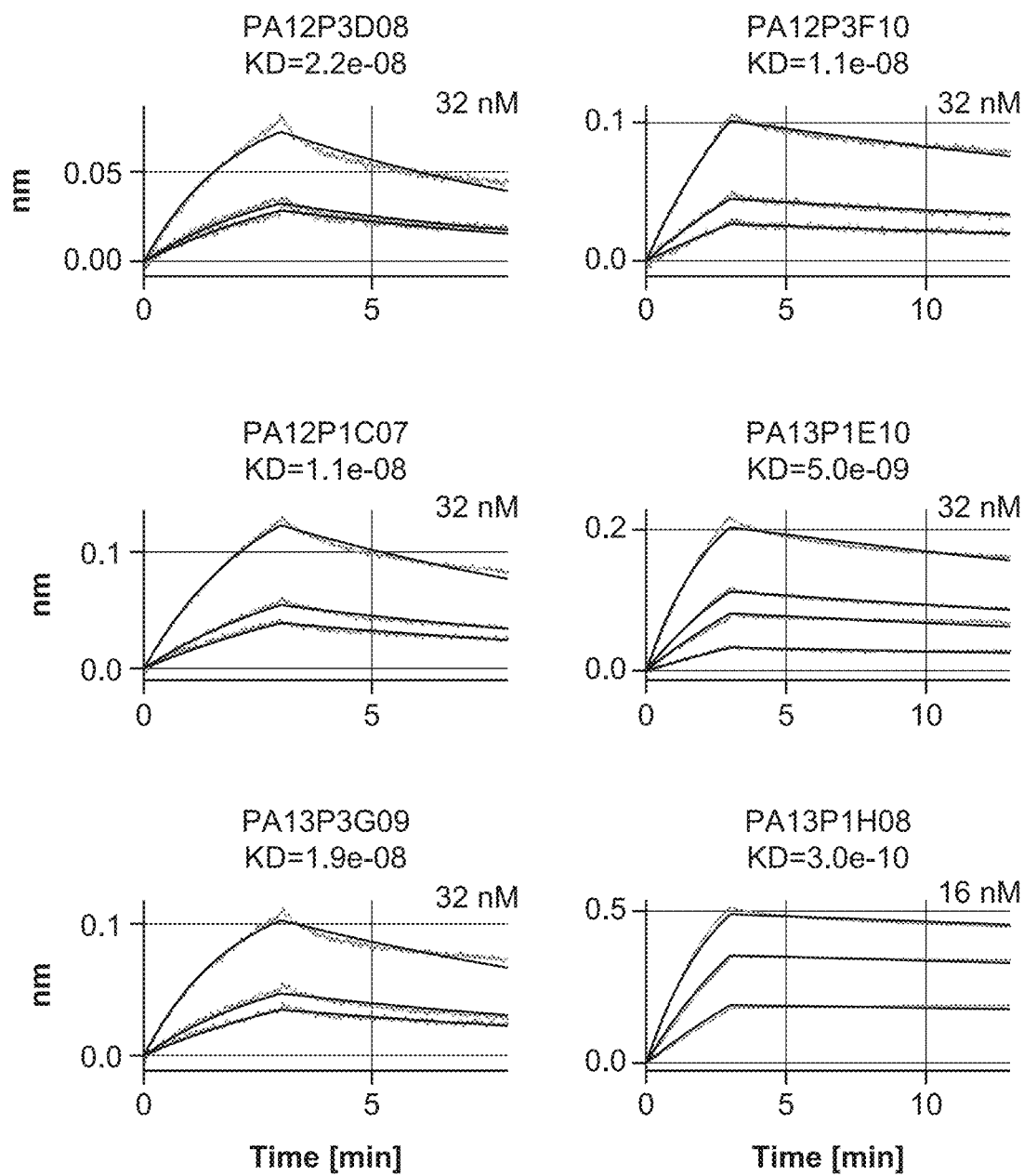
Figure 12F:
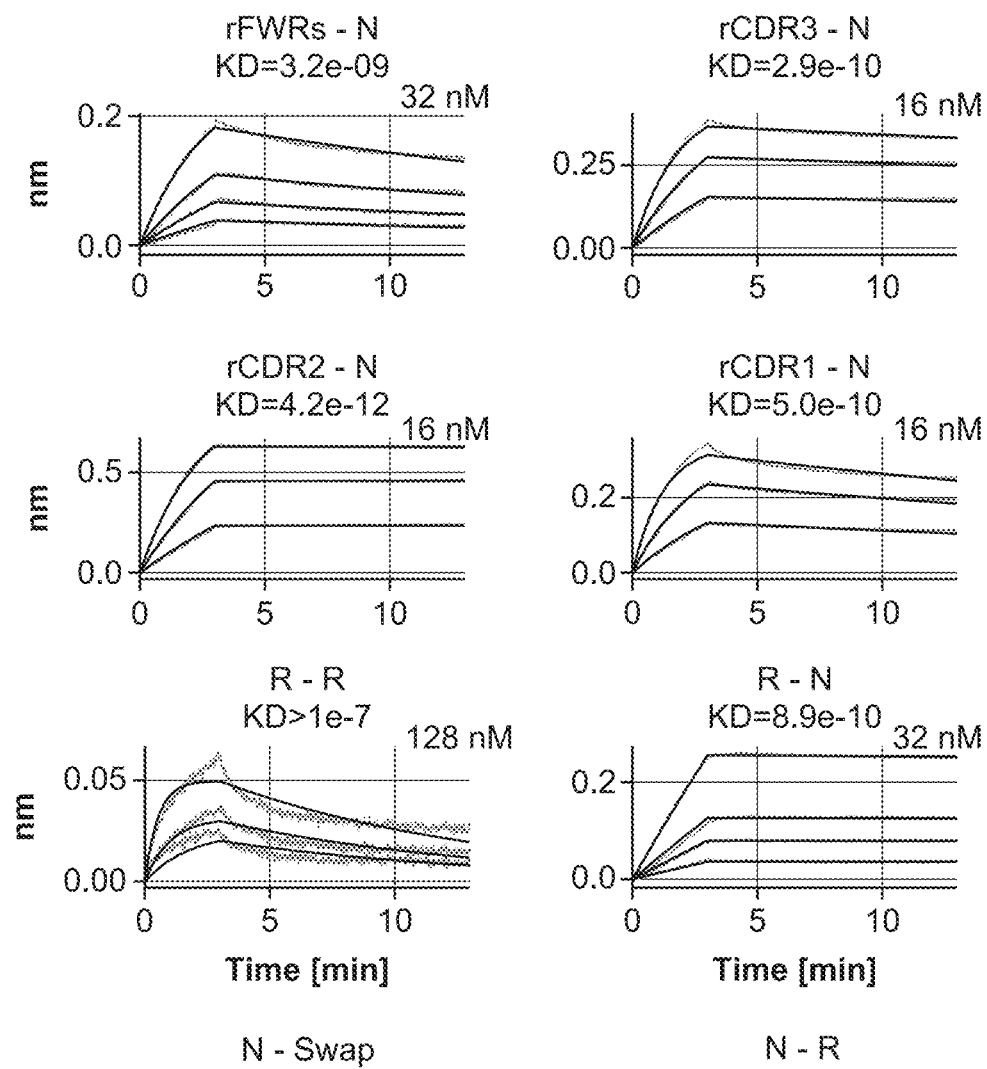
Figure 12G:
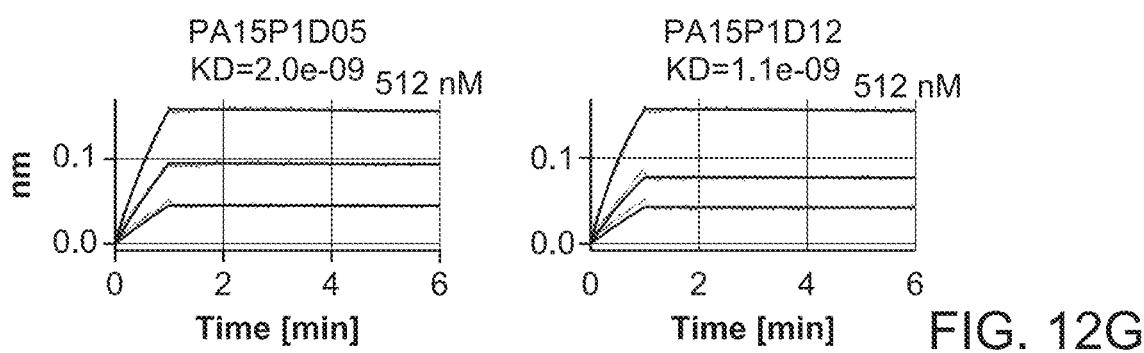
Figure 12H:
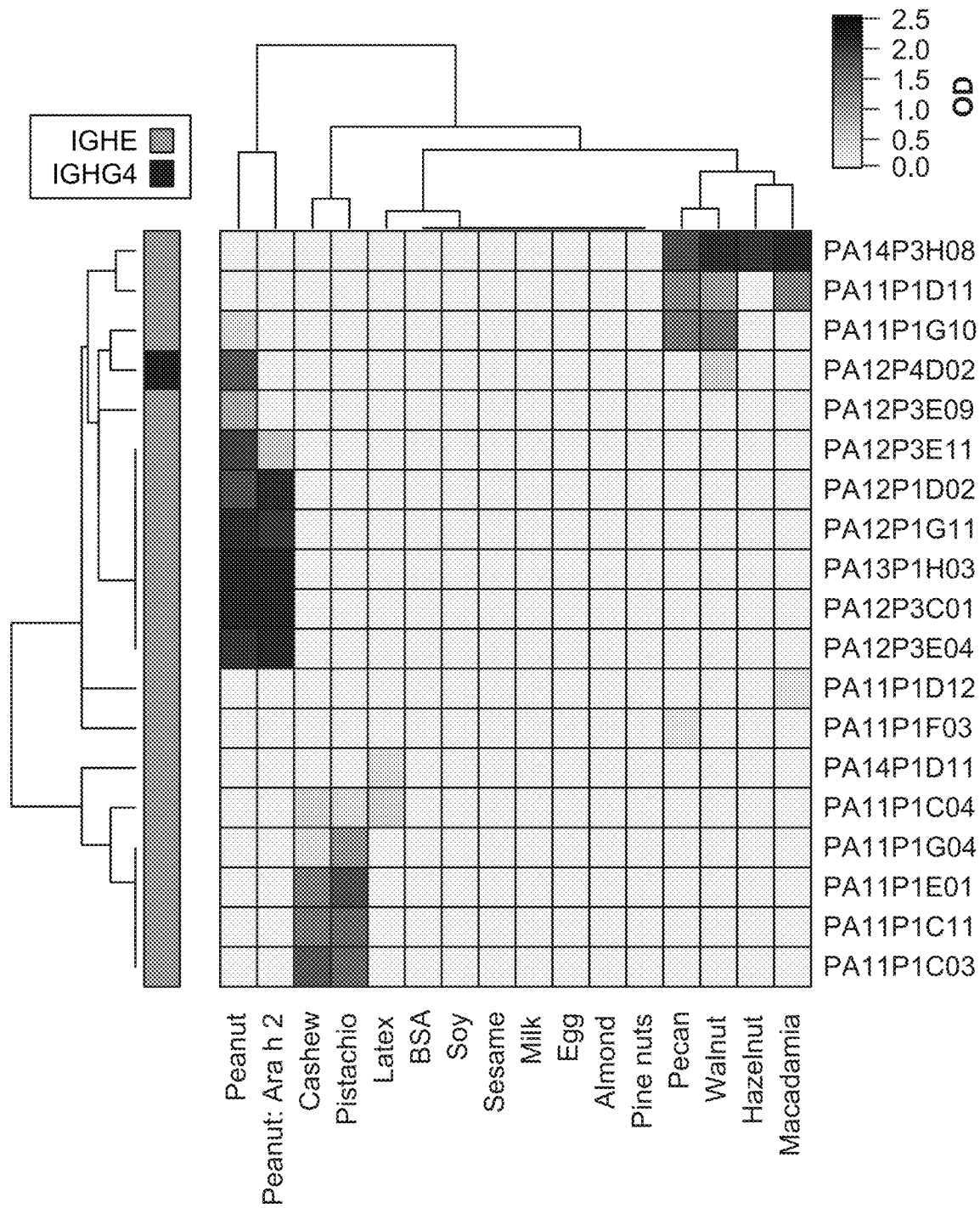
Figure 16:
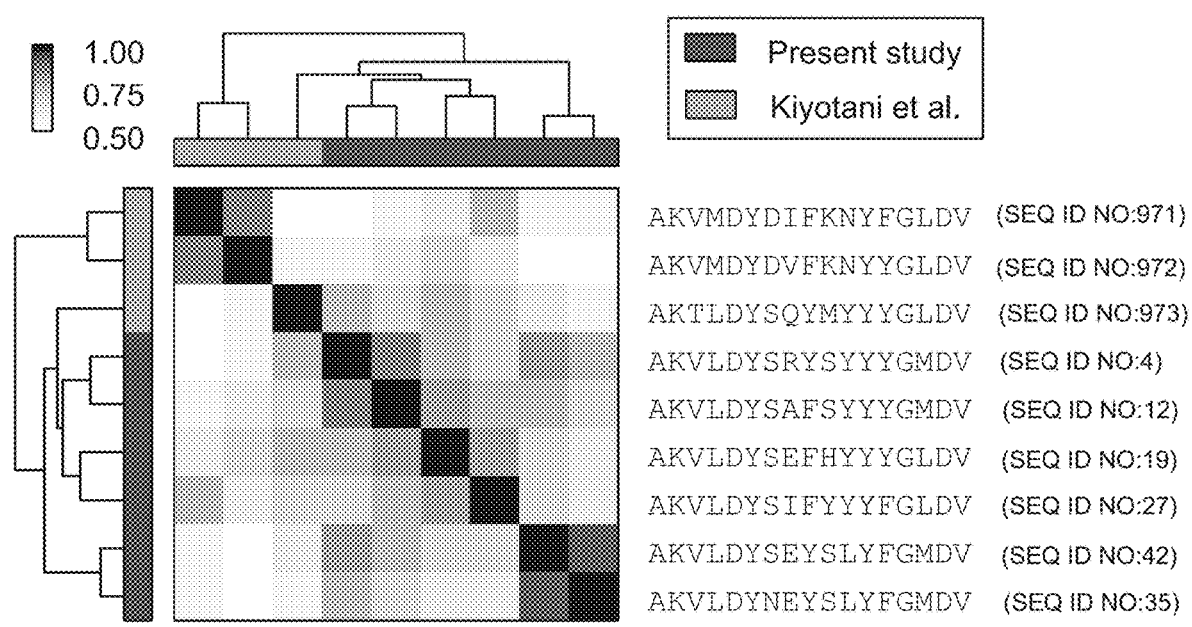
FIG. 16. Pairwise CDR3 sequence identity of the heavy chain CDR3 sequences from clones PA12P3F10, PA12P3D08, PA12P1C07, PA13P1E10, PA13P3G09, and PA13P1H08 (SEQ ID NOs: 19, 35, 42, 12, 27, 4) and three heavy chain CDR3 sequences derived from multiple patients in a separate peanut allergy immune repertoire sequencing study (62). Each sequence from this separate study has an identity of at least 70% with one or more sequences from the present study. All sequences share the IGHV3-30 and IGHJ6 gene segments and have CDR3s 17 amino acids in length.

| SEQ ID NO | Sequence | Description |
|---|---|---|
| 972 | AKVMDYDVFKNYYGLDV | FIG. 16 |
| 973 | AKTLDYSQYMYYYGLDV | FIG. 16 |
| 974 | QHYGRSPPYT | FIG. 12G |
| 975 | QHYGSSPPFT | FIG. 12G |
| 976 | QHYGSLPPFT | FIG. 12G |
| 977 | AAWDDTLVGV | FIG. 12G |
| 978 | AAWDDLVVGV | FIG. 12G |
| 979 | QSTDSSGDYVV | FIG. 12G |
| 980 | QSTDSSLRDVV | FIG. 12G |
| 981 | TSYAGRNIQV | FIG. 12G |
| 982 | SSYAGSNIAV | FIG. 12G |
| 983 | QSYDGSSPVI | FIG. 12G |
| 984 | QSYDTNIVV | FIG. 12G |
| 985 | QSYDSANVV | FIG. 12G |
| 986 | QSYDADNAV | FIG. 12G |
| 987 | SSYTRETALGGV | FIG. 12G |
| 988 | QQYYTTPRT | FIG. 12G |
| 989 | QQYYTTPYT | FIG. 12G |
| 990 | QQYLTTPYT | FIG. 12G |
| 991 | QQYDEWPPFT | FIG. 12G |
| 992 | QQYNHWPPYT | FIG. 12G |
| 993 | GSYKSGSTWV | FIG. 12G |
| 994 | SSYRSGSTWV | FIG. 12G |
| 995 | SSYTSGRTWV | FIG. 12G |
| 996 | SSYTTGRTWV | FIG. 12G |
| 997 | ASRYCTDSGCYLGSFDY | FIG. 12G |
| 998 | ASRYCTDDGCYLGSFDF | FIG. 12G |
| 999 | TRDHGYY | FIG. 12G |
| 1000 | ARDHGYY | FIG. 12G |
| 1001 | ARDPAAGTWWFDP | FIG. 12G |
| 1002 | ARPSAHYYDRGGYNDAFDM | FIG. 12G |
| 1003 | TTGYRTTTTYHGDDAFDI | FIG. 12G |
| 1004 | TTGYRTSTSYHGDDAFDI | FIG. 12G |
| 1005 | ARGPPAVQGYFYYMYV | FIG. 12G |
| 1006 | ARGPPGVHGYFYYTDV | FIG. 12G |
| 1007 | ARDVVRPGSGPRLGFDP | FIG. 12G |
| 1008 | ARDVVRPGRGPRLGFDP | FIG. 12G |

TABLE 1-continued

Sequence Listing

| SEQ ID NO | Sequence | Description |
|---|---|---|
| 1009 | AKEGGSSTSWYSLYHEYEMDV | FIG. 12G |
| 1010 | AHKAAEPGSRDRWFDS | FIG. 12G |
| 1011 | AGGYNNSSFYFDS | FIG. 12G |
| 1012 | AVGYNNSWFYFDY | FIG. 12G |
| 1013 | ARLGHLRGWFDS | FIG. 12G |
| 1014 | VLSQYEFGSSWFYYYRMDV | FIG. 12G |
| 1015 | VLSKYEFGSSWFYYYRMDV | FIG. 12G |
| 1016 | VLSKYEFHSSWFYYYRMDV | FIG. 12G |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A composition comprising a monoclonal antibody, or an antigen binding portion thereof comprising a heavy chain variable region, a light chain variable region, and an IgM, IgD, IgG, or IgA constant region,
wherein the heavy chain variable region comprises:
a heavy chain CDR1 comprising the amino acid sequence of SEQ ID NO:2;
a heavy chain CDR2 comprising the amino acid sequence of SEQ ID NO:3;
a heavy chain CDR3 comprising the amino acid sequence of SEQ ID NO:4; and
wherein the light chain variable region comprises:
a light chain CDR1 comprising the amino acid sequence of SEQ ID NO:6;
a light chain CDR2 comprising the amino acid sequence of SEQ ID NO:7; and
a light chain CDR3 comprising the amino acid sequence of SEQ ID NO:8.

2. The composition of claim 1, wherein the heavy chain variable region has a sequence with at least 90% sequence identity to SEQ ID NO:1 and the light chain variable region has a sequence with at least 90% sequence identity to SEQ ID NO:5.

3. The composition of claim 2, having a heavy chain variable region comprising SEQ ID NO:1 and a light chain variable region comprising SEQ ID NO:5.

4. The composition of claim 1, wherein the antigen-binding portion is a Fab, a F(ab')2, a Fv, a scFv, a bivalent scFv, or a diabody.

5. The composition of claim 3, wherein the monoclonal antibody or antigen binding portion thereof is a Fab or a F(ab')2.

6. The composition of claim 1, wherein the monoclonal antibody or antigen binding portion thereof, comprises an IgG constant region.

7. The composition of claim 1 that is a pharmaceutical composition comprising the monoclonal antibody or antigen binding portion thereof and a pharmaceutically acceptable, diluent, adjuvant, or carrier.

* * * * *

```
                       SEQUENCE LISTING

<160> NUMBER OF SEQ ID NOS: 1019

<210> SEQ ID NO 1
    <211> LENGTH: 124
    <212> TYPE: PRT
    <213> ORGANISM: Artificial Sequence
    <220> FEATURE:
    <223> OTHER INFORMATION: Description of Artificial Sequence: Synthetic
          polypeptide

<400> SEQUENCE: 1

Gln Val Gln Leu Val Asn Ser Gly Gly Val Val Gln Pro Gly Arg
    1               5                   10                  15

Ser Leu Arg Leu Ser Cys Val Ala Ser Gly Phe Thr Phe Ser Thr Phe
                    20                  25                  30

Gly Ile His Trp Val Arg Gln Ala Pro Gly Lys Gly Leu Glu Trp Val
                35                  40                  45

Ala Val Ile Ser Asn Asp Gly Glu Lys Ser Glu Ser Ala Asp Ser Val
            50                  55                  60

Lys Gly Arg Phe Thr Pro Ser Arg Asp Asn Ser Lys Asn Thr Val Tyr
    65                  70                  75                  80

Leu Gln Met Asn Asn Leu Arg Val Glu Asp Thr Ala Val Tyr Tyr Cys
                    85                  90                  95

Ala Lys Val Leu Asp Tyr Ser Arg Tyr Ser Tyr Tyr Tyr Gly Met Asp
                100                 105                 110

Val Trp Gly Gln Gly Thr Thr Val Ile Val Ser Ser
                115                 120

<210> SEQ ID NO 2
    <211> LENGTH: 8
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 2
```

```
Gly Phe Thr Phe Ser Thr Phe Gly
1               5
```

```
<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Ser Asn Asp Gly Glu Lys Ser
1               5
```

```
<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Lys Val Leu Asp Tyr Ser Arg Tyr Ser Tyr Tyr Tyr Gly Met Asp
1               5                   10                  15

Val
```

```
<210> SEQ ID NO 5
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Ile Val Leu Thr Gln Ser Pro Gly Thr Leu Ser Leu Ser Pro Gly
1               5                   10                  15

Gly Arg Gly Thr Leu Ser Cys Arg Thr Ser Gln Thr Ile Asn Asn Ala
                20                  25                  30

His Leu Ala Trp Tyr Gln His Lys Pro Gly Gln Ala Pro Arg Leu Leu
            35                  40                  45

Ile Tyr Gly Ser Ser Glu Arg Ala Thr Gly Val Pro Asp Arg Phe Ser
        50                  55                  60

Gly Ser Gly Ser Gly Ser Asp Phe Thr Leu Thr Ile Ser Ser Leu Glu
65                  70                  75                  80

Ala Glu Asp Phe Ala Val Tyr Tyr Cys Gln His Tyr Gly Arg Ser Pro
                85                  90                  95

Pro Tyr Thr Phe Gly Pro Gly Thr Lys Leu Asp Ile Lys
            100                 105
```

```
<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Thr Ile Asn Asn Ala His
1               5
```

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ser Ser
1

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln His Tyr Gly Arg Ser Pro Pro Tyr Thr
1               5                   10

<210> SEQ ID NO 9
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Asp Ser Gly Gly Val Val Gln Pro Gly Lys
1               5                   10                  15

Ser Leu Arg Leu Ser Cys Val Gly Ser Gly Phe Thr Phe Arg Thr Phe
                20                  25                  30

Gly Ile His Trp Val Arg Gln Ala Pro Gly Lys Gly Leu Glu Trp Val
            35                  40                  45

Ala Val Ile Ser Asn Asp Gly Asn Ser Ala Ser Ala Asp Ser Val
    50                  55                  60

Lys Gly Arg Phe Thr Thr Ser Arg Asp Asn Ser Lys Asn Thr Val Tyr
65                  70                  75                  80

Leu Gln Ile Asn Ser Leu Arg Pro Glu Asp Thr Ala Ile Tyr Tyr Cys
                85                  90                  95

Ala Lys Val Leu Asp Tyr Ser Ala Phe Ser Tyr Tyr Tyr Gly Met Asp
                100                 105                 110

Val Trp Gly Gln Gly Thr Thr Val Ile Val Ser Ser
        115                 120

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Phe Thr Phe Arg Thr Phe Gly
1               5

```
<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Ser Asn Asp Gly Gly Asn Ser
1               5

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Lys Val Leu Asp Tyr Ser Ala Phe Ser Tyr Tyr Tyr Gly Met Asp
1               5                   10                  15

Val

<210> SEQ ID NO 13
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Ile Val Leu Thr Gln Ser Pro Gly Thr Leu Ser Leu Ser Pro Gly
1               5                   10                  15

Glu Arg Gly Thr Leu Ser Cys Arg Thr Ser Gln Pro Ile Ser Arg Ala
            20                  25                  30

His Leu Ala Trp Tyr Gln His Lys Ala Gly Gln Ala Pro Arg Leu Leu
        35                  40                  45

Ile Tyr Gly Ser Thr Glu Arg Ala Ala Gly Ile Pro Glu Arg Phe Ser
    50                  55                  60

Gly Gly Gly Ser Gly Ser Asp Phe Thr Leu Thr Ile Ser Ser Leu Glu
65                  70                  75                  80

Ala Glu Asp Phe Ala Val Tyr Tyr Cys Gln His Tyr Gly Arg Ser Pro
                85                  90                  95

Pro Tyr Thr Phe Gly Gln Gly Thr Lys Val Glu Ile Lys
            100                 105

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Pro Ile Ser Arg Ala His
1               5

<210> SEQ ID NO 15
<211> LENGTH: 3
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 15

Gly Ser Thr
1

<210> SEQ ID NO 16
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Val Glu Ser Gly Gly Gly Val Val Gln Pro Gly Gly
1               5                   10                  15

Ser Leu Thr Leu Ser Cys Val Gly Ser Gly Phe Thr Phe Ser His Tyr
            20                  25                  30

Ala Ile His Trp Val Arg Gln Ala Pro Gly Lys Gly Leu Glu Trp Val
        35                  40                  45

Ala Val Ile Ser Asn Val Gly Thr Thr Arg Asp Tyr Ala Asp Ser Leu
    50                  55                  60

Lys Gly Arg Leu Thr Ile Ser Arg Glu Asn Ser Gln Ser Thr Val Phe
65                  70                  75                  80

Leu Gln Met Asn Ser Leu Arg Ala Asp Asp Thr Ala Ile Tyr Tyr Cys
                85                  90                  95

Ala Lys Val Leu Asp Tyr Ser Glu Phe His Tyr Tyr Tyr Gly Leu Asp
            100                 105                 110

Val Trp Gly Gln Gly Thr Ala Val Ala Val Ser Ser
        115                 120

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Phe Thr Phe Ser His Tyr Ala
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Ser Asn Val Gly Thr Thr Arg
1               5

<210> SEQ ID NO 19
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 19

Ala Lys Val Leu Asp Tyr Ser Glu Phe His Tyr Tyr Tyr Gly Leu Asp
1               5                   10                  15
Val

<210> SEQ ID NO 20
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Ile Val Leu Thr Gln Ser Pro Gly Thr Leu Ser Leu Ser Pro Gly
1               5                   10                  15

Gln Arg Val Thr Leu Ser Cys Arg Val Ser Gln Ala Ile Pro Thr Met
            20                  25                  30

Tyr Val Ala Trp Tyr Gln Gln Arg Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Gly Gly Ser Gly Thr Asp Phe Thr Leu Thr Ile Asn Arg Leu Glu
65                  70                  75                  80

Pro Glu Asp Ile Ala Val Tyr Tyr Cys Gln His Tyr Ser Asn Ser Pro
                85                  90                  95

Pro Tyr Thr Phe Gly Pro Gly Thr Lys Leu Glu Ile Lys
            100                 105

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Ala Ile Pro Thr Met Tyr
1               5

<210> SEQ ID NO 22
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Thr Ser
1

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 23

Gln His Tyr Ser Asn Ser Pro Pro Tyr Thr
1               5                   10

<210> SEQ ID NO 24
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Glu Gln Leu Val Glu Ser Gly Gly Gly Val Val His Pro Gly Gly
1               5                   10                  15

Ser Leu Arg Leu Ser Cys Val Ala Ser Ala Phe Thr Phe Asn Arg Phe
            20                  25                  30

Gly Met His Trp Val Arg Gln Ala Pro Gly Lys Gly Leu Glu Trp Val
        35                  40                  45

Ala Val Ile Ser Asn Asp Gly Arg Ser Gln Asp Tyr Ala Asp Ser Val
    50                  55                  60

Lys Gly Arg Phe Ile Ile Ser Arg Asp Asn Ser Lys Asn Thr Leu Tyr
65                  70                  75                  80

Leu Gln Leu Asn Ser Leu Arg Phe Glu Asp Thr Ala Val Tyr Tyr Cys
                85                  90                  95

Ala Lys Val Leu Asp Tyr Ser Ile Phe Tyr Tyr Phe Gly Leu Asp
            100                 105                 110

Val Trp Gly Gln Gly Thr Thr Val Thr Val Ser Ser
        115                 120

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Phe Thr Phe Asn Arg Phe Gly
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Ser Asn Asp Gly Arg Ser Gln
1               5

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

-continued

```
Ala Lys Val Leu Asp Tyr Ser Ile Phe Tyr Tyr Phe Gly Leu Asp
1               5                   10                  15

Val

<210> SEQ ID NO 28
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Val Leu Thr Gln Ser Pro Gly Ser Leu Ser Leu Ser Pro Gly
1               5                   10                  15

Glu Arg Ala Thr Leu Ser Cys Arg Ala Gly Gln Ser Leu Ser Ser Lys
            20                  25                  30

Phe Leu Ala Trp Tyr Gln His Lys Pro Gly Gln Ala Pro Arg Leu Leu
        35                  40                  45

Ile Tyr Gly Ala Ser Thr Arg Ala Thr Gly Val Pro Asp Arg Phe Ser
    50                  55                  60

Gly Ser Gly Ser Gly Thr Asp Phe Ser Leu Ile Ile Ser Arg Val Glu
65                  70                  75                  80

Pro Glu Asp Phe Ala Val Tyr Tyr Cys Gln His Tyr Gly Asp Ser Pro
                85                  90                  95

Pro Tyr Thr Phe Gly Gln Gly Thr Lys Val Glu Met Lys
            100                 105

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Ser Leu Ser Ser Lys Phe
1               5

<210> SEQ ID NO 30
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Ala Ser
1

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln His Tyr Gly Asp Ser Pro Pro Tyr Thr
1               5                   10
```

```
<210> SEQ ID NO 32
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Val Glu Ser Gly Gly Gly Val Val Gln Pro Gly Lys
1               5                   10                  15

Ser Leu Arg Leu Ser Cys Ala Ala Ser Ala Phe Thr Phe Arg Arg Phe
            20                  25                  30

Ala Met His Trp Val Arg Gln Ala Pro Gly Lys Gly Leu Glu Trp Val
        35                  40                  45

Ala Val Ile Ser Asp Asn Gly Leu Arg Glu Asp Tyr Glu Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Gly Leu Arg Ala Glu Asp Thr Ala Val Tyr Tyr Cys
                85                  90                  95

Ala Lys Val Leu Asp Tyr Asn Glu Tyr Ser Leu Tyr Phe Gly Met Asp
            100                 105                 110

Val Trp Gly Gln Gly Thr Thr Val Thr Val Ser Ser
        115                 120

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Phe Thr Phe Arg Arg Phe Ala
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ile Ser Asp Asn Gly Leu Arg Glu
1               5

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Lys Val Leu Asp Tyr Asn Glu Tyr Ser Leu Tyr Phe Gly Met Asp
1               5                   10                  15

Val
```

```
<210> SEQ ID NO 36
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Val Leu Thr Gln Ser Pro Ala Thr Leu Ser Leu Ser Pro Gly
1               5                   10                  15

Glu Arg Ala Thr Leu Ser Cys Arg Thr Ser Gln Ala Ile Ser Asn Asn
            20                  25                  30

Phe Leu Ala Trp Tyr Gln Gln Arg Pro Gly Gln Pro Pro Arg Leu Leu
        35                  40                  45

Ile Tyr Ala Ser Ser Arg Arg Ala Thr Asp Thr Pro Asp Arg Phe Thr
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Phe Cys Gln Tyr Tyr Ser Asp Ser Pro
                85                  90                  95

Pro Tyr Thr Phe Gly Pro Gly Thr Lys Leu Glu Ile Lys
            100                 105

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Ala Ile Ser Asn Asn Phe
1               5

<210> SEQ ID NO 38
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Ser Ser
1

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Tyr Tyr Ser Asp Ser Pro Pro Tyr Thr
1               5                   10

<210> SEQ ID NO 40
<211> LENGTH: 124
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 40

Gln Val Gln Leu Glu Glu Ser Gly Gly Gly Val Val Gln Pro Gly Lys
1               5                   10                  15

Ser Leu Arg Leu Ser Cys Val Ala Ser Ala Phe Thr Phe Lys Arg Phe
            20                  25                  30

Ala Met His Trp Val Arg Gln Ala Pro Gly Lys Gly Leu Glu Trp Val
        35                  40                  45

Ala Val Ile Ser Asp Asn Gly Leu Arg Glu Asp Tyr Glu Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Pro Glu Asp Thr Ala Ile Tyr Tyr Cys
                85                  90                  95

Ala Lys Val Leu Asp Tyr Ser Glu Tyr Ser Leu Tyr Phe Gly Met Asp
            100                 105                 110

Val Trp Gly Gln Gly Thr Thr Val Leu Val Ser Ser
        115                 120

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Phe Thr Phe Lys Arg Phe Ala
1               5

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Lys Val Leu Asp Tyr Ser Glu Tyr Ser Leu Tyr Phe Gly Met Asp
1               5                   10                  15

Val

<210> SEQ ID NO 43
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Ile Val Leu Thr Gln Ser Pro Ala Ile Leu Ser Leu Ser Pro Gly
1               5                   10                  15

Asp Arg Ala Thr Leu Ser Cys Arg Thr Ser Gln Thr Val Asn Ser Asn
            20                  25                  30

Phe Leu Ala Trp Tyr Gln Gln Lys Pro Gly Gln Ala Pro Arg Leu Leu
        35                  40                  45
```

-continued

```
Ile Tyr Gly Ala Ser Arg Arg Ala Ile Asp Ile Pro Asp Arg Phe Thr
 50                  55                  60
Gly Ser Gly Ser Gly Thr Glu Phe Thr Leu Thr Ile Ala Arg Leu Glu
 65                  70                  75                  80
Pro Glu Asp Phe Ala Val Tyr Ser Cys Gln His Tyr Ser Asp Ser Pro
                 85                  90                  95
Pro Tyr Thr Phe Gly Gln Gly Thr Lys Leu Glu Ile Lys
                100                 105
```

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Gln Thr Val Asn Ser Asn Phe
 1               5
```

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Gln His Tyr Ser Asp Ser Pro Pro Tyr Thr
 1               5                  10
```

<210> SEQ ID NO 46
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Gln Val His Leu Val Glu Ser Gly Gly Val Val Gln Pro Gly Arg
 1               5                  10                  15
Ser Leu Gly Leu Ser Cys Ala Ala Ser Gly Phe Thr Phe Asn Tyr Tyr
                20                  25                  30
Ala Ile His Trp Val Arg Gln Ala Pro Gly Lys Gly Leu Glu Trp Val
             35                  40                  45
Ala Val Val Ser Phe Asp Gly Asn Ile Ile Tyr Tyr Ala Asp Ser Val
 50                  55                  60
Lys Gly Arg Phe Asn Ile Ser Arg Asp Asn Ser Lys Asn Thr Val Asn
 65                  70                  75                  80
Leu Gln Met Asn Ser Leu Arg Ala Asp Thr Ala Val Tyr Tyr Cys
                 85                  90                  95
Val Arg Asp Gly Glu Tyr Cys Ser Gly Gly Asn Cys Tyr Trp Gly Asp
                100                 105                 110
Phe Asp Tyr Trp Gly Gln Gly Thr Leu Val Thr Val Ser Pro
            115                 120                 125
```

<210> SEQ ID NO 47
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Phe Thr Phe Asn Tyr Tyr Ala
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Ser Phe Asp Gly Asn Ile Ile
1               5

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Arg Asp Gly Glu Tyr Cys Ser Gly Gly Asn Cys Tyr Trp Gly Asp
1               5                   10                  15

Phe Asp Tyr

<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Glu
                20                  25                  30

Tyr Leu Thr Trp Phe Gln Gln Lys Pro Gly Gln Ala Pro Arg Leu Leu
            35                  40                  45

Ile Tyr Gly Ala Phe Asn Arg Ala Thr Gly Ile Pro Asp Arg Phe Ser
        50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ala Asn Trp Trp
                85                  90                  95

Thr Phe Gly Gln Gly Thr Lys Val Glu Ile Lys
            100                 105

<210> SEQ ID NO 51
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 51

Gln Ser Ile Ser Ser Glu Tyr
1               5

<210> SEQ ID NO 52
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Ala Phe
1

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Gln Tyr Ala Asn Trp Trp Thr
1               5

<210> SEQ ID NO 54
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val His Leu Val Glu Ser Gly Gly Val Val Gln Pro Gly Arg
1               5                   10                  15

Ser Leu Gly Leu Ser Cys Val Ala Ser Gly Phe Thr Phe Asn Tyr Tyr
                20                  25                  30

Ala Ile His Trp Val Arg Gln Ala Pro Gly Lys Gly Leu Glu Trp Val
            35                  40                  45

Ala Val Val Ser Phe Asp Gly Asn Ile Ile Tyr Tyr Ala Asp Ser Val
        50                  55                  60

Lys Gly Arg Phe Asn Ile Ser Arg Asp Asn Ser Lys Asn Thr Val Asn
65                  70                  75                  80

Leu Gln Met Asn Ser Leu Arg Pro Asp Asp Thr Ala Val Tyr Tyr Cys
                85                  90                  95

Val Arg Asp Gly Glu Tyr Cys Ser Gly Gly Asn Cys Tyr Trp Gly Asp
                100                 105                 110

Phe Asp His Trp Gly Gln Gly Ser Leu Val Thr Val Ser Pro
            115                 120                 125

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 55

Val Arg Asp Gly Glu Tyr Cys Ser Gly Asn Cys Tyr Trp Gly Asp
1               5                   10                  15

Phe Asp His

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Glu
            20                  25                  30

Tyr Leu Thr Trp Phe Gln Gln Lys Pro Gly Gln Ala Pro Arg Leu Leu
        35                  40                  45

Ile Tyr Gly Ala Phe Asn Arg Ala Thr Gly Ile Pro Asp Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Ala Asn Trp Trp
                85                  90                  95

Thr Phe Gly Gln Gly Thr Lys Val Glu Ile Lys
            100                 105

<210> SEQ ID NO 57
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Asp Tyr Ser Asn Tyr Tyr Tyr Tyr Gly Met Asp
            100                 105                 110

Val Trp Gly Gln Gly Thr Thr Val Thr Val Ser Ser
        115                 120

<210> SEQ ID NO 58
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 58

Gly Phe Thr Phe Ser Ser Tyr Gly
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ile Ser Tyr Asp Gly Ser Asn Lys
1               5

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ala Lys Val Leu Asp Tyr Ser Asn Tyr Tyr Tyr Tyr Gly Met Asp
1               5                   10                  15

Val

<210> SEQ ID NO 61
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Tyr Thr Phe Gly Gln Gly Thr Lys Leu Glu Ile Lys
            100                 105

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 62

Gln Ser Val Ser Ser Ser Tyr
1               5

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gln Tyr Gly Ser Ser Pro Pro Tyr Thr
1               5                   10

<210> SEQ ID NO 64
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Val Asn Ser Gly Gly Val Val Gln Pro Gly Arg
1               5                   10                  15

Ser Leu Arg Leu Ser Cys Val Ala Ser Gly Phe Thr Phe Ser Ser Tyr
                20                  25                  30

Gly Ile His Trp Val Arg Gln Ala Pro Gly Lys Gly Leu Glu Trp Val
            35                  40                  45

Ala Val Ile Ser Asn Asp Gly Glu Lys Ser Glu Ser Ala Asp Ser Val
        50                  55                  60

Lys Gly Arg Phe Thr Pro Ser Arg Asp Asn Ser Lys Asn Thr Val Tyr
65                  70                  75                  80

Leu Gln Met Asn Asn Leu Arg Val Glu Asp Thr Ala Val Tyr Tyr Cys
                85                  90                  95

Ala Lys Val Leu Asp Tyr Ser Arg Tyr Ser Tyr Tyr Gly Met Asp
                100                 105                 110

Val Trp Gly Gln Gly Thr Thr Val Ile Val Ser Ser
            115                 120

<210> SEQ ID NO 65
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Asn Ser Gly Gly Val Val Gln Pro Gly Arg
1               5                   10                  15

Ser Leu Arg Leu Ser Cys Val Ala Ser Gly Phe Thr Phe Ser Thr Phe
                20                  25                  30

Gly Ile His Trp Val Arg Gln Ala Pro Gly Lys Gly Leu Glu Trp Val
            35                  40                  45

Ala Val Ile Ser Tyr Asp Gly Ser Asn Lys Glu Ser Ala Asp Ser Val
        50                  55                  60

```
Lys Gly Arg Phe Thr Pro Ser Arg Asp Asn Ser Lys Asn Thr Val Tyr
 65                  70                  75                  80

Leu Gln Met Asn Asn Leu Arg Val Glu Asp Thr Ala Val Tyr Tyr Cys
                 85                  90                  95

Ala Lys Val Leu Asp Tyr Ser Arg Tyr Ser Tyr Tyr Tyr Gly Met Asp
                100                 105                 110

Val Trp Gly Gln Gly Thr Thr Val Ile Val Ser Ser
            115                 120

<210> SEQ ID NO 66
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Val Asn Ser Gly Gly Val Val Gln Pro Gly Arg
 1               5                  10                  15

Ser Leu Arg Leu Ser Cys Val Ala Ser Gly Phe Thr Phe Ser Thr Phe
                 20                  25                  30

Gly Ile His Trp Val Arg Gln Ala Pro Gly Lys Gly Leu Glu Trp Val
             35                  40                  45

Ala Val Ile Ser Asn Asp Gly Glu Lys Ser Glu Ser Ala Asp Ser Val
         50                  55                  60

Lys Gly Arg Phe Thr Pro Ser Arg Asp Asn Ser Lys Asn Thr Val Tyr
 65                  70                  75                  80

Leu Gln Met Asn Asn Leu Arg Val Glu Asp Thr Ala Val Tyr Tyr Cys
                 85                  90                  95

Ala Lys Val Leu Asp Tyr Ser Asn Tyr Tyr Tyr Tyr Gly Met Asp
                100                 105                 110

Val Trp Gly Gln Gly Thr Thr Val Ile Val Ser Ser
            115                 120

<210> SEQ ID NO 67
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Thr Phe
                 20                  25                  30

Gly Met His Trp Val Arg Gln Ala Pro Gly Lys Gly Leu Glu Trp Val
             35                  40                  45

Ala Val Ile Ser Asn Asp Gly Glu Lys Ser Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Leu Asp Tyr Ser Arg Tyr Ser Tyr Tyr Tyr Gly Met Asp
                100                 105                 110
```

```
Val Trp Gly Gln Gly Thr Thr Val Thr Val Ser Ser
        115                 120
```

<210> SEQ ID NO 68
<211> LENGTH: 1284
<212> TYPE: DNA
<213> ORGANISM: Unknown
<220> FEATURE:
<223> OTHER INFORMATION: Description of Unknown:
      Nucleotide sequence for IgE heavy chain constant region

<400> SEQUENCE: 68

```
gcctccacac agagcccatc cgtcttcccc ttgacccgct gctgcaaaaa cattccctcc      60
aatgccacct ccgtgactct gggctgcctg gccacgggct acttcccgga gccggtgatg     120
gtgacctggg acacaggctc cctcaacggg acaactatga ccttaccagc caccaccctc     180
acgctctctg gtcactatgc caccatcagc ttgctgaccg tctcgggtgc gtgggccaag     240
cagatgttca cctgccgtgt ggcacacact ccatcgtcca cagactgggt cgacaacaaa     300
accttcagcg tctgctccag ggacttcacc ccgcccaccg tgaagatctt acagtcgtcc     360
tgcgacggcg gcgggcactt cccccccgacc atccagctcc tgtgcctcgt ctctgggtac     420
accccaggga ctatcaacat cacctggctg gaggacgggc aggtcatgga cgtggacttg     480
tccaccgcct ctaccacgca ggagggtgag ctggcctcca cacaaagcga gctcaccctc     540
agccagaagc actggctgtc agaccgcacc tacacctgcc aggtcaccta tcaaggtcac     600
acctttgagg acagcaccaa gaagtgtgca gattccaacc cgagaggggt gagcgcctac     660
ctaagccggc ccagcccgtt cgacctgttc atccgcaagt cgcccacgat cacctgtctg     720
gtggtggacc tggcacccag caaggggacc gtgaacctga cctggtcccg ggccagtggg     780
aagcctgtga accactccac cagaaaggag gagaagcagc gcaatggcac gttaaccgtc     840
acgtccaccc tgccggtggg cacccgagac tggatcgagg gggagaccta ccagtgcagg     900
gtgacccacc cccacctgcc cagggccctc atgcggtcca cgaccaagac cagcggcccg     960
cgtgctgccc cggaagtcta tgcgtttgcg acgccggagt ggccggggag ccgggacaag    1020
cgcacccteg cctgcctgat ccagaacttc atgcctgagg acatctcggt gcagtggctg    1080
cacaacgagg tgcagctccc ggacgcccgg cacagcacga cgcagccccg caagaccaag    1140
ggctccggct tcttcgtctt cagccgcctg gaggtgacca gggccgaatg ggagcagaaa    1200
gatgagttca tctgccgtgc agtccatgag gcagcgagcc cctcacagac cgtccagcga    1260
gcggtgtctg taaatcccgg taaa                                           1284
```

<210> SEQ ID NO 69
<211> LENGTH: 428
<212> TYPE: PRT
<213> ORGANISM: Unknown
<220> FEATURE:
<223> OTHER INFORMATION: Description of Unknown:
      Amino acid sequence for IgE heavy chain constant region

<400> SEQUENCE: 69

```
Ala Ser Thr Gln Ser Pro Ser Val Phe Pro Leu Thr Arg Cys Cys Lys
1               5                   10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
```

```
            50                  55                  60
His Tyr Ala Thr Ile Ser Leu Leu Thr Val Ser Gly Ala Trp Ala Lys
 65                  70                  75                  80

Gln Met Phe Thr Cys Arg Val Ala His Thr Pro Ser Ser Thr Asp Trp
                 85                  90                  95

Val Asp Asn Lys Thr Phe Ser Val Cys Ser Arg Asp Phe Thr Pro Pro
            100                 105                 110

Thr Val Lys Ile Leu Gln Ser Ser Cys Asp Gly Gly His Phe Pro
            115                 120                 125

Pro Thr Ile Gln Leu Leu Cys Leu Val Ser Gly Tyr Thr Pro Gly Thr
            130                 135                 140

Ile Asn Ile Thr Trp Leu Glu Asp Gly Gln Val Met Asp Val Asp Leu
145                 150                 155                 160

Ser Thr Ala Ser Thr Thr Gln Glu Gly Glu Leu Ala Ser Thr Gln Ser
                165                 170                 175

Glu Leu Thr Leu Ser Gln Lys His Trp Leu Ser Asp Arg Thr Tyr Thr
                180                 185                 190

Cys Gln Val Thr Tyr Gln Gly His Thr Phe Glu Asp Ser Thr Lys Lys
                195                 200                 205

Cys Ala Asp Ser Asn Pro Arg Gly Val Ser Ala Tyr Leu Ser Arg Pro
210                 215                 220

Ser Pro Phe Asp Leu Phe Ile Arg Lys Ser Pro Thr Ile Thr Cys Leu
225                 230                 235                 240

Val Val Asp Leu Ala Pro Ser Lys Gly Thr Val Asn Leu Thr Trp Ser
                245                 250                 255

Arg Ala Ser Gly Lys Pro Val Asn His Ser Thr Arg Lys Glu Glu Lys
                260                 265                 270

Gln Arg Asn Gly Thr Leu Thr Val Thr Ser Thr Leu Pro Val Gly Thr
                275                 280                 285

Arg Asp Trp Ile Glu Gly Glu Thr Tyr Gln Cys Arg Val Thr His Pro
                290                 295                 300

His Leu Pro Arg Ala Leu Met Arg Ser Thr Thr Lys Thr Ser Gly Pro
305                 310                 315                 320

Arg Ala Ala Pro Glu Val Tyr Ala Phe Ala Thr Pro Glu Trp Pro Gly
                325                 330                 335

Ser Arg Asp Lys Arg Thr Leu Ala Cys Leu Ile Gln Asn Phe Met Pro
                340                 345                 350

Glu Asp Ile Ser Val Gln Trp Leu His Asn Glu Val Gln Leu Pro Asp
                355                 360                 365

Ala Arg His Ser Thr Thr Gln Pro Arg Lys Thr Lys Gly Ser Gly Phe
                370                 375                 380

Phe Val Phe Ser Arg Leu Glu Val Thr Arg Ala Glu Trp Glu Gln Lys
385                 390                 395                 400

Asp Glu Phe Ile Cys Arg Ala Val His Glu Ala Ala Ser Pro Ser Gln
                405                 410                 415

Thr Val Gln Arg Ala Val Ser Val Asn Pro Gly Lys
                420                 425

<210> SEQ ID NO 70
<211> LENGTH: 981
<212> TYPE: DNA
<213> ORGANISM: Unknown
<220> FEATURE:
<223> OTHER INFORMATION: Description of Unknown:
      Nucleotide sequence for IgG4 heavy chain constant region
```

<400> SEQUENCE: 70

```
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc atcatgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtggaca agagcaggtg gcaggagggg     900
aatgtcttct catgctccgt gatgcatgag gctctgcaca accactacac acagaagagc     960
ctctccctgt ctctgggtaa a                                                981
```

<210> SEQ ID NO 71
<211> LENGTH: 327
<212> TYPE: PRT
<213> ORGANISM: Unknown
<220> FEATURE:
<223> OTHER INFORMATION: Description of Unknown:
      Amino acid sequence for IgG4 heavy chain constant region

<400> SEQUENCE: 71

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
```

```
                    165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 72
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asp Thr Tyr
            20                  25                  30

Gly Met His Trp Val Arg Gln Ala Pro Gly Lys Gly Pro Glu Trp Val
        35                  40                  45

Ala Val Ile Trp Tyr Asp Gly Thr Arg Glu Asp Tyr Ala Asp Ser Val
    50                  55                  60

Lys Gly Arg Phe Thr Val Ser Arg Asp Asn Ser Lys Ser Thr Leu Phe
65                  70                  75                  80

Leu Gln Met Asn Ser Leu Arg Ala Asp Thr Ala Val Tyr Tyr Cys
                85                  90                  95

Ala Lys Glu His Asn Thr Tyr Phe Ser Asp His Ile Gly Arg Val Gly
            100                 105                 110

Gly Met Asp Val Trp Gly Gln Gly Thr Thr Val Ile Val Ser Ser
        115                 120                 125

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Phe Thr Phe Asp Thr Tyr Gly
```

```
<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Trp Tyr Asp Gly Thr Arg Glu
1               5

<210> SEQ ID NO 75
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Lys Glu His Asn Thr Tyr Phe Ser Asp His Ile Gly Arg Val Gly
1               5                   10                  15

Gly Met Asp Val
            20

<210> SEQ ID NO 76
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu Gln Thr Pro Pro Trp Thr Phe Gly Gln Gly Thr Lys Val Glu Ile
            100                 105                 110

Lys

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Ser Leu Leu His Ser Asn Gly Tyr Asn Tyr
```

<210> SEQ ID NO 78
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Gly Ser
1

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Met Gln Val Leu Gln Thr Pro Pro Trp Thr
1               5                   10

<210> SEQ ID NO 80
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Val Glu Ser Gly Gly Gly Val Val Gln Pro Gly Arg
1               5                   10                  15

Ser Leu Arg Leu Ser Cys Ala Gly Ser Gly Phe Thr Phe Asn Ala Tyr
            20                  25                  30

Gly Leu His Trp Val Arg Gln Ala Pro Gly Lys Gly Leu Glu Trp Val
        35                  40                  45

Ala Gly Ile Tyr Tyr Asp Gly Ser Asn Lys Tyr Tyr Ala Asp Ser Val
    50                  55                  60

Lys Gly Arg Phe Ala Ile Ser Arg Asp Asn Ser Gln Asn Thr Leu Tyr
65                  70                  75                  80

Leu Glu Met Asn Ser Leu Arg Val Glu Asp Thr Ala Val Tyr Tyr Cys
                85                  90                  95

Ala Lys Ala Gly Pro Ile Ala Ser Ile Gly Thr Arg His Thr Phe Asp
            100                 105                 110

His Trp Gly Gln Gly Thr Leu Val Thr Val Ser Ser
        115                 120

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Phe Thr Phe Asn Ala Tyr Gly
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ile Tyr Tyr Asp Gly Ser Asn Lys
1               5

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Lys Ala Gly Pro Ile Ala Ser Ile Gly Thr Arg His Thr Phe Asp
1               5                  10                  15

His

<210> SEQ ID NO 84
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Val Met Thr Gln Ser Pro Asp Ser Leu Ala Val Ser Leu Gly
1               5                  10                  15

Glu Arg Ala Thr Ile Asn Cys Lys Ser Ser Gln Ser Leu Leu Leu Asn
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Gly Arg Phe Ser Gly Asn Gly Ser Val Thr Asp Phe Thr Leu Thr
65                  70                  75                  80

Ile Ser Gly Leu Gln Ala Glu Asp Val Ala Val Tyr Tyr Cys His Gln
                85                  90                  95

Tyr Tyr Thr Thr Ser Tyr Thr Phe Gly Gln Gly Thr Lys Leu Glu Ile
            100                 105                 110

Lys

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Ser Leu Leu Leu Asn Ser Asn Asn Lys Asn Tyr
1               5                  10

```
<210> SEQ ID NO 86
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Trp Ala Ser
1

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

His Gln Tyr Tyr Thr Thr Ser Tyr Thr
1               5

<210> SEQ ID NO 88
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Gln Ser Gly Ala Glu Val Lys Lys Pro Gly Ala
1               5                   10                  15

Ser Val Lys Ile Ser Cys Lys Ala Val Gly Tyr Thr Phe Thr Ser Tyr
            20                  25                  30

Tyr Leu His Trp Val Arg Gln Ala Pro Gly Gln Gly Leu Glu Trp Val
        35                  40                  45

Gly Ile Ile Asp Pro Ser Arg Gly His Arg Asn Tyr Ala Gln Gly Phe
    50                  55                  60

Gln Gly Arg Val Thr Met Thr Ser Asp Thr Ser Thr Ser Thr Val Tyr
65                  70                  75                  80

Met Asp Leu Gly Ser Leu Arg Ser Glu Asp Thr Ala Val Tyr Tyr Cys
                85                  90                  95

Ala Arg Ala Pro Ala Arg Asp His Phe Asp Asn Trp Gly Gln Gly Thr
            100                 105                 110

Pro Val Thr Val Ser Pro
        115

<210> SEQ ID NO 89
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Tyr Thr Phe Thr Ser Tyr Tyr
1               5

<210> SEQ ID NO 90
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ile Asp Pro Ser Arg Gly His Arg
1               5

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Arg Ala Pro Ala Arg Asp His Phe Asp Asn
1               5                   10

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Asp Ile Gln Met Thr Gln Ser Pro Ser Ser Leu Ala Ala Ser Val Gly
1               5                   10                  15

Asp Arg Val Thr Ile Asn Cys Gln Ala Ser Gln Asp Ile Arg Asn Cys
            20                  25                  30

Leu Asn Trp Tyr Gln Gln Pro Gly Lys Ala Pro Lys Leu Leu Ile
        35                  40                  45

Tyr Asp Ala Ser Ile Leu Glu Thr Gly Val Pro Ser Arg Phe Ser Gly
 50                 55                  60

Ser Gly Ser Gly Thr Asp Phe Thr Phe Ser Ile Ser Ser Leu Gln Pro
65                  70                  75                  80

Glu Asp Ile Ala Thr Tyr Tyr Cys Gln Gln Cys Glu Asp Leu Pro Leu
                85                  90                  95

Thr Phe Gly Pro Gly Ser Lys Val Asp Ile Lys
            100                 105

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Asp Ile Arg Asn Cys
1               5

<210> SEQ ID NO 94
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 94

Asp Ala Ser
1

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Gln Cys Glu Asp Leu Pro Leu Thr
1               5

<210> SEQ ID NO 96
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Val Gln Leu Val Gln Ser Gly Ala Glu Val Lys Gln Pro Gly Ser
1               5                   10                  15

Ser Val Lys Val Ser Cys Lys Ala Ser Gly Gly Thr Phe Arg Asn Ser
            20                  25                  30

Ala Leu Ser Trp Val Arg Gln Ala Pro Gly Gln Gly Leu Glu Trp Met
        35                  40                  45

Gly Gly Ile Ile Pro Ile Phe Asp Thr Thr Asn Tyr Ala Gln Glu Phe
    50                  55                  60

Gln Gly Arg Val Thr Ile Thr Ala Asp Lys Ser Thr Thr Thr Ala Tyr
65                  70                  75                  80

Met Glu Leu Ser Ser Leu Lys Ser Glu Asp Thr Ala Val Tyr Tyr Cys
                85                  90                  95

Ala Arg Gly Glu Gly Leu Pro Trp Leu Thr Tyr His Tyr Tyr Gly Met
            100                 105                 110

Asp Val Trp Gly Gln Gly Thr Thr Val Thr Val Ser Ser
        115                 120                 125

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Thr Phe Arg Asn Ser Ala
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

```
Ile Ile Pro Ile Phe Asp Thr Thr
1               5

<210> SEQ ID NO 99
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ala Arg Gly Glu Gly Leu Pro Trp Leu Thr Tyr His Tyr Tyr Gly Met
1               5                   10                  15

Asp Val

<210> SEQ ID NO 100
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Ile Gly Thr
                20                  25                  30

Asp Arg Ile Tyr Trp Phe Gln Gln Lys Pro Gly Ser Pro Pro Gln Tyr
            35                  40                  45

Leu Leu Thr Tyr Lys Ser Asp Ser Asp Glu Gln Arg Gly Ser Gly Val
        50                  55                  60

Pro Ser Arg Phe Ser Gly Ser Lys Asp Val Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Trp Val Phe Gly Gly Gly Thr Lys Leu
            100                 105                 110

Thr Val Leu
        115

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Gly Ile Asn Ile Gly Thr Asp Arg
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102
```

```
Tyr Lys Ser Asp Ser Asp Glu
1               5
```

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

```
Met Ile Trp His Ser Ser Ala Trp Val
1               5
```

<210> SEQ ID NO 104
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

His Trp Ser Trp Ile Arg Gln Pro Pro Gly Lys Gly Leu Gln Trp Ile
        35                  40                  45

Gly Glu Ile Ser His Ser Gly Asn Ala Lys Tyr Asn Pro Ser Leu Lys
    50                  55                  60

Ser Arg Val Ser Ile Ser Val His Met Ser Lys Asn Glu Phe Tyr Leu
65                  70                  75                  80

Asn Leu Thr Ser Val Thr Ala Ala Asp Thr Ala Val Tyr Tyr Cys Ala
                85                  90                  95

Arg Gly Tyr Cys Ser Gly Gly Ser Cys Tyr Tyr Lys Phe Trp Gly Gln
            100                 105                 110

Gly Thr Leu Val Thr Val Ser Ser
        115                 120
```

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

```
Gly Gly Ser Leu Ser Gly Tyr His
1               5
```

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

```
Ile Ser His Ser Gly Asn Ala
```

```
1               5
```

<210> SEQ ID NO 107
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Ala Arg Gly Tyr Cys Ser Gly Gly Ser Cys Tyr Tyr Lys Phe
1               5                   10
```

<210> SEQ ID NO 108
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Gln Ser Val Leu Thr Gln Pro Pro Ser Val Ser Ala Ala Pro Gly Gln
1               5                   10                  15

Lys Val Thr Ile Ser Cys Ser Gly Asn Ser Ser Asn Ile Gly Asn Asn
            20                  25                  30

Tyr Val Ser Trp Phe Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Phe Cys Gly Thr Trp Asp Ser Ser Leu
                85                  90                  95

Arg Thr Gly Val Phe Gly Gly Gly Thr Lys Leu Thr Val Leu
            100                 105                 110
```

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

```
Ser Ser Asn Ile Gly Asn Asn Tyr
1               5
```

<210> SEQ ID NO 110
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

```
Asp Asn Asn
1
```

<210> SEQ ID NO 111
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Thr Trp Asp Ser Ser Leu Arg Thr Gly Val
1               5                   10

<210> SEQ ID NO 112
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Leu Ile Tyr Ser Gly Gly Ser Arg Thr Tyr Tyr Pro Asp Ser Val
    50                  55                  60

Lys Gly Arg Phe Thr Ile Ser Arg Asp Asn Ser Asn Ser Thr Leu Phe
65                  70                  75                  80

Leu Gln Met Asn Ser Leu Arg Val Glu Asp Thr Ala Val Tyr Tyr Cys
                85                  90                  95

Ala Lys Gly Gly Ser Ser Trp Leu Lys Met Asp Tyr Trp Gly Gln Gly
            100                 105                 110

Thr Leu Val Ile Val Ser Ser
        115

<210> SEQ ID NO 113
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Phe Thr Phe Ser Ser Tyr Ala
1               5

<210> SEQ ID NO 114
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Ile Tyr Ser Gly Gly Ser Arg Thr
1               5

<210> SEQ ID NO 115
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 115

Ala Lys Gly Gly Ser Ser Trp Leu Lys Met Asp Tyr
1               5                   10

<210> SEQ ID NO 116
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val Gln Trp Tyr Gln His Leu Pro Gly Thr Ala Pro Lys Leu
        35                  40                  45

Leu Ile Phe Ala Asn Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu
            100                 105                 110

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Ser Ser Asn Ile Gly Ala Gly Tyr Asp
1               5

<210> SEQ ID NO 118
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ala Asn Thr
1

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119
```

```
Gln Ser Tyr Asp Ser Ser Leu Ser Gly Ser Val
1               5                   10
```

<210> SEQ ID NO 120
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Gln Val Gln Leu Val Gln Ser Gly Ala Glu Val Lys Lys Pro Gly Ala
1               5                   10                  15

Ser Val Arg Val Ser Cys Ser Ser Gly Tyr Thr Phe Thr Gly Tyr
            20                  25                  30

Tyr Ile His Trp Val Arg Gln Ala Pro Gly Gln Gly Leu Glu Tyr Met
            35                  40                  45

Gly Arg Ile Asn Pro His Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Asp Asp Thr Ala Val Tyr Tyr Cys
                85                  90                  95

Ala Lys Glu Gly Thr Thr Ala His Ile Phe Asn Trp Phe Asp Pro Trp
            100                 105                 110

Gly Gln Gly Thr Leu Val Thr Val Ser Ser
        115                 120
```

<210> SEQ ID NO 121
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

```
Gly Tyr Thr Phe Thr Gly Tyr Tyr
1               5
```

<210> SEQ ID NO 122
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

```
Ile Asn Pro His Ser Gly Gly Thr
1               5
```

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

```
Ala Lys Glu Gly Thr Thr Ala His Ile Phe Asn Trp Phe Asp Pro
```

<210> SEQ ID NO 124
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asn Trp Tyr Gln Gln Lys Pro Gly Lys Ala Pro Asn Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Leu Phe
                85                  90                  95

Thr Phe Gly Gln Gly Thr Lys Leu Glu Ile Lys
            100                 105

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 125

Gln Ser Ile Asn Ser Tyr
1               5

<210> SEQ ID NO 126
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 126

Thr Ala Ser
1

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 127

Gln Gln Ser Tyr Thr Ser Leu Phe Thr
1               5

<210> SEQ ID NO 128
<211> LENGTH: 127

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Gln Leu Gln Leu Gln Glu Ser Gly Pro Gly Leu Val Lys Pro Ser Glu
1               5                   10                  15

Thr Leu Ser Leu Thr Cys Thr Val Ser Gly Val Ser Ile Asn Ser Thr
            20                  25                  30

Ser Tyr Tyr Trp Gly Trp Met Arg Gln Pro Pro Gly Lys Gly Leu Glu
        35                  40                  45

Trp Ile Gly Asn Ile Tyr Tyr Thr Gly Thr Thr Tyr Tyr Asn Pro Ser
    50                  55                  60

Leu Asn Arg Arg Val Ser Ile Ser Gly Asp Thr Ser Lys Asn Gln Phe
65                  70                  75                  80

Ser Leu Ser Leu Thr Ser Val Thr Ala Ala Asp Thr Ala Val Tyr Tyr
                85                  90                  95

Cys Ala Gly Pro Arg Arg Val Thr Val Phe Gly Ile Leu Leu Met Glu
            100                 105                 110

Ser Phe Asp Val Trp Ser Gln Gly Thr Met Val Thr Val Ser Ser
        115                 120                 125

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Val Ser Ile Asn Ser Thr Ser Tyr Tyr
1               5                   10

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ile Tyr Tyr Thr Gly Thr Thr
1               5

<210> SEQ ID NO 131
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ala Gly Pro Arg Arg Val Thr Val Phe Gly Ile Leu Leu Met Glu Ser
1               5                   10                  15

Phe Asp Val

<210> SEQ ID NO 132
<211> LENGTH: 107
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Arg Asp Asp
            20                  25                  30

Leu Gly Trp Phe Gln Gln Lys Pro Gly Lys Ala Pro Lys Leu Leu Ile
        35                  40                  45

Tyr Thr Ala Ser Thr Leu Gln Ser Gly Val Pro Ser Arg Phe Ser Gly
50                  55                  60

Gly Gly Ser Gly Thr Glu Phe Ile Leu Thr Ile Ser Ser Leu Gln Pro
65                  70                  75                  80

Glu Asp Ile Gly Thr Tyr Tyr Cys Leu Gln Asp Tyr Gly Tyr Pro Trp
                85                  90                  95

Thr Phe Gly Gln Gly Thr Lys Val Glu Ile Lys
            100                 105

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gln Ala Ile Arg Asp Asp
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Leu Gln Asp Tyr Gly Tyr Pro Trp Thr
1               5

<210> SEQ ID NO 135
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Leu Ser Trp Val Arg Gln Ala Pro Gly Lys Gly Leu Glu Trp Val
        35                  40                  45

Ser Ala Ile Ser Gly Arg Asp Ala Ser Thr Tyr Tyr Ala Asp Ser Val
50                  55                  60
```

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Thr Leu Phe Asp Tyr Asp Ser Ser Gly Tyr Phe Asp Phe Asp Tyr Trp
            100                 105                 110

Gly Gln Gly Thr Leu Val Thr Val Ser Ser
        115                 120
```

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

```
Gly Phe Thr Phe Ser Asn Tyr Ala
 1               5
```

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

```
Ile Ser Gly Arg Asp Ala Ser Thr
 1               5
```

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

```
Thr Leu Phe Asp Tyr Asp Ser Ser Gly Tyr Phe Asp Phe Asp Tyr
 1               5                  10                  15
```

<210> SEQ ID NO 139
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

```
Gln Ser Ala Leu Thr Gln Pro Arg Ser Val Ser Gly Ser Pro Gly Gln
 1               5                  10                  15

Ser Val Thr Ile Ser Cys Thr Gly Thr Gly Ser Asp Val Gly Gly Tyr
             20                  25                  30

Asn Tyr Val Ser Trp Tyr Gln His His Pro Gly Lys Ala Pro Lys Leu
         35                  40                  45

Ile Ile Phe Asp Val Thr Lys Arg Pro Ser Val Pro Asp Arg Phe
     50                  55                  60

Ser Gly Ser Lys Ser Gly Tyr Thr Ala Ser Leu Thr Ile Ser Gly Leu
```

```
            65                  70                  75                  80
Gln Ala Glu Asp Glu Ala Val Tyr Tyr Cys Cys Ser Tyr Ala Asn Ser
                85                  90                  95
Tyr Thr Gly Val Phe Gly Thr Gly Thr Lys Val Thr Val Leu
            100                 105                 110
```

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

```
Gly Ser Asp Val Gly Gly Tyr Asn Tyr
1               5
```

<210> SEQ ID NO 141
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

```
Asp Val Thr
1
```

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

```
Cys Ser Tyr Ala Asn Ser Tyr Thr Gly Val
1               5                  10
```

<210> SEQ ID NO 143
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

```
Gln Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Ser Ser His
            20                  25                  30
Val Met His Trp Val Arg Gln Ala Pro Gly Lys Gly Leu Glu Trp Val
        35                  40                  45
Ala Leu Ile Ser Leu Asp Gly Asp Asp Lys Tyr Tyr Ala Asp Ser Val
    50                  55                  60
Asn Gly Arg Val Ala Ile Ser Arg Asp Asn Ser Lys Asn Thr Leu Tyr
65                  70                  75                  80
Leu Gln Val Asn Ser Leu Arg Ser Asp Asp Thr Cys Val Tyr Tyr Cys
                85                  90                  95
```

Ala Arg Gly Gly Arg Trp Asp Tyr Ala Leu Asp Val Trp Gly Gln Gly
            100                 105                 110

Thr Thr Val Thr Val Ser Ser
        115

<210> SEQ ID NO 144
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Phe Thr Phe Ser Ser His Val
1               5

<210> SEQ ID NO 145
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ile Ser Leu Asp Gly Asp Asp Lys
1               5

<210> SEQ ID NO 146
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ala Arg Gly Gly Arg Trp Asp Tyr Ala Leu Asp Val
1               5                   10

<210> SEQ ID NO 147
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Ile Val Met Thr Gln Ser Pro Ala Thr Leu Ser Val Ser Pro Gly
1               5                   10                  15

Glu Arg Ala Thr Leu Ser Cys Arg Val Ser Gln Ser Ile Ser Asn Ser
            20                  25                  30

Leu Ala Trp Tyr Gln Gln Lys Pro Gly Gln Val Pro Arg Leu Leu Ile
        35                  40                  45

Tyr Ala Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Ala Leu Thr Phe Gly Gly Gly Thr Lys Val Glu Ile Lys
            100                 105

<210> SEQ ID NO 148
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gln Ser Ile Ser Asn Ser
1               5

<210> SEQ ID NO 149
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ala Ala Ser
1

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gln Gln Tyr Asn Asn Trp Pro Arg Ala Leu Thr
1               5                   10

<210> SEQ ID NO 151
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Pro Glu Trp Val
        35                  40                  45

Ala Val Ile Ser Tyr Asp Gly Thr Asn Glu Tyr Tyr Met Gly Ser Val
    50                  55                  60

Lys Gly Arg Phe Thr Ile Ser Arg Asp Asn Ser Lys Asn Met Val Asn
65                  70                  75                  80

Leu Gln Met Asn Ser Leu Arg Pro Glu Asp Thr Ala Val Tyr Tyr Cys
                85                  90                  95

Ala Arg Asp Leu Ala Ala Trp Ser Arg Glu Leu Leu Val Phe Asp Gln
            100                 105                 110

Trp Gly Gln Gly Thr Leu Val Thr Val Ser Ser
        115                 120

```
<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Phe Thr Phe Asn Asp Tyr Ala
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ile Ser Tyr Asp Gly Thr Asn Glu
1               5

<210> SEQ ID NO 154
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Arg Asp Leu Ala Ala Trp Ser Arg Glu Leu Leu Val Phe Asp Gln
1               5                   10                  15

<210> SEQ ID NO 155
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Asn Val Leu Thr Gln Ser Pro Gly Thr Leu Ser Leu Ser Pro Gly
1               5                   10                  15

Glu Gly Ala Thr Leu Ser Cys Arg Ala Ser Gln Ser Val Pro Asn Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Pro
                85                  90                  95

Gly Thr Phe Gly Gln Gly Thr Lys Val Glu Ile Lys
            100                 105

<210> SEQ ID NO 156
<211> LENGTH: 7
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 156

Gln Ser Val Pro Asn Thr Tyr
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gln Gln Tyr Gly Arg Ser Pro Gly Thr
1               5

<210> SEQ ID NO 158
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gln Ala Gln Val Val Glu Ser Gly Gly Val Val Gln Pro Gly Thr
1               5                   10                  15

Ser Leu Arg Leu Ser Cys Glu Pro Ser Gly Phe Thr Leu Ser Asp Tyr
            20                  25                  30

Gly Ile His Trp Val Arg Gln Pro Pro Gly Lys Gly Leu Glu Trp Val
        35                  40                  45

Ala Val Ile Trp His Asp Gly Asp Arg Ile Asn Tyr Ala Asp Ser Val
    50                  55                  60

Lys Gly Arg Phe Thr Ile Ser Arg Asp Glu Ser Asp Lys Lys Val His
65                  70                  75                  80

Leu Gln Met Glu Ser Leu Arg Thr Glu Asp Thr Ala Val Tyr Tyr Cys
                85                  90                  95

Ala Arg Gly Thr Leu Pro Arg Asn Cys Arg Gly Met Arg Cys Tyr Gly
            100                 105                 110

Glu Phe Asp His Tyr Tyr Tyr Leu Asp Val Trp Gly Thr Gly Thr Thr
        115                 120                 125

Val Thr Val Ser Ser
    130

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Phe Thr Leu Ser Asp Tyr Gly
1               5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ile Trp His Asp Gly Asp Arg Ile
1               5

<210> SEQ ID NO 161
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ala Arg Gly Thr Leu Pro Arg Asn Cys Arg Gly Met Arg Cys Tyr Gly
1               5                   10                  15

Glu Phe Asp His Tyr Tyr Tyr Leu Asp Val
            20                  25

<210> SEQ ID NO 162
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Ser Val Leu Thr Gln Pro Pro Ser Val Ser Gly Ala Pro Gly Gln
1               5                   10                  15

Arg Val Thr Ile Ser Cys Thr Gly His Ser Ser Asn Ile Gly Ala Asn
            20                  25                  30

Ser Asp Val His Trp Tyr Gln Gln Leu Pro Leu Arg Ala Pro Lys Leu
        35                  40                  45

Leu Ile Phe Gly Thr Ile Asn Arg Ala Ser Gly Val Pro Asp Arg Phe
    50                  55                  60

Ser Gly Ser Arg Ser Gly Thr Ser Ala Ser Leu Val Ile Ser Gly Leu
65                  70                  75                  80

Gln Pro Asp Asp Glu Ala Asp Tyr Tyr Cys Gln Ser Tyr Asp Arg Gly
                85                  90                  95

Leu Ser Ala Tyr Val Phe Gly Ser Gly Thr Arg Val Asp Val Leu
            100                 105                 110

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ser Ser Asn Ile Gly Ala Asn Ser Asp
1               5

<210> SEQ ID NO 164
<211> LENGTH: 3
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 164

Gly Thr Ile
1

<210> SEQ ID NO 165
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gln Ser Tyr Asp Arg Gly Leu Ser Ala Tyr Val
1               5                   10

<210> SEQ ID NO 166
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Asp Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Val Tyr Tyr Cys
                85                  90                  95

Ala Arg Glu Arg Ser Thr Gln Ser Ser Ser Trp Tyr Val Ser Ser Tyr
            100                 105                 110

Tyr Ser Tyr Tyr Gly Met Asp Val Trp Gly Gln Gly Thr Thr Val Thr
        115                 120                 125

Val Ser Ser
    130

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Phe Thr Phe Ser Ser Tyr Trp
1               5

<210> SEQ ID NO 168
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 168

Ile Lys Gln Asp Gly Ser Glu Lys
1               5

<210> SEQ ID NO 169
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Arg Glu Arg Ser Thr Gln Ser Ser Ser Trp Tyr Val Ser Ser Tyr
1               5                   10                  15

Tyr Ser Tyr Tyr Gly Met Asp Val
            20

<210> SEQ ID NO 170
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Ser Ser Glu Leu Thr Gln Asp Pro Ala Val Ser Val Ala Leu Gly Gln
1               5                   10                  15

Thr Val Thr Ile Thr Cys Gln Gly Asp Ser Leu Arg Ser Phe Tyr Ala
            20                  25                  30

Ser Trp Tyr Gln Gln Lys Pro Gly Gln Ala Pro Val Phe Val Ile Tyr
        35                  40                  45

Gly Lys Tyr Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Asp Asn His
                85                  90                  95

Leu Gly Val Phe Gly Gly Gly Thr Lys Leu Thr Val Leu
            100                 105

<210> SEQ ID NO 171
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ser Leu Arg Ser Phe Tyr
1               5

<210> SEQ ID NO 172
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Lys Tyr
1

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Asn Ser Arg Asp Ser Ser Asp Asn His Leu Gly Val
1               5                   10

<210> SEQ ID NO 174
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Val Gln Leu Val Gln Ser Gly Ser Glu Leu Arg Lys Pro Gly Ala
1               5                   10                  15

Ser Val Lys Leu Ser Cys Arg Thr Ser Gly Tyr Thr Phe Ile His Phe
            20                  25                  30

Ala Met Asn Trp Leu Arg Gln Ala Pro Gly Gln Gly Leu Glu Trp Leu
        35                  40                  45

Gly Trp Ile Asn Thr His Ser Gly Asn Pro Thr Tyr Ala Gln Gly Phe
    50                  55                  60

Thr Gly Arg Phe Val Phe Ser Leu Asp Val Ser Ala Gly Thr Ala Tyr
65                  70                  75                  80

Leu Glu Ile Ser Gly Leu Lys Ala Glu Asp Thr Ala Val Tyr Tyr Cys
                85                  90                  95

Ala Arg Glu Arg Tyr Phe Asp Phe Trp Gly Gln Gly Ala Leu Val Ala
            100                 105                 110

Val Ser Ser
        115

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Tyr Thr Phe Ile His Phe Ala
1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

```
Ile Asn Thr His Ser Gly Asn Pro
1               5
```

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

```
Ala Arg Glu Arg Tyr Phe Asp Phe
1               5
```

<210> SEQ ID NO 178
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

```
Gln Ser Val Leu Thr Gln Pro Pro Ser Ala Ser Gly Thr Pro Gly Gln
1               5                   10                  15
Arg Val Thr Ile Ser Cys Ser Gly Thr Ser Ser Asn Ile Gly Lys Asn
            20                  25                  30
Phe Leu Tyr Trp Tyr Gln Gln Val Pro Gly Thr Ala Pro Lys Leu Leu
        35                  40                  45
Ile Tyr Ser Ser Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Arg
65                  70                  75                  80
Ser Glu Asp Glu Ala Asp Tyr Tyr Cys Ala Ala Trp Asp Asp Ser Leu
                85                  90                  95
Ser Gly Trp Val Phe Gly Gly Gly Thr Lys Val Thr Val Leu
            100                 105                 110
```

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

```
Ser Ser Asn Ile Gly Lys Asn Phe
1               5
```

<210> SEQ ID NO 180
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

```
Ser Ser Asn
1
```

```
<210> SEQ ID NO 181
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Ala Trp Asp Asp Ser Leu Ser Gly Trp Val
1               5                   10

<210> SEQ ID NO 182
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Pro Pro Gly Lys Gly Leu Val Trp Val
        35                  40                  45

Ser Arg Ile Ser Gly Asp Gly Thr Gly Thr Ser Tyr Ala Asp Ser Val
    50                  55                  60

Arg Gly Arg Phe Thr Ile Ser Arg Asp Asn Ala Lys Ser Thr Leu Tyr
65                  70                  75                  80

Leu Gln Val Asn Ser Leu Ser Ala Glu Asp Thr Ala Val Tyr Tyr Cys
                85                  90                  95

Thr Arg Asp Gly Gly Arg Asp His Pro Thr Pro Asp Ala Phe Asp Ile
            100                 105                 110

Trp Gly Gln Gly Thr Met Val Thr Val Ser Ser
        115                 120

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Gly Phe Thr Phe Ser Asn Tyr Trp
1               5

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ile Ser Gly Asp Gly Thr Gly Thr
1               5

<210> SEQ ID NO 185
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Thr Arg Asp Gly Gly Arg Asp His Pro Thr Pro Asp Ala Phe Asp Ile
1               5                   10                  15

<210> SEQ ID NO 186
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asp Val Val Met Ala Gln Ser Pro Leu Ser Leu Pro Val Thr Leu Gly
1               5                   10                  15

Gln Pro Ala Ser Ile Ser Cys Arg Ser Ser Gln Ser Leu Val His Ser
                20                  25                  30

Asp Gly Asn Thr Tyr Leu Asn Trp Phe Gln Gln Arg Pro Gly Gln Ser
            35                  40                  45

Pro Arg Arg Leu Ile Tyr Lys Ile Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Arg Thr Phe Gly Gln Gly Thr Lys Leu Glu Ile Lys
                100                 105                 110

<210> SEQ ID NO 187
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gln Ser Leu Val His Ser Asp Gly Asn Thr Tyr
1               5                   10

<210> SEQ ID NO 188
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Lys Ile Ser
1

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 189

Met Gln Gly Thr His Trp Pro Arg Thr
1               5

<210> SEQ ID NO 190
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gln Val Gln Leu Gln Gln Trp Gly Ala Gly Leu Leu Lys Pro Ser Glu
1               5                   10                  15

Thr Leu Ser Leu Thr Cys Val Val Ser Gly Ser Phe Ser Thr His
            20                  25                  30

Tyr Trp Asn Trp Ile Arg Gln Ser Pro Gly Lys Gly Leu Glu Trp Ile
        35                  40                  45

Gly Glu Ile Asn His Ser Gly Asn Thr Asn Tyr Asn Pro Ser Leu Thr
    50                  55                  60

Gly Arg Ala Thr Ile Ser Val Ala Thr Ser Lys Thr Gln Phe Ser Leu
65                  70                  75                  80

Arg Leu Asn Ser Val Thr Ala Ala Asp Thr Ala Val Tyr Phe Cys Ala
                85                  90                  95

Arg Gly Pro Arg Leu Arg Tyr Thr Ala Gly Arg Pro Leu Phe Asp Thr
            100                 105                 110

Trp Gly Gln Gly Thr Leu Val Thr Val Ser Ser
        115                 120

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Gly Ser Phe Ser Thr His Tyr
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ile Asn His Ser Gly Asn Thr
1               5

<210> SEQ ID NO 193
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

```
Ala Arg Gly Pro Arg Leu Arg Tyr Thr Ala Gly Arg Pro Leu Phe Asp
1               5                   10                  15

Thr

<210> SEQ ID NO 194
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ala Phe
            20                  25                  30

Leu Ala Trp Tyr Gln Gln Lys Pro Gly Lys Ala Pro Asn Leu Val Ile
        35                  40                  45

Tyr Lys Ala Ser Ser Leu Asp Ser Gly Val Pro Ser Thr Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Gln Tyr Phe Ser Ser Pro Pro
                85                  90                  95

Thr Phe Gly Gln Gly Thr Lys Val Glu Met Lys
            100                 105

<210> SEQ ID NO 195
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Ser Ile Ser Ala Phe
1               5

<210> SEQ ID NO 196
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Lys Ala Ser
1

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gln Gln Tyr Phe Ser Ser Pro Pro Thr
1               5
```

<210> SEQ ID NO 198
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gln Val Gln Leu Gln Glu Ser Gly Pro Gly Leu Val Lys Pro Ser Gln
1               5                   10                  15

Thr Leu Ser Leu Thr Cys Ala Val Ser Gly Gly Ser Ile Ser Ser Gly
            20                  25                  30

Gly Tyr Tyr Trp Ser Trp Ile Arg Gln Leu Pro Gly Lys Gly Leu Glu
        35                  40                  45

Trp Ile Gly Tyr Ile Tyr Tyr Ser Gly Ser Thr Ser Tyr Asn Pro Ser
    50                  55                  60

Leu Lys Ser Arg Val Thr Ile Ser Val Asp Thr Ser Lys Asn Gln Leu
65                  70                  75                  80

Ser Leu Asn Leu Ser Ser Val Thr Ala Ala Asp Thr Ala Val Tyr Asn
                85                  90                  95

Cys Ala Arg Gly Arg Arg Ile Ser Ile Ser Gly Val Val Thr Pro Leu
            100                 105                 110

Phe Asp Tyr Trp Gly Gln Gly Thr Leu Val Thr Val Ser Ser
        115                 120                 125

<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Gly Ser Ile Ser Ser Gly Gly Tyr Tyr
1               5                   10

<210> SEQ ID NO 200
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ile Tyr Tyr Ser Gly Ser Thr
1               5

<210> SEQ ID NO 201
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ala Arg Gly Arg Arg Ile Ser Ile Ser Gly Val Val Thr Pro Leu Phe
1               5                   10                  15

Asp Tyr

<210> SEQ ID NO 202
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Leu Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Val Pro Leu
                85                  90                  95

Thr Phe Gly Gly Gly Thr Lys Val Glu Ile Lys
            100                 105

<210> SEQ ID NO 203
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gln Gly Ile Ser Ser Trp
1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gln Gln Ala Asn Ser Val Pro Leu Thr
1               5

<210> SEQ ID NO 205
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser His Tyr
            20                  25                  30

Tyr Leu Asn Trp Val Arg Gln Ala Pro Gly Lys Gly Leu Glu Trp Val

```
            35                  40                  45

Ala Cys Ile Ser Asp Arg Ser Glu Asn Val Tyr Tyr Ala Asp Ser Val
 50                  55                  60

Lys Gly Arg Phe Thr Ile Ser Arg Asp Asn Ala Lys Asn Ser Leu Phe
 65                  70                  75                  80

Leu Gln Met Asn Asn Leu Arg Ala Glu Asp Thr Ala Ile Tyr Tyr Cys
                 85                  90                  95

Ala Arg Asp Met Arg Glu Leu Arg Pro Ser Ala Asp Tyr Trp Gly Gln
            100                 105                 110

Gly Thr Leu Val Thr Val Ser Ser
        115                 120

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Phe Thr Phe Ser His Tyr Tyr
1               5

<210> SEQ ID NO 207
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ile Ser Asp Arg Ser Glu Asn Val
1               5

<210> SEQ ID NO 208
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ala Arg Asp Met Arg Glu Leu Arg Pro Ser Ala Asp Tyr
1               5                  10

<210> SEQ ID NO 209
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Glu Ile Val Leu Thr Gln Ser Pro Gly Thr Leu Ser Leu Ser Pro Gly
1               5                  10                  15

Asp Arg Ala Thr Leu Ser Cys Arg Ala Ser Gln Ser Val Asp Gly Asn
            20                  25                  30

Ser Leu Ala Trp Tyr Gln Gln Lys Pro Gly Gln Ala Pro Arg Leu Leu
        35                  40                  45
```

```
Ile Ser Gly Ala Ser Thr Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Val Leu Tyr His Cys Gln Leu Tyr Thr Val Ser Pro
                 85                  90                  95

Arg Tyr Thr Phe Gly Gln Gly Thr Lys Leu Glu Ile Lys
            100                 105

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Gln Ser Val Asp Gly Asn Ser
1               5

<210> SEQ ID NO 211
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gln Leu Tyr Thr Val Ser Pro Arg Tyr Thr
1               5                   10

<210> SEQ ID NO 212
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asp
                 20                  25                  30

Asn Tyr Tyr Trp Gly Trp Ile Arg Gln Pro Pro Gly Lys Gly Pro Leu
            35                  40                  45

Trp Ile Gly Thr Ile Phe Tyr Asn Gly Asp Thr Tyr Tyr Asn Pro Ser
 50                  55                  60

Leu Lys Ser Gln Leu Asn Ile Ser Val Asp Pro Ser Lys Asn Gln Phe
 65                  70                  75                  80

Ser Leu Lys Leu Thr Ser Val Thr Ala Ala Asp Thr Ala Ile Tyr Tyr
                 85                  90                  95

Cys Thr Arg His Asp Ser Tyr Ser Arg Gly Trp Tyr Val Thr His Trp
            100                 105                 110

Gly Gln Gly Thr Leu Val Thr Val Ser Ser
            115                 120

<210> SEQ ID NO 213
<211> LENGTH: 10
<212> TYPE: PRT
```

<213> ORGANISM: Artificial Sequence
<220> FEATURE:
<223> OTHER INFORMATION: Description of Artificial Sequence: Synthetic peptide

<400> SEQUENCE: 213

Gly Gly Ser Ile Ser Ser Asp Asn Tyr Tyr
1               5                   10

<210> SEQ ID NO 214
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 214

Ile Phe Tyr Asn Gly Asp Thr
1               5

<210> SEQ ID NO 215
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 215

Thr Arg His Asp Ser Tyr Ser Arg Gly Trp Tyr Val Thr His
1               5                   10

<210> SEQ ID NO 216
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 216

Glu Ile Val Leu Thr Gln Ser Pro Ala Thr Leu Ser Leu Phe Pro Gly
1               5                   10                  15

Glu Arg Ala Thr Leu Ser Cys Arg Ala Ser Gln Ser Val Thr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Arg Ser Ala Arg Gln Leu
                85                  90                  95

Phe Gly Gly Gly Thr Lys Val Glu Ile Lys
            100                 105

<210> SEQ ID NO 217
<211> LENGTH: 6
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 217

Gln Ser Val Thr Ser Tyr
1               5

<210> SEQ ID NO 218
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gln Gln Arg Ser Ala Arg Gln Leu
1               5

<210> SEQ ID NO 219
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Glu Val Gln Leu Val Glu Ser Gly Gly Gly Leu Val Lys Pro Gly Gly
1               5                   10                  15

Ser Leu Arg Leu Ser Cys Val Ala Ser Gly Leu Thr Phe Arg Asn Ala
            20                  25                  30

Trp Met Thr Trp Val Arg Gln Ala Pro Gly Lys Gly Leu Glu Trp Val
        35                  40                  45

Gly Arg Ile Lys Ser Asn Val Asn Gly Gly Thr Thr Asp Tyr Ala Ala
    50                  55                  60

Pro Val Arg Gly Arg Phe Thr Ile Ser Arg Asp Asp Ser Arg Asp Thr
65                  70                  75                  80

Leu Tyr Leu Gln Met Asn Ser Leu Glu Thr Glu Asp Thr Ala Met Tyr
                85                  90                  95

Tyr Cys Thr Lys Asp Pro Pro Tyr Thr Gly Gly Gly Tyr Cys Gln His
            100                 105                 110

Trp Gly Leu Gly Thr Leu Val Thr Val Ser Ser
        115                 120

<210> SEQ ID NO 220
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Leu Thr Phe Arg Asn Ala Trp
1               5

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221
```

```
Ile Lys Ser Asn Val Asn Gly Gly Thr Thr
1               5                  10
```

<210> SEQ ID NO 222
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

```
Thr Lys Asp Pro Pro Tyr Thr Gly Gly Gly Tyr Cys Gln His
1               5                  10
```

<210> SEQ ID NO 223
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

```
Glu Ile Val Leu Thr Gln Ser Pro Ala Thr Leu Ser Leu Ser Pro Gly
1               5                  10                  15

Glu Ser Ala Thr Leu Ser Cys Arg Ala Ser Gln Ser Val Ser Ser Cys
                20                  25                  30

Leu Ala Trp Tyr Gln Gln Lys Pro Gly Gln Ala Pro Arg Leu Leu Ile
            35                  40                  45

Tyr Asp Ala Ser Thr Arg Ala Pro Gly Ile Pro Gly Arg Phe Ser Gly
    50                  55                  60

Ser Gly Ser Gly Thr Asp Phe Thr Leu Ala Ile Ser Ser Leu Glu Pro
65                  70                  75                  80

Glu Asp Phe Ala Val Tyr Tyr Cys Gln Gln Cys Ser Asn Trp Pro Leu
                85                  90                  95

Thr Phe Gly Arg Gly Thr Arg Leu Glu Ile Lys
            100                 105
```

<210> SEQ ID NO 224
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

```
Gln Ser Val Ser Ser Cys
1               5
```

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

```
Gln Gln Cys Ser Asn Trp Pro Leu Thr
1               5
```

<210> SEQ ID NO 226

```
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Thr Gly
            20                  25                  30

Ala Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Lys Asp Thr Ser Lys Asn Gln Phe
65                  70                  75                  80

Ser Leu Arg Leu Thr Ser Val Thr Ala Ala Asp Thr Ala Val Tyr Tyr
                85                  90                  95

Cys Val Arg Glu Lys Leu Thr Gly Ala Pro Asp Asn Trp Gly Gln Gly
            100                 105                 110

Thr Leu Val Ala Val Ser Ser
        115

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Gly Ser Ile Asn Thr Gly Ala Tyr Tyr
1               5                   10

<210> SEQ ID NO 228
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Val Arg Glu Lys Leu Thr Gly Ala Pro Asp Asn
1               5                   10

<210> SEQ ID NO 229
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Ser Asn Tyr
            20                  25                  30

Leu Ala Trp Phe His Gln Lys Pro Gly Lys Ala Pro Lys Ser Leu Ile
```

```
                35                  40                  45
Tyr Ala Ala Ser Thr Leu His Asp Gly Val Pro Ser Ser Phe Ser Gly
    50                  55                  60

Ser Gly Ser Gly Thr Glu Phe Thr Leu Thr Ile Ser Asp Leu Gln Pro
65                  70                  75                  80

Glu His Phe Gly Thr Tyr Tyr Cys Glu Gln Tyr Asn Ser Tyr Pro Phe
                85                  90                  95

Thr Phe Gly Pro Gly Thr Thr Val Asp Phe Lys
            100                 105

<210> SEQ ID NO 230
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Gln Gly Val Ser Asn Tyr
1               5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Glu Gln Tyr Asn Ser Tyr Pro Phe Thr
1               5

<210> SEQ ID NO 232
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Leu Ser Ser Tyr
            20                  25                  30

Asn Phe Ile Trp Val Arg Gln Ala Pro Gly Gln Gly Leu Glu Trp Met
        35                  40                  45

Gly Gly Ile Leu Pro Val Phe Asp Thr Thr Asn Tyr Ala Gln Lys Phe
    50                  55                  60

Gln Gly Arg Val Thr Ile Thr Ala Asp Lys Ala Thr Ser Thr Ser Tyr
65                  70                  75                  80

Met Glu Leu Ser Ser Leu Thr Ser Glu Asp Thr Ala Val Tyr Tyr Cys
                85                  90                  95

Ala Arg Ala Val Gly Gly Thr His Tyr Tyr Tyr Gly Leu Asp Val
            100                 105                 110

Trp Gly Gln Gly Thr Thr Val Ala Val Ser Ser
        115                 120

<210> SEQ ID NO 233
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Gly Gly Pro Leu Ser Ser Tyr Asn
1               5

<210> SEQ ID NO 234
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ile Leu Pro Val Phe Asp Thr Thr
1               5

<210> SEQ ID NO 235
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ala Arg Ala Val Gly Gly Thr His Tyr Tyr Tyr Tyr Gly Leu Asp Val
1               5                   10                  15

<210> SEQ ID NO 236
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Gly
            20                  25                  30

Asn Gly Tyr Asn Tyr Val Asp Trp Tyr Leu Gln Arg Pro Gly Gln Pro
        35                  40                  45

Pro Gln Leu Leu Ile Tyr Leu Gly Ser Arg Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Leu Gly Val Tyr Tyr Cys Met Gln Ala
                85                  90                  95

Leu Gln Thr Arg Val Thr Phe Gly Pro Gly Thr Lys Val Asp Ile Lys
            100                 105                 110

<210> SEQ ID NO 237
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 237

Gln Ser Leu Leu His Gly Asn Gly Tyr Asn Tyr
1               5                   10

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Met Gln Ala Leu Gln Thr Arg Val Thr
1               5

<210> SEQ ID NO 239
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Met Ser Tyr
                20                  25                  30

Trp Ile Gly Trp Val Arg Gln Lys Pro Gly Lys Gly Leu Glu Trp Met
            35                  40                  45

Gly Ile Ile Phe Pro Gly Asp Ser Asp Thr Arg Tyr Ser Pro Ser Phe
        50                  55                  60

Gln Gly His Val Thr Ile Ser Ala Asp Lys Ser Ile Thr Thr Ala Tyr
65                  70                  75                  80

Leu Gln Trp Asn Ser Leu Glu Ala Ser Asp Thr Ala Ile Tyr Tyr Cys
                85                  90                  95

Ala Thr Leu Asp Gly Asp Tyr Trp Gly Arg Gly Thr Leu Val Thr Val
            100                 105                 110

Ser Ser

<210> SEQ ID NO 240
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gly Tyr Ser Phe Met Ser Tyr Trp
1               5

<210> SEQ ID NO 241
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

```
Ile Phe Pro Gly Asp Ser Asp Thr
1               5

<210> SEQ ID NO 242
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Ala Thr Leu Asp Gly Asp Tyr
1               5

<210> SEQ ID NO 243
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Ser Ser
            20                  25                  30

Ser Ser Asn Lys Asn Tyr Leu Gly Trp Tyr Gln Gln Lys Pro Gly Gln
        35                  40                  45

Pro Pro Lys Leu Leu Ile His Trp Ala Ser Thr Arg Ala Ala Gly Val
    50                  55                  60

Pro Asp Arg Phe Ser Gly Ser Gly Thr Gly Thr Asp Phe Thr Leu Asn
65                  70                  75                  80

Ile Ser Ser Leu Gln Ala Glu Asp Val Ala Val Tyr Tyr Cys Gln Gln
                85                  90                  95

Tyr His Thr Thr Leu Pro Thr Phe Gly Gln Gly Thr Lys Leu Glu Ile
            100                 105                 110

Lys

<210> SEQ ID NO 244
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gln Ser Val Leu Ser Ser Ser Ser Asn Lys Asn Tyr
1               5                   10

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gln Gln Tyr His Thr Thr Leu Pro Thr
1               5
```

<210> SEQ ID NO 246
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Ser
            20                  25                  30

Ala Met Thr Trp Val Arg Gln Ala Pro Gly Lys Gly Leu Glu Trp Val
        35                  40                  45

Ser Thr Ile Ser Gly Asn Gly Asp Thr Thr Tyr Tyr Ala Asp Ser Val
    50                  55                  60

Lys Gly Arg Phe Ser Ile Phe Arg Asp Asn Ser Arg Asn Thr Leu Tyr
65                  70                  75                  80

Val Gln Met Asn Ser Leu Arg Ala Glu Asp Thr Ala Val Tyr Tyr Cys
                85                  90                  95

Ala Arg Tyr Gly Asp His Lys Gly Trp Phe Asp Ser Trp Gly Gln Gly
            100                 105                 110

Thr Leu Val Thr Val Ser Ser
        115

<210> SEQ ID NO 247
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gly Phe Thr Phe Arg Asp Ser Ala
1               5

<210> SEQ ID NO 248
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ile Ser Gly Asn Gly Asp Thr Thr
1               5

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Ala Arg Tyr Gly Asp His Lys Gly Trp Phe Asp Ser
1               5                   10

-continued

```
<210> SEQ ID NO 250
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Glu Leu Val Met Thr Gln Ser Pro Ala Ser Leu Ser Val Ser Pro Gly
1               5                   10                  15

Glu Gly Ala Thr Val Ser Cys Arg Ala Ser Gln Ser Val Gly Ser Asn
            20                  25                  30

Leu Ala Trp Tyr Gln Gln Lys Pro Gly Gln Pro Arg Leu Leu Ile
        35                  40                  45

Tyr Gly Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Lys Val Glu Ile Lys
            100                 105

<210> SEQ ID NO 251
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gln Ser Val Gly Ser Asn
1               5

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gln Gln Tyr Asn Asn Trp Pro Arg Thr
1               5

<210> SEQ ID NO 253
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45
```

```
Gly Ile Ile Asn Pro Ser Asp Gly Ser Lys Thr Tyr Ala Gln Lys Phe
    50                  55                  60
Gln Gly Arg Val Thr Leu Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Gly Asn Gly Tyr Ser Ser Ser Trp Tyr Val Asn Asp Tyr Trp
            100                 105                 110
Gly Gln Gly Thr Leu Val Thr Val Ser Ser
        115                 120

<210> SEQ ID NO 254
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Ile Asn Pro Ser Asp Gly Ser Lys
1               5

<210> SEQ ID NO 255
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ala Arg Gly Asn Gly Tyr Ser Ser Ser Trp Tyr Val Asn Asp Tyr
1               5                   10                  15

<210> SEQ ID NO 256
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Asp Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Leu Thr Asn Ser
                20                  25                  30
Asn Phe Ala Trp Tyr Gln Gln Ile Pro Gly Gln Ala Pro Arg Leu Leu
            35                  40                  45
Ile Tyr Gly Ala Ser Ser Arg Ala Thr Gly Ile Pro Asp Arg Phe Ser
        50                  55                  60
Gly Ser Gly Ser Gly Thr Asp Phe Thr Leu Thr Ile Ser Arg Leu Glu
65                  70                  75                  80
Pro Glu Asp Phe Val Val Tyr Tyr Cys Gln Gln Tyr Gly Arg Ser Pro
                85                  90                  95
Ile Thr Phe Gly Gln Gly Thr Arg Leu Glu Ile Lys
            100                 105

<210> SEQ ID NO 257
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 257

Gln Ser Leu Thr Asn Ser Asn
1               5

<210> SEQ ID NO 258
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gln Gln Tyr Gly Arg Ser Pro Ile Thr
1               5

<210> SEQ ID NO 259
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Thr Lys Tyr
                20                  25                  30

Gly Met His Trp Val Arg Gln Ala Pro Gly Lys Gly Leu Glu Trp Val
            35                  40                  45

Ala Leu Ile Ser Tyr Asp Gly Asn Asn Lys Tyr Tyr Ala Asp Ser Val
        50                  55                  60

Arg Gly Arg Val Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Gly Gln Asp Tyr Pro Phe Trp Ser Gly Ser Thr Phe Glu Tyr
            100                 105                 110

Trp Gly Gln Gly Thr Leu Val Thr Val Ser Ser
        115                 120

<210> SEQ ID NO 260
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Gly Phe Thr Phe Thr Lys Tyr Gly
1               5

<210> SEQ ID NO 261
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 261

Ile Ser Tyr Asp Gly Asn Asn Lys
1               5

<210> SEQ ID NO 262
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ala Arg Gly Gln Asp Tyr Pro Phe Trp Ser Gly Ser Thr Phe Glu Tyr
1               5                   10                  15

<210> SEQ ID NO 263
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Gln Ala Val Val Thr Gln Glu Pro Ser Leu Thr Val Ser Pro Gly Gly
1               5                   10                  15

Thr Val Thr Leu Thr Cys Gly Ser Thr Thr Gly Ala Val Thr Gly Gly
            20                  25                  30

His Phe Pro Tyr Trp Ile Gln Gln Lys Pro Gly Gln Ala Pro Arg Thr
        35                  40                  45

Leu Ile Tyr Asp Ala Thr Asn Arg His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Asp Tyr Tyr Cys Leu Leu Ser Tyr Ser Ser
                85                  90                  95

Ala Thr Phe Leu Ile Phe Gly Gly Gly Thr Lys Leu Thr Val Leu
            100                 105                 110

<210> SEQ ID NO 264
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Thr Gly Ala Val Thr Gly Gly His Phe
1               5

<210> SEQ ID NO 265
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Asp Ala Thr
1

<210> SEQ ID NO 266
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Leu Leu Ser Tyr Ser Ser Ala Thr Phe Leu Ile
1               5                   10

<210> SEQ ID NO 267
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Leu Ser Ser Gly
            20                  25                  30

Ser Tyr Phe Trp Ser Trp Ile Arg Gln Pro Pro Gly Lys Gly Leu Glu
        35                  40                  45

Trp Ile Gly Tyr Ile Ser Phe Arg Gly Asp Thr Asn Tyr Asn Pro Ser
    50                  55                  60

Leu Lys Ser Arg Val Ile Ile Ser Leu Asp Lys Ser Lys Asn Gln Phe
65                  70                  75                  80

Ser Leu Arg Leu Ser Ser Met Thr Pro Ala Asp Thr Ala Val Tyr Tyr
                85                  90                  95

Cys Ala Arg Ser Pro Trp Ile Gln Ser Trp Ser Tyr Tyr Phe Asp Tyr
            100                 105                 110

Trp Gly Gln Gly Thr Leu Val Thr Val Ser Ser
        115                 120

<210> SEQ ID NO 268
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Gly Asp Ser Leu Ser Ser Gly Ser Tyr Phe
1               5                   10

<210> SEQ ID NO 269
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Ile Ser Phe Arg Gly Asp Thr
1               5

<210> SEQ ID NO 270
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Ala Arg Ser Pro Trp Ile Gln Ser Trp Ser Tyr Tyr Phe Asp Tyr
1               5                   10                  15

<210> SEQ ID NO 271
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Asp Ile Gln Met Thr Gln Ser Pro Ser Thr Val Ser Ala Ser Val Gly
1               5                   10                  15

Asp Arg Val Thr Ile Thr Cys Arg Ala Ser Gln Arg Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Gly Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Ile Tyr Tyr Cys Gln Gln Tyr Asn Gly Tyr Pro Trp
                85                  90                  95

Thr Phe Gly Gln Gly Thr Lys Val Glu Ile Lys
            100                 105

<210> SEQ ID NO 272
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Gln Arg Ile Ser Ser Trp
1               5

<210> SEQ ID NO 273
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gln Gln Tyr Asn Gly Tyr Pro Trp Thr
1               5

<210> SEQ ID NO 274
<211> LENGTH: 122
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 274

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Thr Asp
            20                  25                  30

Asn Trp Trp Ser Trp Val Arg Gln Pro Pro Asn Lys Gly Leu Glu Trp
        35                  40                  45

Ile Gly Ala Ile Phe Gln Ser Gly Ser Thr Ile Tyr Asn Pro Ser Leu
    50                  55                  60

Met Ser Arg Val Thr Ile Ser Leu Asp Arg Ser Asn Asn Arg Phe Ser
65                  70                  75                  80

Leu Gln Leu Ile Ser Val Thr Ala Ala Asp Thr Ala Leu Tyr Tyr Cys
                85                  90                  95

Ala Arg Ala Ser Phe His Tyr Gly Ser Gly Asn Tyr Phe Glu Tyr Leu
            100                 105                 110

Gly Gln Gly Thr Leu Val Thr Val Ser Ser
        115                 120

<210> SEQ ID NO 275
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Gly Gly Ser Ile Ser Thr Asp Asn Trp
1               5

<210> SEQ ID NO 276
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Ile Phe Gln Ser Gly Ser Thr
1               5

<210> SEQ ID NO 277
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Ala Arg Ala Ser Phe His Tyr Gly Ser Gly Asn Tyr Phe Glu Tyr
1               5                   10                  15

<210> SEQ ID NO 278
<211> LENGTH: 111
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 278

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Val Gly Thr His
            20                  25                  30

His Val Ser Trp Tyr Gln Gln Leu Pro Gly Thr Ala Pro Lys Leu Leu
        35                  40                  45

Ile Tyr Glu Asn Asp Lys Arg Pro Ser Gly Ile Pro Asn Arg Phe Ser
    50                  55                  60

Gly Ser Lys Ser Gly Thr Ser Ala Thr Leu Ala Ile Ile Gly Leu Gln
65                  70                  75                  80

Thr Gly Asp Glu Ala Asp Tyr Tyr Cys Gly Ser Trp Asp Ser Ser Leu
                85                  90                  95

Ser Ala Phe Trp Val Phe Gly Gly Gly Thr Lys Leu Thr Val Leu
            100                 105                 110

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Ser Ser Asn Val Gly Thr His His
1               5

<210> SEQ ID NO 280
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Glu Asn Asp
1

<210> SEQ ID NO 281
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gly Ser Trp Asp Ser Ser Leu Ser Ala Phe Trp Val
1               5                   10

<210> SEQ ID NO 282
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

```
Gln Val Gln Leu Val Gln Ser Gly Ala Glu Val Lys Lys Pro Gly Ala
1               5                   10                  15

Ser Val Lys Val Ala Cys Lys Ala Ser Gly Tyr Thr Phe Thr Arg Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Asp Ser Gln Lys Phe
    50                  55                  60

Gln Gly Arg Val Thr Ile Thr Arg Asp Thr Ser Ala Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Val Pro Trp Gly Leu Gly Ser Tyr Asn Phe Asp Tyr Trp
            100                 105                 110

Gly Gln Gly Thr Leu Val Ser Ile Ser Ser
            115                 120
```

<210> SEQ ID NO 283
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 283

```
Gly Tyr Thr Phe Thr Arg Tyr Ala
1               5
```

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 284

```
Ile Asn Ala Gly Asn Gly Asn Thr
1               5
```

<210> SEQ ID NO 285
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 285

```
Ala Arg Gly Val Pro Trp Gly Leu Gly Ser Tyr Asn Phe Asp Tyr
1               5                   10                  15
```

<210> SEQ ID NO 286
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 286

```
Gln Thr Val Val Thr Gln Glu Pro Ser Leu Thr Val Ser Pro Gly Gly
1               5                   10                  15
```

-continued

```
Thr Val Thr Leu Ser Cys Ala Ser Asn Thr Gly Ala Val Thr Ser Gly
            20                  25                  30

Tyr Tyr Pro Tyr Trp Phe Gln Gln Lys Pro Gly Gln Ala Pro Arg Thr
        35                  40                  45

Leu Ile Tyr Glu Thr Ser Asn Lys His Pro Trp Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Cys Cys Leu Leu Tyr Tyr Gly Gly
                 85                  90                  95

Thr Trp Val Phe Gly Gly Gly Thr Lys Leu Thr Val Leu
            100                 105

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Thr Gly Ala Val Thr Ser Gly Tyr Tyr
1               5

<210> SEQ ID NO 288
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Glu Thr Ser
1

<210> SEQ ID NO 289
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Leu Leu Tyr Tyr Gly Gly Thr Trp Val
1               5

<210> SEQ ID NO 290
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Ala Pro Gly Lys Gly Leu Glu Trp Val
```

```
                35                  40                  45

Ser Ala Ile Ser Gly Arg Asp Gly Asn Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Leu Tyr Asp Tyr Asp Ser Ser Gly Tyr Phe Asp Phe Asp Tyr Trp
            100                 105                 110

Gly Gln Gly Thr Leu Val Thr Val Ser Ser
        115                 120

<210> SEQ ID NO 291
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Ile Ser Gly Arg Asp Gly Asn Thr
1               5

<210> SEQ ID NO 292
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Thr Leu Tyr Asp Tyr Asp Ser Ser Gly Tyr Phe Asp Phe Asp Tyr
1               5                   10                  15

<210> SEQ ID NO 293
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 293

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Phe
            20                  25                  30

Asn Tyr Val Ser Trp Tyr Gln Gln His Pro Gly Lys Ala Pro Lys Leu
        35                  40                  45

Met Ile Phe Asp Val Thr Gln Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr His Cys Cys Ser Tyr Ala Asn Tyr
                85                  90                  95

Tyr Thr Gly Val Phe Gly Thr Gly Thr Arg Val Thr Val Leu
            100                 105                 110

<210> SEQ ID NO 294
```

<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ser Ser Asp Val Gly Gly Phe Asn Tyr
1               5

<210> SEQ ID NO 295
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Cys Ser Tyr Ala Asn Tyr Tyr Thr Gly Val
1               5                   10

<210> SEQ ID NO 296
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Asn Ile Arg Phe Ala Asp Ser Val
    50                  55                  60

Lys Gly Arg Phe Thr Phe Ser Arg Asp Asn Ala Asn Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ser Arg Thr Val Tyr Gly Asp Ser Pro Leu Ser Tyr Gly
            100                 105                 110

Ile Asp Val Trp Gly Gln Gly Thr Thr Val Thr Val Ser Ser
        115                 120                 125

<210> SEQ ID NO 297
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Ile Asn Ser Asp Gly Ser Asn Ile
1               5

<210> SEQ ID NO 298
<211> LENGTH: 19
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 298

Ala Arg Ala Ser Arg Thr Val Tyr Gly Asp Ser Pro Leu Ser Tyr Gly
1               5                   10                  15

Ile Asp Val

<210> SEQ ID NO 299
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Ser Tyr Ala Leu Thr Gln Pro Pro Ser Val Ser Val Ser Pro Gly Gln
1               5                   10                  15

Thr Ala Ser Ile Thr Cys Ser Gly Asp Lys Leu Gly Asn Lys Phe Ala
            20                  25                  30

Cys Trp Tyr Gln Gln Lys Pro Gly Arg Ser Pro Val Leu Val Ile Tyr
        35                  40                  45

Gln Asp Ser Gln Arg Pro Thr Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Asn Thr His Val
                85                  90                  95

Leu Phe Gly Gly Gly Thr Lys Leu Thr Val Leu
            100                 105

<210> SEQ ID NO 300
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Lys Leu Gly Asn Lys Phe
1               5

<210> SEQ ID NO 301
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Gln Asp Ser
1

<210> SEQ ID NO 302
<211> LENGTH: 10
<212> TYPE: PRT
<213> ORGANISM: Artificial Sequence
<220> FEATURE:
<223> OTHER INFORMATION: Description of Artificial Sequence: Synthetic

```
                    peptide

<400> SEQUENCE: 302

Gln Ala Trp Asp Ser Asn Thr His Val Leu
1               5                   10

<210> SEQ ID NO 303
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Gly Tyr
            20                  25                  30

Gly Met His Trp Val Arg Gln Ala Pro Gly Lys Gly Leu Glu Trp Val
        35                  40                  45

Ala Phe Phe Ser Phe Asp Gly Ser Asn Thr Asp Tyr Val Asp Ser Val
    50                  55                  60

Lys Gly Arg Phe Thr Ile Ser Gly Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Ile Leu Val Leu Pro Ala Ala Val Ser Val Phe Ser Gly
            100                 105                 110

Tyr Tyr Tyr Gly Met Asp Val Trp Gly Gln Gly Thr Thr Val Thr Val
        115                 120                 125

Ser Ser
    130

<210> SEQ ID NO 304
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Gly Phe Thr Phe Ser Gly Tyr Gly
1               5

<210> SEQ ID NO 305
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Phe Ser Phe Asp Gly Ser Asn Thr
1               5

<210> SEQ ID NO 306
<211> LENGTH: 23
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 306

Val Arg Asp Ile Leu Val Leu Pro Ala Ala Val Ser Val Phe Ser Gly
1               5                   10                  15

Tyr Tyr Tyr Gly Met Asp Val
            20

<210> SEQ ID NO 307
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Ile
                85                  90                  95

Thr Phe Gly Gln Gly Thr Arg Leu Glu Ile Lys
            100                 105

<210> SEQ ID NO 308
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Gln Ser Val Arg Ser Tyr
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gln His Arg Ser Asn Trp Pro Ile Thr
1               5

<210> SEQ ID NO 310
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 310

Gln Val Gln Leu Arg Val Ser Gly Pro Gly Leu Val Asn Pro Ser Glu
1               5                   10                  15

Thr Leu Ser Leu Thr Cys Ile Val Ser Gly Asp Ser Leu Arg Asp Tyr
            20                  25                  30

Tyr Trp Ser Trp Ile Arg Gln Ser Pro Gly Lys Gly Leu Glu Trp Ile
        35                  40                  45

Gly Tyr Val Thr Glu Ser Gly Gly Ala His Tyr Asn Pro Ser Leu Glu
    50                  55                  60

Ser Arg Val Thr Ile Ser Val Asp Ala Ser Lys Thr Gln Phe Ser Leu
65                  70                  75                  80

Asn Leu Lys Ser Val Thr Ala Ala Asp Thr Ala Val Tyr Tyr Cys Ala
                85                  90                  95

Arg Asp Ala Tyr Ser Ser Thr Trp Tyr Thr Val Gly Trp Phe Asp Pro
            100                 105                 110

Trp Gly Pro Gly Ser Leu Val Thr Val Ser Ser
        115                 120

<210> SEQ ID NO 311
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gly Asp Ser Leu Arg Asp Tyr Tyr
1               5

<210> SEQ ID NO 312
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Val Thr Glu Ser Gly Gly Ala
1               5

<210> SEQ ID NO 313
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Ala Arg Asp Ala Tyr Ser Ser Thr Trp Tyr Thr Val Gly Trp Phe Asp
1               5                   10                  15

Pro

<210> SEQ ID NO 314
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 314

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Val Gly Val Tyr
            20                  25                  30

Leu Ala Trp Tyr Gln Gln Lys Pro Gly Gln Ala Pro Arg Leu Ile Ile
        35                  40                  45

Tyr Asp Ala Ser Asp Arg Val Ser Gly Val Pro Ala Arg Phe Thr Gly
    50                  55                  60

Ser Gly Ser Gly Thr Asp Phe Thr Leu Thr Ile Thr Ser Leu Glu Pro
65                  70                  75                  80

Glu Asp Phe Ala Val Tyr Phe Cys Gln Gln Arg Thr Ser Gly Leu Thr
                85                  90                  95

Phe Gly Gly Gly Thr Thr Leu Glu Ile Lys
            100                 105

<210> SEQ ID NO 315
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gln Asp Val Gly Val Tyr
1               5

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gln Gln Arg Thr Ser Gly Leu Thr
1               5

<210> SEQ ID NO 317
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Gln Val Glu Leu Val Glu Ser Gly Gly Gly Val Val Gln Pro Gly Arg
1               5                   10                  15

Ser Leu Arg Leu Ser Cys Val Ala Ser Gly Phe Thr Phe Ser Asp Tyr
            20                  25                  30

Gly Met His Trp Val Arg Gln Ala Pro Gly Lys Gly Leu Glu Trp Val
        35                  40                  45

Ala Val Ile Trp Phe Asp Gly Ser Ser Lys Tyr Tyr Ala Asp Ser Val
    50                  55                  60

Lys Gly Arg Phe Thr Ile Ser Arg Asp Asp Ser Lys Asn Thr Val Phe
65                  70                  75                  80

Met Gln Met Asn Asn Val Arg Val Glu Asp Thr Ala Val Tyr Tyr Cys
```

```
                    85                  90                  95

Ala Arg Glu Gln Trp Leu Gly Thr Glu Tyr Phe Gln Asn Trp Gly Gln
            100                 105                 110

Gly Thr Leu Val Thr Val Ser Ser
        115                 120

<210> SEQ ID NO 318
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Gly Phe Thr Phe Ser Asp Tyr Gly
1               5

<210> SEQ ID NO 319
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Ile Trp Phe Asp Gly Ser Ser Lys
1               5

<210> SEQ ID NO 320
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Ala Arg Glu Gln Trp Leu Gly Thr Glu Tyr Phe Gln Asn
1               5                   10

<210> SEQ ID NO 321
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Glu Ile Val Met Thr Gln Ser Pro Ala Thr Leu Ser Leu Phe Pro Gly
1               5                   10                  15

Glu Arg Ala Thr Leu Ser Cys Arg Ala Ser Gln Ser Val Ala Gly Asn
            20                  25                  30

Leu Ala Trp Tyr Gln Gln Lys Pro Gly Gln Ala Pro Arg Leu Leu Ile
        35                  40                  45

Tyr Glu Ala Ser Thr Arg Ala Thr Asp Ile Pro Ala Arg Phe Ser Gly
    50                  55                  60

Ser Gly Ser Glu Thr Glu Phe Thr Leu Thr Ile Ser Ser Leu Gln Ser
65                  70                  75                  80

Glu Asp Phe Ala Val Tyr Tyr Cys Gln Gln Tyr Lys Lys Trp Leu Ile
                85                  90                  95
```

Thr Phe Gly Gln Gly Thr Arg Leu Glu Ile Lys
            100                 105

<210> SEQ ID NO 322
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gln Ser Val Ala Gly Asn
1               5

<210> SEQ ID NO 323
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Glu Ala Ser
1

<210> SEQ ID NO 324
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Gln Gln Tyr Lys Lys Trp Leu Ile Thr
1               5

<210> SEQ ID NO 325
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Gln Leu Gln Leu Gln Gln Trp Gly Ala Gly Leu Val Lys Pro Ser Glu
1               5                   10                  15

Thr Leu Ser Leu Thr Cys Thr Val Ser Gly Gly Ser Leu Ser Gly His
            20                  25                  30

Phe Trp Ser Trp Ile Arg Gln Ser Pro Glu Lys Gly Leu Glu Trp Ile
        35                  40                  45

Gly Glu Ile Asn His Ser Gly Arg Lys Asn Tyr Asn Pro Ser Leu Met
    50                  55                  60

Ile Arg Val Asp Ile Ser Ile Asp Thr Ser Lys Asn Gln Phe Ser Met
65                  70                  75                  80

Arg Met Thr Ser Leu Thr Ala Ala Asp Ser Ala Val Tyr Tyr Cys Ala
                85                  90                  95

Arg Val Gly Arg Asn Ile Val Asp Thr Asp Asp Ala Phe Asp Val Trp
            100                 105                 110

Gly Arg Gly Thr Leu Val Thr Val Ser Ser
        115                 120

<210> SEQ ID NO 326
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Gly Gly Ser Leu Ser Gly His Phe
1               5

<210> SEQ ID NO 327
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Ile Asn His Ser Gly Arg Lys
1               5

<210> SEQ ID NO 328
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Ala Arg Val Gly Arg Asn Ile Val Asp Thr Asp Asp Ala Phe Asp Val
1               5                   10                  15

<210> SEQ ID NO 329
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Glu Ile Val Leu Thr Gln Ser Pro Gly Thr Leu Ser Leu Ser Pro Gly
1               5                   10                  15

Asp Thr Val Thr Leu Ser Cys Arg Ala Ser Gln Thr Ile Asp Ser Ile
            20                  25                  30

Tyr Leu Ala Trp Tyr Gln Gln Arg Pro Gly Gln Ala Pro Arg Leu Leu
        35                  40                  45

Ile Tyr Gly Ala Ser Thr Arg Ala Thr Gly Thr Pro Asp Arg Phe Ser
    50                  55                  60

Gly Gly Gly Ser Gly Thr Asp Phe Thr Leu Thr Ile Thr Arg Leu Glu
65                  70                  75                  80

Pro Glu Asp Phe Ala Val Tyr Phe Cys Gln Gln Tyr Gly Thr Ser Pro
                85                  90                  95

Pro Ile Thr Phe Gly Arg Gly Thr Arg Leu Glu Ile Lys
            100                 105

<210> SEQ ID NO 330
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 330

Gln Thr Ile Asp Ser Ile Tyr
1               5

<210> SEQ ID NO 331
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Gln Gln Tyr Gly Thr Ser Pro Pro Ile Thr
1               5                   10

<210> SEQ ID NO 332
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Gln Val Gln Leu Leu Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asn Ile His Trp Val Arg Gln Ala Pro Gly Gln Ser Phe Glu Trp Met
        35                  40                  45

Gly Trp Ile His Val Gly Asn Gly Glu Thr Lys Tyr Ser Gln Asn Phe
    50                  55                  60

Gln Asp Arg Val Ala Ile Thr Arg Asp Thr Ser Ala Asn Thr Val Tyr
65                  70                  75                  80

Met Glu Leu Ser Pro Leu Arg Ser Glu Asp Thr Ala Leu Tyr Tyr Cys
                85                  90                  95

Val Arg Asp His Val Thr Ala Ile Val Val Gly Leu Phe Asp Pro Trp
            100                 105                 110

Gly Gln Gly Thr Leu Val Thr Val Ser Ser
        115                 120

<210> SEQ ID NO 333
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gly Tyr Thr Phe Thr Ser Tyr Asn
1               5

<210> SEQ ID NO 334
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 334

Ile His Val Gly Asn Gly Glu Thr
1               5

<210> SEQ ID NO 335
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Val Arg Asp His Val Thr Ala Ile Val Val Gly Leu Phe Asp Pro
1               5                   10                  15

<210> SEQ ID NO 336
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Gln Ser Ala Leu Thr Gln Pro Ala Ser Val Ser Gly Ser Pro Gly Gln
1               5                   10                  15

Ser Ile Thr Ile Ser Cys Ser Gly Thr Ser Thr Asp Val Gly Ala Tyr
            20                  25                  30

Lys Tyr Val Ser Trp Tyr Gln His Pro Gly Arg Ser Pro Lys Val
        35                  40                  45

Ile Leu Tyr Glu Val Asp Asn Arg Pro Ser Gly Val Ser Ile Arg Phe
    50                  55                  60

Ser Gly Ser Lys Ser Gly Asn Thr Ala Ser Leu Thr Ile Ser Gly Leu
65                  70                  75                  80

Arg Ala Glu Asp Glu Ala Asp Tyr Tyr Cys Ser Ser Phe Thr Ser Ser
                85                  90                  95

Ser Thr Trp Val Phe Gly Gly Gly Thr Lys Val Thr Val Leu
            100                 105                 110

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Ser Thr Asp Val Gly Ala Tyr Lys Tyr
1               5

<210> SEQ ID NO 338
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Glu Val Asp
1

<210> SEQ ID NO 339
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Ser Ser Phe Thr Ser Ser Ser Thr Trp Val
1               5                   10

<210> SEQ ID NO 340
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ser Ile Ser Trp Val Arg Gln Ala Pro Gly Gln Gly Leu Glu Trp Met
        35                  40                  45

Gly Gly Ile Ile Pro Ile Phe Gly Ser Gly Ser Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Ser Ser Asp Asp Thr Ala Val Tyr Tyr Cys
                85                  90                  95

Ala Arg Gly Glu Ser Pro Ser Asn Phe Val Tyr Tyr Gly Met Asp Val
            100                 105                 110

Trp Gly Gln Gly Thr Thr Val Thr Val Ser Ser
        115                 120

<210> SEQ ID NO 341
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Gly Gly Thr Phe Ser Ser Tyr Ser
1               5

<210> SEQ ID NO 342
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ile Ile Pro Ile Phe Gly Ser Gly
1               5

<210> SEQ ID NO 343
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Ala Arg Gly Glu Ser Pro Ser Asn Phe Val Tyr Tyr Gly Met Asp Val
1               5                   10                  15

<210> SEQ ID NO 344
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Asp Ile Val Leu Thr Gln Ser Pro Leu Ser Leu Pro Val Thr Pro Gly
1               5                   10                  15

Glu Pro Ala Ser Ile Ser Cys Arg Ser Ser His Ser Leu Leu His Ser
                20                  25                  30

Asn Gly Tyr Asn His Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Leu Val Thr Phe Gly Pro Gly Thr Lys Val Asp Ile Lys
            100                 105                 110

<210> SEQ ID NO 345
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

His Ser Leu Leu His Ser Asn Gly Tyr Asn His
1               5                   10

<210> SEQ ID NO 346
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Met Gln Ala Leu Leu Val Thr
1               5

<210> SEQ ID NO 347
<211> LENGTH: 121
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 347

Glu Val Lys Val Val Glu Ser Gly Gly Gly Leu Val Gln Pro Gly Gly
1               5                   10                  15

Ser Leu Arg Leu Ser Cys Ala Ala Ser Glu Phe Thr Phe Thr Tyr Tyr
            20                  25                  30

Trp Met Ser Trp Ile Arg Gln Ala Pro Gly Lys Gly Leu Glu Trp Val
        35                  40                  45

Ala Asn Val Asn Gly Asp Ala Thr Glu Lys Tyr Tyr Val Asp Ser Val
    50                  55                  60

Lys Gly Arg Phe Thr Ile Ser Arg Asp Asn Pro Lys Lys Thr Val Tyr
65                  70                  75                  80

Leu Gln Met Asn Ser Leu Arg Val Glu Asp Thr Ala Val Tyr Tyr Cys
                85                  90                  95

Ala Arg Val Gly Thr Thr Val Val Asn Asp Gly Phe Asp Leu Trp Gly
            100                 105                 110

Leu Gly Thr Met Val Thr Val Ser Ser
        115                 120

<210> SEQ ID NO 348
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 348

Glu Phe Thr Phe Thr Tyr Tyr Trp
1               5

<210> SEQ ID NO 349
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 349

Val Asn Gly Asp Ala Thr Glu Lys
1               5

<210> SEQ ID NO 350
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 350

Ala Arg Val Gly Thr Thr Val Val Asn Asp Gly Phe Asp Leu
1               5                   10

<210> SEQ ID NO 351
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 351

Ser Tyr Val Leu Thr Gln Ser His Ser Val Ser Val Ala Pro Gly Gln
1               5                   10                  15

Thr Ala Arg Ile Thr Cys Gly Gly Glu Asn Ile Gly Gly Lys Gly Val
            20                  25                  30

His Trp Tyr Gln Gln Lys Pro Gly Gln Ala Pro Leu Leu Val Val Ser
        35                  40                  45

Ser Asp Thr Gly Arg Arg Ser Val Thr Pro Asp Arg Phe Ser Gly Ser
    50                  55                  60

Asn Ser Gly Asp Thr Ala Thr Leu Ile Ile Ser Arg Val Glu Ala Gly
65                  70                  75                  80

Asp Glu Ala Asp Tyr Tyr Cys Gln Val Trp Asp Pro Thr Ser Glu Tyr
                85                  90                  95

Val Phe Gly Ser Gly Thr Lys Val Thr Val Leu
            100                 105

<210> SEQ ID NO 352
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Asn Ile Gly Gly Lys Gly
1               5

<210> SEQ ID NO 353
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ser Asp Thr
1

<210> SEQ ID NO 354
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Gln Val Trp Asp Pro Thr Ser Glu Tyr Val
1               5                   10

<210> SEQ ID NO 355
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

```
Gln Leu Gln Leu Gln Glu Ser Gly Ser Gly Leu Val Lys Pro Ser Gln
1               5                   10                  15

Thr Leu Ser Leu Thr Cys Ala Val Ser Gly Gly Ser Ile Ser Ser Gly
            20                  25                  30

Asp Tyr Ser Trp Ser Trp Ile Arg Gln Pro Pro Gly Lys Gly Leu Glu
        35                  40                  45

Trp Ile Gly Phe Arg Tyr Tyr Ser Gly Thr Thr Phe Tyr Asn Pro Ser
    50                  55                  60

Leu Glu Ser Arg Leu Thr Ile Ser Ile Asp Arg Ser Thr Asn Gln Phe
65                  70                  75                  80

Ser Leu Gln Leu Thr Ser Val Thr Ala Ala Asp Thr Ala Val Tyr Phe
                85                  90                  95

Cys Ala Ser Phe Arg Pro Leu Leu Arg Phe Leu Asp Pro Glu Gly Leu
                100                 105                 110

Phe Glu Tyr Trp Gly Gln Gly Ile Leu Val Thr Val Ser Ser
            115                 120                 125
```

<210> SEQ ID NO 356
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

```
Gly Gly Ser Ile Ser Ser Gly Asp Tyr Ser
1               5                   10
```

<210> SEQ ID NO 357
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

```
Arg Tyr Tyr Ser Gly Thr Thr
1               5
```

<210> SEQ ID NO 358
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

```
Ala Ser Phe Arg Pro Leu Leu Arg Phe Leu Asp Pro Glu Gly Leu Phe
1               5                   10                  15

Glu Tyr
```

<210> SEQ ID NO 359
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

-continued

```
Glu Leu Val Met Thr Gln Ser Pro Ala Thr Leu Ser Val Ser Pro Gly
1               5                   10                  15

Ala Arg Ala Thr Leu Ser Cys Arg Ala Ser Pro Gly Ala Asn Ser His
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asp Trp Pro Tyr
                85                  90                  95

Thr Phe Gly Gln Gly Thr Lys Leu Glu Ile Lys
            100                 105
```

<210> SEQ ID NO 360
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

```
Pro Gly Ala Asn Ser His
1               5
```

<210> SEQ ID NO 361
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

```
Gln Gln Tyr Asn Asp Trp Pro Tyr Thr
1               5
```

<210> SEQ ID NO 362
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

```
Gln Val Gln Leu Val Gln Ser Gly Ala Ala Val Lys Lys Pro Gly Ala
1               5                   10                  15

Ser Val Arg Ile Ser Cys Glu Ala Ser Gly Tyr Thr Phe Thr Gly Tyr
            20                  25                  30

Asn Ile His Trp Val Arg Gln Ala Pro Gly Gln Gly Leu Glu Trp Met
        35                  40                  45

Gly Trp Val Asn Pro Asn Asn Gly Gly Thr Lys Phe Ala Gln Lys Phe
    50                  55                  60

Glu Gly Trp Val Thr Met Thr Val Ala Thr Ser Ile Asn Thr Val Tyr
65                  70                  75                  80

Met Glu Leu Thr Gly Leu Lys Ser Gly Asp Thr Ala Val Tyr Phe Cys
                85                  90                  95

Ala Arg Asp His Gly Asp Ser Phe Asp Gln Trp Gly Gln Gly Thr Leu
```

```
                100               105               110
Val Thr Val Ser Ser
        115

<210> SEQ ID NO 363
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Gly Tyr Thr Phe Thr Gly Tyr Asn
1               5

<210> SEQ ID NO 364
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Val Asn Pro Asn Asn Gly Gly Thr
1               5

<210> SEQ ID NO 365
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Ala Arg Asp His Gly Asp Ser Phe Asp Gln
1               5                   10

<210> SEQ ID NO 366
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Glu Ile Val Leu Thr Gln Ser Pro Asp Thr Leu Ser Leu Ser Pro Gly
1               5                   10                  15

Asp Arg Ala Thr Leu Ser Cys Arg Ala Ser His Ser Leu Asn Asn Asp
            20                  25                  30

Tyr Leu Ala Trp Tyr Gln His Arg Pro Gly Gln Ala Pro Arg Leu Leu
        35                  40                  45

Ile Tyr Gly Thr Ser His Gly Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Thr Glu Asp Phe Ala Val Tyr Tyr Cys His His Tyr Gly Lys Ser Leu
                85                  90                  95

Phe Pro Phe Gly Pro Gly Thr Lys Val Asp Ile Lys
                100                 105
```

<210> SEQ ID NO 367
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

His Ser Leu Asn Asn Asp Tyr
1               5

<210> SEQ ID NO 368
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

His His Tyr Gly Lys Ser Leu Phe Pro
1               5

<210> SEQ ID NO 369
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Thr Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg Lys His Thr Ser Gly Trp Tyr Asp Arg Gly Gly Asp
            100                 105                 110

Val Trp Gly Gln Gly Thr Thr Val Thr Val Ser Ser
        115                 120

<210> SEQ ID NO 370
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Gly Phe Thr Phe Ser Gly Ser Ala
1               5

<210> SEQ ID NO 371

-continued

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Ile Arg Ser Lys Ala Asn Thr Tyr Ala Thr
1               5                   10

<210> SEQ ID NO 372
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Thr Arg Lys His Thr Ser Gly Trp Tyr Asp Arg Gly Gly Asp Val
1               5                   10                  15

<210> SEQ ID NO 373
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105

<210> SEQ ID NO 374
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Gln Asp Ile Ser Asn Tyr
1               5

<210> SEQ ID NO 375
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 375

Gln Gln Tyr Asp Asn Leu Pro Leu Thr
1               5

<210> SEQ ID NO 376
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Val Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Asp Cys Thr Val Thr Asp Ala Pro Leu Ser Tyr Trp Gly Gln
            100                 105                 110

Gly Thr Leu Val Thr Val Ser Ser
        115                 120

<210> SEQ ID NO 377
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Gly Phe Thr Val Ser Asn Tyr Ala
1               5

<210> SEQ ID NO 378
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ile Ser Gly Ser Gly Gly Ser Thr
1               5

<210> SEQ ID NO 379
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Ala Ile Asp Cys Thr Val Thr Asp Ala Pro Leu Ser Tyr
1               5                   10

<210> SEQ ID NO 380
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Ala Ile Gln Met Thr Gln Ser Pro Ser Ser Leu Ser Pro Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Arg
                85                  90                  95

Thr Phe Gly Gln Gly Thr Lys Val Glu Ile Lys
            100                 105

<210> SEQ ID NO 381
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Gln Gly Ile Arg Asn Asp
1               5

<210> SEQ ID NO 382
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Leu Gln Asp Tyr Asn Tyr Pro Arg Thr
1               5

<210> SEQ ID NO 383
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 383

Gln Val Gln Leu Glu Gln Ser Gly Ala Glu Val Arg Lys Pro Gly Ser
1               5                   10                  15

```
Ser Val Lys Val Ser Cys Lys Ala Ser Gly Thr Thr Phe Ser Asn His
            20                  25                  30

Ala Met Ser Trp Val Arg Gln Ala Pro Gly Gln Gly Leu Glu Trp Met
        35                  40                  45

Gly Gly Ile Ile Pro Leu Val Asp Lys Ser Met Tyr Ala Leu Lys Phe
50                  55                  60

Gln Gly Arg Val Thr Ile Thr Ala Asp Glu Ser Arg Asn Thr Val Tyr
65                  70                  75                  80

Met Glu Leu Ser Ser Leu Gly Ser Glu Asp Thr Ala Val Tyr Tyr Cys
                85                  90                  95

Ala Arg Ser Phe Ala Asp Ile Thr Thr Phe Gly Phe Val Val Asn Phe
            100                 105                 110

His Tyr Tyr Tyr Thr Leu Asp Val Trp Gly Gln Gly Thr Pro Val Thr
        115                 120                 125

Val Ser Ser
    130

<210> SEQ ID NO 384
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 384

Gly Thr Thr Phe Ser Asn His Ala
1               5

<210> SEQ ID NO 385
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Ile Ile Pro Leu Val Asp Lys Ser
1               5

<210> SEQ ID NO 386
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ala Arg Ser Phe Ala Asp Ile Thr Thr Phe Gly Phe Val Val Asn Phe
1               5                   10                  15

His Tyr Tyr Tyr Thr Leu Asp Val
            20

<210> SEQ ID NO 387
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 387
```

```
Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Asp Asn
            20                  25                  30

Tyr Val Gln Trp Phe Gln Gln Arg Pro Gly Ser Ala Pro Thr Thr Leu
        35                  40                  45

Ile Tyr Glu Asp Asn Arg Arg Pro Ser Gly Val Pro Asp Arg Phe Ser
    50                  55                  60

Gly Ser Val Asp Ser Ser Asn Ser Ala Ser Leu Thr Ile Ser Gly
65                  70                  75                  80

Leu Lys Pro Glu Asp Glu Ala Asp Tyr Tyr Cys Gln Ser Tyr Asp Thr
                85                  90                  95

Thr Gln Arg Val Phe Gly Gly Gly Thr Lys Leu Thr Val Leu
            100                 105                 110

<210> SEQ ID NO 388
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Ser Gly Ser Ile Ala Asp Asn Tyr
1               5

<210> SEQ ID NO 389
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Glu Asp Asn
1

<210> SEQ ID NO 390
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Gln Ser Tyr Asp Thr Thr Gln Arg Val
1               5

<210> SEQ ID NO 391
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 391

Gln Leu Gln Leu Gln Glu Ser Gly Ser Arg Leu Val Lys Pro Ser Gln
1               5                   10                  15

Thr Leu Ser Leu Thr Cys Ala Val Ser Gly Gly Ser Ile Asn Ser Gly
```

```
                    20                  25                  30

Gly Tyr Ser Trp Ser Trp Ile Arg Gln Pro Gly Lys Gly Leu Glu
            35                  40                  45

Trp Ile Gly Asn Ile Tyr His Gly Glu Thr Thr His Tyr Asn Pro Ser
        50                  55                  60

Leu Lys Ser Arg Val Thr Ile Ser Ile Asp Lys Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Ala Pro Leu Gly Asn Tyr Tyr Asp Thr Ser Gly Tyr Leu
            100                 105                 110

Gln Pro Phe Asp Tyr Trp Gly Pro Gly Ala Leu Val Thr Val Ser Ser
        115                 120                 125

<210> SEQ ID NO 392
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Gly Gly Ser Ile Asn Ser Gly Gly Tyr Ser
1               5                   10

<210> SEQ ID NO 393
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ile Tyr His Gly Glu Thr Thr
1               5

<210> SEQ ID NO 394
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Ala Arg Ala Pro Leu Gly Asn Tyr Tyr Asp Thr Ser Gly Tyr Leu Gln
1               5                   10                  15

Pro Phe Asp Tyr
            20

<210> SEQ ID NO 395
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Gly Ile Ile Asn Asp
            20                  25                  30

Leu Gly Trp Tyr Gln Gln Arg Pro Gly Arg Ala Pro Thr Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Ala Asp Phe Ala Thr Tyr Phe Cys Leu Gln Tyr Asn Ser Tyr Pro Pro
                85                  90                  95

Thr Phe Gly Gln Gly Thr Lys Val Glu Ile Lys
            100                 105

<210> SEQ ID NO 396
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Gln Gly Ile Ile Asn Asp
1               5

<210> SEQ ID NO 397
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 397

Leu Gln Tyr Asn Ser Tyr Pro Pro Thr
1               5

<210> SEQ ID NO 398
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 398

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Ile Phe Arg Asp His
            20                  25                  30

Gly Met Ser Trp Val Arg Gln Ala Pro Gly Lys Gly Leu Glu Trp Val
        35                  40                  45

Ser Gly Ile Asn Trp Asn Gly Ala Asn Thr Gly Tyr Ala Asp Ser Val
    50                  55                  60

Lys Gly Arg Ser Thr Ile Ser Arg Asp Asn Ala Lys Asn Ser Leu Tyr
65                  70                  75                  80

Leu Gln Met Ser Ser Leu Arg Ala Asp Asp Thr Ala Leu Tyr His Cys
                85                  90                  95

Val Ser His Asp Tyr Tyr Tyr Gly Leu Asp Val Trp Gly Pro Gly Thr
            100                 105                 110

Thr Val Ile Val Ser Ser

<210> SEQ ID NO 399
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Gly Phe Ile Phe Arg Asp His Gly
1               5

<210> SEQ ID NO 400
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 400

Ile Asn Trp Asn Gly Ala Asn Thr
1               5

<210> SEQ ID NO 401
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 401

Val Ser His Asp Tyr Tyr Tyr Gly Leu Asp Val
1               5                   10

<210> SEQ ID NO 402
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Asp
            20                  25                  30

Asn Tyr Val Ser Trp Tyr Gln Gln His Pro Gly Lys Val Pro Lys Leu
        35                  40                  45

Ile Ile His Asp Val Ser Glu Arg Pro Ser Gly Val Pro Asp Arg Phe
    50                  55                  60

Ser Gly Ser Lys Ser Ala Asn Thr Ala Ser Leu Thr Ile Ser Gly Leu
65                  70                  75                  80

Gln Ala Asp Asp Glu Ala Asp Tyr Tyr Cys Cys Ser Tyr Ala Gly Thr
                85                  90                  95

Tyr Thr Phe Gly Gly Gly Thr Arg Leu Thr Val Leu
            100                 105

<210> SEQ ID NO 403
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 403

Ser Ser Asp Val Gly Gly Asp Asn Tyr
1               5

<210> SEQ ID NO 404
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 404

Asp Val Ser
1

<210> SEQ ID NO 405
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 405

Cys Ser Tyr Ala Gly Thr Tyr Thr
1               5

<210> SEQ ID NO 406
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 406

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln Leu Pro Gly Lys Gly Leu Glu
        35                  40                  45

Trp Ile Gly Tyr Ile Tyr Tyr Ser Gly Ser Thr Tyr Asn Pro Ser
    50                  55                  60

Leu Lys Ser Arg Val Thr Ile Ser Val Asp Thr Ser Lys Asn Gln Leu
65                  70                  75                  80

Ser Leu Asn Leu Ser Ser Val Thr Ala Ala Asp Thr Ala Val Tyr Tyr
                85                  90                  95

Cys Ala Arg Gly Arg Arg Ile Ser Ile Ser Gly Val Val Thr Pro Leu
            100                 105                 110

Phe Asp Tyr Trp Gly Gln Gly Thr Leu Val Thr Val Ser Ser
        115                 120                 125

<210> SEQ ID NO 407
<211> LENGTH: 107
<212> TYPE: PRT
<213> ORGANISM: Artificial Sequence
```

-continued

```
<220> FEATURE:
<223> OTHER INFORMATION: Description of Artificial Sequence: Synthetic
      polypeptide

<400> SEQUENCE: 407

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Val Pro Leu
                85                  90                  95

Thr Phe Gly Gly Gly Thr Lys Val Glu Ile Lys
            100                 105

<210> SEQ ID NO 408
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Gln Val Gln Leu Val Gln Ser Gly Ala Glu Val Lys Lys Pro Gly Ala
1               5                   10                  15

Ser Val Lys Val Ser Cys Gln Ala Ser Gly Tyr Thr Phe Thr Arg Tyr
            20                  25                  30

Asp Ile Asn Trp Val Arg Gln Ala Thr Gly Gln Gly Leu Glu Trp Met
        35                  40                  45

Gly Trp Leu Asn Pro Lys Ser Gly Asp Thr Gly Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Thr Ser Leu Thr Ser Asp Asp Thr Ala Val Tyr Tyr Cys
                85                  90                  95

Ala Arg Gly Val Asp Ala Asn His Trp Gly Gln Gly Ser Leu Val Thr
            100                 105                 110

Val Ser Ser
        115

<210> SEQ ID NO 409
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Gly Tyr Thr Phe Thr Arg Tyr Asp
1               5

<210> SEQ ID NO 410
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Leu Asn Pro Lys Ser Gly Asp Thr
1               5

<210> SEQ ID NO 411
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

Ala Arg Gly Val Asp Ala Asn His
1               5

<210> SEQ ID NO 412
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Asp Ile Val Val Thr Gln Ser Pro Asp Ser Leu Ala Val Ser Leu Gly
1               5                   10                  15

Glu Arg Ala Thr Ile Asn Cys Lys Ser Ser Gln Ser Ile Phe Asp Thr
            20                  25                  30

Ser Ser Asn Lys Asn Tyr Leu Ala Trp Phe Arg Gln Arg Pro Gly Gln
        35                  40                  45

Pro Pro Gln Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Leu Pro His Ala Phe Gly Gln Gly Thr Lys Leu Glu Ile
            100                 105                 110

Lys

<210> SEQ ID NO 413
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Gln Ser Ile Phe Asp Thr Ser Ser Asn Lys Asn Tyr
1               5                   10

<210> SEQ ID NO 414
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 414

His Gln Tyr Tyr Ser Leu Pro His Ala
1               5

<210> SEQ ID NO 415
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Glu Ala Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Ile His Trp Val Arg Gln Ala Pro Gly Lys Gly Leu Val Trp Val
        35                  40                  45

Ser Arg Ile Asn Ser Asp Gly Ser Ser Thr Arg Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Ala Ser Arg Thr Val Tyr Gly Asp Ser Pro Leu Ser Asn Gly
            100                 105                 110

Met Asp Val Trp Gly Gln Gly Thr Lys Val Thr Val Ser Ser
        115                 120                 125

<210> SEQ ID NO 416
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Gly Phe Thr Phe Ser Ser Tyr Tyr
1               5

<210> SEQ ID NO 417
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Ile Asn Ser Asp Gly Ser Ser Thr
1               5

<210> SEQ ID NO 418
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 418

Ala Arg Ala Ser Arg Thr Val Tyr Gly Asp Ser Pro Leu Ser Asn Gly
1               5                   10                  15

Met Asp Val

<210> SEQ ID NO 419
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Phe Ala
            20                  25                  30

Cys Trp Tyr Gln Gln Lys Pro Gly His Ser Pro Val Leu Val Ile Tyr
        35                  40                  45

Gln Asp Asp Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr His Val
                85                  90                  95

Val Phe Gly Gly Gly Thr Lys Leu Thr Val Leu
            100                 105

<210> SEQ ID NO 420
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Lys Leu Gly Asp Lys Phe
1               5

<210> SEQ ID NO 421
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 421

Gln Asp Asp
1

<210> SEQ ID NO 422
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 422

```
Gln Ala Trp Asp Ser Ser Thr His Val Val
1               5                   10

<210> SEQ ID NO 423
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Asn Thr Tyr
            20                  25                  30

Asn Met Asn Trp Val Arg Gln Ala Pro Gly Lys Gly Leu Glu Trp Ile
        35                  40                  45

Ser Asp Ile Thr Ser Ser Gly Ser Met Arg Ser Tyr Ala Asp Ala Val
    50                  55                  60

Lys Gly Arg Phe Thr Ile Ser Arg Asp Asn Ala Lys Asn Ser Leu His
65                  70                  75                  80

Leu Gln Met Asn Ser Leu Arg Val Glu Asp Thr Ala Val Tyr Tyr Cys
                85                  90                  95

Thr Arg Gly Trp His Asp Asp Leu Trp Ser Gly Tyr Ser Tyr Gly Leu
            100                 105                 110

Asp Val Trp Gly Gln Gly Thr Thr Val Thr Val Ser Ser
        115                 120                 125

<210> SEQ ID NO 424
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 424

Gly Phe Ser Phe Asn Thr Tyr Asn
1               5

<210> SEQ ID NO 425
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Ile Thr Ser Ser Gly Ser Met Arg
1               5

<210> SEQ ID NO 426
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Thr Arg Gly Trp His Asp Asp Leu Trp Ser Gly Tyr Ser Tyr Gly Leu
1               5                   10                  15
```

Asp Val

<210> SEQ ID NO 427
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Asp Ile Gln Met Thr Gln Ser Pro Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Arg Pro Gly Lys Ala Pro Arg Cys Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Asn Leu Gln Ala
65                  70                  75                  80

Glu Asp Phe Ala Thr Tyr Tyr Cys Leu Gln His Lys Ser Tyr Pro Leu
                85                  90                  95

Thr Phe Gly Pro Gly Thr Lys Val Asp Ile Lys
            100                 105

<210> SEQ ID NO 428
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 428

Leu Gln His Lys Ser Tyr Pro Leu Thr
1               5

<210> SEQ ID NO 429
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

Gln Leu Leu Leu Leu Gly Pro Gly Pro Gly Val Val Arg Pro Ser Glu
1               5                   10                  15

Thr Leu Ser Leu Thr Cys Asn Val Ser Gly His Ser Ile Thr Asp Ser
            20                  25                  30

Pro Tyr Tyr Trp Gly Trp Ile Arg Gln Ala Pro Gly Lys Gly Leu Glu
        35                  40                  45

Trp Ile Gly His Phe Tyr Tyr Ser Asp Tyr Tyr Tyr Asn Pro Ser
    50                  55                  60

Leu Lys Ser Arg Val Asn Val Ser Val Asp Thr Ser Lys Asn His Leu
65                  70                  75                  80

Phe Leu Ala Leu Thr Ser Val Thr Ala Ala Asp Thr Ala Val Tyr Tyr
                85                  90                  95

Cys Ala Arg Gly Phe Gly Gly Tyr Asp Ser Pro Ile Trp Ala Ile Trp

```
                100                 105                 110
Gly Gln Gly Thr Leu Val Thr Val Ser Ser
        115                 120

<210> SEQ ID NO 430
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 430

Gly His Ser Ile Thr Asp Ser Pro Tyr Tyr
1               5                   10

<210> SEQ ID NO 431
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 431

Phe Tyr Tyr Ser Asp Tyr Thr
1               5

<210> SEQ ID NO 432
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 432

Ala Arg Gly Phe Gly Gly Tyr Asp Ser Pro Ile Trp Ala Ile
1               5                   10

<210> SEQ ID NO 433
<211> LENGTH: 103
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 433

Ser His Ala Val Thr Gln Pro Pro Ser Val Ser Val Ala Pro Gly Gln
1               5                   10                  15

Thr Ala Ser Leu Thr Cys Ala Gly Asp Asp Ile Glu Glu Asn Thr Val
            20                  25                  30

His Trp Tyr Gln Gln Lys Pro Gly Gln Ala Pro Val Leu Val Ile Tyr
        35                  40                  45

Tyr Thr Thr Asp Arg Pro Ser Ala Ile Pro Glu Arg Phe Phe Gly Ser
    50                  55                  60

Lys Ser Gly Asn Thr Ala Thr Leu Ser Ile Ala Arg Val Glu Ala Gly
65                  70                  75                  80

Asp Glu Ala Asp Tyr Tyr Cys Gln Val Ser Asp Arg Val Phe Gly Gly
                85                  90                  95

Gly Thr Lys Leu Thr Val Leu
            100
```

```
<210> SEQ ID NO 434
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 434

Asp Ile Glu Glu Asn Thr
1               5

<210> SEQ ID NO 435
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 435

Tyr Thr Thr
1

<210> SEQ ID NO 436
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 436

Gln Val Ser Asp Arg Val
1               5

<210> SEQ ID NO 437
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 437

Glu Val Gln Leu Val Gln Ser Gly Gly Gly Leu Val Lys Pro Gly Gly
1               5                   10                  15

Ser Leu Arg Leu Ser Cys Ala Ala Ser Gly Ser Thr Leu Thr Asn Tyr
            20                  25                  30

Asn Ile Asn Trp Val Arg Gln Ala Pro Gly Lys Gly Leu Gln Trp Val
        35                  40                  45

Ser Ser Ile Ser Gly Thr Arg Asp Tyr Thr Tyr Tyr Ala Asp Ser Val
    50                  55                  60

Val Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Gly Arg Glu Val Gly Gly Asp Tyr Asp Ser Tyr Asp Trp Gly
            100                 105                 110

Gln Gly Thr Leu Val Thr Val Ser Ser
        115                 120

<210> SEQ ID NO 438
```

```
<210> SEQ ID NO 438
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 438

Gly Ser Thr Leu Thr Asn Tyr Asn
1               5

<210> SEQ ID NO 439
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

Ile Ser Gly Thr Arg Asp Tyr Thr
1               5

<210> SEQ ID NO 440
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

Ala Arg Gly Arg Glu Val Gly Gly Asp Tyr Asp Ser Tyr Asp
1               5                   10

<210> SEQ ID NO 441
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Thr Phe
            20                  25                  30

Leu His Trp Tyr Gln Gln Lys Pro Gly Lys Ala Pro Ser Val Leu Ile
        35                  40                  45

Tyr Gly Ala Ser Asp Leu Lys Thr Gly Val Pro Ser Arg Phe Ser Gly
    50                  55                  60

Ser Gly Ser Gly Thr His Phe Thr Leu Thr Ile Ser Ser Leu Gln Pro
65                  70                  75                  80

Glu Asp Ile Ala Thr Tyr Tyr Cys Gln Gln Tyr Asp His Leu Pro Leu
                85                  90                  95

Thr Phe Gly Gly Gly Thr Lys Val Glu Ile Lys
            100                 105

<210> SEQ ID NO 442
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 442

Gln Asp Ile Ser Thr Phe
1               5

<210> SEQ ID NO 443
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Gln Gln Tyr Asp His Leu Pro Leu Thr
1               5

<210> SEQ ID NO 444
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Ser Arg Leu Gly Trp Ala Tyr Asp Ala Phe Asp Ile Trp Gly
            100                 105                 110

Gln Gly Thr Met Val Thr Val Ser Ser
        115                 120

<210> SEQ ID NO 445
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 445

Gly Phe Thr Val Ser Ser Asn Tyr
1               5

<210> SEQ ID NO 446
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 446

Ile Tyr Ser Gly Gly Ser Thr
1               5

<210> SEQ ID NO 447
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Ala Arg Asp Ser Arg Leu Gly Trp Ala Tyr Asp Ala Phe Asp Ile
1               5                   10                  15

<210> SEQ ID NO 448
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Asp
                85                  90                  95

Gly Thr Phe Gly Gln Gly Thr Lys Val Glu Ile Lys
            100                 105

<210> SEQ ID NO 449
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Met Gln Asp Gly Thr
1               5

<210> SEQ ID NO 450
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Gln Val Gln Leu Val Gln Ser Gly Ser Glu Leu Lys Lys Pro Gly Ala
1               5                   10                  15
```

-continued

```
Ser Val Lys Ala Ser Cys Lys Ala Ser Gly Tyr Thr Phe Ser Asn Tyr
                20                  25                  30

Ala Val Asn Trp Val Arg Gln Ala Pro Gly Gln Gly Leu Glu Trp Met
            35                  40                  45

Gly Trp Ile Asn Thr Lys Thr Gly Asn Pro Thr Tyr Gly Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ala Ala Asp Tyr Gly Glu Pro Tyr Tyr Tyr Gly Met Asp Val
            100                 105                 110

Trp Gly Gln Gly Thr Thr Val Thr Val Ser Ser
        115                 120

<210> SEQ ID NO 451
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Gly Tyr Thr Phe Ser Asn Tyr Ala
1               5

<210> SEQ ID NO 452
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 452

Ile Asn Thr Lys Thr Gly Asn Pro
1               5

<210> SEQ ID NO 453
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 453

Ala Arg Ala Ala Asp Tyr Gly Glu Pro Tyr Tyr Tyr Gly Met Asp Val
1               5                   10                  15

<210> SEQ ID NO 454
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Gln Ser Ala Leu Thr Gln Pro Ala Ser Val Ser Gly Ser Pro Gly Gln
1               5                   10                  15

Ser Ile Thr Ile Ser Cys Thr Gly Thr Asn Ser Asp Val Gly Ser Tyr
                20                  25                  30
```

```
Asn Leu Val Ser Trp Tyr Gln Gln His Pro Gly Lys Ala Pro Lys Phe
            35                  40                  45

Met Ile Tyr Glu Gly Thr Lys Arg Pro Ser Gly Val Ser Asn Arg Phe
     50                  55                  60

Ser Gly Ser Lys Ser Gly His Thr Ala Ser Leu Thr Ile Ser Gly Leu
 65                  70                  75                  80

Gln Ala Glu Asp Glu Ala Asp Tyr Tyr Cys Cys Ser Tyr Ala Gly Thr
                 85                  90                  95

Ser Thr Leu Val Phe Gly Gly Gly Thr Lys Leu Thr Val Leu
            100                 105                 110
```

<210> SEQ ID NO 455
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 455

```
Asn Ser Asp Val Gly Ser Tyr Asn Leu
 1               5
```

<210> SEQ ID NO 456
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 456

```
Glu Gly Thr
 1
```

<210> SEQ ID NO 457
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 457

```
Cys Ser Tyr Ala Gly Thr Ser Thr Leu Val
 1               5                  10
```

<210> SEQ ID NO 458
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Arg Asn Tyr
            20                  25                  30

Trp Met Asn Trp Val Arg Gln Ala Pro Gly Lys Gly Leu Val Trp Val
            35                  40                  45

Ser Arg Ile Asn Ser Glu Gly Ser Ser Thr Ser Tyr Ala Asp Pro Val
```

```
                    50                  55                  60

Lys Gly Arg Phe Thr Ile Ser Arg Asp Asn Ala Lys Asp Thr Leu Tyr
 65                  70                  75                  80

Leu Gln Met Asp Ser Leu Arg Ala Glu Asp Ser Ala Val Tyr Tyr Cys
                    85                  90                  95

Ala Arg Ile Phe Asn Gly Tyr Ile His Val Gly Arg Asp Tyr Trp Gly
                100                 105                 110

Gln Gly Thr Arg Val Thr Val Ser Ser
            115                 120

<210> SEQ ID NO 459
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 459

Gly Phe Thr Phe Arg Asn Tyr Trp
1               5

<210> SEQ ID NO 460
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 460

Ile Asn Ser Glu Gly Ser Ser Thr
1               5

<210> SEQ ID NO 461
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Ala Arg Ile Phe Asn Gly Tyr Ile His Val Gly Arg Asp Tyr
1               5                   10

<210> SEQ ID NO 462
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

Asp Ile Gln Met Thr Gln Ser Pro Ser Thr Leu Ser Ala Ser Ile Gly
1               5                   10                  15

Asp Arg Val Thr Ile Thr Cys Arg Ala Ser Glu Ser Ile Ser Asn Trp
            20                  25                  30

Leu Ala Trp Phe Gln Gln Lys Pro Gly Lys Ala Pro Lys Leu Leu Ile
        35                  40                  45

Tyr Lys Ala Ser Asn Leu Glu Ser Gly Val Pro Ser Arg Phe Ser Gly
    50                  55                  60
```

```
Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Ser Asn Ser Gln
                 85                  90                  95

Thr Phe Gly Gln Gly Thr Lys Leu Asp Leu Lys
            100                 105
```

<210> SEQ ID NO 463
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 463

```
Glu Ser Ile Ser Asn Trp
 1               5
```

<210> SEQ ID NO 464
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 464

```
Gln Gln Tyr Asn Ser Asn Ser Gln Thr
 1               5
```

<210> SEQ ID NO 465
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 465

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
             20                  25                  30

Tyr Trp Asn Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Ala Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Ala Asn Leu Phe Gly Val Ala Leu Arg Arg Val Leu Gly Pro Phe
            100                 105                 110

Asp Tyr Trp Gly Gln Gly Thr Leu Val Thr Val Ser Ser
        115                 120                 125
```

<210> SEQ ID NO 466
<211> LENGTH: 8
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 466

Gly Gly Ser Ile Ser Ser Tyr Tyr
1               5

<210> SEQ ID NO 467
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 467

Ala Arg Ala Asn Leu Phe Gly Val Ala Leu Arg Arg Val Leu Gly Pro
1               5                   10                  15

Phe Asp Tyr

<210> SEQ ID NO 468
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 468

Asp Ile Gln Met Thr Gln Ser Pro Ser Ser Leu Ser Ala Ser Val Gly
1               5                   10                  15

Asp Arg Val Thr Ile Ala Cys Arg Ala Ser Gln Ser Ile Ala Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 469
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 469

Gln Ser Ile Ala Asn Tyr
1               5

<210> SEQ ID NO 470
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 470

Gln Gln Ser Tyr Ser Thr Pro Tyr Thr
1               5

<210> SEQ ID NO 471
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Phe Arg Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Val Gln Met Asn Ser Leu Thr Asp Glu Asp Thr Ala Val Tyr Tyr Cys
                85                  90                  95

Ala Arg Asp Arg Gly Val Thr Thr Arg Gln Phe Ser Tyr Tyr Tyr Tyr
                100                 105                 110

Gly Met Asp Val Trp Gly Gln Gly Thr Thr Val Thr Val Ser Ser
            115                 120                 125

<210> SEQ ID NO 472
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 472

Gly Phe Ser Phe Arg Ser Tyr Gly
1               5

<210> SEQ ID NO 473
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Ala Arg Asp Arg Gly Val Thr Thr Arg Gln Phe Ser Tyr Tyr Tyr Tyr
1               5                   10                  15

Gly Met Asp Val
            20

<210> SEQ ID NO 474
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

```
Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Ser Ile Thr Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Leu Pro Ser Arg Phe Ser Gly
50                  55                  60

Ser Gly Ser Gly Thr Asp Phe Thr Leu Thr Ile Ser Gly Leu Gln Ser
65                  70                  75                  80

Glu Asp Phe Ala Thr Tyr Tyr Cys Gln Gln Tyr Tyr Asn Tyr Pro Gln
                85                  90                  95

Thr Phe Gly Gln Gly Thr Arg Val Glu Ile Lys
            100                 105
```

<210> SEQ ID NO 475
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 475

```
Gln Ser Ile Thr Ser Tyr
1               5
```

<210> SEQ ID NO 476
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 476

```
Gln Gln Tyr Tyr Asn Tyr Pro Gln Thr
1               5
```

<210> SEQ ID NO 477
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 477

```
Glu Val Gln Leu Leu Glu Ser Gly Gly Gln Leu Val Gln Pro Gly Gly
1               5                   10                  15

Ser Leu Arg Leu Ser Cys Gly Ala Phe Gly Phe Thr Phe Gly Asp Ala
            20                  25                  30

Ala Met Thr Trp Val Arg Gln Ala Pro Gly Lys Gly Leu Glu Trp Val
        35                  40                  45

Ser Thr Ile Ser Gly Arg Gly Asp Glu Thr Phe Ser Ala Asp Ser Val
50                  55                  60

Lys Gly Arg Phe Thr Ile Ser Arg Asp Asn Phe Lys Asn Met Leu Tyr
65                  70                  75                  80

Val Gln Met Asn Ser Leu Arg Ala Glu Asp Thr Ala Thr Tyr Tyr Cys
                85                  90                  95
```

```
Ala Arg Leu Gly His Leu Arg Gly Trp Phe Asp Ser Trp Gly Gln Gly
            100                 105                 110

Thr Leu Val Thr Val Ser Ser
        115

<210> SEQ ID NO 478
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Gly Phe Thr Phe Gly Asp Ala Ala
1               5

<210> SEQ ID NO 479
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Ile Ser Gly Arg Gly Asp Glu Thr
1               5

<210> SEQ ID NO 480
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 480

Ala Arg Leu Gly His Leu Arg Gly Trp Phe Asp Ser
1               5                   10

<210> SEQ ID NO 481
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 481

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Gly Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Lys Val Glu Ile Lys
            100                 105
```

<210> SEQ ID NO 482
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Gln Ser Val Ser Ser Asn
1               5

<210> SEQ ID NO 483
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Thr Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Gly Ala
    50                  55                  60

Pro Val Lys Gly Arg Phe Ser Ile Ser Arg Asp Asp Ser Lys Asn Thr
65                  70                  75                  80

Leu Tyr Leu His Met Asn Ser Leu Lys Thr Glu Asp Thr Ala Val Tyr
                85                  90                  95

Tyr Cys Thr Thr Lys Ser Pro Asn Ser Asn Trp Phe Pro Phe Tyr Tyr
            100                 105                 110

Tyr Tyr Tyr Met Asp Val Trp Gly Lys Gly Thr Thr Val Thr Val Ser
        115                 120                 125

Ser

<210> SEQ ID NO 484
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Gly Phe Thr Phe Ser Asp Ala Trp
1               5

<210> SEQ ID NO 485
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Ile Lys Ser Lys Thr Asp Gly Gly Thr Thr

```
1               5                   10
```

<210> SEQ ID NO 486
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

```
Thr Thr Lys Ser Pro Asn Ser Asn Trp Phe Pro Phe Tyr Tyr Tyr
1               5                   10                  15

Tyr Met Asp Val
            20
```

<210> SEQ ID NO 487
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 487

```
Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Phe Val Ser Trp Tyr Gln Gln His Pro Gly Lys Ala Pro Gln Leu
        35                  40                  45

Met Ile Tyr Asp Val Thr Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Tyr Ser Tyr Ala Ala Ser
                85                  90                  95

Ser Leu Tyr Val Phe Gly Thr Gly Thr Lys Val Thr Val Leu
            100                 105                 110
```

<210> SEQ ID NO 488
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

```
Ser Ser Asp Val Gly Gly Tyr Asn Phe
1               5
```

<210> SEQ ID NO 489
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

```
Tyr Ser Tyr Ala Ala Ser Ser Leu Tyr Val
1               5                   10
```

<210> SEQ ID NO 490
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 490

Gln Leu Gln Leu Gln Glu Ser Gly Pro Gly Leu Val Lys Pro Ser Glu
1               5                   10                  15

Thr Leu Ser Leu Ile Cys Thr Val Ser Gly Gly Ala Ile Thr Ser Ser
            20                  25                  30

Thr Phe Tyr Trp Ala Trp Ile Arg Gln Pro Pro Gly Arg Gly Leu Glu
        35                  40                  45

Trp Ile Gly Ser Met Tyr Tyr Ser Gly Ser Thr Tyr Tyr Asn Leu Ser
    50                  55                  60

Leu Lys Ser Arg Val Ile Ile Ser Val Asn Thr Ser Lys Asn Gln Phe
65                  70                  75                  80

Ser Leu Thr Leu Thr Ser Ala Thr Ala Thr Asp Met Ala Val Tyr Tyr
                85                  90                  95

Cys Val Arg His Thr Leu His Asp Tyr Gly Ser Gly Ser Phe Pro Asp
            100                 105                 110

Tyr Ser Tyr Gly Met Asp Val Trp Gly Gln Gly Thr Thr Val Thr Val
        115                 120                 125

Ser Ser
    130

<210> SEQ ID NO 491
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Gly Gly Ala Ile Thr Ser Ser Thr Phe Tyr
1               5                   10

<210> SEQ ID NO 492
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Met Tyr Tyr Ser Gly Ser Thr
1               5

<210> SEQ ID NO 493
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 493

Val Arg His Thr Leu His Asp Tyr Gly Ser Gly Ser Phe Pro Asp Tyr
1               5                   10                  15

Ser Tyr Gly Met Asp Val
            20

<210> SEQ ID NO 494
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 494

Glu Ile Val Leu Thr Gln Ser Pro Ala Thr Leu Ser Leu Phe Pro Gly
1               5                   10                  15

Glu Arg Gly Thr Leu Ser Cys Arg Ala Ser Gln Ser Val Ser His
            20                  25                  30

Leu Ile Trp Tyr Gln Gln Lys Pro Gly Gln Ala Pro Arg Val Leu Ile
        35                  40                  45

Phe Asp Ala Thr Asn Arg Ala Thr Gly Ile Pro Ala Arg Phe Ser Gly
    50                  55                  60

Ser Gly Ser Gly Thr Asp Phe Thr Leu Thr Ile Ser Asn Leu Glu Pro
65                  70                  75                  80

Glu Asp Tyr Gly Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 495
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Gln Ser Val Ser Ser His
1               5

<210> SEQ ID NO 496
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 496

Gln Gln Arg Ser Asn Trp Pro Leu Thr
1               5

<210> SEQ ID NO 497
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 497

Glu Val Gln Leu Leu Glu Ser Gly Gly Gly Leu Val Gln Pro Gly Gly
1               5                   10                  15

Ser Leu Lys Leu Ser Cys Val Ala Ser Gly Phe Thr Phe Ser Ser Tyr 20                  25                  30
Ala Met Met Trp Val Arg Gln Ala Pro Gly Lys Gly Leu Glu Trp Ile
                35                  40                  45

Ser Ser Ile Ser Ser Gly Gly Ser Thr Tyr Tyr Ala Asp Ser Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Ser His Cys Ser Thr Thr Ser Cys Pro Arg Ala Phe Tyr Tyr
                100                 105                 110

Tyr Gly Met Asp Val Trp Gly Gln Gly Thr Thr Val Thr Val Ser Ser
                115                 120                 125

<210> SEQ ID NO 498
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Ile Ser Ser Ser Gly Gly Ser Thr
1               5

<210> SEQ ID NO 499
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 499

Ala Lys Ser His Cys Ser Thr Thr Ser Cys Pro Arg Ala Phe Tyr Tyr
1               5                   10                  15

Tyr Gly Met Asp Val
            20

<210> SEQ ID NO 500
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 500

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Thr Thr Tyr
                20                  25                  30

Leu Asn Trp Tyr Gln Gln Lys Pro Gly Lys Ala Pro Lys Leu Leu Ile
                35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Ser Leu Ser Ser Leu Gln Pro
65                  70                  75                  80

Glu Asp Ser Ala Thr Tyr Tyr Cys Gln Gln Ser Tyr Ser Thr Leu Gly
                85                  90                  95

Ala Phe Gly Gly Gly Thr Lys Val Glu Ile Lys
            100                 105

<210> SEQ ID NO 501
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Gln Thr Ile Thr Thr Tyr
1               5

<210> SEQ ID NO 502
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Gln Gln Ser Tyr Ser Thr Leu Gly Ala
1               5

<210> SEQ ID NO 503
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 503

Gln Val His Leu Gln Glu Ser Gly Pro Gly Leu Val Lys Pro Ser Gly
1               5                   10                  15

Thr Leu Ser Leu Thr Cys Thr Val Ser Gly Gly Ser Ile Ser Thr Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Gly Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Arg Leu Arg Ser Val Thr Ala Ala Asp Thr Ala Val Tyr Tyr Cys Ala
                85                  90                  95

Arg Glu Ile Asp Ser Arg Met Asp Arg Trp Gly Gln Gly Thr Leu Val
            100                 105                 110

Thr Val Ser Ser
        115

<210> SEQ ID NO 504
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Gly Gly Ser Ile Ser Thr Tyr Tyr

```
<210> SEQ ID NO 505
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Ile Tyr Tyr Gly Gly Thr Thr
1               5

<210> SEQ ID NO 506
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Ala Arg Glu Ile Asp Ser Arg Met Asp Arg
1               5                   10

<210> SEQ ID NO 507
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

Ser Tyr Ala Leu Thr Gln Pro Pro Ser Val Ser Val Ala Pro Gly Lys
1               5                   10                  15

Thr Ala Arg Ile Thr Cys Gly Gly Asp Asn Ile Gly Ser Lys Thr Val
            20                  25                  30

His Trp Tyr His Gln Lys Pro Gly Gln Ala Pro Val Leu Val Ile Tyr
        35                  40                  45

Tyr Asp Ser Asn Arg Pro Ser Gly Ile Ser Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Asn Ser Asp His
                85                  90                  95

Arg Ile Phe Gly Gly Gly Thr Lys Leu Thr Val Leu
            100                 105

<210> SEQ ID NO 508
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Asn Ile Gly Ser Lys Thr
1               5

<210> SEQ ID NO 509
<211> LENGTH: 3
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

Tyr Asp Ser
1

<210> SEQ ID NO 510
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Gln Val Trp Asp Ser Asn Ser Asp His Arg Ile
1               5                   10

<210> SEQ ID NO 511
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

Gln Val Gln Leu Val Gln Ser Gly Ala Glu Val Arg Lys Pro Gly Ser
1               5                   10                  15

Ser Val Lys Val Ser Cys Lys Ala Ser Gly Gly Thr Phe Ser Asn Asn
            20                  25                  30

Pro Ile Thr Trp Val Arg Gln Ala Pro Gly Gln Gly Leu Glu Trp Met
        35                  40                  45

Gly Trp Ile Ile Pro Ile Phe Asn Thr Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Lys Ser Glu Asp Thr Ala Leu Phe Tyr Cys
                85                  90                  95

Ala Arg Asp Arg Ala His Ala Tyr Cys Asn Asn Gly Val Cys Tyr Thr
            100                 105                 110

Thr Asp Ala Phe Asp Val Trp Gly Gln Gly Thr Leu Val Thr Val Ser
        115                 120                 125

Ser

<210> SEQ ID NO 512
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Gly Gly Thr Phe Ser Asn Asn Pro
1               5

<210> SEQ ID NO 513
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

Ile Ile Pro Ile Phe Asn Thr Thr
1               5

<210> SEQ ID NO 514
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Ala Arg Asp Arg Ala His Ala Tyr Cys Asn Asn Gly Val Cys Tyr Thr
1               5                   10                  15

Thr Asp Ala Phe Asp Val
            20

<210> SEQ ID NO 515
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 515

Glu Thr Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Arg Tyr
                20                  25                  30

Leu Ala Trp Tyr Gln His Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Ser Ala Val Tyr Tyr Cys Gln Gln Gly Thr Asp Trp Leu Thr
                85                  90                  95

Phe Gly Gly Gly Thr Lys Val Glu Ile Lys
            100                 105

<210> SEQ ID NO 516
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Gln Ser Val Gly Arg Tyr
1               5

<210> SEQ ID NO 517
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 517

Gln Gln Gly Thr Asp Trp Leu Thr
1               5

<210> SEQ ID NO 518
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 518

Gln Val Gln Leu Val Glu Ser Gly Gly Gly Leu Val Lys Pro Gly Gly
1               5                   10                  15

Ser Leu Arg Leu Ser Cys Ala Ala Ser Gly Ile Thr Phe Ser Asp Asn
            20                  25                  30

Tyr Met Thr Trp Ile Arg Gln Ala Pro Gly Lys Gly Leu Glu Trp Val
        35                  40                  45

Ser Tyr Ile Ser Ser Ser Gly Thr Asn Ile Phe Tyr Ala Asp Ser Leu
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Thr Leu Met Thr Gly Ser Ser Leu Tyr Phe Asp Tyr Trp Gly
            100                 105                 110

Gln Gly Thr Gln Val Thr Val Ser Ser
        115                 120

<210> SEQ ID NO 519
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Gly Ile Thr Phe Ser Asp Asn Tyr
1               5

<210> SEQ ID NO 520
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Ile Ser Ser Ser Gly Thr Asn Ile
1               5

<210> SEQ ID NO 521
<211> LENGTH: 14
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 521

Ala Arg Thr Leu Met Thr Gly Ser Ser Leu Tyr Phe Asp Tyr
1               5                   10

<210> SEQ ID NO 522
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 522

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Leu Ala Ile Ser Gly Val Gln Ala Glu
65                  70                  75                  80

Asp Glu Ala Asp Tyr Tyr Cys Gln Ser Ala Asp Ile Arg Val Thr Glu
                85                  90                  95

Ser Val Leu Phe Gly Gly Gly Thr Lys Leu Thr Val Leu
            100                 105

<210> SEQ ID NO 523
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Ala Leu Pro Lys Gln Tyr
1               5

<210> SEQ ID NO 524
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Lys Asp Ser
1

<210> SEQ ID NO 525
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Gln Ser Ala Asp Ile Arg Val Thr Glu Ser Val Leu
```

```
1               5                   10
```

<210> SEQ ID NO 526
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 526

```
Glu Val His Leu Leu Glu Ser Gly Gly His Leu Val Gln Pro Gly Gly
1               5                   10                  15

Ser Leu Arg Leu Ala Cys Ala Val Ser Gly Phe Thr Phe Ser Asp Ser
            20                  25                  30

Ala Met Thr Trp Val Arg Gln Ala Pro Gly Lys Gly Leu Glu Trp Val
        35                  40                  45

Ser Thr Ile Ser Gly Arg Gly Asp Glu Thr Phe Phe Ala Asp Ser Val
    50                  55                  60

Lys Gly Arg Phe Ser Ile Phe Arg Asp Asn Ser Asn Ser Val Leu Tyr
65                  70                  75                  80

Val Gln Met Asn Ser Leu Arg Ala Glu Asp Thr Ala Thr Tyr Tyr Cys
                85                  90                  95

Ala Arg Tyr Gly His His Lys Gly Trp Phe Asp Ser Trp Gly Gln Gly
            100                 105                 110

Thr Leu Val Thr Val Ser Ser
        115
```

<210> SEQ ID NO 527
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

```
Gly Phe Thr Phe Ser Asp Ser Ala
1               5
```

<210> SEQ ID NO 528
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

```
Ala Arg Tyr Gly His His Lys Gly Trp Phe Asp Ser
1               5                   10
```

<210> SEQ ID NO 529
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 529

```
Glu Ile Val Met Thr Gln Ser Pro Ala Thr Leu Ser Val Ser Pro Gly
1               5                   10                  15
```

```
Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Ile Gly Ile Pro Ala Gly Phe Ser Gly
 50                  55                  60

Ser Gly Ser Gly Thr Glu Phe Thr Leu Thr Ile Ser Ser Leu Gln Ser
 65                  70                  75                  80

Glu Asp Ser Ala Val Tyr Tyr Cys Gln Gln Tyr Asn Asn Trp Pro Arg
                 85                  90                  95

Thr Phe Gly Gln Gly Thr Lys Val Glu Ile Lys
            100                 105
```

<210> SEQ ID NO 530
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 530

```
Gln Val Gln Leu Val Gln Ser Gly Thr Glu Val Lys Lys Pro Gly Ala
 1               5                  10                  15

Ser Val Lys Val Ser Cys Lys Ala Ser Gly Tyr Thr Phe Ser Ser Phe
                20                  25                  30

Gly Ile Thr Trp Val Arg Gln Ala Pro Gly Gln Gly Leu Glu Trp Met
             35                  40                  45

Gly Trp Ile Ser Ala Tyr Asn Gly Asn Thr Lys Tyr Ala Gln Ala Val
 50                  55                  60

Gln Gly Arg Val Thr Leu Thr Thr Asp Thr Ser Thr Thr Thr Ala Tyr
 65                  70                  75                  80

Met Glu Leu Arg Ser Leu Arg Ser Asn Asp Thr Ala Val Tyr Phe Cys
                 85                  90                  95

Ala Arg Glu Gly Ile Glu His Leu Val Val Glu Gly Arg Gly Pro Gly
            100                 105                 110

Gly Asp Cys Trp Gly Gln Gly Thr Leu Val Ile Val Ser Ser
            115                 120                 125
```

<210> SEQ ID NO 531
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

```
Gly Tyr Thr Phe Ser Ser Phe Gly
 1               5
```

<210> SEQ ID NO 532
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 532

```
Ile Ser Ala Tyr Asn Gly Asn Thr
```

```
<210> SEQ ID NO 533
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Ala Arg Glu Gly Ile Glu His Leu Val Val Glu Gly Arg Gly Pro Gly
1               5                   10                  15

Gly Asp Cys

<210> SEQ ID NO 534
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 534

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Glu Tyr Thr
                20                  25                  30

Ser Trp Tyr Gln Gln Lys Ser Gly Gln Ala Pro Val Leu Val Ile Tyr
            35                  40                  45

Glu Asp Ile Lys Arg Pro Ser Gly Ile Pro Glu Arg Phe Ser Gly Ser
        50                  55                  60

Ser Ser Gly Thr Met Ala Ser Leu Thr Ile Ser Gly Ala Gln Val Asp
65                  70                  75                  80

Asp Glu Ala Asp Tyr Tyr Cys Tyr Ser Thr Thr Ser Gly Asp His
                85                  90                  95

Lys Val Phe Gly Gly Gly Thr Lys Leu Thr Val Leu
            100                 105

<210> SEQ ID NO 535
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Ala Leu Pro Lys Glu Tyr
1               5

<210> SEQ ID NO 536
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 536

Glu Asp Ile
1
```

```
<210> SEQ ID NO 537
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Tyr Ser Thr Asp Thr Ser Gly Asp His Lys Val
1               5                   10

<210> SEQ ID NO 538
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 538

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Arg Glu Trp Val
        35                  40                  45

Ala Ala Leu Ser Tyr Asp Gly Ser Ser Thr Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Thr Arg Val Pro Tyr Gly Glu Gly Arg Ala Ala Asn Asp Tyr Trp Gly
            100                 105                 110

Gln Gly Thr Leu Val Thr Val Ser Ser
        115                 120

<210> SEQ ID NO 539
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Leu Ser Tyr Asp Gly Ser Ser Thr
1               5

<210> SEQ ID NO 540
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Thr Arg Val Pro Tyr Gly Glu Gly Arg Ala Ala Asn Asp Tyr
1               5                   10

<210> SEQ ID NO 541
<211> LENGTH: 107
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 541

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Asn Ile Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln His Tyr Asn Thr Tyr Ser Arg
                85                  90                  95

Ser Phe Gly Gly Gly Thr Glu Val Ala Ile Lys
            100                 105

<210> SEQ ID NO 542
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 542

Gln Ser Ile Gly Ser Trp
1               5

<210> SEQ ID NO 543
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 543

Gln His Tyr Asn Thr Tyr Ser Arg Ser
1               5

<210> SEQ ID NO 544
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 544

Gln Val Gln Leu Val Gln Ser Gly Ala Glu Val Lys Thr Pro Gly Ser
1               5                   10                  15

Ser Val Lys Val Ser Cys Thr Ala Ser Gly Asp Ser Phe Ser Arg Tyr
            20                  25                  30

Ala Ile Asn Trp Val Arg Gln Ala Pro Gly Gln Gly Leu Glu Trp Val
        35                  40                  45

Gly Lys Ile Val Pro Val Phe Gly Ala Ala Ser Tyr Ala Gln Lys Phe
    50                  55                  60
```

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ile Val Lys Leu Ser Thr Met Pro Pro Val Tyr Trp Gly
            100                 105                 110

Gln Gly Thr Leu Val Thr Val Ser Ser
        115                 120

<210> SEQ ID NO 545
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545

Gly Asp Ser Phe Ser Arg Tyr Ala
1               5

<210> SEQ ID NO 546
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Ile Val Pro Val Phe Gly Ala Ala
1               5

<210> SEQ ID NO 547
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 547

Ala Arg Gly Ile Val Lys Leu Ser Thr Met Pro Pro Val Tyr
1               5                   10

<210> SEQ ID NO 548
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 548

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Ser Glu Val Ser Arg Phe Ser Gly Val Pro
    50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Val Gly Val Tyr Tyr Cys Met Gln Gly
                    85                  90                  95

Ile His His Leu Thr Phe Gly Pro Gly Thr Lys Val Asp Ile Lys
                100                 105                 110
```

<210> SEQ ID NO 549
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

```
Gln Ser Leu Leu His Ser Asp Gly Lys Thr Tyr
1               5                   10
```

<210> SEQ ID NO 550
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 550

```
Glu Val Ser
1
```

<210> SEQ ID NO 551
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

```
Met Gln Gly Ile His His Leu Thr
1               5
```

<210> SEQ ID NO 552
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 552

```
Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Val Ser Asp Ser
                20                  25                  30

Ala Tyr Tyr Trp Ser Trp Ile Arg Gln Pro Pro Gly Gly Gly Leu Glu
            35                  40                  45

Phe Ile Gly Tyr Val Tyr Asn Ser Gly Ser Thr Asn Tyr Asn Pro Ser
        50                  55                  60

Leu Lys Ser Arg Val Thr Ile Ser Val Asp Thr Ser Lys Asn Gln Phe
65                  70                  75                  80

Ser Leu Ser Leu Ser Ser Leu Thr Ala Ala Asp Thr Ala Val Tyr Tyr
                85                  90                  95
```

-continued

```
Cys Ala Arg Tyr Cys Ser Ser Thr Ser Cys Tyr Val Arg Ser Ser Asp
            100                 105                 110

Val Asn Trp Phe Asp Pro Trp Gly Gln Gly Thr Leu Val Ile Val Ser
        115                 120                 125

Ser

<210> SEQ ID NO 553
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Gly Gly Ser Val Ser Asp Ser Ala Tyr Tyr
1               5                   10

<210> SEQ ID NO 554
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Val Tyr Asn Ser Gly Ser Thr
1               5

<210> SEQ ID NO 555
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 555

Ala Arg Tyr Cys Ser Ser Thr Ser Cys Tyr Val Arg Ser Ser Asp Val
1               5                   10                  15

Asn Trp Phe Asp Pro
            20

<210> SEQ ID NO 556
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 556

Glu Ile Val Leu Thr Gln Ser Pro Gly Thr Leu Ser Ser Ser Pro Gly
1               5                   10                  15

Glu Ser Ala Thr Leu Ser Cys Arg Ala Ser Gln Ser Leu Gly Thr Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

-continued

```
Glu Asp Phe Ala Val Tyr Tyr Cys His Gln Arg Ser His Trp Leu Thr
                85                  90                  95
Phe Gly Gly Gly Thr Lys Val Glu Ile Lys
            100                 105

<210> SEQ ID NO 557
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Gln Ser Leu Gly Thr Tyr
1               5

<210> SEQ ID NO 558
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 558

His Gln Arg Ser His Trp Leu Thr
1               5

<210> SEQ ID NO 559
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 559

Glu Ala Gln Leu Leu Glu Ser Gly Gly Gly Leu Val Gln Pro Gly Gly
1               5                   10                  15
Ser Leu Arg Leu Ser Cys Ala Ala Ser Gly Phe Asn Phe Ser Asn Tyr
            20                  25                  30
Ala Met Thr Trp Val Arg Gln Ala Pro Gly Lys Gly Leu Glu Trp Val
        35                  40                  45
Ser Ala Ile Ser Ser Gly Gly Thr Thr Tyr Tyr Ala Asp Ser Val
    50                  55                  60
Lys Gly Arg Phe Thr Ile Ser Arg Asp Asn Ser Lys Asn Thr Val Tyr
65                  70                  75                  80
Leu Gln Met Asn Ser Leu Lys Asp Ala Asp Ser Ala Leu Tyr Tyr Cys
                85                  90                  95
Ala Lys Pro Gly Arg Ala Val Val Arg Leu Ser Tyr Phe Asp Ser
            100                 105                 110
Trp Gly Gln Gly Thr Leu Val Thr Val Ser Ser
        115                 120

<210> SEQ ID NO 560
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560
```

```
Gly Phe Asn Phe Ser Asn Tyr Ala
1               5

<210> SEQ ID NO 561
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Ile Ser Ser Gly Gly Gly Thr Thr
1               5

<210> SEQ ID NO 562
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Ala Lys Pro Gly Arg Ala Val Val Val Arg Leu Ser Tyr Phe Asp Ser
1               5                   10                  15

<210> SEQ ID NO 563
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 563

Gln Ser Val Leu Thr Gln Pro Pro Ser Val Ser Ala Ala Pro Gly Gln
1               5                   10                  15

Lys Val Ser Ile Ser Cys Ser Gly Ser Gly Ser Asn Ile Ala Asn His
                20                  25                  30

Tyr Val Ser Trp Tyr Gln His Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Thr Val Val Val Phe Gly Gly Gly Thr Lys Leu Thr Val Leu
            100                 105                 110

<210> SEQ ID NO 564
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 564

Gly Ser Asn Ile Ala Asn His Tyr
1               5
```

<210> SEQ ID NO 565
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 565

Gly Thr Trp Asp Ser Ser Leu Thr Val Val Val
1               5                   10

<210> SEQ ID NO 566
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 566

Gln Ile Thr Leu Lys Glu Ser Gly Pro Thr Leu Val Lys Pro Thr Glu
1               5                   10                  15

Thr Leu Thr Leu Thr Cys Thr Phe Ser Gly Phe Ser Leu Thr Thr Ser
            20                  25                  30

Gly Val Ala Val Gly Trp Val Arg Gln Pro Pro Gly Lys Ala Leu Glu
        35                  40                  45

Trp Leu Ala Leu Ile Tyr Trp Asp Asp Asp Glu Arg Tyr Thr Pro Ser
    50                  55                  60

Leu Lys Ser Arg Leu Thr Ile Thr Lys Asp Thr Ser Lys Ser Gln Val
65                  70                  75                  80

Val Leu Thr Met Thr Asn Met Asp Pro Val Asp Thr Ala Thr Tyr Phe
                85                  90                  95

Cys Val His Cys Glu Gly Pro Asp Ile Leu Leu Val Pro Ala Ala Tyr
            100                 105                 110

Phe Phe Asp Phe Trp Gly Gln Gly Thr Leu Val Thr Val Ser Ser
        115                 120                 125

<210> SEQ ID NO 567
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 567

Gly Phe Ser Leu Thr Thr Ser Gly Val Ala
1               5                   10

<210> SEQ ID NO 568
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 568

Ile Tyr Trp Asp Asp Asp Glu
1               5

<210> SEQ ID NO 569
<211> LENGTH: 19

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Val His Cys Glu Gly Pro Asp Ile Leu Leu Val Pro Ala Ala Tyr Phe
1               5                   10                  15

Phe Asp Phe

<210> SEQ ID NO 570
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 570

Glu Ile Val Leu Thr Gln Ser Pro Gly Thr Leu Ser Leu Ser Pro Gly
1               5                   10                  15

Asp Arg Ala Thr Leu Ser Cys Arg Ala Ser Gln Ser Val Ser Arg Arg
            20                  25                  30

Tyr Leu Ala Trp Tyr Gln Gln Ser Pro Gly Gln Ala Pro Arg Leu Leu
        35                  40                  45

Ile Ser Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Met Tyr Tyr Cys Gln Gln Tyr Gly Ser Ser Thr
                85                  90                  95

Gly Thr Phe Gly Gln Gly Thr Lys Val Glu Met Lys
            100                 105

<210> SEQ ID NO 571
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 571

Gln Ser Val Ser Arg Arg Tyr
1               5

<210> SEQ ID NO 572
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Gln Gln Tyr Gly Ser Ser Thr Gly Thr
1               5

<210> SEQ ID NO 573
<211> LENGTH: 127
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 573

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ser
            20                  25                  30

Gly Tyr Tyr Trp Ser Trp Ile Arg Gln His Pro Gly Lys Gly Leu Glu
        35                  40                  45

Trp Ile Gly Tyr Ile Asn Tyr Ile Gly Gly Thr Tyr Tyr Asn Pro Ser
    50                  55                  60

Leu Arg Ser Arg Val Thr Met Ser Val Asp Thr Ser Lys Asn Gln Phe
65                  70                  75                  80

Ser Leu Arg Leu Ser Ser Val Ser Ala Ala Asp Thr Ala Val Tyr Tyr
                85                  90                  95

Cys Ala Ser Thr His Ser Tyr Gly Asp Tyr Ser Arg Asp Tyr Tyr Tyr
            100                 105                 110

Gly Val Asp Val Trp Gly Gln Gly Thr Thr Val Thr Ile Ser Ser
        115                 120                 125

<210> SEQ ID NO 574
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Gly Gly Ser Ile Ser Ser Ser Gly Tyr Tyr
1               5                   10

<210> SEQ ID NO 575
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Ile Asn Tyr Ile Gly Gly Thr
1               5

<210> SEQ ID NO 576
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Ala Ser Thr His Ser Tyr Gly Asp Tyr Ser Arg Asp Tyr Tyr Tyr Gly
1               5                   10                  15

Val Asp Val

<210> SEQ ID NO 577
<211> LENGTH: 108
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 577

Glu Ile Val Leu Thr Gln Ser Pro Ala Thr Leu Ser Leu Ser Pro Gly
1               5                   10                  15

Asp Arg Ala Thr Leu Ser Cys Arg Thr Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Ala Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Cys Ala Gly Ser Pro
                85                  90                  95

Phe Thr Phe Gly Pro Gly Thr Lys Val Asp Leu Lys
            100                 105

<210> SEQ ID NO 578
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Gln Gln Cys Ala Gly Ser Pro Phe Thr
1               5

<210> SEQ ID NO 579
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 579

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn His Arg Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Pro Gly Leu Ser Ile Ala Val Ala Gly Pro Phe Asp Tyr
            100                 105                 110

Trp Gly Gln Gly Thr Leu Val Thr Val Ser Ser
        115                 120

<210> SEQ ID NO 580
<211> LENGTH: 8
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 580

Gly Phe Thr Phe Ser Asp Tyr Ala
1               5

<210> SEQ ID NO 581
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Ile Ser Tyr Asp Gly Asn His Arg
1               5

<210> SEQ ID NO 582
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 582

Ala Arg His Pro Gly Leu Ser Ile Ala Val Ala Gly Pro Phe Asp Tyr
1               5                   10                  15

<210> SEQ ID NO 583
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 583

Glu Ile Val Met Thr Gln Ser Pro Ala Thr Leu Ser Val Ser Pro Gly
1               5                   10                  15

Glu Arg Ala Thr Leu Ser Cys Gly Ala Ser Gln Ser Val Ser Ser Asn
            20                  25                  30

Leu Ala Trp Tyr Gln Gln Lys Pro Gly Gln Ala Pro Arg Leu Leu Phe
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Leu Tyr Tyr Cys Gln Gln Tyr Asn Asn Trp Pro Trp
                85                  90                  95

Thr Phe Gly Gln Gly Thr Lys Val Asp Ile Lys
            100                 105

<210> SEQ ID NO 584
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 584

Gln Gln Tyr Asn Asn Trp Pro Trp Thr
1               5

<210> SEQ ID NO 585
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 585

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Arg Asp
            20                  25                  30

Gly Ile Thr Trp Val Arg Gln Ala Pro Gly Gln Gly Leu Glu Trp Met
        35                  40                  45

Gly Trp Ile Ser Ala Asn Asn Asp Phe Thr Asp Tyr Ala Gln Lys Phe
    50                  55                  60

Gln Gly Arg Leu Thr Met Thr Thr Asp Thr Ser Thr Asn Thr Ala Tyr
65                  70                  75                  80

Met Glu Leu Arg Ser Leu Arg Ser Asp Asp Thr Ala Val Tyr Tyr Cys
                85                  90                  95

Ala Arg Gln Val Ile Thr Val Leu Gly Tyr Ser Tyr Gly Met Asp Val
            100                 105                 110

Trp Gly Gln Gly Thr Thr Val Thr Val Ser Ser
        115                 120

<210> SEQ ID NO 586
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Gly Tyr Thr Phe Asn Arg Asp Gly
1               5

<210> SEQ ID NO 587
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 587

Ile Ser Ala Asn Asn Asp Phe Thr
1               5

<210> SEQ ID NO 588
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588

Ala Arg Gln Val Ile Thr Val Leu Gln Tyr Ser Tyr Gly Met Asp Val
1               5                   10                  15

<210> SEQ ID NO 589
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 589

Asp Ile Gln Met Thr Gln Phe Pro Ser Ser Leu Ser Ala Ser Val Gly
1               5                   10                  15

Asp Arg Val Thr Ile Thr Cys Arg Ala Ser Gln Ser Ile Ser Arg Tyr
                20                  25                  30

Leu Asn Trp Tyr Gln Gln Thr Pro Gly Lys Ala Pro Lys Leu Leu Ile
            35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Thr Ala Pro Leu
                85                  90                  95

Thr Phe Gly Gly Gly Thr Arg Val Glu Ile Lys
            100                 105

<210> SEQ ID NO 590
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 590

Gln Ser Ile Ser Arg Tyr
1               5

<210> SEQ ID NO 591
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 591

Gln Gln Ser Asp Thr Ala Pro Leu Thr
1               5

<210> SEQ ID NO 592
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 592

Gln Val Gln Leu Val Glu Ser Gly Gly Gly Leu Val Thr Pro Gly Gly
1               5                   10                  15

Ser Leu Arg Leu Ser Cys Thr Val Ser Gly Phe Thr Leu Ser Asp Tyr
                20                  25                  30

```
Tyr Met Ser Trp Ile Arg Gln Ala Pro Gly Lys Gly Leu Asp Trp Leu
        35                  40                  45

Ser Tyr Ile Ser Gly Ser Gly Asp Asn Lys Asn Tyr Ala Asp Ser Val
    50                  55                  60

Arg Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Pro Ser Gly Gly Tyr Ser Pro Gly Val Val Leu Trp
            100                 105                 110

Gly Gln Gly Thr Leu Val Thr Val Ser Ser
        115                 120

<210> SEQ ID NO 593
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Gly Phe Thr Leu Ser Asp Tyr Tyr
1               5

<210> SEQ ID NO 594
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Ile Ser Gly Ser Gly Asp Asn Lys
1               5

<210> SEQ ID NO 595
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 595

Ala Arg Glu Phe Pro Ser Gly Gly Tyr Ser Pro Gly Val Val Leu
1               5                   10                  15

<210> SEQ ID NO 596
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 596

Asn Phe Val Leu Thr Gln Pro His Ser Val Ser Glu Ser Pro Gly Lys
1               5                   10                  15

Thr Val Thr Ile Ser Cys Ala Arg Ser Ser Gly Ser Ile Ala Gly Ser
            20                  25                  30

Phe Val Gln Trp Tyr Gln Gln Arg Pro Gly Ser Ser Pro Thr Thr Val
```

```
                35                  40                  45
Ile Tyr Glu Asp Thr Arg Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Thr Asn Pro Trp Val Phe Gly Gly Gly Thr Lys Leu Thr Val Leu
            100                 105                 110

<210> SEQ ID NO 597
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Ser Gly Ser Ile Ala Gly Ser Phe
 1               5

<210> SEQ ID NO 598
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 598

Glu Asp Thr
 1

<210> SEQ ID NO 599
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 599

Gln Ser Tyr Asp Ser Thr Asn Pro Trp Val
 1               5                  10

<210> SEQ ID NO 600
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 600

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Val Ile Tyr Ser Gly Gly Ser Arg Thr Tyr Tyr Ala Asp Ser Ala
     50                  55                  60
```

```
Lys Gly Arg Phe Thr Ile Ser Arg Asp Asn Ser Lys Asn Met Leu Tyr
 65                  70                  75                  80

Leu Gln Met Asn Ser Leu Arg Ala Glu Asp Thr Ala Val Tyr Tyr Cys
                 85                  90                  95

Thr Lys Asn Asp Tyr Asp Ser Ser Gly Tyr Phe Asp Phe Asp Asn Trp
            100                 105                 110

Gly Gln Gly Thr Leu Val Thr Val Ser Ser
        115                 120
```

<210> SEQ ID NO 601
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

```
Thr Lys Asn Asp Tyr Asp Ser Ser Gly Tyr Phe Asp Phe Asp Asn
 1               5                  10                  15
```

<210> SEQ ID NO 602
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 602

```
Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr His Cys Ser Ser Tyr Thr Ser Ser
                 85                  90                  95

Ser Thr Trp Val Phe Gly Gly Gly Thr Lys Leu Thr Val Leu
            100                 105                 110
```

<210> SEQ ID NO 603
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

```
Ser Ser Asp Val Gly Gly Tyr Asn Tyr
 1               5
```

<210> SEQ ID NO 604
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 604

Ser Ser Tyr Thr Ser Ser Ser Thr Trp Val
1               5                   10

<210> SEQ ID NO 605
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 605

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Val Tyr Ser Gly Gly Ser Gly Thr Tyr Tyr Ala Asp Ser Val
    50                  55                  60

Lys Gly Arg Phe Thr Ile Ser Arg Asp Asp Ser Thr Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Asp Ser Phe Gly Glu Leu Asp Leu Asp Ser Trp Gly
            100                 105                 110

Gln Gly Thr Leu Val Ser Val Ser Ser
        115                 120

<210> SEQ ID NO 606
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Val Tyr Ser Gly Gly Ser Gly Thr
1               5

<210> SEQ ID NO 607
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 607

Ala Lys Asp Arg Asp Ser Phe Gly Glu Leu Asp Leu Asp Ser
1               5                   10

<210> SEQ ID NO 608
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 608

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Lys Asn Lys Asn Tyr Leu Ala Trp Tyr Gln Gln Arg Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Leu Gln
                85                  90                  95

Tyr Tyr Asn Ile Pro Arg Thr Phe Gly Gln Gly Thr Lys Leu Glu Ile
            100                 105                 110

Lys

<210> SEQ ID NO 609
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 609

Gln Ser Val Leu Tyr Ser Ser Lys Asn Lys Asn Tyr
1               5                   10

<210> SEQ ID NO 610
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 610

Leu Gln Tyr Tyr Asn Ile Pro Arg Thr
1               5

<210> SEQ ID NO 611
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 611

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Leu Ser Trp Val Arg Gln Pro Pro Gly Lys Gly Leu Glu Trp Val
        35                  40                  45

Ser Val Ile Tyr Ser Gly Gly Ser Arg Thr Tyr Tyr Ala Asp Ala Ala
    50                  55                  60

Lys Gly Arg Phe Thr Ile Ser Arg Asp Asn Ser Lys Asn Met Leu Tyr
65                  70                  75                  80
```

-continued

```
Leu Gln Met Asn Ser Leu Arg Ala Glu Asp Thr Ala Val Tyr Tyr Cys
                85                  90                  95

Thr Lys His Asp Tyr Asp Ser Ser Gly Tyr Phe Asp Phe Asp Asn Trp
           100                 105                 110

Gly Gln Gly Thr Leu Val Thr Val Ser Ser
        115                 120

<210> SEQ ID NO 612
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 612

Thr Lys His Asp Tyr Asp Ser Ser Gly Tyr Phe Asp Phe Asp Asn
1               5                   10                  15

<210> SEQ ID NO 613
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 613

Glu Val Gln Leu Val Glu Ser Gly Gly Gly Val Ala Arg Pro Gly Gly
1               5                   10                  15

Ser Leu Arg Leu Ser Cys Ala Ala Ser Gly Phe Thr Phe Asp Asp Tyr
            20                  25                  30

Gly Met Ser Trp Val Arg Gln Ala Pro Gly Lys Gly Leu Glu Trp Val
        35                  40                  45

Ser Gly Ile Asn Trp Asn Gly Ser Thr Asn Tyr Ala Asp Ser Val
    50                  55                  60

Lys Gly Arg Phe Ile Ile Ser Arg Asp Asn Gly Lys Asn Ser Leu Tyr
65                  70                  75                  80

Leu Gln Met Asn Ser Leu Arg Ala Glu Asp Thr Ala Phe Tyr His Cys
                85                  90                  95

Ala Arg Arg Gly Asn Phe Tyr Tyr Tyr Gly Met Asp Val Trp Gly Gln
            100                 105                 110

Gly Thr Thr Val Thr Val Ser Ser
        115                 120

<210> SEQ ID NO 614
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 614

Gly Phe Thr Phe Asp Asp Tyr Gly
1               5

<210> SEQ ID NO 615
<211> LENGTH: 8
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 615

Ile Asn Trp Asn Gly Gly Ser Thr
1               5

<210> SEQ ID NO 616
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 616

Ala Arg Arg Gly Asn Phe Tyr Tyr Tyr Gly Met Asp Val
1               5                   10

<210> SEQ ID NO 617
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 617

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Asn Ser Thr Trp
            20                  25                  30

Leu Ala Trp Tyr Gln Gln Lys Pro Gly Lys Ala Pro Glu Leu Leu Ile
        35                  40                  45

Phe Asp Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Gln Arg Phe Pro Leu
                85                  90                  95

Thr Phe Gly Gly Gly Thr Lys Val Glu Ile Lys
            100                 105

<210> SEQ ID NO 618
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 618

Gln Gly Asn Ser Thr Trp
1               5

<210> SEQ ID NO 619
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 619

Gln Gln Ala Gln Arg Phe Pro Leu Thr

<210> SEQ ID NO 620
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 620

Gln Val Gln Leu Val Gln Ser Gly Ser Glu Leu Arg Arg Pro Gly Ala
1               5                   10                  15

Ser Val Lys Val Ser Cys Lys Thr Ser Gly Tyr Ala Phe Thr His Phe
                20                  25                  30

Ala Met Asn Trp Leu Arg Gln Ala Pro Gly Gln Gly Leu Glu Trp Leu
            35                  40                  45

Gly Trp Ile Asn Thr His Ser Gly Asn Pro Thr Tyr Ala Gln Gly Phe
        50                  55                  60

Thr Gly Arg Ile Val Phe Ser Leu Asp Thr Ser Ala Gly Thr Ala Tyr
65                  70                  75                  80

Leu Glu Ile Ser Ser Leu Lys Ala Glu Asp Thr Ala Val Tyr Tyr Cys
                85                  90                  95

Ala Arg Glu Arg Tyr Phe Asp Phe Trp Gly Gln Gly Thr Leu Val Ala
            100                 105                 110

Val Ser Ser
        115

<210> SEQ ID NO 621
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 621

Gly Tyr Ala Phe Thr His Phe Ala
1               5

<210> SEQ ID NO 622
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 622

Gln Ser Val Leu Thr Gln Pro Pro Ser Ala Ser Gly Thr Pro Gly Gln
1               5                   10                  15

Arg Val Thr Ile Ser Cys Ser Gly Thr Asn Ser Asn Ile Gly Lys Asn
                20                  25                  30

Phe Leu Tyr Trp Tyr Gln Gln Leu Pro Gly Thr Ala Pro Lys Leu Leu
            35                  40                  45

Ile Phe Ser Ser Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Asn Leu
                85                  90                  95

```
Ser Gly Trp Val Phe Gly Gly Gly Thr Lys Val Thr Val Leu
            100                 105                 110

<210> SEQ ID NO 623
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 623

Asn Ser Asn Ile Gly Lys Asn Phe
1               5

<210> SEQ ID NO 624
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 624

Ala Ala Trp Asp Asp Asn Leu Ser Gly Trp Val
1               5                   10

<210> SEQ ID NO 625
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 625

Gln Val Gln Leu Gln Glu Ser Gly Pro Gly Leu Val Lys Pro Ser Glu
1               5                   10                  15

Ala Leu Ser Leu Thr Cys Ser Val Ser Asp Gly Ser Val Ser Ser Gly
            20                  25                  30

Ser Tyr Tyr Trp Thr Trp Ile Arg Gln Pro Pro Gly Lys Gly Leu Glu
        35                  40                  45

Trp Ile Gly Cys Ile His Tyr Ser Gly Arg Thr Asn Tyr Asn Pro Ser
    50                  55                  60

Leu Lys Ser Arg Val Thr Ile Ser Ile Asp Thr Ser Lys Asn Gln Phe
65                  70                  75                  80

Ser Leu Gln Leu Ser Ser Val Thr Ala Val Asp Thr Ala Val Tyr Tyr
                85                  90                  95

Cys Ala Arg Asp Arg Gly Glu Tyr Asp Phe Trp Arg Val Arg Tyr Tyr
            100                 105                 110

Gly Met Asp Val Trp Gly Gln Gly Thr Thr Val Thr Val Ser Ser
        115                 120                 125

<210> SEQ ID NO 626
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 626

Asp Gly Ser Val Ser Ser Gly Ser Tyr Tyr
```

```
<210> SEQ ID NO 627
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 627

Ile His Tyr Ser Gly Arg Thr
1               5

<210> SEQ ID NO 628
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 628

Ala Arg Asp Arg Gly Glu Tyr Asp Phe Trp Arg Val Arg Tyr Tyr Gly
1               5                   10                  15

Met Asp Val

<210> SEQ ID NO 629
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 629

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Tyr
                20                  25                  30

Asn Tyr Val Ser Trp Tyr Gln Gln His Pro Gly Lys Ala Pro Lys Leu
            35                  40                  45

Leu Ile Tyr Asp Phe Ser Asn Arg Pro Ser Gly Val Ser Asp Arg Phe
        50                  55                  60

Ser Gly Ser Lys Ser Gly Asn Thr Ala Ser Leu Thr Ile Ser Gly Leu
65                  70                  75                  80

Arg Ala Glu Asp Glu Ser Asp Tyr Tyr Cys Thr Ser Tyr Thr Asn Thr
                85                  90                  95

Asn Thr Arg Leu Phe Gly Gly Gly Thr Lys Leu Thr Val Leu
            100                 105                 110

<210> SEQ ID NO 630
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 630

Ser Ser Asp Val Gly Asp Tyr Asn Tyr
1               5
```

```
-continued

<210> SEQ ID NO 631
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 631

Asp Phe Ser
1

<210> SEQ ID NO 632
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 632

Thr Ser Tyr Thr Asn Thr Asn Thr Arg Leu
1               5                   10

<210> SEQ ID NO 633
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 633

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Gly Leu His Trp Val Arg Gln Ala Pro Gly Gln Arg Pro Glu Trp Met
        35                  40                  45

Gly Trp Ile Asn Ala Gly Asn Gly Asn Arg Lys Tyr Ser Glu Arg Phe
    50                  55                  60

Gln Ala Arg Val Thr Phe Thr Arg Asp Thr Ser Ala Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Leu Thr Ala Ala His Phe Asp Tyr Trp Gly Gln
            100                 105                 110

Gly Thr Gln Val Thr Val Ser Ser
        115                 120

<210> SEQ ID NO 634
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634

Gly Tyr Thr Phe Ile Ser Tyr Gly
1               5

<210> SEQ ID NO 635
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 635

Ile Asn Ala Gly Asn Gly Asn Arg
1               5

<210> SEQ ID NO 636
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 636

Ala Arg Asp Arg Leu Thr Ala Ala Ala His Phe Asp Tyr
1               5                   10

<210> SEQ ID NO 637
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 637

Glu Ile Val Met Thr Gln Ser Pro Ala Thr Leu Ser Val Ser Leu Gly
1               5                   10                  15

Glu Arg Ala Thr Leu Ser Cys Arg Ala Ser Gln Ser Val Ser Ser Asp
            20                  25                  30

Leu Ala Trp Tyr Gln Gln Lys Pro Gly Gln Ala Pro Arg Leu Leu Met
        35                  40                  45

Tyr Gly Ala Ser Thr Arg Ala Thr Gly Phe Pro Ala Arg Phe Thr Gly
    50                  55                  60

Ser Gly Ser Gly Pro Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Phe
                85                  90                  95

Thr Phe Gly Gly Gly Thr Lys Val Glu Ile Lys
            100                 105

<210> SEQ ID NO 638
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 638

Gln Ser Val Ser Ser Asp
1               5

<210> SEQ ID NO 639
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 639

Gln Gln Tyr Asn Asn Trp Pro Phe Thr
1               5

<210> SEQ ID NO 640
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 640

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Thr Ser Ser
            20                  25                  30

Ala Val Gly Val Gly Trp Ile Arg Gln Pro Pro Gly Lys Ala Leu Glu
        35                  40                  45

Trp Leu Ala Leu Ile Tyr Gly Asp Asp Lys Arg Tyr Ser Pro Ser
    50                  55                  60

Leu Lys Arg Arg Leu Thr Ile Thr Lys Asp Thr Ser Lys Asn Gln Val
65                  70                  75                  80

Val Leu Thr Met Thr Asp Val Asp Pro Val Asp Thr Ala Thr Tyr Tyr
                85                  90                  95

Cys Ala His Arg Arg Leu Thr Ile Pro Leu Leu Met Val Ala Ala Asp
            100                 105                 110

Ala Phe Asp Ile Trp Gly Pro Gly Thr Met Val Ile Val Ser Ser
        115                 120                 125

<210> SEQ ID NO 641
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 641

Gly Phe Ser Leu Thr Ser Ser Ala Val Gly
1               5                   10

<210> SEQ ID NO 642
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 642

Ile Tyr Gly Asp Asp Asp Lys
1               5

<210> SEQ ID NO 643
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 643

```
Ala His Arg Arg Leu Thr Ile Pro Leu Leu Met Val Ala Ala Asp Ala
1               5                   10                  15

Phe Asp Ile

<210> SEQ ID NO 644
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 644

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ser Arg Trp
            20                  25                  30

Leu Ala Trp Tyr Gln Gln Lys Pro Gly Lys Ala Pro Lys Leu Leu Ile
        35                  40                  45

Tyr Arg Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Phe His Thr
                85                  90                  95

Phe Gly Gln Gly Thr Lys Leu Glu Ile Lys
            100                 105

<210> SEQ ID NO 645
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 645

Gln Ser Val Ser Arg Trp
1               5

<210> SEQ ID NO 646
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 646

Arg Ala Ser
1

<210> SEQ ID NO 647
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 647

Gln Gln Tyr Ser Ser Phe His Thr
1               5
```

<210> SEQ ID NO 648
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 648

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Thr Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Ala Asp Thr Ala Val Tyr Tyr Cys
                85                  90                  95

Ala Arg Asp Gly Gly Arg Ser Gly Tyr Phe Asp Asp Tyr Trp Gly Gln
            100                 105                 110

Gly Thr Leu Val Thr Val Ser Ser
        115                 120

<210> SEQ ID NO 649
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 649

Gly Phe Ile Phe Ser Thr Tyr Ser
1               5

<210> SEQ ID NO 650
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 650

Ile Ser Ser Ser Ser Asn Thr Ile
1               5

<210> SEQ ID NO 651
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 651

Ala Arg Asp Gly Gly Arg Ser Gly Tyr Phe Asp Asp Tyr
1               5                   10

```
<210> SEQ ID NO 652
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 652

Gln Leu Val Leu Thr Gln Ser Pro Ala Ser Ala Ser Leu Gly Ala
1               5                   10                  15

Ser Val Lys Leu Thr Cys Thr Leu Ser Asn Gly His Ile Asn Tyr Ala
                20                  25                  30

Ile Ala Trp His Gln Gln Pro Asp Lys Gly Pro Arg Tyr Leu Leu
        35                  40                  45

Asn Leu Lys Ser Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Gly Leu Gln Ser Glu Asp Glu Ala Asp Tyr Tyr Cys Gln Thr Trp Gly
                85                  90                  95

Thr Gly Ile Gln Val Phe Gly Gly Gly Thr Lys Leu Thr Val Leu
            100                 105                 110

<210> SEQ ID NO 653
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 653

Asn Gly His Ile Asn Tyr Ala
1               5

<210> SEQ ID NO 654
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 654

Leu Lys Ser Asp Gly Ser His
1               5

<210> SEQ ID NO 655
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 655

Gln Thr Trp Gly Thr Gly Ile Gln Val
1               5

<210> SEQ ID NO 656
<211> LENGTH: 122
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 656

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Gly Val Trp Phe Gly Glu Leu Phe Pro Phe Asp Tyr Trp
            100                 105                 110

Gly Gln Gly Thr Leu Gly Thr Val Ser Ser
        115                 120

<210> SEQ ID NO 657
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 657

Gly Gly Ser Phe Ser Gly Tyr Tyr
1               5

<210> SEQ ID NO 658
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 658

Ile Asn His Ser Gly Ser Thr
1               5

<210> SEQ ID NO 659
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 659

Ala Arg Gly Arg Gly Val Trp Phe Gly Glu Leu Phe Pro Phe Asp Tyr
1               5                   10                  15

<210> SEQ ID NO 660
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 660

Gln Gly Gly Leu Thr Gln Pro Pro Ser Val Ser Lys Gly Leu Arg Gln
1               5                   10                  15

Thr Ala Thr Leu Thr Cys Thr Gly Asn Ser Asn Asn Val Gly Asn Gln
            20                  25                  30

Gly Ala Ala Trp Leu Gln Gln His Gln Gly His Pro Pro Lys Leu Leu
        35                  40                  45

Ser Tyr Arg Asn Asn Asn Arg Pro Ser Gly Ile Ser Glu Arg Phe Ser
    50                  55                  60

Ala Ser Arg Ser Gly Asn Thr Ala Ser Leu Thr Ile Thr Gly Leu Gln
65                  70                  75                  80

Pro Glu Asp Glu Ala Asp Tyr Tyr Cys Ser Ala Trp Asp Ser Ser Leu
                85                  90                  95

Ser Ala Val Val Phe Gly Gly Gly Thr Lys Leu Thr Val Leu
            100                 105                 110

<210> SEQ ID NO 661
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 661

Ser Asn Asn Val Gly Asn Gln Gly
1               5

<210> SEQ ID NO 662
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 662

Arg Asn Asn
1

<210> SEQ ID NO 663
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 663

Ser Ala Trp Asp Ser Ser Leu Ser Ala Val Val
1               5                   10

<210> SEQ ID NO 664
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 664

Gln Val Gln Leu Gln Gln Trp Gly Ala Gly Leu Leu Lys Pro Ser Glu
1               5                   10                  15
```

```
Thr Leu Ser Leu Asn Cys Thr Val Tyr His Gly Ser Leu Ser Thr Ser
            20                  25                  30

Tyr Trp Ser Trp Ile Arg Gln Pro Pro Gly Arg Gly Leu Glu Trp Ile
        35                  40                  45

Gly Glu Ile Asn Asp Ser Gly Ala Thr Asn Tyr Asn Pro Ser Leu Lys
 50                  55                  60

Ser Arg Val Ile Ile Ser Val Asp Thr Ser Lys Asp Gln Phe Ser Leu
65                  70                  75                  80

Lys Leu Thr Ser Val Thr Ala Ala Asp Thr Ala Met Tyr Tyr Cys Ala
                85                  90                  95

Arg Ala Pro Leu Leu Trp Val Gly Glu Ser Phe Phe Tyr Tyr Phe Asp
            100                 105                 110

Ser Trp Gly Gln Gly Ile Leu Val Thr Val Ser Ser
        115                 120
```

<210> SEQ ID NO 665
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 665

```
His Gly Ser Leu Ser Thr Ser Tyr
1               5
```

<210> SEQ ID NO 666
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 666

```
Ile Asn Asp Ser Gly Ala Thr
1               5
```

<210> SEQ ID NO 667
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 667

```
Ala Arg Ala Pro Leu Leu Trp Val Gly Glu Ser Phe Phe Tyr Tyr Phe
1               5                   10                  15

Asp Ser
```

<210> SEQ ID NO 668
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 668

```
Asp Ile Gln Met Thr Gln Ser Pro Ser Ser Leu Ser Ala Ser Val Gly
1               5                   10                  15
```

-continued

```
Asp Arg Val Ser Ile Thr Cys Arg Ala Gly Gln Ser Ile Asp Thr Tyr
            20                  25                  30

Leu Asn Trp Tyr Gln His Lys Pro Gly Lys Ala Pro Asp Leu Leu Ile
        35                  40                  45

Tyr Thr Thr Ser Thr Leu His Ser Gly Val Pro Ser Arg Phe Ser Gly
 50                  55                  60

Ser Gly Ser Gly Thr Asp Phe Thr Leu Thr Ile Thr Ser Leu Gln Pro
 65                  70                  75                  80

Glu Asp Phe Ala Ile Tyr Tyr Cys Gln Gln Ser Tyr Lys Ser Pro Tyr
                85                  90                  95

Thr Phe Gly Gln Gly Thr Lys Val Glu Ile Lys
            100                 105
```

<210> SEQ ID NO 669
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 669

```
Gln Ser Ile Asp Thr Tyr
 1               5
```

<210> SEQ ID NO 670
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 670

```
Thr Thr Ser
 1
```

<210> SEQ ID NO 671
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 671

```
Gln Gln Ser Tyr Lys Ser Pro Tyr Thr
 1               5
```

<210> SEQ ID NO 672
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 672

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
```

```
                35                  40                  45
Gly Ile Ile Asn Pro Ser Gly Gly Thr Thr Ser Ser Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Leu Tyr Tyr Cys
                85                  90                  95

Ala Arg Asp Arg Glu Gln Lys Val Gly Gly Ala Pro Leu His Trp Gly
            100                 105                 110

Gln Gly Thr Leu Val Thr Val Ser Ser
        115                 120

<210> SEQ ID NO 673
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 673

Ile Asn Pro Ser Gly Gly Thr Thr
1               5

<210> SEQ ID NO 674
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 674

Ala Arg Asp Arg Glu Gln Lys Val Gly Gly Ala Pro Leu His
1               5                   10

<210> SEQ ID NO 675
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 675

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Ser Phe Thr Ile Ser Ser Leu Gln Pro
65                  70                  75                  80

Glu Asp Ile Ala Thr Tyr Tyr Cys Gln Gln Tyr Asp Asn Phe Ala Leu
                85                  90                  95

Thr Phe Gly Gly Gly Thr Lys Val Glu Ile Lys
            100                 105

<210> SEQ ID NO 676
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 676

Gln Gln Tyr Asp Asn Phe Ala Leu Thr
1               5

<210> SEQ ID NO 677
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 677

Glu Val Gln Leu Leu Glu Ser Gly Gly Gly Leu Val Gln Pro Gly Val
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Tyr Ser Gly Gly Asn Ile Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asp Asn Leu Arg Ala Glu Asp Thr Ala Leu Tyr Tyr Cys
                85                  90                  95

Ala Lys His Asp Tyr Asp Ser Ser Gly Tyr Phe Asp Phe Asp Tyr Trp
            100                 105                 110

Gly His Gly Thr Leu Val Thr Val Ser Ser
        115                 120

<210> SEQ ID NO 678
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 678

Ile Tyr Ser Gly Gly Asn Ile Ile
1               5

<210> SEQ ID NO 679
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 679

Ala Lys His Asp Tyr Asp Ser Ser Gly Tyr Phe Asp Phe Asp Tyr
1               5                   10                  15

<210> SEQ ID NO 680
<211> LENGTH: 110
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 680

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Arg Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Cys Ser Tyr Thr Ser Ser
                85                  90                  95

Ser Thr Trp Val Phe Gly Gly Gly Thr Lys Leu Thr Val Leu
            100                 105                 110
```

<210> SEQ ID NO 681
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 681

```
Ser Arg Asp Val Gly Gly Tyr Asn Tyr
1               5
```

<210> SEQ ID NO 682
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 682

```
Asp Val Asn
1
```

<210> SEQ ID NO 683
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 683

```
Cys Ser Tyr Thr Ser Ser Ser Thr Trp Val
1               5                   10
```

<210> SEQ ID NO 684
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 684

Gln Val Gln Leu Gln Glu Ser Gly Pro Gly Leu Val Lys Pro Ser Gly
1               5                   10                  15

Thr Leu Ser Leu Thr Cys Ala Val Ser Gly Ala Ser Ile Ser Asn Ser
            20                  25                  30

Ala Trp Trp Asn Trp Val Arg Gln Pro Pro Arg Gly Gly Leu Glu Trp
        35                  40                  45

Val Gly Glu Ile Tyr Pro Ser Gly Ser Thr Asn Tyr Thr Pro Ser Leu
50                  55                  60

Lys Ser Arg Ala Thr Ile Leu Leu Asp Glu Ser Arg Asn Glu Phe Ser
65                  70                  75                  80

Leu Lys Leu Asn Ser Val Thr Ala Ala Asp Thr Ala Val Tyr Tyr Cys
                85                  90                  95

Ala Arg Gly Arg Leu Glu Asp Cys Asn Gly Gly Val Cys Tyr Phe Phe
            100                 105                 110

Asp Asn Trp Gly Gln Gly Ile Leu Val Ser Val Ser Ser
        115                 120                 125

<210> SEQ ID NO 685
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 685

Gly Ala Ser Ile Ser Asn Ser Ala Trp
1               5

<210> SEQ ID NO 686
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 686

Ile Tyr Pro Ser Gly Ser Thr
1               5

<210> SEQ ID NO 687
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 687

Ala Arg Gly Arg Leu Glu Asp Cys Asn Gly Gly Val Cys Tyr Phe Phe
1               5                   10                  15

Asp Asn

<210> SEQ ID NO 688
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 688

Asp Ile Glu Met Thr Gln Ser Pro Ser Thr Leu Ser Ala Ser Val Gly
1               5                   10                  15

Asp Arg Val Thr Ile Thr Cys Arg Ala Asn Tyr Gly Ile Gly Ala Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Leu Arg Phe Ser Gly
50                  55                  60

Ser Gly Ser Gly Thr Glu Phe Thr Leu Ser Ile Ser Gly Leu Gln Pro
65                  70                  75                  80

Asp Asp Phe Ala Thr Tyr Tyr Cys His Gln Tyr Ser Thr Tyr Pro Ile
                85                  90                  95

Thr Phe Gly Gln Gly Thr Arg Leu Glu Ile Lys
            100                 105

<210> SEQ ID NO 689
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 689

Tyr Gly Ile Gly Ala Trp
1               5

<210> SEQ ID NO 690
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 690

His Gln Tyr Ser Thr Tyr Pro Ile Thr
1               5

<210> SEQ ID NO 691
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 691

Gln Val Gln Leu Val Glu Ser Gly Gly Gly Val Val Gln Pro Gly Arg
1               5                   10                  15

Ser Leu Thr Leu Ser Cys Ala Ala Ser Gly Phe Asn Phe Lys Thr Tyr
            20                  25                  30

Gly Met His Trp Val Arg Gln Ala Pro Gly Lys Gly Leu Glu Trp Val
        35                  40                  45

Ala Val Ile Tyr His Asp Gly Asn Asp Lys Phe Tyr Ala Asp Ser Val
50                  55                  60

Lys Gly Arg Phe Thr Ile Ser Arg Asp Asn Ser Lys Asn Thr Leu Tyr
65                  70                  75                  80

Val Gln Met Ser Ser Leu Arg Ala Asp Asp Thr Ala Ile Tyr Tyr Cys
                85                  90                  95

```
Ala Lys Gly Ile Phe Ser Ser Gly Tyr His Tyr Gly Met Asp Val Trp
            100                 105                 110

Gly Gln Gly Thr Ala Val Ile Val Ser Ser
        115                 120

<210> SEQ ID NO 692
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 692

Gly Phe Asn Phe Lys Thr Tyr Gly
1               5

<210> SEQ ID NO 693
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 693

Ile Tyr His Asp Gly Asn Asp Lys
1               5

<210> SEQ ID NO 694
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 694

Ala Lys Gly Ile Phe Ser Ser Gly Tyr His Tyr Gly Met Asp Val
1               5                   10                  15

<210> SEQ ID NO 695
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 695

Asp Ile Gln Met Thr Gln Ser Pro Ser Ser Leu Ser Ala Ser Leu Gly
1               5                   10                  15

Asp Ser Val Thr Ile Thr Cys Leu Ala Ser Gln Gly Ile Lys Glu Phe
            20                  25                  30

Leu Ser Trp Phe Gln Gln Lys Pro Gly Gln Ala Pro Lys Leu Leu Ile
        35                  40                  45

Tyr Asp Ala Ser Ser Ser His Ser Gly Val Pro Ser Arg Phe Ser Gly
    50                  55                  60

Ser Gly Ser Ala Thr His Phe Thr Leu Thr Ile Ser Ser Leu Gln Pro
65                  70                  75                  80

Asp Asp Ile Ala Thr Tyr Tyr Cys Gln Gln Tyr His Gln Val Pro Leu
                85                  90                  95

Thr Phe Gly Gln Gly Thr Arg Leu Glu Ile Lys
            100                 105
```

-continued

<210> SEQ ID NO 696
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 696

Gln Gly Ile Lys Glu Phe
1               5

<210> SEQ ID NO 697
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 697

Gln Gln Tyr His Gln Val Pro Leu Thr
1               5

<210> SEQ ID NO 698
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 698

Glu Val Arg Leu Val Glu Ser Gly Gly Gly Leu Ile Gln Pro Gly Gly
1               5                   10                  15

Ser Leu Arg Leu Ser Cys Ala Ala Ser Gly Phe Asn Val Ser Ser Asp
            20                  25                  30

Tyr Met Asn Trp Val Arg Gln Ala Pro Gly Lys Gly Leu Glu Trp Val
        35                  40                  45

Ser Val Leu Tyr Ser Ser Gly Phe Thr Tyr Tyr Ala Asp Ser Val Arg
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Val Ala Leu Phe Gly Glu Pro Leu Val Asp Ser Trp Gly Gln Gly
            100                 105                 110

Thr Leu Val Thr Val Ser Ser
        115

<210> SEQ ID NO 699
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 699

Gly Phe Asn Val Ser Ser Asp Tyr
1               5

<210> SEQ ID NO 700
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 700

Leu Tyr Ser Ser Gly Phe Thr
1               5

<210> SEQ ID NO 701
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 701

Ala Arg Val Ala Leu Phe Gly Glu Pro Leu Val Asp Ser
1               5                   10

<210> SEQ ID NO 702
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 702

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ile Ser Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys Gln Gln Tyr Asn Asn Trp Pro Trp
                85                  90                  95

Thr Phe Gly Gln Gly Thr Lys Val Glu Ile Lys
            100                 105

<210> SEQ ID NO 703
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 703

Gly Ala Ile
1

<210> SEQ ID NO 704
<211> LENGTH: 6
<212> TYPE: PRT
<213> ORGANISM: Arachis hypogaea

```
<400> SEQUENCE: 704

Asp Pro Tyr Ser Pro Ser
1               5

<210> SEQ ID NO 705
<211> LENGTH: 11
<212> TYPE: PRT
<213> ORGANISM: Arachis hypogaea

<400> SEQUENCE: 705

Asp Ser Tyr Gly Arg Asp Pro Tyr Ser Pro Ser
1               5                   10

<210> SEQ ID NO 706
<211> LENGTH: 11
<212> TYPE: PRT
<213> ORGANISM: Arachis hypogaea

<400> SEQUENCE: 706

Tyr Ser Pro Ser Gln Asp Pro Tyr Ser Pro Ser
1               5                   10

<210> SEQ ID NO 707
<211> LENGTH: 10
<212> TYPE: PRT
<213> ORGANISM: Arachis hypogaea

<400> SEQUENCE: 707

Pro Asp Arg Arg Asp Pro Tyr Ser Pro Ser
1               5                   10

<210> SEQ ID NO 708
<211> LENGTH: 151
<212> TYPE: PRT
<213> ORGANISM: Arachis hypogaea

<400> SEQUENCE: 708

Arg Gln Gln Trp Glu Leu Gln Gly Asp Arg Arg Cys Gln Ser Gln Leu
1               5                   10                  15

Glu Arg Ala Asn Leu Arg Pro Cys Glu Gln His Leu Met Gln Lys Ile
            20                  25                  30

Gln Arg Asp Glu Asp Ser Tyr Gly Arg Asp Pro Tyr Ser Pro Ser Gln
        35                  40                  45

Asp Pro Tyr Ser Pro Ser Gln Asp Pro Asp Arg Arg Asp Pro Tyr Ser
    50                  55                  60

Pro Ser Pro Tyr Asp Arg Arg Gly Ala Gly Ser Ser Gln His Gln Glu
65                  70                  75                  80

Arg Cys Cys Asn Glu Leu Asn Glu Phe Glu Asn Asn Gln Arg Cys Met
                85                  90                  95

Cys Glu Ala Leu Gln Gln Ile Met Glu Asn Gln Ser Asp Arg Leu Gln
            100                 105                 110

Gly Arg Gln Gln Glu Gln Gln Phe Lys Arg Glu Leu Arg Asn Leu Pro
        115                 120                 125

Gln Gln Cys Gly Leu Arg Ala Pro Gln Arg Cys Asp Leu Glu Val Glu
    130                 135                 140

Ser Gly Gly Arg Asp Arg Tyr
145                 150

<210> SEQ ID NO 709
```

<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 709

Glu Val Gln Leu Val Ala Ser Gly Gly Gly Leu Ile His Pro Gly Gly
1               5                   10                  15

Ser Leu Arg Leu Ser Cys Glu Ala Ser Gly Phe Ser Phe Ser Arg Phe
            20                  25                  30

Trp Met Tyr Trp Val Arg Gln Ser Pro Gly Glu Gly Leu Val Trp Val
        35                  40                  45

Ala Arg Leu Ser Gly Asp Gly Thr Val Thr Asn Tyr Ala Asp Ser Met
    50                  55                  60

Glu Gly Arg Val Thr Ile Ser Arg Asp Asn Val Lys Asn Thr Leu Phe
65                  70                  75                  80

Leu Glu Met Asn Ser Leu Arg Glu Gly Asp Thr Gly Ile Tyr Tyr Cys
                85                  90                  95

Ala Arg Lys Asp Cys Pro Ser Leu Ser Cys Gln Leu Asp Tyr Trp Gly
            100                 105                 110

Gln Gly Val Gln Val Thr Val Ser Ser
        115                 120

<210> SEQ ID NO 710
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 710

Gly Phe Ser Phe Ser Arg Phe Trp
1               5

<210> SEQ ID NO 711
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 711

Leu Ser Gly Asp Gly Thr Val Thr
1               5

<210> SEQ ID NO 712
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 712

Ala Arg Lys Asp Cys Pro Ser Leu Ser Cys Gln Leu Asp Tyr
1               5                   10

<210> SEQ ID NO 713
<211> LENGTH: 110
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 713

Gln Ser Val Leu Thr Gln Pro Pro Ser Val Ser Ala Ala Pro Gly Gln
1               5                   10                  15

Lys Val Thr Ile Ser Cys Ser Gly Ser Thr Ser Asn Ile Gly Lys Asn
            20                  25                  30

Tyr Val Ser Trp Tyr Gln His Phe Pro Gly Ala Ala Pro Lys Leu Leu
        35                  40                  45

Ile Phe Asp Asn Asp Lys Arg Pro Ser Gly Ile Pro Asp Arg Phe Ser
    50                  55                  60

Gly Ser Arg Ser Gly Thr Ser Ala Thr Leu Asp Ile Thr Gly Leu Gln
65                  70                  75                  80

Thr Gly Asp Glu Ala Asp Tyr Phe Cys Ala Thr Trp Asp Ser Arg Leu
                85                  90                  95

Ser Ala Asp Val Phe Gly Ser Gly Thr Thr Val Ser Val Leu
            100                 105                 110

<210> SEQ ID NO 714
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 714

Thr Ser Asn Ile Gly Lys Asn Tyr
1               5

<210> SEQ ID NO 715
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 715

Asp Asn Asp
1

<210> SEQ ID NO 716
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 716

Ala Thr Trp Asp Ser Arg Leu Ser Ala Asp Val
1               5                   10

<210> SEQ ID NO 717
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 717

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asn Phe Ser Asn Phe
            20                  25                  30

Ala Val Ser Trp Val Arg Gln Thr Pro Gly Lys Gly Leu Glu Trp Val
        35                  40                  45

Ser Ala Ile Leu Gly Ser Arg Ser Val Thr Tyr Tyr Ala Asp Ser Val
    50                  55                  60

Lys Gly Arg Phe Thr Ile Ser Arg Asp Lys Ser Lys Asn Ala Leu Tyr
65                  70                  75                  80

Leu Gln Met Asp Ser Leu Arg Ala Glu Asp Thr Ala Ile Tyr Tyr Cys
                85                  90                  95

Ala Lys Leu Phe Phe Met Pro Tyr Ser His Asp Asp Ser Gly Asp Tyr
            100                 105                 110

Trp Gly Gln Gly Thr Leu Val Ala Val Ser Ser
        115                 120

<210> SEQ ID NO 718
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 718

Gly Phe Asn Phe Ser Asn Phe Ala
1               5

<210> SEQ ID NO 719
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 719

Ile Leu Gly Ser Arg Ser Val Thr
1               5

<210> SEQ ID NO 720
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 720

Ala Lys Leu Phe Phe Met Pro Tyr Ser His Asp Asp Ser Gly Asp Tyr
1               5                   10                  15

<210> SEQ ID NO 721
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 721

-continued

```
Gln Leu Val Leu Thr Gln Ser Pro Ser Ala Ser Leu Gly Ala
1               5                   10                  15

Ser Val Lys Leu Thr Cys Thr Leu Ser Ser Asp His Arg Ser Tyr Ala
            20                  25                  30

Ile Ala Trp His Gln Gln Pro Gly Lys Gly Pro Arg Tyr Leu Met
                35                  40                  45

Lys Val Asn Arg Asp Gly Ser His Ile Lys Gly Asp Gly Ile Pro His
        50                  55                  60

Arg Phe Ser Gly Ser Ser Val Thr Glu Arg Tyr Leu Ile Ile Ser
65                  70                  75                  80

Ser Leu Gln Ser Glu Asp Glu Ala Asp Tyr Tyr Cys Gln Ser Trp Asp
                85                  90                  95

Thr Gly Ile Gln Val Phe Gly Gly Gly Thr Arg Leu Thr Val Val
                100                 105                 110
```

<210> SEQ ID NO 722
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 722

```
Ser Asp His Arg Ser Tyr Ala
1               5
```

<210> SEQ ID NO 723
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 723

```
Val Asn Arg Asp Gly Ser His
1               5
```

<210> SEQ ID NO 724
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 724

```
Gln Ser Trp Asp Thr Gly Ile Gln Val
1               5
```

<210> SEQ ID NO 725
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 725

```
Gln Val Gln Leu Gln Glu Ser Gly Leu Gly Leu Val Lys Pro Ser Gly
1               5                   10                  15

Thr Leu Ser Leu Thr Cys Ala Val Ser Gly Gly Pro Met Asn Ser Ser
            20                  25                  30
```

```
Tyr Trp Trp Ser Trp Val Arg Gln Ser Pro Gly Gly Leu Glu Trp
        35                  40                  45

Ile Gly Gln Ile Ser His Tyr Thr Asn Thr Lys Tyr Asn Pro Ser Phe
 50                  55                  60

Lys Asn Arg Val Ser Ile Ser Ile Asp Lys Ser Lys Asn Glu Phe Ser
 65                  70                  75                  80

Leu Arg Leu Thr Tyr Val Thr Gly Ala Asp Thr Gly Val Tyr Tyr Cys
                 85                  90                  95

Val Gly Glu Arg Asp Trp Lys Asp Pro Asn Trp Phe Asp Pro Trp Gly
                100                 105                 110

Gln Gly Arg Leu Val Thr Val Ser Ser
        115                 120

<210> SEQ ID NO 726
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 726

Gly Gly Pro Met Asn Ser Ser Tyr Trp
1               5

<210> SEQ ID NO 727
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 727

Ile Ser His Tyr Thr Asn Thr
1               5

<210> SEQ ID NO 728
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 728

Val Gly Glu Arg Asp Trp Lys Asp Pro Asn Trp Phe Asp Pro
1               5                   10

<210> SEQ ID NO 729
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 729

Gln Ser Val Leu Thr Gln Pro Pro Ser Val Ser Gly Ala Pro Gly Gln
1               5                   10                  15

Arg Val Thr Ile Ser Cys Thr Gly Ser Asn Ser Asn Ile Gly Ala Gly
                20                  25                  30

Gln Asp Val His Trp Tyr Gln His Phe Pro Gly Thr Ala Pro Lys Leu
```

```
            35                  40                  45
Val Ile Tyr Gly Asn Ser Asn Arg Pro Ser Gly Val Pro Asp Arg Phe
 50                  55                  60

Ser Gly Ser Lys Ser Gly Thr Ser Ala Ser Leu Ala Ile Ser Gly Leu
65                  70                  75                  80

Gln Ala Asp Asp Glu Ala Asp Tyr Tyr Cys Gln Ser Tyr Asp Lys Ser
                85                  90                  95

Leu Ser Ser Ser Leu Phe Gly Gly Gly Thr Lys Leu Thr Val Leu
            100                 105                 110

<210> SEQ ID NO 730
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 730

Asn Ser Asn Ile Gly Ala Gly Gln Asp
1               5

<210> SEQ ID NO 731
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 731

Gly Asn Ser
1

<210> SEQ ID NO 732
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 732

Gln Ser Tyr Asp Lys Ser Leu Ser Ser Ser Leu
1               5                   10

<210> SEQ ID NO 733
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 733

Gln Val Gln Leu Gln Glu Ser Gly Pro Gly Leu Val Lys Pro Ser Glu
1               5                   10                  15

Thr Leu Ser Leu Ser Cys Asn Val Ser Gly Gly Ser Ile Arg Gly His
            20                  25                  30

Tyr Trp Ser Trp Ile Arg Gln Ser Pro Gly Lys Arg Leu Glu Trp Leu
        35                  40                  45

Gly Tyr Ile Tyr Gln Ser Gly Tyr Thr Lys Tyr Asn Pro Ser Leu Lys
    50                  55                  60
```

Ser Arg Val Ser Ile Ser Leu Asp Thr Ser Lys Asn Lys Phe Ser Leu
65                  70                  75                  80

Asn Leu Lys Ser Val Thr Thr Ala Asp Thr Ala Val Tyr Tyr Cys Ala
            85                  90                  95

Gly Arg Val Ala Glu Arg Gly Gly Asp Gln Phe Asp Phe Trp Gly Gln
            100                 105                 110

Gly Thr Leu Val Thr Val Ser Ser
            115                 120

<210> SEQ ID NO 734
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 734

Gly Gly Ser Ile Arg Gly His Tyr
1               5

<210> SEQ ID NO 735
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 735

Ile Tyr Gln Ser Gly Tyr Thr
1               5

<210> SEQ ID NO 736
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 736

Ala Gly Arg Val Ala Glu Arg Gly Gly Asp Gln Phe Asp Phe
1               5                   10

<210> SEQ ID NO 737
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 737

Ser Tyr Glu Leu Thr Gln Ser Pro Ser Leu Ser Val Ser Pro Gly Gln
1               5                   10                  15

Thr Ala Ser Ile Thr Cys Ser Gly Glu Asn Leu Gly Glu Lys His Ala
            20                  25                  30

Ser Trp Tyr Gln Gln Lys Ser Gly Gln Ser Pro Val Leu Val Ile Tyr
        35                  40                  45

Gln Asp Thr Lys Arg Pro Ala Gly Ile Pro Glu Arg Phe Ser Gly Ser
    50                  55                  60

Asn Ser Gly Ser Thr Ala Thr Leu Thr Ile Ser Gly Thr Gln Pro Met
65                  70                  75                  80

```
Asp Glu Ala Asp Tyr Phe Cys Gln Ala Trp Asp Ala Asn Thr Ala Asn
                85                  90                  95

Val Ile Phe Gly Gly Gly Thr Met Leu Thr Val Leu
            100                 105

<210> SEQ ID NO 738
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 738

Asn Leu Gly Glu Lys His
1               5

<210> SEQ ID NO 739
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 739

Gln Asp Thr
1

<210> SEQ ID NO 740
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 740

Gln Ala Trp Asp Ala Asn Thr Ala Asn Val Ile
1               5                   10

<210> SEQ ID NO 741
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 741

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Thr Ile His Trp Val Arg Gln Thr Ser Gly Lys Gly Leu Glu Trp Val
        35                  40                  45

Gly Arg Ile Gly Ser Lys Ala Thr Ser Tyr Ala Thr Ala Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Phe Cys Thr Arg Arg Tyr Tyr Asp Thr Thr Lys Ser Val Leu Val Val
```

```
                100                 105                 110
Ser Asp Ser Trp Gly Gln Gly Thr Leu Val Thr Val Ser Ser
        115                 120                 125

<210> SEQ ID NO 742
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 742

Gly Phe Thr Phe Ser Gly Ser Thr
1               5

<210> SEQ ID NO 743
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 743

Ile Gly Ser Lys Ala Thr Ser Tyr Ala Thr
1               5                   10

<210> SEQ ID NO 744
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 744

Thr Arg Arg Tyr Tyr Asp Thr Thr Lys Ser Val Leu Val Val Ser Asp
1               5                   10                  15

Ser

<210> SEQ ID NO 745
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 745

Ser Tyr Glu Leu Thr Gln Pro Pro Ser Met Ser Val Ser Pro Gly Gln
1               5                   10                  15

Thr Ala Arg Ile Thr Cys Ser Gly Asp Val Leu Ala Lys Gln Phe Ala
            20                  25                  30

Tyr Trp Tyr Gln Gln Lys Pro Gly Gln Ala Pro Val Leu Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Ile Ile Thr Leu Thr Ile Ser Gly Val Gln Ala Glu
65                  70                  75                  80

Asp Glu Ala Asp Tyr Tyr Cys Gln Ser Ala Asp Ser Ser Gly Thr Ser
                85                  90                  95

Trp Val Phe Gly Gly Gly Thr Lys Leu Thr Val Leu
```

<210> SEQ ID NO 746
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 746

Val Leu Ala Lys Gln Phe
1               5

<210> SEQ ID NO 747
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 747

Lys Asp Ser
1

<210> SEQ ID NO 748
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 748

Gln Ser Ala Asp Ser Ser Gly Thr Ser Trp Val
1               5                   10

<210> SEQ ID NO 749
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 749

Gln Leu Leu Leu Gln Glu Ser Gly Pro Gly Leu Val Lys Pro Ser Glu
1               5                   10                  15

Thr Leu Ser Leu Ser Cys Thr Val Ser Ala Gly Ser Ile Thr Ser Ile
            20                  25                  30

Asn Tyr Ser Trp Gly Trp Ile Arg Gln Pro Pro Gly Lys Gly Leu Glu
        35                  40                  45

Trp Ile Ala Ser Val Tyr Phe Ser Gly Ser Ile Tyr Tyr Asn Pro Ser
    50                  55                  60

Leu Lys Ser Arg Val Ala Ile Ser Val Asp Thr Ser Lys Asn Thr Phe
65                  70                  75                  80

Ser Leu Asn Leu Thr Ser Val Thr Ala Ala Asp Thr Ala Val Tyr Tyr
                85                  90                  95

Cys Ala Arg Leu Arg Leu Asp Thr Gly Arg Asp Ser Ser Gly Leu Ser
            100                 105                 110

Tyr Arg Glu His Phe Asp Tyr Trp Ala Gln Gly Thr Leu Val Thr Val
        115                 120                 125

```
Ser Ser
    130

<210> SEQ ID NO 750
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 750

Ala Gly Ser Ile Thr Ser Ile Asn Tyr Ser
1               5                   10

<210> SEQ ID NO 751
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 751

Val Tyr Phe Ser Gly Ser Ile
1               5

<210> SEQ ID NO 752
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 752

Ala Arg Leu Arg Leu Asp Thr Gly Arg Asp Ser Ser Gly Leu Ser Tyr
1               5                   10                  15

Arg Glu His Phe Asp Tyr
            20

<210> SEQ ID NO 753
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 753

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Met Trp
            20                  25                  30

Leu Ala Trp Phe Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Gln Tyr Asn Ser Tyr Leu Phe
                85                  90                  95

Thr Phe Gly Pro Gly Thr Lys Val Asp Ile Lys
            100                 105
```

<210> SEQ ID NO 754
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 754

Gln Ser Ile Gly Met Trp
1               5

<210> SEQ ID NO 755
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 755

Gln Gln Tyr Asn Ser Tyr Leu Phe Thr
1               5

<210> SEQ ID NO 756
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 756

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Ser Ser
                20                  25                  30

Trp Ile Gly Trp Val Arg Gln Met Pro Gly Lys Gly Leu Glu Trp Met
            35                  40                  45

Gly Ile Ile His Pro Gly Asp Ser Asp Thr Arg Tyr Ser Pro Ser Phe
        50                  55                  60

Gln Gly Gln Val Thr Ile Ser Ala Asp Lys Ser Leu Thr Thr Ala Phe
65                  70                  75                  80

Leu Gln Trp Ser Ser Leu Lys Thr Ser Asp Thr Ala Ile Tyr Tyr Cys
                85                  90                  95

Ala Arg His Gly Ser Thr Met Leu Trp Gly Asp Ala Phe Asp Ile Trp
            100                 105                 110

Gly Gln Gly Thr Met Val Thr Val Ser Ser
        115                 120

<210> SEQ ID NO 757
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 757

Gly Tyr Asn Phe Thr Ser Ser Trp
1               5

```
<210> SEQ ID NO 758
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 758

Ile His Pro Gly Asp Ser Asp Thr
1               5

<210> SEQ ID NO 759
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 759

Ala Arg His Gly Ser Thr Met Leu Trp Gly Asp Ala Phe Asp Ile
1               5                   10                  15

<210> SEQ ID NO 760
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 760

Ser Tyr Glu Leu Thr Gln Pro Pro Ser Val Ser Leu Ser Pro Gly Gln
1               5                   10                  15

Thr Ala Arg Ile Thr Cys Ser Gly Asp Ala Leu Pro Lys His Tyr Ala
            20                  25                  30

Tyr Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gln Ser Ser Asp Ser Thr Gly Glu Val
                85                  90                  95

Phe Gly Gly Gly Thr Lys Leu Thr Val Leu
            100                 105

<210> SEQ ID NO 761
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 761

Ala Leu Pro Lys His Tyr
1               5

<210> SEQ ID NO 762
<211> LENGTH: 3
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 762

Lys Asp Thr
1

<210> SEQ ID NO 763
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 763

Gln Ser Ser Asp Ser Thr Gly Glu Val
1               5

<210> SEQ ID NO 764
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 764

Gln Val Gln Leu Val Gln Ser Gly Ala Glu Val Lys Lys Pro Gly Ala
1               5                   10                  15

Ser Val Met Leu Ser Cys Lys Ala Ser Gly Tyr Ile Phe Thr Asn Ser
            20                  25                  30

Asp Ile Asn Trp Val Arg Gln Ala Pro Gly Gln Gly Pro Glu Trp Met
        35                  40                  45

Gly Trp Met Asn Pro Lys Ser Gly Asn Thr Gly Tyr Glu Gln Lys Phe
    50                  55                  60

Gln Gly Arg Val Thr Met Thr Thr Asn Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Ser Thr Gly Ala Val Ala Gly Asn Phe Asp Tyr Trp Gly Gln
            100                 105                 110

Gly Thr Pro Val Thr Val Ser Ser
        115                 120

<210> SEQ ID NO 765
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 765

Gly Tyr Ile Phe Thr Asn Ser Asp
1               5

<210> SEQ ID NO 766
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 766

Met Asn Pro Lys Ser Gly Asn Thr
1               5

<210> SEQ ID NO 767
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 767

Ala Arg Ser Thr Gly Ala Val Ala Gly Asn Phe Asp Tyr
1               5                   10

<210> SEQ ID NO 768
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 768

Glu Ile Val Met Thr Gln Ser Pro Ala Thr Leu Ser Val Ser Leu Gly
1               5                   10                  15

Asp Arg Ala Thr Leu Ser Cys Arg Ala Ser Gln Ser Ile Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Ile Arg Ile Thr Asp Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ile Tyr Phe Cys Gln Gln Tyr Asn Asn Trp Arg Thr
                85                  90                  95

Phe Gly Gln Gly Thr Arg Val Glu Leu Lys
            100                 105

<210> SEQ ID NO 769
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 769

Gln Ser Ile Ser Arg Asn
1               5

<210> SEQ ID NO 770
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 770

Gln Gln Tyr Asn Asn Trp Arg Thr
1               5

<210> SEQ ID NO 771
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 771

His Val Gln Leu Gln Glu Ser Gly Pro Gly Leu Val Lys Ser Ser Glu
1               5                   10                  15

Thr Leu Ser Leu Thr Cys Asn Val Ser Ser Asp Ser Phe Ser Asp His
            20                  25                  30

Tyr Trp Ser Trp Val Arg Gln Pro Ala Gly Lys Gly Leu Gln Trp Leu
        35                  40                  45

Gly Arg Ile Tyr Asn Thr Gly Thr Thr Tyr Asn Pro Ser Leu Asn
    50                  55                  60

Arg Arg Ile Thr Met Ser Val Asp Thr Ser Lys Asn Gln Phe Ser Leu
65                  70                  75                  80

Arg Leu Thr Ser Val Thr Ala Ala Asp Thr Ala Val Tyr Tyr Cys Ala
                85                  90                  95

Ala Arg His Tyr His Tyr Asp Lys Thr Ile Trp Gly Gln Gly Thr Leu
            100                 105                 110

Val Thr Val Ser Ser
        115

<210> SEQ ID NO 772
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 772

Ser Asp Ser Phe Ser Asp His Tyr
1               5

<210> SEQ ID NO 773
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 773

Ile Tyr Asn Thr Gly Thr Thr
1               5

<210> SEQ ID NO 774
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 774

Ala Ala Arg His Tyr His Tyr Asp Lys Thr Ile
1               5                   10

```
<210> SEQ ID NO 775
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 775

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Pro Glu Asp Glu Ala Asp Phe Tyr Cys Gln Ser Tyr Asp Ser
                85                  90                  95

Asp Asp Arg Glu Val Phe Gly Gly Gly Thr Arg Leu Thr Val Leu
            100                 105                 110

<210> SEQ ID NO 776
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 776

Ser Gly Ser Ile Ala Ser Asn Tyr
1               5

<210> SEQ ID NO 777
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 777

Gln Ser Tyr Asp Ser Asp Asp Arg Glu Val
1               5                   10

<210> SEQ ID NO 778
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 778

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45
```

```
Gly Trp Ile Ser Ala Tyr Asn Gly Asn Thr Thr Tyr Ala Gln Asn Phe
 50                  55                  60

His Ala Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Phe Cys
                 85                  90                  95

Ala Arg Thr Ser Ala Arg Thr Ile Thr Ile Phe Gly Val Leu Ile Pro
            100                 105                 110

Ala Gly Leu Asn Leu Asp Tyr Trp Gly Gln Gly Thr Leu Val Thr Val
        115                 120                 125

Ser Ser
    130

<210> SEQ ID NO 779
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 779

Gly Tyr Thr Phe Thr Thr Tyr Gly
 1               5

<210> SEQ ID NO 780
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 780

Ala Arg Thr Ser Ala Arg Thr Ile Thr Ile Phe Gly Val Leu Ile Pro
 1               5                  10                  15

Ala Gly Leu Asn Leu Asp Tyr
             20

<210> SEQ ID NO 781
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 781

Gln Ser Ala Leu Thr Gln Pro Ala Ser Val Ser Gly Ser Pro Gly Gln
 1               5                  10                  15

Ser Ile Thr Ile Ser Cys Thr Gly Thr Gly Ser Asp Val Gly Arg Tyr
             20                  25                  30

Asn Tyr Val Ser Trp Tyr Gln Gln His Pro Gly Lys Ala Pro Lys Phe
         35                  40                  45

Met Ile Tyr Asp Val Ser Asn Arg Pro Ser Gly Val Ser Asn Arg Phe
 50                  55                  60

Ser Ala Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Ser Thr
                 85                  90                  95

Ser Thr Leu Val Phe Gly Gly Gly Thr Lys Leu Thr Val Leu
```

<210> SEQ ID NO 782
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 782

Gly Ser Asp Val Gly Arg Tyr Asn Tyr
1               5

<210> SEQ ID NO 783
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 783

Ser Ser Tyr Thr Ser Thr Ser Thr Leu Val
1               5                   10

<210> SEQ ID NO 784
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 784

Gln Val Asp Leu Val Glu Ser Gly Gly Gly Tyr Val Lys Ser Gly Gly
1               5                   10                  15

Ser Leu Arg Leu Ser Cys Ala Ala Ser Gly Phe Arg Phe Ser Asp Tyr
                20                  25                  30

Tyr Met Ser Trp Val Arg Gln Ala Pro Gly Lys Gly Leu Glu Trp Leu
            35                  40                  45

Ser His Ile Ser Ser Asp Ser Ser Asp Thr Asn Tyr Ala Asp Ser Val
        50                  55                  60

Lys Gly Arg Phe Ser Ile Ser Arg Asp Asn Ala Lys Asn Ser Val Phe
65                  70                  75                  80

Leu Gln Met Asn Thr Leu Arg Ala Glu Asp Thr Ala Val Tyr Tyr Cys
                85                  90                  95

Ala Arg Asn Ala Leu Thr Asn Ala Tyr Asp Met Ser Gly Phe Arg Asn
            100                 105                 110

Trp Gly Gln Gly Ile Leu Val Thr Val Ser Ser
        115                 120

<210> SEQ ID NO 785
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 785

Gly Phe Arg Phe Ser Asp Tyr Tyr
1               5

<210> SEQ ID NO 786
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 786

Ile Ser Ser Asp Ser Ser Asp Thr
1               5

<210> SEQ ID NO 787
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 787

Ala Arg Asn Ala Leu Thr Asn Ala Tyr Asp Met Ser Gly Phe Arg Asn
1               5                   10                  15

<210> SEQ ID NO 788
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 788

Asn Phe Met Leu Thr Gln Pro His Ser Val Ser Glu Ser Pro Gly Lys
1               5                   10                  15

Thr Val Ile Leu Ser Cys Thr Arg Ser Ser Gly Ser Ile Ala Thr Asn
            20                  25                  30

Tyr Val Arg Trp Tyr Gln Gln Arg Pro Gly Ser Ala Pro Thr Thr Val
        35                  40                  45

Ile Tyr Glu Asp Ser Arg Arg Pro Ser Ser Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Arg Thr Glu Asp Glu Ala Asp Tyr Tyr Cys Gln Ser Phe Asp Thr
                85                  90                  95

Ser Ser Arg Lys Val Val Phe Gly Gly Gly Thr Lys Leu Thr Val Leu
            100                 105                 110

<210> SEQ ID NO 789
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 789

Ser Gly Ser Ile Ala Thr Asn Tyr
1               5

<210> SEQ ID NO 790
<211> LENGTH: 3
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 790

Glu Asp Ser
1

<210> SEQ ID NO 791
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 791

Gln Ser Phe Asp Thr Ser Ser Arg Lys Val Val
1               5                   10

<210> SEQ ID NO 792
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 792

Gln Val Thr Leu Arg Glu Ser Gly Pro Ala Leu Val Glu Val Thr Gln
1               5                   10                  15

Thr Val Thr Leu Thr Cys Asn Phe Ser Gly Phe Ser Leu His Thr Arg
            20                  25                  30

Gly Met Tyr Val Asn Trp Ile Arg Gln Pro Pro Gly Lys Ala Leu Glu
        35                  40                  45

Trp Leu Ala Val Ile Asn Trp Asp Asp Asp Lys Tyr Tyr Thr Pro Ser
    50                  55                  60

Leu Lys Asn Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Asp Tyr Gly Gly Tyr Gly Pro Glu Gly Phe Asp Tyr
            100                 105                 110

Trp Gly Gln Gly Thr Leu Val Thr Val Ser Ser
        115                 120

<210> SEQ ID NO 793
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 793

Gly Phe Ser Leu His Thr Arg Gly Met Tyr
1               5                   10

<210> SEQ ID NO 794
<211> LENGTH: 7
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 794

Ile Asn Trp Asp Asp Asp Lys
1               5

<210> SEQ ID NO 795
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 795

Ala Arg Thr Asp Tyr Gly Gly Tyr Gly Pro Glu Gly Phe Asp Tyr
1               5                   10                  15

<210> SEQ ID NO 796
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 796

Glu Ile Val Met Thr Gln Ser Pro Ala Thr Leu Ser Val Ser Pro Gly
1               5                   10                  15

Glu Ser Ala Thr Leu Ser Cys Arg Ala Ser Gln Ser Val Arg Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Pro Gly Val Pro Ala Arg Phe Thr Gly
    50                  55                  60

Ser Glu Ser Gly Arg Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Tyr Thr Phe Gly Gln Gly Thr Lys Leu Glu Ile Lys
            100                 105

<210> SEQ ID NO 797
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 797

Gln Ser Val Arg Ser Asn
1               5

<210> SEQ ID NO 798
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 798

Gln Gln Tyr Asn Asn Trp Pro Pro Tyr Thr

```
1               5                   10

<210> SEQ ID NO 799
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 799

Gln Val Gln Leu Val Glu Ser Gly Gly Gly Val Val Gln Pro Gly Arg
1               5                   10                  15

Ser Leu Arg Leu Ser Cys Val Ala Ser Gly Phe Asp Leu Asn Ala Tyr
            20                  25                  30

Gly Met His Trp Val Arg Gln Ala Pro Gly Lys Gly Leu Asp Trp Val
        35                  40                  45

Ala Ala Thr Ser Arg Gly Gly Thr Lys Lys Tyr Tyr Ala Asp Ser Val
    50                  55                  60

Lys Gly Arg Phe Thr Ile Ser Arg Asp Val Ser Lys Asn Thr Leu Tyr
65                  70                  75                  80

Leu Gln Met Gly Ser Leu Arg Thr Gly Asp Thr Ala Ile Tyr Tyr Cys
                85                  90                  95

Gly Val Gly Met Glu Asp Val Phe Asp Ile Trp Gly Gln Gly Thr Met
            100                 105                 110

Val Thr Val Ser Pro
        115

<210> SEQ ID NO 800
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 800

Gly Phe Asp Leu Asn Ala Tyr Gly
1               5

<210> SEQ ID NO 801
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 801

Thr Ser Arg Gly Gly Thr Lys Lys
1               5

<210> SEQ ID NO 802
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 802

Gly Val Gly Met Glu Asp Val Phe Asp Ile
1               5                   10
```

<210> SEQ ID NO 803
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 803

Gln Ser Val Leu Thr Gln Pro Pro Ser Val Ser Ala Ala Pro Gly Gln
1               5                   10                  15

Lys Val Thr Ile Ser Cys Ser Glu Asn Asn Ser Asn Ile Gly Asn Arg
            20                  25                  30

Asn Val Ser Trp Tyr Gln Gln Leu Pro Gly Lys Ala Pro Lys Leu Phe
        35                  40                  45

Ile Tyr Asp Asn Asn Glu Arg Pro Ser Gly Ile Pro Ala Arg Phe Ser
    50                  55                  60

Gly Ser Lys Ser Gly Thr Ser Ala Thr Leu Val Ile Thr Gly Leu Gln
65                  70                  75                  80

Thr Gly Asp Glu Ala Asp Tyr Tyr Cys Gly Thr Trp Asp Arg Ser Leu
                85                  90                  95

Ser Val Trp Val Phe Gly Gly Gly Thr Lys Leu Thr Val Leu
            100                 105                 110

<210> SEQ ID NO 804
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 804

Asn Ser Asn Ile Gly Asn Arg Asn
1               5

<210> SEQ ID NO 805
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 805

Gly Thr Trp Asp Arg Ser Leu Ser Val Trp Val
1               5                   10

<210> SEQ ID NO 806
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 806

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Met Arg Ser Gly
            20                  25                  30

Asp Tyr Tyr Trp Ser Trp Ile Arg Gln Pro Pro Gly Lys Gly Leu Glu
        35                  40                  45

```
Trp Ile Gly Tyr Ile Tyr Phe Thr Gly Ser Ser Tyr Tyr Asn Pro Ser
    50                  55                  60

Leu Lys Ser Arg Ala Thr Ile Ser Val Asp Thr Ser Lys Asn Gln Phe
65                  70                  75                  80

Ser Leu Lys Leu Asn Ser Val Thr Ala Ala Asp Thr Ala Val Tyr Phe
                85                  90                  95

Cys Ala Arg Gly Val Asp Val Asp Leu Thr Phe Phe Asp Cys Trp Gly
            100                 105                 110

His Gly Thr Leu Val Thr Val Ser Ser
        115                 120

<210> SEQ ID NO 807
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 807

Gly Gly Ser Met Arg Ser Gly Asp Tyr Tyr
1               5                   10

<210> SEQ ID NO 808
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 808

Ile Tyr Phe Thr Gly Ser Ser
1               5

<210> SEQ ID NO 809
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 809

Ala Arg Gly Val Asp Val Asp Leu Thr Phe Phe Asp Cys
1               5                   10

<210> SEQ ID NO 810
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 810

Ser Tyr Val Leu Thr Gln Pro Pro Ser Val Ser Leu Ala Pro Gly Lys
1               5                   10                  15

Thr Ala Arg Ile Thr Cys Gly Gly Asn Asn Ile Gly Asn Lys Ser Val
                20                  25                  30

His Trp Tyr Gln Gln Lys Pro Gly Gln Ala Pro Val Leu Val Ile Tyr
            35                  40                  45

Tyr Asp Ser Asp Arg Pro Ser Gly Ile Pro Glu Arg Phe Ser Gly Ser
```

```
                50                  55                  60
Asn Ser Gly Asn Thr Ala Thr Leu Thr Ile Asn Arg Val Glu Ala Gly
 65                  70                  75                  80

Asp Glu Ala Asp Tyr His Cys Gln Val Trp Asp Ser Ser Thr Asp His
                 85                  90                  95

Arg Val Phe Gly Glu Gly Thr Lys Leu Thr Val Leu
            100                 105
```

<210> SEQ ID NO 811
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 811

```
Asn Ile Gly Asn Lys Ser
 1               5
```

<210> SEQ ID NO 812
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 812

```
Gln Val Trp Asp Ser Ser Thr Asp His Arg Val
 1               5                  10
```

<210> SEQ ID NO 813
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 813

```
Gln Val Gln Leu Gln Gln Trp Gly Ala Gly Leu Leu Lys Pro Ser Glu
 1               5                  10                  15

Thr Leu Ser Leu Thr Cys Thr Val Ile Gly Thr Ser Phe Ser Asn Tyr
             20                  25                  30

Tyr Trp Ser Trp Ile Arg Gln Pro Pro Gly Lys Gly Leu Gln Trp Ile
         35                  40                  45

Gly Glu Ile Thr His Ser Asp Ser Ala Asn Tyr Asn Pro Ser Leu Lys
     50                  55                  60

Ser Arg Val Ile Ile Ser Ile Asp Ser Ser Lys Asn Gln Leu Ser Leu
 65                  70                  75                  80

Asn Leu Ser Ser Val Thr Ala Ala Asp Thr Ala Val Tyr Tyr Cys Ala
                 85                  90                  95

Arg Gly Ser Lys Asp Tyr Tyr Asp Arg Ser Thr Phe Ser Trp Phe Asp
            100                 105                 110

Pro Trp Gly Gln Gly Thr Leu Val Thr Val Ser Ser
        115                 120
```

<210> SEQ ID NO 814
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 814

Gly Thr Ser Phe Ser Asn Tyr Tyr
1               5

<210> SEQ ID NO 815
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 815

Ile Thr His Ser Asp Ser Ala
1               5

<210> SEQ ID NO 816
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 816

Ala Arg Gly Ser Lys Asp Tyr Tyr Asp Arg Ser Thr Phe Ser Trp Phe
1               5                   10                  15

Asp Pro

<210> SEQ ID NO 817
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 817

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Asn Ile Ser Asn Lys
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Val Pro Ala Arg Phe Ser Cys
    50                  55                  60

Ser Val Ser Gly Thr Ala Phe Thr Leu Thr Ile Asn Arg Leu Gln Ser
65                  70                  75                  80

Glu Asp Phe Ala Val Tyr Tyr Cys Gln Gln Tyr Tyr Tyr Trp Pro Pro
                85                  90                  95

Pro Tyr Thr Phe Gly His Gly Thr Lys Leu Glu Ile Lys
            100                 105

<210> SEQ ID NO 818
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 818

Gln Asn Ile Ser Asn Lys
1               5

<210> SEQ ID NO 819
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 819

Gln Gln Tyr Tyr Tyr Trp Pro Pro Pro Tyr Thr
1               5                   10

<210> SEQ ID NO 820
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 820

Gln Val Gln Leu Val Glu Ser Gly Gly Gly Phe Val Lys Pro Gly Gly
1               5                   10                  15

Ser Leu Arg Leu Ser Cys Ala Val Ser Gly Phe Thr Phe Ser Asp Tyr
            20                  25                  30

Tyr Met Ser Trp Val Arg Gln Ala Pro Gly Lys Gly Leu Glu Trp Leu
        35                  40                  45

Ser His Ile Ser Ser Asp Gly Ser Asp Thr Asn Tyr Ala Asp Ser Val
    50                  55                  60

Lys Gly Arg Phe Ser Ile Ser Arg Asp Asn Ala Lys Asn Ser Val Phe
65                  70                  75                  80

Leu Gln Met Asn Thr Leu Arg Val Glu Asp Thr Ala Val Tyr Tyr Cys
                85                  90                  95

Ala Arg Asn Ala Leu Thr Asn Ala Tyr Asp Met Ser Gly Phe Arg Asn
            100                 105                 110

Trp Gly Gln Gly Thr Leu Val Thr Val Ser Ser
        115                 120

<210> SEQ ID NO 821
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 821

Gly Phe Thr Phe Ser Asp Tyr Tyr
1               5

<210> SEQ ID NO 822
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 822

```
Ile Ser Ser Asp Gly Ser Asp Thr
1               5
```

<210> SEQ ID NO 823
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 823

```
Asn Phe Met Leu Thr Gln Pro His Ser Val Ser Glu Ser Pro Gly Lys
1               5                   10                  15

Thr Val Ile Leu Ser Cys Thr Arg Ser Ser Gly Ser Ile Ala Ser Asn
            20                  25                  30

Tyr Val Arg Trp Tyr Gln Gln Arg Pro Gly Ser Ala Pro Thr Thr Val
        35                  40                  45

Ile Tyr Glu Asp Ser Arg Arg Pro Ser Ser Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Phe Asp Ser
                85                  90                  95

Ser Ser Arg Lys Val Val Phe Gly Gly Gly Thr Lys Leu Thr Val Leu
            100                 105                 110
```

<210> SEQ ID NO 824
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 824

```
Gln Ser Phe Asp Ser Ser Ser Arg Lys Val Val
1               5                   10
```

<210> SEQ ID NO 825
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 825

```
Gln Val Gln Leu Leu Gln Ser Gly Pro Glu Val Lys Gln Pro Gly Ala
1               5                   10                  15

Ser Val Gln Val Ser Cys Gln Thr Ser Gly Tyr Thr Phe Thr Gly Tyr
            20                  25                  30

Tyr Ile His Trp Val Arg Gln Ala Pro Gly Gln Gly Leu Glu Trp Val
        35                  40                  45

Gly Trp Ile Asn Pro Asn Arg Gly His Thr Asn Tyr Gly Pro Ala Phe
    50                  55                  60

Gln Gly Arg Leu Thr Leu Thr Ala Asp Thr Ser Ser Ser Thr Ala Tyr
65                  70                  75                  80

Leu Glu Leu Thr Arg Leu Arg Ser Asp Asp Thr Ala Val Tyr Tyr Cys
                85                  90                  95
```

```
Ala Arg Asp Arg Leu Thr Gly Gly Arg Asp Ala Phe Glu Ile Trp Gly
            100                 105                 110

Gln Gly Thr Met Leu Ile Val Ser Ser
        115                 120

<210> SEQ ID NO 826
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 826

Ile Asn Pro Asn Arg Gly His Thr
1               5

<210> SEQ ID NO 827
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 827

Ala Arg Asp Arg Leu Thr Gly Gly Arg Asp Ala Phe Glu Ile
1               5                   10

<210> SEQ ID NO 828
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 828

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Ser Val Ala Ser Ser Leu Gln Asp Gly Val Pro Pro Arg Phe Ser Gly
    50                  55                  60

Ser Arg Ser Gly Thr Glu Phe Thr Leu Thr Ile Ser Ser Leu Gln Pro
65                  70                  75                  80

Glu Asp Phe Ala Ile Tyr Tyr Cys Gln Gln Ser Tyr Ser Leu Ser Trp
                85                  90                  95

Thr Phe Gly Gln Gly Thr Lys Val Glu Ile Lys
            100                 105

<210> SEQ ID NO 829
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 829

Gln Ser Ile Ser Ser Tyr
1               5
```

<210> SEQ ID NO 830
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 830

Val Ala Ser
1

<210> SEQ ID NO 831
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 831

Gln Gln Ser Tyr Ser Leu Ser Trp Thr
1               5

<210> SEQ ID NO 832
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 832

Gln Val Gln Leu Val Gln Ser Gly Ala Glu Val Lys Gln Pro Gly Ala
1               5                   10                  15

Ser Val Gln Val Ala Cys Gln Thr Ser Gly Tyr Ile Phe Thr Ala Tyr
            20                  25                  30

Tyr Ile His Trp Leu Arg Gln Ala Pro Gly Gln Gly Leu Glu Trp Val
        35                  40                  45

Gly Trp Ile Asn Pro Asn Arg Gly His Thr Asn Tyr Ala Pro Gly Phe
    50                  55                  60

Gln Gly Arg Leu Thr Leu Thr Ala Asp Thr Ser Ser Ser Thr Ala Tyr
65                  70                  75                  80

Leu Ala Leu Thr Arg Leu Ala Ser Asp Thr Ala Val Tyr Tyr Cys
                85                  90                  95

Ala Arg Asp Arg Leu Thr Gly Gly Arg Asp Ala Phe Glu Ile Trp Gly
            100                 105                 110

Gln Gly Thr Met Leu Ile Val Ser Ser
        115                 120

<210> SEQ ID NO 833
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 833

Gly Tyr Ile Phe Thr Ala Tyr Tyr
1               5

```
<210> SEQ ID NO 834
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 834

Asp Ile Gln Leu Thr Gln Ser Pro Ser Leu Ser Ala Ser Val Gly
1               5                   10                  15

Asp Arg Val Thr Ile Thr Cys Arg Ala Ser Gln Ser Val Ser Ser Tyr
                20                  25                  30

Leu Asn Trp Tyr Gln Gln Lys Pro Gly Glu Ala Pro Lys Leu Leu Ile
            35                  40                  45

Ser Ala Ala Ser Ser Leu Gln Asp Gly Val Pro Pro Arg Phe Ser Gly
        50                  55                  60

Ser Arg Ser Gly Thr Glu Phe Thr Leu Thr Ile Ser Ser Leu Gln Pro
65                  70                  75                  80

Glu Asp Phe Ala Ile Tyr Tyr Cys Gln Gln Ser Tyr Ser Leu Trp Trp
                85                  90                  95

Thr Phe Gly Gln Gly Thr Lys Val Glu Ile Lys
            100                 105

<210> SEQ ID NO 835
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 835

Gln Ser Val Ser Ser Tyr
1               5

<210> SEQ ID NO 836
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 836

Gln Gln Ser Tyr Ser Leu Trp Trp Thr
1               5

<210> SEQ ID NO 837
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 837

Gln Leu Gln Leu Gln Glu Ser Gly Ser Gly Leu Val Lys Pro Ser Gln
1               5                   10                  15

Thr Leu Ser Leu Thr Cys Asp Val Ser Gly Asp Ser Met Asn Asp Asp
                20                  25                  30

Val Tyr Thr Trp Ser Trp Ile Arg Gln Pro Pro Gly Arg Gly Leu Glu
            35                  40                  45
```

Trp Ile Gly Tyr Ile Ser His Thr Gly Asn Thr Phe Tyr Asn Ser Ser
         50                  55                  60

Leu Gln Ser Arg Val Thr Met Ser Val Asp Thr Ser Lys Asn Gln Phe
 65                  70                  75                  80

Ser Leu Lys Leu Ser Ser Val Thr Ile Ala Asp Thr Ala Val Tyr Tyr
                 85                  90                  95

Cys Ala Arg Leu Thr Phe Leu Phe Ser Ala Pro Phe Ser Ser Phe Asn
             100                 105                 110

Trp Phe Asp Pro Trp Gly Gln Gly Ile Leu Val Thr Val Ser Ser
             115                 120                 125

<210> SEQ ID NO 838
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 838

Gly Asp Ser Met Asn Asp Asp Val Tyr Thr
1               5                   10

<210> SEQ ID NO 839
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 839

Ile Ser His Thr Gly Asn Thr
1               5

<210> SEQ ID NO 840
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 840

Ala Arg Leu Thr Phe Leu Phe Ser Ala Pro Phe Ser Ser Phe Asn Trp
1               5                   10                  15

Phe Asp Pro

<210> SEQ ID NO 841
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 841

Gln Ser Val Leu Thr Gln Pro Pro Ser Val Ser Gly Ala Pro Gly Gln
1               5                   10                  15

Thr Ile Thr Ile Ser Cys Thr Gly Thr Pro Ser Asn Phe Gly Ala Asp
            20                  25                  30

Tyr Asp Val His Trp Tyr Gln Gln Arg Pro Gly Thr Ala Pro Lys Leu
        35                  40                  45

```
Leu Ile Phe Ala Asp Lys His Arg Pro Ser Gly Val Pro Asp Arg Phe
 50                  55                  60

Ser Gly Ser Arg Ser Gly Thr Ser Ala Ser Leu Ala Ile Ser Gly Leu
 65                  70                  75                  80

Gln Ala Glu Asp Glu Ala Asp Tyr Tyr Cys Gln Ser Tyr Asp Ser Gly
                 85                  90                  95

Val Val Gly Leu Trp Val Phe Gly Gly Gly Thr Lys Val Thr Val Leu
            100                 105                 110

<210> SEQ ID NO 842
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 842

Pro Ser Asn Phe Gly Ala Asp Tyr Asp
1               5

<210> SEQ ID NO 843
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 843

Ala Asp Lys
1

<210> SEQ ID NO 844
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 844

Gln Ser Tyr Asp Ser Gly Val Val Gly Leu Trp Val
1               5                   10

<210> SEQ ID NO 845
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 845

Gln Val Gln Leu Gln Gln Trp Gly Ala Gly Leu Leu Lys Pro Ser Glu
1               5                   10                  15

Thr Leu Ser Leu Thr Cys Gly Val His Gly Gly Ser Leu Asn Asn Tyr
            20                  25                  30

Tyr Trp Ser Trp Ile Arg Gln Pro Pro Gly Lys Gly Leu Glu Trp Ile
        35                  40                  45

Gly Glu Val Tyr His Ser Gly Ser Ile Asn Tyr Asn Pro Ser Leu Lys
    50                  55                  60

Ser Arg Val Thr Met Ser Val Asp Thr Ser Lys Asn Gln Phe Ser Phe
65                  70                  75                  80
```

```
Asn Leu Ser Ser Val Thr Ala Ala Asp Thr Ala Val Tyr Tyr Cys Ala
                85                  90                  95

Arg Gly Ala Tyr Asp Ser Arg Gly Phe Trp Thr Leu Asp Ala Phe Asn
            100                 105                 110

Thr Trp Gly Gln Gly Thr Met Val Ile Val Ser Ser
        115                 120

<210> SEQ ID NO 846
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 846

Gly Gly Ser Leu Asn Asn Tyr Tyr
1               5

<210> SEQ ID NO 847
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 847

Val Tyr His Ser Gly Ser Ile
1               5

<210> SEQ ID NO 848
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 848

Ala Arg Gly Ala Tyr Asp Ser Arg Gly Phe Trp Thr Leu Asp Ala Phe
1               5                   10                  15

Asn Thr

<210> SEQ ID NO 849
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 849

Asp Ile Gln Met Thr Gln Ser Pro Ser Ala Leu Ser Ala Ser Leu Gly
1               5                   10                  15

Asp Arg Val Thr Ile Thr Cys Arg Ala Ser Glu Ser Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Asp Asp Phe Ala Thr Tyr Tyr Cys His Gln Tyr Asn Arg Tyr Ser Tyr
                85                  90                  95

Thr Phe Gly Gln Gly Thr Lys Leu Asp Ile Lys
            100                 105

<210> SEQ ID NO 850
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 850

Glu Ser Ile Asn Ser Trp
1               5

<210> SEQ ID NO 851
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 851

His Gln Tyr Asn Arg Tyr Ser Tyr Thr
1               5

<210> SEQ ID NO 852
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 852

Glu Val Leu Leu Leu Glu Ser Gly Gly Gly Leu Val His Pro Gly Gly
1               5                   10                  15

Thr Leu Arg Leu Ser Cys Ala Ala Ser Gly Phe Thr Phe Arg Asn Ser
            20                  25                  30

Ala Met Thr Trp Val Arg Gln Ala Pro Gly Lys Gly Leu Glu Trp Val
        35                  40                  45

Ser Ser Ile Gly Gly Ser Gly Ala Lys Ser Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Thr Leu Arg Val Asp Asp Thr Ala Ile Tyr Tyr Cys
                85                  90                  95

Ala Lys Asp Gln Leu Asn Cys Tyr Asp Leu Trp Ser Gly Asp Tyr Cys
            100                 105                 110

Trp Phe Asp Thr Trp Gly Gln Gly Thr Leu Val Thr Val Ser Ser
        115                 120                 125

<210> SEQ ID NO 853
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 853

Gly Phe Thr Phe Arg Asn Ser Ala
1               5

<210> SEQ ID NO 854
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 854

Ile Gly Gly Ser Gly Ala Lys Ser
1               5

<210> SEQ ID NO 855
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 855

Ala Lys Asp Gln Leu Asn Cys Tyr Asp Leu Trp Ser Gly Asp Tyr Cys
1               5                   10                  15

Trp Phe Asp Thr
            20

<210> SEQ ID NO 856
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 856

Gln Ser Val Leu Ile Gln Pro Pro Ser Ala Ser Gly Thr Pro Gly Gln
1               5                   10                  15

Arg Val Thr Ile Ser Cys Ser Gly Ser Asn Ser Asn Ile Gly Ser Asn
            20                  25                  30

Tyr Val Cys Trp Tyr Gln His Leu Pro Gly Gly Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Leu
                85                  90                  95

Ser Gly Ser Trp Val Phe Gly Gly Gly Thr Lys Leu Thr Val Leu
            100                 105                 110

<210> SEQ ID NO 857
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 857
```

Asn Ser Asn Ile Gly Ser Asn Tyr
1               5

<210> SEQ ID NO 858
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 858

Ala Ala Trp Asp Asp Ser Leu Ser Gly Ser Trp Val
1               5                   10

<210> SEQ ID NO 859
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 859

Glu Val Gln Leu Leu Glu Ser Gly Gly Gly Leu Val Gln Pro Gly Gly
1               5                   10                  15

Ser Leu Arg Leu Ser Cys Ala Val Ser Gly Leu Lys Phe Ser Ser Tyr
            20                  25                  30

Ala Met Ser Trp Val Arg Gln Ala Pro Gly Lys Gly Leu Glu Trp Val
        35                  40                  45

Ser Val Val Ser Gly Ser Ser Gly Ser Thr Phe Tyr Ala Val Ser Val
    50                  55                  60

Glu Gly Arg Phe Ser Ile Ser Arg Asp Asn Ser Asn Asn Met Leu Tyr
65                  70                  75                  80

Met Asp Met His Ser Leu Arg Val Glu Asp Thr Ala Lys Tyr Tyr Cys
                85                  90                  95

Ala Lys Val Val Gly Trp Tyr Tyr Asp Arg Asn Gly Asn Arg Arg Pro
            100                 105                 110

Lys Gly Phe Arg Ala Phe Asp Val Trp Gly Gln Gly Thr Met Val Ile
        115                 120                 125

Val Ser Ser
    130

<210> SEQ ID NO 860
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 860

Gly Leu Lys Phe Ser Ser Tyr Ala
1               5

<210> SEQ ID NO 861
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 861

Val Ser Gly Ser Ser Gly Ser Thr
1               5

<210> SEQ ID NO 862
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 862

Ala Lys Val Val Gly Trp Tyr Tyr Asp Arg Asn Gly Asn Arg Arg Pro
1               5                   10                  15

Lys Gly Phe Arg Ala Phe Asp Val
            20

<210> SEQ ID NO 863
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 863

Gln Ser Val Leu Thr Gln Pro Pro Ser Ala Ser Gly Thr Pro Gly Gln
1               5                   10                  15

Arg Ile Thr Ile Ala Cys Ser Gly Thr Thr Ser Asn Ile Gly Gly Asn
            20                  25                  30

Ser Val Asn Trp Tyr Gln Gln Phe Pro Gly Ala Ala Pro Arg Leu Leu
        35                  40                  45

Ile Phe Asp Tyr Asp Gln Arg Pro Ser Gly Val Pro Ala Arg Phe Ser
    50                  55                  60

Gly Ser Ser Ser Gly Ser Ser Gly Tyr Leu Ala Ile Ser Gly Leu Gln
65                  70                  75                  80

Ser Glu Asp Glu Ala Asp Tyr Tyr Cys Ser Ser Trp Asp Asp Asn Leu
                85                  90                  95

Asn Gly Trp Val Phe Gly Gly Gly Thr Lys Leu Thr Val Leu
            100                 105                 110

<210> SEQ ID NO 864
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 864

Thr Ser Asn Ile Gly Gly Asn Ser
1               5

<210> SEQ ID NO 865
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 865

Asp Tyr Asp

```
<210> SEQ ID NO 866
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 866

Ser Ser Trp Asp Asp Asn Leu Asn Gly Trp Val
1               5                   10

<210> SEQ ID NO 867
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 867

Glu Val Gln Leu Leu Glu Ser Gly Gly Gly Leu Val Gln Pro Gly Gly
1               5                   10                  15

Ser Leu Arg Leu Ser Cys Val Ala Ser Gly Phe Thr Phe Ser Gly His
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Lys Thr Val Asp
65                  70                  75                  80

Leu Gln Met Asn Asn Leu Arg Ala Glu Asp Thr Ala Ile Tyr Tyr Cys
                85                  90                  95

Ala Lys Asp Leu His Phe Asp Thr Ser Gly Tyr Tyr Tyr Ser Met Ile
            100                 105                 110

Phe Asp Tyr Trp Gly Gln Gly Thr Leu Val Pro Val Ser Ser
        115                 120                 125

<210> SEQ ID NO 868
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 868

Gly Phe Thr Phe Ser Gly His Ala
1               5

<210> SEQ ID NO 869
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 869

Ala Lys Asp Leu His Phe Asp Thr Ser Gly Tyr Tyr Tyr Ser Met Ile
1               5                   10                  15
```

Phe Asp Tyr

<210> SEQ ID NO 870
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 870

Gln Ser Ala Leu Ala Gln Pro Ala Ser Val Ser Gly Ser Pro Gly Gln
1               5                   10                  15

Ser Ile Thr Ile Ser Cys Thr Gly Thr Ser Ser Asp Ile Ser Asp Tyr
            20                  25                  30

Asn Tyr Val Ser Trp Tyr Gln Gln His Pro Gly Lys Ala Pro Lys Leu
        35                  40                  45

Ile Leu Tyr Asp Val Asn Asn Arg Pro Ser Gly Val Ser Ser Arg Phe
50                  55                  60

Ser Gly Ser Lys Ser Gly Asp Thr Ala Ser Leu Thr Ile Ser Gly Leu
65                  70                  75                  80

Gln Pro Glu Asp Glu Ala Asp Tyr Tyr Cys Ser Ser Tyr Thr Ser Thr
            85                  90                  95

Lys Ile Phe Gly Gly Gly Thr Lys Val Thr Val Leu
        100                 105

<210> SEQ ID NO 871
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 871

Ser Ser Asp Ile Ser Asp Tyr Asn Tyr
1               5

<210> SEQ ID NO 872
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 872

Ser Ser Tyr Thr Ser Thr Lys Ile
1               5

<210> SEQ ID NO 873
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 873

Glu Val Gln Leu Leu Glu Ser Gly Gly Gly Leu Leu Gln Leu Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
            35                  40                  45

Ser Leu Ile Thr Gly Ser Gly Gly Asn Thr Tyr Tyr Ala Asp Ser Val
 50                  55                  60

Lys Gly Arg Phe Thr Ile Ser Arg Asp Asn Ser Lys Asn Thr Leu Phe
 65                  70                  75                  80

Leu Gln Met Asn Ser Leu Arg Val Glu Asp Thr Ala Ile Tyr Tyr Cys
                 85                  90                  95

Val Lys Thr Asp Phe Tyr Asp Ser Ser Gly Tyr Tyr Phe His Asp Ala
                100                 105                 110

Phe His Ile Trp Gly Gln Gly Thr Met Val Thr Val Ser Ser
        115                 120                 125

<210> SEQ ID NO 874
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 874

Gly Phe Thr Phe Ser Ser Tyr Val
1               5

<210> SEQ ID NO 875
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 875

Ile Thr Gly Ser Gly Gly Asn Thr
1               5

<210> SEQ ID NO 876
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 876

Val Lys Thr Asp Phe Tyr Asp Ser Ser Gly Tyr Tyr Phe His Asp Ala
1               5                   10                  15

Phe His Ile

<210> SEQ ID NO 877
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 877

Gln Thr Val Val Thr Gln Glu Pro Ser Leu Thr Val Ser Pro Gly Gly
1               5                   10                  15

Thr Val Thr Leu Thr Cys Ala Ser Ser Thr Gly Ser Val Thr Ser Gly
                20                  25                  30

```
Tyr Tyr Pro Asn Trp Phe Gln Gln Lys Pro Gly Gln Ala Pro Arg Thr
            35                  40                  45

Leu Ile Tyr Gly Thr Ser Asn Lys His Ser Trp Thr Pro Ala Arg Phe
 50                  55                  60

Ser Gly Ser Leu Leu Gly Gly Lys Ala Ala Leu Thr Leu Ser Asp Val
 65                  70                  75                  80

Gln Pro Glu Asp Glu Ala Glu Tyr Tyr Cys Leu Leu Tyr Tyr Gly Gly
                 85                  90                  95

Ala Tyr Val Phe Gly Thr Gly Thr Lys Val Thr Val Leu
                100                 105
```

<210> SEQ ID NO 878
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 878

```
Thr Gly Ser Val Thr Ser Gly Tyr Tyr
 1               5
```

<210> SEQ ID NO 879
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 879

```
Leu Leu Tyr Tyr Gly Gly Ala Tyr Val
 1               5
```

<210> SEQ ID NO 880
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 880

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ile Arg Tyr
                20                  25                  30

Asp Ile His Trp Val Arg Gln Ala Thr Gly Gln Gly Leu Glu Trp Met
            35                  40                  45

Gly Trp Met Asn Pro Asn Asn Gly Lys Ser Gly Phe Ala Gln Lys Phe
 50                  55                  60

Glu Gly Arg Val Thr Leu Thr Arg Asn Thr Ser Val Ser Thr Tyr
 65                  70                  75                  80

Met Gln Leu Ser Ser Leu Gly Leu Glu Asp Thr Ala Val Tyr Tyr Cys
                 85                  90                  95

Val Arg Ala Gly Tyr Ser Tyr Gly Trp Gly Phe Asp Tyr Trp Gly Gln
                100                 105                 110

Gly Ser Leu Val Thr Val Ser Ser
            115                 120
```

```
<210> SEQ ID NO 881
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 881

Gly Tyr Thr Phe Ile Arg Tyr Asp
1               5

<210> SEQ ID NO 882
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 882

Met Asn Pro Asn Asn Gly Lys Ser
1               5

<210> SEQ ID NO 883
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 883

Val Arg Ala Gly Tyr Ser Tyr Gly Trp Gly Phe Asp Tyr
1               5                   10

<210> SEQ ID NO 884
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 884

Asn Phe Thr Leu Thr Gln Pro His Ser Val Ser Gly Ser Pro Gly Lys
1               5                   10                  15

Thr Val Thr Ile Ser Cys Thr Arg Ser Ser Gly Gly Ile Ala Ser Ser
            20                  25                  30

His Val Gln Trp Tyr Gln Gln Arg Pro Ala Ser Ala Pro Thr Thr Leu
        35                  40                  45

Ile Phe Glu Asp Asp Gln Arg Ser Ser Gly Val Pro Asp Arg Phe Ser
    50                  55                  60

Gly Ser Ile Asp Thr Ser Ser Asn Ser Ala Tyr Leu Thr Ile Ser Gly
65                  70                  75                  80

Leu Glu Ala Glu Asp Glu Ala Asp Tyr Tyr Cys Gln Ser Tyr Asp Asn
                85                  90                  95

Ser Met Trp Val Phe Gly Gly Gly Ser Lys Val Thr Val Leu
            100                 105                 110

<210> SEQ ID NO 885
<211> LENGTH: 8
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 885

Ser Gly Gly Ile Ala Ser Ser His
1               5

<210> SEQ ID NO 886
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 886

Glu Asp Asp
1

<210> SEQ ID NO 887
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 887

Gln Ser Tyr Asp Asn Ser Met Trp Val
1               5

<210> SEQ ID NO 888
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 888

His Val Gln Leu Val Gln Ser Gly Ala Asp Val Lys Lys Pro Gly Ser
1               5                   10                  15

Ser Val Lys Val Ser Cys Lys Phe Ser Gly Gly Thr Phe Asn Asn Asp
                20                  25                  30

Ser Ile Asn Trp Val Arg Gln Ala Pro Gly Gln Gly Leu Glu Trp Met
            35                  40                  45

Gly Val Ile Met Pro Phe Phe Gly Ala Thr Arg Phe Ala Pro Lys Phe
        50                  55                  60

Gln Gly Arg Val Thr Leu Thr Ala Asp Lys Phe Thr Ser Thr Gly Tyr
65                  70                  75                  80

Met Glu Leu Gly Ser Leu Lys Ser Asp Asp Thr Ala Val Tyr Tyr Cys
                85                  90                  95

Ala Arg Asp Lys Pro Pro Asp Asp Lys Trp Ala Asp Tyr Gly Met Asp
                100                 105                 110

Val Trp Gly Gln Gly Thr Thr Val Thr Val Ser Ser
            115                 120

<210> SEQ ID NO 889
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 889

Gly Gly Thr Phe Asn Asn Asp Ser
1               5

<210> SEQ ID NO 890
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 890

Ile Met Pro Phe Phe Gly Ala Thr
1               5

<210> SEQ ID NO 891
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 891

Ala Arg Asp Lys Pro Asp Asp Lys Trp Ala Asp Tyr Gly Met Asp
1               5                   10                  15

Val

<210> SEQ ID NO 892
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 892

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Val
                20                  25                  30

Tyr Trp Tyr Gln Gln Lys Thr Gly Gln Ala Pro Val Leu Val Ile Tyr
            35                  40                  45

Lys Asp Thr Glu Arg Pro Ser Gly Ile Pro Glu Arg Phe Ser Gly Ser
    50                  55                  60

Thr Ser Gly Thr Thr Val Thr Leu Thr Ile Ser Gly Val Gln Ala Asp
65                  70                  75                  80

Asp Glu Ala Asp Tyr Phe Cys Gln Ser Ala Asp Arg Asn Ala Asn Tyr
                85                  90                  95

Arg Val Phe Gly Gly Gly Thr Lys Leu Thr Val Leu
                100                 105

<210> SEQ ID NO 893
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 893

```
Gln Ser Ala Asp Arg Asn Ala Asn Tyr Arg Val
1               5                   10
```

<210> SEQ ID NO 894
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 894

```
Gln Leu Gln Leu Gln Glu Ser Gly Ser Gly Leu Val Lys Pro Ser Gln
1               5                   10                  15

Thr Leu Ser Leu Thr Cys Ala Val Ser Gly Ser Ile Thr Ser Gly
            20                  25                  30

Thr Tyr Ser Trp Thr Trp Ile Arg Gln Ser Pro Glu Lys Gly Leu Glu
        35                  40                  45

Trp Ile Gly Tyr Ile Tyr Tyr Thr Gly Ser Thr Tyr Tyr Asn Pro Ser
    50                  55                  60

Leu Gly Arg Arg Val Thr Ile Ser Gly Asp Thr Ser Asn Asn Glu Phe
65                  70                  75                  80

Ser Leu Asn Leu Lys Ser Val Thr Ala Ala Asp Thr Ala Val Tyr Tyr
                85                  90                  95

Cys Ala Arg Gly Ile His Arg Gly Gly Val Leu Asp Phe Trp Gly Gln
            100                 105                 110

Gly Ile Leu Val Thr Val Ser Ser
        115                 120
```

<210> SEQ ID NO 895
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 895

```
Gly Gly Ser Ile Thr Ser Gly Thr Tyr Ser
1               5                   10
```

<210> SEQ ID NO 896
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 896

```
Ile Tyr Tyr Thr Gly Ser Thr
1               5
```

<210> SEQ ID NO 897
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 897

```
Ala Arg Gly Ile His Arg Gly Gly Val Leu Asp Phe
1               5                   10
```

<210> SEQ ID NO 898
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 898

Glu Ile Val Leu Thr Gln Ser Pro Ala Thr Leu Pro Leu Ser Pro Gly
1               5                   10                  15

Glu Arg Ala Thr Leu Ser Cys Arg Ala Ser Gln Ser Leu Asp Lys Tyr
            20                  25                  30

Leu Ala Trp Tyr Gln Gln Lys Pro Gly Gln Ala Pro Arg Leu Leu Ile
        35                  40                  45

Tyr Asp Thr Ser Lys Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Arg Asn Asn Trp Pro Pro
                85                  90                  95

Tyr Thr Phe Gly Gln Gly Thr Lys Val Glu Met Lys
            100                 105

<210> SEQ ID NO 899
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 899

Gln Ser Leu Asp Lys Tyr
1               5

<210> SEQ ID NO 900
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 900

Asp Thr Ser
1

<210> SEQ ID NO 901
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 901

Gln Gln Arg Asn Asn Trp Pro Pro Tyr Thr
1               5                   10

<210> SEQ ID NO 902
<211> LENGTH: 119
<212> TYPE: PRT

<213> ORGANISM: Artificial Sequence
<220> FEATURE:
<223> OTHER INFORMATION: Description of Artificial Sequence: Synthetic
    polypeptide

<400> SEQUENCE: 902

Gln Val Leu Leu Val Gln Ser Gly Ser Glu Val Lys Asn Pro Gly Ala
1               5                   10                  15

Ser Ile Arg Val Ser Cys Lys Thr Ser Gly Tyr Met Phe Thr Asn Asn
            20                  25                  30

Gly Ile Ala Trp Val Arg Glu Val Pro Thr Gln Gly Leu Glu Trp Met
        35                  40                  45

Gly Trp Ile Ser Thr Tyr Ser Gly Ala Thr His Tyr Ala Pro Asn Leu
    50                  55                  60

His Gly Arg Ile Thr Met Thr Ala Asp Thr Ser Ala Ser Thr Ala Tyr
65                  70                  75                  80

Met Glu Leu Arg Ser Leu Gln Ser Gly Asp Thr Gly Val Tyr Tyr Cys
                85                  90                  95

Ala Arg Leu Trp Phe Gly Lys Leu Gly Leu Asp Phe Trp Gly Gln Gly
            100                 105                 110

Thr Gln Val Thr Val Ser Ser
        115

<210> SEQ ID NO 903
<211> LENGTH: 8
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 903

Gly Tyr Met Phe Thr Asn Asn Gly
1               5

<210> SEQ ID NO 904
<211> LENGTH: 8
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 904

Ile Ser Thr Tyr Ser Gly Ala Thr
1               5

<210> SEQ ID NO 905
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 905

Ala Arg Leu Trp Phe Gly Lys Leu Gly Leu Asp Phe
1               5                   10

<210> SEQ ID NO 906
<211> LENGTH: 111
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 906

Gln Ser Val Leu Thr Gln Pro Pro Ser Ala Ser Gly Thr Pro Gly Gln
1               5                   10                  15

Arg Val Ile Ile Ser Cys Ser Gly Ser Thr Ser Asn Ile Gly Thr Lys
            20                  25                  30

Thr Val Asn Trp Tyr Gln His Leu Pro Gly Thr Ala Pro Lys Leu Leu
        35                  40                  45

Ile Tyr Asn Asn Asn Gln Arg Pro Ser Gly Val Pro Asp Arg Phe Ser
    50                  55                  60

Gly Ser Lys Ser Gly Thr Ser Ala Ser Leu Thr Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Arg Gly Leu Phe Gly Pro Gly Thr Lys Val Thr Val Leu
            100                 105                 110

<210> SEQ ID NO 907
<211> LENGTH: 8
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 907

Thr Ser Asn Ile Gly Thr Lys Thr
1               5

<210> SEQ ID NO 908
<211> LENGTH: 3
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 908

Asn Asn Asn
1

<210> SEQ ID NO 909
<211> LENGTH: 12
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 909

Ala Ala Trp Asp Asp Ser Leu Asn Gly Arg Gly Leu
1               5                   10

<210> SEQ ID NO 910
<211> LENGTH: 124
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 910

```
Gln Val Glu Val Val Glu Ser Gly Gly Gly Val Val Gln Pro Gly Lys
1               5                   10                  15

Ser Leu Arg Leu Ser Cys Ala Ala Ser Gly Phe Lys Phe Asn Val Tyr
            20                  25                  30

Gly Ile His Trp Val Arg Gln Ala Pro Gly Lys Gly Leu Glu Trp Val
            35                  40                  45

Ala Val Val Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Thr Tyr
65                  70                  75                  80

Leu Gln Met Asp Ser Leu Arg Val Asp Asp Thr Ala Val Tyr Tyr Cys
                85                  90                  95

Ala Arg Glu Leu Gln Tyr Ser Asn Tyr Asp Tyr Phe Tyr Ala Met Asp
            100                 105                 110

Val Trp Gly Gln Gly Thr Thr Val Thr Val Ser Ser
            115                 120
```

```
<210> SEQ ID NO 911
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 911

Gly Phe Lys Phe Asn Val Tyr Gly
1               5
```

```
<210> SEQ ID NO 912
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 912

Val Trp Tyr Asp Gly Ser Asn Lys
1               5
```

```
<210> SEQ ID NO 913
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 913

Ala Arg Glu Leu Gln Tyr Ser Asn Tyr Asp Tyr Phe Tyr Ala Met Asp
1               5                   10                  15

Val
```

```
<210> SEQ ID NO 914
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 914
```

```
Asp Ile Gln Met Thr Gln Ser Pro Pro Ser Leu Ser Ala Ser Val Gly
1               5                   10                  15

Asp Arg Val Thr Ile Thr Cys Arg Ala Ser Gln Asp Ile Asp Asn Tyr
            20                  25                  30

Leu Val Trp Phe Gln Gln Lys Pro Gly Arg Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Tyr
                85                  90                  95

Thr Phe Gly Gln Gly Thr Lys Leu Glu Ile Lys
            100                 105

<210> SEQ ID NO 915
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 915

Gln Asp Ile Asp Asn Tyr
1               5

<210> SEQ ID NO 916
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 916

Gln Gln Tyr Asn Ser Phe Pro Tyr Thr
1               5

<210> SEQ ID NO 917
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 917

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Ser Ser His
            20                  25                  30

Tyr Trp Ser Trp Ile Arg Gln Pro Pro Gly Arg Gly Leu Glu Trp Ile
        35                  40                  45

Ala Tyr Ile Ser Tyr Ser Gly Arg Thr Lys Tyr Asn Pro Ser Leu Lys
    50                  55                  60

Ser Arg Val Thr Ile Ser Glu Asp Thr Ser Lys Asn Gln Phe Ser Leu
65                  70                  75                  80

Lys Leu Ser Ser Val Thr Pro Ala Asp Thr Ala Val Tyr Tyr Cys Ala
                85                  90                  95

Arg Ile Tyr Gly Asp Tyr Gly Pro Phe Ile Asp Tyr Trp Gly Gln Gly
```

Thr Leu Val Thr Val Ser Ser
            115

<210> SEQ ID NO 918
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 918

Gly Gly Ser Ile Ser Ser His Tyr
1               5

<210> SEQ ID NO 919
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 919

Ile Ser Tyr Ser Gly Arg Thr
1               5

<210> SEQ ID NO 920
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 920

Ala Arg Ile Tyr Gly Asp Tyr Gly Pro Phe Ile Asp Tyr
1               5                   10

<210> SEQ ID NO 921
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 921

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Thr Tyr
            20                  25                  30

Leu Asn Trp Tyr Gln Gln Lys Pro Gly Thr Ala Pro Met Leu Leu Ile
        35                  40                  45

Tyr Gly Ala Tyr Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Ser Leu Pro Leu
                85                  90                  95

Thr Phe Gly Gly Gly Thr Lys Val Glu Ile Lys
            100                 105

<210> SEQ ID NO 922
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 922

Gln Thr Ile Ser Thr Tyr
1               5

<210> SEQ ID NO 923
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 923

Gly Ala Tyr
1

<210> SEQ ID NO 924
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 924

Gln Gln Ser Ser Ser Leu Pro Leu Thr
1               5

<210> SEQ ID NO 925
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 925

Gln Glu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp His Tyr Trp Ser Trp Leu Arg Gln Thr Pro Gly Lys Gly Leu Glu
        35                  40                  45

Trp Ile Gly Tyr Ile Tyr Arg Gly Asn Thr Asn Tyr Asn Pro Ser
    50                  55                  60

Leu Glu Ser Arg Ile Thr Met Ser Val Asp Thr Ser Lys Asn Gln Phe
65                  70                  75                  80

Ser Leu Lys Leu Ser Ser Val Thr Ala Ala Asp Thr Gly Val Tyr Tyr
                85                  90                  95

Cys Ala Arg Asp Arg Arg Leu Leu Phe Trp Phe Gly Gln Gly Pro Glu
            100                 105                 110

Thr Phe Asp Ile Trp Gly Pro Gly Thr Met Val Thr Val Ser Ser
        115                 120                 125

<210> SEQ ID NO 926

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 926

Gly Gly Ser Ile Ser Ser Gly Asp His Tyr
1               5                   10

<210> SEQ ID NO 927
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 927

Ile Tyr Tyr Arg Gly Asn Thr
1               5

<210> SEQ ID NO 928
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 928

Ala Arg Asp Arg Arg Leu Leu Phe Trp Phe Gly Gln Gly Pro Glu Thr
1               5                   10                  15

Phe Asp Ile

<210> SEQ ID NO 929
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 929

Asp Ile Gln Met Thr Gln Ser Pro Ser Ile Leu Ser Ala Ser Val Gly
1               5                   10                  15

Asp Arg Val Thr Ile Thr Cys Arg Ala Ser Gln Asn Ile Asn His Trp
            20                  25                  30

Leu Ala Trp Tyr Gln Gln Lys Pro Gly Lys Ala Pro Lys Leu Leu Ile
        35                  40                  45

Tyr Met Ala Ser Ser Leu Glu Asn Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Gly
                85                  90                  95

Thr Phe Gly His Gly Thr Lys Val Asp Ile Lys
            100                 105

<210> SEQ ID NO 930
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 930

Gln Asn Ile Asn His Trp
1               5

<210> SEQ ID NO 931
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 931

Met Ala Ser
1

<210> SEQ ID NO 932
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 932

Gln Gln Tyr Asn Ser Tyr Ser Gly Thr
1               5

<210> SEQ ID NO 933
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 933
tactgtgcga aagttcttga ctacagtgaa tttcattact attacggttt ggacgtctgg      60
ggccaaggga ccgcggtcgc cgtctcctca g                                     91

<210> SEQ ID NO 934
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 934
tactgtgcga aagttcttga ctacaatgag tactctctct acttcggtat ggacgtctgg      60
ggccaaggga ccacggtcac cgtctcctca g                                     91

<210> SEQ ID NO 935
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 935
tactgtgcga aagttcttga ctacagtgaa tactctctct acttcggtat ggacgtctgg      60
```

```
ggccaaggga ccacggtcct tgtctcctca g                                    91

<210> SEQ ID NO 936
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 936
tactgtgcga aggtccttga ctacagtagg tactccctatt attacgggat ggacgtctgg    60
ggccagggga ccacggtcat cgtctcctca g                                    91

<210> SEQ ID NO 937
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 937
tactgtgcta aggtccttga ctacagtgca ttctcctatt attatgggat ggacgtctgg     60
ggccagggga ccacggtcat cgtctcctca g                                    91

<210> SEQ ID NO 938
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 938
tattgtgcga aagtccttga ctacagtatt ttctattact atttcggcct ggacgtctgg     60
ggccaaggga ccacggtcac cgtctcctca g                                    91

<210> SEQ ID NO 939
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 939
tactgtgcga aaga                                                       14

<210> SEQ ID NO 940
<211> LENGTH: 4
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 940 tyct                                                                  4

<210> SEQ ID NO 941
<211> LENGTH: 16
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 941
tgactacagt aactac                                                      16

<210> SEQ ID NO 942
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 942
attactacta ctactacggt atggacgtct ggggccaagg gaccacggtc accgtctcct      60
cag                                                                    63

<210> SEQ ID NO 943
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 943

Tyr Cys Ala Lys
1

<210> SEQ ID NO 944
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 944

Val Leu Asp Tyr Ser Asn Tyr
1               5

<210> SEQ ID NO 945
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 945

Asn Tyr Tyr Tyr Tyr Tyr Gly Met Asp Val Trp Gly Gln Gly Thr Thr
1               5                   10                  15

Val Thr Val Ser Ser
            20

<210> SEQ ID NO 946
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 946
```

-continued

Tyr Cys Ala Lys Val Leu Asp Tyr Ser Asn Tyr Tyr Tyr Tyr Gly
1               5                   10                  15

Met Asp Val Trp Gly Gln Gly Thr Thr Val Thr Val Ser Ser
            20                  25                  30

<210> SEQ ID NO 947
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 947

Tyr Cys Ala Lys Val Leu Asp Tyr Ser Glu Phe His Tyr Tyr Gly
1               5                   10                  15

Leu Asp Val Trp Gly Gln Gly Thr Ala Val Ala Val Ser Ser
            20                  25                  30

<210> SEQ ID NO 948
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 948

Tyr Cys Ala Lys Val Leu Asp Tyr Asn Glu Tyr Ser Leu Tyr Phe Gly
1               5                   10                  15

Met Asp Val Trp Gly Gln Gly Thr Thr Val Thr Val Ser Ser
            20                  25                  30

<210> SEQ ID NO 949
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 949

Tyr Cys Ala Lys Val Leu Asp Tyr Ser Glu Tyr Ser Leu Tyr Phe Gly
1               5                   10                  15

Met Asp Val Trp Gly Gln Gly Thr Thr Val Leu Val Ser Ser
            20                  25                  30

<210> SEQ ID NO 950
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 950

Tyr Cys Ala Lys Val Leu Asp Tyr Ser Arg Tyr Ser Tyr Tyr Gly
1               5                   10                  15

Met Asp Val Trp Gly Gln Gly Thr Thr Val Ile Val Ser Ser
            20                  25                  30

<210> SEQ ID NO 951
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 951

Tyr Cys Ala Lys Val Leu Asp Tyr Ser Ala Phe Ser Tyr Tyr Gly
1               5                   10                  15

Met Asp Val Trp Gly Gln Gly Thr Thr Val Ile Val Ser Ser
            20                  25                  30

<210> SEQ ID NO 952
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 952

Tyr Cys Ala Lys Val Leu Asp Tyr Ser Ile Phe Tyr Tyr Tyr Phe Gly
1               5                   10                  15

Leu Asp Val Trp Gly Gln Gly Thr Thr Val Thr Val Ser Ser
            20                  25                  30

<210> SEQ ID NO 953
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 953
gcagtgtatt actgtcagca ttacagtaat tcaccccccgt acactttttgg cccggggacc    60 aagttggaga tcaaac                                                      76

<210> SEQ ID NO 954
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 954
gcagtgtatt tctgtcagta ctatagtgac tcacctccgt acactttttgg cccggggacc    60 aagctggaga tcaaac                                                      76

<210> SEQ ID NO 955
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 955
gcagtgtatt cctgtcaaca ctatagtgac tcacctcctt acactttttgg ccaggggacc    60 aaactggaga tcaaac                                                      76

<210> SEQ ID NO 956
<211> LENGTH: 76
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 956
gcagtttatt actgtcagca ctatggtagg tcacctccgt acactttggg cccggggacc    60
aagctggaca tcaaac                                                    76

<210> SEQ ID NO 957
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 957
gcagtatatt actgtcaaca ctatggtagg tcacctccat acactttggg ccaggggacc    60
aaagtggaga tcaaac                                                    76

<210> SEQ ID NO 958
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 958
gcagtgtact actgtcagca ctatggagac tcacctccgt acacctttgg ccaggggacg    60
aaagtggaga tgaaac                                                    76

<210> SEQ ID NO 959
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 959
gcagtgtatt actgtcagca gtatggtagc tcacctcc                            38

<210> SEQ ID NO 960
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 960
tgtacacttt tggccagggg accaagctgg agatcaaac                           39

<210> SEQ ID NO 961
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 961

Ala Val Tyr Tyr Cys Gln Gln Tyr Gly Ser Ser Pro
1               5                   10
```

<210> SEQ ID NO 962
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 962

Pro Tyr Thr Phe Gly Gln Gly Thr Lys Leu Glu Ile Lys
1               5                   10

<210> SEQ ID NO 963
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 963

Ala Val Tyr Tyr Cys Gln Gln Tyr Gly Ser Ser Pro Pro Tyr Thr Phe
1               5                   10                  15

Gly Gln Gly Thr Lys Leu Glu Ile Lys
            20                  25

<210> SEQ ID NO 964
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 964

Ala Val Tyr Tyr Cys Gln His Tyr Ser Asn Ser Pro Pro Tyr Thr Phe
1               5                   10                  15

Gly Pro Gly Thr Lys Leu Glu Ile Lys
            20                  25

<210> SEQ ID NO 965
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 965

Ala Val Tyr Phe Cys Gln Tyr Tyr Ser Asp Ser Pro Pro Tyr Thr Phe
1               5                   10                  15

Gly Pro Gly Thr Lys Leu Glu Ile Lys
            20                  25

<210> SEQ ID NO 966
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 966

Ala Val Tyr Ser Cys Gln His Tyr Ser Asp Ser Pro Pro Tyr Thr Phe
1               5                   10                  15

Gly Gln Gly Thr Lys Leu Glu Ile Lys
            20                  25

<210> SEQ ID NO 967
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 967

Ala Val Tyr Tyr Cys Gln His Tyr Gly Arg Ser Pro Pro Tyr Thr Phe
1               5                   10                  15

Gly Pro Gly Thr Lys Leu Asp Ile Lys
            20                  25

<210> SEQ ID NO 968
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 968

Ala Val Tyr Tyr Cys Gln His Tyr Gly Arg Ser Pro Pro Tyr Thr Phe
1               5                   10                  15

Gly Gln Gly Thr Lys Val Glu Ile Lys
            20                  25

<210> SEQ ID NO 969
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 969

Ala Val Tyr Tyr Cys Gln His Tyr Gly Asp Ser Pro Pro Tyr Thr Phe
1               5                   10                  15

Gly Gln Gly Thr Lys Val Glu Met Lys
            20                  25

<210> SEQ ID NO 970
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 970

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro

```
                65                  70                  75                  80
Glu Asp Phe Ala Val Tyr Tyr Cys Gln Gln Arg Ser Asn Trp Pro Pro
                    85                  90                  95
Gly Phe Thr Phe Gly Pro Gly Thr Lys Val Asp Ile Lys
            100                 105
```

<210> SEQ ID NO 971
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 971

```
Ala Lys Val Met Asp Tyr Asp Ile Phe Lys Asn Tyr Phe Gly Leu Asp
1               5                   10                  15
Val
```

<210> SEQ ID NO 972
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 972

```
Ala Lys Val Met Asp Tyr Asp Val Phe Lys Asn Tyr Tyr Gly Leu Asp
1               5                   10                  15
Val
```

<210> SEQ ID NO 973
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 973

```
Ala Lys Thr Leu Asp Tyr Ser Gln Tyr Met Tyr Tyr Tyr Gly Leu Asp
1               5                   10                  15
Val
```

<210> SEQ ID NO 974
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 974

```
Gln His Tyr Gly Arg Ser Pro Pro Tyr Thr
1               5                   10
```

<210> SEQ ID NO 975
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 975

Gln His Tyr Gly Ser Ser Pro Pro Phe Thr
1               5                   10

<210> SEQ ID NO 976
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 976

Gln His Tyr Gly Ser Leu Pro Pro Phe Thr
1               5                   10

<210> SEQ ID NO 977
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 977

Ala Ala Trp Asp Asp Thr Leu Val Gly Val
1               5                   10

<210> SEQ ID NO 978
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 978

Ala Ala Trp Asp Asp Leu Val Val Gly Val
1               5                   10

<210> SEQ ID NO 979
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 979

Gln Ser Thr Asp Ser Ser Gly Asp Tyr Val Val
1               5                   10

<210> SEQ ID NO 980
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 980

Gln Ser Thr Asp Ser Ser Leu Arg Asp Val Val
1               5                   10

<210> SEQ ID NO 981
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 981

Thr Ser Tyr Ala Gly Arg Asn Ile Gln Val
1               5                   10

<210> SEQ ID NO 982
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 982

Ser Ser Tyr Ala Gly Ser Asn Ile Ala Val
1               5                   10

<210> SEQ ID NO 983
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 983

Gln Ser Tyr Asp Gly Ser Ser Pro Val Ile
1               5                   10

<210> SEQ ID NO 984
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 984

Gln Ser Tyr Asp Thr Asn Ile Val Val
1               5

<210> SEQ ID NO 985
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 985

Gln Ser Tyr Asp Ser Ala Asn Val Val
1               5

<210> SEQ ID NO 986
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 986

Gln Ser Tyr Asp Ala Asp Asn Ala Val
1               5
```

<210> SEQ ID NO 987
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 987

Ser Ser Tyr Thr Arg Glu Thr Ala Leu Gly Gly Val
1               5                   10

<210> SEQ ID NO 988
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 988

Gln Gln Tyr Tyr Thr Thr Pro Arg Thr
1               5

<210> SEQ ID NO 989
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 989

Gln Gln Tyr Tyr Thr Thr Pro Tyr Thr
1               5

<210> SEQ ID NO 990
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 990

Gln Gln Tyr Leu Thr Thr Pro Tyr Thr
1               5

<210> SEQ ID NO 991
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 991

Gln Gln Tyr Asp Glu Trp Pro Pro Phe Thr
1               5                   10

<210> SEQ ID NO 992
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 992

Gln Gln Tyr Asn His Trp Pro Pro Tyr Thr
1               5                   10

<210> SEQ ID NO 993
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 993

Gly Ser Tyr Lys Ser Gly Ser Thr Trp Val
1               5                   10

<210> SEQ ID NO 994
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 994

Ser Ser Tyr Arg Ser Gly Ser Thr Trp Val
1               5                   10

<210> SEQ ID NO 995
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 995

Ser Ser Tyr Thr Ser Gly Arg Thr Trp Val
1               5                   10

<210> SEQ ID NO 996
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 996

Ser Ser Tyr Thr Thr Gly Arg Thr Trp Val
1               5                   10

<210> SEQ ID NO 997
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 997

Ala Ser Arg Tyr Cys Thr Asp Ser Gly Cys Tyr Leu Gly Ser Phe Asp
1               5                   10                  15

Tyr
```

```
<210> SEQ ID NO 998
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 998

Ala Ser Arg Tyr Cys Thr Asp Asp Gly Cys Tyr Leu Gly Ser Phe Asp
1               5                   10                  15

Phe

<210> SEQ ID NO 999
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 999

Thr Arg Asp His Gly Tyr Tyr
1               5

<210> SEQ ID NO 1000
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1000

Ala Arg Asp His Gly Tyr Tyr
1               5

<210> SEQ ID NO 1001
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1001

Ala Arg Asp Pro Ala Ala Gly Thr Trp Trp Phe Asp Pro
1               5                   10

<210> SEQ ID NO 1002
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1002

Ala Arg Pro Ser Ala His Tyr Tyr Asp Arg Gly Gly Tyr Asn Asp Ala
1               5                   10                  15

Phe Asp Met

<210> SEQ ID NO 1003
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 1003

Thr Thr Gly Tyr Arg Thr Thr Thr Tyr His Gly Asp Asp Ala Phe
1               5                   10                  15

Asp Ile

<210> SEQ ID NO 1004
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1004

Thr Thr Gly Tyr Arg Thr Ser Thr Ser Tyr His Gly Asp Asp Ala Phe
1               5                   10                  15

Asp Ile

<210> SEQ ID NO 1005
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1005

Ala Arg Gly Pro Pro Ala Val Gln Gly Tyr Phe Tyr Tyr Met Tyr Val
1               5                   10                  15

<210> SEQ ID NO 1006
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1006

Ala Arg Gly Pro Pro Gly Val His Gly Tyr Phe Tyr Tyr Thr Asp Val
1               5                   10                  15

<210> SEQ ID NO 1007
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1007

Ala Arg Asp Val Val Arg Pro Gly Ser Gly Pro Arg Leu Gly Phe Asp
1               5                   10                  15

Pro

<210> SEQ ID NO 1008
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 1008

Ala Arg Asp Val Val Arg Pro Gly Arg Gly Pro Arg Leu Gly Phe Asp
1               5                   10                  15

Pro

<210> SEQ ID NO 1009
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1009

Ala Lys Glu Gly Gly Ser Ser Thr Ser Trp Tyr Ser Leu Tyr His Glu
1               5                   10                  15

Tyr Glu Met Asp Val
            20

<210> SEQ ID NO 1010
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1010

Ala His Lys Ala Ala Glu Pro Gly Ser Arg Asp Arg Trp Phe Asp Ser
1               5                   10                  15

<210> SEQ ID NO 1011
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1011

Ala Gly Gly Tyr Asn Asn Ser Ser Phe Tyr Phe Asp Ser
1               5                   10

<210> SEQ ID NO 1012
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1012

Ala Val Gly Tyr Asn Asn Ser Trp Phe Tyr Phe Asp Tyr
1               5                   10

<210> SEQ ID NO 1013
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1013

Ala Arg Leu Gly His Leu Arg Gly Trp Phe Asp Ser
1               5                   10
```

```
<210> SEQ ID NO 1014
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1014

Val Leu Ser Gln Tyr Glu Phe Gly Ser Ser Trp Phe Tyr Tyr Tyr Arg
1               5                   10                  15

Met Asp Val

<210> SEQ ID NO 1015
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1015

Val Leu Ser Lys Tyr Glu Phe Gly Ser Ser Trp Phe Tyr Tyr Tyr Arg
1               5                   10                  15

Met Asp Val

<210> SEQ ID NO 1016
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1016

Val Leu Ser Lys Tyr Glu Phe His Ser Ser Trp Phe Tyr Tyr Tyr Arg
1               5                   10                  15

Met Asp Val

<210> SEQ ID NO 1017
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1017

Gly Ser Gly Ser Gly Ser Gly
1               5

<210> SEQ ID NO 1018
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1018

Tyr Pro Tyr Asp Val Pro Asp Tyr Ala Gly
1               5                   10

<210> SEQ ID NO 1019
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1019

Ala Lys His Asp Tyr Asp Ser Ser Gly Tyr Phe Asp Glu Asp Tyr
1               5                   10                  15
```